(12) United States Patent
Kim et al.

(10) Patent No.: US 8,748,442 B2
(45) Date of Patent: Jun. 10, 2014

(54) SGC STIMULATORS

(75) Inventors: Charles Kim, Cambridge, MA (US);
Takashi Nakai, Newton, MA (US);
Thomas Wai-Ho Lee, Lexington, MA (US); Joel Moore, Lexington, MA (US);
Nicholas Robert Perl, Brookline, MA (US); Jason Rohde, Andover, MA (US);
Rajesh R Iyengar, West Newton, MA (US); Ara Mermerian, Melrose, MA (US); Angelika Fretzen, Somerville, MA (US)

(73) Assignee: Ironwood Pharmaceuticals, Inc., Cambridge, MA (US)

( * ) Notice: Subject to any disclaimer, the term of this patent is extended or adjusted under 35 U.S.C. 154(b) by 47 days.

(21) Appl. No.: 13/174,676

(22) Filed: Jun. 30, 2011

(65) Prior Publication Data

US 2012/0184516 A1      Jul. 19, 2012

Related U.S. Application Data

(60) Provisional application No. 61/360,236, filed on Jun. 30, 2010, provisional application No. 61/406,845, filed on Oct. 26, 2010, provisional application No. 61/474,563, filed on Apr. 12, 2011.

(51) Int. Cl.
| | | |
|---|---|---|
| A01N 43/54 | (2006.01) | |
| A61K 31/505 | (2006.01) | |
| A01N 43/40 | (2006.01) | |
| A61K 31/44 | (2006.01) | |
| C07D 401/00 | (2006.01) | |
| C07D 403/00 | (2006.01) | |
| C07D 405/00 | (2006.01) | |
| C07D 409/00 | (2006.01) | |
| C07D 411/00 | (2006.01) | |
| C07D 413/00 | (2006.01) | |
| C07D 417/00 | (2006.01) | |
| C07D 419/00 | (2006.01) | |

(52) U.S. Cl.
USPC ......... 514/269; 514/341; 544/333; 546/275.4

(58) Field of Classification Search
USPC .............. 514/269, 341; 544/333; 546/275.4
See application file for complete search history.

(56) References Cited

U.S. PATENT DOCUMENTS

| | | | |
|---|---|---|---|
| 3,169,966 A | 2/1965 | Schmidt et al. | |
| 3,228,946 A | 1/1966 | Schmidt et al. | |
| 3,250,761 A | 5/1966 | Schmidt et al. | |
| 5,470,862 A | 11/1995 | Lin et al. | |
| 6,028,072 A | 2/2000 | Lee et al. | |
| 2010/0075964 A1 | 3/2010 | Busch et al. | |

FOREIGN PATENT DOCUMENTS

| | | |
|---|---|---|
| BE | 612971 | 7/1962 |
| BE | 627392 | 1/1963 |
| BE | 627394 | 1/1963 |
| DE | 1197088 | 9/1962 |
| DE | 19744026 | 10/1997 |
| DE | 19744027 | 10/1997 |
| DE | 19649460 | 5/1998 |
| EP | 1433788 | 12/2002 |
| EP | 1479678 | 11/2004 |
| FR | 1403372 | 7/1964 |
| WO | 9307138 | 4/1993 |
| WO | 9715570 | 5/1997 |
| WO | 9827091 | 6/1998 |
| WO | 9856785 | 12/1998 |
| WO | 0009500 | 2/2000 |
| WO | 0039083 | 7/2000 |
| WO | 0187287 | 11/2001 |
| WO | 0218350 | 3/2002 |
| WO | 03000659 | 1/2003 |
| WO | 03026649 | 4/2003 |
| WO | 03039539 | 5/2003 |
| WO | 2004013135 | 2/2004 |
| WO | 2004016606 | 2/2004 |
| WO | 2004069158 | 8/2004 |
| WO | 2006104141 | 10/2006 |
| WO | 2006114313 | 11/2006 |
| WO | 2007002559 | 1/2007 |

(Continued)

OTHER PUBLICATIONS

Zabel et. al., European Journal of Inorganic Chemistry, 2008, Wiley-VCH, pp. 3648-3654.*

(Continued)

*Primary Examiner* — Sarah Pihonak
(74) *Attorney, Agent, or Firm* — Heslin Rothenberg Farley & Mesiti P.C.

(57) ABSTRACT

Compounds of Formula I are described. They are useful as stimulators of sGC, particularly NO-independent, heme-dependent stimulators. These compounds may be useful for treating, preventing or managing various disorders that are herein disclosed.

Formula I

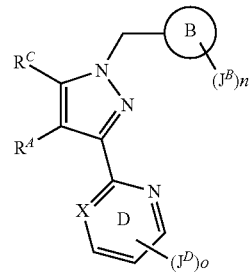

79 Claims, No Drawings

(56) References Cited

FOREIGN PATENT DOCUMENTS

| | | |
|---|---|---|
| WO | 2007014054 | 2/2007 |
| WO | 2008004096 | 1/2008 |
| WO | 2008024390 | 2/2008 |
| WO | 2008141731 | 11/2008 |
| WO | 2009067600 | 5/2009 |
| WO | 2009076454 | 6/2009 |
| WO | 2009143039 | 11/2009 |
| WO | 2010015656 | 2/2010 |
| WO | 2010015657 | 2/2010 |
| WO | 2010/054762 | 5/2010 |
| WO | 2010/054763 | 5/2010 |
| WO | 2010054762 | 5/2010 |
| WO | 2010054763 | 5/2010 |

OTHER PUBLICATIONS

Sawyer et. al., Journal of Medicinal Chemistry, 2003, American Chemical Society, vol. 46, No. 19, pp. 3953-3956.*

Structures of some compounds found in STN substructure searches in File Registry with dates of STN entries shown with each of the compound records.

Skinner, Philip J. et al., "Fluorinated pyrazole acids are agonists of the high affinity niacin receptor GPR109a", Bioorganic & Medicinal Chemistry Letters (2007), 17(20), 5620-5623, Elsevier Ltd., ISSN: 0960-894X.

Yonetoku, Yasuhiro et al., "Novel potent and selective calcium-release-activated calcium (CRAC) channel inhibitors. Synthesis and inhibitory activity of aryl-3-triflouoromethylpyrazoles", Bioorganic & Medicinal Chemistry (2006), 14(15), 5370-5383, Elsevier B.V.

Zhang, Jidong et al., "Potent nonpetide endothelin antagonists: synthesis and structure-activity relationships of pyrazole-5-carboxylic acids", Medicinal Chemistry, Hoechst Marion Roussel, Bioorganic & Medicinal Chemistry Letters (2000), 10(22), 2575-2578, Elsevier Science Ltd., ISSN: 0960-894X.

Takshasi, Masahiko et al., "Ring transformation of 1, 2, 4, 5-tetrazines to 4-aminopyrazoles by cyanotrimethysilane", Faculty English, Ibaraki University, Hitachi, 316, Japan Tetrahedron Letters (1987), 28(19), 2139-42, TELEAY; ISSN: 0040-4039.

Zabel, Dirk et al., "Iron and cobalt complexes of tridentate N-donor ligands in ethylene polymerization: efficient shielding of the active sites by simple phenyl groups", Fachbereich Chemie, Technische Universitaet Kaiserlautern, European Journal of Inorganic Chemistry (2008), (23), 3648-3654, ISSN: 1434-1948, Wiley-VCH Verlag GmbH Co.

Bouabdallah, Ibrahim et al., "Catecholase activities of two C-C linked bipyrazole N-donor ligands with copper (II) salts", Laboratory of Organic Chemistry, Macromolecular and Natural Products, Dept. of Chemistry, Faculty of Sciences, University Mohammed the First, Oujda, 60000, Morocco, Journal Marocain de Chimie Heterocyclique (2007), 6(1), 21-25.

Bouabdallah, Ibrahim et al., 1, 1'-Dibenzyl-5, 5'-dipehenyl-3, 3'-bipyrazole, Laboratoire de Chimie Organique Physique, Dept. de Chimi, Faculte des Sciences, Universite Mohammed First, Oujda, 6000, Morocco, ISSN: 1422-8599, 2006.

Kalluraya, Balakrishna et al., Reactions of aryl/aryloxyacet hydrazides with acetylenic ketones, Dept of Studies in Chemistry, Mangalore University, Mangalagangothri, 574 199, India, Indian Journal of Heterocyclic Chemistry (1999), 8(4), 309-314.

Jaehnisch, K. et al., Furylvinyl halides. X. Reactions of β-fur-2-yl-β-chloro-α-cyanoacrylic acid derivative with hydrazines, Zentralinst. Organic Chemical, Akad. Wiss. DDR, Berlin-Adlershof, DDR-1199, Ger. Dem. Rep., Journal fuer Praktische Chemie (Leipzig) (1989), 331(4), 552-8. ISSN: 0021-8383.

Kost, A.N. et al., "Condensation of 1-acylpyrazolines", Mosk. Gos. University im. Lomonosova, Moscow, USSR Khimiya Geterotsiklicheskikh Soedinenii (1974), (9), 1268-70. ISSN: 0132-6244.

Kost, A.N. et al., "The effect of phosphoryl chlorid on 1-acetyl-3, 5, 5-trimethylpyrazoline. A new synthesis of bipyrazoles", Mosk. Gos. University im. Lomonosova, Moscow, USSR, Doklady Akademii Nauk SSSR (1968), 179(2) 337-40, ISSN: 0002-3264.

Khalil, A. et al., "Phase-Transfer Catalyzed Alkylation and 3-Substituted-1H-pyrazol-2-in-5-ones in the Absence or Presence of Carbon Disulphide", Phosphorus, Sulfur Silicon Relat. Elem. (2005), 180(2), 479-496.

Tarrago, Georges et al., "Orientation de la reaction d'alkylation des pyrazoles dans des conditions neutres et en catalyse par transfert de phase", J. Heterocycl. Chemical (1980), 17(1), 137-142.

Boubdallah Ibrahim et al., "Regioselective synthesis and crystal structure of 1, 1'-dibenzyl-5, 5'-diisopropyl-3-3'-bipyrazole", Journal Marocain de Chimie Heterocylclique (2004), 3(1), pp. 39-44.

Goodell, John R. et al., "Identification of Compounds with Anti-West Nile Virus Activity", Journal of Medicinal Chemistry (2006),49(6), pp. 2127-2137.

Rostom, Sherif A. F.; Polysubstituted pyrazoles, part 6. Synthesis of some 1-(4-chlorophenyl)-4-hydroxy-1H-pyrazol-3-carbonl derivatives linked to nitrogenous heterocyclic ring systems as potential antitumor agents, Biorganic & Medicinal Chemistry (2010), 18(7), pp. 2767-2776.

Ye, Long et al., "Pyrazolylthiazole as ΔF508-Cystic Fibrosis Transmembrane Conductance Regulator Correctors with Improved Hydrophilicity Compared to Bithiazoles", Journal of Medicinal Chemistry (2010), 53(9), 3772-3781.

Bonacorso, Helio G. et al., "Synthesis of new trihalomethylated and non-symmetrical substituted 2-(1H-pyrazolyl)-5-(1H-pyrazolylcarbonyl)pyridines", Journal of the Brazilian Chemical Society (2009), 20(3), 509-517.

Sakya, Subas M. et al., "Facile microwave assisted decarbonylation of 4-formyl group in 5-alkyl amino substituted pyrazoles", Tetrahedron Letters (2008), 49(14), 2280-2282, CODEN: TELEAY; ISSN: 0040-4039.

Suen, Yat Fan et al., "A Novel Route to Fully Substituted 1H-Pyrazoles", Journal of Organic Chemistry (2005), 70(21), 8468-8471, CODEN: JOCEAH; ISSN: 0022-3263.

Amer, Fathy A. et al., "Synthesis of 4,4'-aryldihydrazono-3-(3'-pyridyl)-2-pyrazolin-4,5-diones and 1-aryl-3-(3'-pyridyl)-4,4'-arylbisazo-5-aryliminopyrazoles and their application as disazo disperse dyes", Journal of Chemical Technology and Biotechnology (1979-1982) (1980), 30(2), 78-84, CODEN: JCTBDC; ISSN: 0142-0356.

* cited by examiner

SGC STIMULATORS

This application claims the benefits of U.S. Provisional Application Nos. 61/360,236, filed Jun. 30, 2010, 61/406,845, filed Oct. 26, 2010 and 61/474,563, filed Apr. 12, 2011, the disclosures of which applications are hereby incorporated by reference.

FIELD OF THE INVENTION

The present disclosure relates to stimulators of soluble guanylate cyclase (sGC), pharmaceutical formulations thereof and their use, alone or in combination with one or more additional agents, for treating and/or preventing various diseases, wherein an increase in the concentration of nitric oxide (NO) might be desirable.

BACKGROUND OF THE INVENTION

Soluble guanylate cyclase (sGC) is the primary receptor for nitric oxide (NO) in vivo. sGC can be activated via both NO-dependent and NO-independent mechanisms. In response to this activation, sGC converts GTP into the secondary messenger cyclic GMP (cGMP). The increased level of cGMP, in turn, modulates the activity of downstream effectors including protein kinases, phosphodiesterases (PDEs), and ion channels.

In the body, NO is synthesized from arginine and oxygen by various nitric oxide synthase (NOS) enzymes and by sequential reduction of inorganic nitrate. Three distinct isoforms of NOS have been identified: inducible NOS (iNOS or NOS II) found in activated macrophage cells; constitutive neuronal NOS (nNOS or NOS I), involved in neurotransmission and long term potentiation; and constitutive endothelial NOS (eNOS or NOS III) which regulates smooth muscle relaxation and blood pressure.

Experimental and clinical evidence indicates that reduced bioavailability and/or responsiveness to endogenously produced NO contributes to the development of cardiovascular, endothelial, renal and hepatic disease, as well as erectile dysfunction. In particular, the NO signaling pathway is altered in cardiovascular diseases, including, for instance, systemic and pulmonary hypertension, heart failure, stroke, thrombosis and atherosclerosis.

Pulmonary hypertension (PH) is a disease characterized by sustained elevation of blood pressure in the pulmonary vasculature (pulmonary artery, pulmonary vein and pulmonary capillaries), which results in right heart hypertrophy, eventually leading to right heart failure and death. In PH, the bioactivity of NO and other vasodilators such as prostacyclin is reduced, whereas the production of endogenous vasoconstrictors such as endothelin is increased, resulting in excessive pulmonary vasoconstriction. sGC stimulators have been used to treat PH because they promote smooth muscle relaxation, which leads to vasodilation.

Treatment with NO-independent sGC stimulators also promoted smooth muscle relaxation in the corpus cavernosum of healthy rabbits, rats and humans, causing penile erection, indicating that sGC stimulators are useful for treating erectile dysfunction.

NO-independent, heme-dependent, sGC stimulators, such as those disclosed herein, have several important differentiating characteristics, including crucial dependency on the presence of the reduced prosthetic heme moiety for their activity, strong synergistic enzyme activation when combined with NO and stimulation of the synthesis of cGMP by direct stimulation of sGC, independent of NO. The benzylindazole compound YC-1 was the first sGC stimulator to be identified. Additional sGC stimulators with improved potency and specificity for sGC have since been developed. These compounds have been shown to produce anti-aggregatory, anti-proliferative and vasodilatory effects.

Since compounds that stimulate sGC in an NO-independent manner offer considerable advantages over other current alternative therapies, there is a need to develop novel stimulators of sGC. They would be useful in the prevention, management and treatment of disorders such as pulmonary hypertension, arterial hypertension, heart failure, atherosclerosis, inflammation, thrombosis, renal fibrosis and failure, liver cirrhosis, erectile dysfunction and other cardiovascular disorders.

SUMMARY OF THE INVENTION

The present invention is directed to compounds according to Formula I, or pharmaceutically acceptable salts thereof,

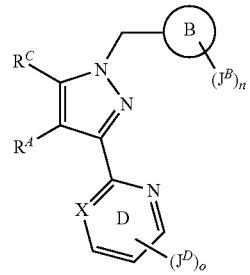

Formula I wherein:

ring B is a phenyl or a 6-membered heteroaryl ring, containing 1 or 2 nitrogen atoms in the ring;

n is an integer selected from 0 to 3;

each $J^B$ is independently selected from halogen, —CN, —NO$_2$, a $C_{1-6}$ aliphatic, —OR$^B$ or a $C_{3-8}$ cycloaliphatic group; wherein each said $C_{1-6}$ aliphatic and each said $C_{3-8}$ cycloaliphatic group is optionally and independently substituted with up to 3 instances of $R^3$;

each $R^B$ is independently selected from hydrogen, a $C_{1-6}$ aliphatic or a $C_{3-8}$ cycloaliphatic;

wherein each said $C_{1-6}$ aliphatic and each said $C_{3-8}$ cycloaliphatic ring is optionally and independently substituted with up to 3 instances of $R^3$;

each $R^3$ is independently selected from halogen, —CN, $C_{1-4}$ alkyl, $C_{1-4}$ haloalkyl, —O($C_{1-4}$ alkyl) or —O($C_{1-4}$ haloalkyl);

X is selected from N, C-$J^D$ or C—H;

o is an integer selected from 0 to 3;

each $J^D$ is independently selected from halogen, —NO$_2$, —OR$^D$, —SR$^D$, —C(O)R$^D$, —C(O)OR$^D$, —C(O)N(R$^D$)$_2$, —CN, —N(R$^D$)$_2$, —N(R$^d$)C(O)R$^D$, —N(R$^d$)C(O)OR$^D$, —SO$_2$R$^D$, —SO$_2$N(R$^D$)$_2$, —N(R$^d$)SO$_2$R$^D$, a $C_{1-6}$ aliphatic, —(C$_{1-6}$ aliphatic)-R$^D$, a $C_{3-8}$ cycloaliphatic ring, a 6 to 10-membered aryl ring, a 4 to 8-membered heterocyclic ring or a 5 to 10-membered heteroaryl ring; wherein each said 4 to 8-membered heterocyclic ring and each said 5 to 10-membered heteroaryl ring contains between 1 and 3 heteroatoms independently selected from O, N or S; and wherein each said $C_{1-6}$ aliphatic, each said $C_{3-8}$ cycloaliphatic ring, each said 6 to 10-membered aryl ring, each said 4 to 8-membered heterocyclic ring and each said 5 to 10-membered heteroaryl ring is optionally and independently substituted with up to 3 instances of $R^5$;

each $R^D$ is independently selected from hydrogen, a $C_{1-6}$ aliphatic, —$(C_{1-6}$ aliphatic$)$-$R^f$, a $C_{3-8}$ cycloaliphatic ring, a 4 to 8-membered heterocyclic ring, phenyl or a 5 to 6-membered heteroaryl ring; wherein each said 4 to 8-membered heterocylic ring and each said 5 to 6-membered heteroaryl ring contains between 1 and 3 heteroatoms independently selected from O, N or S; and wherein each said $C_{1-6}$ aliphatic, each said $C_{3-8}$ cycloaliphatic ring, each said 4 to 8-membered heterocyclic ring, each said phenyl and each said 5 to 6-membered heteroaryl ring is optionally and independently substituted with up to 3 instances of $R^5$;

each $R^d$ is independently selected from hydrogen, a $C_{1-6}$ aliphatic, —$(C_{1-6}$ aliphatic$)$-$R^f$, a $C_{3-8}$ cycloaliphatic ring, a 4 to 8-membered heterocyclic ring, phenyl or a 5 to 6-membered heteroaryl ring; wherein each said heterocylic ring and each said heteroaryl ring contains between 1 and 3 heteroatoms independently selected from O, N or S; and wherein each said $C_{1-6}$ aliphatic, each said $C_{3-8}$ cycloaliphatic ring, each said 4 to 8-membered heterocyclic ring, each said phenyl and each said 5 to 6-membered heteroaryl ring is optionally and independently substituted by up to 3 instances of $R^5$;

each $R^f$ is independently selected from a $C_{3-8}$ cycloaliphatic ring, a 4 to 8-membered heterocyclic ring, phenyl or a 5 to 6-membered heteroaryl ring; wherein each said heterocylic ring and each said heteroaryl ring contains between 1 and 3 heteroatoms independently selected from O, N or S; and wherein each said $C_{1-6}$ aliphatic, each said $C_{3-8}$ cycloaliphatic ring, each said 4 to 8-membered heterocyclic ring, each said phenyl and each said 5 to 6-membered heteroaryl ring is optionally and independently substituted by up to 3 instances of $R^5$;

alternatively, two instances of $R^D$ linked to the same nitrogen atom of $J^D$, together with said nitrogen atom of $J^D$, form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of $R^5$; or alternatively, one instance of $R^D$ linked to a carbon, oxygen or sulfur atom of $J^D$ and one instance of $R^d$ linked to a nitrogen atom of the same P, together with said carbon, oxygen or sulfur and said nitrogen atom of that same $J^D$, form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of $R^5$;

each $R^5$ is independently selected from halogen, —CN, —$NO_2$, $C_{1-4}$ alkyl, a $C_{7-12}$ aralkyl, $C_{3-8}$ cycloalkyl ring, $C_{1-4}$ haloalkyl, $C_{1-4}$ cyanoalkyl, —$OR^6$, —$SR^6$, —$OCOR^6$, —$COR^6$, —$C(O)OR^6$, —$C(O)N(R^6)_2$, —$N(R^6)C(O)R^6$, —$N(R^6)_2$, —$SO_2R^6$, —$SO_2N(R^6)_2$, —$N(R^6)SO_2R^6$, phenyl or an oxo group; wherein each said phenyl group is optionally and independently substituted with up to 3 instances of halogen, —OH, —$NH_2$, —NH$(C_{1-4}$ alkyl$)$, —$N(C_{1-4}$ alkyl$)_2$, —$NO_2$, —CN, $C_{1-4}$ alkyl, $C_{1-4}$ haloalkyl, —$O(C_{1-4}$ alkyl$)$ or —$O(C_{1-4}$ haloalkyl$)$; and wherein each said $C_{7-12}$ aralkyl and each said cycloalkyl group is optionally and independently substituted with up to 3 instances of halogen;

each $R^6$ is independently selected from hydrogen, a $C_{1-4}$ alkyl, a $C_{2-4}$ alkenyl, phenyl, a $C_{7-12}$ aralkyl or a $C_{3-8}$ cycloalkyl ring; wherein each said $C_{1-4}$ alkyl, each said $C_{2-4}$ alkenyl, each said phenyl, each said $C_{7-12}$ aralkyl and each said cycloalkyl group is optionally and independently substituted with up to 3 instances of halogen;

alternatively, two instances of $R^6$ linked to the same nitrogen atom of $R^5$, together with said nitrogen atom of $R^5$, form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S; or alternatively, one instance of $R^6$ linked to a nitrogen atom of $R^5$ and one instance of $R^6$ linked to a carbon or sulfur atom of the same $R^5$, together with said nitrogen and said carbon or sulfur atom of the same $R^5$, form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S;

or, alternatively, two $J^D$ groups attached to two vicinal ring D atoms, taken together with said two vicinal ring D atoms, form a 5 to 7-membered heterocycle resulting in a fused ring D wherein said 5 to 7-membered heterocycle contains from 1 to 3 heteroatoms independently selected from N, O or S; and wherein said 5 to 7-membered heterocycle is optionally and independently substituted by up to 3 instances of halogen, —OH, —$NH_2$, —NH$(C_{1-4}$ alkyl$)$, —$N(C_{1-4}$ alkyl$)_2$, —CN, $C_{1-4}$ alkyl, $C_{1-4}$ haloalkyl, —$O(C_{1-4}$ alkyl$)$, —$O(C_{1-4}$ haloalkyl$)$, oxo or phenyl; wherein said phenyl is optionally and independently substituted by up to three instances of halogen, —OH, —$NH_2$, —NH$(C_{1-4}$ alkyl$)$, —$N(C_{1-4}$ alkyl$)_2$, —$NO_2$, —CN, $C_{1-4}$ alkyl, $C_{1-4}$ haloalkyl, —$O(C_{1-4}$ alkyl$)$ or haloalkyl$)$;

$R^C$ is selected from —CN, $C_{1-6}$ alkyl or a ring C;

ring C is a phenyl ring, a monocyclic 5 or 6-membered heteroaryl ring, a bicyclic 8 to 10-membered heteroaryl ring, a monocyclic 3 to 10-membered cycloaliphatic ring, or a monocyclic 4 to 10-membered heterocycle; wherein said monocyclic 5 or 6-membered heteroaryl ring, said bicyclic 8 to 10-membered heteroaryl ring, or said monocyclic 4 to 10-membered heterocycle contain between 1 and 4 heteroatoms selected from N, O or S; wherein said monocyclic 5 or 6-membered heteroaryl ring is not a 1,3,5-triazinyl ring; and wherein said phenyl, monocyclic 5 to 6-membered heteroaryl ring, bicyclic 8 to 10-membered heteroaryl ring, or monocyclic 4 to 10-membered heterocycle is optionally and independently substituted with up to 3 instances of $J^C$;

each $J^C$ is independently selected from halogen, —CN, —$NO_2$, a $C_{1-6}$ aliphatic, —$OR^H$, —$SR^H$, —$N(R^H)_2$, a $C_{3-8}$ cycloaliphatic ring or a 4 to 8-membered heterocyclic ring; wherein said 4 to 8-membered heterocyclic ring contains 1 or 2 heteroatoms independently selected from N, O or S; wherein each said $C_{1-6}$ aliphatic, each said $C_{3-8}$ cycloaliphatic ring and each said 4 to 8-membered heterocyclic ring, is optionally and independently substituted with up to 3 instances of $R^7$; or alternatively, two $J^C$ groups attached to two vicinal ring C atoms, taken together with said two vicinal ring C atoms, form a 5 to 7-membered heterocycle resulting in a fused ring C; wherein said 5 to 7-membered heterocycle contains from 1 to 2 heteroatoms independently selected from N, O or S;

each $R^H$ is independently selected from hydrogen, a $C_{1-6}$ aliphatic, a $C_{3-8}$ cycloaliphatic ring or a 4 to 8-membered heterocyclic ring; wherein each said 4 to 8-membered heterocylic ring contains between 1 and 3 heteroatoms independently selected from O, N or S; and wherein each said $C_{1-6}$ aliphatic, each said $C_{3-8}$ cycloaliphatic ring, each said 4 to 8-membered heterocyclic ring, is optionally and independently substituted with up to 3 instances of $R^7$;

alternatively, two instances of $R^H$ linked to the same nitrogen atom of $J^C$, together with said nitrogen atom of $J^C$, form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of $R^7$; or each $R^7$ is independently selected from halogen, —CN, —NO$_2$, $C_{1-4}$ alkyl, $C_{1-4}$ haloalkyl, $C_{3-8}$ cycloalkyl ring, —OR$^8$, —SR$^8$, —N(R$^8$)$_2$, or an oxo group; wherein each said cycloalkyl group is optionally and independently substituted with up to 3 instances of halogen;

each $R^8$ is independently selected from hydrogen, a $C_{1-4}$ alkyl, $C_{1-4}$ haloalkyl or a $C_{3-8}$ cycloalkyl ring; wherein each said cycloalkyl group is optionally and independently substituted with up to 3 instances of halogen;

alternatively, two instances of $R^8$ linked to the same nitrogen atom of $R^7$, together with said nitrogen atom of $R^7$, form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S;

$R^A$ is selected from hydrogen, halogen, $C_{1-4}$ alkyl or $C_{1-4}$ haloalkyl;

with the proviso that when ring B is unsubstituted phenyl and ring D is unsubstituted pyrimidinyl (X is N and o is zero), $R^C$ is not methyl or ethyl.

The invention also provides a method of treating or preventing a disease, health condition or disorder in a subject in need thereof, comprising administering; alone or in combination therapy, a therapeutically or prophylactically effective amount of the compound of Formula I or a pharmaceutically acceptable salt thereof to the subject; wherein the disease, health condition or disorder is a peripheral or cardiac vascular disorder/condition, or a urogenital system disorder that can benefit from sGC stimulation.

DETAILED DESCRIPTION OF THE INVENTION

Reference will now be made in detail to certain embodiments of the invention, examples of which are illustrated in the accompanying structures and formulae. While the invention will be described in conjunction with the enumerated embodiments, it will be understood that they are not intended to limit the invention to those embodiments. Rather, the invention is intended to cover all alternatives, modifications and equivalents that may be included within the scope of the present invention as defined by the claims. The present invention is not limited to the methods and materials described herein but include any methods and materials similar or equivalent to those described herein that could be used in the practice of the present invention. In the event that one or more of the incorporated literature references, patents or similar materials differ from or contradict this application, including but not limited to defined terms, term usage, described techniques or the like, this application controls.

DEFINITIONS AND GENERAL TERMINOLOGY

For purposes of this disclosure, the chemical elements are identified in accordance with the Periodic Table of the Elements, CAS version, and the Handbook of Chemistry and Physics, 75$^{th}$ Ed. 1994. Additionally, general principles of organic chemistry are described in "Organic Chemistry", Thomas Sorrell, University Science Books, Sausalito: 1999, and "March's Advanced Organic Chemistry", 5$^{th}$ Ed., Smith, M. B. and March, J. eds. John Wiley & Sons, New York: 2001, which are herein incorporated by reference in their entirety.

As described herein, compounds of Formula I may be optionally substituted with one or more substituents, such as illustrated generally below, or as exemplified by particular classes, subclasses, and species of the invention. The phrase "optionally substituted" is used interchangeably with the phrase "substituted or unsubstituted." In general, the term "substituted", refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. If a substituent radical or structure is not identified or defined as "optionally substituted", the substituent radical or structure is not substituted. As will be apparent to one of ordinary skill in the art, groups such as —H, halogen, —NO$_2$, —CN, —OH, —NH$_2$ or —OCF$_3$ would not be substitutable groups.

The phrase "up to", as used herein, refers to zero or any integer number that is equal or less than the number following the phrase. For example, "up to 3" means any one of 0, 1, 2, or 3. As described herein, a specified number range of atoms includes any integer therein. For example, a group having from 1-4 atoms could have 1, 2, 3 or 4 atoms. When any variable occurs more than one time at any position, its definition on each occurrence is independent from every other occurrence.

Selection of substituents and combinations envisioned by this disclosure are only those that result in the formation of stable or chemically feasible compounds. Such choices and combinations will be apparent to those of ordinary skill in the art and may be determined without undue experimentation. The term "stable", as used herein, refers to compounds that are not substantially altered when subjected to conditions to allow for their production, detection, and, in some embodiments, their recovery, purification, and use for one or more of the purposes disclosed herein. In some embodiments, a stable compound or chemically feasible compound is one that is not substantially altered when kept at a temperature of 25° C. or less, in the absence of moisture or other chemically reactive conditions, for at least a week.

A compound, such as the compounds of Formula I or other compounds herein disclosed, may be present in its free form (e.g. an amorphous form, or a crystalline form or polymorphs). Under certain conditions, compounds may also form salts. As used herein, the term co-form is synonymous with the term multi-component crystalline form. When one of the components in the co-form has clearly transferred a proton to the other component, the resulting co-form is referred to as a "salt". The formation of a salt is determined by how large the difference is in the pKas between the partners that form the mixture.

Unless only one of the isomers is drawn or named specifically, structures depicted herein are also meant to include all stereoisomeric (e.g., enantiomeric, diastereomeric, atropoisomeric and cis-trans isomeric) forms of the structure; for example, the R and S configurations for each asymmetric center, Ra and Sa configurations for each asymmetric axis, (Z) and (E) double bond configurations, and cis and trans conformational isomers. Therefore, single stereochemical isomers as well as racemates, and mixtures of enantiomers, diastereomers, and cis-trans isomers (double bond or conformational) of the present compounds are within the scope of the present disclosure. Unless otherwise stated, all tautomeric forms of the compounds of the present disclosure are within the scope of the disclosure.

The present disclosure also embraces isotopically-labeled compounds which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$, and $^{125}I$, respectively. Certain isotopically-labeled compounds of the present invention (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$, and $^{18}F$ are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

The term "aliphatic" or "aliphatic group", as used herein, means a straight-chain (i.e., unbranched) or branched, substituted or unsubstituted hydrocarbon chain that is completely saturated or that contains one or more units of unsaturation. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms. In other embodiments, aliphatic groups contain 1-4 aliphatic carbon atoms and in yet other embodiments, aliphatic groups contain 1-3 aliphatic carbon atoms. Suitable aliphatic groups include, but are not limited to, linear or branched, substituted or unsubstituted alkyl, alkenyl, or alkynyl groups. Specific examples of aliphatic groups include, but are not limited to: methyl, ethyl, propyl, butyl, isopropyl, isobutyl, vinyl, sec-butyl, tert-butyl, butenyl, propargyl, acetylene and the like.

The term "alkyl", as used herein, refers to a saturated linear or branched-chain monovalent hydrocarbon radical. Unless otherwise specified, an alkyl group contains 1-20 carbon atoms (e.g., 1-20 carbon atoms, 1-10 carbon atoms, 1-8 carbon atoms, 1-6 carbon atoms, 1-4 carbon atoms or 1-3 carbon atoms). Examples of alkyl groups include, but are not limited to, methyl, ethyl, n-propyl, isopropyl, n-butyl, isobutyl, s-butyl, t-butyl, pentyl, hexyl, heptyl, octyl and the like.

The term "alkenyl" refers to a linear or branched-chain monovalent hydrocarbon radical with at least one site of unsaturation, i.e., a carbon-carbon, $sp^{2}$ double bond, wherein the alkenyl radical includes radicals having "cis" and "trans" orientations, or alternatively, "E" and "Z" orientations. Unless otherwise specified, an alkenyl group contains 2-20 carbon atoms (e.g., 2-20 carbon atoms, 2-10 carbon atoms, 2-8 carbon atoms, 2-6 carbon atoms, 2-4 carbon atoms or 2-3 carbon atoms). Examples include, but are not limited to, vinyl, allyl and the like.

The term "alkynyl" refers to a linear or branched monovalent hydrocarbon radical with at least one site of unsaturation, i.e., a carbon-carbon sp triple bond. Unless otherwise specified, an alkynyl group contains 2-20 carbon atoms (e.g., 2-20 carbon atoms, 2-10 carbon atoms, 2-8 carbon atoms, 2-6 carbon atoms, 2-4 carbon atoms or 2-3 carbon atoms). Examples include, but are not limited to, ethynyl, propynyl, and the like.

The term "carbocyclic" refers to a ring system formed only by carbon and hydrogen atoms. Unless otherwise specified, throughout this disclosure, carbocycle is used as a synonym of "non-aromatic carbocycle" or "cycloaliphatic". In some instances the term can be used in the phrase "aromatic carbocycle", and in this case it refers to an "aryl group" as defined below.

The term "cycloaliphatic" (or "non-aromatic carbocycle", "non-aromatic carbocyclyl", "non-aromatic carbocyclic") refers to a cyclic hydrocarbon that is completely saturated or that contains one or more units of unsaturation but which is not aromatic, and which has a single point of attachment to the rest of the molecule. Unless otherwise specified, a cycloaliphatic group may be monocyclic, bicyclic, tricyclic, fused, spiro or bridged. In one embodiment, the term "cycloaliphatic" refers to a monocyclic $C_{3}$-$C_{12}$ hydrocarbon or a bicyclic $C_{7}$-$C_{12}$ hydrocarbon. In some embodiments, any individual ring in a bicyclic or tricyclic ring system has 3-7 members. Suitable cycloaliphatic groups include, but are not limited to, cycloalkyl, cycloalkenyl, and cycloalkynyl. Examples of aliphatic groups include cyclopropyl, cyclobutyl, cyclopentyl, cyclopentenyl, cyclohexyl, cyclohexenyl, cycloheptyl, cycloheptenyl, norbornyl, cyclooctyl, cyclononyl, cyclodecyl, cycloundecyl, cyclododecyl, and the like.

The term "cycloaliphatic" also includes polycyclic ring systems in which the non-aromatic carbocyclic ring can be "fused" to one or more aromatic or non-aromatic carbocyclic or heterocyclic rings or combinations thereof, as long as the radical or point of attachment is on the non-aromatic carbocyclic ring.

"Heterocycle" (or "heterocyclyl" or "heterocyclic), as used herein, refers to a ring system in which one or more ring members are an independently selected heteroatom, which is completely saturated or that contains one or more units of unsaturation but which is not aromatic, and which has a single point of attachment to the rest of the molecule. Unless otherwise specified, through this disclosure, heterocycle is used as a synonym of "non-aromatic heterocycle". In some instances the term can be used in the phrase "aromatic heterocycle", and in this case it refers to a "heteroaryl group" as defined below. The term heterocycle also includes fused, spiro or bridged heterocyclic ring systems. Unless otherwise specified, a heterocycle may be monocyclic, bicyclic or tricyclic. In some embodiments, the heterocycle has 3-18 ring members in which one or more ring members is a heteroatom independently selected from oxygen, sulfur or nitrogen, and each ring in the system contains 3 to 7 ring members. In other embodiments, a heterocycle may be a monocycle having 3-7 ring members (2-6 carbon atoms and 1-4 heteroatoms) or a bicycle having 7-10 ring members (4-9 carbon atoms and 1-6 heteroatoms). Examples of bicyclic heterocyclic ring systems include, but are not limited to: adamantanyl, 2-oxa-bicyclo[2.2.2]octyl, 1-aza-bicyclo[2.2.2]octyl.

As used herein, the term "heterocycle" also includes polycyclic ring systems wherein the heterocyclic ring is fused with one or more aromatic or non-aromatic carbocyclic or heterocyclic rings, or with combinations thereof, as long as the radical or point of attachment is on the heterocyclic ring.

Examples of heterocyclic rings include, but are not limited to, the following monocycles: 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl; and the following bicycles: 3-1H-benzimidazol-2-one, 3-(1-alkyl)-benzimidazol-2-one, indolinyl, tetrahydroquinolinyl, tetrahydroisoquinolinyl, benzothiolane, benzodithiane, and 1,3-dihydroimidazol-2-one.

As used herein, the term "aryl" (as in "aryl ring" or "aryl group"), used alone or as part of a larger moiety, as in "aralkyl", "aralkoxy", "aryloxyalkyl", refers to a carbocyclic ring system wherein at least one ring in the system is aromatic and has a single point of attachment to the rest of the molecule. Unless otherwise specified, an aryl group may be monocyclic, bicyclic or tricyclic and contain 6-18 ring members. The term also includes polycyclic ring systems where the aryl ring is fused with one or more aromatic or non-aromatic carbocyclic or heterocyclic rings, or with combinations thereof, as long as the radical or point of attachment is in the aryl ring. Examples of aryl rings include, but are not limited to, phenyl, naphthyl, indanyl, indenyl, tetralin, fluorenyl, and anthracenyl.

The term "aralkyl" refers to a radical having an aryl ring substituted with an alkylene group, wherein the open end of the alkylene group allows the aralkyl radical to bond to another part of the compound of Formula I. The alkylene group is a bivalent, straight-chain or branched, saturated hydrocarbon group. As used herein, the term "$C_{7-12}$ aralkyl" means an aralkyl radical wherein the total number of carbon atoms in the aryl ring and the alkylene group combined is 7 to 12. Examples of "aralkyl" include, but not limited to, a phenyl ring substituted by a $C_{1-6}$ alkylene group, e.g., benzyl and phenylethyl, and a naphthyl group substituted by a $C_{1-2}$ alkylene group.

The term "heteroaryl" (or "heteroaromatic" or "heteroaryl group" or "aromatic heterocycle") used alone or as part of a larger moiety as in "heteroaralkyl" or "heteroarylalkoxy" refers to a ring system wherein at least one ring in the system is aromatic and contains one or more heteroatoms, wherein each ring in the system contains 3 to 7 ring members and which has a single point of attachment to the rest of the molecule. Unless otherwise specified, a heteroaryl ring system may be monocyclic, bicyclic or tricyclic and have a total of five to fourteen ring members. In one embodiment, all rings in a heteroaryl system are aromatic. Also included in this definition are heteroaryl radicals where the heteroaryl ring is fused with one or more aromatic or non-aromatic carbocyclic or heterocyclic rings, or combinations thereof, as long as the radical or point of attachment is in the heteroaryl ring. Bicyclic 6, 5 heteroaromatic system, as used herein, for example, is a six membered heteroaromatic ring fused to a second five membered ring wherein the radical or point of attachment is on the six-membered ring.

Heteroaryl rings include, but are not limited to the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, benzopyrazinyl, benzopyranonyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

As used herein, "cyclo" (or "cyclic", or "cyclic moiety") encompasses mono-, bi- and tri-cyclic ring systems including cycloaliphatic, heterocyclic, aryl or heteroaryl, each of which has been previously defined.

"Fused" bicyclic ring systems comprise two rings which share two adjoining ring atoms.

"Bridged" bicyclic ring systems comprise two rings which share three or four adjacent ring atoms. As used herein, the term "bridge" refers to an atom or a chain of atoms connecting two different parts of a molecule. The two atoms that are connected through the bridge (usually but not always, two tertiary carbon atoms) are referred to as "bridgeheads". In addition to the bridge, the two bridgeheads are connected by at least two of individual atoms or chains of atoms. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.2.3]nonyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.03,7]nonyl. "Spiro" bicyclic ring systems share only one ring atom (usually a quaternary carbon atom) between the two rings.

The term "ring atom" refers to an atom such as C, N, O or S that is part of the ring of an aromatic group, a cycloaliphatic group or a heteroaryl ring. A "substitutable ring atom" is a ring carbon or nitrogen atom bonded to at least one hydrogen atom. The hydrogen can be optionally replaced with a suitable substituent group. Thus, the term "substitutable ring atom" does not include ring nitrogen or carbon atoms which are shared when two rings are fused. In addition, "substitutable ring atom" does not include ring carbon or nitrogen atoms when the structure depicts that they are already attached to one or more moiety other than hydrogen and no hydrogens are available for substitution.

"Heteroatom" refers to one or more of oxygen, sulfur, nitrogen, phosphorus, or silicon, including any oxidized form of nitrogen, sulfur, phosphorus, or silicon, the quaternized form of any basic nitrogen, or a substitutable nitrogen of a heterocyclic or heteroaryl ring, for example N (as in 3,4-dihydro-2H-pyrrolyl), NH (as in pyrrolidinyl) or $NR^+$ (as in N-substituted pyrrolidinyl).

In some embodiments, two independent occurrences of a variable may be taken together with the atom(s) to which each variable is bound to form a 5-8-membered, heterocyclyl, aryl, or heteroaryl ring or a 3-8-membered cycloalkyl ring. Exemplary rings that are formed when two independent occurrences of a substituent are taken together with the atom(s) to which each variable is bound include, but are not limited to the following: a) two independent occurrences of a substituent that are bound to the same atom and are taken together with that atom to form a ring, where both occurrences of the substituent are taken together with the atom to which they are bound to form a heterocyclyl, heteroaryl, carbocyclyl or aryl ring, wherein the group is attached to the rest of the molecule by a single point of attachment; and b) two independent occurrences of a substituent that are bound to different atoms and are taken together with both of those atoms to form a heterocyclyl, heteroaryl, carbocyclyl or aryl ring, wherein the ring that is formed has two points of attachment with the rest of the molecule. For example, where a phenyl group is substituted with two occurrences of $R^o$ as in Formula D1:

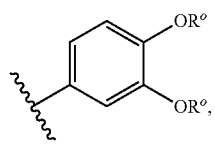

these two occurrences of $R^o$ are taken together with the oxygen atoms to which they are bound to form a fused 6-membered oxygen containing ring as in Formula D2:

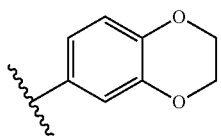

It will be appreciated that a variety of other rings can be formed when two independent occurrences of a substituent are taken together with the atom(s) to which each substituent is bound and that the examples detailed above are not intended to be limiting.

In some embodiments, an alkyl or aliphatic chain can be optionally interrupted with another atom or group. This means that a methylene unit of the alkyl or aliphatic chain can optionally be replaced with said other atom or group. Unless otherwise specified, the optional replacements form a chemically stable compound. Optional interruptions can occur both within the chain and/or at either end of the chain; i.e. both at the point of attachment(s) to the rest of the molecule and/or at the terminal end. Two optional replacements can also be adjacent to each other within a chain so long as it results in a chemically stable compound. Unless otherwise specified, if the replacement or interruption occurs at a terminal end of the chain, the replacement atom is bound to an H on the terminal end. For example, if —CH$_2$CH$_2$CH$_3$ were optionally interrupted with —O—, the resulting compound could be —OCH$_2$CH$_3$, —CH$_2$OCH$_3$, or —CH$_2$CH$_2$OH. In another example, if the divalent linker —CH$_2$CH$_2$CH$_2$— were optionally interrupted with —O—, the resulting compound could be —OCH$_2$CH$_2$—, —CH$_2$OCH$_2$—, or —CH$_2$CH$_2$O—. The optional replacements can also completely replace all of the carbon atoms in a chain. For example, a C$_3$ aliphatic can be optionally replaced by —N(R')—, —C(O)—, and —N(R')— to form —N(R')C(O)N(R')— (a urea).

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., $R^X$O(O)C-alkyl is an example of a carboxy group used terminally. A group is internal when the group is present in the middle of a substituent at the end of the substituent bound to the rest of the chemical structure. Alkylcarboxy (e.g., alkyl-C(O)O— or alkyl-O(CO)—) and alkylcarboxyaryl (e.g., alkyl-C(O)O-aryl- or alkyl-O(CO)-aryl-) are examples of carboxy groups used internally.

As described herein, a bond drawn from a substituent to the center of one ring within a multiple-ring system (as shown below), represents substitution of the substituent at any substitutable position in any of the rings within the multiple ring system. For example, formula D3 represents possible substitution in any of the positions shown in formula D4:

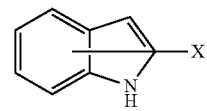

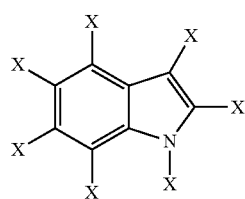

This also applies to multiple ring systems fused to optional ring systems (which would be represented by dotted lines). For example, in Formula D5, X is an optional substituent both for ring A and ring B.

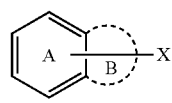

If, however, two rings in a multiple ring system each have different substituents drawn from the center of each ring, then, unless otherwise specified, each substituent only represents substitution on the ring to which it is attached. For example, in Formula D6, Y is an optional substituent for ring A only, and X is an optional substituent for ring B only.

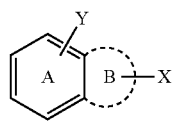

As used herein, the terms "alkoxy" or "alkylthio" refer to an alkyl group, as previously defined, attached to the molecule, or to another chain or ring, through an oxygen ("alkoxy" i.e., —O-alkyl) or a sulfur ("alkylthio" i.e., —S-alkyl) atom.

The terms $C_{n-m}$ "alkoxyalkyl", $C_{n-m}$ "alkoxyalkenyl", $C_{n-m}$ "alkoxyaliphatic", and $C_{n-m}$ "alkoxyalkoxy" mean alkyl, alkenyl, aliphatic or alkoxy, as the case may be, substituted with one or more alkoxy groups, wherein the combined total number of carbons of the alkyl and alkoxy groups, alkenyl and alkoxy groups, aliphatic and alkoxy groups or alkoxy and alkoxy groups, combined, as the case may be, is between the values of n and m. For example, a $C_{4-6}$ alkoxyalkyl has a total of 4-6 carbons divided between the alkyl and alkoxy portion; e.g. it can be —CH$_2$OCH$_2$CH$_2$CH$_3$, —CH$_2$CH$_2$OCH$_2$CH$_3$ or —CH$_2$CH$_2$CH$_2$OCH$_3$.

When the moieties described in the preceding paragraph are optionally substituted, they can be substituted in either or both of the portions on either side of the oxygen or sulfur. For example, an optionally substituted $C_4$ alkoxyalkyl could be, for instance, —CH$_2$CH$_2$OCH$_2$(Me)CH$_3$ or —CH$_2$(OH)OCH$_2$CH$_2$CH$_3$; a $C_5$ alkoxyalkenyl could be, for instance, —CH=CHOCH$_2$CH$_2$CH$_3$ or —CH=CHCH$_2$OCH$_2$CH$_3$.

The term aryloxy, arylthio, benzyloxy or benzylthio, refer to an aryl or benzyl group attached to the molecule, or to another chain or ring, through an oxygen ("aryloxy", benzyloxy e.g., —O-Ph, —OCH$_2$Ph) or sulfur ("arylthio" e.g., —S-Ph, —S—CH$_2$Ph) atom. Further, the terms "aryloxyalkyl", "benzyloxyalkyl" "aryloxyalkenyl" and "aryloxyaliphatic" mean alkyl, alkenyl or aliphatic, as the case may be, substituted with one or more aryloxy or benzyloxy groups, as the case may be. In this case, the number of atoms for each aryl, aryloxy, alkyl, alkenyl or aliphatic will be indicated separately. Thus, a 5-6-membered aryloxy($C_{1-4}$ alkyl) is a 5-6 membered aryl ring, attached via an oxygen atom to a $C_{1-4}$ alkyl chain which, in turn, is attached to the rest of the molecule via the terminal carbon of the $C_{1-4}$ alkyl chain.

As used herein, the terms "halogen" or "halo" mean F, Cl, Br, or I.

The terms "haloalkyl", "haloalkenyl", "haloaliphatic", and "haloalkoxy" mean alkyl, alkenyl, aliphatic or alkoxy, as the case may be, substituted with one or more halogen atoms. For example a $C_{1-3}$ haloalkyl could be —CFHCH$_2$CHF$_2$ and a $C_{1-2}$ haloalkoxy could be —OC(Br)HCHF$_2$. This term includes perfluorinated alkyl groups, such as —CF$_3$ and —CF$_2$CF$_3$.

As used herein, the term "cyano" refers to —CN or —C≡N.

The terms "cyanoalkyl", "cyanoalkenyl", "cyanoaliphatic", and "cyanoalkoxy" mean alkyl, alkenyl, aliphatic or alkoxy, as the case may be, substituted with one or more cyano groups. For example a $C_{1-3}$ cyanoalkyl could be —C(CN)$_2$CH$_2$CH$_3$ and a $C_{1-2}$ cyanoalkenyl could be =CHC(CN)H$_2$.

As used herein, an "amino" group refers to —NH$_2$.

The terms "aminoallyl", "aminoalkenyl", "aminoaliphatic", and "aminoalkoxy" mean alkyl, alkenyl, aliphatic or alkoxy, as the case may be, substituted with one or more amino groups. For example a $C_{1-3}$ aminoallyl could be —CH(NH$_2$)CH$_2$CH$_2$NH$_2$ and a $C_{1-2}$ aminoalkoxy could be —OCH$_2$CH$_2$NH$_2$.

The term "hydroxyl" or "hydroxy" refers to —OH.

The terms "hydroxyalkyl", "hydroxyalkenyl", "hydroxyaliphatic", and "hydroxyalkoxy" mean alkyl, alkenyl, aliphatic or alkoxy, as the case may be, substituted with one or more —OH groups. For example a $C_{1-3}$ hydroxyalkyl could be —CH$_2$(CH$_2$OH)CH$_3$ and a $C_4$ hydroxyalkoxy could be —OCH$_2$C(CH$_3$)(OH)CH$_3$.

As used herein, a "carbonyl", used alone or in connection with another group refers to —C(O)— or —C(O)H. For example, as used herein, an "alkoxycarbonyl," refers to a group such as —C(O)O(alkyl).

As used herein, an "oxo" refers to =O, wherein oxo is usually, but not always, attached to a carbon atom (e.g., it can also be attached to a sulfur atom). An aliphatic chain can be optionally interrupted by a carbonyl group or can optionally be substituted by an oxo group, and both expressions refer to the same: e.g. —CH$_2$—C(O)—CH$_3$.

As used herein, in the context of resin chemistry (e.g. using solid resins or soluble resins or beads), the term "linker" refers to a bifunctional chemical moiety attaching a compound to a solid support or soluble support.

In all other situations, a "linker", as used herein, refers to a divalent group in which the two free valences are on different atoms (e.g. carbon or heteroatom) or are on the same atom but can be substituted by two different substituents. For example, a methylene group can be $C_1$ alkyl linker (—CH$_2$—) which can be substituted by two different groups, one for each of the free valences (e.g. as in Ph-CH$_2$-Ph, wherein methylene acts as a linker between two phenyl rings). Ethylene can be $C_2$ alkyl linker (—CH$_2$CH$_2$—) wherein the two free valences are on different atoms. The amide group, for example, can act as a linker when placed in an internal position of a chain (e.g. —CONH—). A linker can be the result of interrupting an aliphatic chain by certain functional groups or of replacing methylene units on said chain by said functional groups. E.g. a linker can be a $C_{1-6}$ aliphatic chain in which up to two methylene units are substituted by —C(O)— or —NH— (as in —CH$_2$—NH—CH$_2$—C(O)—CH$_2$— or —CH$_2$—NH—C(O)—CH$_2$—). An alternative way to define the same —CH$_2$—NH—CH$_2$—C(O)—CH$_2$— and —CH$_2$—NH—C(O)—CH$_2$— groups is as a $C_3$ alkyl chain optionally interrupted by up to two —C(O)— or —NH— moieties. Cyclic groups can also form linkers: e.g. a 1,6-cyclohexanediyl can be a linker between two R groups, as in

A linker can additionally be optionally substituted in any portion or position.

Divalent groups of the type R—CH= or R$_2$C=, wherein both free valences are in the same atom and are attached to the same substituent, are also possible. In this case, they will be referred to by their IUPAC accepted names. For instance an alkylidene (such as, for example, a methylidene (=CH$_2$) or an ethylidene (=CH—CH$_3$)) would not be encompassed by the definition of a linker in this disclosure.

The term "protecting group", as used herein, refers to an agent used to temporarily block one or more desired reactive sites in a multifunctional compound. In certain embodiments, a protecting group has one or more, or preferably all, of the following characteristics: a) reacts selectively in good yield to give a protected substrate that is stable to the reactions occurring at one or more of the other reactive sites; and b) is selectively removable in good yield by reagents that do not attack the regenerated functional group. Exemplary protecting groups are detailed in Greene, T. W. et al., "Protective Groups in Organic Synthesis", Third Edition, John Wiley & Sons, New York: 1999, the entire contents of which is hereby incorporated by reference. The term "nitrogen protecting group", as used herein, refers to an agents used to temporarily block one or more desired nitrogen reactive sites in a multifunctional compound. Preferred nitrogen protecting groups also possess the characteristics exemplified above, and certain exemplary nitrogen protecting groups are detailed in Chapter 7 in Greene, T. W., Wuts, P. G in "Protective Groups in Organic Synthesis", Third Edition, John Wiley & Sons, New York: 1999, the entire contents of which are hereby incorporated by reference.

As used herein, the term "displaceable moiety" or "leaving group" refers to a group that is associated with an aliphatic or aromatic group as defined herein and is subject to being displaced by nucleophilic attack by a nucleophile.

As used herein, "amide coupling agent" or "amide coupling reagent" means a compound that reacts with the hydroxyl moiety of a carboxy moiety thereby rendering it susceptible to nucleophilic attack. Exemplary amide coupling agents include DIC (diisopropylcarbodiimide), EDCI (1-ethyl-3-(3-dimethylaminopropyl)carbodiimide), DCC (dicyclohexylcarbodiimide), BOP (benzotriazol-1-yloxy-tris (dimethylamino)-phosphonium hexafluorophosphate), pyBOP ((benzotriazol-1-yloxy)tripyrrolidinophosphonium hexafluorophosphate), etc.

Compound Embodiments

The present invention is directed to compounds according to Formula I, or pharmaceutically acceptable salts thereof,

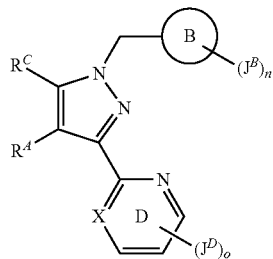

Formula I wherein:
ring B is a phenyl or a 6-membered heteroaryl ring, containing 1 or 2 nitrogen atoms in the ring;
n is an integer selected from 0 to 3;
each $J^B$ is independently selected from halogen, —CN, —NO$_2$, a $C_{1-6}$ aliphatic, —OR$^B$ or a $C_{3-8}$ cycloaliphatic group; wherein each said $C_{1-6}$ aliphatic and each said $C_{3-8}$ cycloaliphatic group is optionally and independently substituted with up to 3 instances of R$^3$;
each R$^B$ is independently selected from hydrogen, a $C_{1-6}$ aliphatic or a $C_{3-8}$ cycloaliphatic; wherein each said $C_{1-6}$ aliphatic and each said $C_{3-8}$ cycloaliphatic ring is optionally and independently substituted with up to 3 instances of R$^3$;
each R$^3$ is independently selected from halogen, —CN, $C_{1-4}$ alkyl, $C_{1-4}$ haloalkyl, —O($C_{1-4}$ alkyl) or —O($C_{1-4}$ haloalkyl);
X is selected from N, C-J$^D$ or C—H;
o is an integer selected from 0 to 3;
each $J^D$ is independently selected from halogen, —NO$_2$, —OR$^D$, —SR$^D$, —C(O)R$^D$, —C(O)OR$^D$, —C(O)N(R$^D$)$_2$, —CN, —N(R$^D$)$_2$, —N(R$^d$)C(O)R$^D$, —N(R$^d$)C(O)OR$^D$, —SO$_2$R$^D$, —SO$_2$N(R$^D$)$_2$, —N(R$^d$)SO$_2$R$^D$, a $C_{1-6}$ aliphatic, —($C_{1-6}$ aliphatic)-R$^D$, a $C_{3-8}$ cycloaliphatic ring, a 6 to 10-membered aryl ring, a 4 to 8-membered heterocyclic ring or a 5 to 10-membered heteroaryl ring; wherein each said 4 to 8-membered heterocylic ring and each said 5 to 10-membered heteroaryl ring contains between 1 and 3 heteroatoms independently selected from O, N or S; and wherein each said $C_{1-6}$ aliphatic, each said $C_{3-8}$ cycloaliphatic ring, each said 6 to 10-membered aryl ring, each said 4 to 8-membered heterocyclic ring and each said 5 to 10-membered heteroaryl ring is optionally and independently substituted with up to 3 instances of R$^5$;
each R$^D$ is independently selected from hydrogen, a $C_{1-6}$ aliphatic, —($C_{1-6}$ aliphatic)-R$^f$, a $C_{3-8}$ cycloaliphatic ring, a 4 to 8-membered heterocyclic ring, phenyl or a 5 to 6-membered heteroaryl ring; wherein each said 4 to 8-membered heterocylic ring and each said 5 to 6-membered heteroaryl ring contains between 1 and 3 heteroatoms independently selected from O, N or S; and wherein each said $C_{1-6}$ aliphatic, each said $C_{3-8}$ cycloaliphatic ring, each said 4 to 8-membered heterocyclic ring, each said phenyl and each said 5 to 6-membered heteroaryl ring is optionally and independently substituted with up to 3 instances of R$^5$;
each R$^d$ is independently selected from hydrogen, a $C_{1-6}$ aliphatic, —($C_{1-6}$ aliphatic)-R$^f$, a $C_{3-8}$ cycloaliphatic ring, a 4 to 8-membered heterocyclic ring, phenyl or a 5 to 6-membered heteroaryl ring; wherein each said heterocylic ring and each said heteroaryl ring contains between 1 and 3 heteroatoms independently selected from O, N or S; and wherein each said $C_{1-6}$ aliphatic, each said $C_{3-8}$ cycloaliphatic ring, each said 4 to 8-membered heterocyclic ring, each said phenyl and each said 5 to 6-membered heteroaryl ring is optionally and independently substituted by up to 3 instances of R$^5$;
each R$^f$ is independently selected from a $C_{3-8}$ cycloaliphatic ring, a 4 to 8-membered heterocyclic ring, phenyl or a 5 to 6-membered heteroaryl ring; wherein each said heterocylic ring and each said heteroaryl ring contains between 1 and 3 heteroatoms independently selected from O, N or S; and wherein each said $C_{1-6}$ aliphatic, each said $C_{3-8}$ cycloaliphatic ring, each said 4 to 8-membered heterocyclic ring, each said phenyl and each said 5 to 6-membered heteroaryl ring is optionally and independently substituted by up to 3 instances of R$^5$;
alternatively, two instances of R$^D$ linked to the same nitrogen atom of J$^D$, together with said nitrogen atom of J$^D$, form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of R$^5$; or
alternatively, one instance of R$^D$ linked to a carbon, oxygen or sulfur atom of J$^D$ and one instance of R$^d$ linked to a nitrogen atom of the same J$^D$, together with said carbon, oxygen or sulfur and said nitrogen atom of that same P, form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of $R^5$;

each $R^5$ is independently selected from halogen, —CN, —NO$_2$, $C_{1-4}$ alkyl, a $C_{7-12}$ aralkyl, $C_{3-8}$ cycloalkyl ring, $C_{1-4}$ haloalkyl, $C_{1-4}$ cyanoalkyl, —OR$^6$, —SR$^6$, —COR$^6$, —OCOR$^6$, —C(O)OR$^6$, —C(O)N(R$^6$)$_2$, —N(R$^6$)C(O)R$^6$, —N(R$^6$)$_2$, —SO$_2$R$^6$, —SO$_2$N(R$^6$)$_2$, —N(R$^6$)SO$_2$R$^6$, phenyl or an oxo group; wherein each said phenyl group is optionally and independently substituted with up to 3 instances of halogen, —OH, —NH$_2$, —NH(C$_{1-4}$ alkyl), —N(C$_{1-4}$ alkyl)$_2$, —NO$_2$, —CN, C$_{1-4}$ alkyl, C$_{1-4}$ haloalkyl, —O(C$_{1-4}$ alkyl) or —O(C$_{1-4}$ haloalkyl); and wherein each said C$_{7-12}$ aralkyl and each said cycloalkyl group is optionally and independently substituted with up to 3 instances of halogen;

each $R^6$ is independently selected from hydrogen, a $C_{1-4}$ alkyl, a $C_{2-4}$ alkenyl, phenyl, a $C_{7-12}$ aralkyl or a $C_{3-8}$ cycloalkyl ring; wherein each said $C_{1-4}$ alkyl, each said $C_{2-4}$ alkenyl, each said phenyl, each said $C_{7-12}$ aralkyl and each said cycloalkyl group is optionally and independently substituted with up to 3 instances of halogen;

alternatively, two instances of $R^6$ linked to the same nitrogen atom of $R^5$, together with said nitrogen atom of $R^5$, form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S; or alternatively, one instance of $R^6$ linked to a nitrogen atom of $R^5$ and one instance of $R^6$ linked to a carbon or sulfur atom of the same $R^5$, together with said nitrogen and said carbon or sulfur atom of the same $R^5$, form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S;

or, alternatively, two $J^D$ groups attached to two vicinal ring D atoms, taken together with said two vicinal ring D atoms, form a 5 to 7-membered heterocycle resulting in a fused ring D wherein said 5 to 7-membered heterocycle contains from 1 to 3 heteroatoms independently selected from N, O or S; and wherein said 5 to 7-membered heterocycle is optionally and independently substituted by up to 3 instances of halogen, —OH, —NH$_2$, —NH(C$_{1-4}$ alkyl), —N(C$_{1-4}$ allyl)$_2$, —CN, C$_{1-4}$ alkyl, C$_{1-4}$ haloalkyl, —O(C$_{1-4}$ alkyl), —O(C$_{1-4}$ haloalkyl), oxo or phenyl; wherein said phenyl is optionally and independently substituted by up to three instances of halogen, —OH, —NH$_2$, —NH(C$_{1-4}$ alkyl), —N(C$_{1-4}$ alkyl)$_2$, —NO$_2$, —CN, C$_{1-4}$ alkyl, C$_{1-4}$ haloalkyl, —O(C$_{1-4}$ alkyl) or —O(C$_{1-4}$ haloalkyl);

$R^C$ is selected from —CN, C$_{1-6}$ alkyl or a ring C;

ring C is a phenyl ring, a monocyclic 5 or 6-membered heteroaryl ring, a bicyclic 8 to 10-membered heteroaryl ring, a monocyclic 3 to 10-membered cycloaliphatic ring, or a monocyclic 4 to 10-membered heterocycle; wherein said monocyclic 5 or 6-membered heteroaryl ring, said bicyclic 8 to 10-membered heteroaryl ring, or said monocyclic 4 to 10-membered heterocycle contain between 1 and 4 heteroatoms selected from N, O or S; wherein said monocyclic 5 or 6 membered heterocyclic ring is not a 1,3,5-triazinyl ring and wherein said phenyl, monocyclic 5 to 6-membered heteroaryl ring, bicyclic 8 to 10-membered heteroaryl ring, or monocyclic 4 to 10-membered heterocycle is optionally and independently substituted with up to 3 instances of $J^C$;

each $J^C$ is independently selected from halogen, —CN, —NO$_2$, a C$_{1-6}$ aliphatic, —OR$^H$, —SR$^H$, —N(R$^H$)$_2$, a C$_{3-8}$ cycloaliphatic ring or a 4 to 8-membered heterocyclic ring; wherein said 4 to 8-membered heterocyclic ring contains 1 or 2 heteroatoms independently selected from N, O or S; wherein each said C$_{1-6}$ aliphatic, each said C$_{3-8}$ cycloaliphatic ring and each said 4 to 8-membered heterocyclic ring, is optionally and independently substituted with up to 3 instances of $R^7$; or alternatively, two $J^C$ groups attached to two vicinal ring C atoms, taken together with said two vicinal ring C atoms, form a 5 to 7-membered heterocycle resulting in a fused ring C; wherein said 5 to 7-membered heterocycle contains from 1 to 2 heteroatoms independently selected from N, O or S;

each $R^H$ is independently selected from hydrogen, a C$_{1-6}$ aliphatic, a C$_{3-8}$ cycloaliphatic ring or a 4 to 8-membered heterocyclic ring; wherein each said 4 to 8-membered heterocylic ring contains between 1 and 3 heteroatoms independently selected from O, N or S; and wherein each said C$_{1-6}$ aliphatic, each said C$_{3-8}$ cycloaliphatic ring, each said 4 to 8-membered heterocyclic ring, is optionally and independently substituted with up to 3 instances of $R^7$;

alternatively, two instances of $R^H$ linked to the same nitrogen atom of $J^C$, together with said nitrogen atom of $J^C$, form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of $R^7$; or each $R^7$ is independently selected from halogen, —CN, —NO$_2$, C$_{1-4}$ alkyl, C$_{1-4}$ haloalkyl, C$_{3-8}$ cycloalkyl ring, —OR$^8$, —SR$^8$, —N(R$^8$)$_2$, or an oxo group; wherein each said cycloalkyl group is optionally and independently substituted with up to 3 instances of halogen;

each $R^8$ is independently selected from hydrogen, a C$_{1-4}$ alkyl, C$_{1-4}$ haloalkyl or a C$_{3-8}$ cycloalkyl ring; wherein each said cycloalkyl group is optionally and independently substituted with up to 3 instances of halogen;

alternatively, two instances of $R^8$ linked to the same nitrogen atom of $R^7$, together with said nitrogen atom of $R^7$, form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S; $R^A$ is selected from hydrogen, halogen, C$_{1-4}$ alkyl or C$_{1-4}$ haloalkyl, with the proviso that when ring B is unsubstituted phenyl and ring D is unsubstituted pyrimidinyl (X is N and o is zero), $R^C$ is not methyl or ethyl.

In another aspect, the invention is directed to a compound of Formula I, or pharmaceutically acceptable salts thereof,

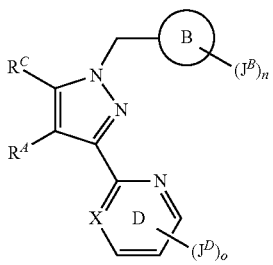

Formula I wherein:
ring B is a phenyl or a 6-membered heteroaryl ring, containing 1 or 2 nitrogen atoms in the ring;
n is an integer selected from 0 to 3;
each $J^B$ is independently selected from halogen, —CN, —NO$_2$, a $C_{1-6}$ aliphatic, —OR$^B$ or a $C_{3-8}$ cycloaliphatic group; wherein each said $C_{1-6}$ aliphatic and each said $C_{3-8}$ cycloaliphatic group is optionally and independently substituted with up to 3 instances of $R^3$;
each $R^B$ is independently selected from hydrogen, a $C_{1-6}$ aliphatic or a $C_{3-8}$ cycloaliphatic; wherein each said $C_{1-6}$ aliphatic and each said $C_{3-8}$ cycloaliphatic ring is optionally and independently substituted with up to 3 instances of $R^3$;
each $R^3$ is independently selected from halogen, —CN, $C_{1-4}$ alkyl, $C_{1-4}$ haloalkyl, —O($C_{1-4}$ alkyl) or —O($C_{1-4}$ haloalkyl);
X is selected from N, C-$J^D$ or C—H;
o is an integer selected from 0 to 3;
each $J^D$ is independently selected from halogen, —NO$_2$, —OR$^D$, —SR$^D$, —C(O)R$^D$, —C(O)OR$^D$, —C(O)N(R$^D$)$_2$, —CN, —N(R$^D$)$_2$, —N(R$^d$)C(O)R$^D$, —N(R$^d$)C(O)OR$^D$, —SO$_2$R$^D$, —SO$_2$N(R$^D$)$_2$, —N(R$^d$)SO$_2$R$^D$, a $C_{1-6}$ aliphatic, —(C$_{1-6}$ aliphatic)-R$^D$, a $C_{3-8}$ cycloaliphatic ring, a 6 to 10-membered aryl ring, a 4 to 8-membered heterocyclic ring or a 5 to 10-membered heteroaryl ring; wherein each said 4 to 8-membered heterocylic ring and each said 5 to 10-membered heteroaryl ring contains between 1 and 3 heteroatoms independently selected from O, N or S; and wherein each said $C_{1-6}$ aliphatic, each said $C_{3-8}$ cycloaliphatic ring, each said 6 to 10-membered aryl ring, each said 4 to 8-membered heterocyclic ring and each said 5 to 10-membered heteroaryl ring is optionally and independently substituted with up to 3 instances of $R^5$;
each $R^D$ is independently selected from hydrogen, a $C_{1-6}$ aliphatic, —(C$_{1-6}$ aliphatic)-R$^f$, a $C_{3-8}$ cycloaliphatic ring, a 4 to 8-membered heterocyclic ring, phenyl or a 5 to 6-membered heteroaryl ring; wherein each said 4 to 8-membered heterocylic ring and each said 5 to 6-membered heteroaryl ring contains between 1 and 3 heteroatoms independently selected from O, N or S; and wherein each said $C_{1-6}$ aliphatic, each said $C_{3-8}$ cycloaliphatic ring, each said 4 to 8-membered heterocyclic ring, each said phenyl and each said 5 to 6-membered heteroaryl ring is optionally and independently substituted with up to 3 instances of $R^5$;
each $R^d$ is independently selected from hydrogen, a $C_{1-6}$ aliphatic, —(C$_{1-6}$ aliphatic)-R$^f$, a $C_{3-8}$ cycloaliphatic ring, a 4 to 8-membered heterocyclic ring, phenyl or a 5 to 6-membered heteroaryl ring; wherein each said heterocylic ring and each said heteroaryl ring contains between 1 and 3 heteroatoms independently selected from O, N or S; and wherein each said $C_{1-6}$ aliphatic, each said $C_{3-8}$ cycloaliphatic ring, each said 4 to 8-membered heterocyclic ring, each said phenyl and each said 5 to 6-membered heteroaryl ring is optionally and independently substituted by up to 3 instances of $R^5$;
each $R^f$ is independently selected from a $C_{3-8}$ cycloaliphatic ring, a 4 to 8-membered heterocyclic ring, phenyl or a 5 to 6-membered heteroaryl ring; wherein each said heterocylic ring and each said heteroaryl ring contains between 1 and 3 heteroatoms independently selected from O, N or S; and wherein each said $C_{1-6}$ aliphatic, each said $C_{3-8}$ cycloaliphatic ring, each said 4 to 8-membered heterocyclic ring, each said phenyl and each said 5 to 6-membered heteroaryl ring is optionally and independently substituted by up to 3 instances of $R^5$;
alternatively, two instances of $R^D$ linked to the same nitrogen atom of $J^D$, together with said nitrogen atom of $J^D$, form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of $R^5$; or
alternatively, one instance of $R^D$ linked to a carbon, oxygen or sulfur atom of $J^D$ and one instance of $R^d$ linked to a nitrogen atom of the same $J^D$, together with said carbon, oxygen or sulfur and said nitrogen atom of that same $J^D$, form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of $R^5$;
each $R^5$ is independently selected from halogen, —CN, —NO$_2$, $C_{1-4}$ alkyl, a $C_{7-12}$ aralkyl, $C_{3-8}$ cycloalkyl ring, $C_{1-4}$ haloalkyl, $C_{1-4}$ cyanoalkyl, —OR$^6$, —SR$^6$, —COR$^6$, —C(O)OR$^6$, —C(O)N(R$^6$)$_2$, —N(R$^6$)C(O)R$^6$, —N(R$^6$)$_2$, —SO$_2$R$^6$, —SO$_2$N(R$^6$)$_2$, —N(R$^6$)SO$_2$R$^6$, phenyl or an oxo group; wherein each said phenyl group is optionally and independently substituted with up to 3 instances of halogen, —OH, —NH$_2$, —NH(C$_{1-4}$ alkyl), —N(C$_{1-4}$ alkyl)$_2$, —NO$_2$, —CN, C$_{1-4}$ alkyl, C$_{1-4}$ haloalkyl, —O(C$_{1-4}$ alkyl) or —O(C$_{1-4}$ haloalkyl); and wherein each said C$_{7-12}$ aralkyl and each said cycloalkyl group is optionally and independently substituted with up to 3 instances of halogen;
each $R^6$ is independently selected from hydrogen, a $C_{1-4}$ alkyl, a $C_{2-4}$ alkenyl, phenyl, a $C_{7-12}$ aralkyl or a $C_{3-8}$ cycloalkyl ring; wherein each said $C_{1-4}$ alkyl, each said $C_{2-4}$ alkenyl, each said phenyl, each said $C_{7-12}$ aralkyl and each said cycloalkyl group is optionally and independently substituted with up to 3 instances of halogen;
alternatively, two instances of $R^6$ linked to the same nitrogen atom of $R^5$, together with said nitrogen atom of $R^5$, form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S; or
alternatively, one instance of $R^6$ linked to a nitrogen atom of $R^5$ and one instance of $R^6$ linked to a carbon or sulfur atom of the same $R^5$, together with said nitrogen and said carbon or sulfur atom of the same $R^5$, form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S;

or, alternatively, two $J^D$ groups attached to two vicinal ring D atoms, taken together with said two vicinal ring D atoms, form a 5 to 7-membered heterocycle resulting in a fused ring D wherein said 5 to 7-membered heterocycle contains from 1 to 3 heteroatoms independently selected from N, O or S; and wherein said 5 to 7-membered heterocycle is optionally and independently substituted by up to 3 instances of halogen, —OH, —NH$_2$, —NH(C$_{1-4}$ alkyl), —N(C$_{1-4}$ alkyl)$_2$, —CN, C$_{1-4}$ alkyl, C$_{1-4}$ haloalkyl, —O(C$_{1-4}$ alkyl), —O(C$_{1-4}$ haloalkyl) or oxo;

$R^C$ is selected from —CN, C$_{1-6}$ alkyl or a ring C;

ring C is a phenyl ring, a monocyclic 5 or 6-membered heteroaryl ring, a bicyclic 8 to 10-membered heteroaryl ring, a monocyclic 3 to 10-membered cycloaliphatic ring, or a monocyclic 4 to 10-membered heterocycle; wherein said monocyclic 5 or 6-membered heteroaryl ring, said bicyclic 8 to 10-membered heteroaryl ring, or said monocyclic 4 to 10-membered heterocycle contain between 1 and 4 heteroatoms selected from N, O or S; wherein said phenyl, monocyclic 5 to 6-membered heteroaryl ring, bicyclic 8 to 10-membered heteroaryl ring, or monocyclic 4 to 10-membered heterocycle is optionally and independently substituted with up to 3 instances of $J^C$;

each $J^C$ is independently selected from halogen, —CN, —NO$_2$, a C$_{1-6}$ aliphatic, —OR$^H$, —SR$^H$, —N(R$^H$)$_2$, a C$_{3-8}$ cycloaliphatic ring or a 4 to 8-membered heterocyclic ring; wherein said 4 to 8-membered heterocyclic ring contains 1 or 2 heteroatoms independently selected from N, O or S; wherein each said C$_{1-6}$ aliphatic, each said C$_{3-8}$ cycloaliphatic ring and each said 4 to 8-membered heterocyclic ring, is optionally and independently substituted with up to 3 instances of R$^7$; or alternatively, two $J^C$ groups attached to two vicinal ring C atoms, taken together with said two vicinal ring C atoms, form a 5 to 7-membered heterocycle resulting in a fused ring C; wherein said 5 to 7-membered heterocycle contains from 1 to 2 heteroatoms independently selected from N, O or S;

each $R^H$ is independently selected from hydrogen, a C$_{1-6}$ aliphatic, a C$_{3-8}$ cycloaliphatic ring or a 4 to 8-membered heterocyclic ring; wherein each said 4 to 8-membered heterocylic ring contains between 1 and 3 heteroatoms independently selected from O, N or S; and wherein each said C$_{1-6}$ aliphatic, each said C$_{3-8}$ cycloaliphatic ring, each said 4 to 8-membered heterocyclic ring, is optionally and independently substituted with up to 3 instances of R$^7$;

alternatively, two instances of $R^H$ linked to the same nitrogen atom of $J^C$, together with said nitrogen atom of $J^C$, form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of R$^7$; or each R$^7$ is independently selected from halogen, —CN, —NO$_2$, C$_{1-4}$ alkyl, C$_{1-4}$ haloalkyl, C$_{3-8}$ cycloalkyl ring, —OR$^8$, —SR$^8$, —N(R$^8$)$_2$, or an oxo group; wherein each said cycloalkyl group is optionally and independently substituted with up to 3 instances of halogen;

each R$^8$ is independently selected from hydrogen, a C$_{1-4}$ alkyl, C$_{1-4}$ haloalkyl or a C$_{3-8}$ cycloalkyl ring; wherein each said cycloalkyl group is optionally and independently substituted with up to 3 instances of halogen;

alternatively, two instances of R$^8$ linked to the same nitrogen atom of R$^7$, together with said nitrogen atom of R$^7$, form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S; R$^A$ is selected from hydrogen, halogen, C$_{1-4}$ alkyl or C$_{1-4}$ haloalkyl, with the proviso that when ring B is unsubstituted phenyl and ring D is unsubstituted pyrimidinyl (X is N and o is zero), $R^C$ is not methyl or ethyl.

In another aspect, the invention is directed to a compound of Formula I, or pharmaceutically acceptable salts thereof,

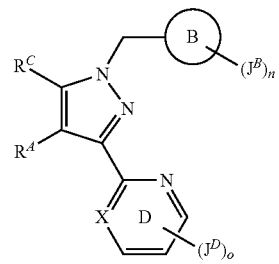

Formula I wherein:

ring B is a phenyl or a 6-membered heteroaryl ring, containing 1 or 2 nitrogen atoms in the ring;

n is an integer selected from 0 to 3;

each $J^B$ is independently selected from halogen, —CN, —NO$_2$, a C$_{1-6}$ aliphatic, —OR$^B$ or a C$_{3-8}$ cycloaliphatic group; wherein each said C$_{1-6}$ aliphatic and each said C$_{3-8}$ cycloaliphatic group is optionally and independently substituted with up to 3 instances of R$^3$;

each R$^B$ is independently selected from hydrogen, a C$_{1-6}$ aliphatic or a C$_{3-8}$ cycloaliphatic; wherein each said C$_{1-6}$ aliphatic and each said C$_{3-8}$ cycloaliphatic ring is optionally and independently substituted with up to 3 instances of R$^3$;

each R$^3$ is independently selected from halogen, —CN, C$_{1-4}$ alkyl, C$_{1-4}$ haloalkyl, —O(C$_{1-4}$ alkyl) or —O(C$_{1-4}$ haloalkyl);

X is selected from N, C-$J^D$ or C—H;

o is an integer selected from 0 to 3;

each $J^D$ is independently selected from halogen, —NO$_2$, —OR$^D$, —SR$^D$, —C(O)R$^D$, —C(O)OR$^D$, —C(O)N(R$^D$)$_2$, —CN, —N(R$^D$)$_2$, —N(R$^d$)C(O)R$^D$, —N(R$^d$)C(O)OR$^D$, —SO$_2$R$^D$, —SO$_2$N(R$^D$)$_2$, —N(R$^d$)SO$_2$R$^D$, a C$_{1-6}$ aliphatic, —(C$_{1-6}$ aliphatic)-R$^D$, a C$_{3-8}$ cycloaliphatic ring, a 6 to 10-membered aryl ring, a 4 to 8-membered heterocyclic ring or a 5 to 10-membered heteroaryl ring; wherein each said 4 to 8-membered heterocylic ring and each said 5 to 10-membered heteroaryl ring contains between 1 and 3 heteroatoms independently selected from O, N or S; and wherein each said C$_{1-6}$ aliphatic, each said C$_{3-8}$ cycloaliphatic ring, each said 6 to 10-membered aryl ring, each said 4 to 8-membered heterocyclic ring and each said 5 to 10-membered heteroaryl ring is optionally and independently substituted with up to 3 instances of R$^5$;

each R$^D$ is independently selected from hydrogen, a C$_{1-6}$ aliphatic, —(C$_{1-6}$ aliphatic)-R$^f$, a C$_{3-8}$ cycloaliphatic ring, a 4 to 8-membered heterocyclic ring, phenyl or a 5 to 6-membered heteroaryl ring; wherein each said 4 to 8-membered heterocylic ring and each said 5 to 6-membered heteroaryl ring contains between 1 and 3 heteroatoms independently selected from O, N or S; and wherein each said $C_{1-6}$ aliphatic, each said $C_{3-8}$ cycloaliphatic ring, each said 4 to 8-membered heterocyclic ring, each said phenyl and each said 5 to 6-membered heteroaryl ring is optionally and independently substituted with up to 3 instances of $R^5$;

each $R^d$ is independently selected from hydrogen, a $C_{1-6}$ aliphatic, —($C_{1-6}$ aliphatic)-$R^f$, a $C_{3-8}$ cycloaliphatic ring, a 4 to 8-membered heterocyclic ring, phenyl or a 5 to 6-membered heteroaryl ring; wherein each said heterocylic ring and each said heteroaryl ring contains between 1 and 3 heteroatoms independently selected from O, N or S; and wherein each said $C_{1-6}$ aliphatic, each said $C_{3-8}$ cycloaliphatic ring, each said 4 to 8-membered heterocyclic ring, each said phenyl and each said 5 to 6-membered heteroaryl ring is optionally and independently substituted by up to 3 instances of $R^5$;

each $R^f$ is independently selected from a $C_{3-8}$ cycloaliphatic ring, a 4 to 8-membered heterocyclic ring, phenyl or a 5 to 6-membered heteroaryl ring; wherein each said heterocylic ring and each said heteroaryl ring contains between 1 and 3 heteroatoms independently selected from O, N or S; and wherein each said $C_{1-6}$ aliphatic, each said $C_{3-8}$ cycloaliphatic ring, each said 4 to 8-membered heterocyclic ring, each said phenyl and each said 5 to 6-membered heteroaryl ring is optionally and independently substituted by up to 3 instances of $R^5$;

alternatively, two instances of $R^D$ linked to the same nitrogen atom of $J^D$, together with said nitrogen atom of $J^D$, form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of $R^5$; or alternatively, one instance of $R^D$ linked to a carbon, oxygen or sulfur atom of $J^D$ and one instance of $R^d$ linked to a nitrogen atom of the same P, together with said carbon, oxygen or sulfur and said nitrogen atom of that same $J^D$, form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of $R^5$;

each $R^5$ is independently selected from halogen, —CN, —NO$_2$, $C_{1-4}$ alkyl, a $C_{7-12}$ aralkyl, $C_{3-8}$ cycloalkyl ring, $C_{1-4}$ haloalkyl, $C_{1-4}$ cyanoalkyl, —OR$^6$, —SR$^6$, —COR$^6$, —C(O)OR$^6$, —C(O)N(R$^6$)$_2$, —N(R$^6$)C(O)R$^6$, —N(R$^6$)$_2$, —SO$_2$R$^6$, —SO$_2$N(R$^6$)$_2$, —N(R$^6$)SO$_2$R$^6$, phenyl or an oxo group; wherein each said phenyl group is optionally and independently substituted with up to 3 instances of halogen, —OH, —NH$_2$, —NH($C_{1-4}$ alkyl), —N($C_{1-4}$ alkyl)$_2$, —NO$_2$, —CN, $C_{1-4}$ alkyl, $C_{1-4}$ haloalkyl, —O($C_{1-4}$ alkyl) or —O($C_{1-4}$ haloalkyl); and wherein each said $C_{7-12}$ aralkyl and each said cycloalkyl group is optionally and independently substituted with up to 3 instances of halogen;

each $R^6$ is independently selected from hydrogen, a $C_{1-4}$ alkyl, a $C_{2-4}$ alkenyl, phenyl, a $C_{7-12}$ aralkyl or a $C_{3-8}$ cycloalkyl ring; wherein each said $C_{1-4}$ alkyl, each said $C_{2-4}$ alkenyl, each said phenyl, each said $C_{7-12}$ aralkyl and each said cycloalkyl group is optionally and independently substituted with up to 3 instances of halogen;

alternatively, two instances of $R^6$ linked to the same nitrogen atom of $R^5$, together with said nitrogen atom of $R^5$, form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S; or alternatively, one instance of $R^6$ linked to a nitrogen atom of $R^5$ and one instance of $R^6$ linked to a carbon or sulfur atom of the same $R^5$, together with said nitrogen and said carbon or sulfur atom of the same $R^5$, form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S;

or, alternatively, two $J^D$ groups attached to two vicinal ring D atoms, taken together with said two vicinal ring D atoms, form a 5 to 7-membered heterocycle resulting in a fused ring D wherein said 5 to 7-membered heterocycle contains from 1 to 3 heteroatoms independently selected from N, O or S; and wherein said 5 to 7-membered heterocycle is optionally and independently substituted by up to 3 instances of halogen, —OH, —NH$_2$, —NH($C_{1-4}$ alkyl), —N($C_{1-4}$ alkyl)$_2$, —CN, $C_{1-4}$ alkyl, $C_{1-4}$ haloalkyl, —O($C_{1-4}$ alkyl), —O($C_{1-4}$ haloalkyl) or oxo;

$R^C$ is selected from —CN, $C_{1-6}$ alkyl or a ring C;

ring C is a phenyl ring, a monocyclic 5 or 6-membered heteroaryl ring, a bicyclic 8 to 10-membered heteroaryl ring, a monocyclic 3 to 10-membered cycloaliphatic ring, or a monocyclic 4 to 10-membered heterocycle; wherein said monocyclic 5 or 6-membered heteroaryl ring, said bicyclic 8 to 10-membered heteroaryl ring, or said monocyclic 4 to 10-membered heterocycle contain between 1 and 4 heteroatoms selected from N, O or S; wherein said monocyclic 5 or 6-membered heteroaryl ring is not a 1,3,5-triazinyl ring; and wherein said phenyl, monocyclic 5 to 6-membered heteroaryl ring, bicyclic 8 to 10-membered heteroaryl ring, or monocyclic 4 to 10-membered heterocycle is optionally and independently substituted with up to 3 instances of $J^C$;

each $J^C$ is independently selected from halogen, —CN, —NO$_2$, a $C_{1-6}$ aliphatic, —OR$^H$, —SR$^H$, —N(R$^H$)$_2$, a $C_{3-8}$ cycloaliphatic ring or a 4 to 8-membered heterocyclic ring; wherein said 4 to 8-membered heterocyclic ring contains 1 or 2 heteroatoms independently selected from N, O or S; wherein each said $C_{1-6}$ aliphatic, each said $C_{3-8}$ cycloaliphatic ring and each said 4 to 8-membered heterocyclic ring, is optionally and independently substituted with up to 3 instances of $R^7$; or alternatively, two $J^C$ groups attached to two vicinal ring C atoms, taken together with said two vicinal ring C atoms, form a 5 to 7-membered heterocycle resulting in a fused ring C; wherein said 5 to 7-membered heterocycle contains from 1 to 2 heteroatoms independently selected from N, O or S;

each $R^H$ is independently selected from hydrogen, a $C_{1-6}$ aliphatic, a $C_{3-8}$ cycloaliphatic ring or a 4 to 8-membered heterocyclic ring; wherein each said 4 to 8-membered heterocylic ring contains between 1 and 3 heteroatoms independently selected from O, N or S; and wherein each said $C_{1-6}$ aliphatic, each said $C_{3-8}$ cycloaliphatic ring, each said 4 to 8-membered heterocyclic ring, is optionally and independently substituted with up to 3 instances of $R^7$;

alternatively, two instances of $R^H$ linked to the same nitrogen atom of $J^C$, together with said nitrogen atom of $J^C$, form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of $R^7$; or each $R^7$ is independently selected from halogen, —CN, —NO$_2$, C$_{1-4}$ alkyl, C$_{1-4}$ haloalkyl, C$_{3-8}$ cycloalkyl ring, —OR$^8$, —SR$^8$, —N(R$^8$)$_2$, or an oxo group; wherein each said cycloalkyl group is optionally and independently substituted with up to 3 instances of halogen;

each $R^8$ is independently selected from hydrogen, a C$_{1-4}$ alkyl, C$_{1-4}$ haloalkyl or a C$_{3-8}$ cycloalkyl ring; wherein each said cycloalkyl group is optionally and independently substituted with up to 3 instances of halogen;

alternatively, two instances of $R^8$ linked to the same nitrogen atom of $R^7$, together with said nitrogen atom of $R^7$, form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S; $R^A$ is selected from hydrogen, halogen, C$_{1-4}$ alkyl or C$_{1-4}$ haloalkyl, with the proviso that when ring B is unsubstituted phenyl and ring D is unsubstituted pyrimidinyl (X is N and o is zero), $R^C$ is not methyl or ethyl.

In another aspect, the invention is directed to a compound of Formula I, or pharmaceutically acceptable salts thereof,

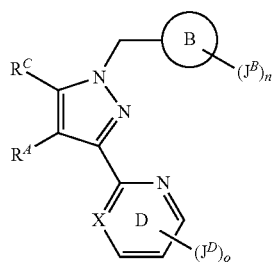

Formula I wherein:
ring B is a phenyl or a 6-membered heteroaryl ring, containing 1 or 2 nitrogen atoms in the ring;
n is an integer selected from 0 to 3;
each $J^B$ is independently selected from halogen, —CN, —NO$_2$, a C$_{1-6}$ aliphatic, —OR$^B$ or a C$_{3-8}$ cycloaliphatic group; wherein each said C$_{1-6}$ aliphatic and each said C$_{3-8}$ cycloaliphatic group is optionally and independently substituted with up to 3 instances of $R^3$;

each $R^B$ is independently selected from hydrogen, a C$_{1-6}$ aliphatic or a C$_{3-8}$ cycloaliphatic; wherein each said C$_{1-6}$ aliphatic and each said C$_{3-8}$ cycloaliphatic ring is optionally and independently substituted with up to 3 instances of $R^3$;

each $R^3$ is independently selected from halogen, —CN, C$_{1-4}$ alkyl, C$_{1-4}$ haloalkyl, —O(C$_{1-4}$ alkyl) or —O(C$_{1-4}$ haloalkyl);

X is selected from N, C-$J^D$ or C—H;
o is an integer selected from 0 to 3;
each $J^D$ is independently selected from halogen, —NO$_2$, —OR$^D$, —SR$^D$, —C(O)R$^D$, —C(O)OR$^D$, —C(O)N(R$^D$)$_2$, —CN, —N(R$^D$)$_2$, —N(R$^d$)C(O)R$^D$, —N(R$^d$)C(O)OR$^D$, —SO$_2$R$^D$, —SO$_2$N(R$^D$)$_2$, —N(R$^d$)SO$_2$R$^D$, a C$_{1-6}$ aliphatic, —(C$_{1-6}$ aliphatic)-R$^D$, a C$_{3-8}$ cycloaliphatic ring, a 6 to 10-membered aryl ring, a 4 to 8-membered heterocyclic ring or a 5 to 10-membered heteroaryl ring; wherein each said 4 to 8-membered heterocyclic ring and each said 5 to 10-membered heteroaryl ring contains between 1 and 3 heteroatoms independently selected from O, N or S; and wherein each said C$_{1-6}$ aliphatic, each said C$_{3-8}$ cycloaliphatic ring, each said 6 to 10-membered aryl ring, each said 4 to 8-membered heterocyclic ring and each said 5 to 10-membered heteroaryl ring is optionally and independently substituted with up to 3 instances of $R^5$;

each $R^D$ is independently selected from hydrogen, a C$_{1-6}$ aliphatic, —(C$_{1-6}$ aliphatic)-R$^f$, a C$_{3-8}$ cycloaliphatic ring, a 4 to 8-membered heterocyclic ring, phenyl or a 5 to 6-membered heteroaryl ring; wherein each said 4 to 8-membered heterocylic ring and each said 5 to 6-membered heteroaryl ring contains between 1 and 3 heteroatoms independently selected from O, N or S; and wherein each said C$_{1-6}$ aliphatic, each said C$_{3-8}$ cycloaliphatic ring, each said 4 to 8-membered heterocyclic ring, each said phenyl and each said 5 to 6-membered heteroaryl ring is optionally and independently substituted with up to 3 instances of $R^5$;

each $R^d$ is independently selected from hydrogen, a C$_{1-6}$ aliphatic, —(C$_{1-6}$ aliphatic)-R$^f$, a C$_{3-8}$ cycloaliphatic ring, a 4 to 8-membered heterocyclic ring, phenyl or a 5 to 6-membered heteroaryl ring; wherein each said heterocyclic ring and each said heteroaryl ring contains between 1 and 3 heteroatoms independently selected from O, N or S; and wherein each said C$_{1-6}$ aliphatic, each said C$_{3-8}$ cycloaliphatic ring, each said 4 to 8-membered heterocyclic ring, each said phenyl and each said 5 to 6-membered heteroaryl ring is optionally and independently substituted by up to 3 instances of $R^5$;

each $R^f$ is independently selected from a C$_{3-8}$ cycloaliphatic ring, a 4 to 8-membered heterocyclic ring, phenyl or a 5 to 6-membered heteroaryl ring; wherein each said heterocyclic ring and each said heteroaryl ring contains between 1 and 3 heteroatoms independently selected from O, N or S; and wherein each said C$_{1-6}$ aliphatic, each said C$_{3-8}$ cycloaliphatic ring, each said 4 to 8-membered heterocyclic ring, each said phenyl and each said 5 to 6-membered heteroaryl ring is optionally and independently substituted by up to 3 instances of $R^5$;

alternatively, two instances of $R^D$ linked to the same nitrogen atom of $J^D$, together with said nitrogen atom of P, form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of $R^5$; or alternatively, one instance of $R^D$ linked to a carbon, oxygen or sulfur atom of $J^D$ and one instance of $R^d$ linked to a nitrogen atom of the same $J^D$, together with said carbon, oxygen or sulfur and said nitrogen atom of that same $J^D$, form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of $R^5$;

each $R^5$ is independently selected from halogen, —CN, —NO$_2$, C$_{1-4}$ alkyl, a C$_{7-12}$ aralkyl, C$_{3-8}$ cycloalkyl ring, C$_{1-4}$ haloalkyl, C$_{1-4}$ cyanoalkyl, —OR$^6$, —SR$^6$, —COR$^6$, —C(O)OR$^6$, —C(O)N(R$^6$)$_2$, —N(R$^6$)C(O)R$^6$, —N(R$^6$)$_2$, —$SO_2R^6$, —$SO_2N(R^6)_2$, —$N(R^6)SO_2R^6$, phenyl or an oxo group; wherein each said phenyl group is optionally and independently substituted with up to 3 instances of halogen, —OH, —$NH_2$, —$NH(C_{1-4}$ alkyl), —$N(C_{1-4}$ allyl$)_2$, —$NO_2$, —CN, $C_{1-4}$ alkyl, $C_{1-4}$ haloalkyl, —$O(C_{1-4}$ alkyl) or —$O(C_{1-4}$ haloalkyl); and wherein each said $C_{7-12}$ aralkyl and each said cycloalkyl group is optionally and independently substituted with up to 3 instances of halogen;

each $R^6$ is independently selected from hydrogen, a $C_{1-4}$ alkyl, a $C_{2-4}$ alkenyl, phenyl, a $C_{7-12}$ aralkyl or a $C_{3-8}$ cycloalkyl ring; wherein each said $C_{1-4}$ alkyl, each said $C_{2-4}$ alkenyl, each said phenyl, each said $C_{7-12}$ aralkyl and each said cycloalkyl group is optionally and independently substituted with up to 3 instances of halogen;

alternatively, two instances of $R^6$ linked to the same nitrogen atom of $R^5$, together with said nitrogen atom of $R^5$, form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S; or alternatively, one instance of $R^6$ linked to a nitrogen atom of $R^5$ and one instance of $R^6$ linked to a carbon or sulfur atom of the same $R^5$, together with said nitrogen and said carbon or sulfur atom of the same $R^5$, form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S;

or, alternatively, two $J^D$ groups attached to two vicinal ring D atoms, taken together with said two vicinal ring D atoms, form a 5 to 7-membered heterocycle resulting in a fused ring D wherein said 5 to 7-membered heterocycle contains from 1 to 3 heteroatoms independently selected from N, O or S; and wherein said 5 to 7-membered heterocycle is optionally and independently substituted by up to 3 instances of halogen, —OH, —$NH_2$, —$NH(C_{1-4}$ alkyl), —$N(C_{1-4}$ allyl$)_2$, —CN, $C_{1-4}$ alkyl, $C_{1-4}$ haloalkyl, —$O(C_{1-4}$ alkyl), —$O(C_{1-4}$ haloalkyl), oxo or phenyl; wherein said phenyl is optionally and independently substituted by up to three instances of halogen, —OH, —$NH_2$, —$NH(C_{1-4}$ alkyl), —$N(C_{1-4}$ alkyl$)_2$, —$NO_2$, —CN, $C_{1-4}$ alkyl, $C_{1-4}$ haloalkyl, —$O(C_{1-4}$ alkyl) or —$O(C_{1-4}$ haloalkyl);

$R^C$ is selected from —CN, $C_{1-6}$ alkyl or a ring C;

ring C is a phenyl ring, a monocyclic 5 or 6-membered heteroaryl ring, a bicyclic 8 to 10-membered heteroaryl ring, a monocyclic 3 to 10-membered cycloaliphatic ring, or a monocyclic 4 to 10-membered heterocycle; wherein said monocyclic 5 or 6-membered heteroaryl ring, said bicyclic 8 to 10-membered heteroaryl ring, or said monocyclic 4 to 10-membered heterocycle contain between 1 and 4 heteroatoms selected from N, O or S; wherein said monocyclic 5 or 6-membered heteroaryl ring is not a 1,3,5-triazinyl ring; and wherein said phenyl, monocyclic 5 to 6-membered heteroaryl ring, bicyclic 8 to 10-membered heteroaryl ring, or monocyclic 4 to 10-membered heterocycle is optionally and independently substituted with up to 3 instances of $J^C$;

each is independently selected from halogen, —CN, —$NO_2$, a $C_{1-6}$ aliphatic, —$OR^H$, —$SR^H$, —$N(R^H)_2$, a $C_{3-8}$ cycloaliphatic ring or a 4 to 8-membered heterocyclic ring; wherein said 4 to 8-membered heterocyclic ring contains 1 or 2 heteroatoms independently selected from N, O or S; wherein each said $C_{1-6}$ aliphatic, each said $C_{3-8}$ cycloaliphatic ring and each said 4 to 8-membered heterocyclic ring, is optionally and independently substituted with up to 3 instances of $R^7$; or alternatively, two $J^C$ groups attached to two vicinal ring C atoms, taken together with said two vicinal ring C atoms, form a 5 to 7-membered heterocycle resulting in a fused ring C; wherein said 5 to 7-membered heterocycle contains from 1 to 2 heteroatoms independently selected from N, O or S;

each $R^H$ is independently selected from hydrogen, a $C_{1-6}$ aliphatic, a $C_{3-8}$ cycloaliphatic ring or a 4 to 8-membered heterocyclic ring; wherein each said 4 to 8-membered heterocylic ring contains between 1 and 3 heteroatoms independently selected from O, N or S; and wherein each said $C_{1-6}$ aliphatic, each said $C_{3-8}$ cycloaliphatic ring, each said 4 to 8-membered heterocyclic ring, is optionally and independently substituted with up to 3 instances of $R^7$;

alternatively, two instances of $R^H$ linked to the same nitrogen atom of $J^C$, together with said nitrogen atom of $J^C$, form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of $R^7$; or each $R^7$ is independently selected from halogen, —CN, —$NO_2$, $C_{1-4}$ alkyl, $C_{1-4}$ haloalkyl, $C_{3-8}$ cycloalkyl ring, —$OR^8$, —$SR^8$, —$N(R^8)_2$, or an oxo group; wherein each said cycloalkyl group is optionally and independently substituted with up to 3 instances of halogen;

each $R^8$ is independently selected from hydrogen, a $C_{1-4}$ alkyl, $C_{1-4}$ haloalkyl or a $C_{3-8}$ cycloalkyl ring; wherein each said cycloalkyl group is optionally and independently substituted with up to 3 instances of halogen;

alternatively, two instances of $R^8$ linked to the same nitrogen atom of $R^7$, together with said nitrogen atom of $R^7$, form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S; $R^A$ is selected from hydrogen, halogen, $C_{1-4}$ alkyl or $C_{1-4}$ haloalkyl, with the proviso that when ring B is unsubstituted phenyl and ring D is unsubstituted pyrimidinyl (X is N and o is zero), $R^C$ is not methyl or ethyl.

In some embodiments of Formula I, ring B is phenyl. In some embodiments, said phenyl ring is unsubstituted and n=0. In other embodiments, ring B is substituted phenyl, and n is an integer selected between 1 and 3.

In some embodiments of Formula I wherein ring B is substituted phenyl, each $J^B$ is independently selected from halogen, a $C_{1-6}$ aliphatic or —$OR^B$. In some embodiments, each $J^B$ is independently selected from a halogen atom. In some embodiments, when $J^B$ is independently selected from a halogen atom, each $J^B$ can be independently selected from fluoro or chloro, or each $J^B$ is fluoro. In other embodiments, each $J^B$ is independently selected from a $C_{1-6}$ aliphatic. In some embodiments, each $J^B$ is methyl or ethyl. In other embodiments, each $J^B$ is methyl. In still other embodiments of Formula I, wherein ring B is substituted phenyl, each $J^B$ is independently selected from —$OR^B$; wherein each $R^B$ is hydrogen or a $C_{1-6}$ alkyl. In some embodiments, each $R^B$ is methyl, ethyl, propyl or isopropyl.

In some of the above embodiments, wherein ring B is substituted phenyl, n is 1 or 2 and each $J^B$ is independently selected from fluoro, chloro, methyl or methoxy. In other embodiments of Formula I, ring B is a 6-membered heteroaryl ring. In some embodiments, n=0 and the 6-membered heteroaryl ring in unsubstituted. In other embodiments, ring B is a substituted pyridyl ring and n is an integer selected between 1 and 3. In other embodiments, ring B is a substituted pyrimidinyl ring and n is selected between 1 and 3. In some of the above embodiments, wherein ring B is substituted pyridine or pyrimidine, n is 1 or 2 and each $J^B$ is independently selected from fluoro, chloro, methyl or methoxy.

In some embodiments of Formula I, at least one $J^B$ is ortho to the attachment of the methylene linker between ring B and the pyrazolyl ring. In some embodiments, said ortho $J^B$ is independently selected from a halogen atom. In other embodiments, said ortho $J^B$ is selected from fluoro or chloro. In further embodiments, said ortho $J^B$ is fluoro.

In some embodiments of Formula I, X in ring D is C-$J^D$ or C—H. In other embodiments X in ring D is N.

In some embodiments of Formula I, ring D is unsubstituted and o is 0. In other embodiments of Formula I, o is an integer selected from 1 to 3.

In those embodiments of Formula I wherein ring D is substituted, each $J^D$ is independently selected from halogen, a $C_{1-6}$ aliphatic, —N(R$^D$)$_2$, —N(R$^d$)C(O)R$^D$, —N(R$^d$)C(O)OR$^D$, —SO$_2$R$^D$, —SO$_2$N(R$^D$)$_2$, —N(R$^d$)SO$_2$R$^D$, —SR$^D$, —OR$^D$ or an optionally substituted $C_{3-8}$ cycloaliphatic ring. In other embodiments, each $J^D$ is independently selected from a halogen atom. In still other embodiments, each $J^D$ is selected from chloro or fluoro. In some embodiments, each $J^D$ is independently selected from a $C_{1-6}$ aliphatic or a $C_{3-8}$ cycloaliphatic ring. In other embodiments, each $J^D$ is selected from methyl, ethyl, propyl, cyclobutyl, cyclopropyl or isopropyl. In still embodiments, each $J^D$ is methyl, ethyl or cyclopropyl. In other embodiments of Formula I, each $J^D$ is independently selected from —N(R$^D$)$_2$, —N(R$^d$)C(O)R$^D$, —N(R$^d$)C(O)OR$^D$, —SO$_2$R$^D$, —SO$_2$N(R$^D$)$_2$, —N(R$^d$)SO$_2$R$^D$ or —OR$^D$. In some embodiments, each R$^d$ is independently selected from a $C_{1-4}$ alkyl or hydrogen and each R$^D$ is independently selected from hydrogen or $C_{1-4}$ alkyl. In other embodiments, each R$^d$ is independently selected from hydrogen or methyl and each R$^D$ is independently selected from hydrogen, methyl, ethyl, propyl or isopropyl. In still other embodiments, each R$^d$ and each R$^D$ is independently selected from hydrogen or methyl. In some of the above embodiments, wherein ring D is substituted, o is 1. In other embodiments, o is 2. In other embodiments o is 3.

In some embodiments of Formula I, wherein ring D is substituted, o is 1, 2 or 3 and each $J^D$ is independently selected from methyl, fluoro, —N(R$^D$)$_2$, —N(R$^d$)C(O)R$^D$, —N(R$^d$)C(O)OR$^D$, —SO$_2$R$^D$, —SO$_2$N(R$^D$)$_2$ or —N(R$^d$)SO$_2$R$^D$; wherein each R$^d$ and each R$^D$ is independently selected from hydrogen or methyl.

In some embodiments of Formula I, R$^C$ is —CN.

In other embodiments of Formula I, R$^C$ is a $C_{1-6}$ alkyl. In some embodiments R$^C$ is selected from methyl, ethyl, propyl, isopropyl or butyl.

In still other embodiments of Formula I, R$^C$ is a ring C.

In some embodiments of Formula, R$^C$ is a phenyl ring, a monocyclic 5 to or 6-membered heteroaryl ring, a monocyclic 3 to 10-membered cycloaliphatic ring or a monocyclic 4 to 10-membered heterocycle; each of them optionally and independently substituted by up to 6 instances of $J^C$. In other embodiments of Formula I, ring C is a phenyl ring, a monocyclic 5 to 6-membered heteroaryl ring, a monocyclic 3 to 6-membered cycloaliphatic ring or a monocyclic 4 to 6-membered heterocycle; each of them optionally and independently substituted with up to 3 instances of $J^C$.

In some embodiments of Formula I, R$^C$ is a monocyclic 3 to 6-membered cycloaliphatic ring, optionally and independently substituted with up to 2 instances of $J^C$. In other embodiments, ring C is cyclopropyl, cyclobutyl, cyclopentyl or cyclohexyl. In other embodiments of Formula I, R$^C$ is a ring C which is a 4-membered cycloaliphatic ring substituted by 1 to 3 instances of f, a 5-membered cycloaliphatic ring substituted by 1 to 4 instances of $J^C$ or a 6-membered cycloaliphatic ring substituted by 1 to 5 instances of $J^C$; wherein each $J^C$ is independently selected from halogen or a $C_{1-6}$ aliphatic.

In other embodiments of Formula I, R$^C$ is phenyl, optionally and independently substituted by up to 5 instances of $J^C$. In some embodiments, ring C is phenyl and it is unsubstituted. In other embodiments, it is substituted by 1 to 3 instances of $J^C$; wherein each $J^C$ is independently selected from halogen, a $C_{1-6}$ aliphatic, —NH$_2$, —CN or —O($C_{1-6}$ aliphatic). In other embodiments, each $J^C$ is independently selected from halogen, —NH$_2$, —CN, $C_{1-6}$ alkyl or —O($C_{1-4}$ alkyl). In still other embodiments, ring C is phenyl substituted by 1 to 2 instances of $J^C$ and each $J^C$ is selected from fluoro, chloro, methyl, —CN or —OCH$_3$.

In still other embodiments of Formula I, R$^C$ is a 5 to 6-membered heteroaryl ring and is optionally and independently substituted by up to 5 instances of $J^C$. In some embodiments, said 5 to 6-membered heteroaryl ring is unsubstituted. In other embodiments, it is substituted with 1 to 3 instances of $J^C$. In some of these embodiments, the 5 to 6-membered heteroaryl ring can be selected from thienyl, thiazolyl, oxadiazolyl, oxazolyl, isooxazolyl, tetrazolyl, pyrrolyl, triazolyl, furanyl, pyridinyl, pyrimidinyl, pyrazinyl or pyridazinyl. In other embodiments, the heteroaryl ring C is selected from furanyl, thienyl, thiazolyl, 1,3,4-oxadiazolyl, pyridinyl, pyrimidinyl or pyrazin-3-yl. In still other embodiments, the heteroaryl ring C is selected from thienyl, thiazolyl, 1,3,4-oxadiazolyl or pyridinyl. In further embodiments, said 5 to 6-membered heteroaryl ring is selected from furan-2-yl, furan-3-yl, thien-3-yl, thien-2-yl, thiazol-2-yl, pyridin-2-yl, pyridin-3-yl, pyridin-4-yl, pyrimidin-2-yl or pyrimidin-4-yl; and is optionally substituted with up to 2 instances of $J^C$.

In some embodiments of Formula I, ring C is a 5 to 6-membered heteroaryl ring and it is substituted by 1 to 5 instances of $J^C$; wherein each $J^C$ is independently selected from halogen, a $C_{1-6}$ aliphatic, —CN, —NH$_2$ or —O($C_{1-6}$ aliphatic). In other embodiments, ring C is thienyl or pyridinyl substituted by 1 to 3 instances of $J^C$ and each $J^C$ is independently selected from a halogen, $C_{1-6}$ aliphatic —NH$_2$ or —O($C_{1-4}$ alkyl). In still other embodiments, ring C is substituted by 1 to 3 instances of $J^C$ and each $J^C$ is independently selected from a $C_{1-6}$ aliphatic. In further embodiments, said $C_{1-6}$ aliphatic is selected from methyl, ethyl, propyl or isopropyl. In yet other embodiments, ring C is substituted by 1 to 3 instances of $J^C$ and each $J^C$ is independently selected from a halogen atom, —NH$_2$, methyl or —OCH$_3$. In other embodiments, ring C is a 5-6 membered heteroaryl and it is substituted by 1 or 2 instances of $J^C$; wherein each $J^C$ is selected from fluoro, chloro, bromo, methyl, —CN, —NH$_2$ or —OCH$_3$.

In some embodiments of Formula I, ring C is a bicyclic 7 to 10-membered heteroaryl ring. In other embodiments, ring C is benzofuran-2-yl, furo[3,2-b]pyridinyl, furo[2,3-b]pyridinyl, benzothienyl or indolyl. In still other embodiments, ring C is benzofuran-2-yl, furo[3,2-b]pyridinyl or benzothienyl.

In some embodiments, the compounds of the invention are represented by structural Formula II:

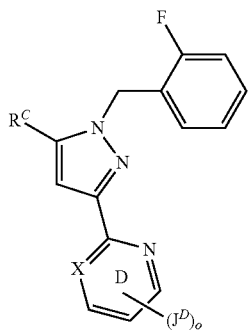

Formula II

In some embodiments of Formula II, X in ring D is C—H. In other embodiments X in ring D is N.

In some embodiments of Formula II, ring D is unsubstituted and o is 0. In other embodiments of Formula II, o is an integer from 1 to 3.

In those embodiments of Formula II wherein ring D is substituted, each $J^D$ is independently selected from halogen, a $C_{1-6}$ aliphatic, —N($R^D$)$_2$, —N($R^d$)C(O)$R^D$, —N($R^d$)C(O)O$R^D$, —SO$_2$$R^D$, —SO$_2$N($R^D$)$_2$, —N($R^d$)SO$_2$$R^D$, —S$R^D$, —O$R^D$ or an optionally substituted $C_{3-8}$ cycloaliphatic ring. In other embodiments, each $J^D$ is independently selected from a halogen atom. In still other embodiments, each $J^D$ is selected from chloro or fluoro. In some embodiments, each $J^D$ is independently selected from a $C_{1-6}$ aliphatic or a $C_{3-8}$ cycloaliphatic ring. In other embodiments, each $J^D$ is selected from methyl, ethyl, propyl, cyclobutyl, cyclopropyl or isopropyl. In still embodiments, each $J^D$ is methyl, ethyl or cyclopropyl. In other embodiments of Formula II, each $J^D$ is independently selected from —N($R^D$)$_2$, —N($R^d$)C(O)$R^D$, —N($R^d$)C(O)O$R^D$, —SO$_2$$R^D$, —SO$_2$N($R^D$)$_2$, —N($R^d$)SO$_2$$R^D$ or —O$R^D$. In some embodiments, each $R^d$ is independently selected from a $C_{1-4}$ alkyl or hydrogen and each $R^D$ is independently selected from hydrogen or $C_{1-4}$ alkyl. In other embodiments, each $R^d$ is independently selected from hydrogen or methyl and each $R^D$ is independently selected from hydrogen, methyl, ethyl, propyl or isopropyl. In still other embodiments, each $R^d$ and each $R^D$ is independently selected from hydrogen or methyl. In some of the above embodiments, wherein ring D is substituted, o is 1. In other embodiments, o is 2. In other embodiments, o is 3.

In some embodiments of Formula II, wherein ring D is substituted, o is 1, 2 or 3 and each $J^D$ is independently selected from methyl, fluoro, —N($R^D$)$_2$, —N($R^d$)C(O)$R^D$, —N($R^d$)C(O)O$R^D$, —SO$_2$$R^D$, —SO$_2$N($R^D$)$_2$ or —N($R^d$)SO$_2$$R^D$; wherein each $R^d$ and each $R^D$ is independently selected from hydrogen or methyl.

In some embodiments of Formula II, $R^C$ is —CN.

In other embodiments of Formula II, $R^C$ is a $C_{1-6}$ alkyl. In some embodiments $R^C$ is selected from methyl, ethyl, propyl, isopropyl or butyl. In still other embodiments of Formula II, $R^C$ is a ring C.

In some embodiments of Formula II, wherein $R^C$ is a phenyl ring, a monocyclic 5 to or 6-membered heteroaryl ring, a monocyclic 3 to 10-membered cycloaliphatic ring or a monocyclic 4 to 10-membered heterocycle; each of them optionally and independently substituted with up to 6 instances of $J^C$. In other embodiments of Formula II, ring C is a phenyl ring, a monocyclic 5 to 6-membered heteroaryl ring, a monocyclic 3 to 6-membered cycloaliphatic ring or a monocyclic 4 to 6-membered heterocycle; each of them optionally and independently substituted with up to 3 instances of $J^C$.

In some embodiments of Formula II, $R^C$ is a monocyclic 3 to 6-membered cycloaliphatic ring, optionally and independently substituted with up to 2 instances of $J^C$. In other embodiments, ring C is cyclopropyl, cyclobutyl, cyclopentyl or cyclohexyl. In other embodiments of Formula II, $R^C$ is a ring C which is a 4-membered cycloaliphatic ring substituted by 1 to 3 instances of $J^C$, a 5-membered cycloaliphatic ring substituted by 1 to 4 instances of $J^C$ or a 6-membered cycloaliphatic ring substituted by 1 to 5 instances of $J^C$; wherein each $J^C$ is independently selected from halogen or a $C_{1-6}$ aliphatic.

In other embodiments of Formula II, $R^C$ is phenyl, optionally and independently substituted by up to 5 instances of $J^C$. In some embodiments, ring C is phenyl and it is unsubstituted. In other embodiments, it is substituted by 1 to 3 instances of $J^C$; wherein each $J^C$ is independently selected from halogen, a $C_{1-6}$ aliphatic, —NH$_2$, —CN or —O($C_{1-6}$ aliphatic). In other embodiments, each $J^C$ is independently selected from halogen, —NH$_2$, —CN, $C_{1-6}$ alkyl or —O($C_{1-4}$ alkyl). In still other embodiments, ring C is phenyl substituted by 1 to 2 instances of $J^C$ and each $J^C$ is selected from fluoro, chloro, methyl, —CN or —OCH$_3$.

In still other embodiments of Formula II, $R^C$ is a 5 to 6-membered heteroaryl ring and is optionally and independently substituted by up to 5 instances of $J^C$. In some embodiments, said 5 to 6-membered heteroaryl ring is unsubstituted. In other embodiments, it is substituted with 1 to 3 instances of $J^C$. In some of these embodiments, the 5 to 6-membered heteroaryl ring can be selected from thienyl, thiazolyl, oxadiazolyl, oxazolyl, isooxazolyl, tetrazolyl, pyrrolyl, triazolyl, furanyl, pyridinyl, pyrimidinyl, pyrazinyl or pyridazinyl. In other embodiments, the heteroaryl ring C is selected from furanyl, thienyl, thiazolyl, 1,3,4-oxadiazolyl, pyridinyl, pyrimidinyl or pyrazin-3-yl. In still other embodiments, the heteroaryl ring C is selected from thienyl, thiazolyl, 1,3,4-oxadiazolyl or pyridinyl. In further embodiments, said 5 to 6-membered heteroaryl ring is selected from furan-2-yl, furan-3-yl, thien-3-yl, thien-2-yl, thiazol-2-yl, pyridin-2-yl, pyridin-3-yl, pyridin-4-yl, pyrimidin-2-yl or pyrimidin-4-yl; and is optionally substituted with up to 2 instances of $J^C$.

In some embodiments of Formula II, ring C is a 5 to 6-membered heteroaryl ring and it is substituted by 1 to 5 instances of $J^C$; wherein each $J^C$ is independently selected from halogen, a $C_{1-6}$ aliphatic, —CN, —NH$_2$ or —O($C_{1-6}$ aliphatic). In other embodiments, ring C is thienyl or pyridinyl substituted by 1 to 3 instances of $J^C$ and each $J^C$ is independently selected from a halogen, $C_{1-6}$ aliphatic —NH$_2$ or —O($C_{1-4}$ alkyl). In still other embodiments, ring C is substituted by 1 to 3 instances of $J^C$ and each $J^C$ is independently selected from a $C_{1-6}$ aliphatic. In further embodiments, said $C_{1-6}$ aliphatic is selected from methyl, ethyl, propyl or isopropyl. In yet other embodiments, ring C is substituted by 1 to 3 instances of $J^C$ and each $J^C$ is independently selected from a halogen atom, —NH$_2$, methyl or —OCH$_3$. In other embodiments, ring C is a 5-6 membered heteroaryl and it is substituted by 1 or 2 instances of $J^C$; wherein each $J^C$ is selected from fluoro, chloro, bromo, methyl, —CN, —NH$_2$ or —OCH$_3$.

In some embodiments of Formula II, ring C is a bicyclic 7 to 10-membered heteroaryl ring. In other embodiments, ring C is benzofuran-2-yl, furo[3,2-b]pyridinyl, furo[2,3-b]pyridinyl, benzothienyl or indolyl. In still other embodiments, ring C is benzofuran-2-yl, furo[3,2-b]pyridinyl or benzothienyl.

In some embodiments, the compounds of the invention are represented by structural Formula III or Formula IV:

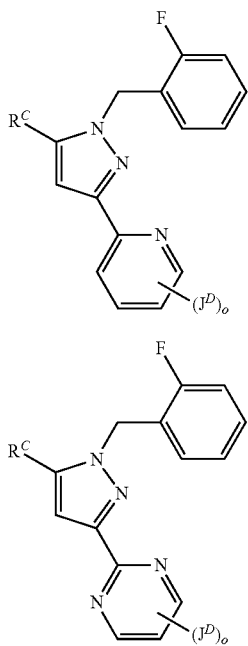

Formula III

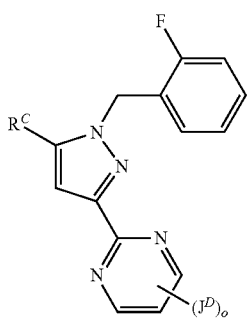

Formula IV

In some embodiments of Formula III and Formula IV, o is 0 and $J^D$ is not present. In other embodiments of Formula III and Formula IV, o is an integer from 1 to 3.

In those embodiments of Formula III and Formula IV wherein ring D is substituted, each $J^D$ is independently selected from halogen, a $C_{1-6}$ aliphatic, —N($R^D$)$_2$, —N($R^d$)C(O)$R^D$, —N($R^d$)C(O)O$R^D$, —SO$_2R^D$, —SO$_2$N($R^D$)$_2$, —N($R^d$)SO$_2R^D$, —S$R^D$, —O$R^D$ or an optionally substituted $C_{3-8}$ cycloaliphatic ring. In other embodiments, each $J^D$ is independently selected from a halogen atom. In still other embodiments, each $J^D$ is selected from chloro or fluoro. In some embodiments, each $J^D$ is independently selected from a $C_{1-6}$ aliphatic or a $C_{3-8}$ cycloaliphatic ring. In other embodiments, each $J^D$ is selected from methyl, ethyl, propyl, cyclobutyl, cyclopropyl or isopropyl. In still embodiments, each $J^D$ is methyl, ethyl or cyclopropyl. In other embodiments of Formula III and Formula IV, each JP is independently selected from —N($R^D$)$_2$, —N($R^d$)C(O)$R^D$, —N($R^d$)C(O)O$R^D$, —SO$_2R^D$, —SO$_2$N($R^D$)$_2$, —N($R^d$)SO$_2R^D$ or —O$R^D$. In some embodiments, each $R^d$ is independently selected from a $C_{1-4}$ alkyl or hydrogen and each $R^D$ is independently selected from hydrogen or $C_{1-4}$ alkyl. In other embodiments, each $R^d$ is independently selected from hydrogen or methyl and each $R^D$ is independently selected from hydrogen, methyl, ethyl, propyl or isopropyl. In still other embodiments, each $R^d$ and each $R^D$ is independently selected from hydrogen or methyl. In some of the above embodiments, wherein ring D is substituted, o is 1. In other embodiments, o is 2 or 3.

In some embodiments of Formula III and Formula IV, wherein ring D is substituted, o is 1, 2 or 3 and each $J^D$ is independently selected from methyl, fluoro, —N($R^D$)$_2$, —N($R^d$)C(O)$R^D$, —N($R^d$)C(O)O$R^D$, —SO$_2R^D$, —SO$_2$N($R^D$)$_2$ or —N($R^d$)SO$_2R^D$; wherein each $R^d$ and each $R^D$ is independently selected from hydrogen or methyl.

In some embodiments of Formula III and Formula IV, $R^C$ is —CN.

In other embodiments of Formula III and Formula IV, $R^C$ is a $C_{1-6}$ alkyl. In some embodiments $R^C$ is selected from methyl, ethyl, propyl, isopropyl or butyl. In still other embodiments of Formula III and Formula IV, $R^C$ is a ring C.

In some embodiments of Formula III and Formula IV, wherein $R^C$ is a phenyl ring, a monocyclic 5 to or 6-membered heteroaryl ring, a monocyclic 3 to 10-membered cycloaliphatic ring or a monocyclic 4 to 10-membered heterocycle; each of them optionally and independently substituted by up to 6 instances of $J^C$. In other embodiments of Formula II, ring C is a phenyl ring, a monocyclic 5 to 6-membered heteroaryl ring, a monocyclic 3 to 6-membered cycloaliphatic ring or a monocyclic 4 to 6-membered heterocycle; each of them optionally and independently substituted with up to 3 instances of $J^C$.

In some embodiments of Formula III and Formula IV, $R^C$ is a monocyclic 3 to 6-membered cycloaliphatic ring, optionally and independently substituted with up to 2 instances of $J^C$. In other embodiments, ring C is cyclopropyl, cyclobutyl, cyclopentyl or cyclohexyl. In other embodiments of Formula III and Formula IV, $R^C$ is a ring C which is a 4-membered cycloaliphatic ring substituted by 1 to 3 instances of $J^C$, a 5-membered cycloaliphatic ring substituted by 1 to 4 instances of $J^C$ or a 6-membered cycloaliphatic ring substituted by 1 to 5 instances of $J^C$; wherein each $J^C$ is independently selected from halogen or a $C_{1-6}$ aliphatic.

In other embodiments of Formula III and Formula IV, $R^C$ is phenyl, optionally and independently substituted by up to 5 instances of $J^C$. In some embodiments, ring C is phenyl and it is unsubstituted. In other embodiments, it is substituted by 1 to 3 instances of $J^C$; wherein each $J^C$ is independently selected from halogen, a $C_{1-6}$ aliphatic, —NH$_2$, —CN or —O($C_{1-6}$ aliphatic). In other embodiments, each $J^C$ is independently selected from halogen, —NH$_2$, —CN, $C_{1-6}$ alkyl or —O($C_{1-4}$ alkyl). In still other embodiments, ring C is phenyl substituted by 1 to 2 instances of $J^C$ and each $J^C$ is selected from fluoro, chloro, methyl, —CN or —OCH$_3$.

In still other embodiments of Formula III and Formula IV, $R^C$ is a 5 to 6-membered heteroaryl ring and is optionally and independently substituted by up to 5 instances of $J^C$. In some embodiments, said 5 to 6-membered heteroaryl ring is unsubstituted. In other embodiments, it is substituted with 1 to 3 instances of $J^C$. In some of these embodiments, the 5 to 6-membered heteroaryl ring can be selected from thienyl, thiazolyl, oxadiazolyl, oxazolyl, isooxazolyl, tetrazolyl, pyrrolyl, triazolyl, furanyl, pyridinyl, pyrimidinyl, pyrazinyl or pyridazinyl. In other embodiments of Formula III and Formula IV, $R^C$ is oxazolyl optionally and independently substituted by up to 5 instances of $J^C$. In other embodiments, the heteroaryl ring C is selected from furanyl, thienyl, thiazolyl, 1,3,4-oxadiazolyl, pyridinyl, pyrimidinyl or pyrazin-3-yl. In still other embodiments, the heteroaryl ring C is selected from thienyl, thiazolyl, 1,3,4-oxadiazolyl or pyridinyl. In further embodiments, said 5 to 6-membered heteroaryl ring is selected from furan-2-yl, furan-3-yl, thien-3-yl, thien-2-yl, thiazol-2-yl, pyridin-2-yl, pyridin-3-yl, pyridin-4-yl, pyrimidin-2-yl or pyrimidin-4-yl; and is optionally substituted with up to 2 instances of $J^C$.

In other embodiments of Formula IV, $R^C$ is oxazolyl optionally and independently substituted by up to 5 instances of $J^C$. In these embodiments, $J^D$ can be —N($R^d$)C(O)O$R^D$ or —N($R^D$)$_2$.

In some embodiments of Formula III and Formula IV, ring C is a 5 to 6-membered heteroaryl ring and it is substituted by 1 to 5 instances of $J^C$; wherein each $J^C$ is independently selected from halogen, a $C_{1-6}$ aliphatic, —CN, —NH$_2$ or —O($C_{1-6}$ aliphatic). In other embodiments, ring C is thienyl or pyridinyl substituted by 1 to 3 instances of $J^C$ and each $J^C$ is independently selected from a halogen, $C_{1-6}$ aliphatic —NH$_2$ or —O(C$_{1-4}$ alkyl). In still other embodiments, ring C is substituted by 1 to 3 instances of J$^C$ and each J$^C$ is independently selected from a C$_{1-6}$ aliphatic. In further embodiments, said C$_{1-6}$ aliphatic is selected from methyl, ethyl, propyl or isopropyl. In yet other embodiments, ring C is substituted by 1 to 3 instances of J$^C$ and each J$^C$ is independently selected from a halogen atom, —NH$_2$, methyl or —OCH$_3$. In other embodiments, ring C is a 5-6 membered heteroaryl and it is substituted by 1 or 2 instances of J$^C$; wherein each J$^C$ is selected from fluoro, chloro, bromo, methyl, —CN, —NH$_2$ or —OCH$_3$.

In some embodiments of Formula III and Formula IV, ring C is a bicyclic 7 to 10-membered heteroaryl ring. In other embodiments, ring C is benzofuran-2-yl, furo[3,2-b]pyridinyl, furo[2,3-b]pyridinyl, benzothienyl or indolyl. In still other embodiments, ring C is benzofuran-2-yl, furo[3,2-b]pyridinyl or benzothienyl.

In some embodiments of Formula III and Formula IV, J$^D$ is —N(R$^d$)C(O)OR$^D$ or —N(R$^D$)$_2$, or two J$^D$ groups attached to two vicinal ring D atoms, taken together with said two vicinal ring D atoms, form a 5-membered heterocycle containing from 1 to 3 heteroatoms independently selected from N, O or S resulting in a fused ring D wherein said 5-membered heterocycle is optionally and independently substituted by up to 3 instances of halogen, —OH, —NH$_2$, —NH(C$_{1-4}$ alkyl), —N(C$_{1-4}$ alkyl)$_2$, —CN, C$_{1-4}$ alkyl, C$_{1-4}$ haloalkyl, —O(C$_{1-4}$ alkyl), —O(C$_{1-4}$ haloalkyl) or oxo.

In some embodiments, the compounds of the invention are represented by one of structural Formulae VA-VF:

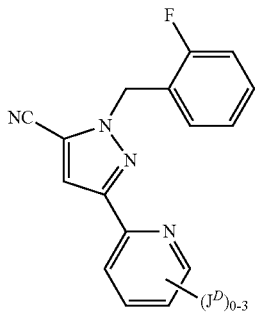

VA

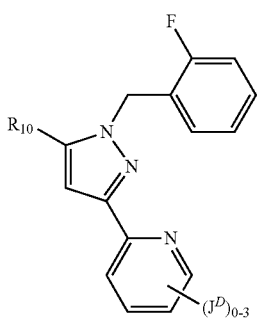

VB

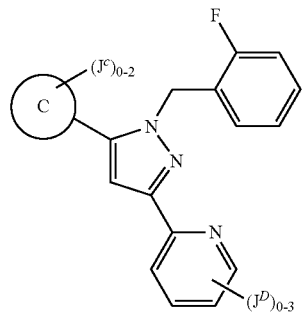

VC

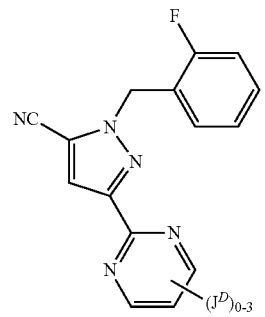

VD

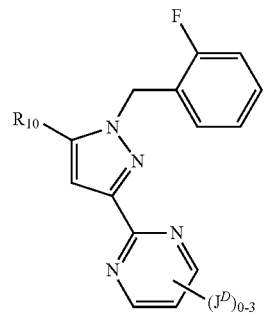

VE

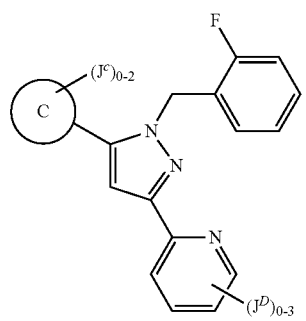

VF wherein the symbol of the letter C surrounded by a circle represents ring C and wherein R$^{10}$ is a C$_{1-4}$ alkyl group and Ring C is a phenyl, a pyridine, a thiofuranyl, a furanyl, a thiazolyl, a 4-6 membered cycloaliphatic ring or a 4-6 membered heterocyclic ring.

In some embodiments of Formulae VA to VF, each J$^D$ is independently selected from halogen, a C$_{1-6}$ aliphatic, —N(R$^D$)$_2$, —N(R$^d$)C(O)R$^D$, —N(R$^d$)C(O)OR$^D$, —SO$_2$R$^D$, —SO$_2$N(R$^D$)$_2$, —N(R$^d$)SO$_2$R$^D$, —SR$^D$, —OR$^D$ or an optionally substituted C$_{3-8}$ cycloaliphatic ring. In other embodiments, each J$^D$ is independently selected from a halogen atom. In still other embodiments, each J$^D$ is selected from chloro or fluoro. In some embodiments, each J$^D$ is independently selected from a C$_{1-6}$ aliphatic or a C$_{3-8}$ cycloaliphatic ring. In other embodiments, each $J^D$ is selected from methyl, ethyl, propyl, cyclobutyl, cyclopropyl or isopropyl. In still embodiments, each $J^D$ is methyl, ethyl or cyclopropyl. In other embodiments of Formulae VA-VF, each $J^D$ is independently selected from $N(R^D)_2$, $-N(R^d)C(O)R^D$, $-N(R^d)C(O)OR^D$, $-SO_2R^D$, $-SO_2N(R^D)_2$, $-N(R^d)SO_2R^D$ or $-OR^D$. In some embodiments, each $R^d$ is independently selected from a $C_{1-4}$ alkyl or hydrogen and each $R^D$ is independently selected from hydrogen or $C_{1-4}$ alkyl. In other embodiments, each $R^d$ is independently selected from hydrogen or methyl and each $R^D$ is independently selected from hydrogen, methyl, ethyl, propyl or isopropyl. In still other embodiments, each $R^d$ and each $R^D$ is independently selected from hydrogen or methyl. In some of the above embodiments, wherein ring D is substituted, o is 1. In other embodiments, o is 2. In other embodiments, o is 3.

In some embodiments of Formulae VA-VF, o is 1, 2 or 3 and each $J^D$ is independently selected from methyl, fluoro, $-N(R^D)_2$, $-N(R^d)C(O)R^D$, $-N(R^d)C(O)OR^D$, $-SO_2R^D$, $-SO_2N(R^D)_2$ or $-N(R^d)SO_2R^D$; wherein each $R^d$ and each $R^D$ is independently selected from hydrogen or methyl.

For compounds of Formulae VC and VF, Ring C is a phenyl ring, a monocyclic 5 to or 6-membered heteroaryl ring, a monocyclic 3 to 10-membered cycloaliphatic ring or a monocyclic 4 to 10-membered heterocycle; each of them optionally and independently substituted by up to 2 instances of $J^C$. In some embodiments of Formulae VC and VF, ring C is a phenyl ring, a monocyclic 5 to 6-membered heteroaryl ring, a monocyclic 3 to 6-membered cycloaliphatic ring or a monocyclic 4 to 6-membered heterocycle; each of them optionally and independently substituted with up to 2 instances of $J^C$.

In some embodiments of Formula VC and Formula VF, $R^C$ is a monocyclic 3 to 6-membered cycloaliphatic ring, optionally and independently substituted with up to 2 instances of $J^C$. In other embodiments, ring C is cyclopropyl, cyclobutyl, cyclopentyl or cyclohexyl. In other embodiments of Formula VC and Formula VF, ring C is a 4-membered cycloaliphatic ring substituted by 0 to 2 instances of $J^C$, a 5-membered cycloaliphatic ring substituted by 0 to 2 instances of $J^C$ or a 6-membered cycloaliphatic ring substituted by 0 to 2 instances of $J^C$; wherein each $J^C$ is independently selected from halogen or a $C_{1-6}$ aliphatic.

In other embodiments of Formula VC and Formula VF, ring C is phenyl, optionally and independently substituted by up to 2 instances of $J^C$. In some embodiments, ring C is phenyl and it is unsubstituted. In other embodiments, it is substituted by 1 to 2 instances of $J^C$; wherein each $J^C$ is independently selected from halogen, a $C_{1-6}$ aliphatic, $-NH_2$, $-CN$ or $-O(C_{1-6}$ aliphatic). In other embodiments, each $J^C$ is independently selected from halogen, $-NH_2$, $-CN$, $C_{1-6}$ alkyl or $-O(C_{1-4}$ alkyl). In still other embodiments, ring C is phenyl substituted by 1 to 2 instances of $J^C$ and each $J^C$ is selected from fluoro, chloro, methyl, $-CN$ or $-OCH_3$.

In still other embodiments of Formula VC and Formula VF, ring C is a 5 to 6-membered heteroaryl ring and is optionally and independently substituted by up to 2 instances of $J^C$. In some embodiments, said 5 to 6-membered heteroaryl ring is unsubstituted. In other embodiments, it is substituted with 1 or 2 instances of $J^C$. In some of these embodiments, the 5 to 6-membered heteroaryl ring can be selected from thienyl, thiazolyl, oxadiazolyl, oxazolyl, isooxazolyl, tetrazolyl, pyrrolyl, triazolyl, furanyl, pyridinyl, pyrimidinyl, pyrazinyl or pyridazinyl. In other embodiments, the heteroaryl ring C is selected from furanyl, thienyl, thiazolyl, 1,3,4-oxadiazolyl, pyridinyl, pyrimidinyl or pyrazin-3-yl. In still other embodiments, the heteroaryl ring C is selected from thienyl, thiazolyl, 1,3,4-oxadiazolyl or pyridinyl. In further embodiments, said 5 to 6-membered heteroaryl ring is selected from furan-2-yl, furan-3-yl, thien-3-yl, thien-2-yl, thiazol-2-yl, pyridin-2-yl, pyridin-3-yl, pyridin-4-yl, pyrimidin-2-yl or pyrimidin-4-yl; and is optionally substituted with up to 2 instances of $J^C$.

In some embodiments of Formula VC and Formula VF, ring C is a 5 to 6-membered heteroaryl ring and it is substituted by 0 to 2 instances of $J^C$; wherein each $J^C$ is independently selected from halogen, a $C_{1-6}$ aliphatic, $-CN$, $-NH_2$ or $-O(C_{1-6}$ aliphatic). In other embodiments, ring C is thienyl or pyridinyl substituted by 0 to 2 instances of $J^C$ and each $J^C$ is independently selected from a halogen, $C_{1-6}$ aliphatic $-NH_2$ or $-O(C_{1-4}$ alkyl). In still other embodiments, ring C is substituted by 1 to 3 instances of $J^C$ and each $J^C$ is independently selected from a $C_{1-6}$ aliphatic. In further embodiments, said $C_{1-6}$ aliphatic is selected from methyl, ethyl, propyl or isopropyl. In yet other embodiments, ring C is substituted by 1 or 2 instances of $J^C$ and each $J^C$ is independently selected from a halogen atom, $-NH_2$, methyl or $-OCH_3$. In other embodiments, ring C is a 5-6 membered heteroaryl and it is substituted by 1 or 2 instances of $J^C$; wherein each $J^C$ is selected from fluoro, chloro, bromo, methyl, $-CN$, $-NH_2$ or $-OCH_3$.

In some embodiments of Formula VC and Formula VF, ring C is a bicyclic 7 to 10-membered heteroaryl ring. In other embodiments, ring C is benzofuran-2-yl, furo[3,2-b]pyridinyl, furo[2,3-b]pyridinyl, benzothienyl or indolyl. In still other embodiments, ring C is benzofuran-2-yl, furo[3,2-b]pyridinyl or benzothienyl.

The compounds of the invention are defined herein by their chemical structures and/or chemical names. Where a compound is referred to by both a chemical structure and a chemical name, and the chemical structure and chemical name conflict, the chemical structure is determinative of the compound's identity.

In some embodiments, compounds of Formula I are selected from those listed in Tables 1A, 1B, 1C and 1D herein.

TABLE 1A

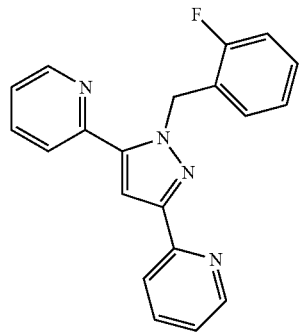

I-1

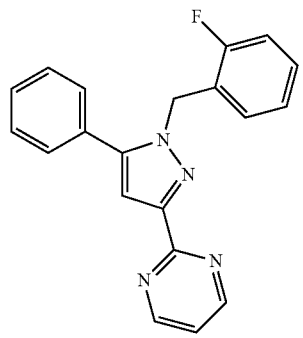

I-2

TABLE 1A-continued
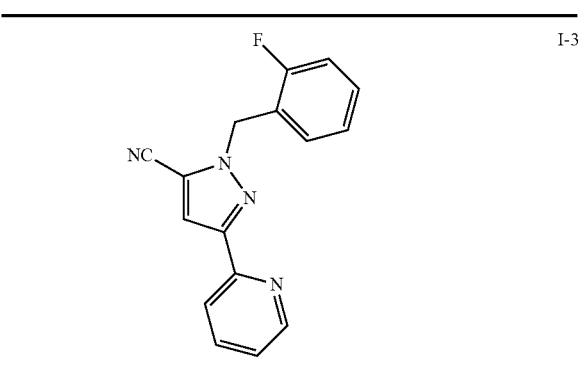
I-3
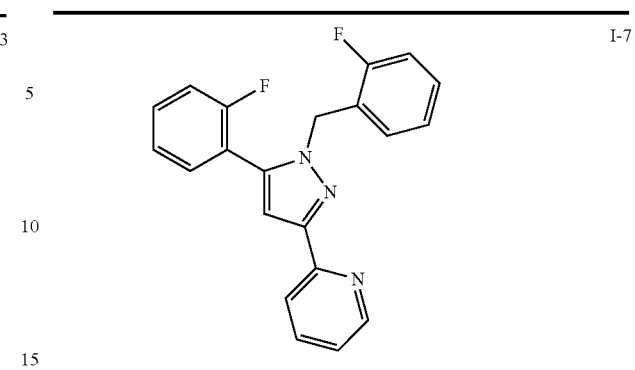
I-7
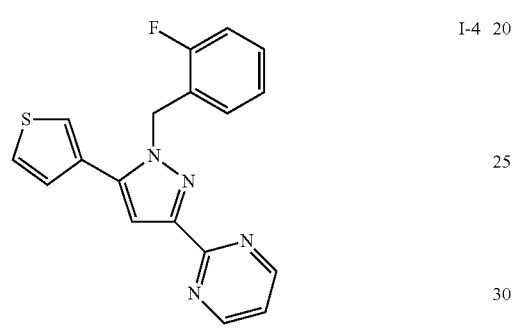
I-4
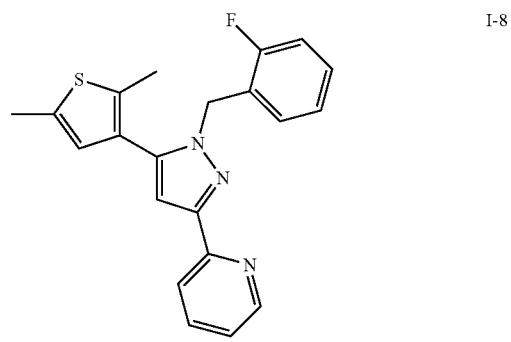
I-8
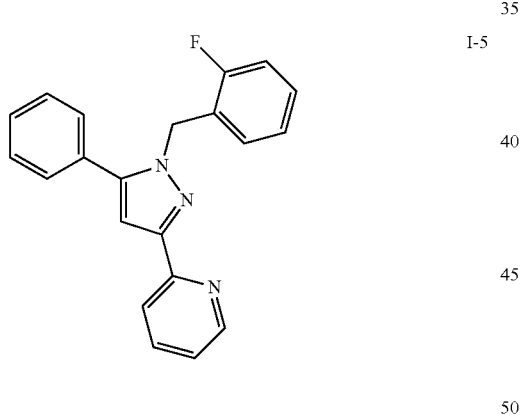
I-5
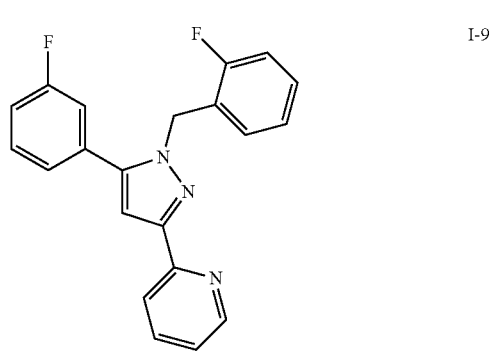
I-9
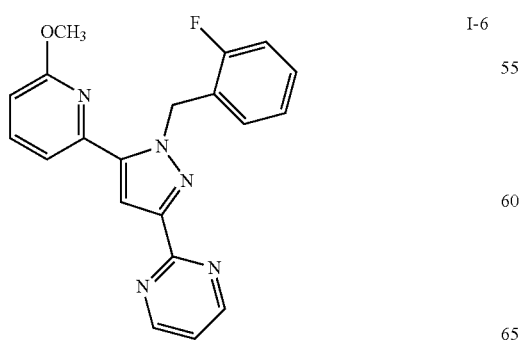
I-6
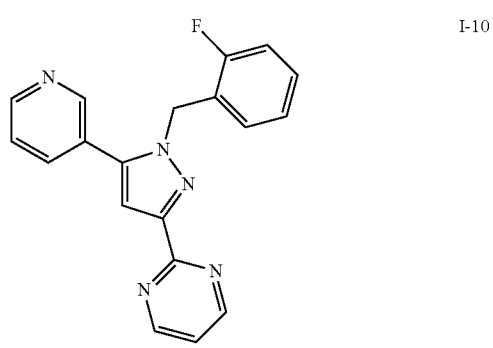
I-10

TABLE 1A-continued
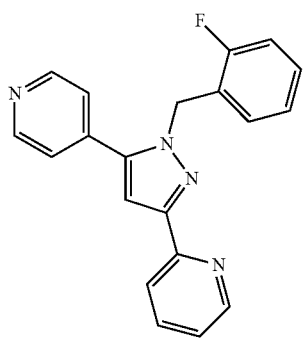 I-11
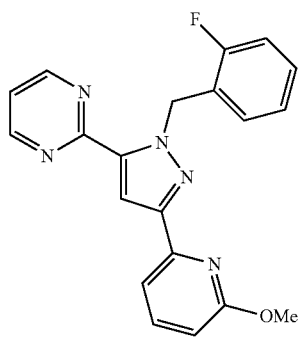 I-15
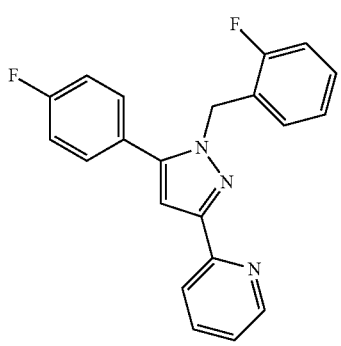 I-12
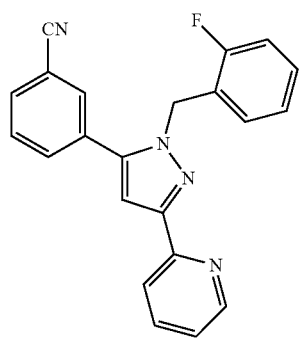 I-16
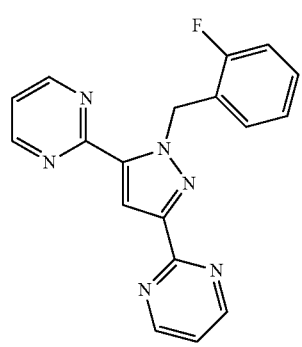 I-13
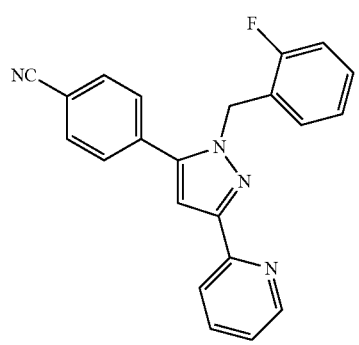 I-17
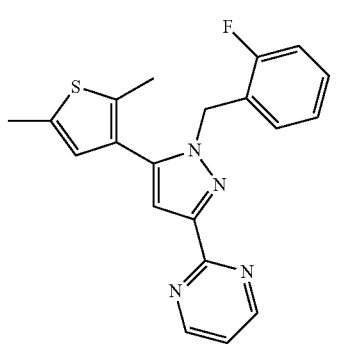 [SMILES: Cc1cc(-c2cc(-c3ncccn3)nn2Cc2ccccc2F)c(C)s1] I-14
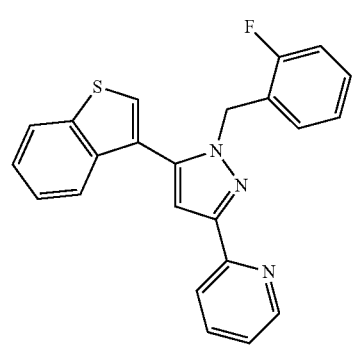 [SMILES: Fc1ccccc1Cn1nc(-c2ccccn2)cc1-c1csc2ccccc12] I-18

TABLE 1A-continued
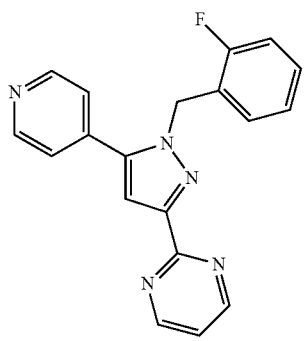
I-19
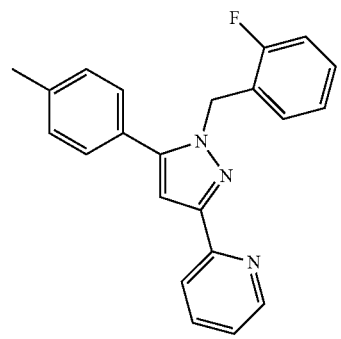
I-23
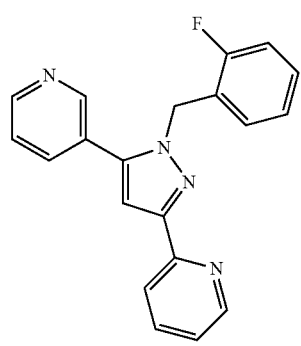
I-20
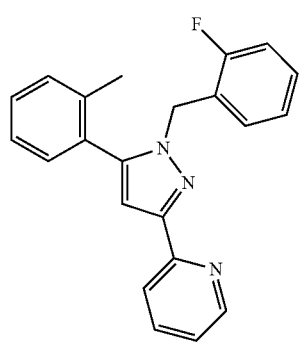
I-24
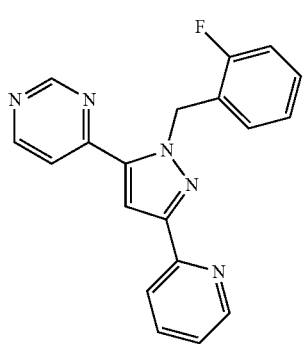 [SMILES: Fc1ccccc1Cn1nc(-c2ccccn2)cc1-c1ccncn1]
I-21
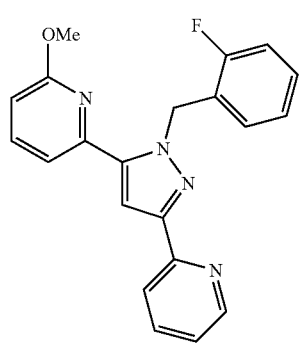
I-25
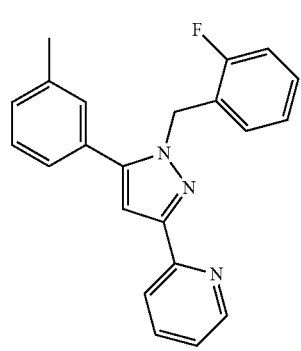
I-22
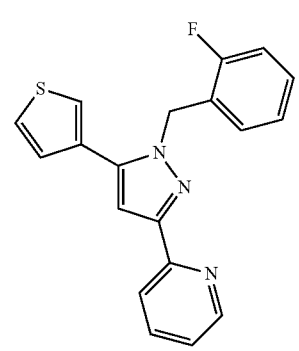 [SMILES: Fc1ccccc1Cn1nc(-c2ccccn2)cc1-c1ccsc1]
I-26

TABLE 1A-continued
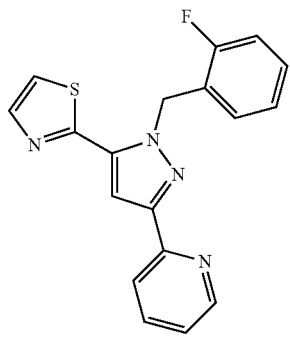 [SMILES: Fc1ccccc1Cn1nc(-c2ccccn2)cc1-c1nccs1]
I-27
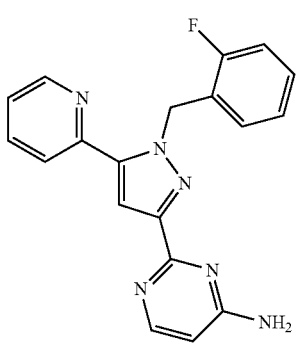
I-31
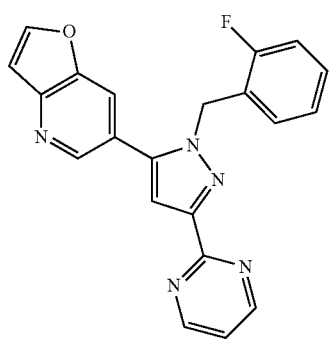 [SMILES: Fc1ccccc1Cn1nc(-c2ncccn2)cc1-c1cnc2ccoc2c1]
I-32
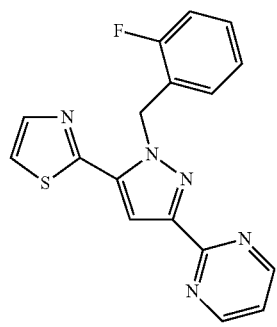 [SMILES: Fc1ccccc1Cn1nc(-c2ncccn2)cc1-c1nccs1]
I-33
TABLE 1A-continued
I-34
I-35
I-36
I-37
I-38

TABLE 1A-continued
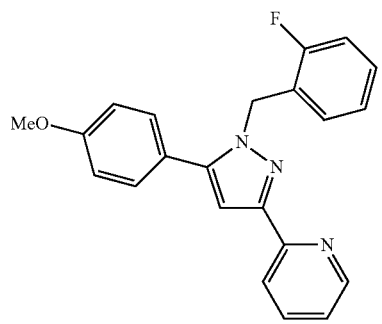 [SMILES: COc1ccc(-c2cc(-c3ccccn3)nn2Cc2ccccc2F)cc1] I-40
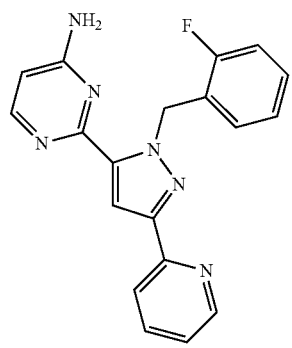 [SMILES: Nc1ccnc(-c2cc(-c3ccccn3)nn2Cc2ccccc2F)n1] I-41
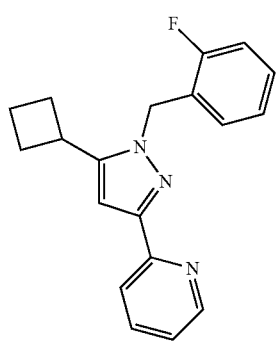 [SMILES: Fc1ccccc1Cn1nc(-c2ccccn2)cc1C1CCC1] I-42
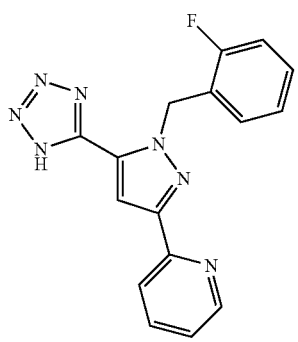 [SMILES: Fc1ccccc1Cn1nc(-c2ccccn2)cc1-c1nnn[nH]1] I-43
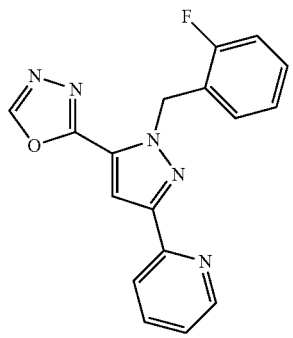 [SMILES: Fc1ccccc1Cn1nc(-c2ccccn2)cc1-c1nnco1] I-45
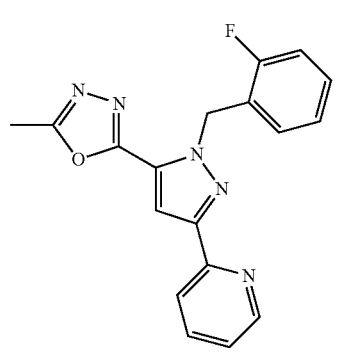 [SMILES: Cc1nnc(-c2cc(-c3ccccn3)nn2Cc2ccccc2F)o1] I-46
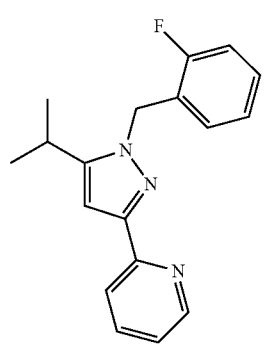 [SMILES: CC(C)c1cc(-c2ccccn2)nn1Cc1ccccc1F] I-47
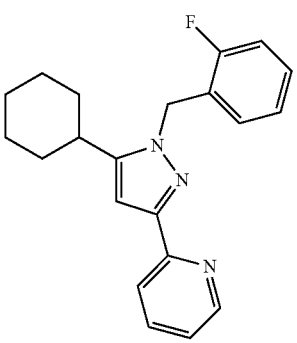 [SMILES: Fc1ccccc1Cn1nc(-c2ccccn2)cc1C1CCCCC1] I-48

TABLE 1A-continued
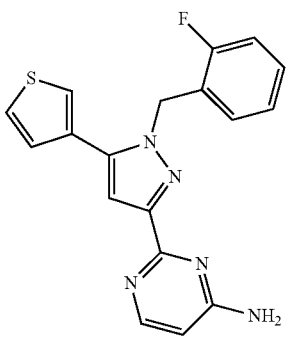 [SMILES: Nc1ccnc(-c2cc(-c3ccsc3)n(Cc3ccccc3F)n2)n1]
I-49
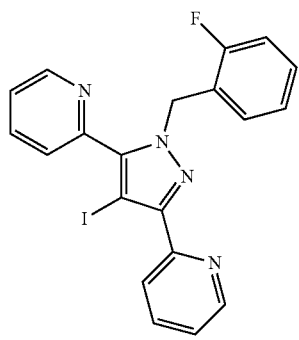
I-53
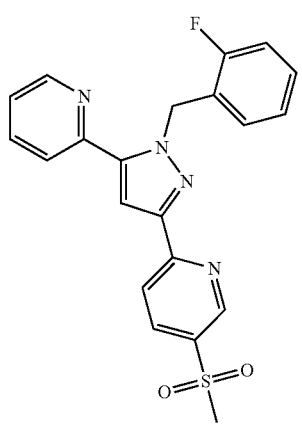 [SMILES: CS(=O)(=O)c1ccc(-c2cc(-c3ccccn3)n(Cc3ccccc3F)n2)nc1]
I-50
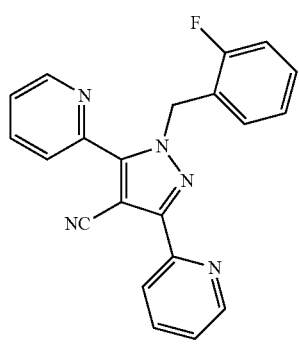
I-54
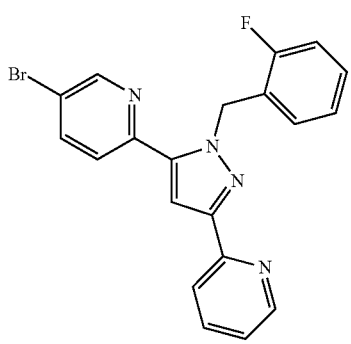 [SMILES: Fc1ccccc1Cn1nc(-c2ccccn2)cc1-c1ccc(Br)cn1]
I-51
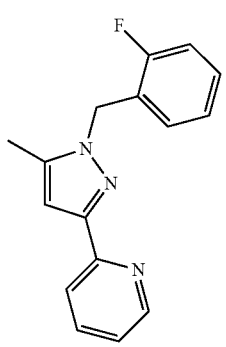
I-55
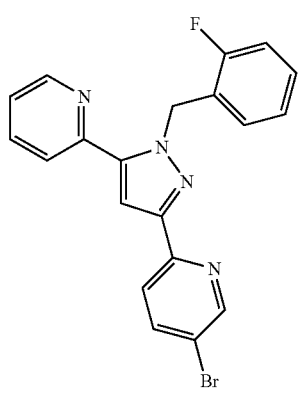 [SMILES: Fc1ccccc1Cn1nc(-c2ccc(Br)cn2)cc1-c1ccccn1]
I-52
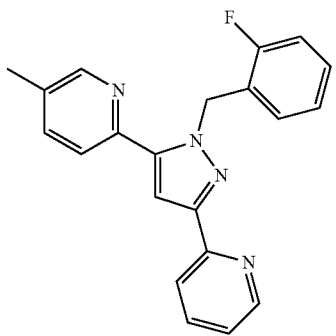 [SMILES: Cc1ccc(-c2cc(-c3ccccn3)nn2Cc2ccccc2F)nc1]
I-56

TABLE 1A-continued
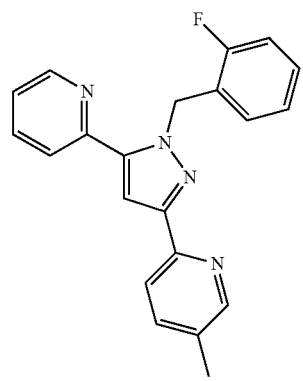 [SMILES: Cc1ccc(-c2cc(-c3ccccn3)n(Cc3ccccc3F)n2)nc1]
I-57
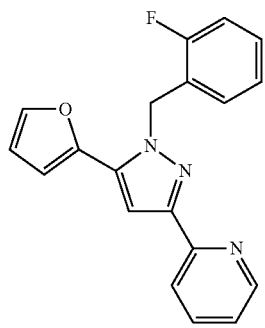
I-61
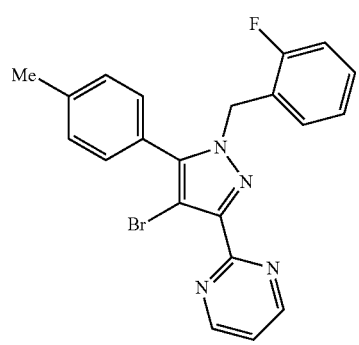 [SMILES: Cc1ccc(-c2c(Br)c(-c3ncccn3)nn2Cc2ccccc2F)cc1]
I-58
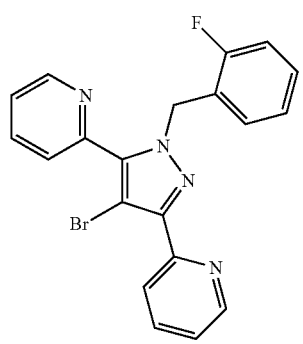
I-62
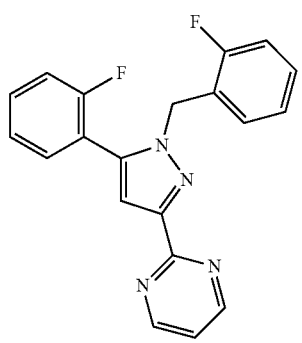 [SMILES: Fc1ccccc1Cn1nc(-c2ncccn2)cc1-c1ccccc1F]
I-59
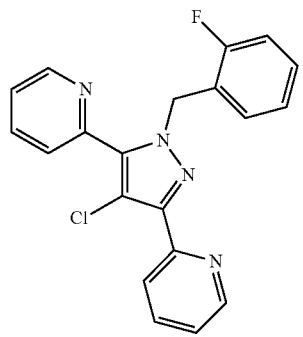
I-63
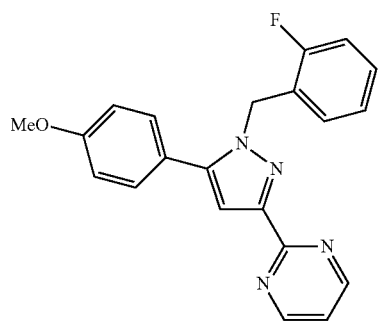 [SMILES: COc1ccc(-c2cc(-c3ncccn3)nn2Cc2ccccc2F)cc1]
I-60
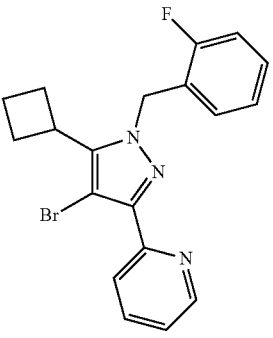 [SMILES: Fc1ccccc1Cn1nc(-c2ccccn2)c(Br)c1C1CCC1]
I-64

TABLE 1A-continued
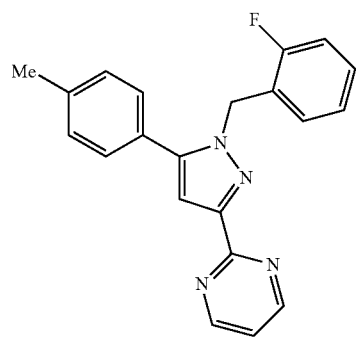
I-65
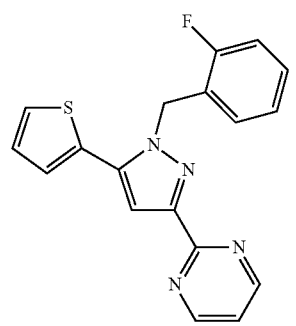 [SMILES: Fc1ccccc1Cn1nc(-c2ncccn2)cc1-c1cccs1]
I-66
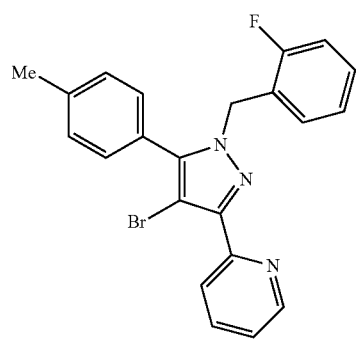
I-67
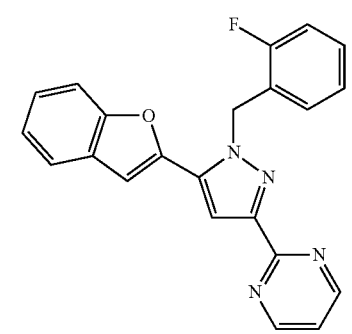 [SMILES: Fc1ccccc1Cn1nc(-c2ncccn2)cc1-c1cc2ccccc2o1]
I-68
TABLE 1A-continued
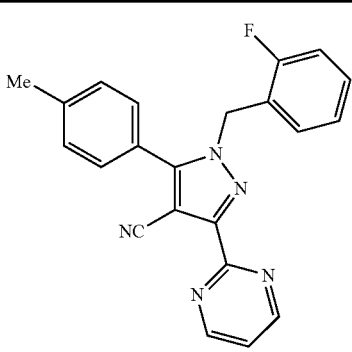
I-69
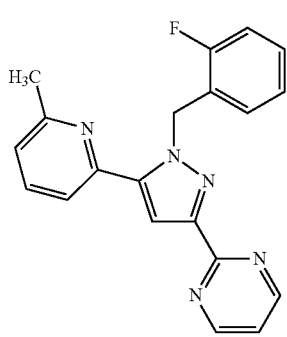 [SMILES: Cc1cccc(-c2cc(-c3ncccn3)nn2Cc2ccccc2F)n1]
I-70
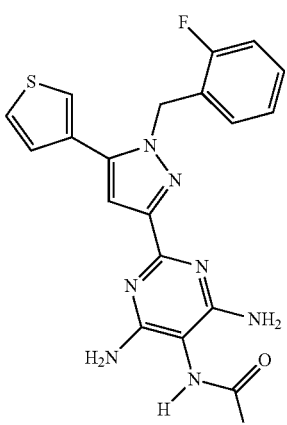
I-71
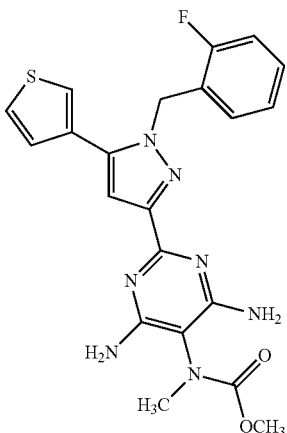
I-72

TABLE 1A-continued
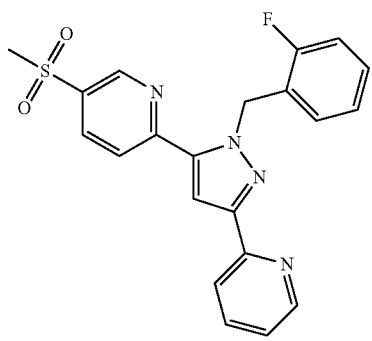 [SMILES: CS(=O)(=O)c1ccc(-c2cc(-c3ccccn3)nn2Cc2ccccc2F)nc1]
I-73
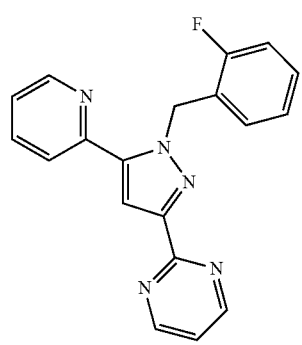
I-75
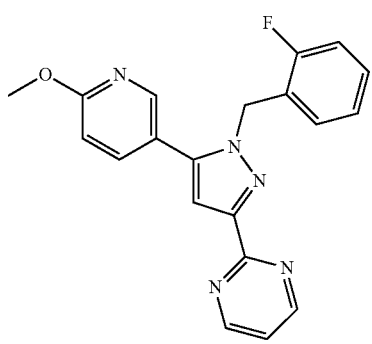 [SMILES: COc1ccc(-c2cc(-c3ncccn3)nn2Cc2ccccc2F)cn1]
I-77
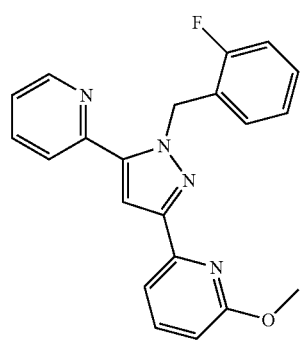 [SMILES: COc1cccc(-c2cc(-c3ccccn3)n(Cc3ccccc3F)n2)n1]
I-78
TABLE 1A-continued
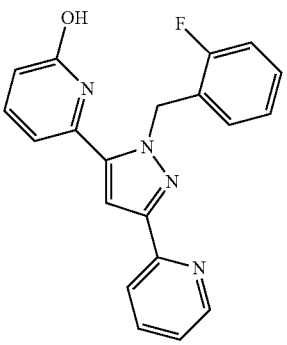 [SMILES: Oc1cccc(-c2cc(-c3ccccn3)nn2Cc2ccccc2F)n1]
I-79
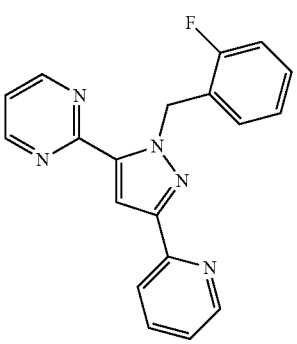
I-80
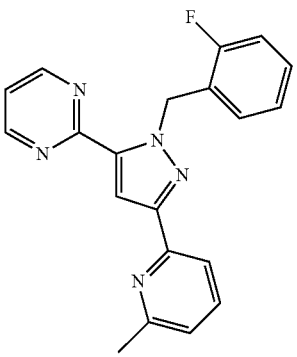 [SMILES: Cc1cccc(-c2cc(-c3ncccn3)n(Cc3ccccc3F)n2)n1]
I-81
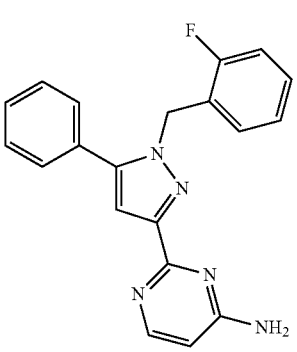 [SMILES: Nc1ccnc(-c2cc(-c3ccccc3)n(Cc3ccccc3F)n2)n1]
I-82

TABLE 1A-continued
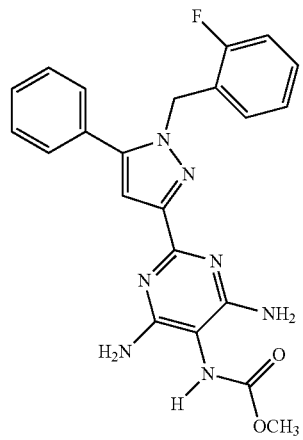 [SMILES: COC(=O)Nc1c(N)nc(-c2cc(-c3ccccc3)n(Cc3ccccc3F)n2)nc1N]
I-83
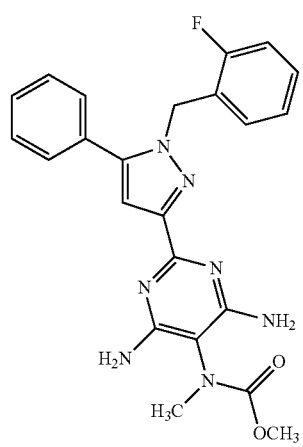
I-84
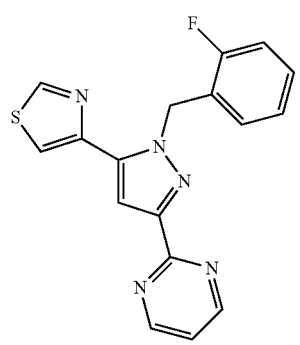 [SMILES: Fc1ccccc1Cn1nc(-c2ncccn2)cc1-c1cscn1]
I-85
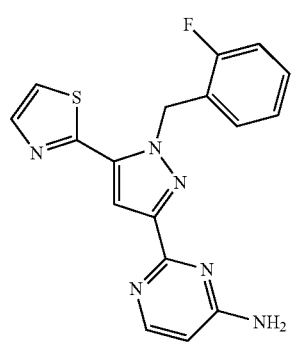 [SMILES: Nc1ccnc(-c2cc(-c3nccs3)n(Cc3ccccc3F)n2)n1]
I-86
TABLE 1A-continued
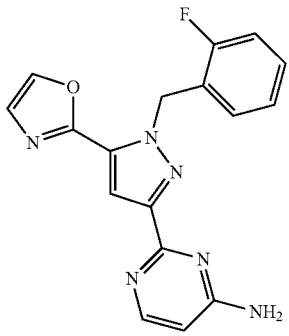 [SMILES: Nc1ccnc(-c2cc(-c3ncco3)n(Cc3ccccc3F)n2)n1]
I-87
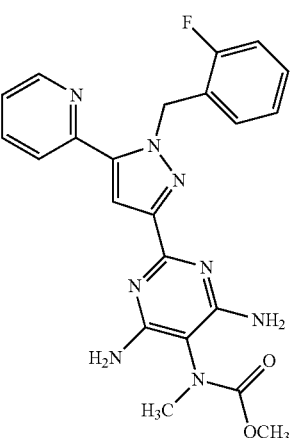
I-88
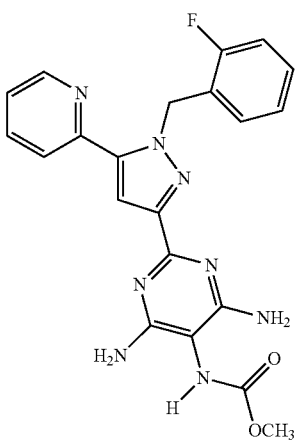 [SMILES: COC(=O)Nc1c(N)nc(-c2cc(-c3ccccn3)n(Cc3ccccc3F)n2)nc1N]
I-89
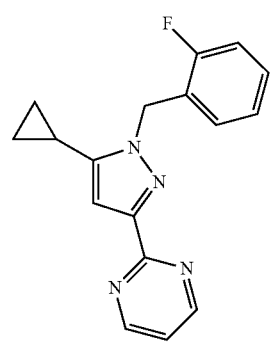 [SMILES: Fc1ccccc1Cn1nc(-c2ncccn2)cc1C1CC1]
I-90

TABLE 1A-continued
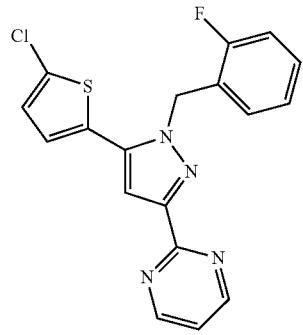 [SMILES: Fc1ccccc1Cn1nc(-c2ncccn2)cc1-c1ccc(Cl)s1]
I-91
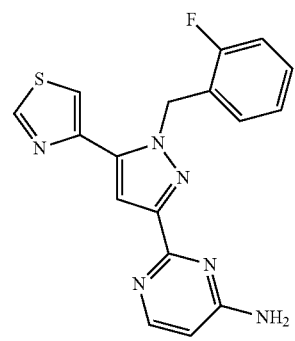 [SMILES: Nc1ccnc(-c2cc(-c3cscn3)n(Cc3ccccc3F)n2)n1]
I-92
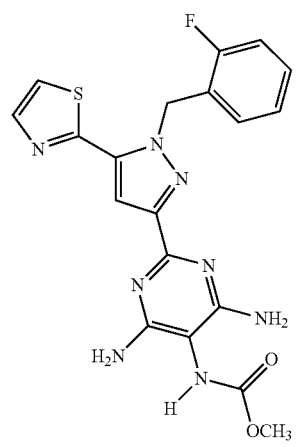 [SMILES: COC(=O)Nc1c(N)nc(-c2cc(-c3nccs3)n(Cc3ccccc3F)n2)nc1N]
I-93
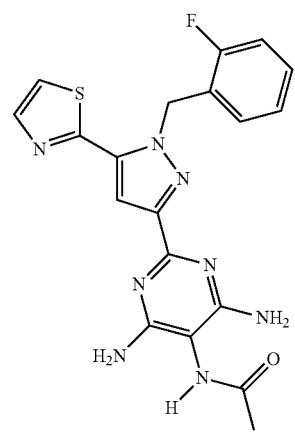 [SMILES: CC(=O)Nc1c(N)nc(-c2cc(-c3nccs3)n(Cc3ccccc3F)n2)nc1N]
I-94
TABLE 1A-continued
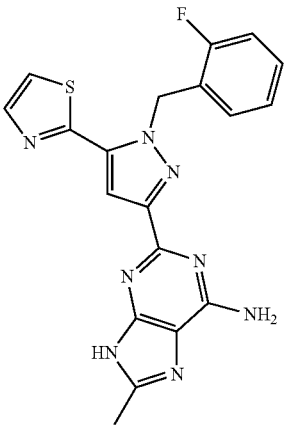 [SMILES: Cc1nc2c(N)nc(-c3cc(-c4nccs4)n(Cc4ccccc4F)n3)nc2[nH]1]
I-95
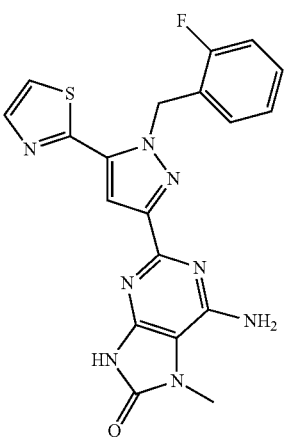 [SMILES: Cn1c(=O)[nH]c2nc(-c3cc(-c4nccs4)n(Cc4ccccc4F)n3)nc(N)c21]
I-96
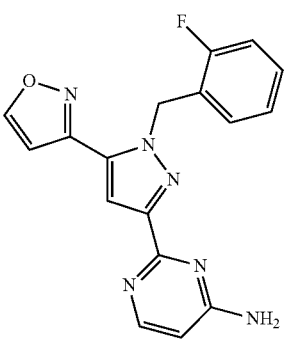 [SMILES: Nc1ccnc(-c2cc(-c3ccon3)n(Cc3ccccc3F)n2)n1]
I-97
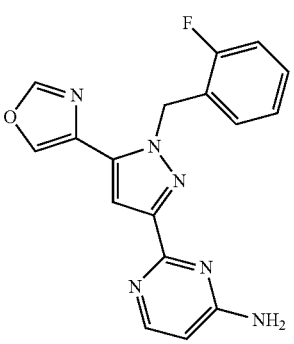 [SMILES: Nc1ccnc(-c2cc(-c3cocn3)n(Cc3ccccc3F)n2)n1]
I-98

TABLE 1A-continued
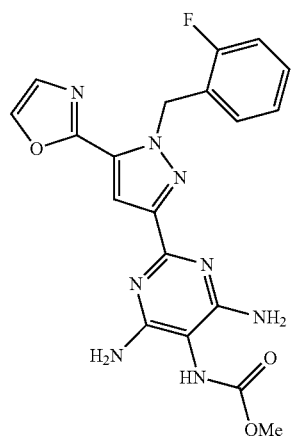 [SMILES: COC(=O)Nc1c(N)nc(-c2cc(-c3ncco3)n(Cc3ccccc3F)n2)nc1N]
I-99
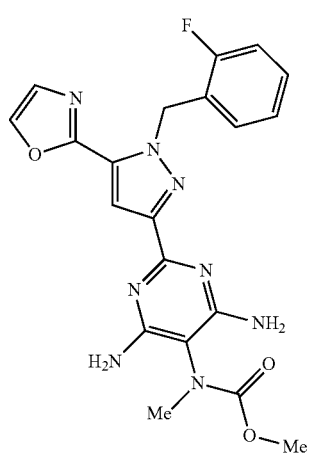 [SMILES: COC(=O)N(C)c1c(N)nc(-c2cc(-c3ncco3)n(Cc3ccccc3F)n2)nc1N]
I-100
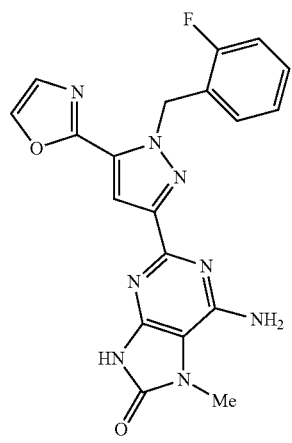 [SMILES: Cn1c(=O)[nH]c2nc(-c3cc(-c4ncco4)n(Cc4ccccc4F)n3)nc(N)c21]
I-101
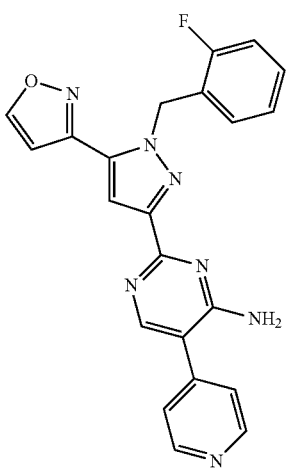 [SMILES: Nc1nc(-c2cc(-c3ccon3)n(Cc3ccccc3F)n2)ncc1-c1ccncc1]
I-102
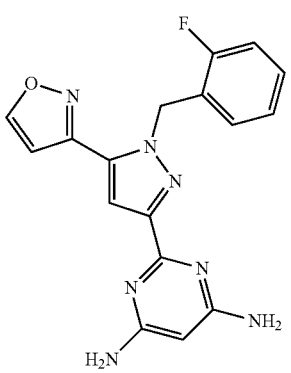 [SMILES: Nc1cc(N)nc(-c2cc(-c3ccon3)n(Cc3ccccc3F)n2)n1]
I-103
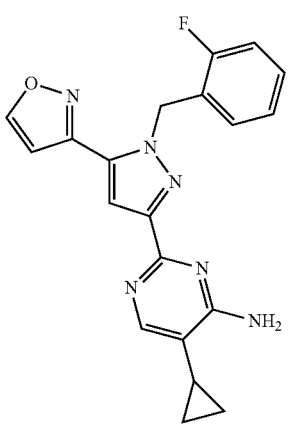 [SMILES: Nc1nc(-c2cc(-c3ccon3)n(Cc3ccccc3F)n2)ncc1C1CC1]
I-104

TABLE 1A-continued
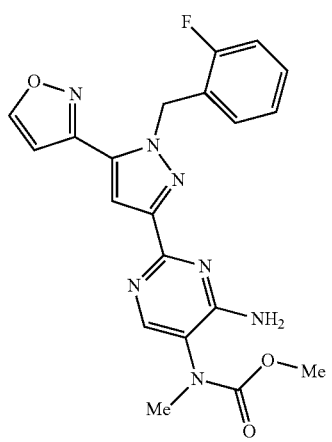 [SMILES: COC(=O)N(C)c1cnc(-c2cc(-c3ccon3)n(Cc3ccccc3F)n2)nc1N]
I-105
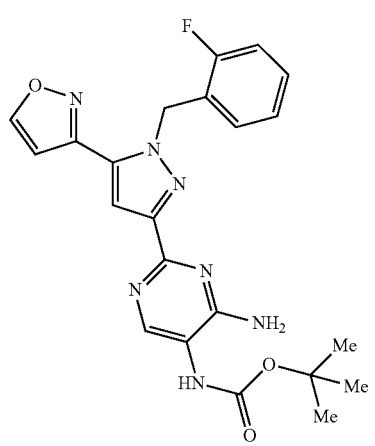 [SMILES: CC(C)(C)OC(=O)Nc1cnc(-c2cc(-c3ccon3)n(Cc3ccccc3F)n2)nc1N]
I-106
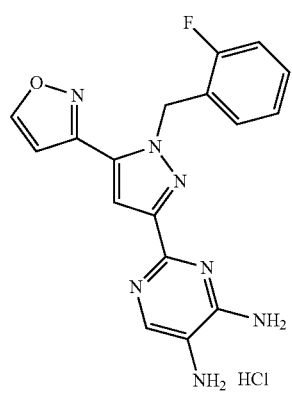 [SMILES: Nc1cnc(-c2cc(-c3ccon3)n(Cc3ccccc3F)n2)nc1N ; Cl]
I-107
TABLE 1A-continued
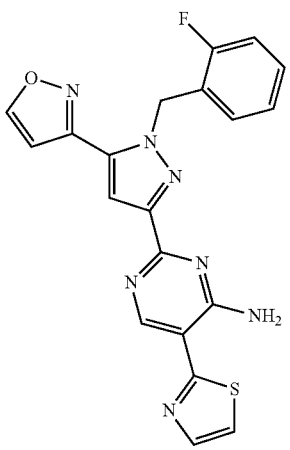 [SMILES: Nc1nc(-c2cc(-c3ccon3)n(Cc3ccccc3F)n2)ncc1-c1nccs1]
I-108
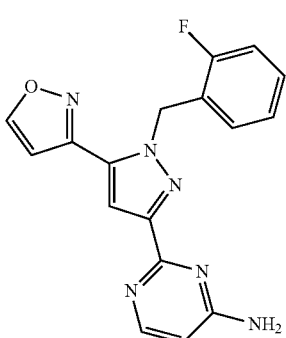
I-109
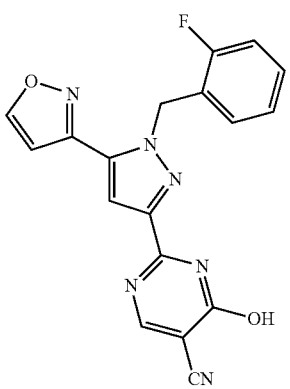 [SMILES: N#Cc1cnc(-c2cc(-c3ccon3)n(Cc3ccccc3F)n2)nc1O]
I-110
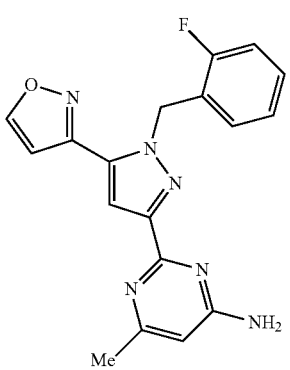 [SMILES: Cc1cc(N)nc(-c2cc(-c3ccon3)n(Cc3ccccc3F)n2)n1]
I-111

TABLE 1A-continued
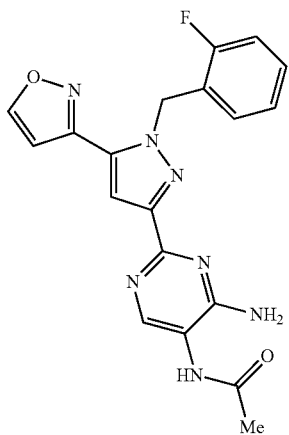 [SMILES: CC(=O)Nc1cnc(-c2cc(-c3ccon3)n(Cc3ccccc3F)n2)nc1N]
I-112
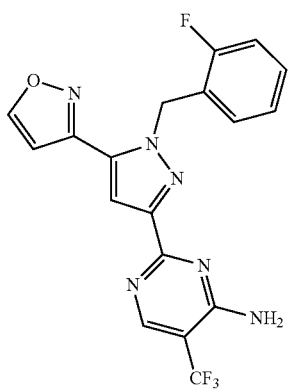 [SMILES: Nc1nc(-c2cc(-c3ccon3)n(Cc3ccccc3F)n2)ncc1C(F)(F)F]
I-113
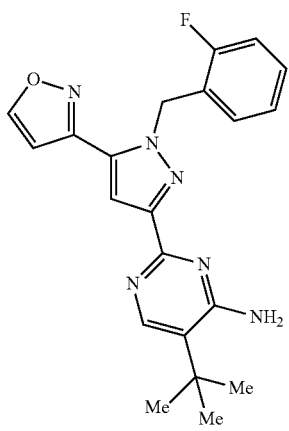 [SMILES: CC(C)(C)c1cnc(-c2cc(-c3ccon3)n(Cc3ccccc3F)n2)nc1N]
I-114
TABLE 1A-continued
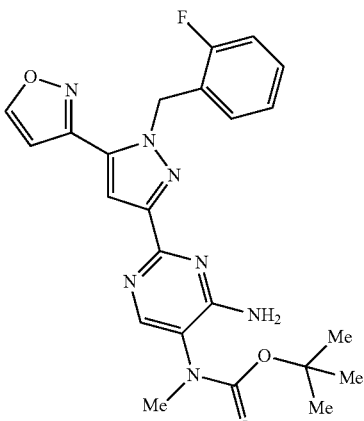
I-115
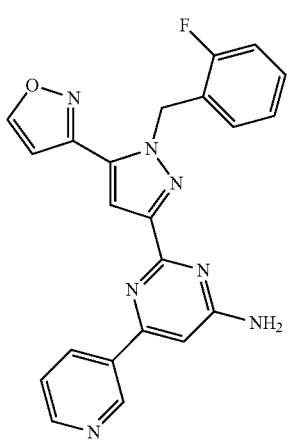
I-116
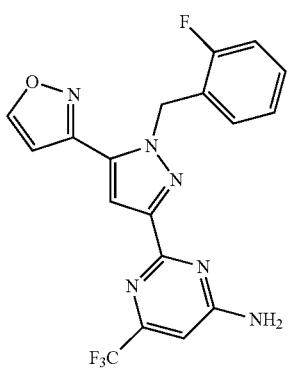
I-117
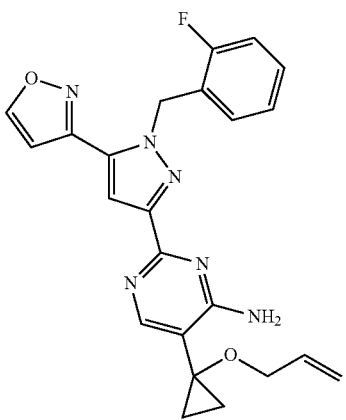 [SMILES: C=CCOC1(c2cnc(-c3cc(-c4ccon4)n(Cc4ccccc4F)n3)nc2N)CC1]
I-118

TABLE 1A-continued
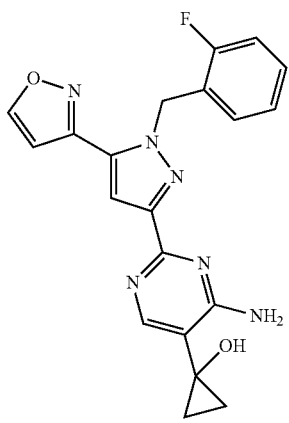 [SMILES: Nc1nc(-c2cc(-c3ccon3)n(Cc3ccccc3F)n2)ncc1C1(O)CC1]
I-119
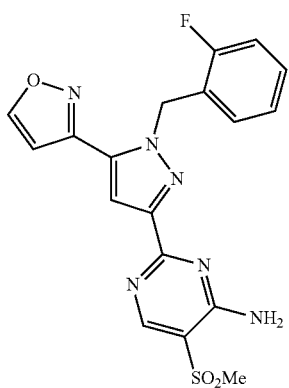 [SMILES: CS(=O)(=O)c1cnc(-c2cc(-c3ccon3)n(Cc3ccccc3F)n2)nc1N]
I-120
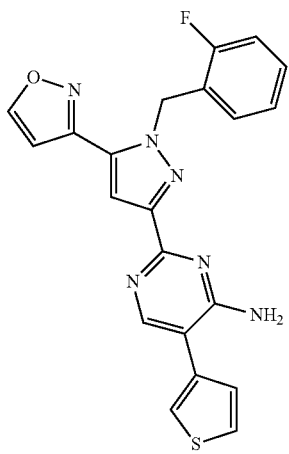 [SMILES: Nc1nc(-c2cc(-c3ccon3)n(Cc3ccccc3F)n2)ncc1-c1ccsc1]
I-121
TABLE 1A-continued
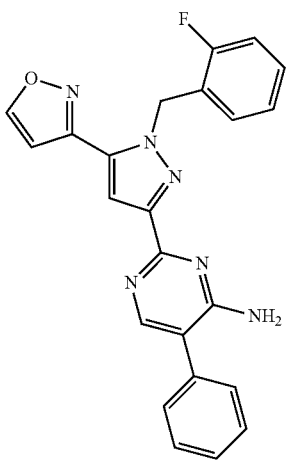 [SMILES: Nc1nc(-c2cc(-c3ccon3)n(Cc3ccccc3F)n2)ncc1-c1ccccc1]
I-122
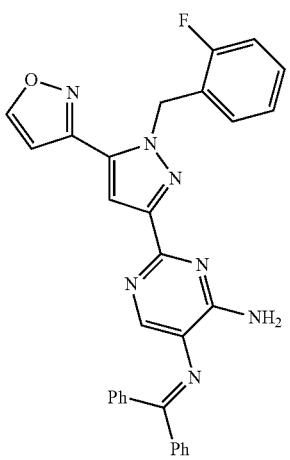 [SMILES: Nc1nc(-c2cc(-c3ccon3)n(Cc3ccccc3F)n2)ncc1N=C(c1ccccc1)c1ccccc1]
I-123
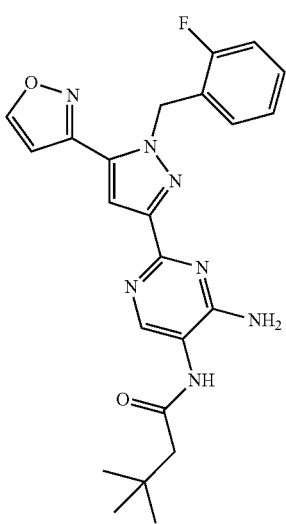 [SMILES: CC(C)(C)CC(=O)Nc1cnc(-c2cc(-c3ccon3)n(Cc3ccccc3F)n2)nc1N]
I-124

TABLE 1A-continued
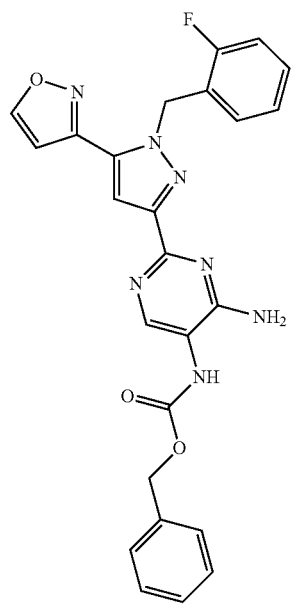 [SMILES: Nc1nc(-c2cc(-c3ccon3)n(Cc3ccccc3F)n2)ncc1NC(=O)OCc1ccccc1]
I-125
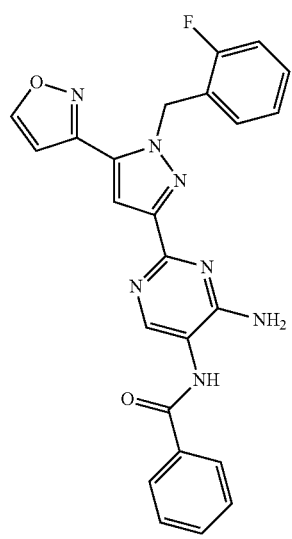 [SMILES: Nc1nc(-c2cc(-c3ccon3)n(Cc3ccccc3F)n2)ncc1NC(=O)c1ccccc1]
I-126
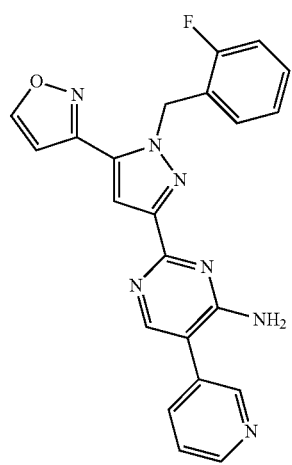 [SMILES: Nc1nc(-c2cc(-c3ccon3)n(Cc3ccccc3F)n2)ncc1-c1cccnc1]
I-127
TABLE 1A-continued
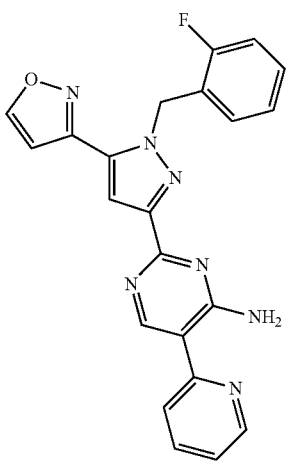 [SMILES: Nc1nc(-c2cc(-c3ccon3)n(Cc3ccccc3F)n2)ncc1-c1ccccn1]
I-128
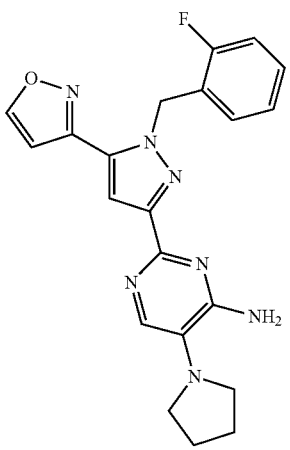 [SMILES: Nc1nc(-c2cc(-c3ccon3)n(Cc3ccccc3F)n2)ncc1N1CCCC1]
I-129
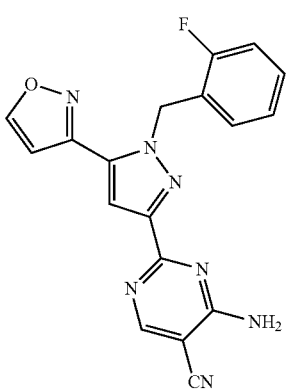
I-130

TABLE 1A-continued
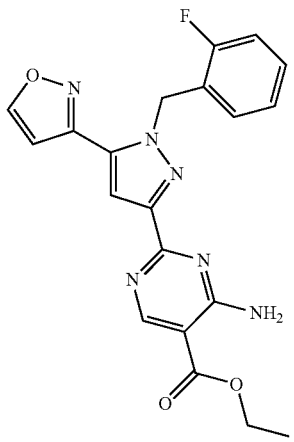 [SMILES: CCOC(=O)c1cnc(-c2cc(-c3ccon3)n(Cc3ccccc3F)n2)nc1N]
I-131
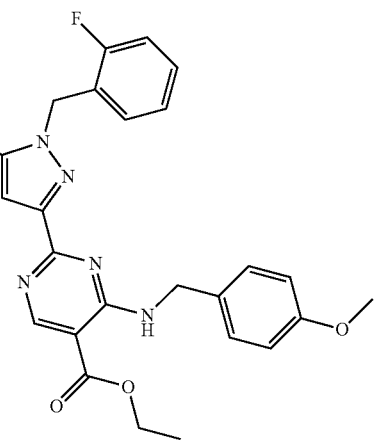
I-134
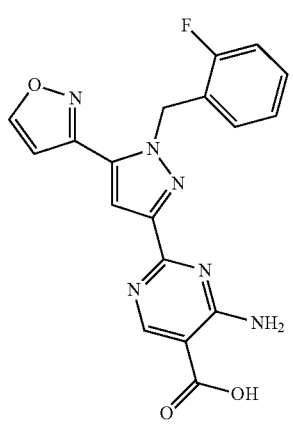 [SMILES: Nc1nc(-c2cc(-c3ccon3)n(Cc3ccccc3F)n2)ncc1C(=O)O]
I-132
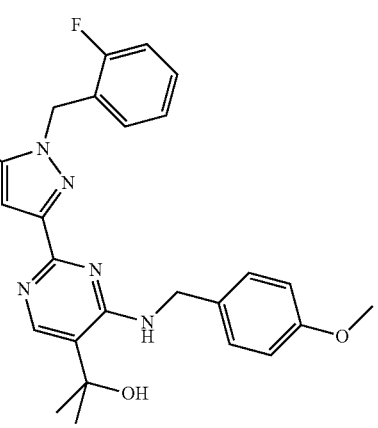
I-135
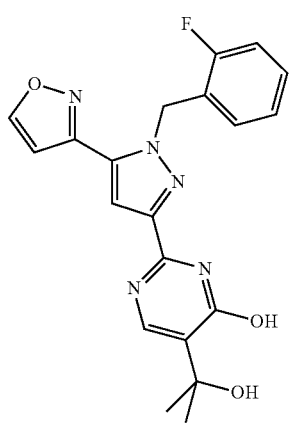 [SMILES: CC(C)(O)c1cnc(-c2cc(-c3ccon3)n(Cc3ccccc3F)n2)nc1O]
I-133
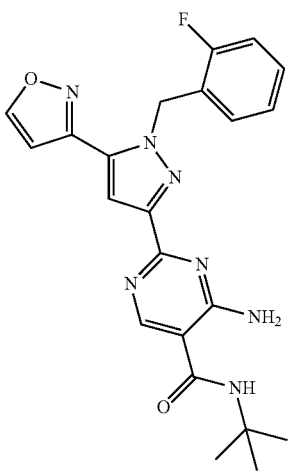 [SMILES: CC(C)(C)NC(=O)c1cnc(-c2cc(-c3ccon3)n(Cc3ccccc3F)n2)nc1N]
I-136

TABLE 1A-continued
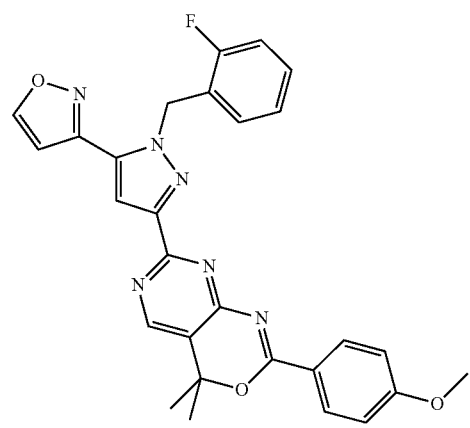 [SMILES: COc1ccc(C2=Nc3nc(-c4cc(-c5ccon5)n(Cc5ccccc5F)n4)ncc3C(C)(C)O2)cc1]
I-137
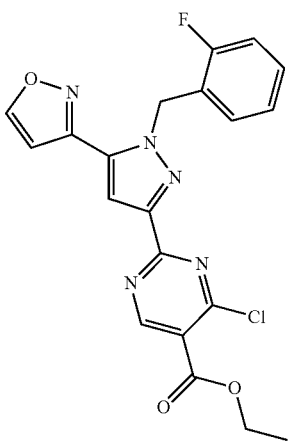
I-140
TABLE 1B
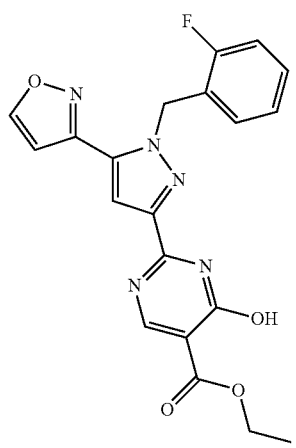
I-138
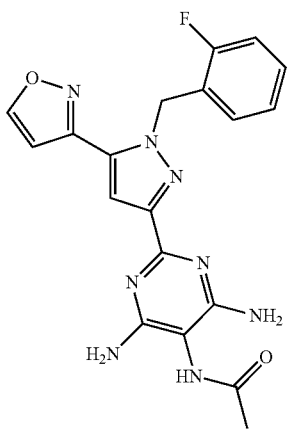 [SMILES: CC(=O)Nc1c(N)nc(-c2cc(-c3ccon3)n(Cc3ccccc3F)n2)nc1N]
I-141
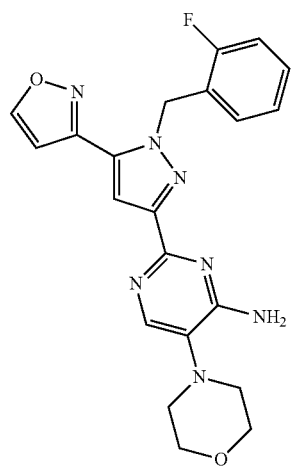
I-139
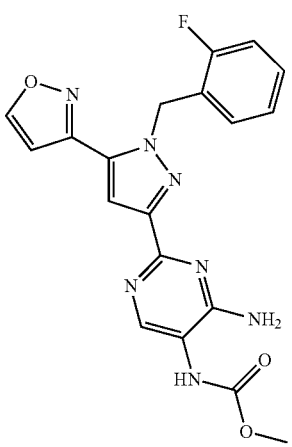 [SMILES: COC(=O)Nc1cnc(-c2cc(-c3ccon3)n(Cc3ccccc3F)n2)nc1N]
I-142

TABLE 1B-continued
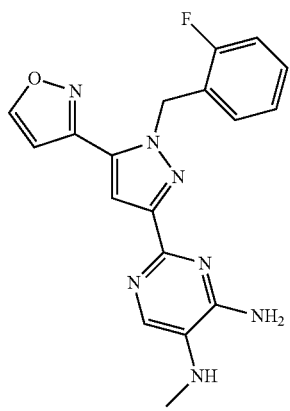 [SMILES: CNc1cnc(-c2cc(-c3ccon3)n(Cc3ccccc3F)n2)nc1N]
I-143
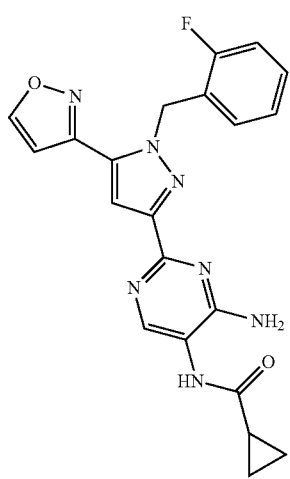 [SMILES: Nc1nc(-c2cc(-c3ccon3)n(Cc3ccccc3F)n2)ncc1NC(=O)C1CC1]
I-144
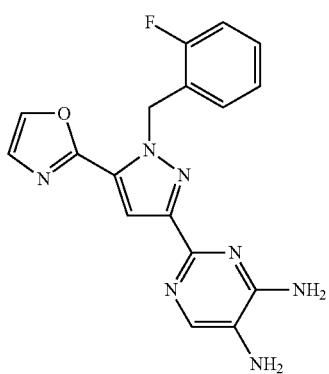
I-145
TABLE 1B-continued
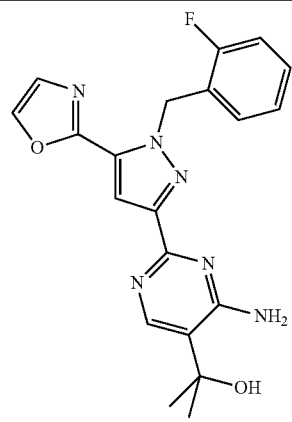
I-146
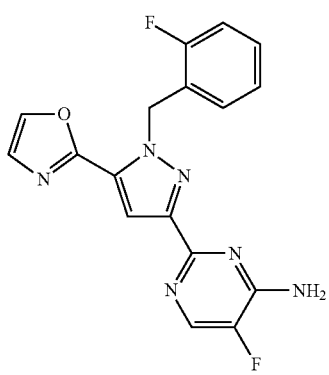 [SMILES: Nc1nc(-c2cc(-c3ncco3)n(Cc3ccccc3F)n2)ncc1F]
I-147
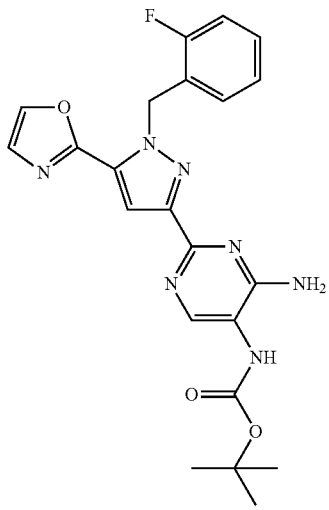 [SMILES: CC(C)(C)OC(=O)Nc1cnc(-c2cc(-c3ncco3)n(Cc3ccccc3F)n2)nc1N]
I-148
I-149

| | |
|---|---|
| 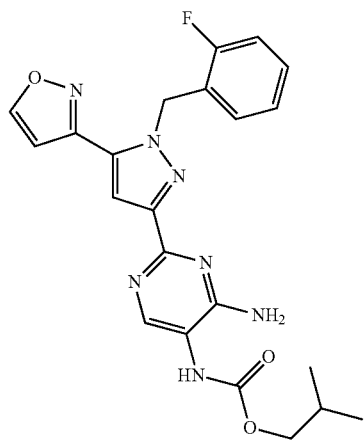 [SMILES: CC(C)COC(=O)Nc1cnc(-c2cc(-c3ccon3)n(Cc3ccccc3F)n2)nc1N] | I-150 |
| 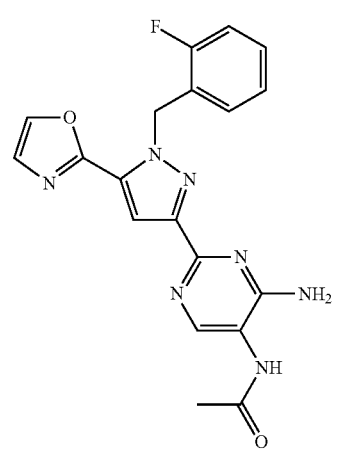 [SMILES: CC(=O)Nc1cnc(-c2cc(-c3ncco3)n(Cc3ccccc3F)n2)nc1N] | I-151 |
| 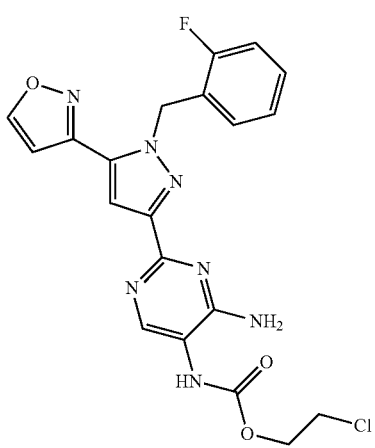 [SMILES: Nc1nc(-c2cc(-c3ccon3)n(Cc3ccccc3F)n2)ncc1NC(=O)OCCCl] | I-152 |
| 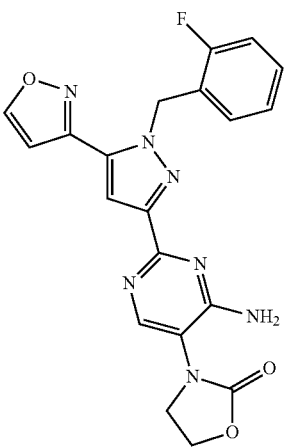 [SMILES: Nc1nc(-c2cc(-c3ccon3)n(Cc3ccccc3F)n2)ncc1N1CCOC1=O] | I-153 |
| 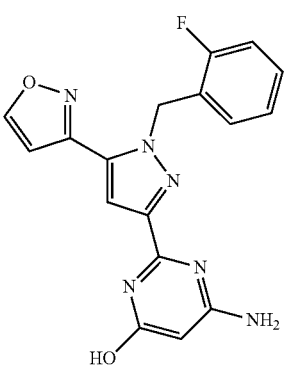 [SMILES: Nc1cc(O)nc(-c2cc(-c3ccon3)n(Cc3ccccc3F)n2)n1] | I-154 |
| 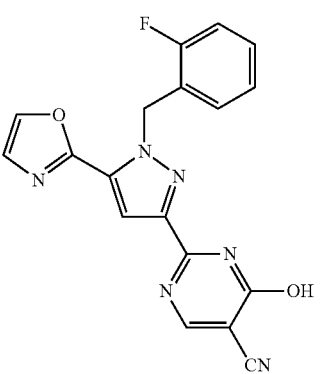 [SMILES: N#Cc1cnc(-c2cc(-c3ncco3)n(Cc3ccccc3F)n2)nc1O] | I-155 |

TABLE 1B-continued
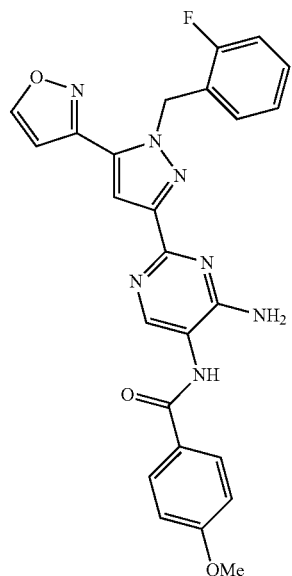 [SMILES: COc1ccc(C(=O)Nc2cnc(-c3cc(-c4ccon4)n(Cc4ccccc4F)n3)nc2N)cc1]
I-156
I-157
I-158
TABLE 1B-continued
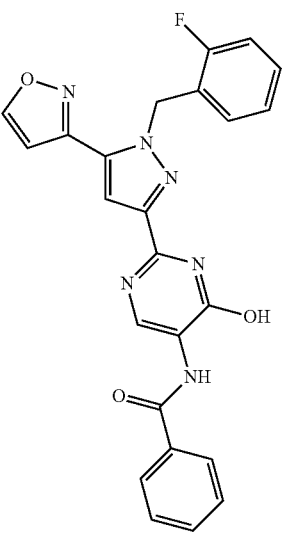 [SMILES: O=C(Nc1cnc(-c2cc(-c3ccon3)n(Cc3ccccc3F)n2)nc1O)c1ccccc1]
I-159
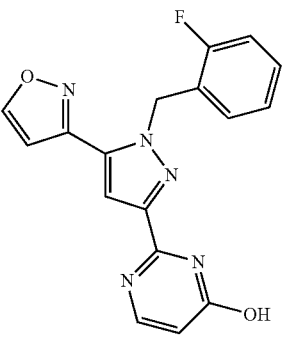 [SMILES: Oc1ccnc(-c2cc(-c3ccon3)n(Cc3ccccc3F)n2)n1]
I-160
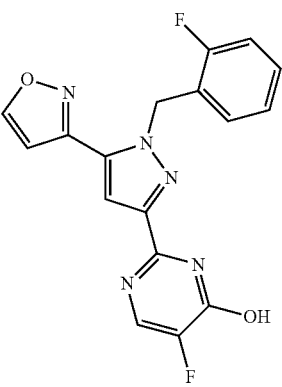 [SMILES: Oc1nc(-c2cc(-c3ccon3)n(Cc3ccccc3F)n2)ncc1F]
I-161

TABLE 1B-continued
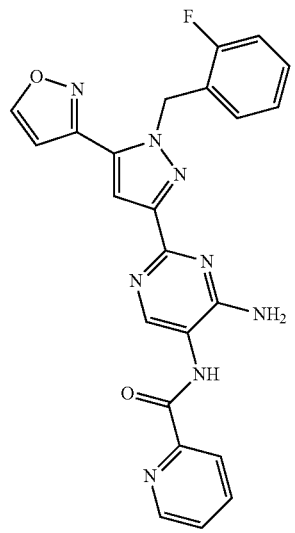 [SMILES: Nc1nc(-c2cc(-c3ccon3)n(Cc3ccccc3F)n2)ncc1NC(=O)c1ccccn1]
I-162
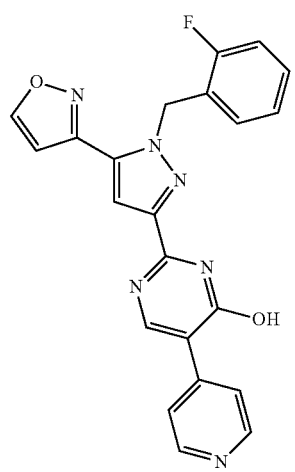 [SMILES: Oc1nc(-c2cc(-c3ccon3)n(Cc3ccccc3F)n2)ncc1-c1ccncc1]
I-163
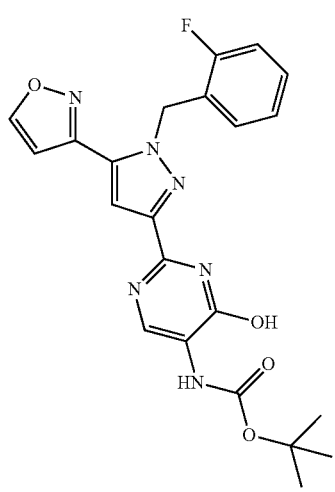 [SMILES: CC(C)(C)OC(=O)Nc1cnc(-c2cc(-c3ccon3)n(Cc3ccccc3F)n2)nc1O]
I-164
TABLE 1B-continued
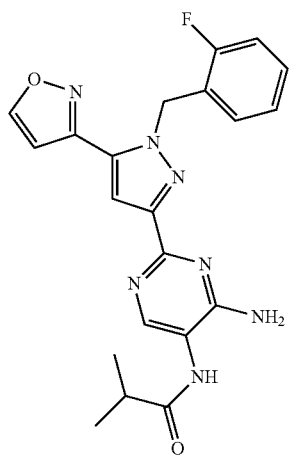 [SMILES: CC(C)C(=O)Nc1cnc(-c2cc(-c3ccon3)n(Cc3ccccc3F)n2)nc1N]
I-165
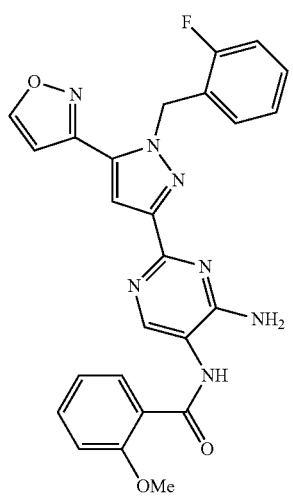 [SMILES: COc1ccccc1C(=O)Nc1cnc(-c2cc(-c3ccon3)n(Cc3ccccc3F)n2)nc1N]
I-166
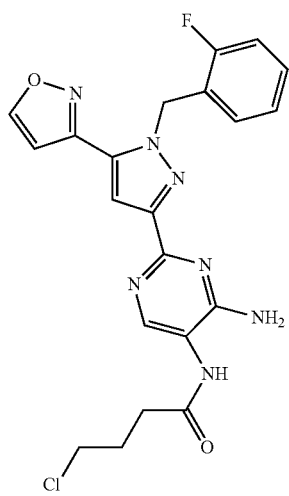 [SMILES: Nc1nc(-c2cc(-c3ccon3)n(Cc3ccccc3F)n2)ncc1NC(=O)CCCCl]
I-167

TABLE 1B-continued
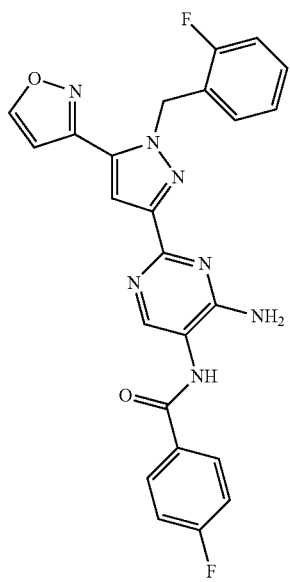 [SMILES: Nc1nc(-c2cc(-c3ccon3)n(Cc3ccccc3F)n2)ncc1NC(=O)c1ccc(F)cc1]
I-168
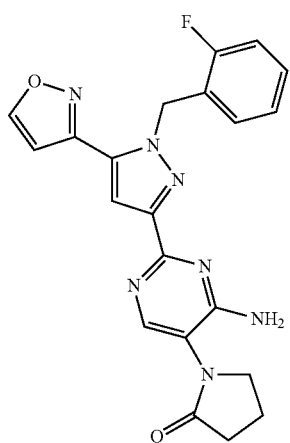 [SMILES: Nc1nc(-c2cc(-c3ccon3)n(Cc3ccccc3F)n2)ncc1N1CCCC1=O]
I-169
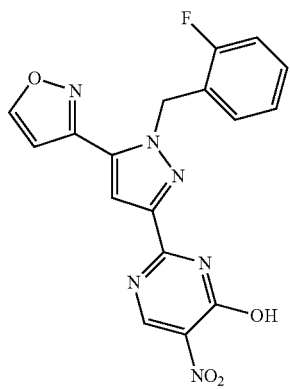 [SMILES: O=[N+]([O-])c1cnc(-c2cc(-c3ccon3)n(Cc3ccccc3F)n2)nc1O]
I-170
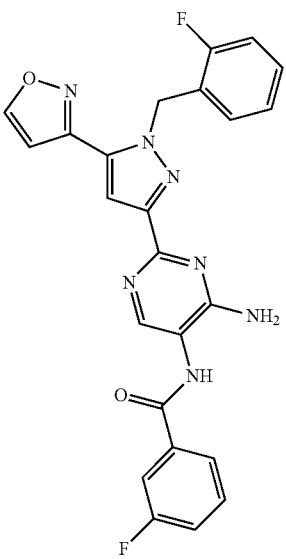 [SMILES: Nc1nc(-c2cc(-c3ccon3)n(Cc3ccccc3F)n2)ncc1NC(=O)c1cccc(F)c1]
I-171
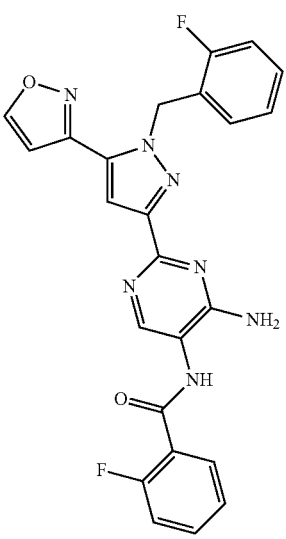
I-172
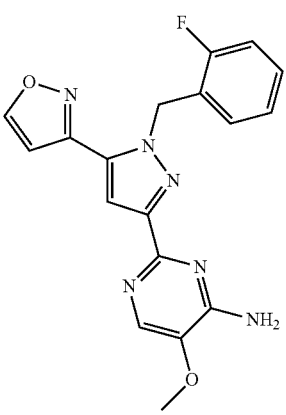 [SMILES: COc1cnc(-c2cc(-c3ccon3)n(Cc3ccccc3F)n2)nc1N]
I-173

TABLE 1B-continued
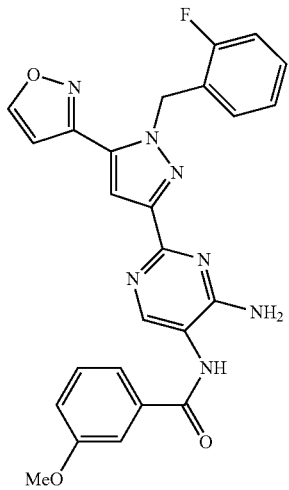 [SMILES: COc1cccc(C(=O)Nc2cnc(-c3cc(-c4ccon4)n(Cc4ccccc4F)n3)nc2N)c1]
I-174
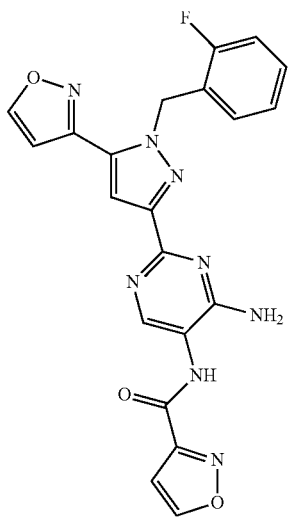 [SMILES: Nc1nc(-c2cc(-c3ccon3)n(Cc3ccccc3F)n2)ncc1NC(=O)c1ccon1]
I-175
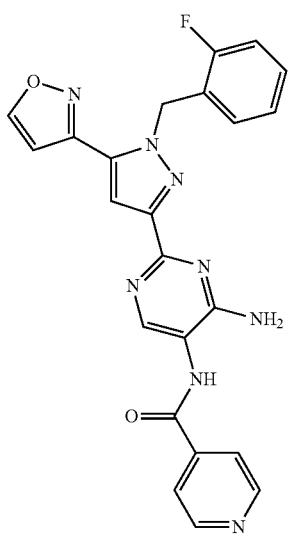
I-176
TABLE 1B-continued
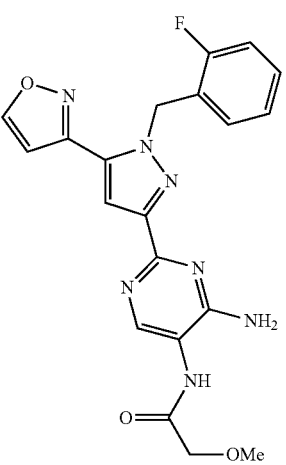 [SMILES: COCC(=O)Nc1cnc(-c2cc(-c3ccon3)n(Cc3ccccc3F)n2)nc1N]
I-177
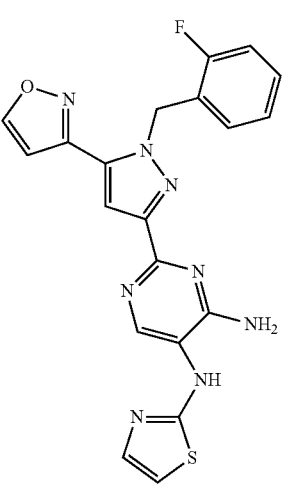 [SMILES: Nc1nc(-c2cc(-c3ccon3)n(Cc3ccccc3F)n2)ncc1Nc1nccs1]
I-178
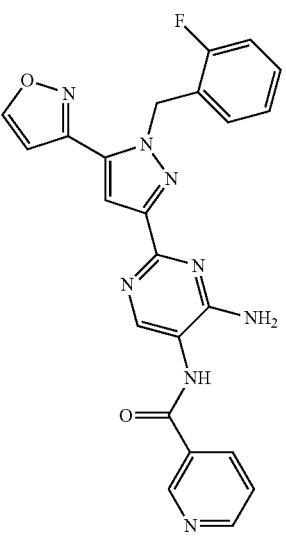 [SMILES: Nc1nc(-c2cc(-c3ccon3)n(Cc3ccccc3F)n2)ncc1NC(=O)c1cccnc1]
I-179

TABLE 1B-continued
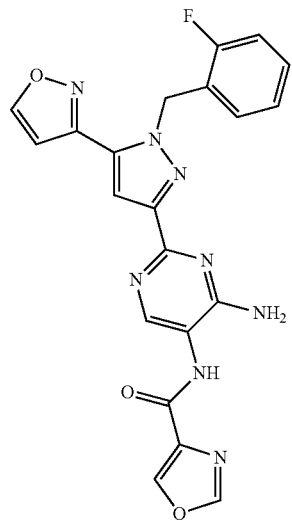 [SMILES: Nc1nc(-c2cc(-c3ccon3)n(Cc3ccccc3F)n2)ncc1NC(=O)c1cocn1]
I-180
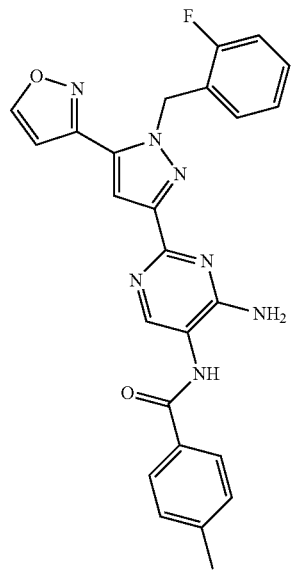 [SMILES: Cc1ccc(C(=O)Nc2cnc(-c3cc(-c4ccon4)n(Cc4ccccc4F)n3)nc2N)cc1]
I-181
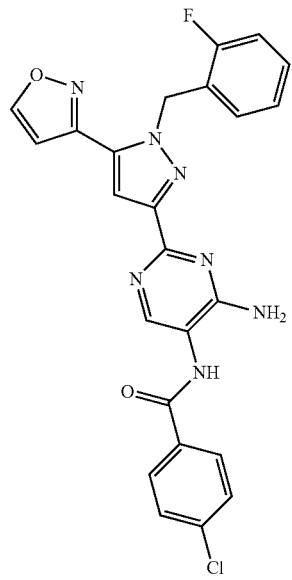
I-182
TABLE 1B-continued
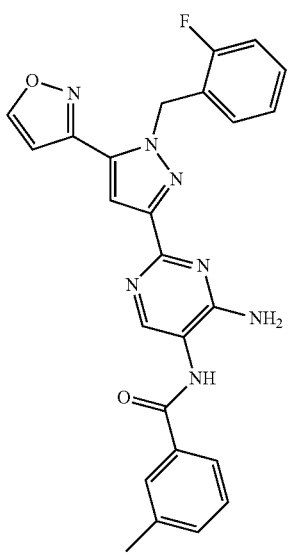 [SMILES: Cc1cccc(C(=O)Nc2cnc(-c3cc(-c4ccon4)n(Cc4ccccc4F)n3)nc2N)c1]
I-183
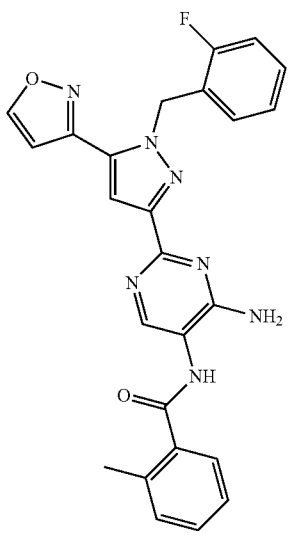 [SMILES: Cc1ccccc1C(=O)Nc1cnc(-c2cc(-c3ccon3)n(Cc3ccccc3F)n2)nc1N]
I-184
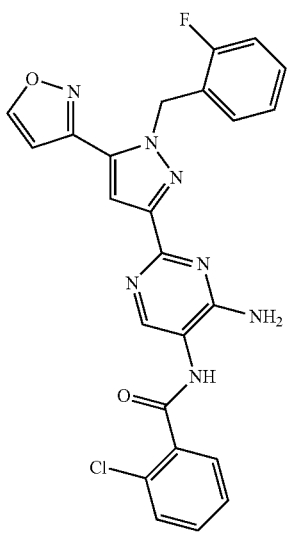 [SMILES: Nc1nc(-c2cc(-c3ccon3)n(Cc3ccccc3F)n2)ncc1NC(=O)c1ccccc1Cl]
I-185

TABLE 1B-continued
I-186
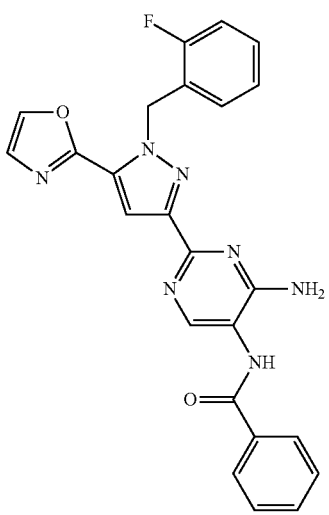 [SMILES: Nc1nc(-c2cc(-c3ncco3)n(Cc3ccccc3F)n2)ncc1NC(=O)c1ccccc1]
I-187
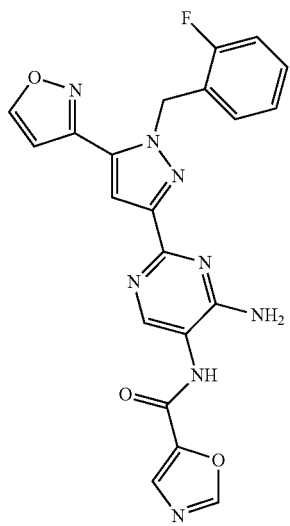 [SMILES: Nc1nc(-c2cc(-c3ccon3)n(Cc3ccccc3F)n2)ncc1NC(=O)c1cnco1]
I-188
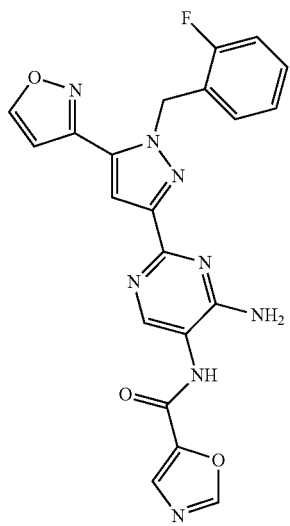 [SMILES: Nc1nc(-c2cc(-c3ccon3)n(Cc3ccccc3F)n2)ncc1NC(=O)c1cnco1]
TABLE 1B-continued
I-189
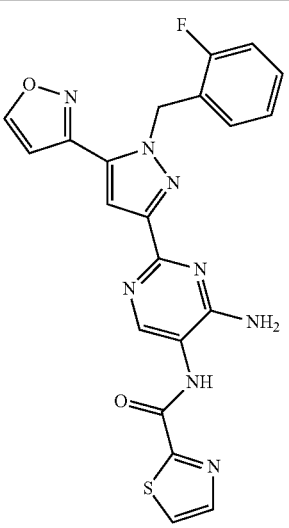 [SMILES: Nc1nc(-c2cc(-c3ccon3)n(Cc3ccccc3F)n2)ncc1NC(=O)c1nccs1]
I-190
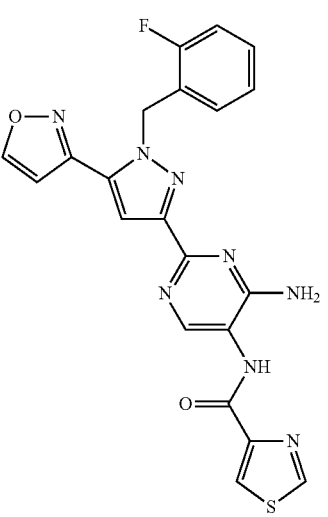 [SMILES: Nc1nc(-c2cc(-c3ccon3)n(Cc3ccccc3F)n2)ncc1NC(=O)c1cscn1]
I-191
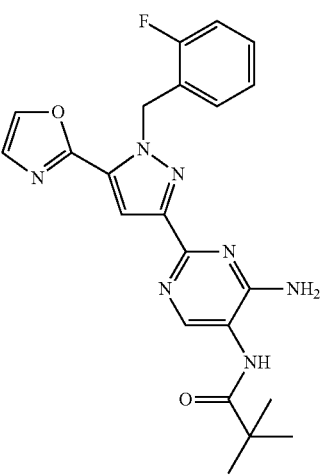 [SMILES: CC(C)(C)C(=O)Nc1cnc(-c2cc(-c3ncco3)n(Cc3ccccc3F)n2)nc1N]

TABLE 1B-continued
I-192
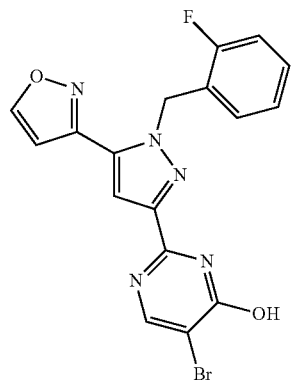 [SMILES: Oc1nc(-c2cc(-c3ccon3)n(Cc3ccccc3F)n2)ncc1Br]
I-193
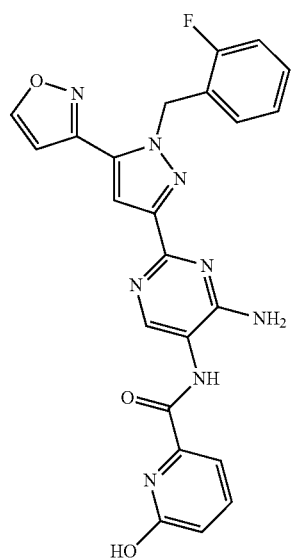 [SMILES: Nc1nc(-c2cc(-c3ccon3)n(Cc3ccccc3F)n2)ncc1NC(=O)c1cccc(O)n1]
I-194
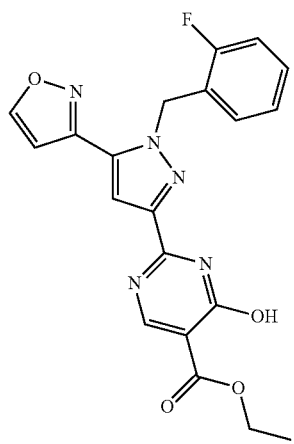 [SMILES: CCOC(=O)c1cnc(-c2cc(-c3ccon3)n(Cc3ccccc3F)n2)nc1O]
TABLE 1B-continued
I-195
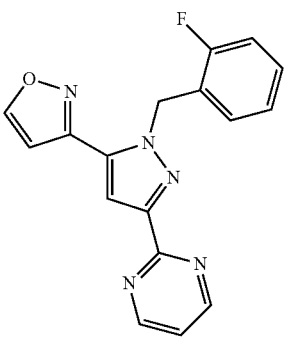
I-196
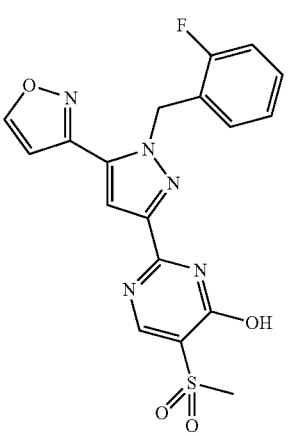 [SMILES: CS(=O)(=O)c1cnc(-c2cc(-c3ccon3)n(Cc3ccccc3F)n2)nc1O]
I-197
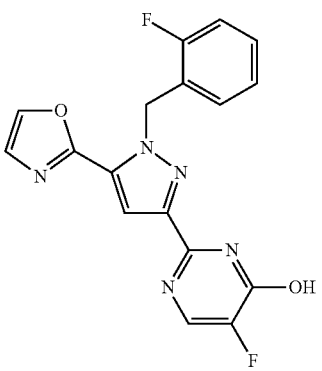 [SMILES: Oc1nc(-c2cc(-c3ncco3)n(Cc3ccccc3F)n2)ncc1F]
I-198
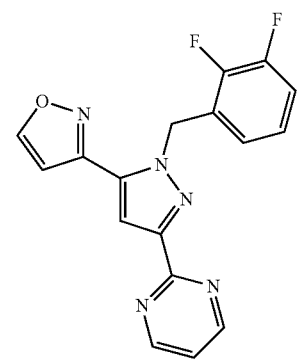 [SMILES: Fc1cccc(Cn2nc(-c3ncccn3)cc2-c2ccon2)c1F]

TABLE 1B-continued
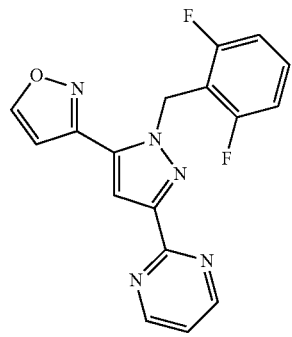 [SMILES: Fc1cccc(F)c1Cn1nc(-c2ncccn2)cc1-c1ccon1]
I-199
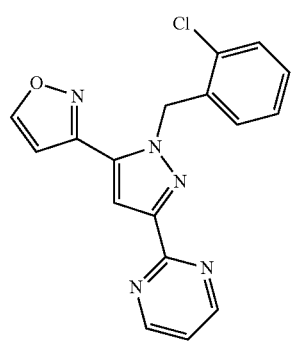
I-200
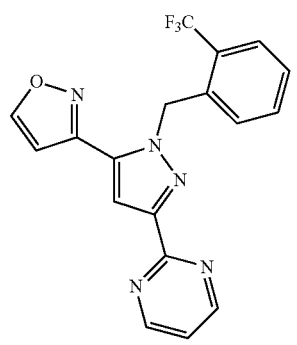 [SMILES: FC(F)(F)c1ccccc1Cn1nc(-c2ncccn2)cc1-c1ccon1]
I-201
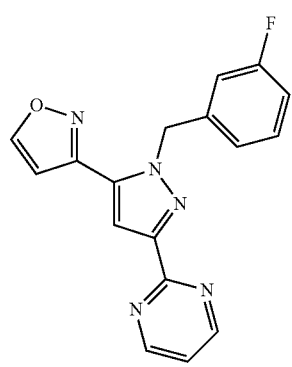 [SMILES: Fc1cccc(Cn2nc(-c3ncccn3)cc2-c2ccon2)c1]
I-202
TABLE 1B-continued
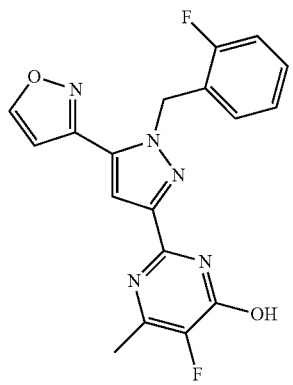 [SMILES: Cc1nc(-c2cc(-c3ccon3)n(Cc3ccccc3F)n2)nc(O)c1F]
I-203
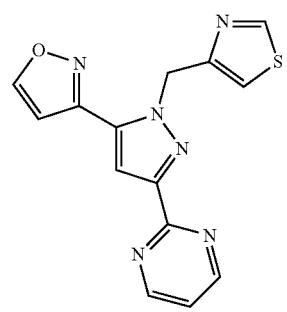 [SMILES: c1cnc(-c2cc(-c3ccon3)n(Cc3cscn3)n2)nc1]
I-204
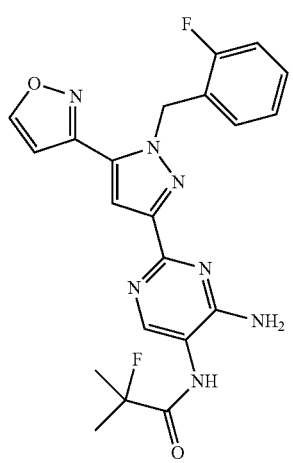 [SMILES: CC(C)(F)C(=O)Nc1cnc(-c2cc(-c3ccon3)n(Cc3ccccc3F)n2)nc1N]
I-205
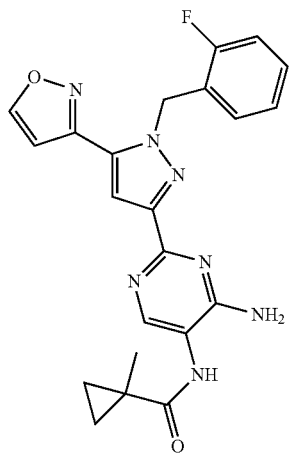 [SMILES: CC1(C(=O)Nc2cnc(-c3cc(-c4ccon4)n(Cc4ccccc4F)n3)nc2N)CC1]
I-206

TABLE 1B-continued
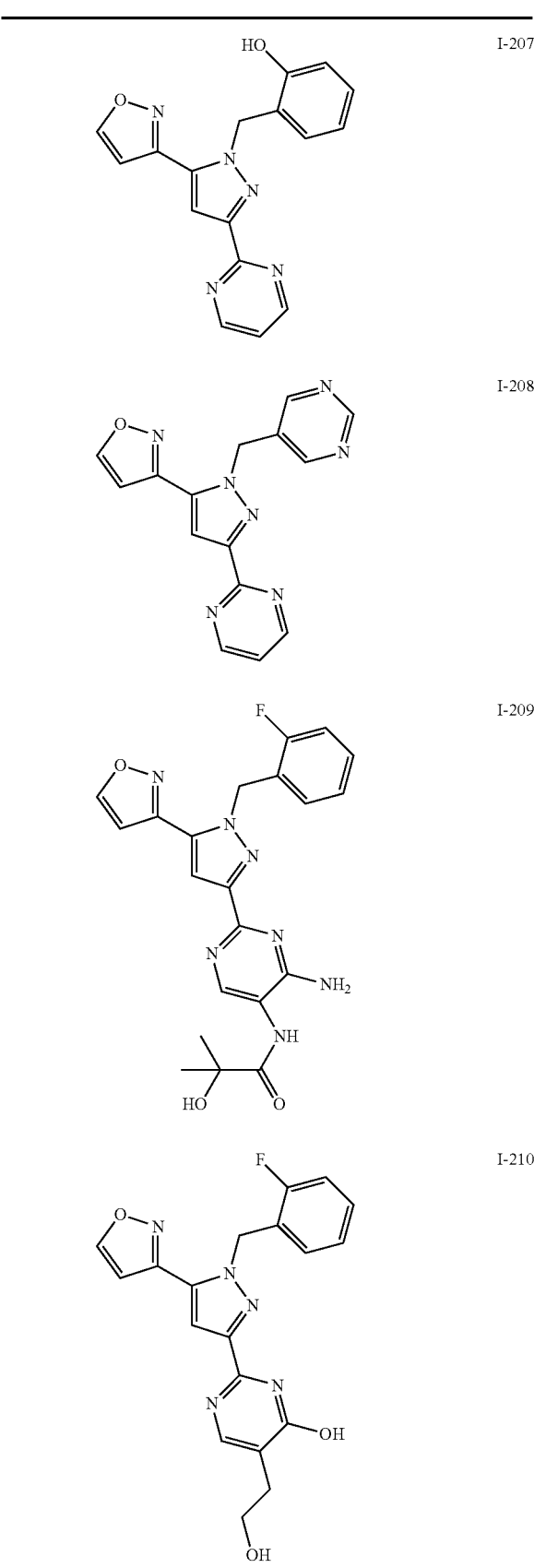
I-207
I-208
I-209
I-210
TABLE 1B-continued
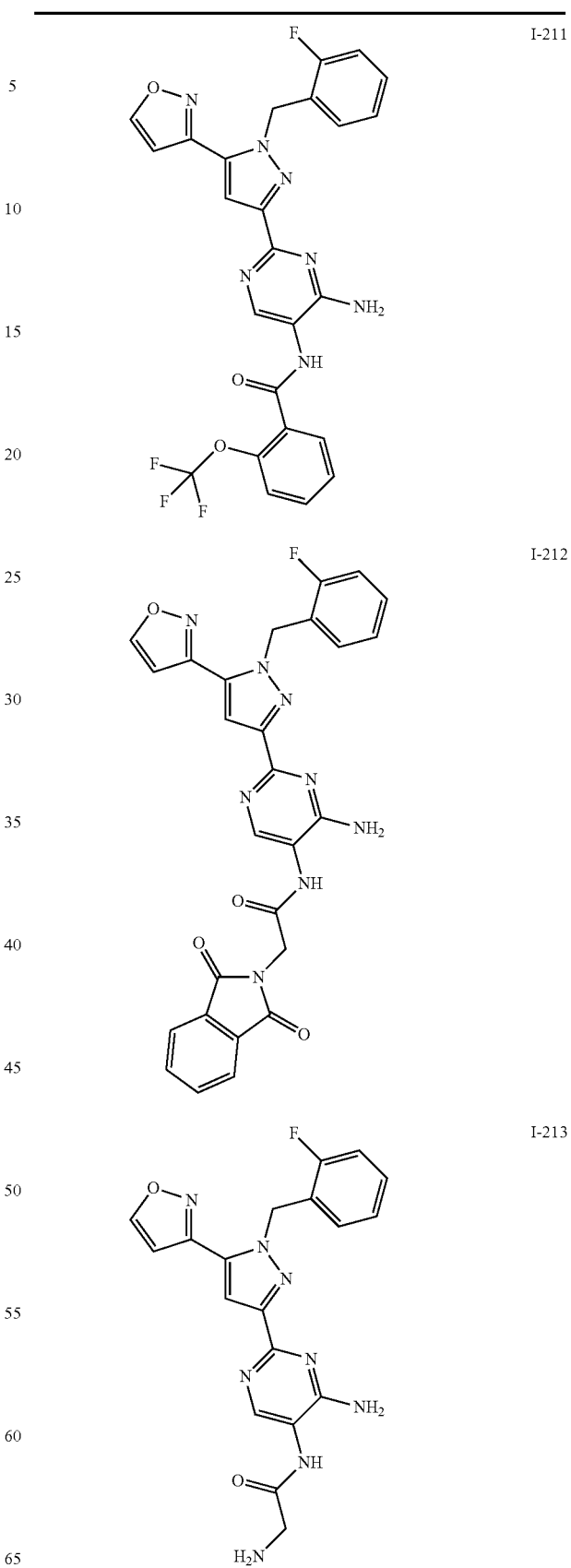
I-211
I-212
I-213

TABLE 1B-continued
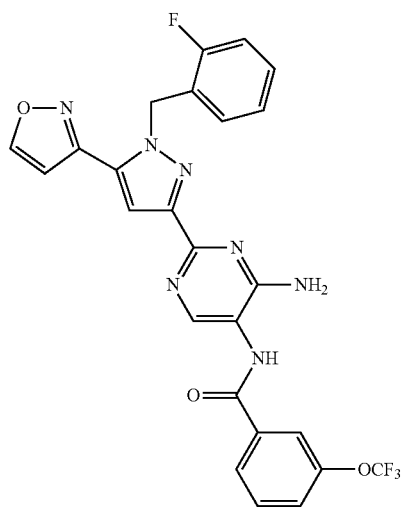 [SMILES: Nc1nc(-c2cc(-c3ccon3)n(Cc3ccccc3F)n2)ncc1NC(=O)c1cccc(OC(F)(F)F)c1]
I-214
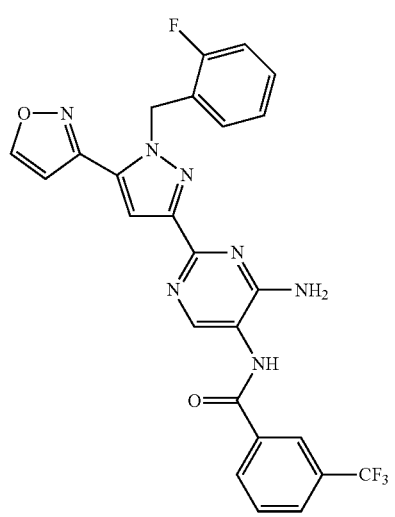 [SMILES: Nc1nc(-c2cc(-c3ccon3)n(Cc3ccccc3F)n2)ncc1NC(=O)c1cccc(C(F)(F)F)c1]
I-215
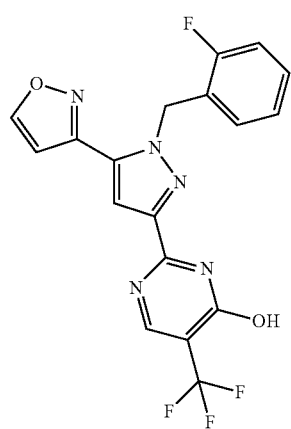 [SMILES: Oc1nc(-c2cc(-c3ccon3)n(Cc3ccccc3F)n2)ncc1C(F)(F)F]
I-216
TABLE 1B-continued
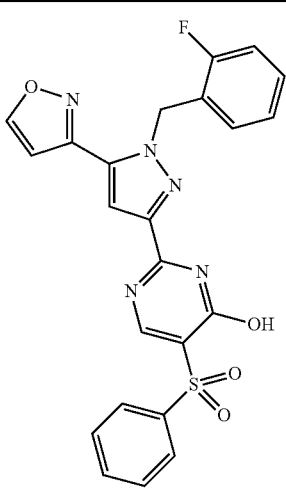
I-217
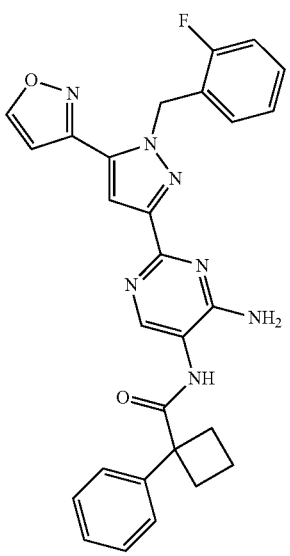 [SMILES: Nc1nc(-c2cc(-c3ccon3)n(Cc3ccccc3F)n2)ncc1NC(=O)C1(c2ccccc2)CCC1]
I-218
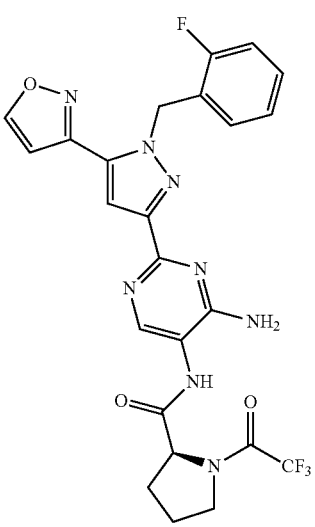 [SMILES: Nc1nc(-c2cc(-c3ccon3)n(Cc3ccccc3F)n2)ncc1NC(=O)[C@@H]1CCCN1C(=O)C(F)(F)F]
I-219

TABLE 1B-continued
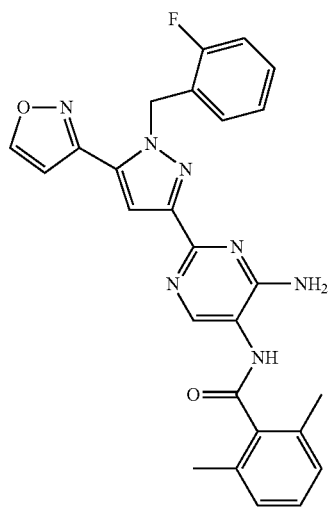 [SMILES: Cc1cccc(C)c1C(=O)Nc1cnc(-c2cc(-c3ccon3)n(Cc3ccccc3F)n2)nc1N]
I-220
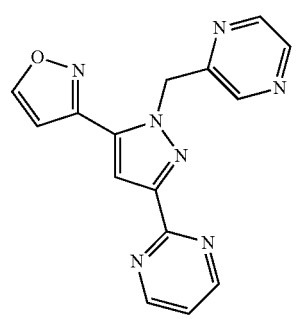 [SMILES: c1cnc(-c2cc(-c3ccon3)n(Cc3cnccn3)n2)nc1]
I-221
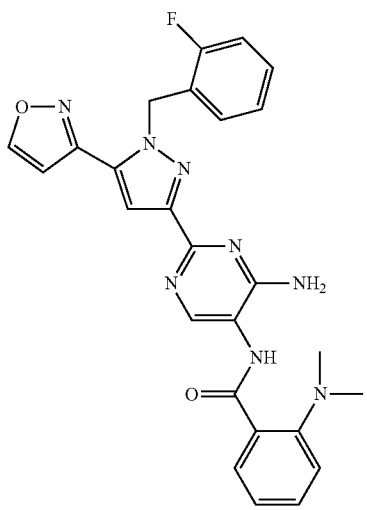 [SMILES: CN(C)c1ccccc1C(=O)Nc1cnc(-c2cc(-c3ccon3)n(Cc3ccccc3F)n2)nc1N]
I-222
TABLE 1B-continued
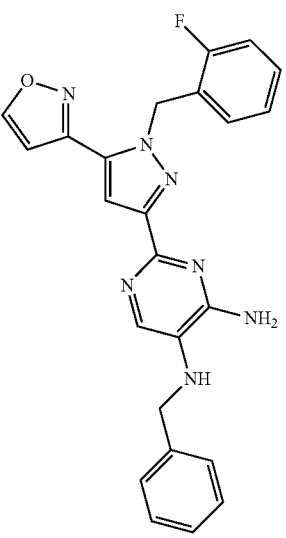 [SMILES: Nc1nc(-c2cc(-c3ccon3)n(Cc3ccccc3F)n2)ncc1NCc1ccccc1]
I-223
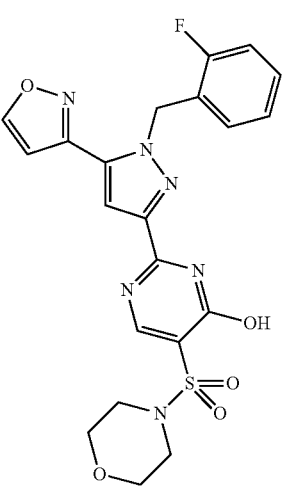 [SMILES: O=S(=O)(c1cnc(-c2cc(-c3ccon3)n(Cc3ccccc3F)n2)nc1O)N1CCOCC1]
I-224
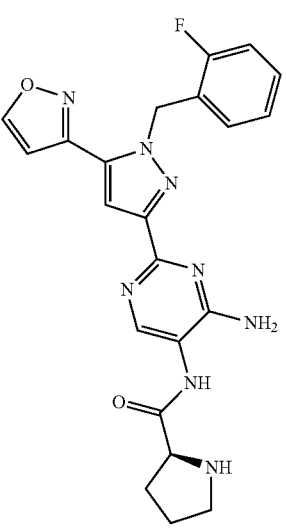 [SMILES: Nc1nc(-c2cc(-c3ccon3)n(Cc3ccccc3F)n2)ncc1NC(=O)[C@@H]1CCCN1]
I-225

TABLE 1B-continued
I-226
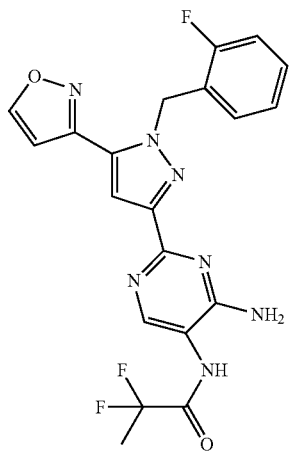 [SMILES: CC(F)(F)C(=O)Nc1cnc(-c2cc(-c3ccon3)n(Cc3ccccc3F)n2)nc1N]
I-227
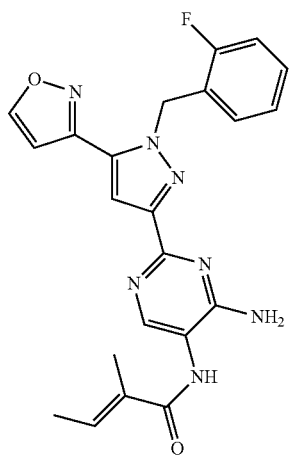 [SMILES: C/C=C(\C)C(=O)Nc1cnc(-c2cc(-c3ccon3)n(Cc3ccccc3F)n2)nc1N]
I-228
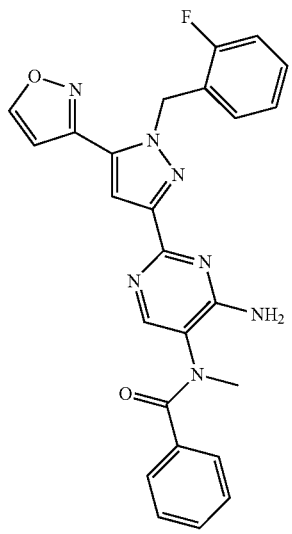 [SMILES: CN(C(=O)c1ccccc1)c1cnc(-c2cc(-c3ccon3)n(Cc3ccccc3F)n2)nc1N]
TABLE 1B-continued
I-229
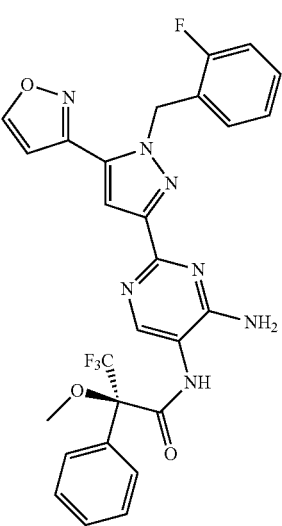 [SMILES: CO[C@@](C(=O)Nc1cnc(-c2cc(-c3ccon3)n(Cc3ccccc3F)n2)nc1N)(c1ccccc1)C(F)(F)F]
I-230
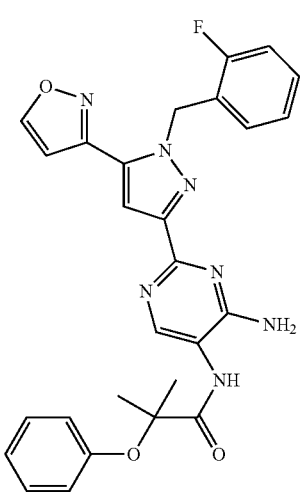 [SMILES: CC(C)(Oc1ccccc1)C(=O)Nc1cnc(-c2cc(-c3ccon3)n(Cc3ccccc3F)n2)nc1N]
I-231
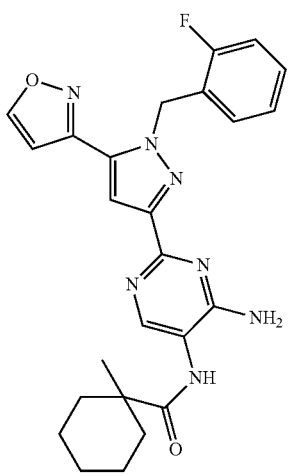 [SMILES: CC1(C(=O)Nc2cnc(-c3cc(-c4ccon4)n(Cc4ccccc4F)n3)nc2N)CCCCC1]

TABLE 1B-continued
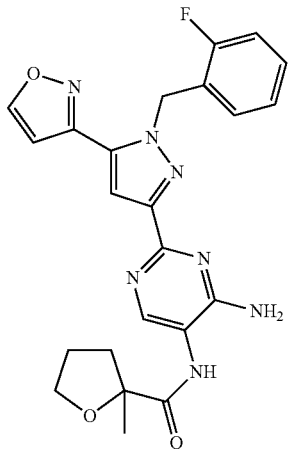 [SMILES: CC1(C(=O)Nc2cnc(-c3cc(-c4ccon4)n(Cc4ccccc4F)n3)nc2N)CCCO1]
I-232
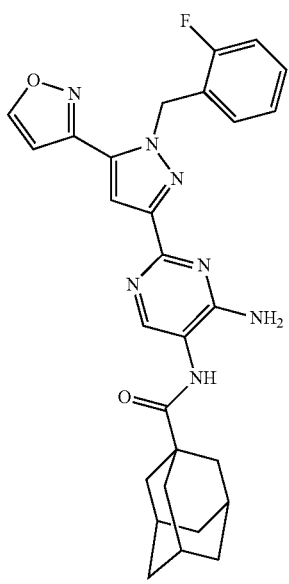 [SMILES: Nc1nc(-c2cc(-c3ccon3)n(Cc3ccccc3F)n2)ncc1NC(=O)C12CC3CC(CC(C3)C1)C2]
I-233
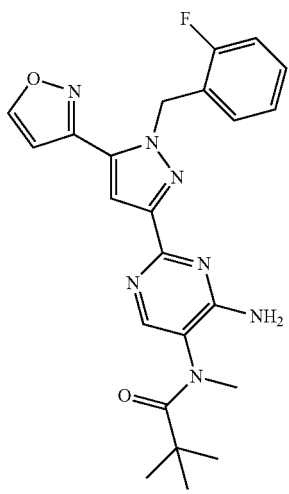 [SMILES: CN(C(=O)C(C)(C)C)c1cnc(-c2cc(-c3ccon3)n(Cc3ccccc3F)n2)nc1N]
I-234
TABLE 1B-continued
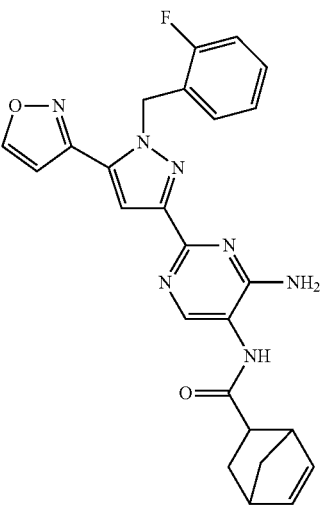 [SMILES: Nc1nc(-c2cc(-c3ccon3)n(Cc3ccccc3F)n2)ncc1NC(=O)C1CC2C=CC1C2]
I-235
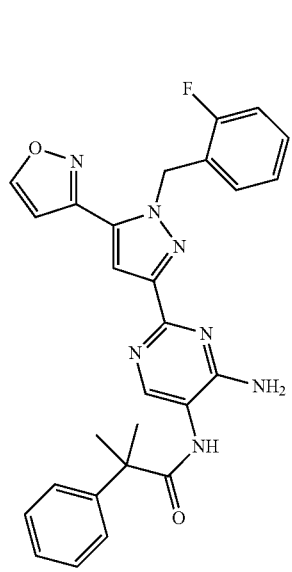 [SMILES: CC(C)(C(=O)Nc1cnc(-c2cc(-c3ccon3)n(Cc3ccccc3F)n2)nc1N)c1ccccc1]
I-236
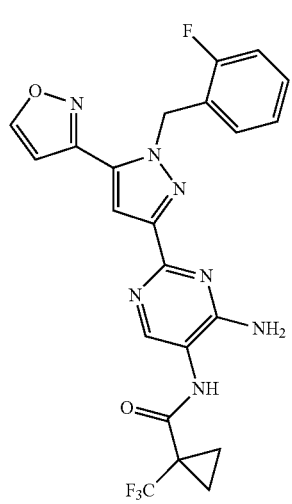 [SMILES: Nc1nc(-c2cc(-c3ccon3)n(Cc3ccccc3F)n2)ncc1NC(=O)C1(C(F)(F)F)CC1]
I-237

TABLE 1B-continued
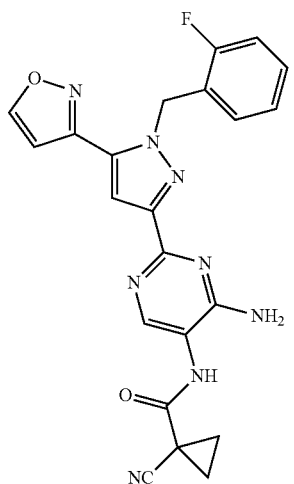 [SMILES: N#CC1(C(=O)Nc2cnc(-c3cc(-c4ccon4)n(Cc4ccccc4F)n3)nc2N)CC1]
I-238
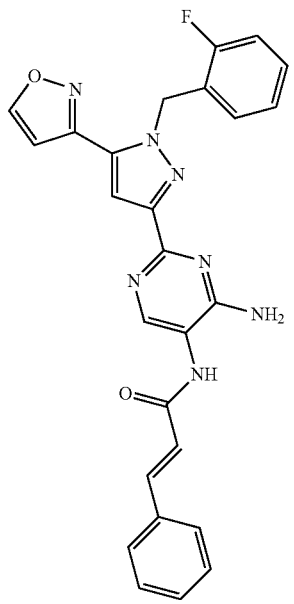 [SMILES: Nc1nc(-c2cc(-c3ccon3)n(Cc3ccccc3F)n2)ncc1NC(=O)/C=C/c1ccccc1]
I-239
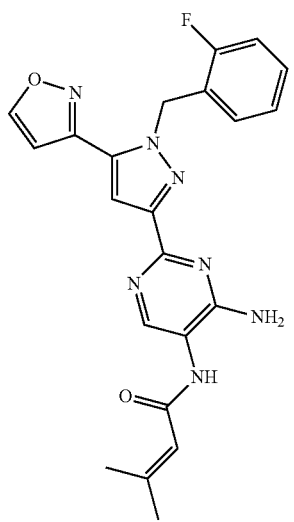 [SMILES: CC(C)=CC(=O)Nc1cnc(-c2cc(-c3ccon3)n(Cc3ccccc3F)n2)nc1N]
I-240
TABLE 1B-continued
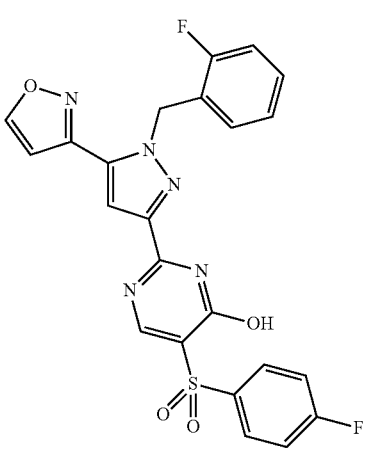 [SMILES: O=S(=O)(c1ccc(F)cc1)c1cnc(-c2cc(-c3ccon3)n(Cc3ccccc3F)n2)nc1O]
I-241
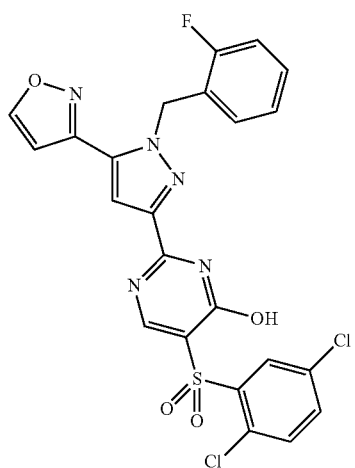 [SMILES: O=S(=O)(c1cc(Cl)ccc1Cl)c1cnc(-c2cc(-c3ccon3)n(Cc3ccccc3F)n2)nc1O]
I-242
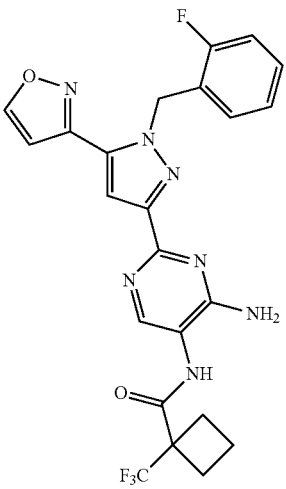 [SMILES: Nc1nc(-c2cc(-c3ccon3)n(Cc3ccccc3F)n2)ncc1NC(=O)C1(C(F)(F)F)CCC1]
I-243

TABLE 1B-continued
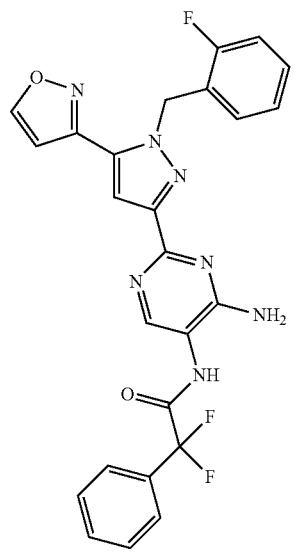 [SMILES: Nc1nc(-c2cc(-c3ccon3)n(Cc3ccccc3F)n2)ncc1NC(=O)C(F)(F)c1ccccc1]
I-244
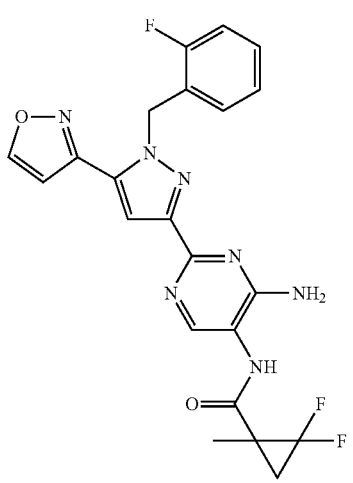 [SMILES: CC1(C(=O)Nc2cnc(-c3cc(-c4ccon4)n(Cc4ccccc4F)n3)nc2N)CC1(F)F]
I-245
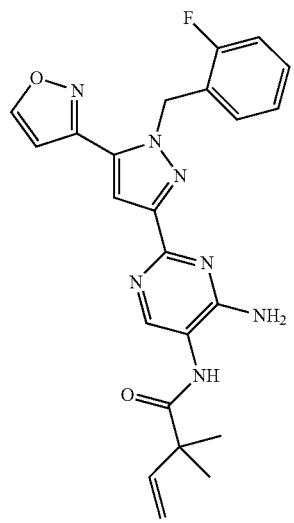 [SMILES: C=CC(C)(C)C(=O)Nc1cnc(-c2cc(-c3ccon3)n(Cc3ccccc3F)n2)nc1N]
I-246
TABLE 1B-continued
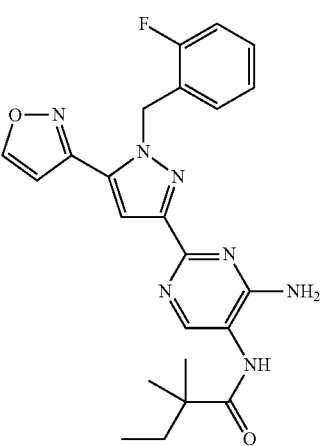 [SMILES: CCC(C)(C)C(=O)Nc1cnc(-c2cc(-c3ccon3)n(Cc3ccccc3F)n2)nc1N]
I-247
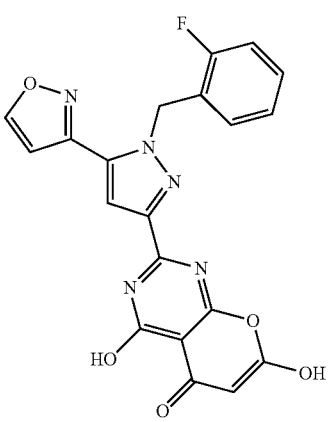 [SMILES: O=c1cc(O)oc2nc(-c3cc(-c4ccon4)n(Cc4ccccc4F)n3)nc(O)c12]
I-248
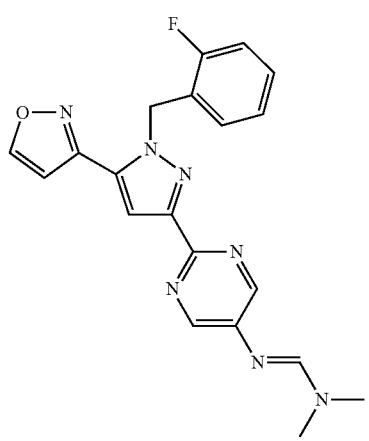 [SMILES: CN(C)/C=N/c1cnc(-c2cc(-c3ccon3)n(Cc3ccccc3F)n2)nc1]
I-249

TABLE 1B-continued
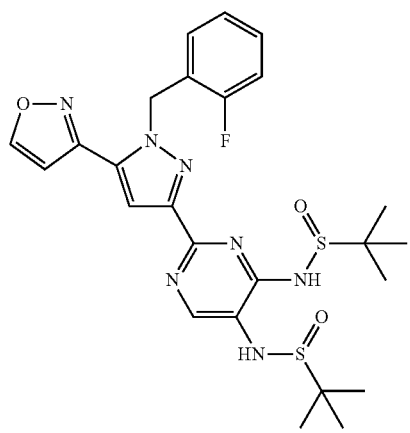 [SMILES: CC(C)(C)S(=O)Nc1cnc(-c2cc(-c3ccon3)n(Cc3ccccc3F)n2)nc1NS(=O)C(C)(C)C]
I-250
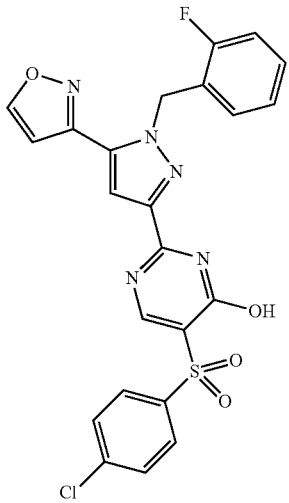
I-253
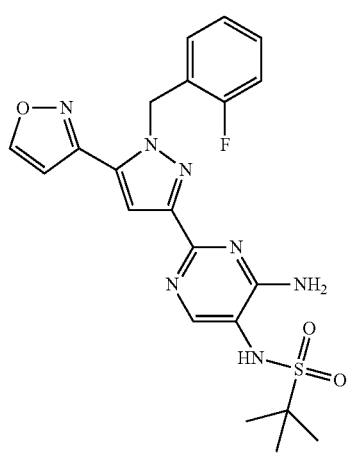 [SMILES: CC(C)(C)S(=O)(=O)Nc1cnc(-c2cc(-c3ccon3)n(Cc3ccccc3F)n2)nc1N]
I-251
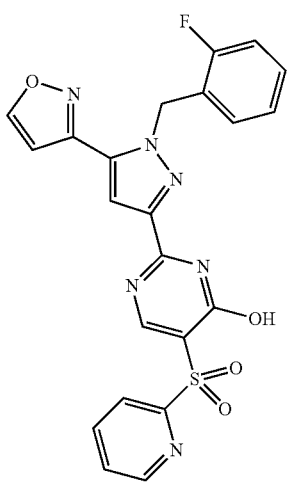
I-254
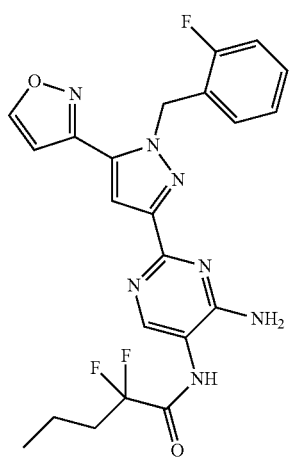 [SMILES: CCCC(F)(F)C(=O)Nc1cnc(-c2cc(-c3ccon3)n(Cc3ccccc3F)n2)nc1N]
I-252
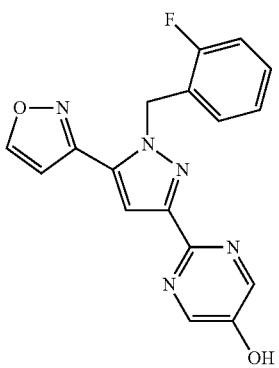 [SMILES: Oc1cnc(-c2cc(-c3ccon3)n(Cc3ccccc3F)n2)nc1]
I-255

TABLE 1B-continued
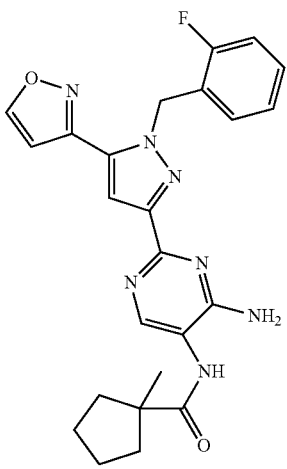 [SMILES: CC1(C(=O)Nc2cnc(-c3cc(-c4ccon4)n(Cc4ccccc4F)n3)nc2N)CCCC1]
I-256
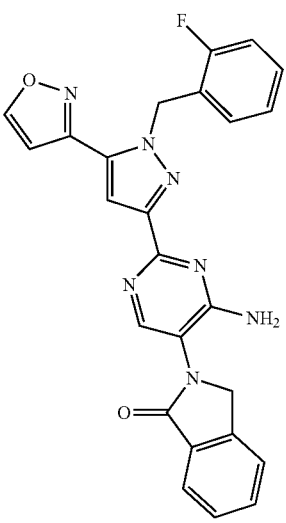
I-259
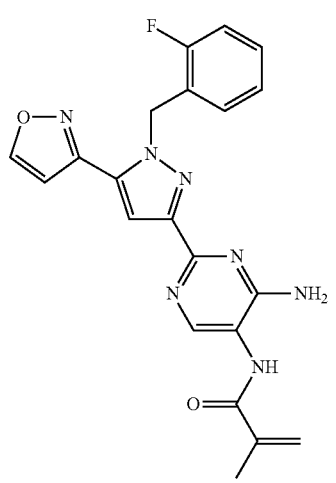 [SMILES: C=C(C)C(=O)Nc1cnc(-c2cc(-c3ccon3)n(Cc3ccccc3F)n2)nc1N]
I-257
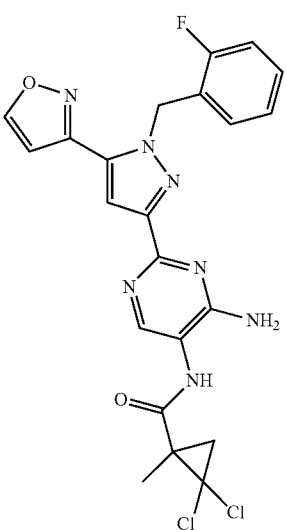 [SMILES: CC1(C(=O)Nc2cnc(-c3cc(-c4ccon4)n(Cc4ccccc4F)n3)nc2N)CC1(Cl)Cl]
I-260
I-258
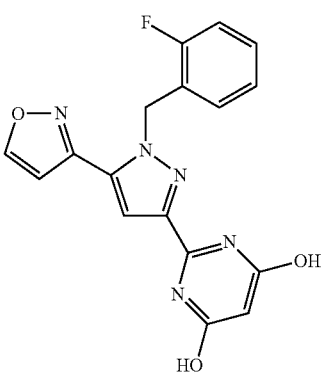 [SMILES: Oc1cc(O)nc(-c2cc(-c3ccon3)n(Cc3ccccc3F)n2)n1]
I-261

TABLE 1B-continued
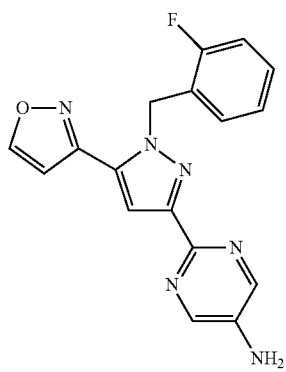 [SMILES: Nc1cnc(-c2cc(-c3ccon3)n(Cc3ccccc3F)n2)nc1]
I-262
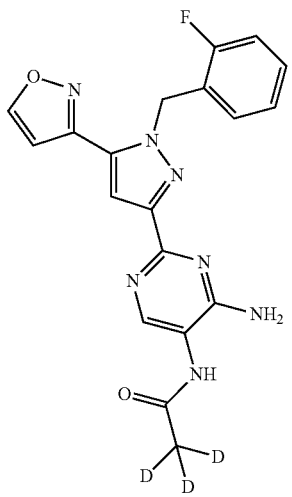 [SMILES: [2H]C([2H])([2H])C(=O)Nc1cnc(-c2cc(-c3ccon3)n(Cc3ccccc3F)n2)nc1N]
I-263
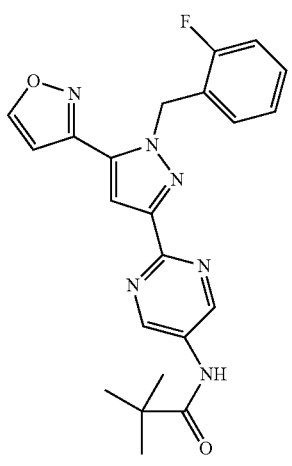 [SMILES: CC(C)(C)C(=O)Nc1cnc(-c2cc(-c3ccon3)n(Cc3ccccc3F)n2)nc1]
I-264
TABLE 1B-continued
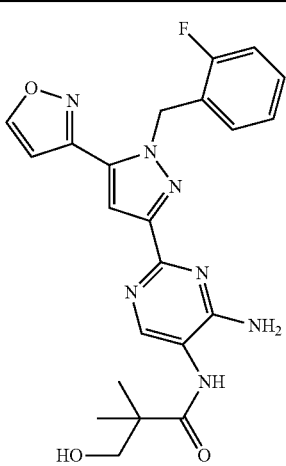
I-265
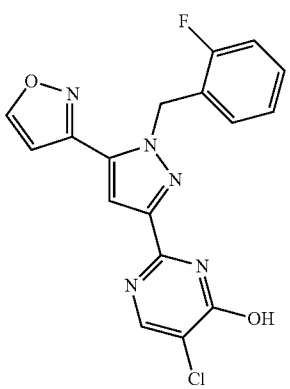
I-266
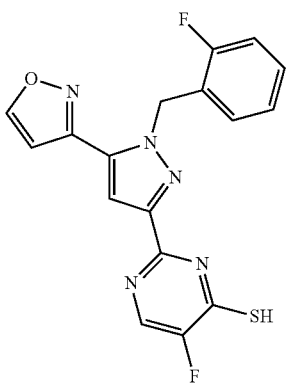 [SMILES: Fc1ccccc1Cn1nc(-c2ncc(F)c(S)n2)cc1-c1ccon1]
I-267

TABLE 1B-continued
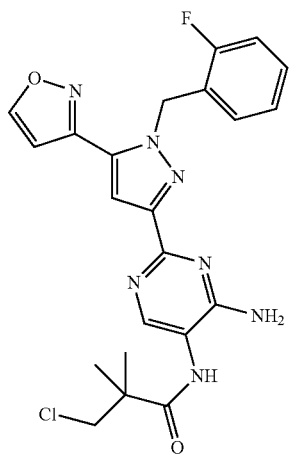 [SMILES: CC(C)(CCl)C(=O)Nc1cnc(-c2cc(-c3ccon3)n(Cc3ccccc3F)n2)nc1N]
I-268
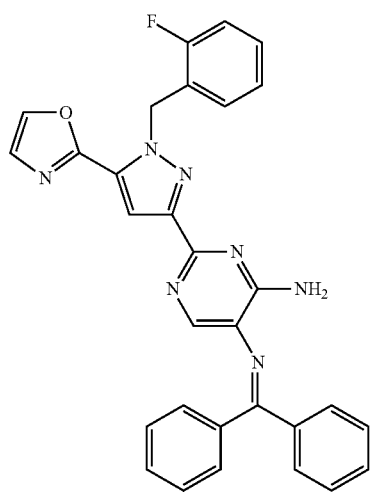 [SMILES: Nc1nc(-c2cc(-c3ncco3)n(Cc3ccccc3F)n2)ncc1N=C(c1ccccc1)c1ccccc1]
I-269
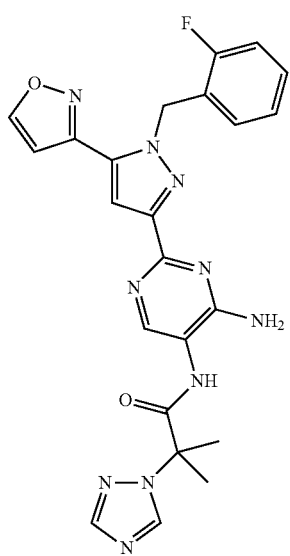 [SMILES: CC(C)(C(=O)Nc1cnc(-c2cc(-c3ccon3)n(Cc3ccccc3F)n2)nc1N)n1cncn1]
I-270
TABLE 1B-continued
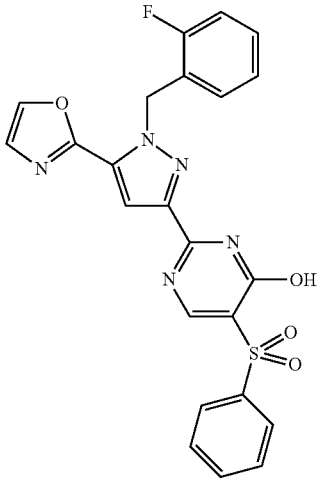 [SMILES: O=S(=O)(c1ccccc1)c1cnc(-c2cc(-c3ncco3)n(Cc3ccccc3F)n2)nc1O]
I-271
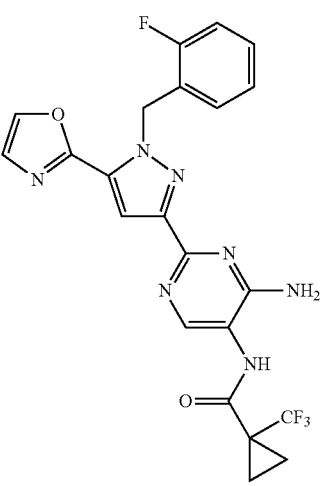 [SMILES: Nc1nc(-c2cc(-c3ncco3)n(Cc3ccccc3F)n2)ncc1NC(=O)C1(C(F)(F)F)CC1]
I-272
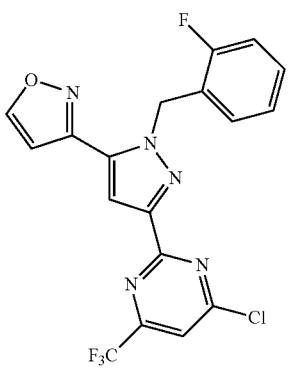
I-273

TABLE 1B-continued
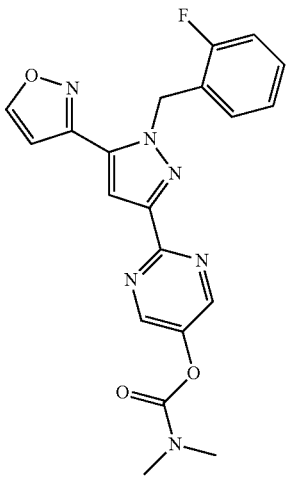 [SMILES: CN(C)C(=O)Oc1cnc(-c2cc(-c3ccon3)n(Cc3ccccc3F)n2)nc1]
I-274
TABLE 1C
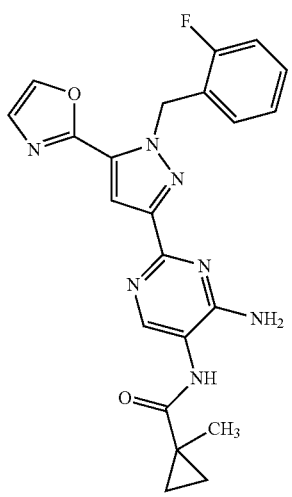 [SMILES: CC1(C(=O)Nc2cnc(-c3cc(-c4ncco4)n(Cc4ccccc4F)n3)nc2N)CC1]
I-275
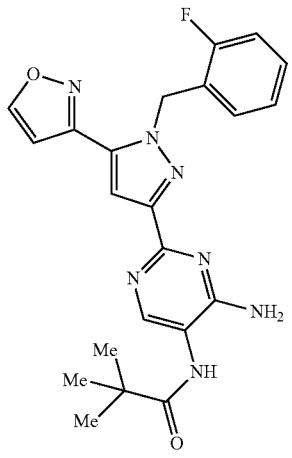 [SMILES: CC(C)(C)C(=O)Nc1cnc(-c2cc(-c3ccon3)n(Cc3ccccc3F)n2)nc1N]
I-277
TABLE 1C-continued
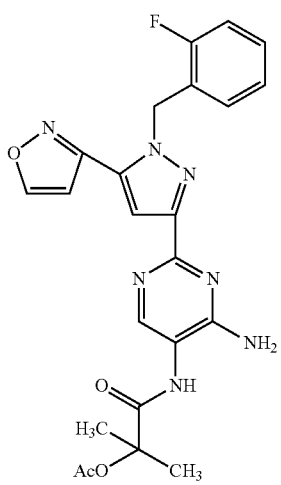 [SMILES: CC(=O)OC(C)(C)C(=O)Nc1cnc(-c2cc(-c3ccon3)n(Cc3ccccc3F)n2)nc1N]
I-278
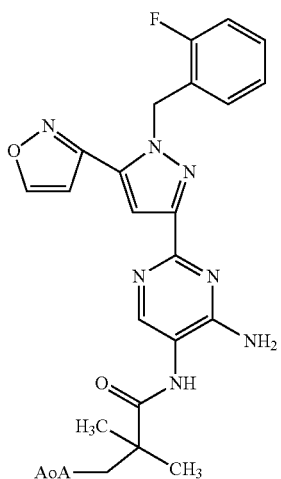
I-280
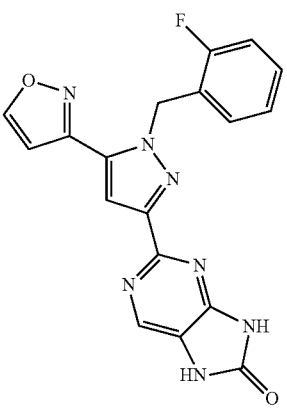 [SMILES: O=c1[nH]c2cnc(-c3cc(-c4ccon4)n(Cc4ccccc4F)n3)nc2[nH]1]
I-281

TABLE 1C-continued
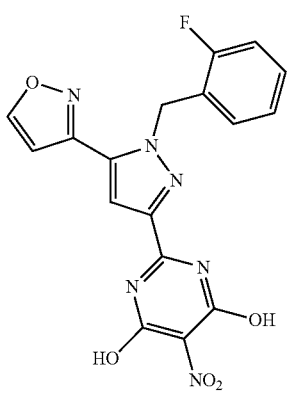 [SMILES: O=[N+]([O-])c1c(O)nc(-c2cc(-c3ccon3)n(Cc3ccccc3F)n2)nc1O]
I-282
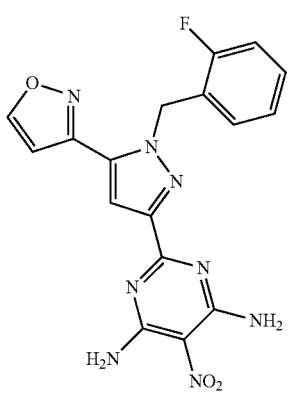
I-283
TABLE 1D
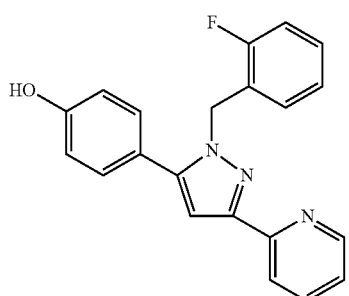
I-310
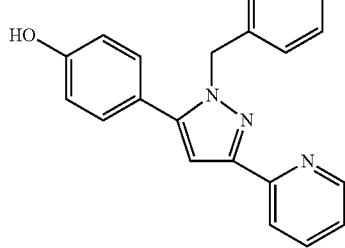
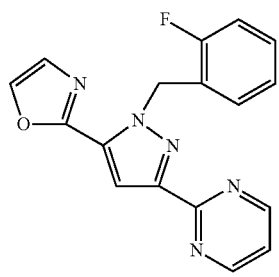
I-309
TABLE 1D-continued
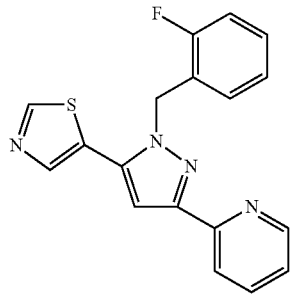 [SMILES: Fc1ccccc1Cn1nc(-c2ccccn2)cc1-c1cncs1]
I-311
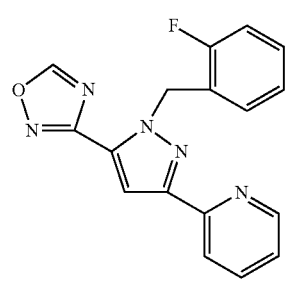 [SMILES: Fc1ccccc1Cn1nc(-c2ccccn2)cc1-c1ncon1]
I-304
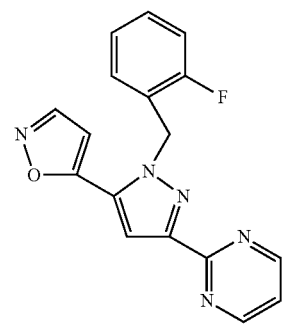 [SMILES: Fc1ccccc1Cn1nc(-c2ncccn2)cc1-c1ccno1]
I-305
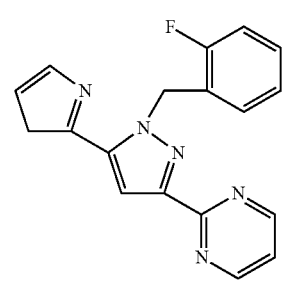 [SMILES: Fc1ccccc1Cn1nc(-c2ncccn2)cc1C1=NC=CC1]
I-306
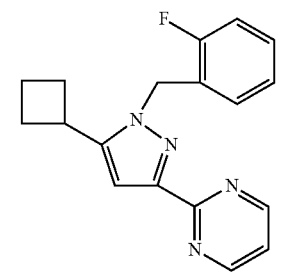 [SMILES: Fc1ccccc1Cn1nc(-c2ncccn2)cc1C1CCC1]
I-307

TABLE 1D-continued
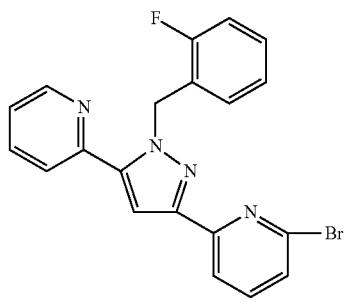 [SMILES: Fc1ccccc1Cn1nc(-c2cccc(Br)n2)cc1-c1ccccn1] I-308
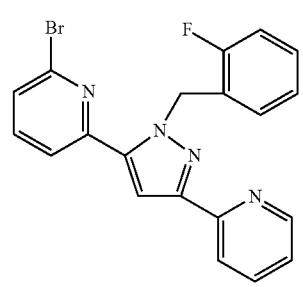 [SMILES: Fc1ccccc1Cn1nc(-c2ccccn2)cc1-c1cccc(Br)n1] I-313
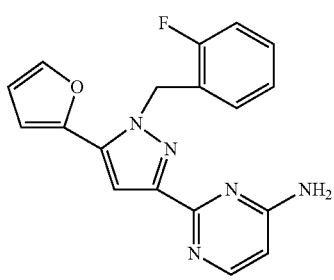 [SMILES: Nc1ccnc(-c2cc(-c3ccco3)n(Cc3ccccc3F)n2)n1] I-284
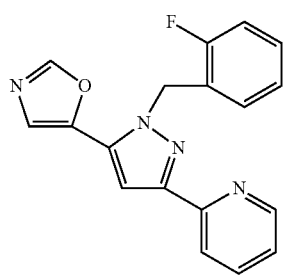 [SMILES: Fc1ccccc1Cn1nc(-c2ccccn2)cc1-c1cnco1] I-285
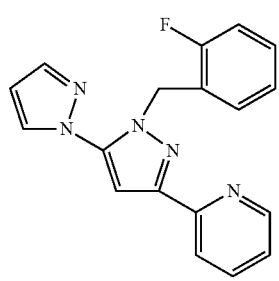 [SMILES: Fc1ccccc1Cn1nc(-c2ccccn2)cc1-n1cccn1] I-286
TABLE 1D-continued
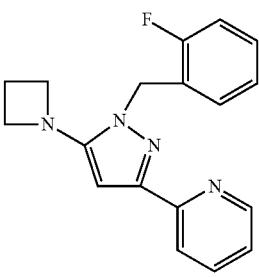 [SMILES: Fc1ccccc1Cn1nc(-c2ccccn2)cc1N1CCC1] I-287
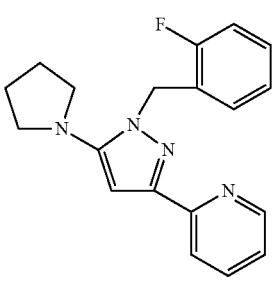 [SMILES: Fc1ccccc1Cn1nc(-c2ccccn2)cc1N1CCCC1] I-288
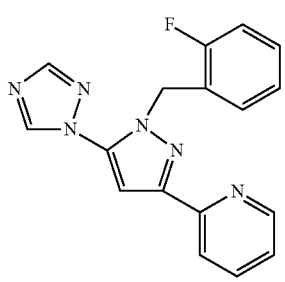 [SMILES: Fc1ccccc1Cn1nc(-c2ccccn2)cc1-n1cncn1] I-289
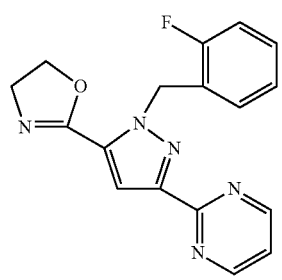 [SMILES: Fc1ccccc1Cn1nc(-c2ncccn2)cc1C1=NCCO1] I-290
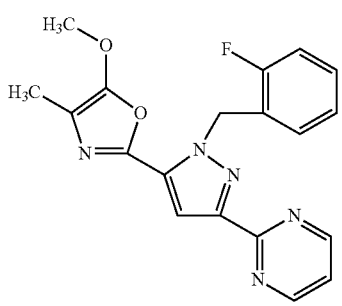 [SMILES: COc1oc(-c2cc(-c3ncccn3)nn2Cc2ccccc2F)nc1C] I-291

TABLE 1D-continued
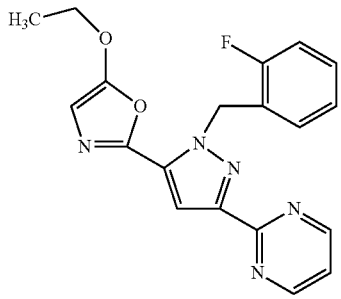 [SMILES: CCOc1cnc(-c2cc(-c3ncccn3)nn2Cc2ccccc2F)o1]
I-292
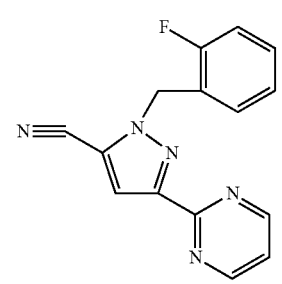 [SMILES: N#Cc1cc(-c2ncccn2)nn1Cc1ccccc1F]
I-293
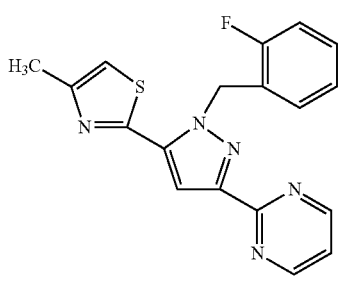 [SMILES: Cc1csc(-c2cc(-c3ncccn3)nn2Cc2ccccc2F)n1]
I-294
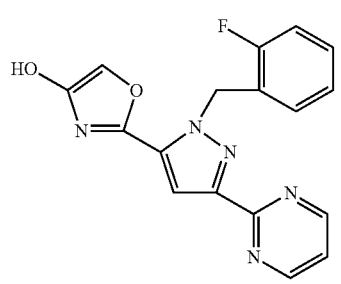 [SMILES: Oc1coc(-c2cc(-c3ncccn3)nn2Cc2ccccc2F)n1]
I-295
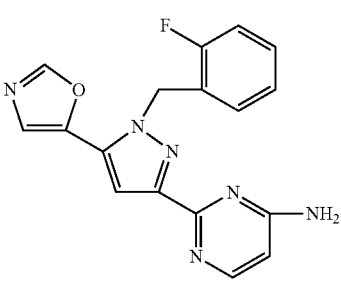 [SMILES: Nc1ccnc(-c2cc(-c3cnco3)n(Cc3ccccc3F)n2)n1]
I-296
TABLE 1D-continued
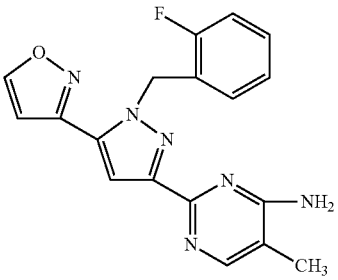 [SMILES: Cc1cnc(-c2cc(-c3ccon3)n(Cc3ccccc3F)n2)nc1N]
I-297
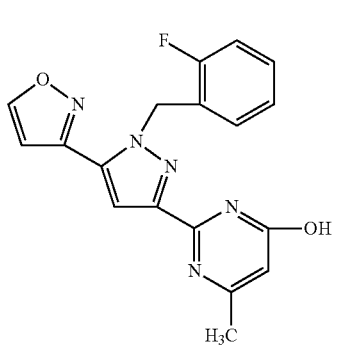 [SMILES: Cc1cc(O)nc(-c2cc(-c3ccon3)n(Cc3ccccc3F)n2)n1]
I-298
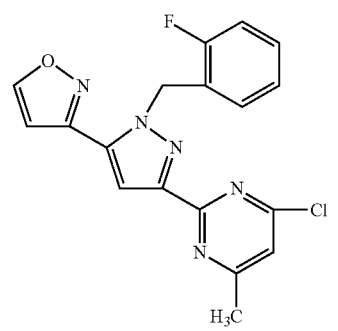
I-299
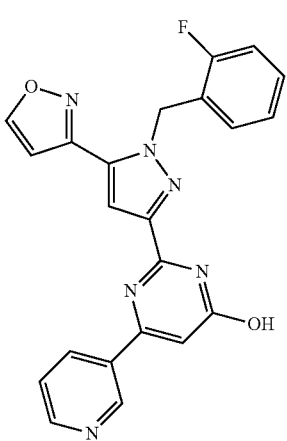
I-300

TABLE 1D-continued

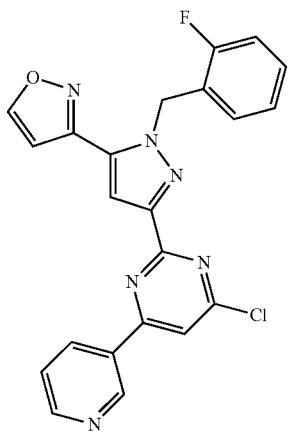 [SMILES: Fc1ccccc1Cn1nc(-c2nc(Cl)cc(-c3cccnc3)n2)cc1-c1ccon1]

I-301

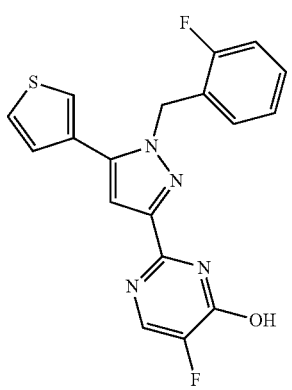 [SMILES: Oc1nc(-c2cc(-c3ccsc3)n(Cc3ccccc3F)n2)ncc1F]

I-302

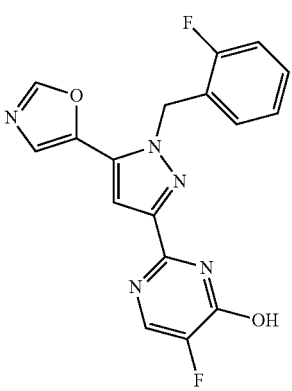 [SMILES: Oc1nc(-c2cc(-c3cnco3)n(Cc3ccccc3F)n2)ncc1F]

I-303

TABLE 1D-continued

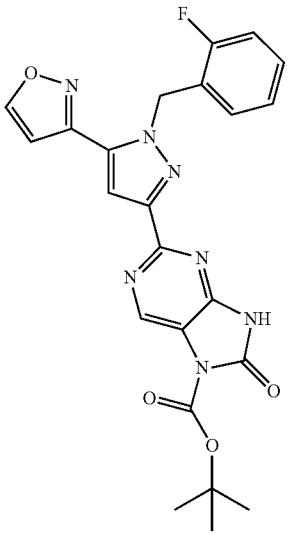

I-312

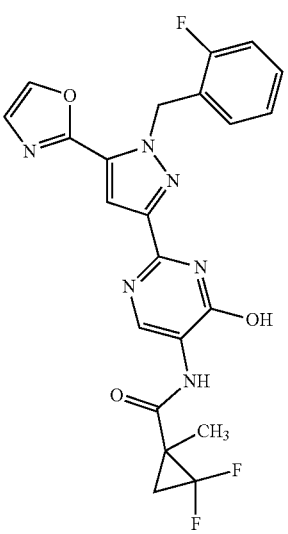

I-276

Methods of Preparing the Compounds

The compounds of Formula I may be prepared according to the schemes and examples depicted and described below. Unless otherwise specified, the starting materials and various intermediates may be obtained from commercial sources, prepared from commercially available compounds or prepared using well-known synthetic methods. Another aspect of the present invention is a process for preparing the compounds of Formula I as disclosed herein.

General synthetic procedures for the compounds of this invention are described below. The synthetic schemes are presented as examples and do not limit the scope of the invention in any way.

I. General Procedure A

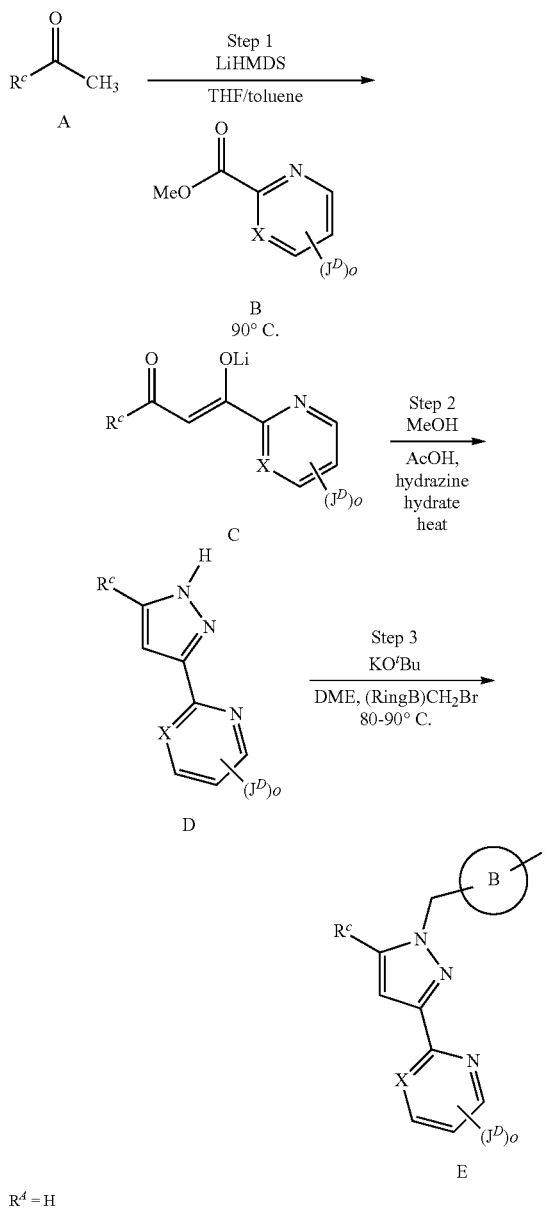

Step 1: Dione Enolate Formation:

To a cooled solution of ketone A in THF, LiHMDS (e.g., 1.05-1.1 eq, 1.0 M in toluene) is added. The reaction is allowed to warm to room temperature, then charged with ester B (1.0 eq). At this time, the reaction is cooled and stirred at that temperature until judged complete (e.g., using either TLC or LC/MS analysis). Once the reaction is complete (reaction time was typically 1-3 h), the product dione enolate C is precipitated using excess diethyl ether, and then filtered and dried. This solid can be used in Step 2, i.e., the cyclization step, without any further purification.

Step 2: Pyrazole Formation:

Dione enolate C is diluted with methanol and consecutively charged with AcOH (e.g., 1-3 eq) and hydrazine hydrate (e.g., 1.0 eq). The reaction mixture is heated and stirred until cyclization is deemed complete (e.g., by LC/MS analysis). Once complete (reaction time was typically less than 10 min), the reaction mixture is concentrated and the resulting pyrazole D can be used in Step 3, i.e., the alkylation step, without any further purification. In some cases, upon cooling, pyrazole D crashes out of solution and is collected by filtration and dried. In some cases, the pyrazole is purified by $SiO_2$ chromatography using an appropriate gradient of EtOAc in hexanes.

Step 3: Alkylation:

Pyrazole D is dissolved in DME and consecutively charged with potassium tert-butoxide (or an alternative base) and the appropriately substituted benzyl bromide (e.g., 1-3 eq). At this time, the reaction is heated to reflux (or above, when using closed vials as reaction vessels) and can be monitored by LC/MS analysis. Once complete, the reaction solution is allowed to cool and the solids are filtered off. The filtrate is then concentrated and the resulting crude oil can be purified using chromatography on $SiO_2$ with an appropriate solvent gradient (e/g/. ethyl acetate/hexanes or DCM/methanol) to give compound E. The alkylation results in two regioisomers, which are readily separable by a standard chromatographic method.

II. General Procedure B

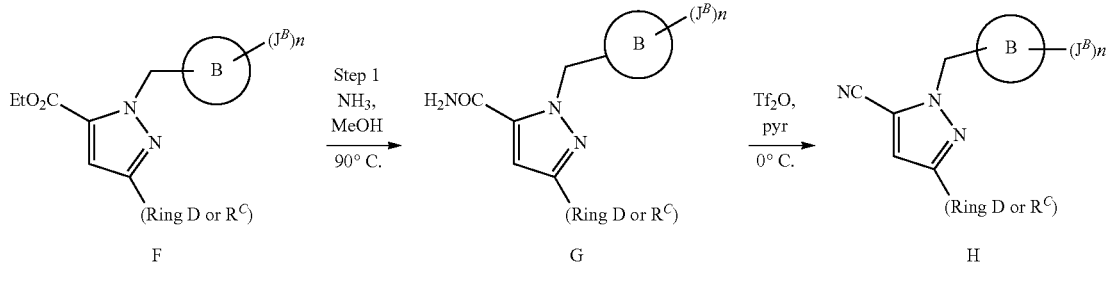

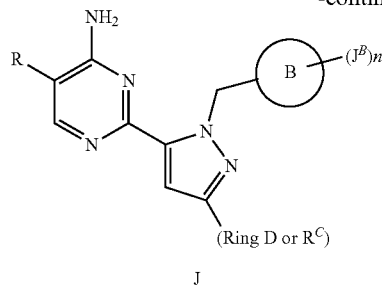 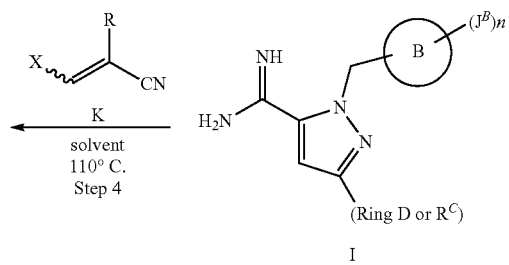

Step 1: Primary Amide Formation:

Ethyl ester F (this is the same as E if it is made according to General Procedure A) is mixed with an excess of a solution of ammonia in methanol (e.g., 7.0 N in methanol) and NaCN (e.g., 0.25 mol %) added as a catalyst. The reaction mixture is then heated and stirred until the reaction is complete (e.g., based on analyses by LC/MS or TLC). Once deemed complete, the reaction mixture is concentrated and the resulting material diluted with DCM and filtered off. The filtrate is concentrated to give amide G, typically obtained as a white foam.

Step 2: Nitrile Formation:

Amide G is dissolved in pyridine (e.g., 0.25M) and cooled (e.g., to 0° C.). Trifluoroacetic anhydride is then added. Once the reaction is complete (e.g., as monitored by LC/MS or TLC), the reaction mixture is diluted with DCM and washed with water. The aqueous portion is back extracted with DCM and the organic portions combined, dried (e.g., with $Na_2SO_4$), filtered, and concentrated under vacuum. The crude oil is purified using chromatography such as $SiO_2$ chromatography and an appropriate solvent gradient (e.g., ethyl acetate/hexanes or DCM/methanol) to give nitrile H, typically obtained as a white foam.

Step 3: Carboximidamide Formation:

Nitrile H is added to a solution of sodium methoxide in methanol (e.g., 95 wt % in methanol) and the reaction mixture is heated (e.g., at 35° C.) and stirred, e.g., for 3-24 h. Acetic acid and ammonium chloride are then added and the mixture stirred at reflux, e.g., for 12-16 h. At this time, the reaction mixture is concentrated, and the remaining crude material is diluted with EtOAc and basified, e.g., by the addition of a saturated solution of sodium carbonate. The heterogeneous reaction mixture is allowed to separate into two layers. The aqueous portion is then extracted with DCM and the organic portions are combined, dried (e.g., with $Na_2SO_4$), filtered, and concentrated. The crude carboximidamide I is used in Step 4, i.e., the cyclization reaction, to generate the targeted pyrimidine.

Step 4: Pyrimidine Formation:

Carboximidamide I is dissolved in an appropriate solvent (e.g., xylene, toluene, or pyridine) and charged with vinyl nitrile K. The reaction mixture is heated at reflux until >90% complete, e.g., as determined by LC/MS analysis. The reaction mixture is then concentrated, DCM added, and the mixture extracted with water. The aqueous portion is then extracted with DCM and the organic portions combined, dried (e.g., with $Na_2SO_4$), filtered, and concentrated. The crude oil is purified by preparative HPLC to give pyrimidine J, as a solid or liquid, as indicated below.

III. General Procedure C-I

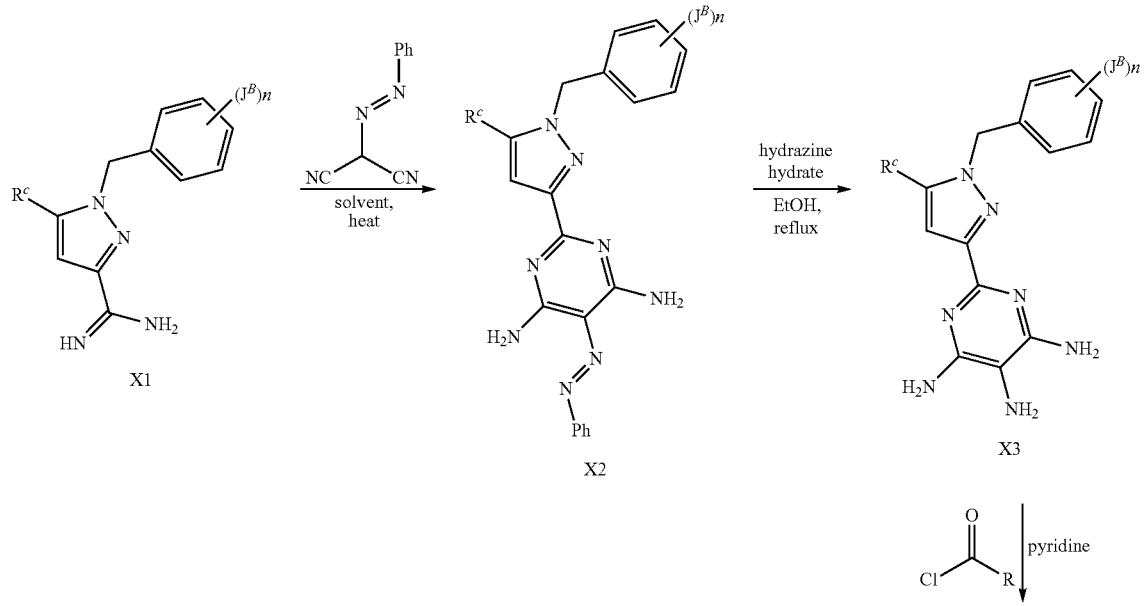

-continued

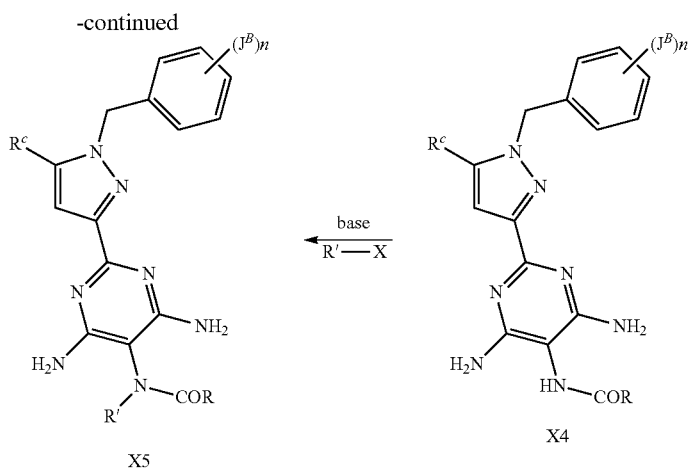

Step 1: Pyrimidine Formation:

Carboximidamide X1 was dissolved in DMF (or ethanol) and charged with NaOMe (1-2 eq). 2-(Phenyldiazenyl)malononitrile (1.1 eq) was added, and the reaction vessel was then capped and heated at 110° C. until >90% complete by LC/MS analysis. The reaction mixture was then diluted with DCM and extracted with NH$_4$Cl (conc., aq). The aqueous portion was then extracted an additional two times with DCM. The organic portions were then combined, dried (Na$_2$SO$_4$), filtered, and concentrated. The crude solid was purified by either precipitation or normal phase chromatography using an appropriate methanol/DCM gradient to give desired pyrimidine X2.

Step 2: Hydrazinolysis:

To a solution of pyrimidine X2 in EtOH was added hydrazine hydrate (>50 eq). Reaction mixture was then heated to reflux and stirred 14-48 h, or until reaction is judged complete by LC/MS analysis. The reaction was then directly concentrated and the crude material was purified by either precipitation, reverse phase preparative HPLC, or by normal phase chromatography using appropriate methanol/DCM gradient to give desired pyrimidine X3.

Step 3: Acylation:

Tri-amino pyrimidine X3 was dissolved in pyridine and cooled to 0° C., at which time the acylating reagent (acyl chloride, chloroformate, etc., 1.0 eq) was added. The reaction was stirred at 0° C. until judged complete by LC/MS analysis (typically <2 h min). The crude reaction was then diluted with DCM and washed with water (2×). The organic portion was then dried, filtered, and concentrated. The crude material was then purified by either precipitation, reverse phase preparative HPLC, or by normal phase chromatography using an appropriate methanol/DCM gradient to give desired pyrimidine X4.

Step 4: Alkylation:

Pyrimidine X4 was dissolved in solvent (most typically DMF) and cooled to 0° C. Base (typically sodium hydride) (1.2 eq) was added followed by the electrophile (intramolecular variants do not require exogenous electrophiles), and the resulting reaction was closely monitored by LC/MS analysis.

Once complete, the reaction was quenched with water and extracted with DCM (3×). The organic portions were then combined, dried (Na$_2$SO$_4$), filtered, and concentrated. The crude oil was purified by either precipitation, reverse phase preparative HPLC, or by normal phase chromatography and a methanol/DCM gradient to give desired pyrimidine X5.

IV. General Procedure C-II

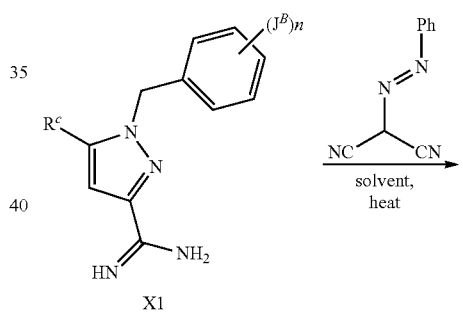

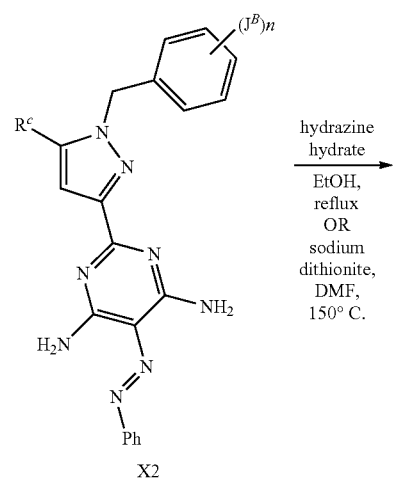

-continued

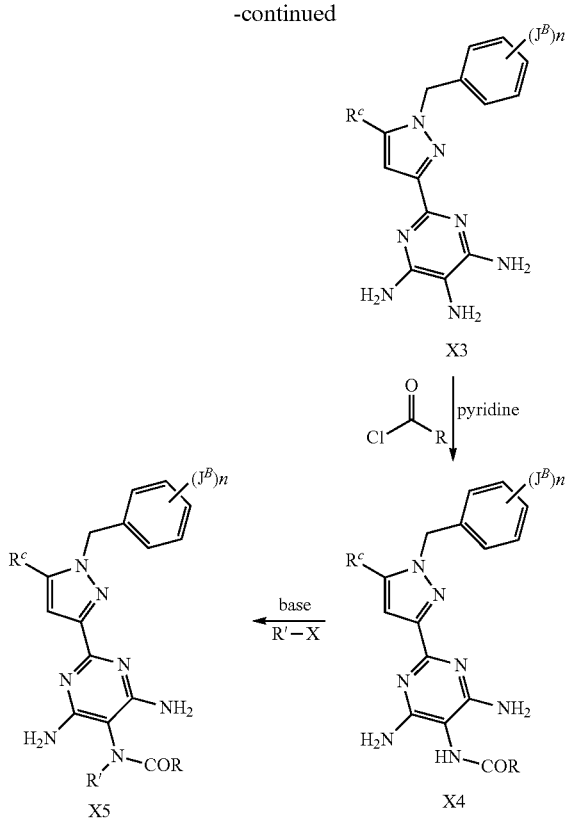

Step 1, Pyrimidine Formation:

Carboximidamide X1 (prepared according to General Procedure B) was dissolved in DMF (or ethanol) and charged with NaOMe (1-2 eq). 2-(Phenyldiazenyl)malononitrile (1.1 eq) was added, and the reaction vessel was then capped and heated at 110° C. until >90% complete by LC/MS analysis. The reaction mixture was then diluted with DCM and extracted with NH$_4$Cl (conc., aq). The aqueous portion was then extracted an additional two times with DCM. The organic portions were then combined, dried (Na$_2$SO$_4$), filtered, and concentrated. The crude solid was purified by either precipitation or normal phase chromatography using an appropriate methanol/DCM gradient to give desired pyrimidine X2.

Step 2, Hydrazinolysis:

To a solution of pyrimidine X2 in EtOH was added hydrazine hydrate (>50 eq). Reaction mixture was then heated to reflux and stirred 14-48 h, or until reaction was judged complete by LC/MS analysis. The reaction was then directly concentrated and the crude material was purified by either precipitation, reverse phase preparative HPLC or by normal phase chromatography using an appropriate methanol/DCM gradient to give desired pyrimidine X3.

Alternative Procedure for Step 2:

To a solution of pyrimidine X2 in DMF was added sodium hydroxide (3 eq as a 2.0N solution) and sodium dithionite (5 eq). Reaction vessel (typically scintillation vial) was then moved to a hot plate set at 150° C. until reaction is judged complete by LC/MS analysis. The reaction was then diluted with DCM and filtered. The filtrate was concentrated and the resulting crude material was purified via flash chromatography (SiO$_2$) using a 0-40% DCM/MeOH gradient to deliver the desired X3.

Step 3, Acylation:

Tri-amino pyrimidine X3 was dissolved in pyridine and cooled to 0° C., at which time the acylating reagent (acyl chloride, chloroformate, etc., 1.0 eq) was added. The reaction was stirred at 0° C. until judged complete by LC/MS analysis (typically <2 h min). The crude reaction was then diluted with DCM and washed with water (2×). The organic portion was then dried, filtered, and concentrated. The crude material was then purified by either precipitation, reverse phase preparative HPLC, or by natural phase chromatography using an appropriate methanol/DCM gradient to give desired pyrimidine X4.

Step 4, Alkylation:

Pyrimidine X4 was dissolved in solvent (most typically DMF) and cooled to 0° C. Base (typically sodium hydride) (1.2 eq) was added followed by the electrophile (intramolecular variants do not require exogenous electrophiles), and the resulting reaction was closely monitored by LC/MS analysis. Once complete, the reaction was quenched with water and extracted with DCM (3 times). The organic portions were then combined, dried (Na$_2$SO$_4$), filtered, and concentrated. The crude oil was purified by either precipitation, reverse phase preparative HPLC, or by normal phase chromatography and a methanol/DCM gradient to give desired pyrimidine X5.

V. General Procedure D

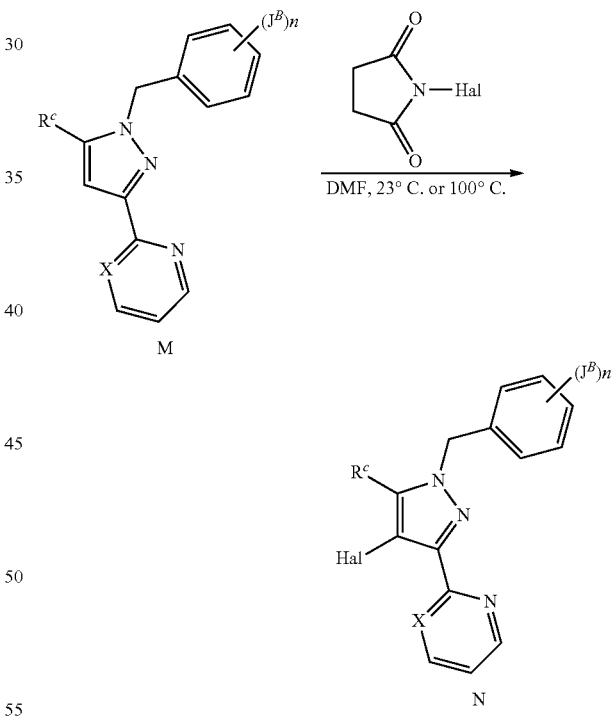

To a solution of pyrazole M in N,N-dimethylformamide was added N-bromosuccinimide (NBS), N-chlorosuccinimide (NCS), or N-iodosuccinimide (NIS) (1.5 equivalents). The solution was stirred at 23° C. (for NBS and NCS) or 100° C. (for NIS) for 3-17 hr until completion as determined by LC/MS analysis. After dilution with saturated aqueous sodium bicarbonate and ethyl acetate, the layers were separated and the aqueous layer was extracted with ethyl acetate (twice). The organics were combined, washed with water (twice), brine, dried over magnesium sulfate, filtered, and the solvent was removed in vacuo. The crude residue was purified by silica gel column chromatography (ethyl acetate/hexanes) to yield the desired product N.

V. General Procedure E

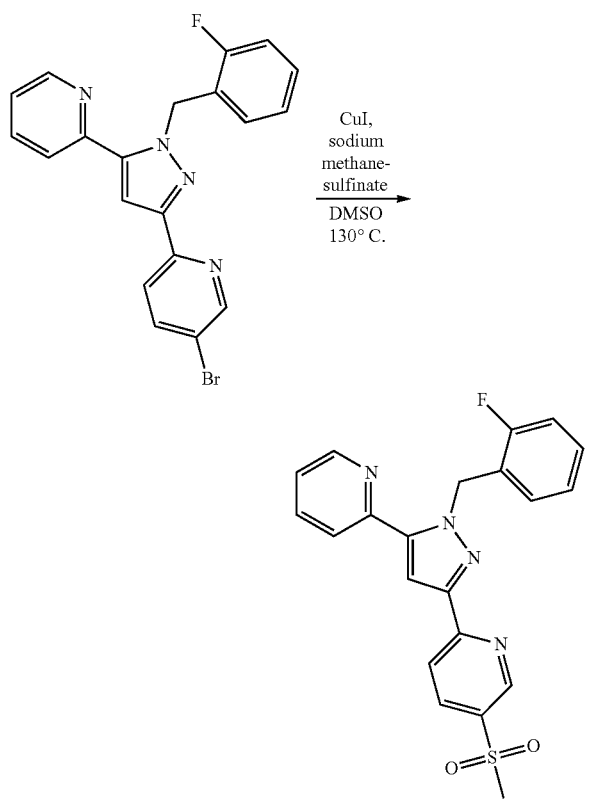

A suspension of 5-bromo-2-(1-(2-fluorobenzyl)-5-(pyridin-2-yl)-1H-pyrazol-3-yl)pyridine, copper(I) iodide (3.0 eq.) and sodium methanesulfinate (3.0 eq.) in DMSO was warmed to 130° C. and stirred at that temperature until completion (by LC/MS analysis). Once complete (reaction time was typically 3-6 h), the reaction solution was cooled to rt and saturated solutions of $NH_4Cl$ and $NaHCO_3$ (2:1 ratio) were added. The resultant mixture was stirred for 1 h and then extracted with EtOAc. The organic phases were dried over $Na_2SO_4$, filtered and conc. The crude product was purified using $SiO_2$ chromatography and an appropriate gradient (ethyl acetate/hexanes) to give 2-(1-(2-fluorobenzyl)-5-(pyridin-2-yl)-1H-pyrazol-3-yl)-5-(methylsulfonyl)pyridine as a white solid (61% yield).

VI. General Procedure F

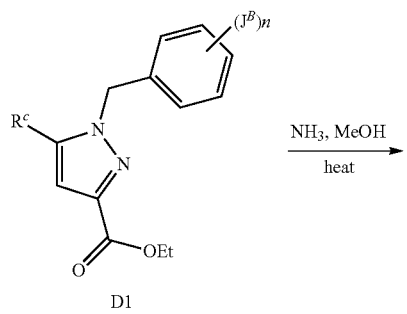

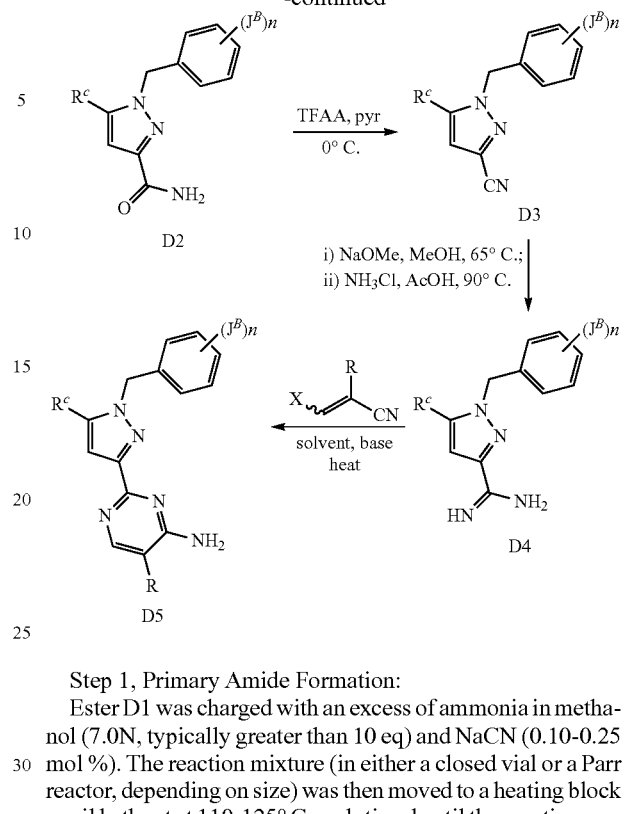

Step 1, Primary Amide Formation:

Ester D1 was charged with an excess of ammonia in methanol (7.0N, typically greater than 10 eq) and NaCN (0.10-0.25 mol %). The reaction mixture (in either a closed vial or a Parr reactor, depending on size) was then moved to a heating block or oil bath set at 110-125° C. and stirred until the reaction was complete. At this time, the reaction mixture was directly concentrated and the resulting material was diluted with DCM and filtered. The filtrate was again concentrated to give amide D2, which was typically carried on to the nitrile formation step without any further purification.

Step 2, Nitrile Formation:

To a cooled (0° C.) solution of amide D2 in pyridine (0.25M), was added trifluoroacetic anhydride (2 eq, fumes). Reaction mixture was stirred at this temperature for ~2 h (or until complete), at which time it was diluted with DCM and extracted with ammonium chloride (sat'd aq). The aqueous portion was then back extracted with additional DCM. The organic portions were then combined, dried (e.g., with $Na_2SO_4$), filtered, and concentrated. The crude oil was then purified using chromatography ($SiO_2$) and an appropriate gradient (e.g., ethyl acetate/hexanes or DCM/methanol) to give nitrile D3.

Step 3, Carboximidamide Formation:

Nitrile D3 (1 eq) was added to a solution of sodium methoxide in methanol (3 eq). The reaction mixture was heated (typically ~65° C.) and stirred for 2-4 h. At this time, acetic acid (1 eq) and ammonium chloride (5 eq) were added and the reaction was refluxed until complete. Once complete, the reaction mixture was concentrated, basified with a sodium carbonate (sat'd aq), and extracted with EtOAc (3×). The organic portions were then combined, dried (e.g., with $Na_2SO_4$), filtered, and concentrated. The crude carboximidamide D4 was carried onto the cyclization reaction without any further purification.

Step 4, Pyrimidine Formation:

Carboximidamide D4 was dissolved in an appropriate solvent (e.g., xylene, toluene, or pyridine) and charged with the appropriate vinyl nitrile (in some cases, 1 eq DBU was added to facilitate cyclization). The reaction mixture was heated at elevated temperature (typically 110° C., but was solvent dependent) until conversion was complete. Once complete, the desired compound was isolated in multiple ways: (1) concentration, then precipitation from diethyl ether; (2) dilution with DCM, washing with water, then purifying the concentrated organic portion with reverse-phase HPLC or SiO$_2$ chromatography; or (3) filtering off precipitated desired compound directly from the reaction mixture VII. General Procedure G

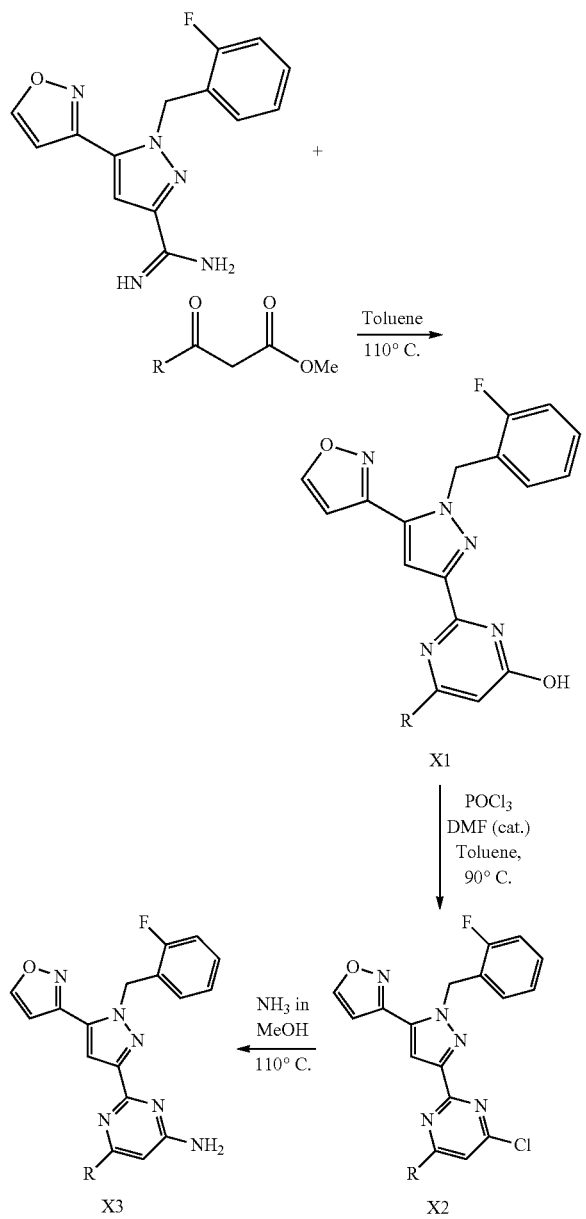

A solution of the requisite 1-(2-fluorobenzyl)-5-(isoxazol-3-yl)-1H-pyrazole-3-carboximidamide (1 equiv) and appropriate β-ketoester (1 equiv) in toluene was heated to 110° C. until consumption of starting material was complete. Evaporation of the solvent in vacuo, followed by purification via silica gel chromatography using the appropriate solvents, gave the desired pyrimidine X1. To a solution of X1 in toluene was added phosphoryl chloride (2.4 equiv), followed by a catalytic amount of N,N-dimethylformamide. The solution was heated to 90° C. until complete consumption of starting material was observed. The resulting suspension was partitioned between water and ethyl acetate. The layers were separated and the aqueous layer was extracted with ethyl acetate. The organics were combined, dried over magnesium sulfate, filtered, and the solvent was removed in vacuo to give the crude residue. Purification by silica gel chromatography using the appropriate solvent system delivered the intermediate aryl chloride X2. Conversion to the desired aminopyrimidine X3 was achieved by treating chloride X2 with 7N ammonia in methanol (100-150 equiv) and heating the solution to 110° C. for 4 h. The solvent was removed in vacuo and purification of the crude residue by silica gel chromatography (methanol in dichloromethane) provided the desired aminopyrimidine X3.

VIII. General Procedure H

General procedure H, described below, may be used to synthesize various compounds, such as Compound I-195.

Compound I-195

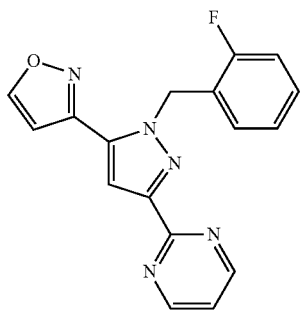 [SMILES: Fc1ccccc1Cn1nc(-c2ncccn2)cc1-c1ccon1]

To a suspension of 3-(3-(pyrimidin-2-yl)-1H-pyrazol-5-yl)isoxazole (Intermediate 8, 73.9 mg, 0.347 mmol) and cesium carbonate (181 mg, 0.555 mmol) in acetonitrile (2 mL) was added 1-(bromomethyl)-2-fluorobenzene (0.059 mL, 0.485 mmol). The suspension was heated to 60° C. for 1 h, at which point the solution had turned faint yellow. LCMS analysis indicated the absence of the starting material. The heterogenous solution was filtered, concentrated, and purified by silica gel chromatography (EtOAc/hex 10-100%). The compound above is the more polar isomer of the alkylation of the central pyrazole. The product was a colorless solid (23%).

$^1$H NMR (400 MHz, CDCl$_3$) δ 8.83 (d, 2H), 8.45 (d, 1H), 7.47 (s, 1H), 7.24 (t, 1H), 7.20-7.15 (m, 1H), 7.02 (td, 1H), 6.96 (td, 1H), 6.84 (td, 1H), 6.59 (d, 1H), 6.03 (s, 2H).

XIX. General Procedure K

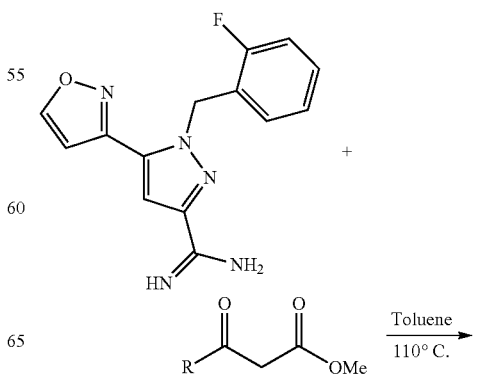

139
-continued

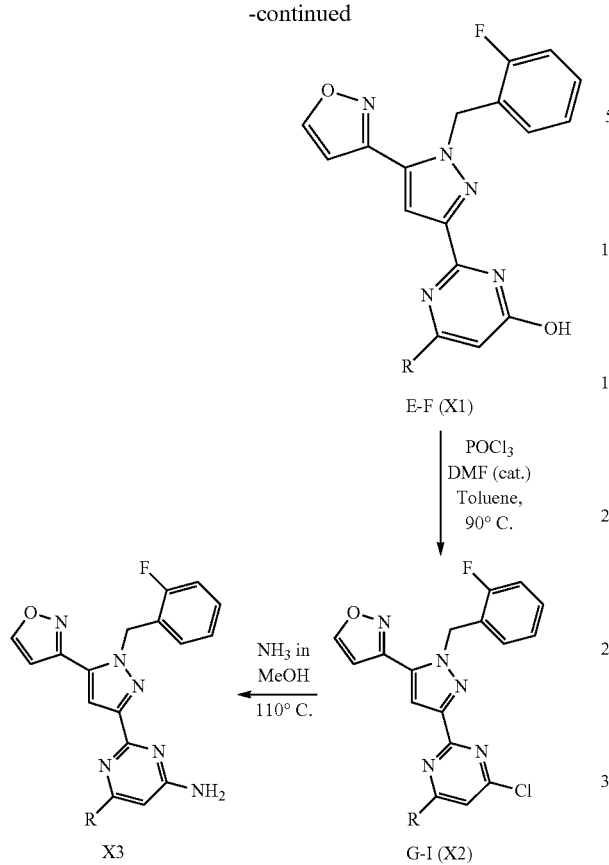

Step 1:

A solution of the requisite 1-(2-fluorobenzyl)-5-(isoxazol-3-yl)-1H-pyrazole-3-carboximidamide (1 equiv) and appropriate β-ketoester (1 equiv) in toluene was heated to 110° C. until consumption of starting material was complete. Evaporation of the solvent in vacuo, followed by purification via silica gel chromatography using the appropriate solvents, gave the desired pyrimidine X1.

Step 2:

To a solution of X1 in toluene was added phosphoryl chloride (2.4 equiv), followed by a catalytic amount of N,N-dimethylformamide. The solution was heated to 90° C. until complete consumption of starting material was observed. The resulting suspension was partitioned between water and ethyl acetate. The layers were separated and the aqueous layer was extracted with ethyl acetate. The organics were combined, dried over magnesium sulfate, filtered, and the solvent was removed in vacuo to give the crude residue. Purification by silica gel chromatography using the appropriate solvent system delivered the intermediate aryl chloride X2.

Step 3:

Conversion to the desired aminopyrimidine X3 was achieved by treating chloride X2 with 7N ammonia in methanol (100-150 equiv) and heating the solution to 110° C. for 4 h. The solvent was removed in vacuo and purification of the crude residue by silica gel chromatography (methanol in dichloromethane) provided the desired aminopyrimidine X3.

140

XX. General Procedure M (Amination)

The following compounds were made utilizing the following amination conditions

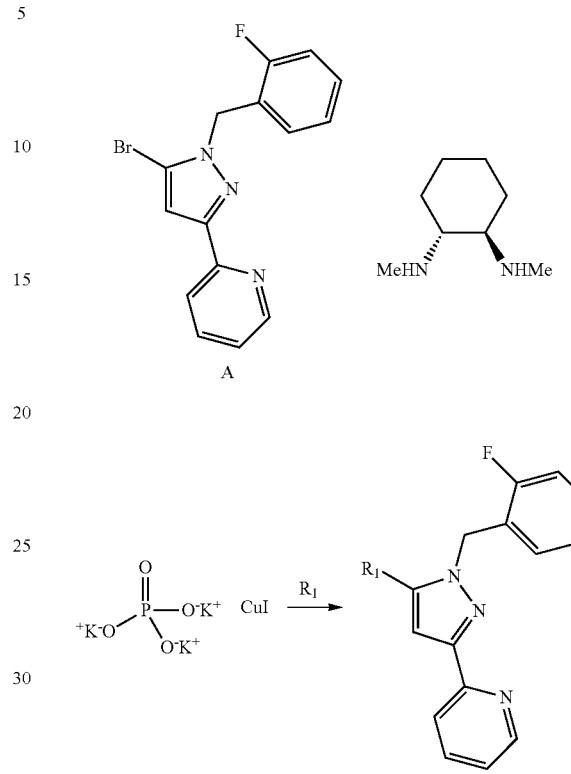

Compound I-286

To a stirring solution of A, (2-(5-bromo-1-(2-fluorobenzyl)-1H-pyrazol-3-yl)pyridine (1 equiv)) in Dioxane was added N1,N2-dimethylcyclohexane-1,2-diamine (0.1 equiv), potassium phosphate (2 equiv), copper(I) iodide (0.1 equiv) and R₁, 1H-pyrazole (1 equiv). The reaction was stirred 16 hr at 110° C. After concentration, product was afforded by both silica gel chromatography as a solid (7.66%).

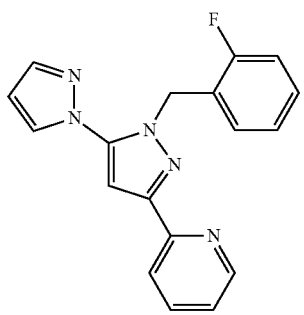 [SMILES: Fc1ccccc1Cn1nc(-c2ccccn2)cc1-n1cccn1]

$^1$H NMR (400 MHz, CDCl$_3$) 8.56-8.57 (m, 1H), 7.93-7.95 (m, 1H), 7.69-7.70 (m, 1H), 7.65-7.69 (m, 1H), 7.54-7.55 (m, 1H), 7.11-7.17 (m, 2H), 6.92-6.96 (m, 3H), 6.91- (s, 1H), 6.36-6.37 (m, 1H), 5.55 (s, 2H).

Compound I-287

To a stirring solution of A, (2-(5-bromo-1-(2-fluorobenzyl)-1H-pyrazol-3-yl)pyridine (1 equiv.)) in Dioxane was added N1,N2-dimethylcyclohexane-1,2-diamine (0.1 equiv), potassium phosphate (2 equiv), copper(I) iodide (0.1 equiv) and R₁, azetidine (1 equiv). The reaction was stirred 16 hr at 110° C. After concentration, product was afforded by both silica gel chromatography as a solid (6.65%).

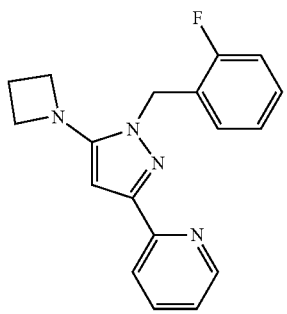 [SMILES: Fc1ccccc1Cn1nc(-c2ccccn2)cc1N1CCC1]

¹H NMR (400 MHz, CDCl₃) 8.62-8.63 (m, 1H), 7.93-7.95 (m, 1H), 7.70 (ddd, 1H), 7.47 (d, 1H), 7.29-7.32 (m, 1H), 7.16-7.20 (m, 2H), 7.07-7.12 (m, 1H), 6.90 (d, 1H), 5.45 (s, 2H), 3.79 (t, 2H), 3.69 (t, 2H), 2.36-2.41 (m, 2H).

Compound I-288

To a stirring solution of A, (2-(5-bromo-1-(2-fluorobenzyl)-1H-pyrazol-3-yl)pyridine (1 equiv.)) in Dioxane was added N1,N2-dimethylcyclohexane-1,2-diamine (0.1 equiv), potassium phosphate (2 equiv), copper(I) iodide (0.1 equiv) and R₁, pyrrolidine (1 equiv). The reaction was stirred 16 hr at 110° C. After concentration, product was afforded by both silica gel chromatography as a solid (16.82%).

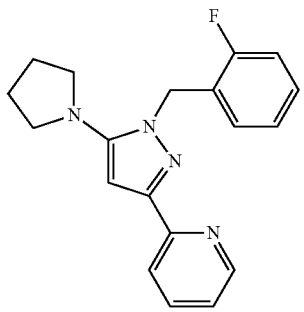 [SMILES: Fc1ccccc1Cn1nc(-c2ccccn2)cc1N1CCCC1]

¹H NMR (400 MHz, CDCl₃) 8.61 (ddd, 1H), 7.95 (ddd, 1H), 7.68 (ddd, 1H), 7.16-7.25 (m, 2H), 7.01-7.07 (m, 2H), 6.93-6.97 (m, 1H), 6.92 (s, 1H), 5.43 (s, 2H), 3.09-3.13 (m, 4H), 1.87-1.90 (m, 4H).

Compound I-289

To a stirring solution of A, (2-(5-bromo-1-(2-fluorobenzyl)-1H-pyrazol-3-yl)pyridine (1 equiv.)) in Dioxane was added N1,N2-dimethylcyclohexane-1,2-diamine (0.1 equiv), potassium phosphate (2 equiv), copper(I) iodide (0.1 equiv) and R₁, 1,2,4-pyrazole (1 equiv). The reaction was stirred 16 hr at 110° C. After concentration, product was afforded by both silica gel chromatography as a solid (2.68%).

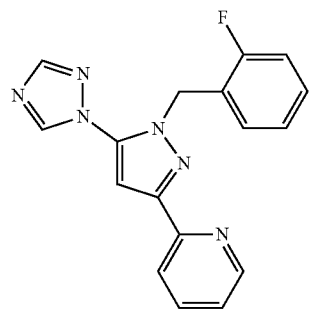 [SMILES: Fc1ccccc1Cn1nc(-c2ccccn2)cc1-n1cncn1]

¹H NMR (400 MHz, CDCl₃) 8.63 (ddd, 1H), 8.24 (s, 1H), 8.17 (s, 1H), 8.01 (ddd, 1H), 7.75 (ddd, 1H), 7.09-7.28 (m, 1H), 7.09 (s, 1H), 7.05-7.06 (m, 1H), 6.97-7.02 (m, 3H), 5.54 (s, 2H).

XXI. General Procedure O

The following compounds were made utilizating the following procedure

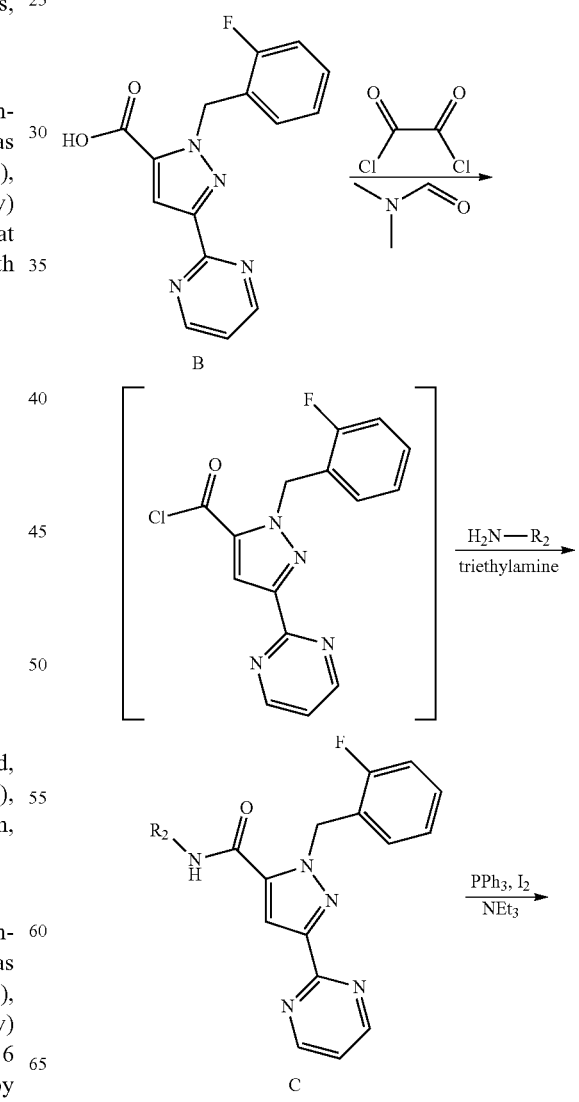

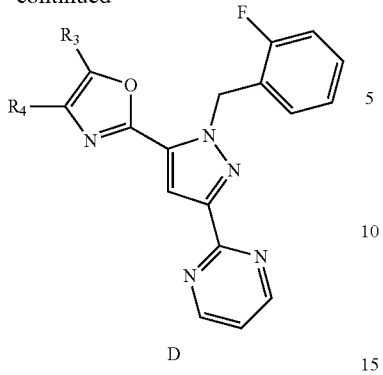

D

Compound I-290

To a solution of B, 1-(2-fluorobenzyl)-3-(pyrimidin-2-yl)-1H-pyrazole-5-carboxylic acid (1 equiv) stirring in DCM was added oxalyl chloride (1.1 equiv) and a catalytic amount of N,N-dimethylformamide. This reaction generated gas and was stirred for 2 hr. The reaction mixture was then concentrated, dried under reduced pressure and subsequently added to a stirring solution of benzene and triethylamine in a 5:1 solution and $R_2$—$NH_2$, 2-bromoethanamine hydrobromide (2 equiv). The temperature was raised to 90° C. and stirred for 16 hr to afford C, where $R_2$ is the closed oxazoline. The reaction was concentrated and purified by silica gel chromatography to afford a solid (10.16%).

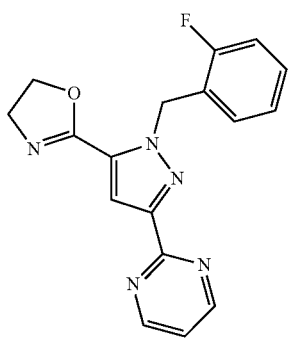 [SMILES: Fc1ccccc1Cn1nc(-c2ncccn2)cc1C1=NCCO1]

$^1$H NMR (400 MHz, CDCl$_3$) 8.81 (d, 2H), 7.55 (s, 1H), 7.21 (t, 1H), 7.16-7.18 (m, 1H), 6.96-7.04 (m, 2H), 6.79-6.83 (m, 1H), 6.09 (s, 2H), 4.35 (t, 2H), 4.03 (t, 2H).

Compound I-291

To a solution of B, 1-(2-fluorobenzyl)-3-(pyrimidin-2-yl)-1H-pyrazole-5-carboxylic acid (1 equiv) stirring in DCM was added oxalyl chloride (1.1 equiv) and a catalytic amount of N,N-dimethylformamide. This reaction generated gas and was stirred for 2 hr. The reaction mixture was then concentrated, dried under reduced pressure and subsequently added to a stirring solution of benzene and triethylamine in a 5:1 solution and $R_2$—$NH_2$, (S)-methyl 2-aminopropanoate hydrochloride (2 equiv) to afford C, where $R_2$ is (S)-methyl 2-aminopropane. This reaction was purified by silica gel chromatography, concentrated and then subsequently treated with triphenylphosphine (2 equiv), iodine (2 equiv) and triethylamine (4 equiv). After stirring for 16 hr under ambient conditions, the reaction was purified by silica gel chromatography to afford D, where $R_3$ is methoxy and $R_4$ is methyl, as desired solid (38.2%).

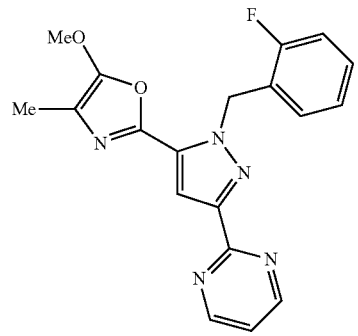 [SMILES: COc1oc(-c2cc(-c3ncccn3)nn2Cc2ccccc2F)nc1C]

$^1$H NMR (400 MHz, CDCl$_3$) 8.82 (d, 2H), 7.52 (d, 1H), 7.20-7.23 (m, 1H), 7.16-7.19 (m, 1H), 6.94-7.04 (m, 2H), 6.85-6.89 (m, 1H), 6.08 (s, 2H), 3.93 (s, 3H), 2.04 (s, 3H).

Compound I-292

To a solution of B, 1-(2-fluorobenzyl)-3-(pyrimidin-2-yl)-1H-pyrazole-5-carboxylic acid (1 equiv) stirring in DCM was added oxalyl chloride (1.1 equiv) and a catalytic amount of N,N-dimethylformamide. This reaction generated gas and was stirred for 2 hr. The reaction mixture was then concentrated, dried under reduced pressure and subsequently added to a stirring solution of benzene and triethylamine in a 5:1 solution and $R_2$—$NH_2$, ethyl 2-aminoacetate to afford C, where $R_2$ is ethyl acetate. This reaction was purified by silica gel chromatography, concentrated and then subsequently treated with triphenylphosphine (2 equiv), iodine (2 equiv) and triethylamine (4 equiv). After stirring for 16 hr under ambient conditions, the reaction was purified by silica gel chromatography to afford D, where $R_3$ is ethoxy and $R_4$ is hydrogen, as desired solid (63.0%).

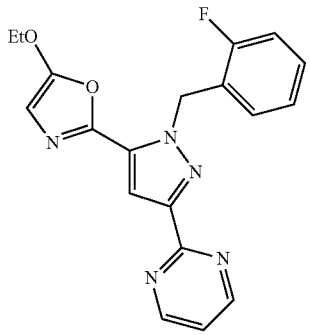 [SMILES: CCOc1cnc(-c2cc(-c3ncccn3)nn2Cc2ccccc2F)o1]

$^1$H NMR (400 MHz, CDCl$_3$) 8.82 (d, 2H), 7.53 (s, 1H), 7.23 (t, 1H), 7.15-7.20 (m, 1H), 7.01-7.05 (m, 1H), 6.96 (dt, 1H), 6.83 (dt, 1H), 6.19 (s, 1H), 6.09 (s, 2H), 4.17 (q, 2H), 1.43 (t, 3H).

Pharmaceutically Acceptable Salts of the Invention.

The phrase "pharmaceutically acceptable salt," as used herein, refers to pharmaceutically acceptable organic or inorganic salts of a compound of Formula I. For use in medicine, the salts of the compounds of Formula I will be pharmaceutically acceptable salts. Other salts may, however, be useful in the preparation of the compounds of Formula I or of their pharmaceutically acceptable salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

Pharmaceutically acceptable salts of the compounds described herein include those derived from suitable inorganic and organic acids and bases. In some embodiments, the salts can be prepared in situ during the final isolation and purification of the compounds. In other embodiments the salts can be prepared from the free form of the compound in a separate synthetic step.

When the compound of Formula I is acidic or contains a sufficiently acidic bioisostere, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particular embodiments include ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine, caffeine, choline, N,N.sup.1-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

When the compound of Formula I is basic or contains a sufficiently basic bioisostere, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particular embodiments include citric, hydrobromic, hydrochloric, maleic, phosphoric, sulfuric and tartaric acids. Other exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

The preparation of the pharmaceutically acceptable salts described above and other typical pharmaceutically acceptable salts is more fully described by Berg et al., "Pharmaceutical Salts," J. Pharm. Sci., 1977:66:149, incorporated here by reference in its entirety.

In addition to the compounds described herein, their pharmaceutically acceptable salts may also be employed in compositions to treat or prevent the herein identified disorders.
Pharmaceutical Compositions and Methods of Administration.

The compounds herein disclosed, and their pharmaceutically acceptable salts thereof may be formulated as pharmaceutical compositions or "formulations".

A typical formulation is prepared by mixing a compound of Formula I, or a pharmaceutically acceptable salt thereof, and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of Formula I is being formulated. Solvents are generally selected based on solvents recognized by persons skilled in the art as safe (GRAS—Generally Regarded as Safe) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include other types of excipients such as one or more buffers, stabilizing agents, antiadherents, surfactants, wetting agents, lubricating agents, emulsifiers, binders, suspending agents, disintegrants, fillers, sorbents, coatings (e.g. enteric or slow release) preservatives, antioxidants, opaquing agents, glidants, processing aids, colorants, sweeteners, perfuming agents, flavoring agents and other known additives to provide an elegant presentation of the drug (i.e., a compound of Formula I or pharmaceutical composition thereof) or aid in the manufacturing of the pharmaceutical product (i.e., medicament).

The formulations may be prepared using conventional dissolution and mixing procedures. For example, the bulk drug substance (i.e., compound of Formula I, a pharmaceutically acceptable salt thereof, or a stabilized form of the compound, such as a complex with a cyclodextrin derivative or other known complexation agent) is dissolved in a suitable solvent in the presence of one or more of the excipients described above. A compound having the desired degree of purity is optionally mixed with pharmaceutically acceptable diluents, carriers, excipients or stabilizers, in the form of a lyophilized formulation, milled powder, or an aqueous solution. Formulation may be conducted by mixing at ambient temperature at the appropriate pH, and at the desired degree of purity, with physiologically acceptable carriers. The pH of the formulation depends mainly on the particular use and the concentration of compound, but may range from about 3 to about 8. When the agent described herein is a solid amorphous dispersion formed by a solvent process, additives may be added directly to the spray-drying solution when forming the mixture such as the additive is dissolved or suspended in the solution as a slurry which can then be spray dried. Alternatively, the additives may be added following spray-drying process to aid in the forming of the final formulated product.

The compound of Formula I or a pharmaceutically acceptable salt thereof is typically formulated into pharmaceutical dosage forms to provide an easily controllable dosage of the drug and to enable patient compliance with the prescribed regimen. Pharmaceutical formulations of compounds of Formula I, or a pharmaceutically acceptable salt thereof, may be prepared for various routes and types of administration. Various dosage forms may exist for the same compound, since different medical conditions may warrant different routes of administration.

The amount of active ingredient that may be combined with the carrier material to produce a single dosage form will vary depending upon the subject treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur. As a general proposition, the initial pharmaceutically effective amount of the inhibitor administered will be in the range of about 0.01-100 mg/kg per dose, namely about 0.1 to 20 mg/kg of patient body weight per day, with the typical initial range of compound used being 0.3 to 15 mg/kg/day.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. The therapeutically or pharmaceutically effective amount of the compound to be administered will be governed by such considerations, and is the minimum amount necessary to ameliorate, cure or treat the disease or disorder or one or more of its symptoms.

The pharmaceutical compositions of Formula I will be formulated, dosed, and administered in a fashion, i.e., amounts, concentrations, schedules, course, vehicles, and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners, such as the age, weight, and response of the individual patient.

The term "prophylactically effective amount" refers to an amount effective in preventing or substantially lessening the chances of acquiring a disease or disorder or in reducing the severity of the disease or disorder before it is acquired or reducing the severity of one or more of its symptoms before the symptoms develop. Roughly, prophylactic measures are divided between primary prophylaxis (to prevent the development of a disease) and secondary prophylaxis (whereby the disease has already developed and the patient is protected against worsening of this process).

Acceptable diluents, carriers, excipients, and stabilizers are those that are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, tretralose or sorbitol; salt-forming counter-ions such as sodium; metal complexes (e.g. Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, e.g., hydroxymethylcellulose or gelatin-microcapsules and poly-(methylmethacylate) microcapsules, respectively; in colloidal drug delivery systems (for example, liposomes, albumin microspheres, microemulsions, nano-particles and nanocapsules) or in macroemulsions. Such techniques are disclosed in Remington's: The Science and Practice of Pharmacy, 21$^{st}$ Edition, University of the Sciences in Philadelphia, Eds., 2005 (hereafter "Remington's").

"Controlled drug delivery systems" supply the drug to the body in a manner precisely controlled to suit the drug and the conditions being treated. The primary aim is to achieve a therapeutic drug concentration at the site of action for the desired duration of time. The term "controlled release" is often used to refer to a variety of methods that modify release of drug from a dosage form. This term includes preparations labeled as "extended release", "delayed release", "modified release" or "sustained release". In general, one can provide for controlled release of the agents described herein through the use of a wide variety of polymeric carriers and controlled release systems including erodible and non-erodible matrices, osmotic control devices, various reservoir devices, enteric coatings and multiparticulate control devices.

"Sustained-release preparations" are the most common applications of controlled release. Suitable examples of sustained-release preparations include semipermeable matrices of solid hydrophobic polymers containing the compound, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers, and poly-D-(−)-3-hydroxybutyric acid.

"Immediate-release preparations" may also be prepared. The objective of these formulations is to get the drug into the bloodstream and to the site of action as rapidly as possible. For instance, for rapid dissolution, most tablets are designed to undergo rapid disintegration to granules and subsequent deaggregation to fine particles. This provides a larger surface area exposed to the dissolution medium, resulting in a faster dissolution rate.

Agents described herein can be incorporated into an erodible or non-erodible polymeric matrix controlled release device. By an erodible matrix is meant aqueous-erodible or water-swellable or aqueous-soluble in the sense of being either erodible or swellable or dissolvable in pure water or requiring the presence of an acid or base to ionize the polymeric matrix sufficiently to cause erosion or dissolution. When contacted with the aqueous environment of use, the erodible polymeric matrix imbibes water and forms an aqueous-swollen gel or matrix that entraps the agent described herein. The aqueous-swollen matrix gradually erodes, swells, disintegrates or dissolves in the environment of use, thereby controlling the release of a compound described herein to the environment of use. One ingredient of this water-swollen matrix is the water-swellable, erodible, or soluble polymer, which may generally be described as an osmopolymer, hydrogel or water-swellable polymer. Such polymers may be linear, branched, or cross linked. The polymers may be homopolymers or copolymers. In certain embodiments, they may be synthetic polymers derived from vinyl, acrylate, methacrylate, urethane, ester and oxide monomers. In other embodiments, they can be derivatives of naturally occurring polymers such as polysaccharides (e.g. chitin, chitosan, dextran and pullulan; gum agar, gum arabic, gum karaya, locust bean gum, gum tragacanth, carrageenans, gum ghatti, guar gum, xanthan gum and scleroglucan), starches (e.g. dextrin and maltodextrin), hydrophilic colloids (e.g. pectin), phosphatides (e.g. lecithin), alginates (e.g. ammonium alginate, sodium, potassium or calcium alginate, propylene glycol alginate), gelatin, collagen, and cellulosics. Cellulosics are cellulose polymer that has been modified by reaction of at least a portion of the hydroxyl groups on the saccharide repeat units with a compound to form an ester-linked or an ether-linked substituent. For example, the cellulosic ethyl cellulose has an ether linked ethyl substituent attached to the saccharide repeat unit, while the cellulosic cellulose acetate has an ester linked acetate substituent. In certain embodiments, the cellulosics for the erodible matrix comprises aqueous-soluble and aqueous-erodible cellulosics can include, for example, ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC). In certain embodiments, the cellulosics comprises various grades of low viscosity (MW less than or equal to 50,000 daltons, for example, the Dow Methocel™ series E5, E15LV, E50LV and K100LY) and high viscosity (MW greater than 50,000 daltons, for example, E4MCR, E10MCR, K4M, K15M and K100M and the Methocel™ K series) HPMC. Other commercially available types of HPMC include the Shin Etsu Metolose 90SH series.

Other materials useful as the erodible matrix material include, but are not limited to, pullulan, polyvinyl pyrrolidone, polyvinyl alcohol, polyvinyl acetate, glycerol fatty acid esters, polyacrylamide, polyacrylic acid, copolymers of ethacrylic acid or methacrylic acid (EUDRAGIT®, Rohm America, Inc., Piscataway, N.J.) and other acrylic acid derivatives such as homopolymers and copolymers of butylmethacrylate, methylmethacrylate, ethylmethacrylate, ethylacrylate, (2-dimethylaminoethyl)methacrylate, and (trimethylaminoethyl)methacrylate chloride.

Alternatively, the agents of the present invention may be administered by or incorporated into a non-erodible matrix device. In such devices, an agent described herein is distributed in an inert matrix. The agent is released by diffusion through the inert matrix. Examples of materials suitable for the inert matrix include insoluble plastics (e.g methyl acrylate-methyl methacrylate copolymers, polyvinyl chloride, polyethylene), hydrophilic polymers (e.g. ethyl cellulose, cellulose acetate, cross linked polyvinylpyrrolidone (also known as crospovidone)), and fatty compounds (e.g. carnauba wax, microcrystalline wax, and triglycerides). Such devices are described further in Remington: The Science and Practice of Pharmacy, 20th edition (2000).

As noted above, the agents described herein may also be incorporated into an osmotic control device. Such devices generally include a core containing one or more agents as described herein and a water permeable, non-dissolving and non-eroding coating surrounding the core which controls the influx of water into the core from an aqueous environment of use so as to cause drug release by extrusion of some or all of the core to the environment of use. In certain embodiments, the coating is polymeric, aqueous-permeable, and has at least one delivery port. The core of the osmotic device optionally includes an osmotic agent which acts to imbibe water from the surrounding environment via such a semi-permeable membrane. The osmotic agent contained in the core of this device may be an aqueous-swellable hydrophilic polymer or it may be an osmogen, also known as an osmagent. Pressure is generated within the device which forces the agent(s) out of the device via an orifice (of a size designed to minimize solute diffusion while preventing the build-up of a hydrostatic pressure head). Non limiting examples of osmotic control devices are disclosed in U.S. patent application Ser. No. 09/495,061.

The amount of water-swellable hydrophilic polymers present in the core may range from about 5 to about 80 wt % (including for example, 10 to 50 wt %). Non limiting examples of core materials include hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP) and cross linked PVP, polyvinyl alcohol (PVA), PVA/PVP copolymers and PVA/PVP copolymers with hydrophobic monomers such as methyl methacrylate, vinyl acetate, and the like, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl cellulose (CEC), sodium alginate, polycarbophil, gelatin, xanthan gum, and sodium starch glycolat. Other materials include hydrogels comprising interpenetrating networks of polymers that may be formed by addition or by condensation polymerization, the components of which may comprise hydrophilic and hydrophobic monomers such as those just mentioned. Water-swellable hydrophilic polymers include but are not limited to PEO, PEG, PVP, sodium croscarmellose, HPMC, sodium starch glycolate, polyacrylic acid and cross linked versions or mixtures thereof.

The core may also include an osmogen (or osmagent). The amount of osmogen present in the core may range from about 2 to about 70 wt % (including, for example, from 10 to 50 wt %). Typical classes of suitable osmogens are water-soluble organic acids, salts and sugars that are capable of imbibing water to thereby effect an osmotic pressure gradient across the barrier of the surrounding coating. Typical useful osmogens include but are not limited to magnesium sulfate, magnesium chloride, calcium chloride, sodium chloride, lithium chloride, potassium sulfate, sodium carbonate, sodium sulfite, lithium sulfate, potassium chloride, sodium sulfate, mannitol, xylitol, urea, sorbitol, inositol, raffinose, sucrose, glucose, fructose, lactose, citric acid, succinic acid, tartaric acid, and mixtures thereof. In certain embodiments, the osmogen is glucose, lactose, sucrose, mannitol, xylitol, sodium chloride, including combinations thereof.

The rate of drug delivery is controlled by such factors as the permeability and thickness of the coating, the osmotic pressure of the drug-containing layer, the degree of hydrophilicity of the hydrogel layer, and the surface area of the device. Those skilled in the art will appreciate that increasing the thickness of the coating will reduce the release rate, while any of the following will increase the release rate: increasing the permeability of the coating; increasing the hydrophilicity of the hydrogel layer; increasing the osmotic pressure of the drug-containing layer; or increasing the device's surface area.

In certain embodiments, entrainment of particles of agents described herein in the extruding fluid during operation of such osmotic device is desirable. For the particles to be well entrained, the agent drug form is dispersed in the fluid before the particles have an opportunity to settle in the tablet core. One means of accomplishing this is by adding a disintegrant that serves to break up the compressed core into its particulate components. Non limiting examples of standard disintegrants include materials such as sodium starch glycolate (e.g., Explotab™ CLV), microcrystalline cellulose (e.g., Avicel™), microcrystalline silicified cellulose (e.g., ProSolv™) and croscarmellose sodium (e.g., Ac-Di-Sol™), and other disintegrants known to those skilled in the art. Depending upon the particular formulation, some disintegrants work better than others. Several disintegrants tend to form gels as they swell with water, thus hindering drug delivery from the device. Non-gelling, non-swelling disintegrants provide a more rapid dispersion of the drug particles within the core as water enters the core. In certain embodiments, non-gelling, non-swelling disintegrants are resins, for example, ion-exchange resins. In one embodiment, the resin is Amberlite™ IRP 88 (available from Rohm and Haas, Philadelphia, Pa.). When used, the disintegrant is present in amounts ranging from about 1-25% of the core agent.

Another example of an osmotic device is an osmotic capsule. The capsule shell or portion of the capsule shell can be semipermeable. The capsule can be filled either by a powder or liquid consisting of an agent described herein, excipients that imbibe water to provide osmotic potential, and/or a water-swellable polymer, or optionally solubilizing excipients. The capsule core can also be made such that it has a bilayer or multilayer agent analogous to the bilayer, trilayer or concentric geometries described above.

Another class of osmotic device useful in this invention comprises coated swellable tablets, for example, as described in EP378404. Coated swellable tablets comprise a tablet core comprising an agent described herein and a swelling material, preferably a hydrophilic polymer, coated with a membrane, which contains holes, or pores through which, in the aqueous use environment, the hydrophilic polymer can extrude and carry out the agent. Alternatively, the membrane may contain polymeric or low molecular weight water-soluble porosigens. Porosigens dissolve in the aqueous use environment, providing pores through which the hydrophilic polymer and agent may extrude. Examples of porosigens are water-soluble polymers such as HPMC, PEG, and low molecular weight compounds such as glycerol, sucrose, glucose, and sodium chloride. In addition, pores may be formed in the coating by drilling holes in the coating using a laser or other mechanical means. In this class of osmotic devices, the membrane material may comprise any film-forming polymer, including polymers which are water permeable or impermeable, providing that the membrane deposited on the tablet core is porous or contains water-soluble porosigens or possesses a macroscopic hole for water ingress and drug release. Embodiments of this class of sustained release devices may also be multilayered, as described, for example, in EP378404.

When an agent described herein is a liquid or oil, such as a lipid vehicle formulation, for example as described in WO05/011634, the osmotic controlled-release device may comprise a soft-gel or gelatin capsule formed with a composite wall and comprising the liquid formulation where the wall comprises a barrier layer formed over the external surface of the capsule, an expandable layer formed over the barrier layer, and a semipermeable layer formed over the expandable layer. A delivery port connects the liquid formulation with the aqueous use environment. Such devices are described, for example, in U.S. Pat. No. 6,419,952, U.S. Pat. No. 6,342,249, U.S. Pat. No. 5,324,280, U.S. Pat. No. 4,672,850, U.S. Pat. No. 4,627,850, U.S. Pat. No. 4,203,440, and U.S. Pat. No. 3,995,631.

As further noted above, the agents described herein may be provided in the form of microparticulates, generally ranging in size from about 10 µm to about 2 mm (including, for example, from about 100 µm to 1 mm in diameter). Such multiparticulates may be packaged, for example, in a capsule such as a gelatin capsule or a capsule formed from an aqueous-soluble polymer such as HPMCAS, HPMC or starch; dosed as a suspension or slurry in a liquid; or they may be formed into a tablet, caplet, or pill by compression or other processes known in the art. Such multiparticulates may be made by any known process, such as wet- and dry-granulation processes, extrusion/spheronization, roller-compaction, melt-congealing, or by spray-coating seed cores. For example, in wet- and dry-granulation processes, the agent described herein and optional excipients may be granulated to form multiparticulates of the desired size.

The agents can be incorporated into microemulsions, which generally are thermodynamically stable, isotropically clear dispersions of two immiscible liquids, such as oil and water, stabilized by an interfacial film of surfactant molecules (Encyclopedia of Pharmaceutical Technology, New York: Marcel Dekker, 1992, volume 9). For the preparation of microemulsions, surfactant (emulsifier), co-surfactant (co-emulsifier), an oil phase and a water phase are necessary. Suitable surfactants include any surfactants that are useful in the preparation of emulsions, e.g., emulsifiers that are typically used in the preparation of creams. The co-surfactant (or "co-emulsifier") is generally selected from the group of polyglycerol derivatives, glycerol derivatives and fatty alcohols. Preferred emulsifier/co-emulsifier combinations are generally although not necessarily selected from the group consisting of: glyceryl monostearate and polyoxyethylene stearate; polyethylene glycol and ethylene glycol palmitostearate; and caprilic and capric triglycerides and oleoyl macrogolglycerides. The water phase includes not only water but also, typically, buffers, glucose, propylene glycol, polyethylene glycols, preferably lower molecular weight polyethylene glycols (e.g., PEG 300 and PEG 400), and/or glycerol, and the like, while the oil phase will generally comprise, for example, fatty acid esters, modified vegetable oils, silicone oils, mixtures of mono-di- and triglycerides, mono- and di-esters of PEG (e.g., oleoyl macrogol glycerides), etc.

The compounds described herein can be incorporated into pharmaceutically-acceptable nanoparticle, nanosphere, and nanocapsule formulations (Delie and Blanco-Prieto, 2005, Molecule 10:65-80). Nanocapsules can generally entrap compounds in a stable and reproducible way. To avoid side effects due to intracellular polymeric overloading, ultrafine particles (sized around 0.1 µm) can be designed using polymers able to be degraded in vivo (e.g. biodegradable poly-alkyl-cyanoacrylate nanoparticles). Such particles are described in the prior art.

Implantable devices coated with a compound of this invention are another embodiment of the present invention. The compounds may also be coated on implantable medical devices, such as beads, or co-formulated with a polymer or other molecule, to provide a "drug depot", thus permitting the drug to be released over a longer time period than administration of an aqueous solution of the drug. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

The formulations include those suitable for the administration routes detailed herein. The formulations may conveniently be presented in unit dosage form and may be prepared by any of the methods well known in the art of pharmacy.

Techniques and formulations generally are found in Remington's. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

The terms "administer", "administering" or "administration" in reference to a compound, composition or formulation of the invention means introducing the compound into the system of the animal in need of treatment. When a compound of the invention is provided in combination with one or more other active agents, "administration" and its variants are each understood to include concurrent and/or sequential introduction of the compound and the other active agents.

The compositions described herein may be administered systemically or locally, e.g.: orally (e.g. using capsules, powders, solutions, suspensions, tablets, sublingual tablets and the like), by inhalation (e.g. with an aerosol, gas, inhaler, nebulizer or the like), to the ear (e.g. using ear drops), topically (e.g. using creams, gels, liniments, lotions, ointments, pastes, transdermal patches, etc), ophthalmically (e.g. with eye drops, ophthalmic gels, ophthalmic ointments), rectally (e.g. using enemas or suppositories), nasally, buccally, vaginally (e.g. using douches, intrauterine devices, vaginal suppositories, vaginal rings or tablets, etc), via an implanted reservoir or the like, or parenterally depending on the severity and type of the disease being treated. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

The pharmaceutical compositions described herein may be orally administered in any orally acceptable dosage form including, but not limited to, capsules, tablets, aqueous suspensions or solutions. Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. Tablets may be uncoated or may be coated by known techniques including microencapsulation to mask an unpleasant taste or to delay disintegration and adsorption in the gastrointestinal tract and thereby provide a sustained action over a longer period. For example, a time delay material such as glyceryl monostearate or glyceryl distearate alone or with a wax may be employed. A water soluble taste masking material such as hydroxypropyl-methylcellulose or hydroxypropyl-cellulose may be employed.

Formulations of a compound of Formula I that are suitable for oral administration may be prepared as discrete units such as tablets, pills, troches, lozenges, aqueous or oil suspensions, dispersible powders or granules, emulsions, hard or soft capsules, e.g. gelatin capsules, syrups or elixirs. Formulations of a compound intended for oral use may be prepared according to any method known to the art for the manufacture of pharmaceutical compositions.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

The active compounds can also be in microencapsulated form with one or more excipients as noted above.

When aqueous suspensions are required for oral use, the active ingredient is combined with emulsifying and suspending agents. If desired, certain sweetening and/or flavoring agents may be added. Syrups and elixirs may be formulated with sweetening agents, for example glycerol, propylene glycol, sorbitol or sucrose. Such formulations may also contain a demulcent, a preservative, flavoring and coloring agents and antioxidant.

Sterile injectable forms of the compositions described herein (e.g. for parenteral administration) may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of injectable formulations.

Oily suspensions may be formulated by suspending the compound of Formula I in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Aqueous suspensions of compounds of Formula I contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound described herein, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsulated matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

The injectable solutions or microemulsions may be introduced into a patient's bloodstream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

Compositions for rectal or vaginal administration are preferably suppositories which can be prepared by mixing the compounds described herein with suitable non-irritating excipients or carriers such as cocoa butter, beeswax, polyethylene glycol or a suppository wax which are solid at ambient temperature but liquid at body temperature and therefore melt in the rectum or vaginal cavity and release the active compound. Other formulations suitable for vaginal administration may be presented as pessaries, tampons, creams, gels, pastes, foams or sprays.

The pharmaceutical compositions described herein may also be administered topically, especially when the target of treatment includes areas or organs readily accessible by topical application, including diseases of the eye, the ear, the skin, or the lower intestinal tract. Suitable topical formulations are readily prepared for each of these areas or organs.

Dosage forms for topical or transdermal administration of a compound described herein include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel. Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum. For treatment of the eye or other external tissues, e.g., mouth and skin, the formulations may be applied as a topical ointment or cream containing the active ingredient(s) in an amount of, for example, 0.075 to 20% w/w. When formulated in an ointment, the active ingredients may be employed with either an oil-based, paraffinic or a water-miscible ointment base.

Alternatively, the active ingredients may be formulated in a cream with an oil-in-water cream base. If desired, the aqueous phase of the cream base may include a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of emulsions prepared using compounds of Formula I may be constituted from known ingredients in a known manner. While the phase may comprise merely an emulsifier (otherwise known as an emulgent), it desirably comprises a mixture of at least one emulsifier with a fat or an oil or with both a fat and an oil. A hydrophilic emulsifier may be included together with a lipophilic emulsifier which acts as a stabilizer. In some embodiments, the emulsifier includes both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulgents and emulsion stabilizers suitable for use in the formulation of compounds of Formula I include Tween™-60, Span™-80, cetostearyl alcohol, benzyl alcohol, myristyl alcohol, glyceryl monostearate and sodium lauryl sulfate.

The pharmaceutical compositions may also be administered by nasal aerosol or by inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents. Formulations suitable for intrapulmonary or nasal administration have a particle size for example in the range of 0.1 to 500 micros (including particles in a range between 0.1 and 500 microns in increments microns such as 0.5, 1, 30, 35 microns, etc) which is administered by rapid inhalation through the nasal passage or by inhalation through the mouth so as to reach the alveolar sacs.

The pharmaceutical composition (or formulation) for use may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

In another aspect, a compound of Formula I or a pharmaceutically acceptable salt thereof may be formulated in a veterinary composition comprising a veterinary carrier. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Therapeutic Methods

The present disclosure relates to stimulators of soluble guanylate cyclase (sGC), pharmaceutical formulations thereof and their use, alone or in combination with one or more additional agents, for treating and/or preventing various diseases, wherein an increase in the concentration of NO might be desirable, such as pulmonary hypertension, arterial hypertension, heart failure, atherosclerosis, inflammation, thrombosis, renal fibrosis and failure, liver cirrhosis, erectile dysfunction and other related cardiovascular disorders.

In one embodiment, the compounds herein disclosed are NO-independent, heme-dependent sGC stimulators that can be used to prevent and/or treat conditions, diseases or disorders in which it is considered desirable to increase the concentration of cGMP. Increased concentration of cGMP leads to vasodilation, inhibition of platelet aggregation and adhesion, anti-hypertensive effects, anti-remodeling effects, anti-apoptotic effects, anti-inflammatory effects and neuronal signal transmission effects. Thus, sGC stimulators may be used to treat and/or prevent a range of diseases and disorders, including but not limited to cardiovascular, endothelial, pulmonary, renal, hepatic and sexual diseases and disorders.

In other embodiments, the compounds here disclosed are sGC stimulators that may be useful in the prevention and/or treatment of diseases and disorders characterized by undesirable reduced bioavailability of and/or sensitivity to NO, such as those associated with conditions of oxidative stress or nitrosative stress.

Specific diseases of disorders which may be treated and/or prevented by administering an sGC stimulator, include but are not limited to: arterial hypertension, pulmonary hypertension, heart failure, stroke, septic shock, atherosclerosis, thrombosis, renal fibrosis, ischemic renal disease and renal failure, liver cirrhosis, erectile dysfunction, male and female sexual dysfunction, sickle cell anemia, asthma, chronic obstructive pulmonary disease, and neuro inflammatory diseases or disorders.

Pulmonary hypertension (PH) is a disease characterized by sustained elevations of blood pressure in the pulmonary vasculature (pulmonary artery, pulmonary vein and pulmonary capillaries), which results in right heart hypertrophy, eventually leading to right heart failure and death. Common symptoms of PH include shortness of breath, dizziness and fainting, all of which are exacerbated by exertion. Without treatment, median life expectancy following diagnosis is 2.8 years. PH exists in many different forms, which are categorized according to their etiology. Categories include pulmonary arterial hypertension (PAH), PH with left heart disease, PH associated with lung diseases and/or hypoxaemia, PH due to chronic thrombotic and/or embolic disease and miscellaneous PH. PAH is rare in the general population, but the prevalence increases in association with certain common conditions such as HIV infection, scleroderma and sickle cell disease. Other forms of PH are generally more common than PAH, and, for instance, the association of PH with chronic obstructive pulmonary disease (COPD) is of particular concern. Current treatment for pulmonary hypertension depends on the stage and the mechanism of the disease.

The compounds according to Formula I of the present invention as well as pharmaceutically acceptable salts thereof, as stimulators of sGC, are useful in the prevention and/or treatment of the following types of diseases, conditions and disorders which can benefit from sGC stimulation:

(1) Peripheral or cardiac vascular disorders/conditions:
  pulmonary hypertension, pulmonary arterial hypertension, and associated pulmonary vascular remodeling (e.g. localized thrombosis and right heart hypertrophy); pulmonary hypertonia; primary pulmonary hypertension, secondary pulmonary hypertension, familial pulmonary hypertension, sporadic pulmonary hypertension, pre-capillary pulmonary hypertension, idiopathic pulmonary hypertension, thrombotic pulmonary arteriopathy, plexogenic pulmonary arteriopathy; pulmonary hypertension associated with or related to: left ventricular dysfunction, hypoxemia, mitral valve disease, constrictive pericarditis, aortic stenosis, cardiomyopathy, mediastinal fibrosis, pulmonary fibrosis, anomalous pulmonary venous drainage, pulmonary venooclusive disease, pulmonary vasculitis, collagen vascular disease, congenital heart disease, pulmonary venous hypertension, interstitial lung disease, sleep-disordered breathing, apnea, alveolar hypoventilation disorders, chronic exposure to high altitude, neonatal lung disease, alveolar-capillary dysplasia, sickle cell disease, other coagulation disorders, chronic thromboembolism, pulmonary embolism (due to tumor, parasites or foreign material), connective tissue disease, lupus, schitosomiasis, sarcoidosis, chronic obstructive pulmonary disease, emphysema, chronic bronchitis, pulmonary capillary hemangiomatosis; histiocytosis X, lymphangiomatosis and compressed pulmonary vessels (such as due to adenopathy, tumor or fibrosing mediastinitis)
  disorders related to high blood pressure and decreased coronary blood flow such as increased acute and chronic coronary blood pressure, arterial hypertension and vascular disorder resulting from cardiac and renal complications (e.g. heart disease, stroke, cerebral ischemia, renal failure); congestive heart failure; thromboembolic disorders and ischemias such as myocardial infarction, stroke, transient ischemic attacks; stable or unstable angina pectoris; arrhythmias; diastolic dysfunction; coronary insufficiency;
  Atherosclerosis (e.g., associated with endothelial injury, platelet and monocyte adhesion and aggregation, smooth muscle proliferation and migration); restenosis (e.g. developed after thrombolysis therapies, percutaneous transluminal angioplasties (PTAs), percutaneous transluminal coronary angioplasties (PTCAs) and bypass); inflammation;
  liver cirrhosis, associated with chronic liver disease, hepatic fibrosis, hepatic stellate cell activation, hepatic fibrous collagen and total collagen accumulation; liver disease of necro-inflammatory and/or of immunological origin; and (2) Urogenital system disorders, such as renal fibrosis and renal failure resulting from chronic kidney diseases or insufficiency (e.g. due to accumulation/deposition and tissue injury, progressive sclerosis, glomerunephritis); prostate hypertrophy; erectile dysfunction; female sexual dysfunction and incontinence.

In some embodiments of the invention, the compounds according to Formula I as well as pharmaceutically acceptable salts thereof are also useful in the prevention and/or treatment of the following types of diseases, conditions and disorders which can benefit from sGC stimulation:

(a) A peripheral or cardiac vascular disorder or health condition selected from: pulmonary hypertension, pulmonary arterial hypertension, and associated pulmonary vascular remodeling, localized pulmonary thrombosis, right heart hypertrophy, pulmonary hypertonia, primary pulmonary hypertension, secondary pulmonary hypertension, familial pulmonary hypertension, sporadic pulmonary hypertension, pre-capillary pulmonary hypertension, idiopathic pulmonary hypertension, thrombotic pulmonary arteriopathy, plexogenic pulmonary arteriopathy; pulmonary hypertension associated with or related to: left ventricular dysfunction, hypoxemia, mitral valve disease, constrictive pericarditis, aortic stenosis, cardiomyopathy, mediastinal fibrosis, pulmonary fibrosis, anomalous pulmonary venous drainage, pulmonary venooclusive disease, pulmonary vasculitis, collagen vascular disease, congenital heart disease, pulmonary venous hypertension, interstitial lung disease, sleep-disordered breathing, apnea, alveolar hypoventilation disorders, chronic exposure to high altitude, neonatal lung disease, alveolar-capillary dysplasia, sickle cell disease, other coagulation disorders, chronic thromboembolism, pulmonary embolism, connective tissue disease, lupus, schitosomiasis, sarcoidosis, chronic obstructive pulmonary disease, emphysema, chronic bronchitis, pulmonary capillary hemangiomatosis; histiocytosis X, lymphangiomatosis or compressed pulmonary vessels;

(b) Liver cirrhosis, or (c) a urogenital system disorder selected from renal fibrosis, renal failure resulting from chronic kidney diseases or insufficiency, erectile dysfunction or female sexual dysfunction.

In other embodiments of the invention, the compounds according to Formula I as well as pharmaceutically acceptable salts thereof are useful in the prevention and/or treatment of the following types of diseases, conditions and disorders which can benefit from sGC stimulation:
  pulmonary hypertension, pulmonary arterial hypertension, and associated pulmonary vascular remodeling, localized pulmonary thrombosis, right heart hypertrophy, pulmonary hypertonia, primary pulmonary hypertension, secondary pulmonary hypertension, familial pulmonary hypertension, sporadic pulmonary hypertension, pre-capillary pulmonary hypertension, idiopathic pulmonary hypertension, thrombotic pulmonary arteriopathy, plexogenic pulmonary arteriopathy or chronic obstructive pulmonary disease, liver cirrhosis, renal fibrosis, renal failure resulting from chronic kidney diseases or insufficiency, erectile dysfunction or female sexual dysfunction.

In still other embodiments, the compounds according to Formula I as well as pharmaceutically acceptable salts thereof are useful in the prevention and/or treatment of the following types of diseases, conditions and disorders which can benefit from sGC stimulation:
  Pulmonary hypertension, pulmonary arterial hypertension, and associated pulmonary vascular remodeling, pulmonary hypertonia, primary pulmonary hypertension, secondary pulmonary hypertension, familial pulmonary hypertension, sporadic pulmonary hypertension, pre-capillary pulmonary hypertension or idiopathic pulmonary hypertension.

The terms, "disease", "disorder" and "condition" may be used interchangeably here to refer to a sGC, cGMP and/or NO mediated medical or pathological condition.

As used herein, the terms "subject" and "patient" are used interchangeably. The terms "subject" and "patient" refer to an animal (e.g., a bird such as a chicken, quail or turkey, or a mammal), specifically a "mammal" including a non-primate (e.g., a cow, pig, horse, sheep, rabbit, guinea pig, rat, cat, dog, and mouse) and a primate (e.g., a monkey, chimpanzee and a human), and more specifically a human. In some embodiments, the subject is a non-human animal such as a farm animal (e.g., a horse, cow, pig or sheep), or a pet (e.g., a dog, cat, guinea pig or rabbit). In some embodiments, the subject is a human.

The invention also provides a method for treating one of these diseases, conditions and disorders in a subject, comprising administering a therapeutically effective amount of the compound of Formula I, or a pharmaceutically acceptable salt thereof, in the subject in need of the treatment. Alternatively, the invention provides the use of the compound of Formula I, or a pharmaceutically acceptable salt thereof, in the treatment of one of these diseases, conditions and disorders in a subject in need of the treatment. The invention further provides a method of making a medicament useful for treating one of these diseases, conditions and disorders comprising using the compound of Formula I, or a pharmaceutically acceptable salt thereof.

The term "biological sample", as used herein, refers to an in vitro or ex vivo sample, and includes, without limitation, cell cultures or extracts thereof; biopsied material obtained from a mammal or extracts thereof; blood, saliva, urine, faeces, semen, tears, lymphatic fluid, ocular fluid, vitreous humour, or other body fluids or extracts thereof.

"Treat", "treating" or "treatment" with regard to a disorder or disease refers to alleviating or abrogating the cause and/or the effects of the disorder or disease. As used herein, the terms "treat", "treatment" and "treating" refer to the reduction or amelioration of the progression, severity and/or duration of a sGC, cGMP and/or NO mediated condition, or the amelioration of one or more symptoms (preferably, one or more discernable symptoms) of said condition (i.e. "managing" without "curing" the condition), resulting from the administration of one or more therapies (e.g., one or more therapeutic agents such as a compound or composition of the invention). In specific embodiments, the terms "treat"; "treatment" and "treating" refer to the amelioration of at least one measurable physical parameter of a sGC, cGMP and/or NO mediated condition. In other embodiments the terms "treat", "treatment" and "treating" refer to the inhibition of the progression of a sGC, cGMP and/or NO mediated condition, either physically by, e.g., stabilization of a discernable symptom or physiologically by, e.g., stabilization of a physical parameter, or both.

The term "preventing" as used herein refers to administering a medicament beforehand to avert or forestall the appearance of one or more symptoms of a disease or disorder. The person of ordinary skill in the medical art recognizes that the term "prevent" is not an absolute term. In the medical art it is understood to refer to the prophylactic administration of a drug to substantially diminish the likelihood or seriousness of a condition, or symptom of the condition and this is the sense intended in this disclosure. The Physician's Desk Reference, a standard text in the field, uses the term "prevent" hundreds of times. As used therein, the term "prevent", "preventing" and "prevention" with regard to a disorder or disease, refer to averting the cause, effects, symptoms or progression of a disease or disorder prior to the disease or disorder fully manifesting itself.

In one embodiment, the methods of the invention are a preventative or "pre-emptive" measure to a patient, specifically a human, having a predisposition (e.g. a genetic predisposition) to developing a sGC, cGMP and/or NO related disease, disorder or symptom.

In other embodiments, the methods of the invention are a preventative or "pre-emptive" measure to a patient, specifically a human, suffering from a disease, disorder or condition that makes him at risk of developing a sGC, cGMP or NO related disease, disorder or symptom.

The compounds and pharmaceutical compositions described herein can be used alone or in combination therapy for the treatment or prevention of a disease or disorder mediated, regulated or influenced by sGC, cGMP and/or NO.

Compounds and compositions here disclosed are also useful for veterinary treatment of companion animals, exotic animals and farm animals, including, without limitation, dogs, cats, mice, rats, hamsters, gerbils, guinea pigs, rabbits, horses, pigs and cattle.

In other embodiments, the invention provides a method of stimulating sGC activity in a biological sample, comprising contacting said biological sample with a compound or composition of the invention. Use of a sGC stimulator in a biological sample is useful for a variety of purposes known to one of skill in the art. Examples of such purposes include, without limitation, biological assays and biological specimen storage.

Combination Therapies

The compounds and pharmaceutical compositions described herein can be used in combination therapy with one or more additional therapeutic agents. For combination treatment with more than one active agent, where the active agents are in separate dosage formulations, the active agents may be administered separately or in conjunction. In addition, the administration of one element may be prior to, concurrent to, or subsequent to the administration of the other agent.

When co-administered with other agents, e.g., when co-administered with another pain medication, an "effective amount" of the second agent will depend on the type of drug used. Suitable dosages are known for approved agents and can be adjusted by the skilled artisan according to the condition of the subject, the type of condition(s) being treated and the amount of a compound described herein being used. In cases where no amount is expressly noted, an effective amount should be assumed. For example, compounds described herein can be administered to a subject in a dosage range from between about 0.01 to about 10,000 mg/kg body weight/day, about 0.01 to about 5000 mg/kg body weight/day, about 0.01 to about 3000 mg/kg body weight/day, about 0.01 to about 1000 mg/kg body weight/day, about 0.01 to about 500 mg/kg body weight/day, about 0.01 to about 300 mg/kg body weight/day, about 0.01 to about 100 mg/kg body weight/day.

When "combination therapy" is employed, an effective amount can be achieved using a first amount of a compound of Formula I or a pharmaceutically acceptable salt thereof and a second amount of an additional suitable therapeutic agent.

In one embodiment of this invention, the compound of Formula I and the additional therapeutic agent are each administered in an effective amount (i.e., each in an amount which would be therapeutically effective if administered alone). In another embodiment, the compound of Structural Formula I and the additional therapeutic agent are each administered in an amount which alone does not provide a therapeutic effect (a sub-therapeutic dose). In yet another embodiment, the compound of Structural Formula I can be administered in an effective amount, while the additional therapeutic agent is administered in a sub-therapeutic dose. In still another embodiment, the compound of Structural Formula I can be administered in a sub-therapeutic dose, while the additional therapeutic agent, for example, a suitable cancer-therapeutic agent is administered in an effective amount.

As used herein, the terms "in combination" or "co-administration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject.

Co-administration encompasses administration of the first and second amounts of the compounds in an essentially simultaneous manner, such as in a single pharmaceutical composition, for example, capsule or tablet having a fixed ratio of first and second amounts, or in multiple, separate capsules or tablets for each. In addition, such co administration also encompasses use of each compound in a sequential manner in either order. When co-administration involves the separate administration of the first amount of a compound of Structural Formulae I and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life and kinetic profile. For example, a compound of Formula I and the second therapeutic agent can be administered in any order within about 24 hours of each other, within about 16 hours of each other, within about 8 hours of each other, within about 4 hours of each other, within about 1 hour of each other or within about 30 minutes of each other.

More, specifically, a first therapy (e.g., a prophylactic or therapeutic agent such as a compound described herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent such as an anti-cancer agent) to a subject.

Examples of other therapeutic agents that may be combined with a compound of this disclosure, either administered separately or in the same pharmaceutical composition, include, but are not limited to:

(1) Endothelium-derived releasing factor (EDRF);
(2) NO donors such as a nitrosothiol, a nitrite, a sydnonimine, a NONOate, a N-nitrosoamine, a N-hydroxyl nitrosamine, a nitrosimine, nitrotyrosine, a diazetine dioxide, an oxatriazole 5-imine, an oxime, a hydroxylamine, a N-hydroxyguanidine, a hydroxyurea or a furoxan. Some examples of these types of compounds include: glyceryl trinitrate (also known as GTN, nitroglycerin, nitroglycerine, and trinitroglycerin), the nitrate ester of glycerol; sodium nitroprusside (SNP), wherein a molecule of nitric oxide is coordinated to iron metal forming a square bipyramidal complex; 3-morpholinosydnonimine (SIN-1), a zwitterionic compound formed by combination of a morpholine and a sydnonimine; S-nitroso-N-acetylpenicillamine (SNAP), an N-acetylated amino acid derivative with a nitrosothiol functional group; diethylenetriamine/NO (DETA/NO), a compound of nitric oxide covalently linked to diethylenetriamine; and NCX 4016, an m-nitroxymethyl phenyl ester of acetyl salicylic acid. More specific examples of some of these classes of NO donors include: the classic nitrovasodilators, such as organic nitrate and nitrite esters, including nitroglycerin, amyl nitrite, isosorbide dinitrate, isosorbide 5-mononitrate, and nicorandil; Isosorbide (Dilatrate®-SR, Imdur®, Ismo®, Isordil®, Isordil®, Titradose®, Monoket®), FK 409 (NOR-3); FR 144420 (NOR-4); 3-morpholinosydnonimine; Linsidomine chlorohydrate ("SIN-1"); S-nitroso-N-acetyl-penicillamine ("SNAP"); AZD3582 (CINOD lead compound), NCX 4016, NCX 701, NCX 1022, HCT 1026, NCX 1015, NCX 950, NCX 1000, NCX 1020, AZD 4717, NCX 1510/NCX 1512, NCX 2216, and NCX 4040 (all available from NicOx S.A.), S-nitrosoglutathione (GSNO), S-nitrosoglutathione mono-ethyl-ester (GSNO-ester), 6-(2-hydroxy-1-methyl-nitrosohydrazino)-N-methyl-1-hexanamine (NOC-9) or diethylamine NONOate. Nitric oxide donors are also as disclosed in U.S. Pat. Nos. 5,155,137, 5,366,997, 5,405,919, 5,650,442, 5,700,830, 5,632,981, 6,290,981, 5,691,423 5,721,365, 5,714,511, 6,511,911, and 5,814,666, Chrysselis et al. (2002) J Med. Chem. 45:5406-9 (such as NO donors 14 and 17), and Nitric Oxide Donors for Pharmaceutical and Biological Research, Eds: Peng George Wang, Tingwei Bill Cai, Naoyuki Taniguchi, Wiley, 2005;

(3) Other substances that enhance cGMP concentrations such as protoporphyrin arachidonic acid and phenyl hydrazine derivatives;

(4) Nitric Oxide Synthase substrates: for example, n-hydroxyguanidine based analogs, such as N[G]-hydroxy-L-arginine (NOHA), 1-(3,4-dimethoxy-2-chlorobenzylideneamino)-3-hydroxyguanidine, and PR5 (1-(3,4-dimethoxy-2-chlorobenzylideneamino)-3-hydroxyguanidine); L-arginine derivatives (such as homo-Arg, homo-NOHA, N-tert-butyloxy- and N-(3-methyl-2-butenyl)oxy-L-arginine, canavanine, epsilon guanidine-carpoic acid, agmatine, hydroxyl-agmatine, and L-tyrosyl-L-arginine); N-alkyl-N'-hydroxyguanidines (such as N-cyclopropyl-N'-hydroxyguanidine and N-butyl-N'-hydroxyguanidine), N-aryl-N'-hydroxyguanidines (such as N-phenyl-N'-hydroxyguanidine and its para-substituted derivatives which bear —F, —Cl, -methyl, —OH substituents, respectively); guanidine derivatives such as 3-(trifluormethyl)propylguanidine; and others reviewed in Cali et al. (2005, Current Topics in Medicinal Chemistry 5:721-736) and disclosed in the references cited therein;

(5) Compounds which enhance eNOS transcription: for example those described in WO 02/064146, WO 02/064545, WO 02/064546 and WO 02/064565, and corresponding patent documents such as US2003/0008915, US2003/0022935, US2003/0022939 and US2003/0055093. Other eNOS transcriptional enhancers including those described in US20050101599 (e.g. 2,2-difluorobenzo[1,3]dioxol-5-carboxylic acid indan-2-ylamide, and 4-fluoro-N-(indan-2-yl)-benzamide), and Sanofi-Aventis compounds AVE3085 and AVE9488 (CA Registry NO. 916514-70-0; Schäfer et al., Journal of Thrombosis and Homeostasis 2005; Volume 3, Supplement 1: abstract number P1487);

(6) NO independent heme-independent sGC activators, including, but not limited to: BAY 58-2667 (see patent publication DE19943635)

165

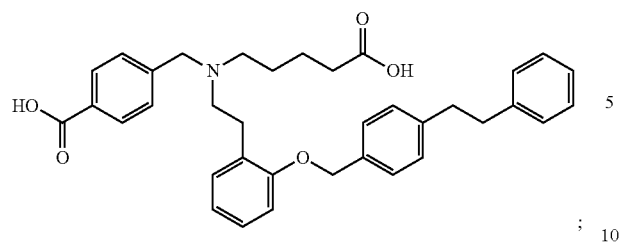

HMR-1766 (ataciguat sodium, see patent publication WO2000002851)

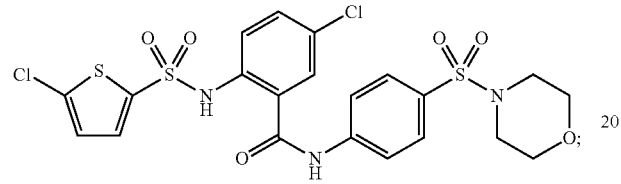

S 3448 (2-(4-chloro-phenylsulfonylamino)-4,5-dimethoxy-N-(4-(thiomorpholine-4-sulfonyl)-phenyl)-benzamide (see patent publications DE19830430 and WO2000002851)

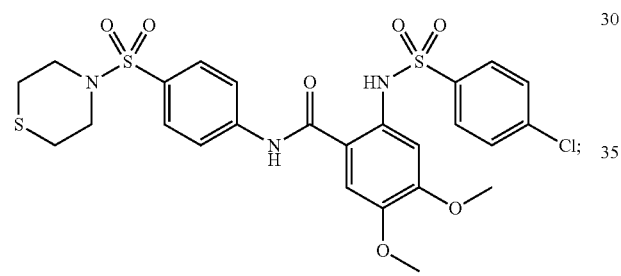

and
HMR-1069 (Sanofi-Aventis).
(7) Heme-dependent sGC stimulators including, but not limited to:
YC-1 (see patent publications EP667345 and DE19744026)

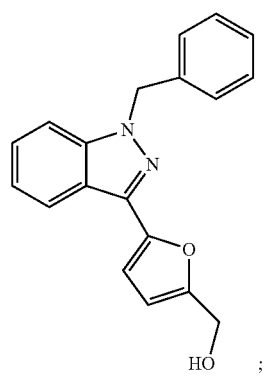 [SMILES: OCc1ccc(-c2nn(Cc3ccccc3)c3ccccc23)o1]

BAY 41-2272 (see patent publications DE19834047 and DE19942809)

166

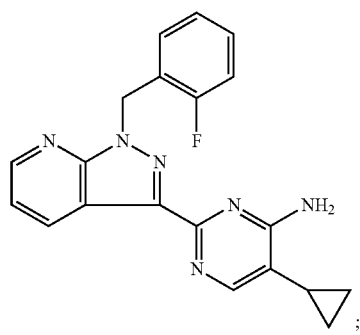 [SMILES: Nc1nc(-c2nn(Cc3ccccc3F)c3ncccc23)ncc1C1CC1]

BAY 41-8543 (see patent publication DE19834044)

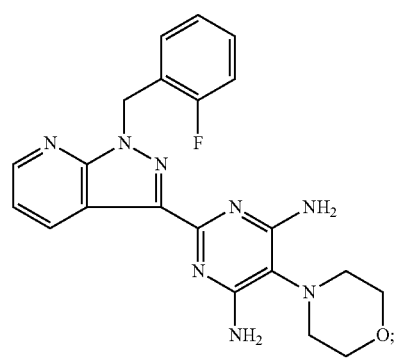 [SMILES: Nc1nc(-c2nn(Cc3ccccc3F)c3ncccc23)nc(N)c1N1CCOCC1]

BAY 63-2521 (see patent publication DE19834044)
CFM-1571 (see patent publication WO2000027394)

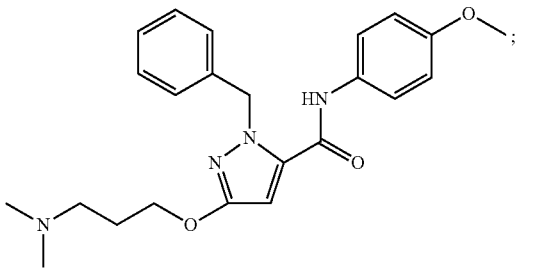

A350-619

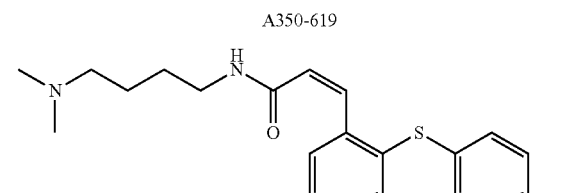

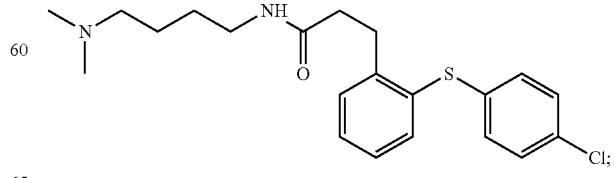

A-344905

-continued

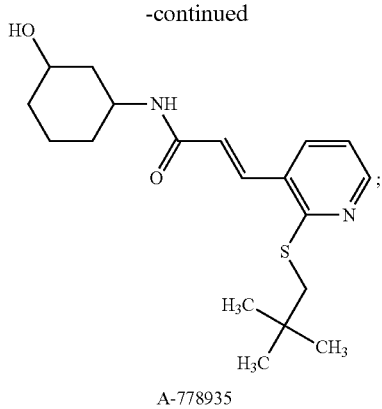
A-778935 and other compounds disclosed in Tetrahedron Letters (2003), 44 (48): 8661-8663.

(8) Compounds that inhibit the degradation of cGMP, such as:

PDE5 inhibitors, such as, for example, Sildenafil (Viagra®) and other related agents such as Avanafil, Lodenafil, Mirodenafil, Sildenafil citrate, Tadalafil (Cialis®), Vardenafil (Levitra®) and Udenafil; Alprostadil; and Dipyridamole;

(9) Calcium channel blockers such as:

Dihydropyridine calcium channel blockers: Amlodipine (Norvasc), Aranidipine (Sapresta), Azelnidipine (Calblock), Barnidipine (HypoCa), Benidipine (Coniel), Cilnidipine (Atelec, Cinalong, Siscard), Clevidipine (Cleviprex), Efonidipine (Landel), Felodipine (Plendil), Lacidipine (Motens, Lacipil), Lercanidipine (Zanidip), Manidipine (Calslot, Madipine), Nicardipine (Cardene, Carden SR), Nifedipine (Procardia, Adalat), Nilvadipine (Nivadil), Nimodipine (Nimotop), Nisoldipine (Baymycard, Sular, Syscor), Nitrendipine (Cardif, Nitrepin, Baylotensin), Pranidipine (Acalas);

Phenylalkylamine calcium channel blockers: Verapamil (Calan, Isoptin)

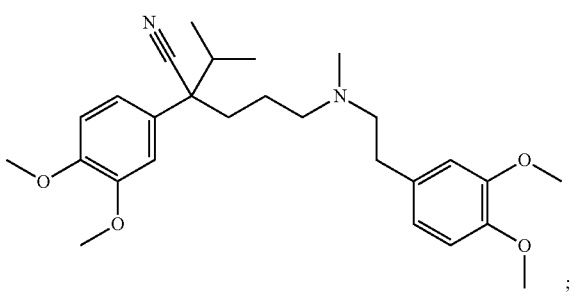

Gallopamil (Procorum, D600);

Benzothiazepines: Diltiazem (Cardizem);

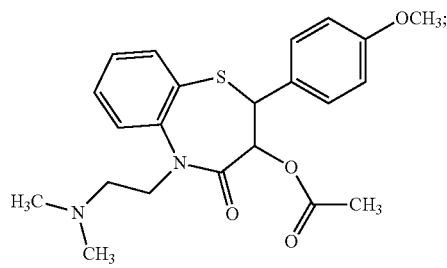 [SMILES: COc1ccc(C2Sc3ccccc3N(CCN(C)C)C(=O)C2OC(C)=O)cc1]

Nonselective calcium channel inhibitors such as: mibefradil, bepridil and fluspirilene, fendiline

(10) Endothelin receptor antagonists (ERAs): for instance the dual ($ET_A$ and $ET_B$) endothelin receptor antagonist Bosentan (marketed as Tracleer®); Sitaxentan, marketed under the name Thelin®; Ambrisentan is marketed as Letairis® in U.S; dual/nonselective endothelin antagonist Actelion-1, that entered clinical trials in 2008;

(11) Prostacyclin derivatives: for instance prostacyclin (prostaglandin $I_2$), Epoprostenol (synthetic prostacyclin, marketed as Flolan®); Treprostinil (Remodulin®) Iloprost (Ilomedin®), Iloprost (marketed as Ventavis®); oral and inhaled forms of Remodulin® that are under development; Beraprost, an oral prostanoid available in Japan and South Korea;

(12) Antihyperlipidemics such as: cholestyramine, colestipol, and colesevelam; statins such as Atorvastatin, Simvastatin, Lovastatin and Pravastatin; Rosuvastatin; also combinations of statins, niacin, intestinal cholesterol absorption-inhibiting supplements (ezetimibe and others, and to a much lesser extent fibrates);

(13) Anticoagulants, such as the following types:
  Coumarins (Vitamin K antagonists): Warfarin® (Coumadin) mostly used in the US and UK; Acenocoumarol® and Phenprocoumon®, mainly used in other countries; Phenindione®;
  Heparin and derivative substances such as: Heparin; low molecular weigh heparin, Fondaparinux and Idraparinux;
  Direct thrombin inhibitors such as: Argatroban, Lepirudin, Bivalirudin and Dabigatran; Ximelagatran (Exanta®), not approved in the US;
  Tissue plasminogen activators, used to dissolve clots and unblock arteries, such as Alteplase;

(14) Antiplatelet drugs: for instance thienopyridines such as Lopidogrel and Ticlopidine; Dipyridamole; Aspirin;

(15) ACE inhibitors, for example the following types:
  Sulthydryl-containing agents such as Captopril (trade name Capoten®), the first ACE inhibitor and Zofenopril;
  Dicarboxylate-containing agents such as Enalapril (Vasotec/Renitec®); Ramipril (Altace/Tritace/Ramace/Ramiwin®); Quinapril (Accupril®) Perindopril (Coversyl/Aceon®), Lisinopril (Lisodur/Lopril/Novatec/Prinivil/Zestril®) and Benazepril (Lotensin®);
  Phosphonate-containing agents such as: Fosinopril;
  Naturally occurring ACE inhibitors such as: Casokinins and lactokinins, which are breakdown products of casein and whey that occur naturally after ingestion of milk products, especially cultured milk; The Lactotripeptides Val-Pro-Pro and Ile-Pro-Pro produced by the probiotic *Lactobacillus helveticus* or derived from casein also have ACE-inhibiting and antihypertensive functions;

(16) Supplemental oxygen therapy;
(17) Beta blockers, such as the following types:
Non-selective agents: Alprenolol®, Bucindolol®, Carteolol®, Carvedilol® (has additional α-blocking activity), Labetalol® (has additional α-blocking activity), Nadolol®, Penbutolol® (has intrinsic sympathomimetic activity), Pindolol® (has intrinsic sympathomimetic activity), Propranolol® and Timolol®;
$\beta_1$-Selective agents: Acebutolol® (has intrinsic sympathomimetic activity), Atenolol®, Betaxolol®, Bisoprolol®, Celiprolol®, Esmolol®, Metoprolol® and Nebivolol®;
$\beta_2$-Selective agents: Butaxamine® (weak α-adrenergic agonist activity);
(18) Antiarrhythmic agents such as the following types:
Type I (sodium channel blockers): Quinidine, Lidocaine, Phenyloin, Propafenone
Type III (potassium channel blockers): Amiodarone, Dofetilide, Sotalol
Type V: Adenosine, Digoxin
(19) Diuretics such as: Thiazide diuretics, e.g., chlorothiazide, chlorthalidone, and hydrochlorothiazide; Loop diuretics, such as furosemide; potassium-sparing diuretics such as amiloride, spironolactone, and triamterene; combinations of these agents;
(20) Exogenous vasodilators such as:
Adenocard®, an adenosine agonist, primarily used as an anti-arrhythmic;
Alpha blockers (which block the vasoconstricting effect of adrenaline);
Atrial natriuretic peptide (ANP);
Ethanol;
Histamine-inducers, which complement proteins C3a, C4a and C5a work by triggering histamine release from mast cells and basophil granulocytes;
Tetrahydrocannabinol (THC), major active chemical in marijuana which has minor vasodilatory effects;
Papaverine, an alkaloid found in the opium poppy *papaver somniferum*;
(21) Bronchodilators: there are two major types of bronchodilator, $\beta_2$ agonists and anticholinergics, exemplified below:
$\beta_2$ agonists: Salbutamol® or albuterol (common brand name: Ventolin) and Terbutaline® are short acting $\beta_2$ agonists for rapid relief of COPD symptoms. Long acting $\beta_2$ agonists (LABAs) such as Salmeterol® and Formoterol®;
anticholinergics: Ipratropium® is the most widely prescribed short acting anticholinergic drug. Tiotropium® is the most commonly prescribed long-acting anticholinergic drug in COPD;
Theophylline®, a bronchodilator and phosphodiesterase inhibitor;
(22) Corticosteroids: such as beclomethasone, methylprednisolone, betamethasone, prednisone, prenisolone, triamcinolone, dexamethasone, fluticasone, flunisolide and hydrocortisone, and corticosteroid analogs such as budesonide
(23) Dietary supplements such as, for example: omega-3 oils; folid acid, niacin, zinc, copper, Korean red ginseng root, ginkgo, pine bark, *Tribulus terrestris*, arginine, *Avena sativa*, horny goat weed, maca root, muira puama, saw palmetto, and Swedish flower pollen; Vitamin C, Vitamin E, Vitamin K2; Testosterone supplements, Zoraxel, Naltrexone, Bremelanotide (formerly PT-141), Melanotan II, hMaxi-K; Prelox: a Proprietary mix/combination of naturally occurring ingredients, L-arginine aspartate and Pycnogenol;
(24) PGD2 receptor antagonists including, but not limited to, compounds described as having PGD2 antagonizing activity in United States Published Applications US20020022218, US20010051624, and US20030055077, PCT Published Applications WO9700853, WO9825919, WO03066046, WO03066047, WO03101961, WO03101981, WO04007451, WO0178697, WO04032848, WO03097042, WO03097598, WO03022814, WO03022813, and WO04058164, European Patent Applications EP945450 and EP944614, and those listed in: Torisu et al. 2004 *Bioorg Med Chem Lett* 14:4557, Torisu et al. 2004 *Bioorg Med Chem Lett* 2004 14:4891, and Torisu et al. 2004 *Bioorg & Med Chem* 2004 12:4685;
(25) Immunosuppressants such as cyclosporine (cyclosporine A, Sandimmune® Neoral®), tacrolimus (FK-506, Prograf®), rapamycin (sirolimus, Rapamune®) and other FK-506 type immunosuppressants, and mycophenolate, e.g., mycophenolate mofetil (CellCept®);
(26) Non-steroidal anti-asthmatics such as β2-agonists (e.g., terbutaline, metaproterenol, fenoterol, isoetharine, albuterol, salmeterol, bitolterol and pirbuterol) and β2-agonist-corticosteroid combinations (e.g., salmeterol-fluticasone (Advair®), formoterol-budesonid (Symbicort®)), theophylline, cromolyn, cromolyn sodium, nedocromil, atropine, ipratropium, ipratropium bromide, leukotriene biosynthesis inhibitors (zileuton, BAY1005);
(27) Non-steroidal anti-inflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone);
(28) Cyclooxygenase-2 (COX-2) inhibitors such as celecoxib (Celebrex®), rofecoxib (Vioxx®), valdecoxib, etoricoxib, parecoxib and lumiracoxib; (opioid analgesics such as codeine, fentanyl, hydromorphone, levorphanol, meperidine, methadone, morphine, oxycodone, oxymorphone, propoxyphene, buprenorphine, butorphanol, dezocine, nalbuphine and pentazocine; and
(29) Anti-diabetic agents such as insulin and insulin mimetics, sulfonylureas (e.g., glyburide, meglinatide), biguanides, e.g., metformin (Glucophage®), α-glucosidase inhibitors (acarbose), thiazolidinone compounds, e.g., rosiglitazone (Avandia®), troglitazone (Rezulin®), ciglitazone, pioglitazone (Actos®) and englitazone.

Kits

The compounds and pharmaceutical formulations described herein may be contained in a kit. The kit may include single or multiple doses of two or more agents, each packaged or formulated individually, or single or multiple doses of two or more agents packaged or formulated in combination. Thus, one or more agents can be present in first container, and the kit can optionally include one or more agents in a second container. The container or containers are placed within a package, and the package can optionally include administration or dosage instructions. A kit can include additional components such as syringes or other means for administering the agents as well as diluents or other means for formulation. Thus, the kits can comprise: a) a pharmaceutical composition comprising a compound described herein and a pharmaceutically acceptable carrier, vehicle or diluent; and b) a container or packaging. The kits may optionally comprise instructions describing a method of using the pharmaceutical compositions in one or more of the methods described herein (e.g. preventing or treating one or more of the diseases and disorders described herein). The kit may optionally comprise a second pharmaceutical composition comprising one or more additional agents described herein for co therapy use, a pharmaceutically acceptable carrier, vehicle or diluent. The pharmaceutical composition comprising the compound described herein and the second pharmaceutical composition contained in the kit may be optionally combined in the same pharmaceutical composition.

A kit includes a container or packaging for containing the pharmaceutical compositions and may also include divided containers such as a divided bottle or a divided foil packet. The container can be, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. It is feasible that more than one container can be used together in a single package to market a single dosage form. For example, tablets may be contained in a bottle which is in turn contained within a box.

An example of a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide written memory aid containing information and/or instructions for the physician, pharmacist or subject regarding when the medication is to be taken. A "daily dose" can be a single tablet or capsule or several tablets or capsules to be taken on a given day. When the kit contains separate compositions, a daily dose of one or more compositions of the kit can consist of one tablet or capsule while a daily dose of another or more compositions of the kit can consist of several tablets or capsules. A kit can take the form of a dispenser designed to dispense the daily doses one at a time in the order of their intended use. The dispenser can be equipped with a memory-aid, so as to further facilitate compliance with the regimen. An example of such a memory-aid is a mechanical counter which indicates the number of daily doses that have been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

EXAMPLES

All references provided in the Examples are herein incorporated by reference. As used herein, all abbreviations, symbols and conventions are consistent with those used in the contemporary scientific literature. See, e.g. Janet S. Dodd, ed., The ACS Style Guide: A Manual for Authors and Editors, $2^{nd}$ Ed., Washington, D.C.: American Chemical Society, 1997, herein incorporated in its entirety by reference.

Example 1

General Procedure A

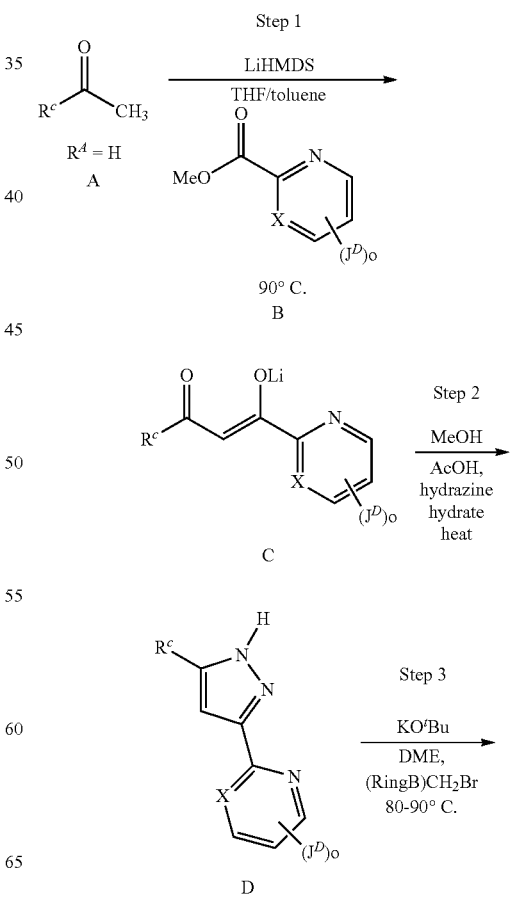

-continued

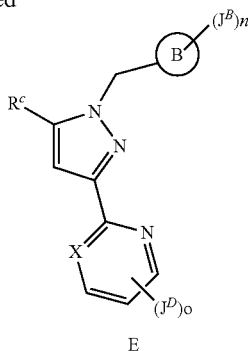

E

Step 1, Dione Enolate Formation:

To a cooled (−78° C.) solution of ketone A in THF, was added LiHMDS (1.05-1.1 eq, 1.0 M in toluene). The reaction was allowed to warm to rt, then charged with ester B (1.0 eq). At this time, the reaction was cooled to −90° C. and stirred at that temperature until judged complete (using either TLC or LC/MS analysis). Once complete (reaction time was typically 1-3 h), the product dione enolate C was precipitated out using excess diethyl ether, and then filtered and dried. This solid was carried onto the cyclization step without any further purification.

Step 2, Pyrazole Formation:

Dione enolate C was diluted with methanol and consecutively charged with AcOH (1-3 eq) and hydrazine hydrate (1.0 eq). The reaction mixture was heated to 60-80° C. and stirred until cyclization was deemed complete (by LC/MS analysis). Once complete (reaction time was typically less than 10 min), the reaction mixture was directly concentrated and the resulting pyrazole 1) was carried onto the alkylation step without any further purification. In some cases, upon cooling, pyrazole D crashed out of solution and was collected by filtration and dried. In other cases, the pyrazole was purified by SiO$_2$ chromatography using an appropriate gradient of EtOAc in hexanes.

Step 3, Alkylation:

Pyrazole D was dissolved in DME and consecutively charged with potassium tert-butoxide (or an alternative base when indicated) and the appropriately substituted benzyl bromide (1-3 eq). At this time, the reaction was heated to reflux (or above, when using closed vials as reaction vessels) and monitored by LC/MS analysis. Once complete, the reaction solution was allowed to cool and all solids filtered off. The filtrate was then concentrated and the resulting crude oil was purified using chromatography on SiO$_2$ with an appropriate solvent gradient (ethyl acetate/hexanes or DCM/methanol) to give compound E (color and physical state below).

It is important to note, that this alkylation process gives rise to two regioisomers. In all cases, these isomers were readily separable by standard chromatographic methods. Structure determination and differentiation within the regioisomeric pair was carried out via NMR spectroscopic methods, including nuclear Overhauser effect (nOe) and correlation spectroscopy (COSY). Furthermore, specific and diagnostic chemical shift trends in spectra generated from standard one-dimensional $^1$HNMR experiments were observed in molecules possessing similar connectivity patterns. These trends, therefore, were also exploited for the purpose of structure elucidation. The structure of one molecule in particular, I-3, was unambiguously assigned via single crystal X-ray diffraction (crystallization was achieved from a mixture of methylene chloride and heptane).

As an illustration of the structure determination process, the protons within compound I-10 were first assigned via COSY. Subsequent irradiation of the benzylic protons @ 5.48 ppm resulted in nOe's of the C-2 (8.64 ppm, 1.1%) and C-4 (7.65 ppm, 1.3%) protons within the 3-pyridyl group, thus proving molecular connectivity. Not surprisingly, irradiation of the corresponding benzylic protons within the other regioisomer resulted in negligible nOe signals.

The Following Compounds were Synthesized Following General Procedure A:

Intermediate 1

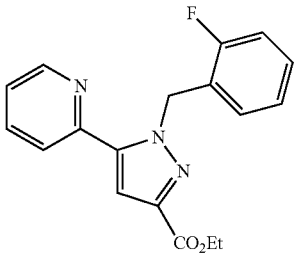 [SMILES: CCOC(=O)c1cc(-c2ccccn2)n(Cc2ccccc2F)n1]

This compound, which could be used as an intermediate for the synthesis of some of the compounds of Formula I, was synthesized as a light-yellow solid following General Procedure A; with diethyl oxalate used as reagent B instead of the reagent as drawn above, NaOEt used as base, and EtOH used as solvent in step 1; and sodium hydride as base, with the appropriate benzyl mesylate as the electrophile, and THF as solvent in step 3. $^1$H NMR (400 MHz, CDCl$_3$) δ 8.62-8.57 (m, 1H), 7.71 (td, 1H), 7.58-7.53 (m, 1H), 7.24-7.20 (m, 1H), 7.20 (s, 1H), 7.19-7.12 (m, 1H), 7.00-6.97 (m, 2H), 6.85-6.79 (m, 1H), 6.12 (s, 2H), 4.45 (q, 2H), 1.42 (t, 3H) ppm.

Intermediate 2

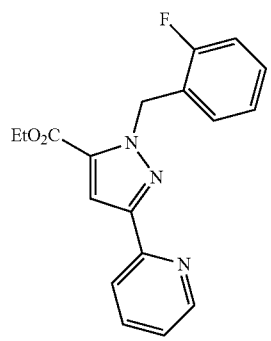 [SMILES: CCOC(=O)c1cc(-c2ccccn2)nn1Cc1ccccc1F]

This compound, that could be used as an intermediate for the synthesis of some of the compounds of Formula I, was synthesized as a light-yellow solid following General Procedure A; with diethyl oxalate used as reagent B, NaOEt used as base, and EtOH used as solvent in step 1; and sodium hydride as base, with the appropriate benzyl mesylate as the electrophile, and THF as solvent in step 3. $^1$H NMR (400 MHz, CDCl$_3$) δ 8.67-8.61 (m, 1H), 8.04-7.99 (m, 1H), 7.77-7.70 (m, 1H), 7.28-7.20 (s, 2H), 7.29 (dd, 1H), 7.10-7.05 (m, 1H), 7.04-6.99 (m, 1H), 6.91-6.86 (m, 1H), 5.93 (s, 2H), 4.31 (q, 2H), 1.33 (d, 3H) ppm.

Intermediate 3

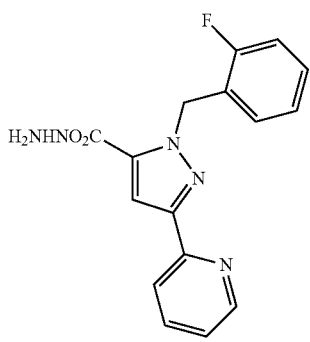

A mixture of intermediate 2 (200 mg) and hydrazine hydrate (1.2 ml) in ethanol (1.2 ml) was heated at 90° C. for 18 h. The mixture was cooled to rt and concentrated under vacuum. The resulting solid was rinsed with a minimal amount of chloroform to give intermediate 3 as white solid in 42% yield. $^1$H NMR (400 MHz, CDCl$_3$) δ 8.63-8.58 (m, 1H), 8.02-7.98 (m, 1H), 7.73 (td, 1H), 7.30 (bs, 1H), 7.25-7.19 (m, 3H), 7.10-6.94 (m, 3H), 5.92 (s, 2H), 4.06-3.99 (m, 2H) ppm.

Intermediate 5

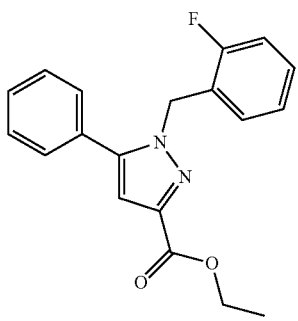 [SMILES: CCOC(=O)c1cc(-c2ccccc2)n(Cc2ccccc2F)n1]

This compound, which could be used as an intermediate for the synthesis of some of the compounds of Formula I, was synthesized as a light-yellow oil (42.2% yield over 3 steps) following General Procedure A; with diethyl oxalate used as reagent B instead of the reagent as drawn above, NaOEt used as base, and EtOH used as solvent in step 1, dione formation; and sodium hydride as base, with the appropriate benzyl mesylate as the electrophile, and THF as solvent in step 3, alkylation. $^1$H NMR (400 MHz, CDCl$_3$) δ 7.42-7.36 (m, 3H), 7.32-7.19 (m, 3H), 7.08-6.95 (m, 2H), 6.91 (s, 1H), 6.90-6.85 (m, 1H), 5.49 (m, 2H), 4.44 (q, 2H), 1.42 (t, 3H) ppm.

Intermediate 7

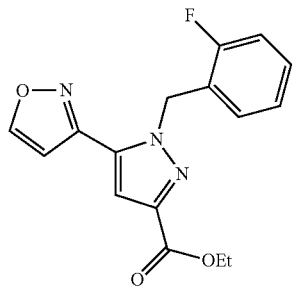 [SMILES: CCOC(=O)c1cc(-c2ccon2)n(Cc2ccccc2F)n1]

This compound, which could be used as an intermediate for the synthesis of some of the compounds of Formula I, was synthesized as a light orange-yellow solid (27-41% yield) following General Procedure A; starting with 3-acetylisoxazole as reagent A, with diethyl oxalate used as reagent B instead of the reagent as drawn above; NaOEt used as base, and EtOH used as solvent in step 1; and sodium hydride as base, with the appropriate benzyl mesylate as the electrophile, and THF as solvent in step 3. $^1$H NMR (400 MHz, CDCl$_3$) δ 8.45 (dd, 1H), 7.24-7.17 (m, 2H), 7.04-6.95 (m, 2H), 6.79 (t, 1H), 6.53 (dd, 1H), 5.94 (s, 2H), 4.42 (q, 2H), 1.40 (t, 3H); MS m/z: 316.0 (M+1).

Compound I-1

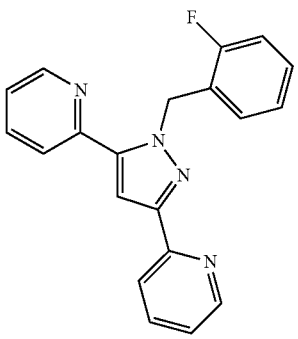 [SMILES: Fc1ccccc1Cn1nc(-c2ccccn2)cc1-c1ccccn1]

This compound was synthesized as a white solid (12% yield over 3 steps) following General Procedure A using 2-acetylpyridine and methyl picolinate in step 1 and 2-fluorobenzyl bromide in step 3. Base and solvent used in step 3 were K2CO3 (3 equiv) and acetonitrile, respectively. 1H NMR (400 MHz, CDCl$_3$) δ 8.64-8.62 (m, 1H), 8.58-8.55 (m, 1H), 8.02 (d, 1H), 7.72-7.61 (m, 3H), 7.33 (s, 1H), 7.21-7.11 (m, 3H), 7.00-6.86 (m, 3H), 6.13 (s, 2H) ppm.

Compound I-2

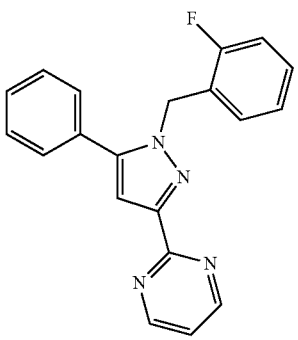 [SMILES: Fc1ccccc1Cn1nc(-c2ncccn2)cc1-c1ccccc1]

This compound was synthesized as an off-white solid (19.2% yield over 3 steps) following General Procedure A using acetophenone and methylpyrimidine-2-carboxylate in step 1 and 2-fluorobenzyl bromide in step 3. $^1$H NMR (400 MHz, CDCl$_3$) δ8.83 (d, 2H), 7.40-7.33 (m, 5H), 7.23-7.18 (m, 1H), 7.21 (t, 1H), 7.18 (s, 1H), 7.04-6.94 (m, 3H), 5.57 (s, 2H) ppm.

Compound I-4

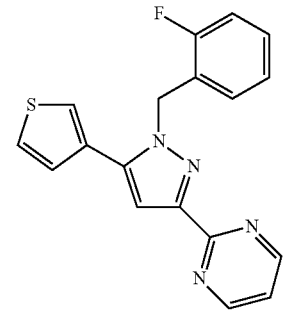 [SMILES: Fc1ccccc1Cn1nc(-c2ncccn2)cc1-c1ccsc1]

This compound was synthesized as a white solid (12.6% yield over 3 steps) following General Procedure A using 2-acetyl-thiophene and methylpyrimidine-2-carboxylate in step 1 and 2-fluorobenzyl bromide in step 3. $^1$H NMR (400 MHz, CDCl$_3$) δ 8.82 (d, 2H), 7.36-7.38 (m, 1H), 7.20-7.26 (m, 4H), 7.12 (dd, 1H), 7.00-7.07 (m, 2H), 6.88-6.92 (m, 1H), 5.63 (s, 2H).

Compound I-5

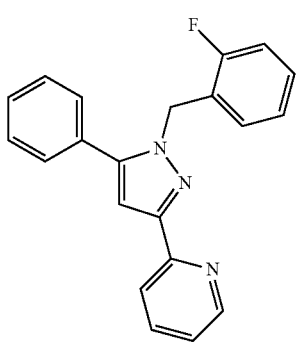

This compound was synthesized as a yellow-orange solid (56% yield over 3 steps) following General Procedure A using acetophenone and methyl picolinate in step 1 and 2-fluorobenzyl bromide in step 3. $^1$H NMR (400 MHz, CDCl$_3$) δ 8.66-8.64 (m, 1H), 8.01 (d, 1H), 7.73 (ddd, 1H), 7.42-7.35 (m, 5H), 7.24-7.21 (m, 2H), 7.06-6.94 (m, 3H), 7.03 (s, 1H), 5.50 (s, 2H) ppm.

Compounds I-6 and I-15

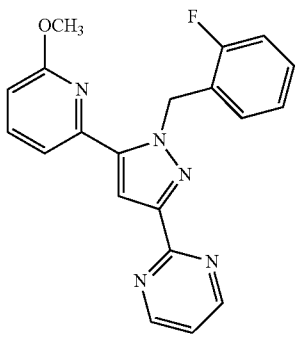

I-6

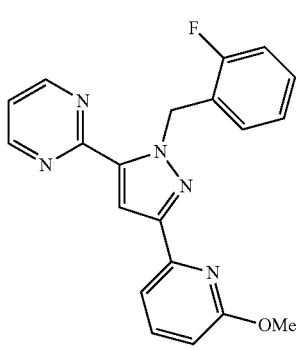

I-15

This compounds were synthesized as a white solid (44% yield over 3 steps) and as an off-white solid (8.2% over 3 steps) following General Procedure A using 1-(6-methoxy-pyridin-2-yl)ethanone and methylpyrimidine-2-carboxylate in step 1 and 2-fluorobenzyl bromide in step 3.

I-6: $^1$H NMR (400 MHz, CDCl$_3$) δ 8.81 (dd, 2H), 7.58 (ddd, 1H), 7.47 (s, 1H), 7.27 (d, 1H), 7.19 (ddd, 1H), 7.14-7.09 (m, 1H), 6.97-6.92 (m, 1H), 6.90 (t, 1H), 6.68 (t, 1H), 6.64 (d, 1H), 6.20 (s, 2H), 3.61 (s, 3H) ppm.

I-15: $^1$H NMR (400 MHz, CDCl$_3$) δ 8.74 (d, 2H), 7.80 (s, 1H), 7.66-7.59 (m, 2H), 7.19-7.15 (m, 1H), 7.15 (t, 1H), 7.04-6.99 (m, 1H), 6.94 (ddd, 1H), 6.84 (ddd, 1H), 6.68 (dd, 1H), 6.22 (s, 2H), 4.40 (s, 3H) ppm.

Compound I-7

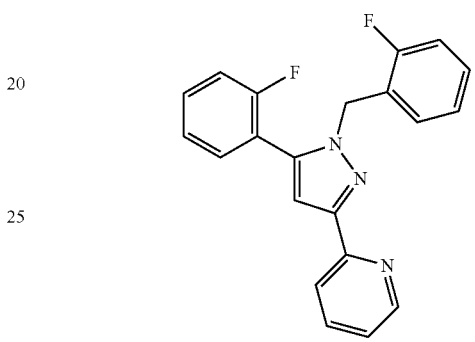

This compound was synthesized as a light-yellow solid (18.8% yield over 3 steps) following General Procedure A using 2-fluoroacetophenone and methyl picolinate in step 1 and 2-fluorobenzyl bromide in step 3. $^1$H NMR (400 MHz, CDCl$_3$) δ 8.66-8.63 (m, 1H), 7.99 (dd, 1H), 7.74-7.70 (m, 1H), 7.43-7.37 (m, 1H), 7.28-7.14 (m, 4H), 7.16 (t, 1H), 7.03 (s, 1H), 7.02-6.91 (m, 3H), 5.42 (s, 2H) ppm.

Compound I-8

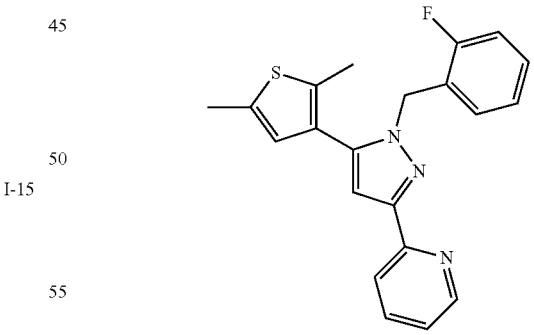

This compound was synthesized as a yellow-orange solid (41.4% yield over 3 steps) following General Procedure A using 1-(2,5-dimethylthiophen-3-yl)ethanone and methyl picolinate in step 1 and 2-fluorobenzyl bromide in step 3. $^1$H NMR (400 MHz, CDCl$_3$) δ 8.65-8.63 (m, 1H), 7.99 (dd, 1H), 7.72-7.68 (m, 1H), 7.23-7.17 (m, 2H), 7.03-6.96 (m, 2H), 6.90-6.86 (m, 1H), 6.89 (s, 1H), 6.43 (s, 1H), 5.36 (s, 2H), 2.38 (s, 3H), 2.24 (s, 3H) ppm.

Compound I-9

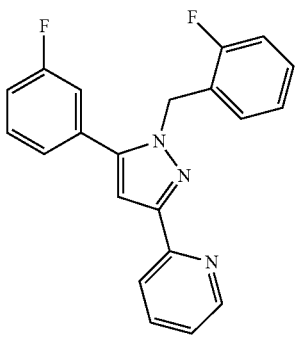 [SMILES: Fc1cccc(-c2cc(-c3ccccn3)nn2Cc2ccccc2F)c1]

This compound was synthesized as an off-white solid (10.6% yield over 3 steps) following General Procedure A using 3-fluoroacetophenone and methyl picolinate in step 1 and 2-fluorobenzyl bromide in step 3. $^1$H NMR (400 MHz, CDCl$_3$) δ 8.66-8.64 (m, 1H), 8.00 (dd, 1H), 7.73 (ddd, 1H), 7.40-7.34 (m, 1H), 7.27-7.21 (m, 2H), 7.15-6.94 (m, 7H), 5.49 (s, 2H) ppm.

Compound I-10

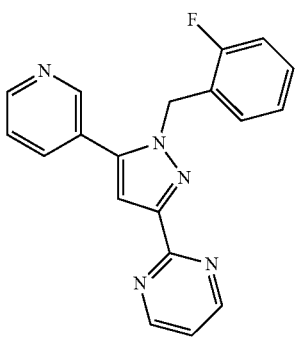

This compound was synthesized as an off-white solid (11.5% yield over 3 steps) following General Procedure A using 3-acetylpyridine and methylpyrimidine-2-carboxylate in step 1 and 2-fluorobenzyl bromide in step 3. $^1$H NMR (400 MHz, CDCl$_3$) δ 8.84 (dd, 2H), 8.64-8.61 (m, 2H), 7.64-7.61 (m, 1H), 7.33 (ddd, 1H), 7.24-7.19 (m, 2H), 7.22 (s, 1H), 7.05-6.95 (m, 3H), 5.56 (s, 2H) ppm.

Compound I-11

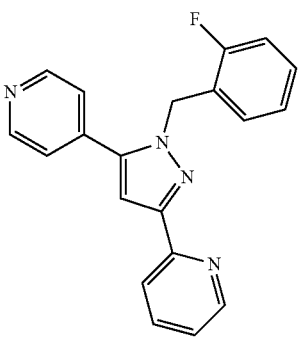 [SMILES: Fc1ccccc1Cn1nc(-c2ccccn2)cc1-c1ccncc1]

This compound was synthesized as a white solid (2.6% yield over 3 steps) following General Procedure A using 4-acetylpyridine and methyl picolinate in step 1 and 2-fluorobenzyl bromide in step 3. $^1$H NMR (400 MHz, CDCl$_3$) δ 8.66-8.65 (m, 2H), 8.01 (ddd, 1H), 7.74 (ddd, 1H), 7.29-7.23 (m, 4H), 7.14 (s, 1H), 7.08-7.02 (m, 2H), 6.99-6.94 (m, 2H), 5.54 (s, 2H) ppm.

Compound I-12

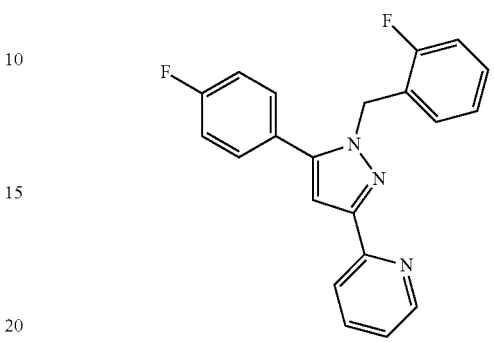

This compound was synthesized as a light-yellow solid (23.6% yield over 3 steps) following General Procedure A using 4-fluoroacetophenone and methyl picolinate in step 1 and 2-fluorobenzyl bromide in step 3. $^1$H NMR (400 MHz, CDCl$_3$) δ 8.65 (d, 1H), 8.00 (d, 1H), 7.23 (ddd, 1H), 7.34-7.21 (m, 4H), 7.11-6.94 (m, 6H), 5.46 (s, 2H) ppm.

Compound I-13

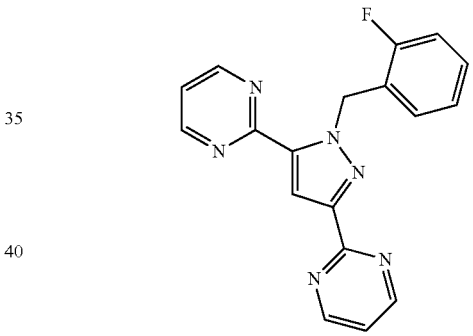

This compound was synthesized as a white solid (2.6% yield over 3 steps) following General Procedure A using 2-acetylpyrimidine and methylpyrimidine-2-carboxylate in step 1 and 2-fluorobenzyl bromide in step 3. $^1$H NMR (400 MHz, CDCl$_3$) δ 8.78 (d, 2H), 8.66 (d, 2H), 7.91 (s, 1H), 7.21-7.19 (m, 2H), 7.16 (t, 1H), 7.07 (t, 1H), 6.99-6.90 (m, 2H), 6.22 (s, 2H) ppm.

Compound I-14

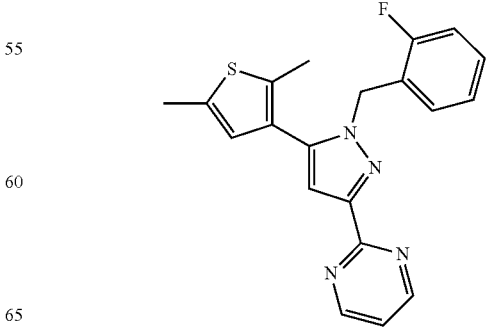

This compound was synthesized as an off-white solid (18.2% yield over 3 steps) following General Procedure A using 1-(2,5-dimethylthiophen-3-yl)ethanone and methyl pyrimidine-2-carboxylate in step 1 and 2-fluorobenzyl bromide in step 3. $^1$H NMR (400 MHz, CDCl$_3$) δ 8.81 (d, 2H), 7.19 (t, 1H), 7.18-7.15 (m, 1H), 7.02 (s, 1H), 7.01-6.87 (m, 3H), 6.40 (s, 1H), 5.43 (s, 2H), 2.36 (s, 3H), 2.20 (s, 3H) ppm.
Compound I-16

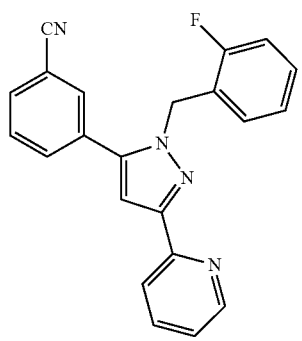 [SMILES: N#Cc1cccc(-c2cc(-c3ccccn3)nn2Cc2ccccc2F)c1]

This compound was synthesized as a light-orange solid (26.2% yield over 3 steps) following General Procedure A using 3-cyanoacetophenone and methyl picolinate in step 1 and 2-fluorobenzyl bromide in step 3. $^1$H NMR (400 MHz, CDCl$_3$) δ 8.66-8.64 (m, 1H), 8.02-7.99 (m, 1H), 7.77-7.73 (m, 1H), 7.70-7.67 (m, 1H), 7.62-7.50 (m, 3H), 7.29-7.23 (m, 2H), 7.09-7.00 (m, 3H), 7.05 (s, 1H), 5.46 (s, 2H) ppm.
Compound I-17

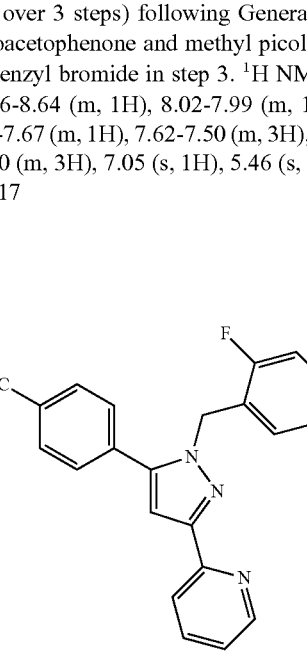

This compound was synthesized as an off-white solid (26.3% yield over 3 steps) following General Procedure A using 4-cyanoacetophenone and methyl picolinate in step 1 and 2-fluorobenzyl bromide in step 3. $^1$H NMR (400 MHz, CDCl$_3$) δ 8.66-8.64 (m, 1H), 8.01 (d, 1H), 7.74 (ddd, 1H), 7.69 (d, 2H), 7.47 (d, 2H), 7.28-7.23 (m, 2H), 7.09 (s, 1H), 7.08-6.97 (m, 3H), 5.49 (s, 2H) ppm.

Compound I-18

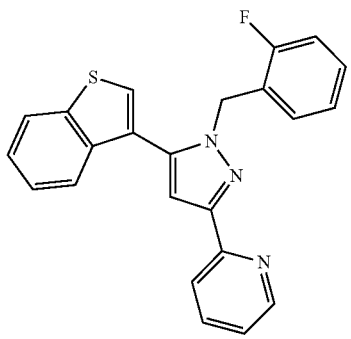

This compound was synthesized as a light yellow solid (38.5% yield over 3 steps) following General Procedure A using 1-(benzo[b]thiophen-3-yl)ethanone and methyl picolinate in step 1 and 2-fluorobenzyl bromide in step 3. Base and solvent used in step 3 were NaH (1 eq) and DMF, respectively. $^1$H NMR (400 MHz, CDCl$_3$) δ 8.68-8.66 (m, 1H), 8.04 (d, 1H), 7.90 (dd, 1H), 7.77-7.73 (m, 2H), 7.43-7.36 (m, 2H), 7.32 (s, 1H), 7.25-7.17 (m, 1H), 7.15 (s, 1H), 7.04-6.94 (m, 2H), 5.46 (s, 2H) ppm.
Compound I-19

This compound was synthesized as a tan solid (13% yield over 3 steps) following General Procedure A using 4-acetylpyridine and methylpyrimidine-2-carboxylate in step 1 and 2-fluorobenzyl bromide in step 3. $^1$H NMR (400 MHz, CDCl$_3$) δ 8.85 (d, 2H), 8.65 (m, 2H), 7.29 (s, 1H), 7.29-7.20 (m, 4H), 7.06-6.95 (m, 3H), 5.62 (s, 2H) ppm. MS: [M+H]= 332.
Compound I-20

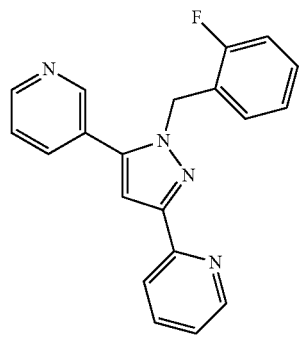

This compound was synthesized as a tan solid (18% yield over 3 steps) following General Procedure A using 3-acetylpyridine and methyl picolinate in step 1 and 2-fluorobenzyl bromide in step 3. $^1$H NMR (400 MHz, CDCl$_3$) δ 8.65 (m, 3H), 8.01 (d, 1H), 7.75 (app. td, 1H), 7.66 (app. dt, 1H), 7.35 (dd, 1H), 7.24 (m, 2H), 7.09 (s, 1H), 7.05 (m, 1H), 6.99 (m, 2H), 5.48 (s, 2H) ppm. MS: [M+H]=331.

Compound I-21

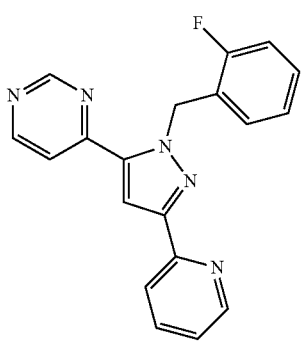 [SMILES: Fc1ccccc1Cn1nc(-c2ccccn2)cc1-c1ccncn1]

This compound was synthesized as a white solid (19% yield over 3 steps) following General Procedure A using 2-acetylpyridine and methylpyrimidine-4-carboxylate in step 1 and 2-fluorobenzyl bromide in step 3. $^1$H NMR (400 MHz, CDCl$_3$) δ 9.18 (d, 1H), 8.75 (d, 1H), 8.65 (m, 1H), 8.05 (d, 1H), 7.76 (app. td, 1H), 7.63 (dd, 1H), 7.53 (s, 1H), 7.25 (m, 1H), 7.19 (m, 1H), 7.03 (m, 1H), 6.96 (app. t, 1H), 6.87 (app. t, 1H), 6.20 (s, 2H) ppm. MS: [M+H]=332.

Compound I-22

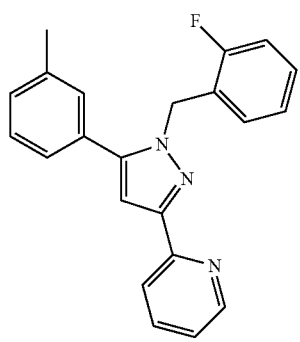 [SMILES: Cc1cccc(-c2cc(-c3ccccn3)nn2Cc2ccccc2F)c1]

This compound was synthesized as a light yellow solid (62% yield over 3 steps) following General Procedure A using 3-methylacetophenone and methyl picolinate in step 1 and 2-fluorobenzyl bromide in step 3. $^1$H NMR (400 MHz, CDCl$_3$) δ 8.65 (d, 1H), 8.00 (d, 1H), 7.73 (app. td, 1H), 7.30-7.13 (m, 6H), 7.07-6.95 (m, 4H), 7.01 (s, 1H), 5.49 (s, 2H), 2.34 (s, 3H) ppm. MS: [M+H]=344.

Compound I-23

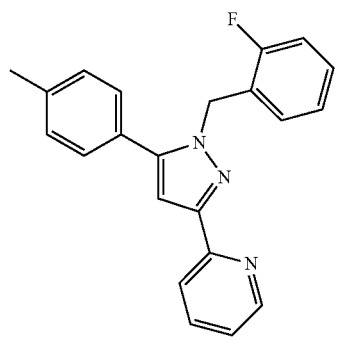

This compound was synthesized as an off-white solid (62% yield over 3 steps) following General Procedure A using 4-methylacetophenone and methyl picolinate in step 1 and 2-fluorobenzyl bromide in step 3. $^1$H NMR (400 MHz, CDCl$_3$) δ 8.65 (d, 1H), 8.00 (d, 1H), 7.72 (app. td, 1H), 7.27-7.19 (m, 6H), 7.03 (m, 2H), 7.00 (s, 1H), 6.94 (app. t, 1H), 5.48 (s, 2H), 2.38 (s, 3H) ppm. MS: [M+H]=344.

Compound I-24

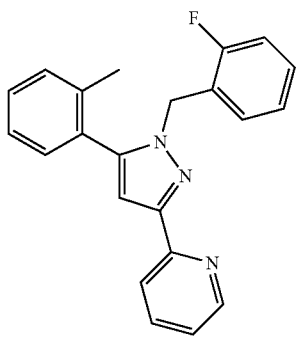 [SMILES: Cc1ccccc1-c1cc(-c2ccccn2)nn1Cc1ccccc1F]

This compound was synthesized as an off-white solid (66% yield over 3 steps) following General Procedure A using 2-methylacetophenone and methyl picolinate in step 1 and 2-fluorobenzyl bromide in step 3. $^1$H NMR (400 MHz, CDCl$_3$) δ 8.65 (d, 1H), 8.01 (d, 1H), 7.72 (app. td, 1H), 7.32 (app. td, 1H), 7.26 (d, 1H), 7.23-7.11 (m, 4H), 7.01 (app. t, 1H), 6.95 (m, 1H), 6.91 (m, 1H), 6.91 (s, 1H), 5.23 (s, 2H), 2.12 (s, 3H) ppm. MS: [M+H]=344.

Compounds I-25 and I-78

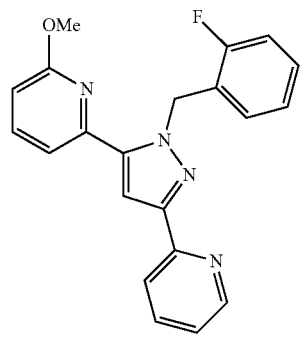

I-25

I-78

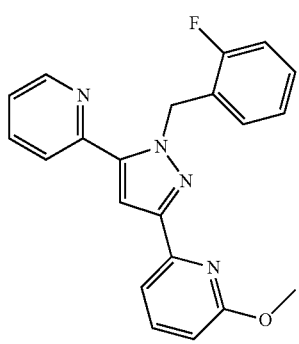

Compound I-27

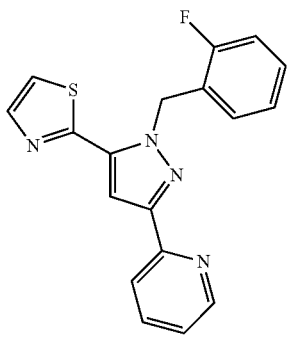 [SMILES: Fc1ccccc1Cn1nc(-c2ccccn2)cc1-c1nccs1]

These compounds were synthesized as a light-yellow solid (24.2% yield over 3 steps) and as a white solid, respectively, following General Procedure A using 1-(pyridin-2-yl)ethanone and methyl picolinate in step 1 and 2-fluorobenzyl bromide in step 3.

I-25: $^1$H NMR (400 MHz, CDCl$_3$) δ 8.67-8.61 (m, 1H), 8.04-7.99 (m, 1H), 7.73-7.67 (m, 1H), 7.60-7.55 (m, 1H), 7.36 (s, 1H), 7.29 (dd, 1H), 7.22-7.18 (m, 1H), 7.18-7.11 (m, 1H), 7.02-6.96 (m, 1H), 6.96-6.91 (m, 1H), 6.74-6.68 (m, 1H), 6.65-6.62 (m, 1H), 6.15 (s, 2H), 3.63 (s, 3H) ppm.

I-78: $^1$H NMR (400 MHz, CDCl$_3$) δ 8.62-8.58 (m, 1H), 7.74-7.64 (m, 1H), 7.66-7.58 (m, 2H), 7.32 (s, 1H), 7.21-7.16 (m, 1H), 7.16-7.11 (m, 1H), 7.01-6.98 (m, 1H), 6.98-6.92 (m, 1H), 6.92-6.87 (m, 1H), 6.68 (dd, 1H), 6.11 (s, 2H), 4.04 (s, 3H) ppm.

Compound I-26

This compound was synthesized as a light yellow solid (8.4% yield over 3 steps) following General Procedure A using 1-(thiazoyl-2-yl)ethanone and methyl picolinate in step 1 and 2-fluorobenzyl bromide in step 3. $^1$H NMR (400 MHz, CDCl$_3$) δ 8.67-8.62 (m, 1H), 8.02 (d, 1H), 7.83 (dd, 1H), 7.77-7.73 (m, 1H), 7.41 (s, 1H), 7.37-7.34 (m, 1H), 7.27-7.21 (m, 1H), 7.17-7.16 (m, 1H), 7.07-7.00 (m, 1H), 7.00-6.95 (m, 1H), 6.93-6.87 (m, 1H), 6.12 (s, 1H) ppm.

Compound I-32

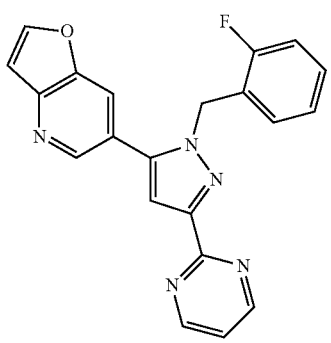 [SMILES: Fc1ccccc1Cn1nc(-c2ncccn2)cc1-c1cnc2ccoc2c1]

This compound was synthesized as a viscous oil (1% yield over 3 steps) following General Procedure A, using 1-(furo[3,2-b]pyridin-6-yl)ethanone and methylpyrimidine-2-carboxylate in step 1 and 2-fluorobenzyl bromide in step 3. $^1$H NMR (400 MHz, CDCl$_3$) 8.85 (d, 2H), 8.56 (d, 1H), 7.92 (d, 1H), 7.70 (q, 1H), 7.23-7.25 (m, 3H), 7.03-7.05 (m, 3H), 6.95-7.00 (m, 1H), 5.59 (s, 2H).

Compound I-33

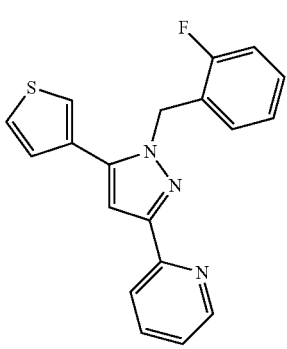

This compound was synthesized as a yellow solid (9.7% yield over 3 steps) following General Procedure A using 1-(thiophen-3-yl)ethanone and methyl picolinate in step 1 and 2-fluorobenzyl bromide in step 3. $^1$H NMR (400 MHz, CDCl$_3$) δ 8.66-8.64 (m, 1H), 7.99 (d, 1H), 7.74-7.66 (m, 1H), 7.35 (dd, 1H), 7.27-7.17 (m, 3H), 7.14-7.11 (m, 1H), 7.07 (s, 1H), 7.06-7.01 (m, 2H), 6.93-6.86 (m, 1H), 5.57 (s, 2H) ppm.

This compound was synthesized as a brown solid (2.5% yield over 3 steps) following General Procedure A using 2-acetyl-thiazole and methylpyrimidine-2-carboxylate in step 1 and 2-fluorobenzyl bromide in step 3. ¹H NMR (400 MHz, CDCl₃) 8.84 (d, 2H), 7.76 (d, 1H), 7.47 (s, 1H), 7.30 (d, 1H), 7.16-7.19 (m, 1H), 7.07-7.13 (m, 1H), 6.86-6.96 (m, 2H), 6.78-6.81 (m, 1H), 6.11 (s, 2H).
Compound I-34

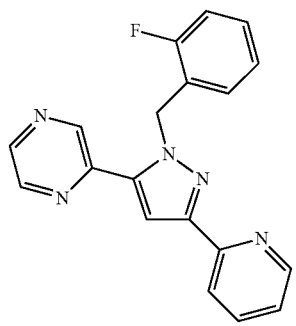 [SMILES: Fc1ccccc1Cn1nc(-c2ccccn2)cc1-c1cnccn1]

This compound was synthesized as a white solid (1.4% yield over 3 steps) following General Procedure A using 2-acetyl-pyridine and methylpyrazine-2-carboxylate in step 1 and 2-fluorobenzyl bromide in step 3. ¹H NMR (400 MHz, CDCl₃) δ 8.96 (d, 1H), 8.66-8.67 (m, 1H), 8.54-8.55 (m, 1H), 8.46 (d, 1H), 8.05 (dt, 1H), 7.75 (dt, 1H), 7.47 (s, 1H), 7.23-7.25 (m, 1H), 7.15-7.20 (m, 1H), 6.94-7.02 (m, 2H), 6.06-6.08 (s, 2H).
Compound I-35

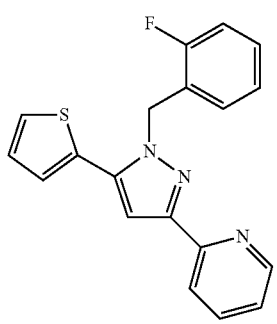 [SMILES: Fc1ccccc1Cn1nc(-c2ccccn2)cc1-c1cccs1]

This compound was synthesized as a white solid (11.7% yield over 3 steps) following General Procedure A using 2-acetyl-thiophene and methyl picolinate in step 1 and 2-fluorobenzyl bromide in step 3. ¹H NMR (400 MHz, CDCl₃) δ 8.65 (td, 1H), 7.99 (dd, 1H), 7.72 (dt, 1H), 7.36 (dd, 1H), 7.20-7.27 (m, 2H), 7.13 (s, 1H), 7.02-7.08 (m, 4H), 6.86 (dt, 1H), 5.62 (s, 2H).
Compound I-36

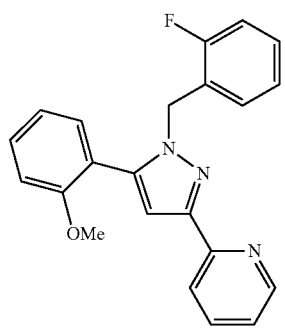

This compound was synthesized as a white solid (11.5% yield over 3 steps) following General Procedure A using 1-(2-methoxyphenyl)ethanone and methyl picolinate in step 1 and 2-fluorobenzyl bromide in step 3. ¹H NMR (400 MHz, CDCl₃) δ 8.60 (dq, 1H), 8.04 (dt, 1H), 7.70 (tq, 1H), 7.63 (td, 1H), 7.31 (tq, 1H), 7.24 (dd, 1H), 7.13-7.20 (m, 3H), 6.91-7.05 (m, 4H), 6.09 (s, 2H), 3.94 (s, 3H).
Compound I-37

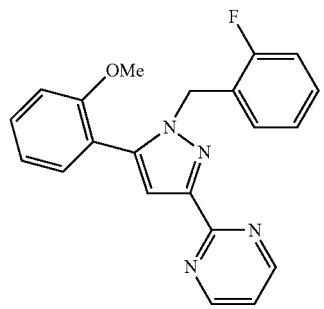 [SMILES: COc1ccccc1-c1cc(-c2ncccn2)nn1Cc1ccccc1F]

This compound was synthesized as a white solid (63.4% yield over 3 steps) following General Procedure A using 1-(2-methoxyphenyl)ethanone and methylpyrimidine-2-carboxylate in step 1 and 2-fluorobenzyl bromide in step 3. ¹H NMR (400 MHz, CDCl₃) δ 8.82 (d, 2H), 7.36-7.40 (m, 1H), 7.11-7.20 (m, 3H), 7.08 (s, 1H), 7.85-7.99 (m, 5H), 5.43 (s, 2H), 3.66 (s, 3H).
Compound I-38

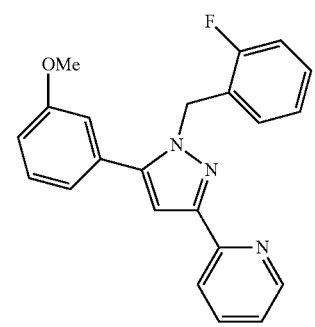 [SMILES: COc1cccc(-c2cc(-c3ccccn3)nn2Cc2ccccc2F)c1]

This compound was synthesized as a white solid (21.8% yield over 3 steps) following General Procedure A using 1-(3-methoxyphenyl)ethanone and methyl picolinate in step 1 and 2-fluorobenzyl bromide in step 3. ¹H NMR (400 MHz, CDCl₃) δ 8.57-8.59 (m, 1H), 7.92-7.94 (d, 1H), 7.66 (dt, 1H), 7.24 (t, 1H), 7.14-7.19 (m, 2H), 6.95-7.00 (m, 3H), 6.85-6.93 (m, 3H), 6.81 (d, 1H), 5.44 (s, 2H), 3.64 (s, 3H).
Compound I-40

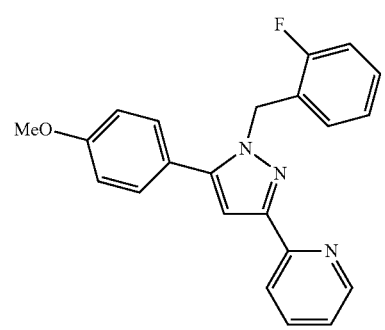

This compound was synthesized as a white solid (16.36% yield over 3 steps) following General Procedure A using 1-(4-methoxyphenyl)ethanone and methyl picolinate in step 1 and 2-fluorobenzyl bromide in step 3. $^1$H NMR (400 MHz, CDCl$_3$) δ 8.64-8.65 (m, 1H), 7.99 (dd, 1H), 7.69-7.73 (m, 1H), 7.25-7.30 (m, 2H), 7.19-7.23 (m, 3H), 6.90-7.05 (m, 5H), 5.47 (s, 2H), 3.82 (s, 3H).

Compound I-42

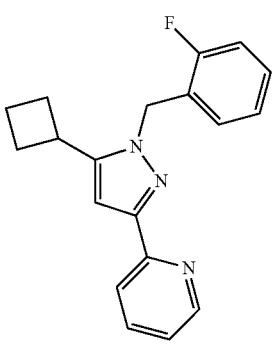 [SMILES: Fc1ccccc1Cn1nc(-c2ccccn2)cc1C1CCC1]

This compound was synthesized as an off-white solid (38.7% yield over 3 steps) following General Procedure A using cyclobutyl methylketone and methyl picolinate in step 1 and 2-fluorobenzyl bromide in step 3. $^1$H NMR (400 MHz, CDCl$_3$) δ 8.64-8.62 (m, 1H), 7.95 (d, 1H), 7.69 (ddd, 1H), 7.25-7.16 (m, 2H), 7.08-6.99 (m, 2H), 6.85 (s, 1H), 6.85-6.79 (m, 1H), 5.36 (s, 2H), 3.45-3.36 (m, 1H), 2.30-2.21 (m, 2H), 2.18-2.08 (m, 2H), 2.03-1.87 (m, 2H) ppm.

Compound I-45

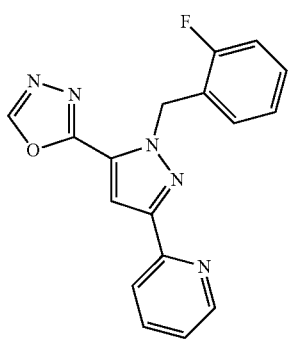 [SMILES: Fc1ccccc1Cn1nc(-c2ccccn2)cc1-c1nnco1]

A mixture of intermediate 3 (110 mg), trimethyl orthoformate (1.2 ml), and p-toluenesulfonic acid monohydrate (13 mg) was heated at reflux for 18 h. The mixture was cooled to rt and concentrated under vacuum. The resulting solid was purified using SiO$_2$ chromatography (ethyl acetate/hexanes) to give I-45 as off-white solid. $^1$H NMR (400 MHz, CDCl$_3$) δ 8.67-8.64 (m, 1H), 8.50-7.47 (m, 1H), 8.05-8.00 (m, 1H), 7.79-7.71 (m, 1H), 7.60 (s, 1H), 7.29-7.20 (m, 2H), 7.10-6.94 (m, 3H), 6.10 (s, 2H) ppm.

Compound I-47

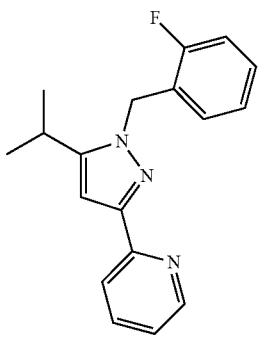 [SMILES: CC(C)c1cc(-c2ccccn2)nn1Cc1ccccc1F]

This compound was synthesized as a white solid (46% yield over 3 steps) following General Procedure A using 3-methyl-2-butanone and methyl picolinate in step 1 and 2-fluorobenzyl bromide in step 3. $^1$H NMR (400 MHz, CDCl$_3$) δ 8.63 (d, 2H), 7.95 (d, 1H), 7.70 (app. td, 1H), 7.23 (m, 1H), 7.18 (m, 1H), 7.06 (m, 1H), 7.02 (app. t, 1H), 6.84 (app. t, 1H), 6.79 (s, 1H), 5.46 (s, 2H), 2.90 (hept, 1H), 1.22 (d, 6H) ppm. MS: [M+H]=296.

Compound I-48

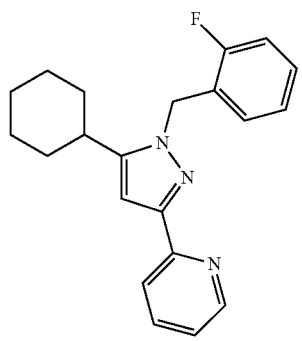 [SMILES: Fc1ccccc1Cn1nc(-c2ccccn2)cc1C1CCCCC1]

This compound was synthesized as a white solid (22% yield over 3 steps) following General Procedure A using 1-cyclohexylethanone and methyl picolinate in step 1 and 2-fluorobenzyl bromide in step 3. $^1$H NMR (400 MHz, CDCl$_3$) δ 8.62 (d, 2H), 7.95 (d, 1H), 7.69 (m, 1H), 7.24 (m, 1H), 7.18 (m, 1H), 7.06 (m, 1H), 7.03 (app. t, 1H), 6.87 (app. t, 1H), 6.75 (s, 1H), 5.44 (s, 2H), 2.53 (m, 1H), 1.84-1.66 (m, 5H), 1.46-1.17 (m, 5H) ppm. MS: [M+H]=336.

Compound I-49

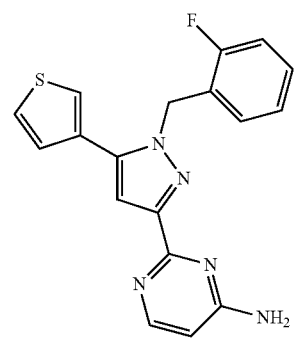

This compound was synthesized as a white solid (3.0% yield over 4 steps—cyclization reaction was 6%) following General Procedure A and using the 3-thiophenyl-derived ketone en route to the required ethyl 1-(2-fluorobenzyl)-5-(thiophen-3-yl)-1H-pyrazole-3-carboxylate starting unit. $^1$H NMR (400 MHz, CDCl$_3$) δ 8.33 (d, 1H), 7.35 (ddd, 1H), 7.23-7.20 (m, 2H), 7.15 (s, 1H), 7.12-7.11 (m, 1H), 7.06-7.00 (m, 2H), 6.84 (ddd, 1H), 6.35 (dd, 1H), 5.63 (s, 2H), 5.05 (bs, 2H) ppm.

Compounds I-51 and I-52

These two compounds were synthesized as a white solid (21% yield over 3 steps) and an off-white solid (17% yield over 3 steps) respectively following General Procedure A using 1-(pyridin-2-yl)ethanone, and methyl 5-bromopicolinate in step 1 and 2-fluorobenzyl bromide in step 3.

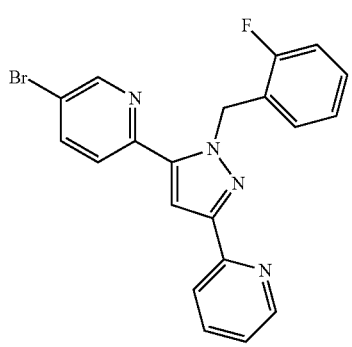

I-51

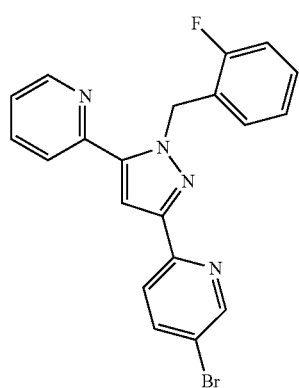

I-52

I-51: $^1$H NMR (400 MHz, CDCl$_3$) δ 8.65 (m, 2H), 8.04 (d, 1H), 7.84 (dd, 1H), 7.74 (app. td, 1H), 7.56 (d, 1H), 7.35 (s, 1H), 7.23 (m, 1H), 7.17 (m, 1H), 7.00 (m, 1H), 6.95 (app. t, 1H), 6.87 (app. t, 1H), 6.08 (s, 2H) ppm. MS: [M+H]=409 and 411.

I-52: $^1$H NMR (400 MHz, CDCl$_3$) δ 8.68 (d, 1H), 8.61 (d, 1H), 7.94 (d, 1H), 7.84 (dd, 1H), 7.73 (app. td, 1H), 7.64 (d, 1H), 7.29 (s, 1H), 7.21 (m, 1H), 7.16 (m, 1H), 6.99 (m, 1H), 6.95 (m, 1H), 6.89 (app. t, 1H), 6.11 (s, 2H) ppm. MS: [M+H]=409 and 411.

Compound I-55

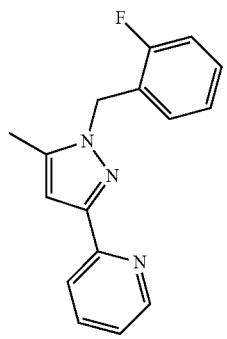 [SMILES: Cc1cc(-c2ccccn2)nn1Cc1ccccc1F]

To a cold solution of intermediate 2 (385 mg) in THF (6.0 ml) at 0° C. and under argon, was added a solution of lithium aluminum hydride (880 μl, 2.0 M in THF). The mixture was removed from the ice bath and stirred at room temperature for 2 h. Upon completion of the reaction, the mixture was cooled to 0° C. and sequentially treated with water (70 μl), 15% sodium hydroxide solution in water (130 μL), and water (70 μl). The resulting precipitate was removed by filtration. The filtrate was concentrated under vacuum to give (1-(2-fluorobenzyl)-3-(pyridin-2-yl)-1H-pyrazol-5-yl)methanol as white solid. In a separate flask, (1-(2-fluorobenzyl)-3-(pyridin-2-yl)-1H-pyrazol-5-yl)methanol (113 mg), lithium chloride (33.8 mg), triethylamine (0.1 ml), and THF were combined (2.0 ml) and cooled to 0° C. To this mixture, was added methanesulfonyl chloride (120 μl). The mixture was gradually warmed to ambient temperature over the course of 16 h. The mixture was diluted with ethyl acetate (100 ml), washed with saturated solution of sodium bicarbonate (20 ml), and brine (20 ml). The organic layer was dried, filtered, and evaporated to give 2-(5-(chloromethyl)-1-(2-fluorobenzyl)-1H-pyrazol-3-yl)pyridine as crude yellow solid. This crude solid (115 mg) was dissolved in THF (1.9 ml) in a separate flask equipped with a stir bar and a balloon filled with argon. The mixture was cooled to 0° C. To this mixture, was added dropwise, a solution of Superhydride (1.1 ml, 1.0 M in THF). The mixture was removed from the ice bath and stirred at room temperature for 24 h. Upon completion of the reaction, the mixture was cooled to 0° C. and sequentially treated with water (120 μl), 15% sodium hydroxide solution in water (240 μL), and water (120 μl). The resulting mixture was diluted in chloroform (100 ml) and washed with brine (50 ml). The organic layer was dried, filtered, and evaporated to give crude solid. The crude solid was purified using SiO$_2$ chromatography (ethyl acetate/hexanes) to give I-55 as off-white solid (44.6% yield over three steps). $^1$H NMR (400 MHz, CDCl$_3$) δ 8.63-8.59 (m, 1H), 7.93-7.89 (m, 1H), 7.68 (td, 1H), 7.27-7.20 (m, 1H), 7.19-7.14 (m, 1H), 7.09-7.01 (m, 2H), 6.93-6.88 (m, 1H), 6.71 (s, 1H), 5.42 (s, 2H), 2.27 (s, 3H) ppm.

Compounds I-56 and I-57

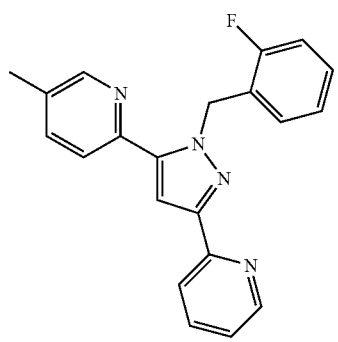

I-56

-continued

I-57

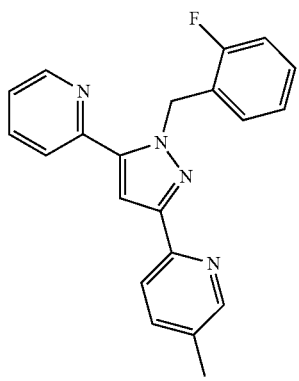

Compound I-60

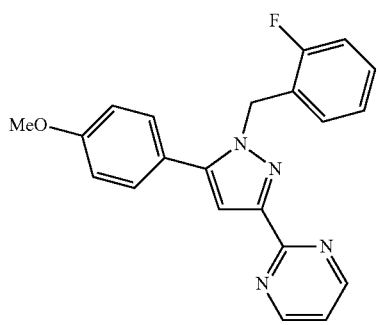

These two compound were synthesized as colorless solids (both <1% isolated yield over 3 steps) following General Procedure A using 1-(5-methylpyridin-2-yl)ethanone hydrochloride and methyl picolinate in step 1 and 2-fluorobenzyl bromide in step 3. (Note—2.1 eq. of LiHMDS was used in step 1)

I-56: ¹H NMR (400 MHz, CDCl₃) δ 8.70 (d, 1H), 8.43 (s, 1H), 8.10 (d, 1H), 7.81 (app. td, 1H), 7.57 (d, 1H), 7.54 (dd, 1H), 7.39 (s, 1H), 7.28 (m, 1H), 7.16 (m, 1H), 6.99 (m, 1H), 6.95 (m, 1H), 6.88 (app. t, 1H), 6.12 (s, 2H), 2.34 (s, 3H) ppm. MS: [M+H]=345.

I-57: ¹H NMR (400 MHz, CDCl₃) δ 8.60 (d, 1H), 8.56 (s, 1H), 8.03 (d, 1H), 7.73 (app. td, 1H), 7.67 (m, 2H), 7.45 (s, 1H), 7.21 (m, 1H), 7.16 (m, 1H), 6.99 (m, 1H), 6.95 (m, 1H), 6.89 (app. t, 1H), 6.13 (s, 2H), 2.41 (s, 3H) ppm. MS: [M+H]= 345.

Compound I-59

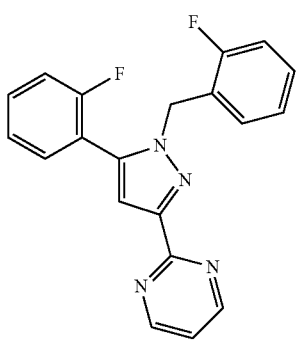

This compound was synthesized as a white solid (59% yield over 3 steps) following General Procedure A using 2-fluoroacetophenone and methylpyrimidine-2-carboxylate in step 1 and 2-fluorobenzyl bromide in step 3. ¹H NMR (400 MHz, CDCl₃) δ 8.83 (d, 2H), 7.43-7.37 (m, 1H), 7.26 (s, 1H), 7.24-7.19 (m, 2H), 7.19-7.12 (m, 3H), 7.00-6.94 (m, 2H), 6.92-6.87 (m, 1H), 5.51 (s, 2H).

This compound was synthesized as a viscous oil that solidified upon standing (60.7% over 3 steps) following General Procedure A using 4-methoxyacetophenone in step 1 and 2-fluorobenzyl bromide in 3.

¹H NMR (400 MHz, CDCl₃) δ 8.81 (d, 2H), 7.23-7.27 (m, 2H), 7.16-7.20 (m, 2H), 7.11 (s, 1H), 6.91-7.02 (m, 3H), 6.88-6.90 (m, 2H), 5.53 (s, 2H), 3.80 (s, 3H).

Compound I-61

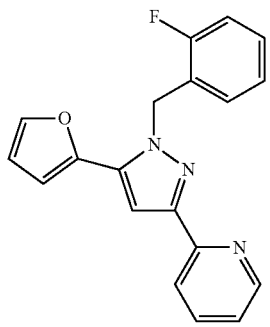 [SMILES: Fc1ccccc1Cn1nc(-c2ccccn2)cc1-c1ccco1]

This compound was synthesized as a solid (58.8% yield over 3 steps) following General Procedure A using 2-acetylfuran in step 1 and 2-fluorobenzyl bromide in step 3.

¹H NMR (400 MHz, CDCl₃) 8.64-8.66 (m, 1H), 7.98 (dq, 1H), 7.70-7.75 (m, 1H), 7.45-7.46 (m, 1H), 7.19-7.26 (m, 3H), 6.98-7.08 (m, 2H), 6.85-6.89 (m, 1H), 6.48 (d, 1H), 6.43-6.45 (m, 1H), 5.73 (s, 2H).

Compound I-65

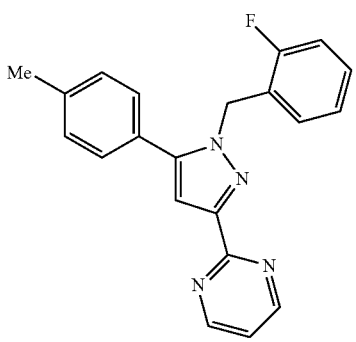 [SMILES: Cc1ccc(-c2cc(-c3ncccn3)nn2Cc2ccccc2F)cc1]

This compound was synthesized as a white solid (35% yield over 3 steps) following General Procedure A using 4-methylacetophenone and methylpyrimidine-2-carboxylate in step 1 and 2-fluorobenzyl bromide in step 3. ¹H NMR (400 MHz, CDCl₃) δ 8.83 (d, 2H), 7.26-7.18 (m, 6H), 7.14 (s, 1H), 7.04-6.93 (m, 3H), 5.56 (s, 2H), 2.38 (s, 3H).

Compound I-66

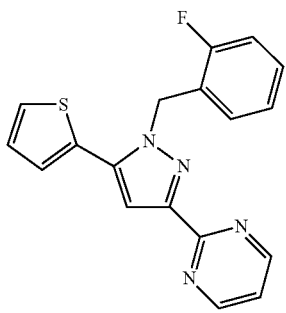 [SMILES: Fc1ccccc1Cn1nc(-c2ncccn2)cc1-c1cccs1]

This compound was synthesized as a solid (28.6% over 3 steps) following General Procedure A and using 2-acetylthiophene in step 1 and 2-fluorobenzyl bromide in step 3. (Note—base and solvent used in step 3 were sodium hydride (1 eq) and DMF, respectively).

¹H NMR (400 MHz, CDCl₃) δ 8.83 (dd, 2H), 7.36-7.38 (m, 1H), 7.21-7.28 (m, 4H), 7.00-7.07 (m, 3H), 6.85-6.89 (m, 1H), 5.69 (s, 2H).

Compound I-68

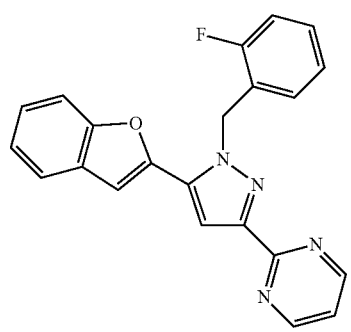 [SMILES: Fc1ccccc1Cn1nc(-c2ncccn2)cc1-c1cc2ccccc2o1]

This compound was synthesized as a solid (8.11% over 3 steps) following General Procedure A and using 2-acetylbenzofuran in step 1 and 2-fluorobenzyl bromide in step 3. (Note—base and solvent used in step 3 were sodium hydride (1 eq) and DMF, respectively).

¹H NMR (400 MHz, CDCl₃) δ 8.83 (dd, 2H), 7.53-7.55 (m, 2H), 7.47 (d, 1H), 7.25-7.32 (m, 1H), 7.17-7.24 (m, 3H), 7.03-7.17 (m, 1H), 6.95-6.97 (m, 2H), 6.85 (s, 1H), 5.93 (s, 2H).

Compounds I-70 and I-81

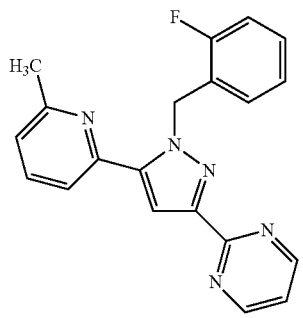
I-70

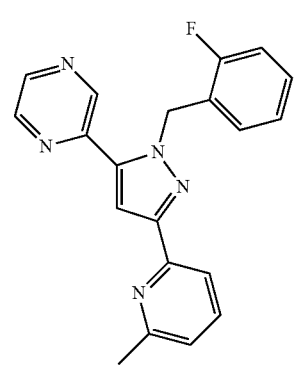
I-81

These two compounds were synthesized as solids (21.1% over 3 steps for the major isomer I-70) following General Procedure A and using 1-(6-methylpyridin-2-yl)ethanone in step 1 and 2-fluorobenzyl bromide in step 3.

I-70: 2-(1-(2-fluorobenzyl)-5-(6-methylpyridin-2-yl)-1H-pyrazol-3-yl)pyrimidine (solid) with 1H NMR (400 MHz, CDCl₃) 8.82-8.84 (m, 2H), 7.56 (t, 1H), 7.42-7.46 (m, 2H), 7.21-7.22 (m, 1H), 7.10-7.12 (m, 1H), 6.86-7.03 (m, 4H), 6.20 (s, 2H), 2.47 (s, 3H)

I-81: 2-(1-(2-fluorobenzyl)-3-(6-methylpyridin-2-yl)-1H-pyrazol-5-yl)pyrimidine (solid) with 1H NMR (400 MHz, CDCl₃) 8.72 (dd, 2H), 7.77-7.80 (m, 2H), 7.62 (t, 1H), 7.10-7.16 (m, 3H), 6.98-7.03 (m, 1H), 6.89-6.93 (m, 1H), 6.78-6.82 (m, 1H), 6.24 (s, 2H), 2.63 (s, 3H).

Compounds I-75 and I-80

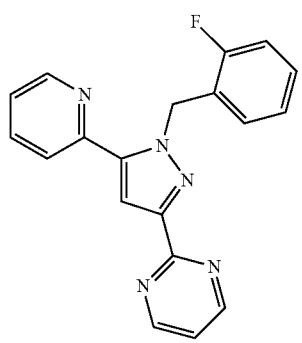
I-75

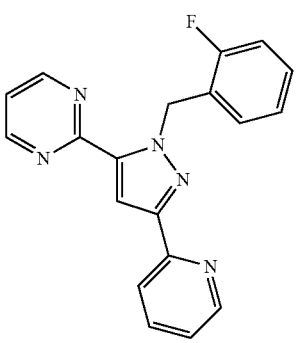

I-80

These two compounds were synthesized as off-white solid (28% over 3 steps and 39% over 3 steps, respectively) following General Procedure A using 1-(pyridin-2-yl)ethanone and methylpyrimidine-2-carboxylate in step 1, dione formation, and 2-fluorobenzyl bromide in step 3, alkylation.

I-75: $^1$H NMR (400 MHz, CDCl$_3$) δ 8.84 (d, 2H), 8.59 (br. d, 1H), 7.71 (d, 1H), 7.64 (app. td, 1H), 7.47 (s, 1H), 7.22 (t, 1H), 7.20 (ddd, 1H), 7.12 (m, 1H), 6.98-6.85 (m, 3H), 6.20 (s, 1H) ppm. MS: [M+H]=332.

I-80: $^1$H NMR (400 MHz, CDCl$_3$) δ 8.73 (d, 2H), 8.68 (br. d, 1H), 7.98 (d, 1H), 7.79 (s, 1H), 7.74 (app. td, 1H), 7.15 (m, 1H), 7.13 (t, 1H), 7.01 (m, 1H), 6.93 (app. t, 1H), 6.85 (app. t, 1H), 6.24 (s, 1H) ppm. MS: [M+H]=332.

Compound I-77

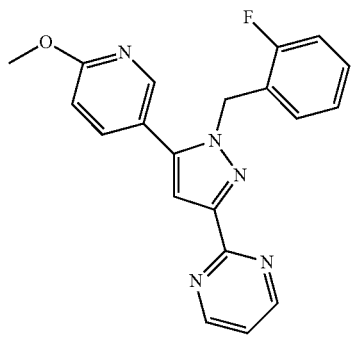 [SMILES: COc1ccc(-c2cc(-c3ncccn3)nn2Cc2ccccc2F)cn1]

Step 1, Dione Formation:

To a cooled (−78° C.) solution of ketone A, 1-(6-methoxypyridin-3-yl)ethanone (0.207 g, 1.369 mmol), was added LiHMDS (1.1 eq, 1.0 M in toluene). The reaction was warmed to rt and stirred for 15 min. At this time, ester B, methyl pyrimidine-2-carboxylate (0.189 g, 1.369 mmol) was added and the reaction was stirred at 90° C. until complete (using TLC and LC/MS analysis). Once complete, the reaction was poured into a solution of ethyl ether to crash out a light tan precipitate that was collected under vacuum filtration and carried on to the next step without any further purification.

Step 2, Pyrazole Formation:

Dione C was dissolved in equal parts MeOH (0.05-0.1M) and acetic acid and treated with hydrazine hydrate (1-3 eq). Reaction was heated to 60° C. and stirred until cyclization was complete (by LC/MS analysis). Once complete, reaction was directly concentrated and taken forward to the next step without any further purification.

Step 3, Alkylation:

Pyrazole D, 2-(5-(6-methoxypyridin-3-yl)-1H-pyrazol-3-yl)pyrimidine, was dissolved in acetonitrile. Potassium carbonate (1.412 g, 10.22 mmol) was added followed by electrophile 1-(bromomethyl)-2-fluorobenzene (0.148 ml, 1.226 mmol). The reaction was heated to 80° C. and stirred until complete by LC/MS analysis. The reaction mixture was concentrated to provide a crude oil which was then purified using SiO2 chromatography and an appropriate gradient (ethyl acetate/hexanes or DCM/methanol) to give a pair of regioisomers, the desired isomer being compound E, 2-(1-(2-fluorobenzyl)-5-(6-methoxypyridin-3-yl)-1H-pyrazol-3-yl)pyrimidine. $^1$H NMR (400 MHz, CDCl$_3$) δ 8.82 (d, 2H), 7.21-7.23 (2H), 7.15 (s, 1H), 6.92-7.13 (m, 6H) 5.53 (s, 2H), 3.96 (s, 3H).

Compound I-79

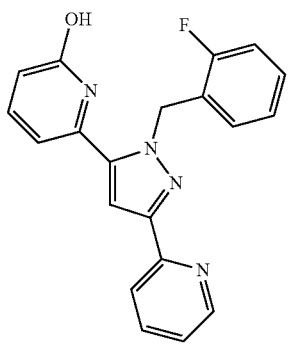 [SMILES: Oc1cccc(-c2cc(-c3ccccn3)nn2Cc2ccccc2F)n1]

A mixture of 2-(1-(2-fluorobenzyl)-3-(pyridin-2-yl)-1H-pyrazol-5-yl)-6-methoxypyridine (Compound I-25; 85.6 mg) and hydrobromic acid (1.2 ml, 33 wt % in acetic acid) in a sealed flask was heated to 100° C. for 18 h. The mixture was poured into ice and basified with saturated solution of sodium bicarbonate. The mixture was extracted with ethyl acetate. The organic portions were combined, dried (with Na$_2$SO$_4$), filtered, and concentrated under vacuum to give crude oil. The crude oil was purified using SiO$_2$ chromatography using ethyl acetate/methanol as gradient to give 6-(1-(2-fluorobenzyl)-3-(pyridin-2-yl)-1H-pyrazol-5-yl)pyridin-2-ol (Compound I-79, 70%) as off white solid. $^1$H NMR (400 MHz, CDCl$_3$) δ 11.54 (bs, 1H), 8.67-8.62 (m, 1H), 8.00-7.94 (m, 1H), 7.74 (td, 1H), 7.42-7.36 (m, 1H), 7.28-7.15 (m, 3H), 7.05-6.93 (m, 3H), 6.56 (d, 1H), 6.27 (d, 1H), 5.61 (s, 2H) ppm.

Compound I-85

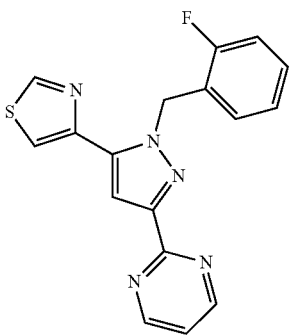 [SMILES: Fc1ccccc1Cn1nc(-c2ncccn2)cc1-c1cscn1]

This compound was synthesized as a white solid (4.3% yield over 3 steps) following General Procedure A using 4-acetylthiazole and methylpyrimidine-2-carboxylate in step 1, dione formation, and 2-fluorobenzyl bromide in step 3, alkylation. $^1$H NMR (400 MHz, CDCl$_3$): δ 8.82-8.00 (m, 3H), 7.51 (d, 1H), 7.40 (s, 1H), 7.20 (t, 1H), 7.17-7.11 (m, 1H), 6.99-6.91 (m, 2H), 6.87-6.83 (m, 1H), 6.03 (s, 2H).

Compound I-90

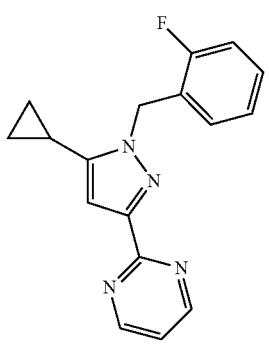 [SMILES: Fc1ccccc1Cn1nc(-c2ncccn2)cc1C1CC1]

This compound was synthesized as a clear, viscous oil (41.6% yield over 3 steps) following General Procedure A using cyclopropyl methyl ketone and methylpyrimidine-2-carboxylate in step 1, dione formation, and 2-fluorobenzyl bromide in step 3, alkylation. $^1$H NMR (400 MHz, CDCl$^3$): δ 8.78 (d, 2H), 7.25-7.20 (m, 1H), 7.17 (t, 1H), 7.08-6.98 (m, 3H), 6.68 (s, 1H), 5.63 (s, 2H), 1.69-1.62 (m, 1H), 0.90 (ddd, 2H), 0.66 (ddd, 2H) ppm.

Compound I-91

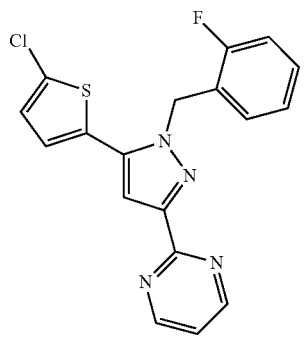 [SMILES: Fc1ccccc1Cn1nc(-c2ncccn2)cc1-c1ccc(Cl)s1]

This compound was synthesized as a white solid (12.6% yield over 3 steps) following General Procedure A using 1-(5-chlorothiophen-2-yl)ethanone and methyl pyrimidine-2-carboxylate in step 1, dione formation, and 2-fluorobenzyl bromide in step 3, alkylation. $^1$H NMR (400 MHz, CDCl$_3$): δ 8.83 (dd, 2H), 7.26-7.22 (m, 3H), 7.08-7.01 (m, 2H), 6.88-6.84 (m, 2H), 6.78 (dd, 1H), 5.66 (s, 2H) ppm.

Example 2

General Procedure B

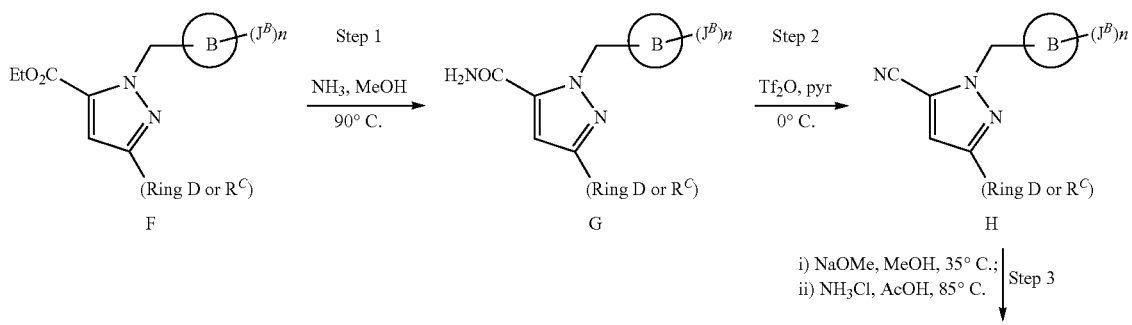

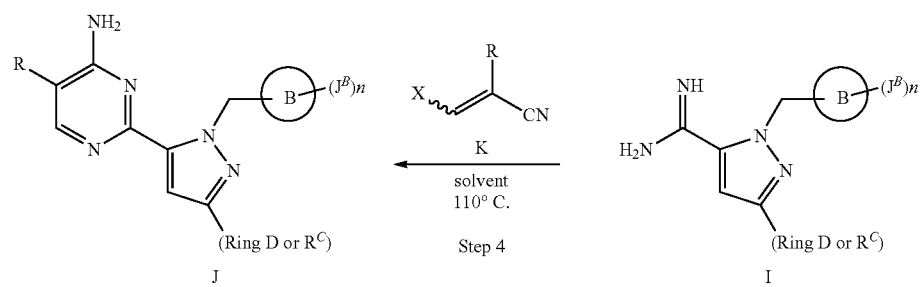

Step 1, Primary Amide Formation:

Ethyl ester F (this is the same as E if it is made according to General Procedure A) was mixed with an excess of a solution of ammonia in methanol (7.0 N in methanol) and NaCN (0.25 mol %) added as a catalyst. The reaction mixture was then heated in a Parr reactor and stirred until the reaction was complete (by LC/MS or TLC). Once deemed complete, the reaction mixture was concentrated and the resulting material diluted with DCM and filtered off. The filtrate was concentrated to give amide G, typically obtained as a white foam.

Step 2, Nitrile Formation:

Amide G was dissolved in pyridine (0.25M) and cooled to 0° C. Trifluoroacetic anhydride was then added. Once the reaction was complete (as monitored by LC/MS or TLC), the reaction mixture was diluted with DCM and washed with water. The aqueous portion was back extracted with DCM and the organic portions combined, dried (e.g., with $Na_2SO_4$), filtered, and concentrated under vacuum. The crude oil was purified using chromatography such as $SiO_2$ chromatography and an appropriate solvent gradient (e.g., ethyl acetate/hexanes or DCM/methanol) to give nitrile H, typically obtained as a white foam.

Step 3, Carboximidamide Formation:

Nitrile H was added to a solution of sodium methoxide in methanol (95 wt % in methanol) and the reaction mixture was heated at 35° C. and stirred, e.g., for 3-24 h. Acetic acid and ammonium chloride were then added and the mixture stirred at reflux, e.g., for 12-16 h. At this time, the reaction mixture was concentrated, and the remaining crude material was diluted with EtOAc and basified, e.g., by the addition of a saturated solution of sodium carbonate. The heterogeneous reaction mixture was allowed to separate into two layers. The aqueous portion was then extracted with DCM and the organic portions were combined, dried (e.g., with $Na_2SO_4$), filtered, and concentrated. The crude carboximidamide I was carried onto the cyclization reaction (step 4) to generate the targeted pyrimidine.

Step 4, Pyrimidine Formation:

Carboximidamide I was dissolved in an appropriate solvent (e.g., xylene, toluene, or pyridine) and charged with vinyl nitrile K. The reaction mixture was heated at reflux until >90% complete, e.g., as determined by LC/MS analysis. The reaction mixture was then concentrated, DCM added, and the mixture extracted with water. The aqueous portion was then extracted with DCM and the organic portions combined, dried (e.g., with $Na_2SO_4$), filtered, and concentrated. The crude oil was purified by preparative HPLC to give pyrimidine J, as a solid or liquid, as indicated below.

The Following Compounds were Synthesized According to General Procedure B

Compound I-3

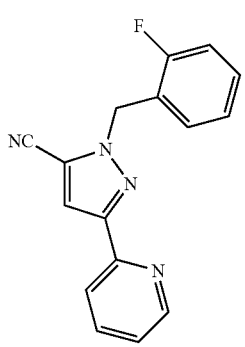 [SMILES: N#Cc1cc(-c2ccccn2)nn1Cc1ccccc1F]

This compound was synthesized as a tan solid (24.2% yield over 2 steps) following General Procedure B, steps 1 and 2 only; with intermediate 2 as reagent F. $^1$H NMR (400 MHz, $CDCl_3$) δ 8.67-8.61 (m, 1H), 7.99-7.93 (m, 1H), 7.77-7.70 (m, 1H), 7.45 (s, 1H), 7.37-7.31 (s, 1H), 7.28-7.19 (m, 2H), 7.16-7.09 (m, 2H), 7.04-6.99 (m, 1H), 5.61 (s, 2H) ppm.

Intermediate 4

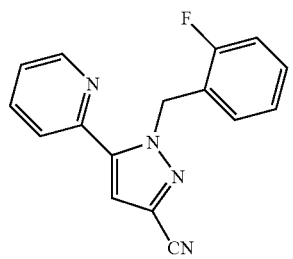 [SMILES: N#Cc1cc(-c2ccccn2)n(Cc2ccccc2F)n1]

This compound, which could be used as an intermediate for the synthesis of some of the compounds of Formula I, was synthesized as a tan solid (16.5% yield over 2 steps) following General Procedure B, steps 1 and 2 only, with intermediate 1 as reagent F. $^1$H NMR (400 MHz, $CDCl_3$) δ 8.68-8.63 (m, 1H), 7.84-7.74 (m, 1H), 7.56-7.50 (m, 1H), 7.34-7.28 (m, 1H), 7.26-7.18 (s, 1H), 7.04-6.99 (m, 2H), 6.99 (s, 1H), 6.99-6.95 (m, 1H), 6.05 (s, 2H) ppm.

Compound I-31

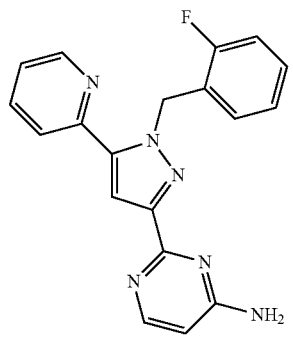 [SMILES: Nc1ccnc(-c2cc(-c3ccccn3)n(Cc3ccccc3F)n2)n1]

This compound was synthesized as a tan solid (4.8% yield over 2 steps) following General Procedure B, with intermediate 4 as reagent H. $^1$H NMR (400 MHz, $CDCl_3$) δ 8.61-8.56 (m, 1H), 7.96-7.88 (m, 1H), 7.76-7.68 (m, 1H), 7.62-7.56 (m, 1H), 7.44 (s, 1H), 7.26-7.22 (s, 1H), 7.16-7.09 (m, 1H), 7.03-6.95 (m, 1H), 6.95-6.88 (m, 2H), 6.68-6.60 (m, 1H), 6.04 (s, 2H), 5.87 (bs, 2H) ppm.

Compound I-41

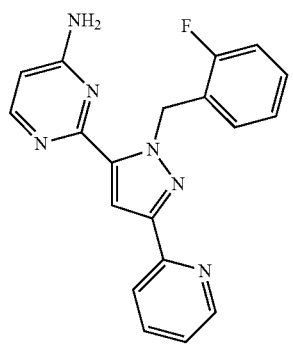 [SMILES: Nc1ccnc(-c2cc(-c3ccccn3)nn2Cc2ccccc2F)n1]

This compound was synthesized as a tan solid (2.6% yield over 2 steps) following General Procedure B, with compound I-3 as reagent H. $^1$H NMR (400 MHz, CDCl$_3$) δ 8.63-8.60 (m, 1H), 8.20-8.15 (m, 1H), 7.91-7.87 (m, 1H), 7.71-7.63 (m, 1H), 7.62 (s, 1H), 7.18-7.13 (s, 1H), 7.12-7.06 (m, 1H), 6.99-6.91 (m, 2H), 6.91-6.79 (m, 2H), 6.13 (s, 2H), 4.79 (bs, 2H) ppm.

Compound I-43

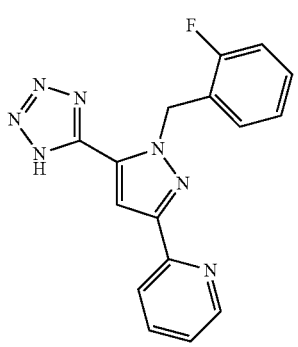 [SMILES: Fc1ccccc1Cn1nc(-c2ccccn2)cc1-c1nnn[nH]1]

A mixture of compound I-3 (184 mg), sodium azide (45 mg), and zinc(II) bromide (74 mg) in a 1:1 water:isopropanol mixture (2 ml) was heated at 130° C. for 24 h. The mixture was cooled to rt and passed through a filter disk to remove solid. The filtrate was concentrated under vacuum to give I-43 as white solid.

$^1$H NMR (400 MHz, CD$_3$OD) δ 8.61-8.52 (m, 1H), 8.01-7.88 (m, 2H), 7.42-7.35 (m, 2H), 7.24-7.16 (m, 1H), 7.05-6.97 (m, 1H), 6.96-6.89 (m, 1H), 6.70 (bs, 1H), 5.98 (s, 2H) ppm.

Compound I-46

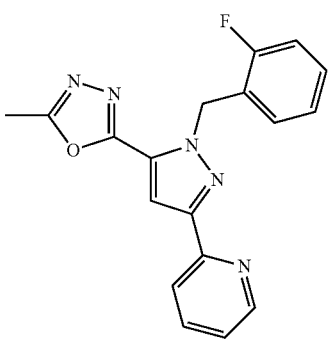 [SMILES: Cc1nnc(-c2cc(-c3ccccn3)nn2Cc2ccccc2F)o1]

A mixture of compound I-43 (124 mg) and acetic anhydride (109 μl) in pyridine (1.9 ml) was heated to 120° C. for 24 h. The mixture was cooled to rt and concentrated under vacuum. The resulting solid was purified using SiO$_2$ chromatography (ethyl acetate/hexanes) to give I-46 as off-white solid. $^1$H NMR (400 MHz, CDCl$_3$) δ 8.66-8.63 (m, 1H), 8.03-7.98 (m, 1H), 7.74 (td, 1H), 7.53 (s, 1H), 7.26-7.20 (m, 2H), 7.09-7.03 (m, 2H), 7.03-6.94 (m, 2H), 6.07 (s, 2H), 2.62 (s, 3H) ppm.

Example 3

General Procedure C-I

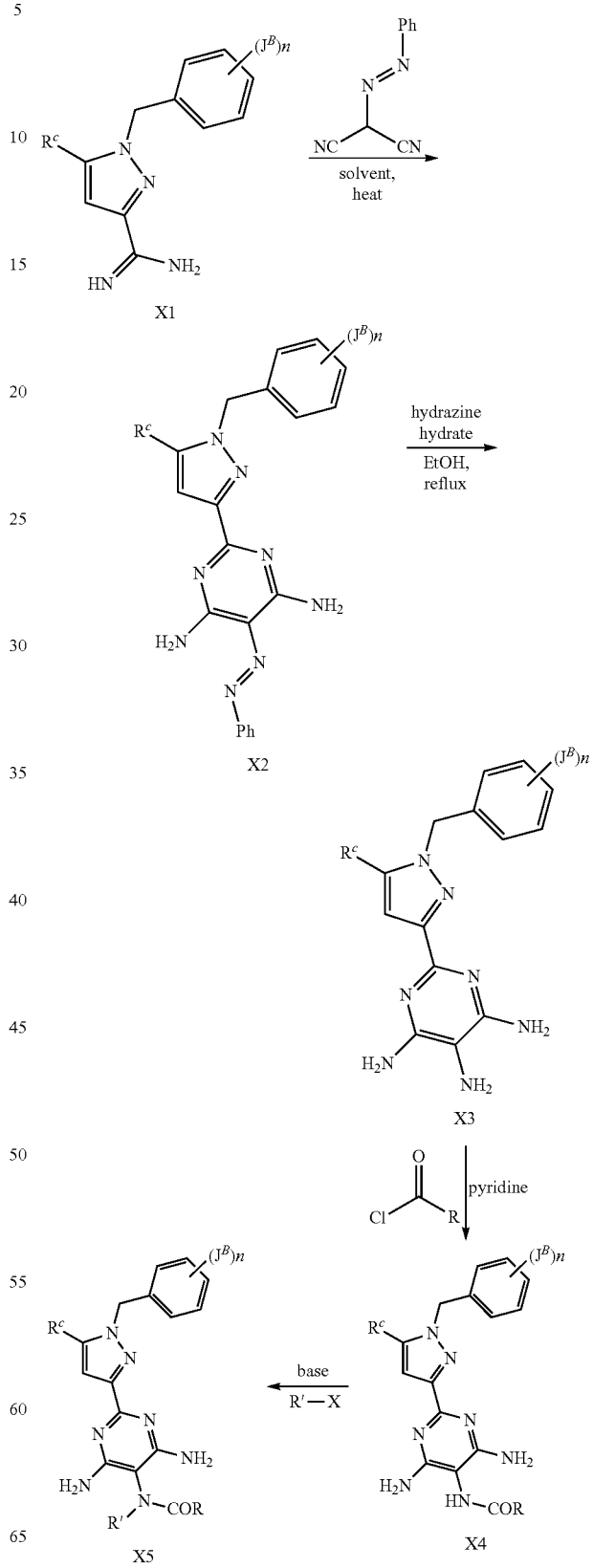

Step 1, Pyrimidine Formation:

Carboximidamide X1 was dissolved in DMF (or ethanol) and charged with NaOMe (1-2 eq). 2-(Phenyldiazenyl)malononitrile (1.1 eq) was added, and the reaction vessel was then capped and heated at 110° C. until >90% complete by LC/MS analysis. The reaction mixture was then diluted with DCM and extracted with NH$_4$Cl (conc., aq). The aqueous portion was then extracted an additional two times with DCM. The organic portions were then combined, dried (Na$_2$SO$_4$), filtered, and concentrated. The crude solid was purified by either precipitation or normal phase chromatography using an appropriate methanol/DCM gradient to give desired pyrimidine X2.

Step 2, Hydrazinolysis:

To a solution of pyrimidine X2 in EtOH was added hydrazine hydrate (>50 eq). Reaction mixture was then heated to reflux and stirred 14-48 h, or until reaction is judged complete by LC/MS analysis. The reaction was then directly concentrated and the crude material was purified by either precipitation, reverse phase preparative HPLC, or by normal phase chromatography using an appropriate methanol/DCM gradient to give desired pyrimidine X3.

Step 3, Acyclation:

Tri-amino pyrimidine X3 was dissolved in pyridine and cooled to 0° C., at which time the acylating reagent (acyl chloride, chloroformate, etc., 1.0 eq) was added. The reaction was stirred at 0° C. until judged complete by LC/MS analysis (typically <2 h min). The crude reaction was then diluted with DCM and washed with water (2×). The organic portion was then dried, filtered, and concentrated. The crude material was then purified by either precipitation, reverse phase preparative HPLC, or by normal phase chromatography using an appropriate methanol/DCM gradient to give desired pyrimidine X4.

Step 4, Alkylation:

Pyrimidine X4 was dissolved in solvent (most typically DMF) and cooled to 0° C. Base (typically sodium hydride) (1.2 eq) was added followed by the electrophile (intramolecular variants do not require exogenous electrophiles), and the resulting reaction was closely monitored by LC/MS analysis. Once complete, the reaction was quenched with water and extracted with DCM (3×). The organic portions were then combined, dried (Na$_2$SO$_4$), filtered, and concentrated. The crude oil was purified by either precipitation, reverse phase preparative HPLC, or by normal phase chromatography and a methanol/DCM gradient to give desired pyrimidine X5.

Compound I-71

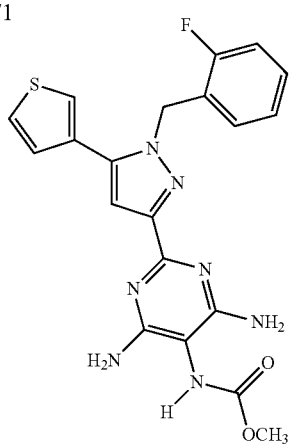

This compound was synthesized as an orange solid (22% yield over 3 steps) following General Procedure C-I using the 3-thiophenyl-derived carboximidamide as the key starting unit in Step 1 and methyl chloroformate as the electrophile in the acylation step. $^1$H NMR (400 MHz, CDCl$_3$) δ 7.34 (dd, 1H), 7.23-7.16 (m, 1H), 7.21 (dd, 1H), 7.11-6.97 (m, 4H), 6.76 (ddd, 1H), 6.47 (bs, 1H), 5.53 (s, 2H), 5.16 (bs, 4H), 3.74 (s, 3H) ppm.

Compound I-72

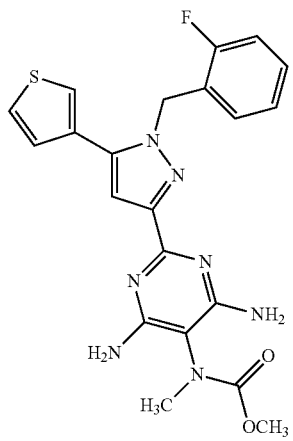 [SMILES: COC(=O)N(C)c1c(N)nc(-c2cc(-c3ccsc3)n(Cc3ccccc3F)n2)nc1N]

This compound was synthesized as a light yellow solid (43% yield from the desmethyl compound) following General Procedure C-I and using sodium hydride (60% in dispersion oil) as the base and DMF as the solvent in the final step. $^1$H NMR (400 MHz, D6-DMSO) δ 7.70-7.69 (m, 1H), 7.68-7.66 (m, 1H), 7.33-7.25 (m, 2H), 7.20-7.15 (m, 1H), 7.11-7.07 (m, 1H), 6.84 (s, 1H), 6.78-6.72 (m, 1H), 5.52 (s, 2H) ppm, 3.62 and 3.50 (s, 3H, rotomeric), 2.96 (s, 3H).

Example 4

General Procedure D

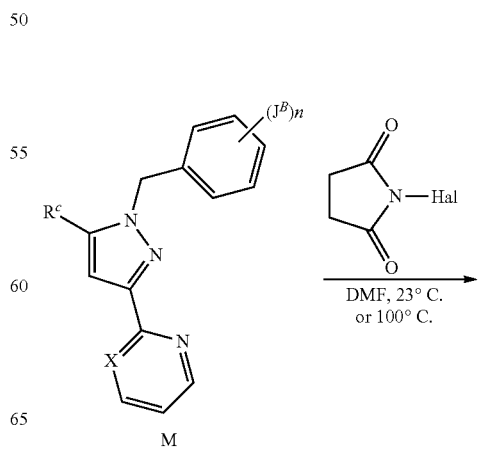

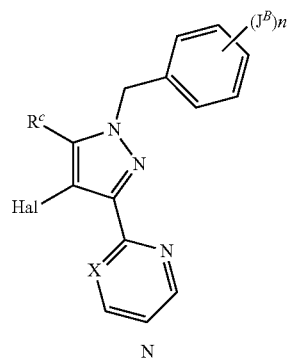

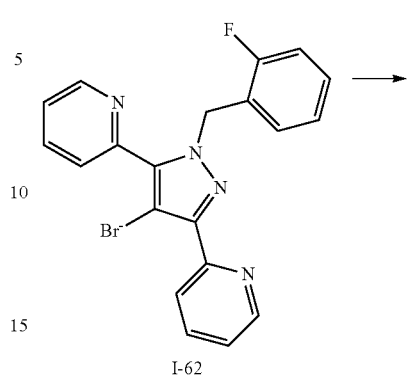

I-62

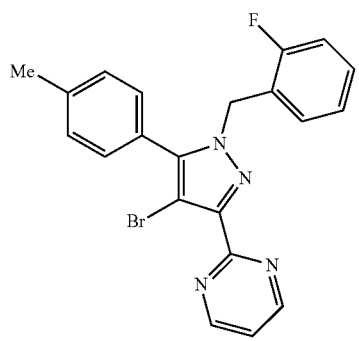

I-54

To a solution of pyrazole M in N,N-dimethylformamide was added N-bromosuccinimide (NBS), N-chlorosuccinimide (NCS), or N-iodosuccinimide (NIS) (1.5 equivalents). The solution was stirred at 23° C. (for NBS and NCS) or 100° C. (for NIS) for 3-17 hr until completion as determined by LC/MS analysis. After dilution with saturated aqueous sodium bicarbonate and ethyl acetate, the layers were separated and the aqueous layer was extracted with ethyl acetate (twice). The organics were combined, washed with water (twice), brine, dried over magnesium sulfate, filtered, and the solvent was removed in vacuo. The crude residue was purified by silica gel column chromatography (ethyl acetate/hexanes) to yield the desired product N.

The Following Compounds were Synthesized Following General Procedure D:

Compound I-53

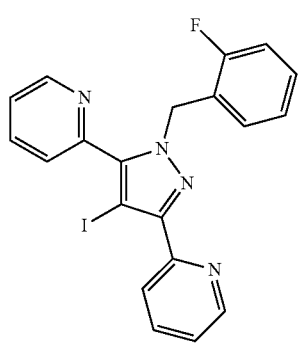 [SMILES: Fc1ccccc1Cn1nc(-c2ccccn2)c(I)c1-c1ccccn1]

This compound was synthesized as a clear oil (73% yield from the starting pyrazole) following General Procedure D using N-iodosuccinimide. $^1$H NMR (400 MHz, CDCl$_3$) δ 8.76-8.73 (m, 2H), 7.96 (d, 1H), 7.79-7.74 (m, 2H), 7.62 (d, 1H), 7.34-7.27 (m, 2H), 7.17-7.11 (m, 1H), 7.00-6.93 (m, 2H), 6.90-6.86 (m, 1H), 5.76 (s, 2H).

Compound I-54

To a suspension of 2,2'-(4-bromo-1-(2-fluorobenzyl)-1H-pyrazole-3,5-diyl)dipyridine (200 mg, 0.489 mmol) in N,N-dimethylformamide (3.4 mL) was added copper (I) cyanide (253 mg, 2.69 mmol). The suspension was stirred at 150° C. for 2 h, at which point LC/MS indicated a complete reaction. The solution was cooled to 23° C. and 5 mL of water, 5 mL of ammonium hydroxide, and 5 mL of ethyl acetate were added. The blue heterogeneous mixture was stirred rapidly for 40 min, and then further diluted with ethyl acetate (150 mL) and water (75 mL). The layers were separated and the aqueous layer was extracted with ethyl acetate (2×75 mL). The organics were combined and washed with water (75 mL) and brine (75 mL), dried over magnesium sulfate, filtered, and the solvent was removed in vacuo to give the crude product as an oil. Purification by silica gel chromatography (hexanes/ethyl acetate) gave 1-(2-fluorobenzyl)-3,5-di(pyridin-2-yl)-1H-pyrazole-4-carbonitrile (161 mg, 0.453 mmol, 93% yield) as a white solid. $^1$H NMR (400 MHz, CDCl$_3$) δ 8.77-8.73 (m, 2H), 8.05-8.03 (m, 1H), 7.96-7.94 (m, 1H), 7.87 (dt, 1H), 7.78 (dt, 1H), 7.40-7.36 (m, 1H), 7.33-7.30 (m, 1H), 7.23-7.17 (m, 1H), 7.07-6.94 (m, 3H), 5.97 (s, 2H).

Compound I-58

This time was synthesized as a white solid (96% yield from the starting pyrazole) following General Procedure D using N-bromosuccinimide. ¹H NMR (400 MHz, CDCl₃) δ 8.90 (d, 2H), 7.29-7.18 (m, 6H), 7.04-7.00 (m, 1H), 6.96-6.92 (m, 2H), 5.47 (s, 2H), 2.41 (s, 3H) ppm.

Compound I-62

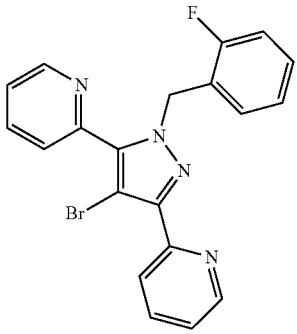 [SMILES: Fc1ccccc1Cn1nc(-c2ccccn2)c(Br)c1-c1ccccn1]

This compound was synthesized as a pale yellow solid (96% yield from the starting pyrazole) following General Procedure D using N-bromosuccinimide. ¹H NMR (400 MHz, CDCl₃) δ 8.76 (d, 1H), 8.73 (d, 1H), 8.01-7.99 (m, 1H), 7.77 (dt, 2H), 7.70-7.68 (m, 1H), 7.33-7.27 (m, 2H), 7.17-7.11 (m, 1H), 7.00-6.95 (m, 2H), 6.93-6.87 (m, 1H), 5.83 (s, 2H).

Compound I-63

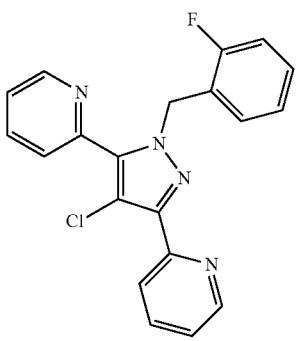 [SMILES: Fc1ccccc1Cn1nc(-c2ccccn2)c(Cl)c1-c1ccccn1]

This compound was synthesized as a white solid (91% yield from the starting pyrazole) following General Procedure D using N-chlorosuccinimide. ¹H NMR (400 MHz, CDCl₃) δ 8.76-8.70 (m, 2H), 8.01-7.99 (m, 1H), 7.78-7.74 (m, 2H), 7.72-7.70 (m, 1H), 7.30-7.25 (m, 2H), 7.16-7.10 (m, 1H), 6.99-6.87 (m, 3H), 5.87 (s, 2H) ppm.

Compound I-64

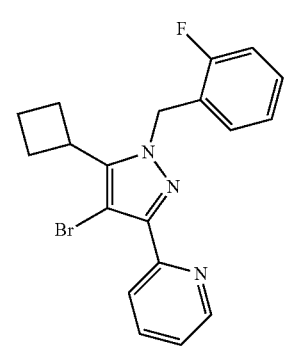 [SMILES: Fc1ccccc1Cn1nc(-c2ccccn2)c(Br)c1C1CCC1]

This compound was synthesized as a clear oil (91% yield from the starting pyrazole) following General Procedure D using N-bromosuccinimide. ¹H NMR (400 MHz, CDCl₃) δ 8.73 (d, 1H), 7.94-7.92 (m, 1H), 7.74 (dt, 1H), 7.31-7.21 (m, 2H), 7.08-7.01 (m, 2H), 6.83-6.79 (m, 1H), 5.47 (s, 2H), 3.57 (quint, 1H), 2.69 (d of quint, 2H), 2.23-2.15 (m, 2H), 2.02-1.85 (m, 2H).

Compound I-67

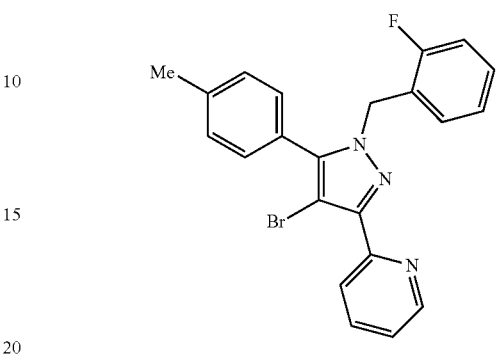

This compound was synthesized as a white solid (87% yield from the starting pyrazole) following General Procedure D using N-bromosuccinimide. ¹H NMR (400 MHz, CDCl₃) δ 8.76-8.77 (m, 1H), 8.03-8.01 (m, 1H), 7.77 (dt, 1H), 7.30-7.19 (m, 6H), 7.06-7.02 (m, 1H), 7.00-6.94 (m, 2H), 5.41 (s, 2H), 2.41 (s, 3H).

Compound I-69

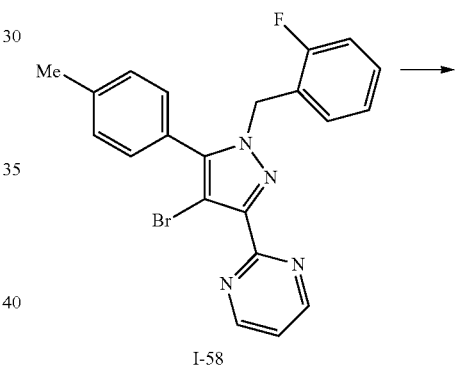

I-58

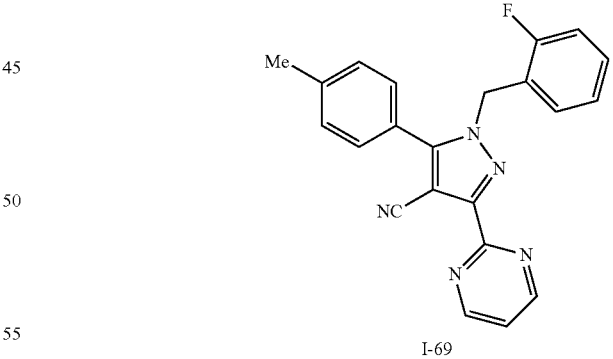

I-69

To a suspension of 2-(4-bromo-1-(2-fluorobenzyl)-5-p-tolyl-1H-pyrazol-3-yl)pyrimidine (145 mg, 0.343 mmol) in N,N-dimethylformamide was added copper(I) cyanide (178 mg, 1.884 mmol). The solution was cooled to 23° C. and 5 mL of water, 5 mL of ammonium hydroxide, and 5 mL of ethyl acetate were added. The blue heterogeneous mixture was stirred rapidly for 45 min, and then further diluted with ethyl acetate (75 mL) and water (50 mL). The layers were separated and the aqueous layer was extracted with ethyl acetate (2×50 mL). The organics were combined and washed with brine (50 mL), dried over magnesium sulfate, filtered, and the solvent was removed in vacuo to give the crude product as an oil. Purification by silica gel chromatography (hexanes/ethyl acetate) gave 1-(2-fluorobenzyl)-3-(pyrimidin-2-yl)-5-p-tolyl-1H-pyrazole-4-carbonitrile (114 mg, 0.309 mmol, 90% yield) as a white solid. $^1$H NMR (400 MHz, CDCl$_3$) δ 8.92 (d, 2H), 7.34-7.23 (m, 6H), 7.09-6.98 (m, 3H), 5.52 (s, 2H), 2.42 (s, 3H).

Example 5

General Procedure E

Compound I-50

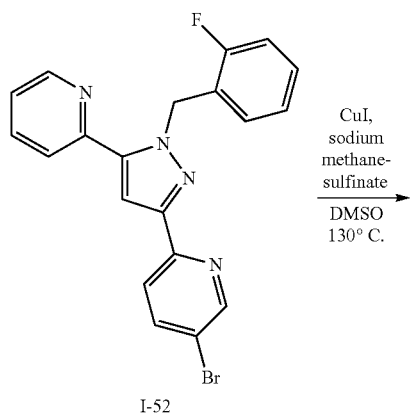

I-52

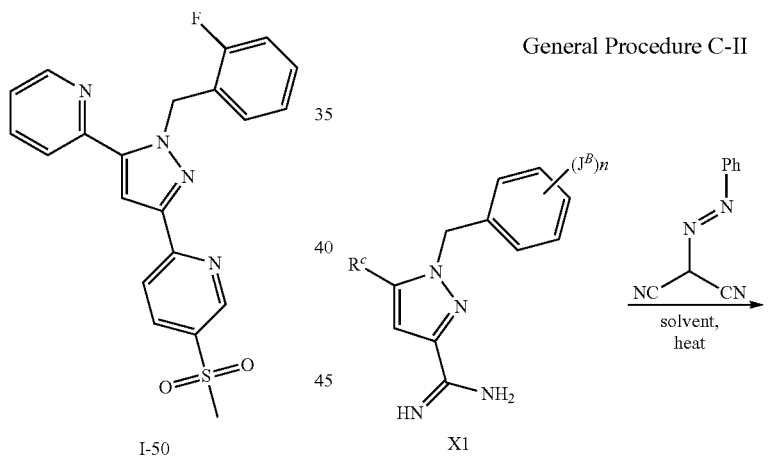

I-50

A suspension of 5-bromo-2-(1-(2-fluorobenzyl)-5-(pyridin-2-yl)-1H-pyrazol-3-yl)pyridine, copper(I) iodide (3.0 eq.) and sodium methanesulfinate (3.0 eq.) in DMSO was warmed to 130° C. and stirred at that temperature until completion (by LC/MS analysis). Once complete (reaction time was typically 3-6 h), the reaction solution was cooled to rt and saturated solutions of NH$_4$Cl and NaHCO$_3$ (2:1 ratio) were added. The resultant mixture was stirred for 1 h and then extracted with EtOAc. The organic phases were dried over Na$_2$SO$_4$, filtered and conc. The crude product was purified using SiO$_2$ chromatography and an appropriate gradient (ethyl acetate/hexanes) to give 2-(1-(2-fluorobenzyl)-5-(pyridin-2-yl)-1H-pyrazol-3-yl)-5-(methylsulfonyl)pyridine as a white solid (61% yield). $^1$H NMR (400 MHz, CDCl$_3$) δ 9.14 (br. s, 1H), 8.63 (d, 1H), 8.23 (m, 2H), 7.75 (app. td, 1H), 7.66 (d, 1H), 7.40 (s, 1H), 7.24 (m, 1H), 7.18 (m, 1H), 7.00 (m, 1H), 6.96 (m, 1H), 6.92 (m, 1H), 6.13 (s, 2H), 3.13 (s, 3H) ppm. MS: [M+H]=409.

The Following Compound was Synthesized Following the Above Procedure E:

Compound I-73

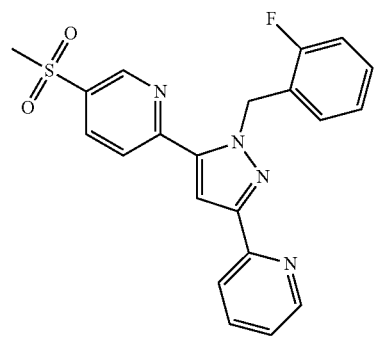 [SMILES: CS(=O)(=O)c1ccc(-c2cc(-c3ccccn3)nn2Cc2ccccc2F)nc1]

This compound was synthesized as a white solid (53% yield) from 5-bromo-2-(1-(2-fluorobenzyl)-3-(pyridin-2-yl)-1H-pyrazol-5-yl)pyridine. $^1$H NMR (400 MHz, CDCl$_3$) δ 9.09 (d, 1H), 8.66 (d, 1H), 8.23 (dd, 1H), 8.07 (d, 1H), 7.86 (d, 1H), 7.76 (app. td, 1H), 7.51 (s, 1H), 7.26 (m, 1H), 7.19 (m, 1H), 7.02 (m, 1H), 6.96 (app. t, 1H), 6.89 (app. t, 1H), 6.14 (s, 2H), 3.12 (s, 3H) ppm. MS: [M+H]=409.

Example 6

General Procedure C-II

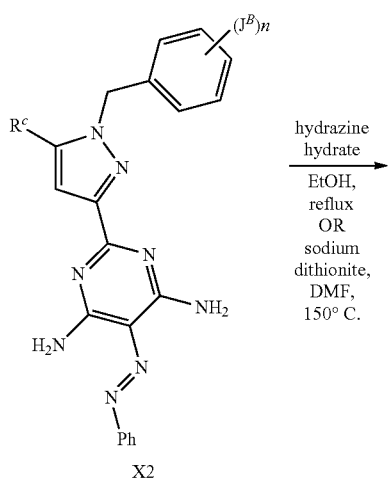

-continued

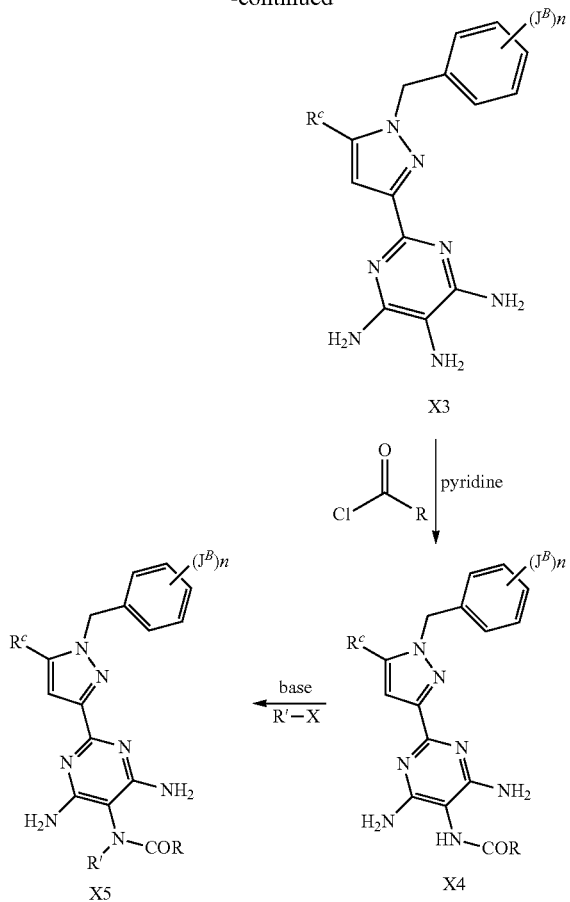

Step 1, Pyrimidine Formation:

Carboximidamide X1 (prepared according to General Procedure B) was dissolved in DMF (or ethanol) and charged with NaOMe (1-2 eq). 2-(Phenyldiazenyl)malononitrile (1.1 eq) was added, and the reaction vessel was then capped and heated at 110° C. until >90% complete by LC/MS analysis. The reaction mixture was then diluted with DCM and extracted with NH$_4$Cl (conc., aq). The aqueous portion was then extracted an additional two times with DCM. The organic portions were then combined, dried (Na$_2$SO$_4$), filtered, and concentrated. The crude solid was purified by either precipitation or normal phase chromatography using an appropriate methanol/DCM gradient to give desired pyrimidine X2.

Step 2, Hydrazinolysis:

To a solution of pyrimidine X2 in EtOH was added hydrazine hydrate (>50 eq). Reaction mixture was then heated to reflux and stirred 14-48 h, or until reaction is judged complete by LC/MS analysis. The reaction was then directly concentrated and the crude material was purified by either precipitation, reverse phase preparative HPLC, or by normal phase chromatography using an appropriate methanol/DCM gradient to give desired pyrimidine X3.

Alternative Procedure for Step 2:

To a solution of pyrimidine X2 in DMF was added sodium hydroxide (3 eq as a 2.0N solution) and sodium dithionite (5 eq). Reaction vessel (typically scintillation vial) was then moved to a hot plate set at 150° C. until reaction is judged complete by LC/MS analysis. The reaction was then diluted with DCM and filtered. The filtrate was concentrated and the resulting crude material was purified via flash chromatography (SiO$_2$) using a 0-40% DCM/MeOH gradient to deliver the desired X3.

Step 3, Acyclation:

Tri-amino pyrimidine X3 was dissolved in pyridine and cooled to 0° C., at which time the acylating reagent (acyl chloride, chloroformate, etc., 1.0 eq) was added. The reaction was stirred at 0° C. until judged complete by LC/MS analysis (typically <2 h min). The crude reaction was then diluted with DCM and washed with water (2×). The organic portion was then dried, filtered, and concentrated. The crude material was then purified by either precipitation, reverse phase preparative HPLC, or by normal phase chromatography using an appropriate methanol/DCM gradient to give desired pyrimidine X4.

Step 4, Alkylation:

Pyrimidine X4 was dissolved in solvent (most typically DMF) and cooled to 0° C. Base (typically sodium hydride) (1.2 eq) was added followed by the electrophile (intramolecular variants do not require exogenous electrophiles), and the resulting reaction was closely monitored by LC/MS analysis. Once complete, the reaction was quenched with water and extracted with DCM (3×). The organic portions were then combined, dried (Na$_2$SO$_4$), filtered, and concentrated. The crude oil was purified by either precipitation, reverse phase preparative HPLC, or by normal phase chromatography and a methanol/DCM gradient to give desired pyrimidine X5.

The Following Compounds were Prepared According to Procedure C-II

Compound I-83

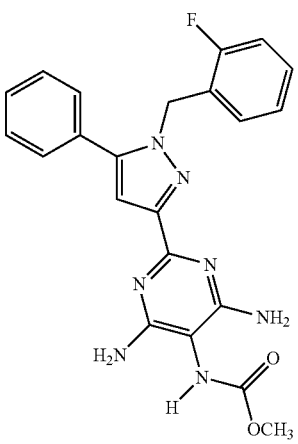 [SMILES: COC(=O)Nc1c(N)nc(-c2cc(-c3ccccc3)n(Cc3ccccc3F)n2)nc1N]

This compound was synthesized as a yellow solid (2.5% yield over 4 steps—cyclization reaction was 100%) following General Procedures F and C-II using acetophenone en route to the required ethyl 1-(2-fluorobenzyl)-5-phenyl-1H-pyrazole-3-carboxylate starting unit. $^1$H NMR (400 MHz, CDCl$_3$): δ 7.42-7.20 (m, 5H), 7.20-7.15 (m, 1H), 7.05-6.90 (m, 2H), 7.02 (s, 1H), 6.84-6.76 (m, 1H), 5.52 (s, 2H), 5.45 (bs, 1H), 5.04 (bs, 4H), 3.77 (s, 3H) ppm.

Compound I-84

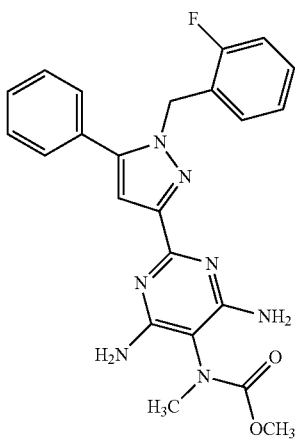 [SMILES: COC(=O)N(C)c1c(N)nc(-c2cc(-c3ccccc3)n(Cc3ccccc3F)n2)nc1N]

This compound was synthesized as an orange solid (21% yield from the des-methyl compound) following General Procedure C-II. NMR (400 MHz, CDCl$_3$): δ 7.37-7.27 (m, 5H), 7.20-7.15 (m, 1H), 7.04-6.93 (m, 2H), 7.01 (s, 1H), 6.84-6.81 (m, 1H), 5.52 (s, 2H), 4.91 (bs, 4H), 3.68 (bs, 3H), 3.15 (s, 3H) ppm.

Compound I-88

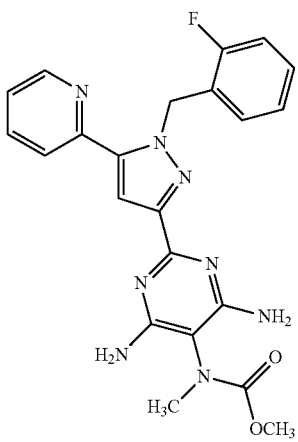 [SMILES: COC(=O)N(C)c1c(N)nc(-c2cc(-c3ccccn3)n(Cc3ccccc3F)n2)nc1N]

This compound was synthesized as an orange solid (21% yield from the corresponding des-methyl compound) following General Procedure C-II using sodium hydride (60% in dispersion oil) as the base and DMF as the solvent in the final step. 1H NMR (400 MHz, CDCl$_3$): δ 8.56 (d, 1H), 7.68 (ddd, 1H), 7.32 (s, 1H), 7.18-7.15 (m, 1H), 7.12-7.07 (m, 1H), 6.96-6.91 (m, 1H), 6.87 (t, 1H), 6.75 (t, 1H), 6.17 (s, 2H), 4.85 (bs, 4H), 3.69 (bs, 3H), 3.17 (s, 3H) ppm.

Compound I-89

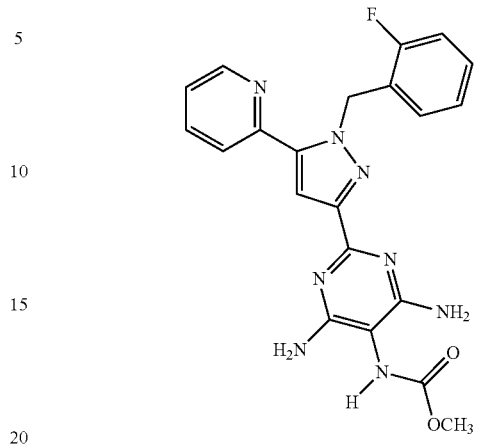

This compound was synthesized as an orange solid (8.0% yield over 3 steps—from the corresponding carboximidamide) following General Procedures F and C-II using 1-(pyridin-2-yl)ethanone en route to the required ethyl 1-(2-fluorobenzyl)-5-(2-pyridyl)-1H-pyrazole-3-carboxylate starting unit. $^1$H NMR (400 MHz, CDCl$_3$): δ 8.55 (d, 1H), 7.79 (bs, 1H), 7.68 (ddd, 1H), 7.30 (s, 1H), 7.19-7.16 (m, 1H), 7.13-7.08 (m, 1H), 6.95-6.86 (m, 2H), 6.75-6.71 (m, 1H), 6.13 (s, 2H), 5.00 (bs, 4H), 3.77 (s, 3H) ppm.

Compound I-93

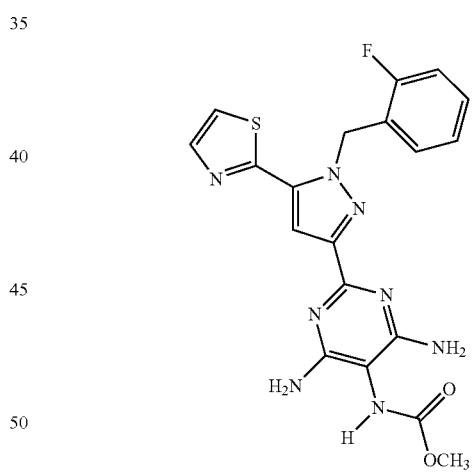

This compound was synthesized as an orange solid (25.7% yield over 3 steps—from the corresponding carboximidamide) following General Procedures F and C-II using 1-(thiazol-2-yl)ethanone en route to the required ethyl 1-(2-fluorobenzyl)-5-(2-thiazolyl)-1H-pyrazole-3-carboxylate starting unit. The cyclization step (step 1) employed EtOH as solvent with 5 equiv of pyridine. Step 2 (cleavage of N=N) exploited sodium hydrosulfite in the presence of sodium hydroxide (2 equiv of a 2N solution). $^1$H NMR (400 MHz, CD$_3$OD): δ 7.95 (d, 1H), 7.74 (d, 1H), 7.51 (s, 1H), 7.31-7.25 (m, 1H), 7.11-7.06 (m, 1H), 7.05 (t, 1H), 6.95 (t, 1H), 6.14 (s, 2H), 3.78 (s, 3H) ppm.

Compound I-94

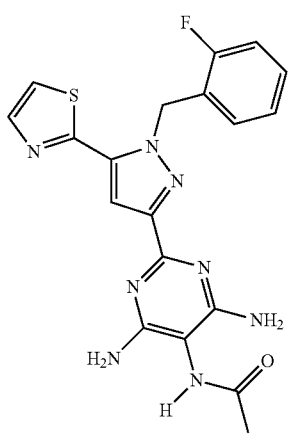 [SMILES: CC(=O)Nc1c(N)nc(-c2cc(-c3nccs3)n(Cc3ccccc3F)n2)nc1N]

This compound was synthesized as a brown solid (81%) following General Procedure C-II via the treatment of the intermediate diazo compound (N=N) with Zn dust in acetic acid (90° C., overnight). ¹H NMR (400 MHz, CD₃OD): δ 7.95 (d, 1H), 7.74 (d, 1H), 7.52 (s, 1H), 7.31-7.26 (m, 1H), 7.11-7.06 (m, 1H), 7.05 (t, 1H), 6.96 (ddd, 1H), 6.15 (s, 2H), 2.19 (s, 3H) ppm.

Compound I-95

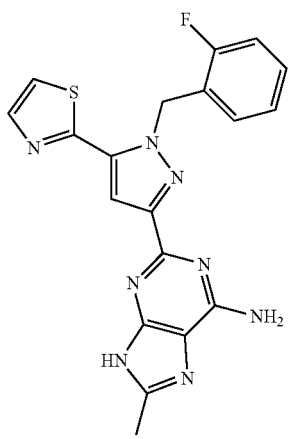 [SMILES: Cc1nc2c(N)nc(-c3cc(-c4nccs4)n(Cc4ccccc4F)n3)nc2[nH]1]

This compound was synthesized as a red solid (15%) by treating I-94 with LiOH (10 equiv) in a solution of THF/MeOH/water (3:1:1) at 90° C., overnight. ¹H NMR (400 MHz, CD₃OD): δ 7.94 (d, 1H), 7.74 (d, 1H), 7.54 (s, 1H), 7.31-7.25 (m, 1H), 7.11-7.06 (m, 1H), 7.04 (t, 1H), 6.97-6.93 (m, 1H), 6.16 (s, 2H), 2.63 (s, 3H) ppm.

Compound I-96

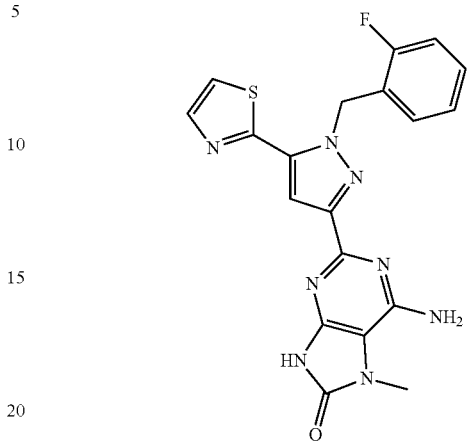

This compound was synthesized as a white solid (13%) by treating I-93 with NaH (large excess) and MeI (1.0 equiv). ¹H NMR (400 MHz, D₆-DMSO): δ 11.59 (s, 1H), 7.98 (d, 1H), 7.91 (d, 1H), 7.36-7.29 (m, 1H), 7.26 (s, 1H), 7.23-7.18 (m, 1H), 7.11 (t, 1H), 6.93 (t, 1H), 6.64 (s, 2H), 6.02 (s, 2H), 3.46 (s, 3H) ppm.

Compound I-99

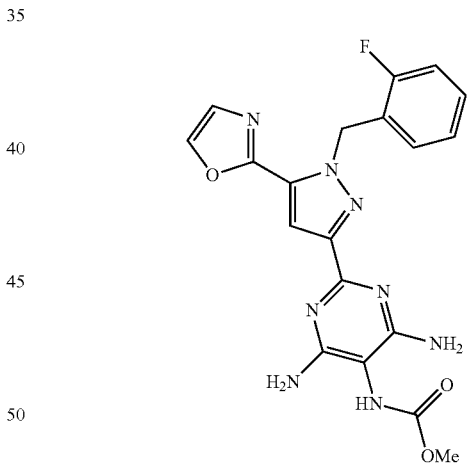

This compound was synthesized as a tan solid (31% yield over 3 steps—from the corresponding carboximidamide) following General Procedures F and C-II using 1-(oxazol-2-yl)ethanone en route to the required ethyl 1-(2-fluorobenzyl)-5-(2-oxazolyl)-1H-pyrazole-3-carboxylate starting unit. Step 2 (cleavage of N=N) exploited sodium hydrosulfite in the presence of sodium hydroxide (2 equiv of a 2N solution). ¹H NMR (400 MHz, CDCl₃): δ 7.67 (s, 1H), 7.53 (s, 1H), 7.19-7.14 (m, 2H), 7.04-6.99 (m, 1H), 6.95-6.91 (t, 1H), 6.74-6.70 (m, 1H), 6.12 (s, 2H), 5.76 (br s, 1H), 4.96 (s, 4H), 3.78 (s, 3H).

Compound I-100

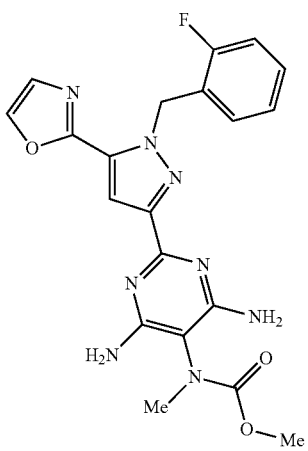 [SMILES: COC(=O)N(C)c1c(N)nc(-c2cc(-c3ncco3)n(Cc3ccccc3F)n2)nc1N]

This compound was synthesized as a tan solid from 1-99 (79% yield, 1.1 equiv NaH and MeI in DMF employed) according to General Procedure C-II. $^1$H NMR (400 MHz, CDCl$_3$): δ 7.67 (s, 1H), 7.53 (s, 1H), 7.19-7.14 (m, 2H), 7.04-6.99 (m, 1H), 6.93 (t, 1H), 6.74-6.71 (m, 1H), 6.13 (s, 2H), 4.83 (s, 4H), 3.70 (br s, 3H), 3.17 (s, 3H).

Compound I-101

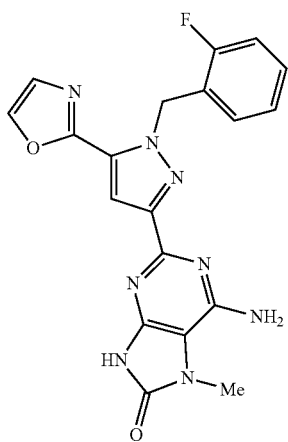 [SMILES: Cn1c(=O)[nH]c2nc(-c3cc(-c4ncco4)n(Cc4ccccc4F)n3)nc(N)c21]

To a solution of methyl 4,6-diamino-2-(1-(2-fluorobenzyl)-5-(oxazol-2-yl)-1H-pyrazol-3-yl)pyrimidin-5-yl(methyl)carbamate (82 mg, 0.19 mmol) in DMF (3.7 mL) at 0° C. was added sodium hydride (60% dispersion in mineral oil, 15 mg, 0.37 mmol). The solution was immediately warmed to ambient temperature and stirred for 45 min. Water (3 mL) was added, and after stirring for 5 minutes, the crude reaction mixture was diluted with ethyl acetete (100 mL) and water (75 mL) and the layers were separated. The aqueous layer was extracted with ethyl acetate (2×50 mL). The organics were combined, washed with water (2×50 mL) and brine (50 mL), dried over magnesium sulfate, and filtered. The solvent was removed in vacuo to give the crude product as an orange solid. The crude material was brought up in ether (10 mL) and the orange solid was filtered off. The procedure was repeated to give 6-amino-2-(1-(2-fluorobenzyl)-5-(oxazol-2-yl)-1H-pyrazol-3-yl)-7-methyl-7H-purin-8(9H)-one (51 mg, 0.13 mmol, 67% yield) as a pink solid. $^1$H NMR (400 MHz, DMSO): δ 11.57 (s, 1H), 8.31 (s, 1H), 7.41 (s, 1H), 7.35-7.31 (m, 2H), 7.25-7.20 (m, 1H), 7.12 (t, 1H), 6.96-6.93 (m, 1H), 6.65 (s, 2H), 6.01 (s, 2H), 3.45 (s, 3H).

Example 7

General Procedure F

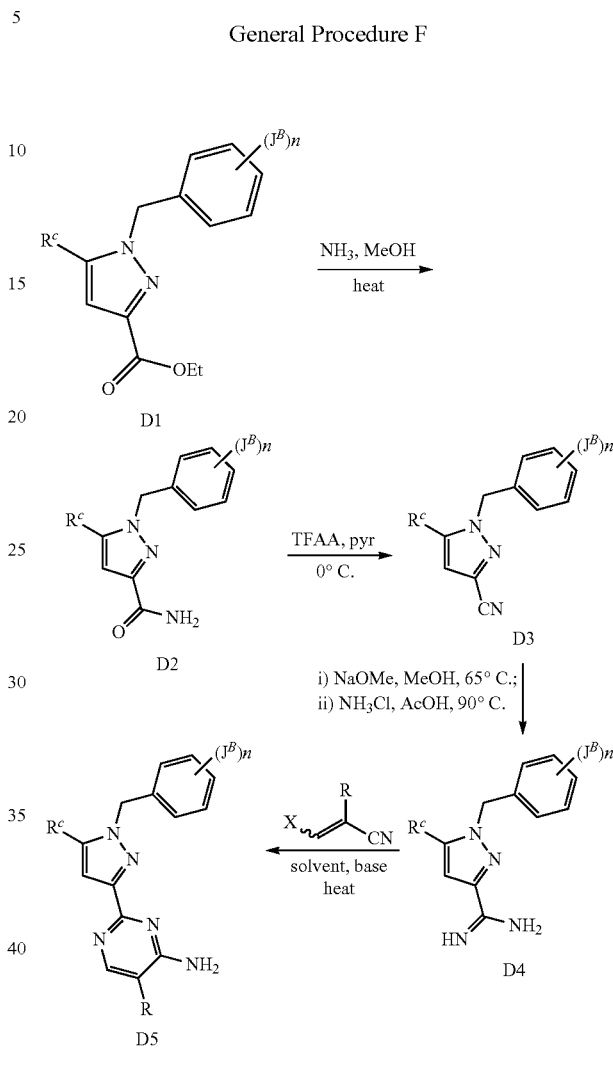

Step 1, Primary Amide Formation:

Ester D1 was charged with an excess of ammonia in methanol (7.0N, typically greater than 10 eq) and NaCN (0.10-0.25 mol %). The reaction mixture (in either a closed vial or a Parr reactor, depending on size) was then moved to a heating block or oil bath set at 110-125° C. and stirred until the reaction was complete. At this time, the reaction mixture was directly concentrated and the resulting material was diluted with DCM and filtered. The filtrate was again concentrated to give amide D2, which was typically carried on to the nitrile formation step without any further purification.

Step 2: Nitrile Formation:

To a cooled (0° C.) solution of amide D2 in pyridine (0.25M), was added trifluoroacetic anhydride (2 eq, fumes). Reaction mixture was stirred at this temperature for ~2 h (or until complete), at which time it was diluted with DCM and extracted with ammonium chloride (sat'd aq). The aqueous portion was then back extracted with additional DCM. The organic portions were then combined, dried (e.g., with Na$_2$SO$_4$), filtered, and concentrated. The crude oil was then purified using chromatography (SiO$_2$) and an appropriate gradient (e.g., ethyl acetate/hexanes or DCM/methanol) to give nitrile D3.

Step 3, Carboximidamide Formation:

Nitrile D3 (1 eq) was added to a solution of sodium methoxide in methanol (3 eq). The reaction mixture was heated (typically ~65° C.) and stirred for 2-4 h. At this time, acetic acid (1 eq) and ammonium chloride (5 eq) were added and the reaction was refluxed until complete. Once complete, the reaction mixture was concentrated, basified with a sodium carbonate (sat'd aq), and extracted with EtOAc (3×). The organic portions were then combined, dried (e.g., with $Na_2SO_4$), filtered, and concentrated. The crude carboximidamide D4 was carried onto the cyclization reaction without any further purification.

Step 4, Pyrimidine Formation:

Carboximidamide D4 was dissolved in an appropriate solvent (e.g., xylene, toluene, or pyridine) and charged with the appropriate vinyl nitrile (in some cases, 1 eq DBU was added to facilitate cyclization). The reaction mixture was heated at elevated temperature (typically 110° C., but was solvent dependent) until conversion was complete. Once complete, the desired compound was isolated in multiple ways: (1) concentration, then precipitation from diethyl ether; (2) dilution with DCM, washing with water, then purifying the concentrated organic portion with reverse-phase HPLC or $SiO_2$ chromatography; or (3) filtering off precipitated desired compound directly from the reaction mixture The Following Compounds were Prepared According to General Scheme F:

Intermediate 6

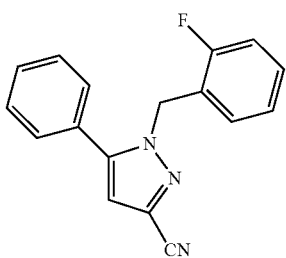 [SMILES: N#Cc1cc(-c2ccccc2)n(Cc2ccccc2F)n1]

This compound, which could be used as an intermediate for the synthesis of some of the compounds of Formula I, was synthesized as a white solid (54.8% yield over 2 steps) following General Procedure F, steps 1 and 2 only. $^1$H NMR (400 MHz, $CDCl_3$) δ 7.50-7.41 (m, 3H), 7.32-7.27 (m, 2H), 7.26 (s, 1H), 7.13-6.93 (m, 3H), 6.73 (s, 1H), 5.41 (s, 2H) ppm.

Compound I-31

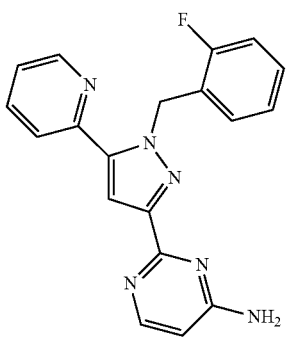 [SMILES: Nc1ccnc(-c2cc(-c3ccccn3)n(Cc3ccccc3F)n2)n1]

This compound was synthesized as a tan solid (4.8% yield over 2 steps) following General Procedure F. $^1$H NMR (400 MHz, $CDCl_3$): δ 8.61-8.56 (m, 1H), 7.96-7.88 (m, 1H), 7.76-7.68 (m, 1H), 7.62-7.56 (m, 1H), 7.44 (s, 1H), 7.26-7.22 (s, 1H), 7.16-7.09 (m, 1H), 7.03-6.95 (m, 1H), 6.95-6.88 (m, 2H), 6.68-6.60 (m, 1H), 6.04 (s, 2H), 5.87 (bs, 2H) ppm.

Compound I-82

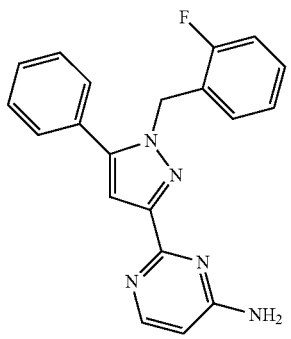 [SMILES: Nc1ccnc(-c2cc(-c3ccccc3)n(Cc3ccccc3F)n2)n1]

This compound was synthesized as a white solid (11% yield over 2 steps from the corresponding nitrile derivative) following General Procedure F, using acetophenone en route to the required ethyl 1-(2-fluorobenzyl)-5-phenyl-1H-pyrazole-3-carboxylate starting unit. EtOH was used as solvent in the cyclization reaction. $^1$H NMR (400 MHz, $CDCl_3$) δ 8.32 (d, 1H), 7.42-7.30 (m, 5H), 7.24-7.15 (m, 1H), 7.10 (s, 1H), 7.05-6.93 (m, 2H), 6.93-6.85 (m, 1H), 6.34 (d, 1H), 5.56 (s, 2H), 5.10 (bs, 2H) ppm.

Compound I-86

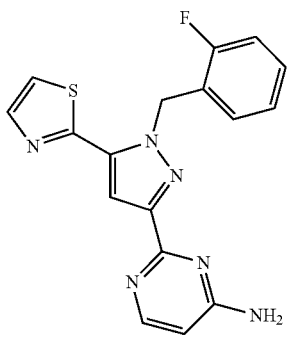

This compound was synthesized as a tan solid (7% yield over 4 steps) following General Procedure F using 1-(thiazol-2-yl)ethanone en route to the required ethyl 1-(2-fluorobenzyl)-5-(thiazol-2-yl)-1H-pyrazole-3-carboxylate starting unit. Pyridine was used as the solvent in the cyclization reaction. $^1$H NMR (400 MHz, $CDCl_3$): δ 8.34 (d, 1H), 7.81 (d, 1H), 7.47 (s, 1H), 7.34 (d, 1H), 7.18-7.13 (m, 1H), 6.99 (t, 1H), 6.93 (t, 1H), 6.79 (t, 1H), 6.37 (d, 1H), 6.17 (s, 2H), 5.09 (bs, 2H) ppm.

Compound I-87

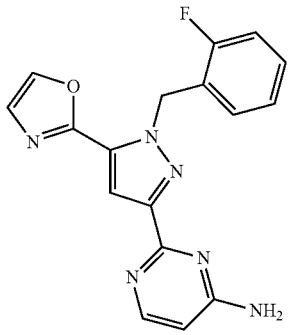

This compound was synthesized as a pink solid (10% yield over 4 steps) following General Procedure F using 2-acetyloxazole en route to the required ethyl 1-(2-fluorobenzyl)-5-(oxazol-2-yl)-1H-pyrazole-3-carboxylate starting compound. Pyridine was used as solvent in the cyclization reaction. $^1$H NMR (400 MHz, CDCl$_3$) δ 8.33 (d, 1H), 7.68 (s, 1H), 7.61 (s, 1H), 7.20-7.16 (m, 2H), 7.05-7.00 (m, 1H), 6.95 (t, 1H), 6.80-6.77 (m, 1H), 6.36 (d, 1H), 6.15 (s, 2H), 5.07 (br s, 2H).

Compound I-92

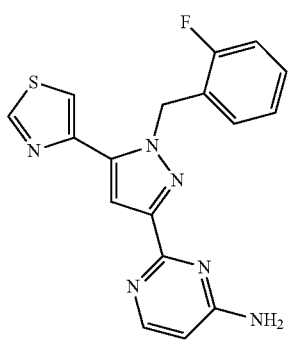

This compound was synthesized as a tan solid (21% yield over 4) following General Procedure F using 1-(thiazol-4-yl)ethanone en route to the required ethyl 1-(2-fluorobenzyl)-5-(thiazol-5-yl)-1H-pyrazole-3-carboxylate starting compound. Pyridine as solvent, along with one equivalent of DBU, was used in the cyclization reaction. $^1$H NMR (400 MHz, D$_6$-DMSO): δ 9.26 (d, 1H), 8.25 (d, 1H), 8.12 (d, 1H), 7.32-7.27 (m, 1H), 7.30 (s, 1H), 7.21-7.16 (m, 1H), 7.08 (t, 1H), 6.92 (bs, 2 h), 6.85 (t, 1H), 6.35 (d, 1H), 5.95 (s, 2H) ppm.

Compound I-97

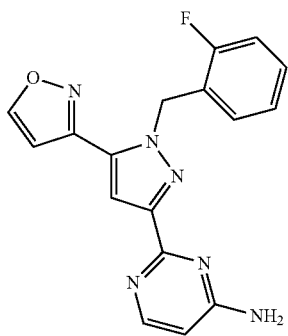

This compound was synthesized as a tan solid (31% yield over 4 steps) following General Procedure F starting from ethyl 1-(2-fluorobenzyl)-5-(isoxazol-3-yl)-1H-pyrazole-3-carboxylate (Intermediate 7). The cyclization reaction (step 4) was conducted in pyridine as a solvent along with one equivalent of DBU. NMR (400 MHz, CDCl$_3$) δ 8.43 (s, 1H), 8.32 (d, 1H), 7.41 (s, 1H), 7.20-7.16 (m, 1H), 7.04-7.00 (m, 1H), 6.95 (t, 1H), 6.79-6.76 (m, 1H), 6.58 (s, 1H), 6.36 (d, 1H), 6.02 (s, 2H), 5.08 (br s, 2H).

Compound I-98

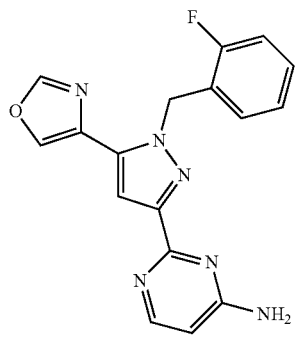 [SMILES: Nc1ccnc(-c2cc(-c3cocn3)n(Cc3ccccc3F)n2)n1]

This compound was synthesized as a brown solid (18% yield over 4 steps) following General Procedure F using 5-acetyloxazole en route to the required ethyl 1-(2-fluorobenzyl)-5-(oxazol-5-yl)-1H-pyrazole-3-carboxylate starting unit. The cyclization reaction (step 4) was conducted in pyridine as a solvent along with one equivalent of 1,8-diazabicyclo[5.4.0]undec-7-ene (DBU). $^1$H NMR (CDCl$_3$/400 MHz): δ 8.29 (d, 1H), 7.90 (d, 1H), 7.80 (d, 1H), 7.27 (s, 1H), 7.21-7.15 (m, 1H), 7.03-6.98 (m, 1H), 6.95 (td, 1H), 6.79 (td, 1H), 6.33 (d, 1H), 5.90 (s, 2H), 5.20 (br s, 2H); MS m/z: 337.3 (M+1).

Compound I-102

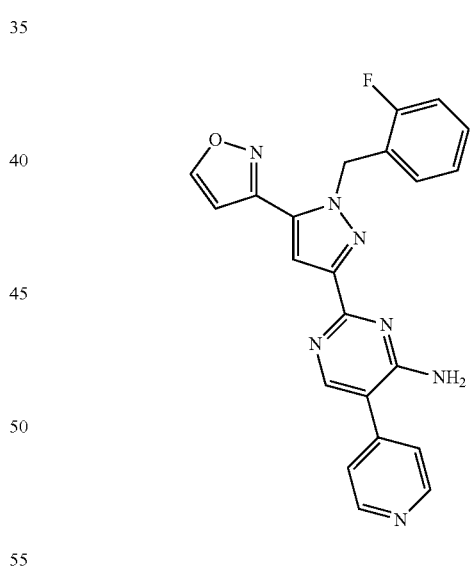

This compound was synthesized as a purple solid (9.4% yield over 4 steps) following General Procedure F using ethyl 1-(2-fluorobenzyl)-5-(isoxazol-3-yl)-1H-pyrazole-3-carboxylate (Intermediate 7) as the starting compound. The cyclization reaction (step 4) was conducted in pyridine in the presence of one equivalent of 1,8-diazabicyclo[5.4.0]undec-7-ene. NMR (400 MHz, CDCl$_3$) δ 8.75 (d, 2H), 8.45 (s, 1H), 8.31 (s, 1H), 7.44-7.42 (m, 3H), 7.22-7.17 (m, 1H), 7.05-7.00 (m, 1H), 6.96 (t, 1H), 6.81-6.77 (m, 1H), 6.59 (s, 1H), 6.03 (s, 2H), 5.32 (br s, 2H).

Compound I-104

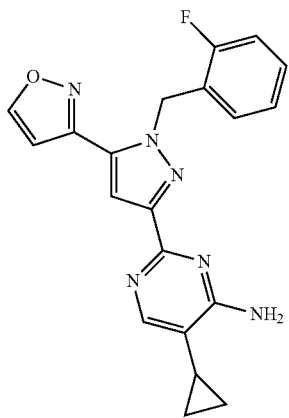 [SMILES: Nc1nc(-c2cc(-c3ccon3)n(Cc3ccccc3F)n2)ncc1C1CC1]

This compound was synthesized as a brown solid (14% yield over 4 steps) following General Procedure F using ethyl 1-(2-fluorobenzyl)-5-(isoxazol-3-yl)-1H-pyrazole-3-carboxylate (Intermediate 7) as the starting compound. The cyclization reaction (step 4) was conducted in the absence of solvent. $^1$H NMR (400 MHz, CDCl$_3$) δ 8.42 (d, 1H), 8.15 (s, 1H), 7.38 (s, 1H), 7.19-7.13 (m, 1H), 7.03-6.98 (m, 1H), 6.93 (t, 1H), 6.76-6.73 (m, 1H), 6.57 (d, 1H), 6.01 (s, 2H), 6.46 (br s, 2H), 1.60-1.53 (m, 1H), 0.97-0.92 (m, 2H), 0.65-0.61 (m, 2H).

Compound I-139

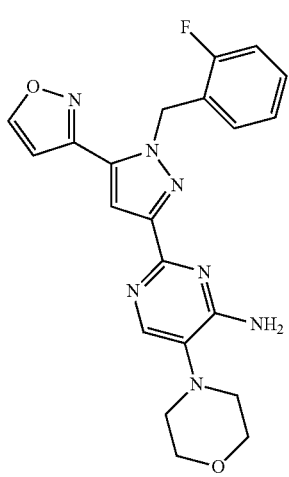 [SMILES: Nc1nc(-c2cc(-c3ccon3)n(Cc3ccccc3F)n2)ncc1N1CCOCC1]

This compound was synthesized as a pink solid (17% yield over 4 steps) following General Procedure F using ethyl 1-(2-fluorobenzyl)-5-(isoxazol-3-yl)-1H-pyrazole-3-carboxylate (Intermediate 7) as the starting compound. The cyclization reaction (step 4) was conducted in the absence of solvent. $^1$H NMR (400 MHz, CDCl$_3$) δ 8.41 (s, 1H), 8.08 (s, 1H), 7.33 (s, 1H), 7.17-7.13 (m, 1H), 7.03-6.97 (m, 1H), 6.93-6.91 (m, 1H), 6.75-6.71 (m, 1H), 6.55 (s, 1H), 5.99 (s, 2H), 5.39 (br s, 2H), 3.83-3.81 (m, 4H), 2.98-2.96 (m, 4H).

Compound I-105

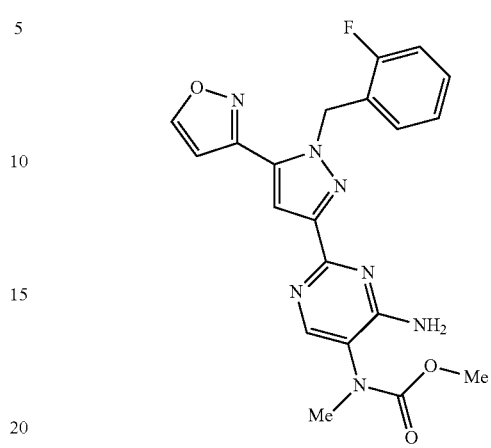

This compound was synthesized as a tan solid (6.0% yield over 4 steps) following General Procedure F using ethyl 1-(2-fluorobenzyl)-5-(isoxazol-3-yl)-1H-pyrazole-3-carboxylate (Intermediate 7) as the starting compound. The cyclization reaction (step 4) was conducted in the absence of solvent. $^1$H NMR (400 MHz, CDCl$_3$) δ 8.42 (s, 1H), 8.20 (br s, 1H), 7.38 (s, 1H), 7.18-7.13 (m, 1H), 7.02-6.97 (m, 1H), 6.92 (t, 1H), 6.77-6.73 (m, 1H), 6.56 (s, 1H), 5.99 (s, 2H), 5.32 (br s, 2H), 3.67 (br s, 3H), 3.21 (s, 3H).

Compound I-106

This compound was synthesized as a brown solid (7.6% yield over 4 steps) following General Procedure F using ethyl 1-(2-fluorobenzyl)-5-(isoxazol-3-yl)-1H-pyrazole-3-carboxylate (Intermediate 7) as the starting compound. The cyclization reaction (step 4) was conducted in the absence of solvent. $^1$H NMR (400 MHz, CDCl$_3$) δ 8.41 (d, 1H), 8.28 (s, 1H), 7.34 (s, 1H), 7.17-7.12 (m, 1H), 7.00-6.95 (m, 1H), 6.91 (t, 1H), 6.77-6.73 (m, 1H), 6.59 (br s, 1H), 6.55 (d, 1H), 5.96 (s, 2H), 5.59 (br s, 2H), 1.44 (s, 9H).

Compound I-108

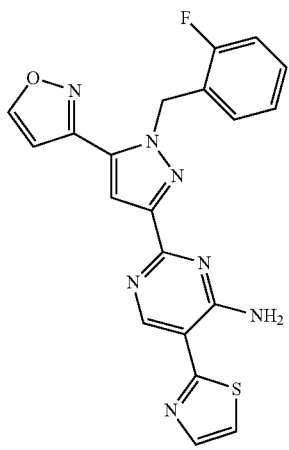 [SMILES: Nc1nc(-c2cc(-c3ccon3)n(Cc3ccccc3F)n2)ncc1-c1nccs1]

This compound was synthesized as a orange solid (3.6% yield over 4 steps) following General Procedure F ethyl 1-(2-fluorobenzyl)-5-(isoxazol-3-yl)-1H-pyrazole-3-carboxylate (Intermediate 7) as the starting compound. The cyclization reaction (step 4) was conducted in the absence of solvent. $^1$H NMR (400 MHz, CDCl$_3$) δ 8.82 (s, 1H), 8.43 (s, 1H), 7.84 (d, 1H), 7.44 (s, 1H), 7.32 (d, 1H), 7.19-7.14 (m, 1H), 7.03-6.99 (m, 1H), 6.96-6.92 (m, 1H), 6.77 (t, 1H), 6.58 (s, 1H), 6.03 (br s, 2H).

Compound I-109

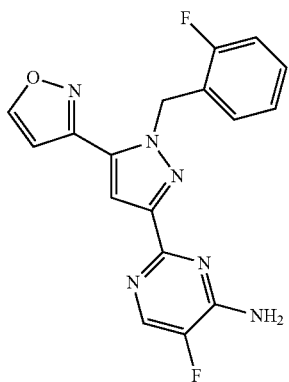

This compound was synthesized as a white solid (8.0% yield over 4 steps) following General Procedure F using ethyl 1-(2-fluorobenzyl)-5-(isoxazol-3-yl)-1H-pyrazole-3-carboxylate (Intermediate 7) as the starting compound. The cyclization reaction (step 4) was conducted in the absence of solvent. $^1$H NMR (400 MHz, DMSO) δ 9.09 (m, 1H), 8.22 (d, 1H), 7.48 (s, 1H), 7.41 (br s, 1H), 7.36-7.31 (m, 1H), 7.24-7.20 (m, 2H), 7.11 (t, 1H), 6.87 (t, 1H), 5.88 (s, 2H).

Compound I-113

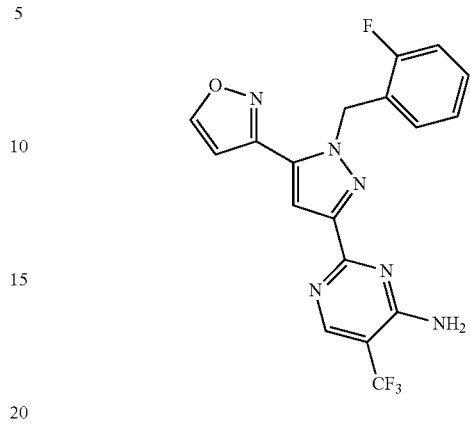

This compound was synthesized as a pale yellow solid (1.3% yield over 4 steps) following General Procedure F, using ethyl 1-(2-fluorobenzyl)-5-(isoxazol-3-yl)-1H-pyrazole-3-carboxylate (Intermediate 7) as the starting compound. The cyclization reaction (step 4) was conducted in the absence of solvent. $^1$H NMR (400 MHz, CDCl$_3$) δ 8.57 (s, 1H), 8.44 (d, 1H), 7.43 (s, 1H), 7.20-7.15 (m, 1H), 7.04-6.99 (m, 1H), 6.94 (t, 1H), 6.78-6.74 (m, 1H), 6.57 (s, 1H), 6.01 (s, 2H), 5.64 (br s, 2H).

Compound I-114

This compound was synthesized as a white solid (26% yield over 4 steps) following General Procedure F using ethyl 1-(2-fluorobenzyl)-5-(isoxazol-3-yl)-1H-pyrazole-3-carboxylate (Intermediate 7) as the starting compound. The cyclization reaction (step 4) was conducted in the absence of solvent. $^1$H NMR (400 MHz, CDCl$_3$) δ 8.40 (d, 1H), 8.30 (s, 1H), 7.37 (s, 1H), 7.18-7.12 (m, 1H), 7.01-6.97 (m, 1H), 6.91 (t, 1H), 6.72 (t, 1H), 6.56 (d, 1H), 5.99 (s, 2H), 5.38 (br s, 2H), 1.38 (s, 9H).

Compound I-115

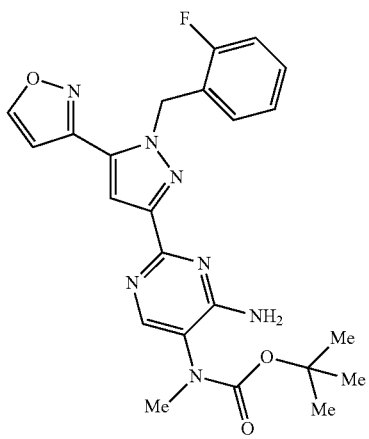 [SMILES: CN(C(=O)OC(C)(C)C)c1cnc(-c2cc(-c3ccon3)n(Cc3ccccc3F)n2)nc1N]

This compound was synthesized as a yellow solid (14% yield over 4 steps) following General Procedure F using Intermediate 7 as the starting compound. The cyclization reaction (step 4) was conducted in the absence of solvent. $^1$H NMR (400 MHz, CDCl$_3$) δ 8.43 (d, 1H), 8.20 (s, 1H), 7.45 (br s, 1H), 7.20-7.14 (m, 1H), 7.03-6.98 (m, 1H), 6.94 (t, 1H), 6.76 (t, 1H), 6.58 (s, 1H), 6.01 (s, 2H), 5.26 (br s, 2H), 3.17 (s, 3H), 1.41 (s, 9H).

Compound I-123

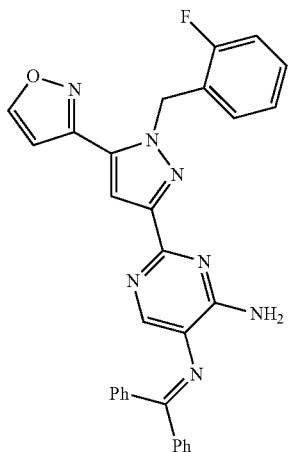 [SMILES: Nc1nc(-c2cc(-c3ccon3)n(Cc3ccccc3F)n2)ncc1N=C(c1ccccc1)c1ccccc1]

This compound was synthesized as an orange glassy solid (15% yield over 4 steps) following General Procedure F starting with Intermediate 7. The cyclization reaction (step 4) was conducted in pyridine with two equivalents of 1,8-diazabicyclo[5.4.0]undec-7-ene. $^1$H NMR (400 MHz, CDCl$_3$) δ 8.39 (d, 1H), 7.79-7.76 (m, 2H), 7.53-7.49 (m, 1H), 7.44-7.40 (m, 2H), 7.37-7.31 (m, 5H), 7.19-7.12 (m, 3H), 7.01-6.96 (m, 1H), 6.94-6.90 (m, 1H), 6.77-6.73 (m, 1H), 6.53 (d, 1H), 5.98 (s, 2H), 5.53 (br s, 2H).

Compound I-107:

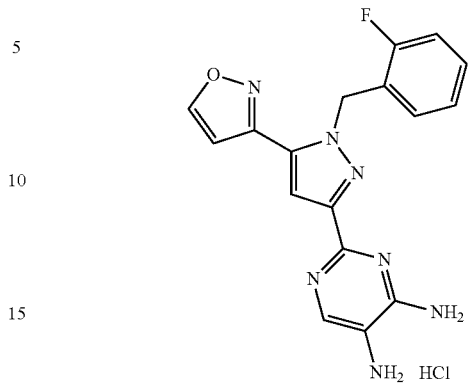

To a solution of N5-(diphenylmethylene)-2-(1-(2-fluorobenzyl)-5-(isoxazol-3-yl)-1H-pyrazol-3-yl)pyrimidine-4,5-diamine (Compound I-123) (0.263 g; 0.510 mmol) in tetrahydrofuran (5.0 mL) was added aqueous 3N hydrochloric acid (1.0 ml, 3.00 mmol). After stirring for 20 minutes, the solvent was evaporated and the residual material was washed with a 5:1 mixture of diethyl ether and hexane to provide compound I-107 (187 mg, 0.485 mmol, 95% yield) as a light brown solid. $^1$H NMR (400 MHz, CD$_3$OD) δ 8.82 (s, 1H), 7.46 (s, 2H), 7.32-7.27 (m, 1H), 7.13-7.06 (m, 2H), 6.98-6.94 (m, 1H), 6.90 (s, 1H), 5.98 (s, 2H).

Compound I-124

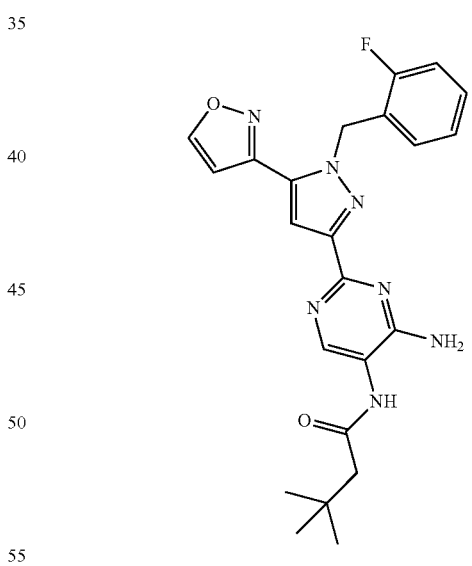

This compound was synthesized as a light tan solid (77%) via the condensation of Compound I-107 (1 equiv) with 3,3-dimethylbutanoyl chloride (3 equiv) in a solution of DCM/pyridine (2:1). Purification was carried out using SiO$_2$ chromatography employing a 0-15% MeOH/DCM gradient following an EtOAc and NH$_4$Cl-based work-up. $^1$H NMR (400 MHz, CD$_3$OD) δ 8.76-8.73 (m, 1H), 8.31-8.29 (m, 1H), 7.43-7.40 (m, 1H), 7.30-7.21 (m, 1H), 7.11-7.00 (m, 2H), 6.86-6.80 (m, 2H), 5.95 (s, 2H), 2.32 (s, 2H), 1.11 (s, 9H) ppm.

Compound I-126

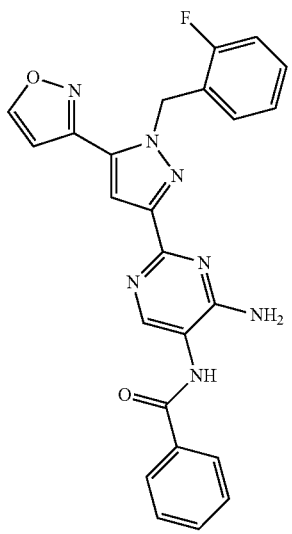

This compound was synthesized as a white solid (35%) via the condensation of Compound I-107 (1 equiv) with benzoyl chloride (5 equiv) in a solution of DCM/pyridine (2:1), giving the bis-benzoylated intermediate that was immediately hydrolyzed with sodium hydroxide (3N, 25 equiv) in methanol. Purification was carried out using $SiO_2$ chromatography employing a 0-15% MeOH/DCM gradient following an EtOAc and $NH_4Cl$-based work-up. $^1H$ NMR (400 MHz, $CDCl_3$) δ 8.73 (bs, 1H), 8.43 (d, 1H), 8.33 (bs, 1H), 7.90 (d, 2H), 7.52-7.48 (m, 1H), 7.39 (t, 2H), 7.32 (s, 1H), 7.14-7.08 (m, 1H), 6.96-6.84 (m, 2H), 6.78-6.72 (m, 1H), 6.56 (d, 1H), 5.84 (s, 2 h), 5.80 (bs, 2H) ppm.
Compound I-125

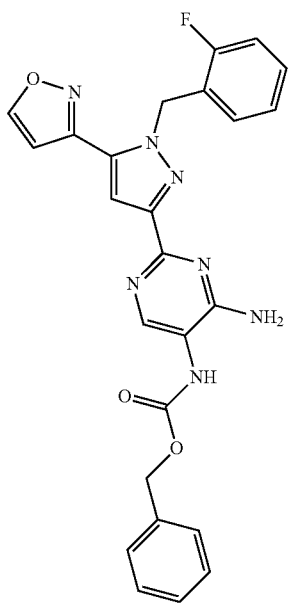 [SMILES: Nc1nc(-c2cc(-c3ccon3)n(Cc3ccccc3F)n2)ncc1NC(=O)OCc1ccccc1]

This compound was synthesized as a light tan solid (58%) via the condensation of Compound I-107 (1 equiv) with benzylchloroformate (9 equiv) in a solution of DCM/pyridine (2:1). Purification was carried out using $SiO_2$ chromatography employing a 0-15% MeOH/DCM gradient following an EtOAc and $NH_4Cl$-based work-up. $^1H$ NMR (400 MHz, $CD_3OD$) δ 8.76-8.74 (m, 1H), 8.38 (bs, 1H), 7.46-7.21 (m, 7H), 7.12-7.00 (m, 2H), 6.87-6.80 (m, 2H), 5.95 (s, 2H), 5.20 (s, 2H) ppm.

Compound I-112

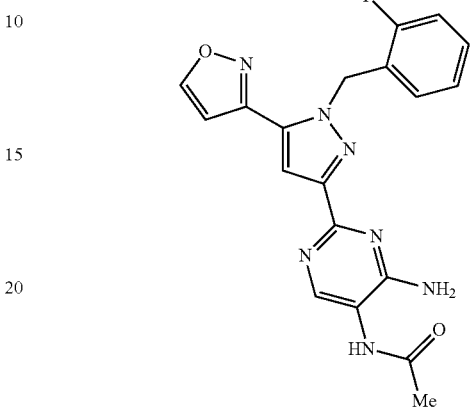

A solution of 2-(1-(2-fluorobenzyl)-5-(isoxazol-3-yl)-1H-pyrazol-3-yl)pyrimidine-4,5-diamine hydrochloride (I-107) (30 mg, 0.077 mmol) in acetic acid (2 mL) was heated to 110° C. for 18 h. After cooling to room temperature, the solution was partitioned between ethyl actetate (50 mL) and saturated aqueous sodium carbonate. The layers were separated and the aqueous layer was extracted with ethyl acetate (2×50 mL). The organics were dried over $MgSO_4$, filtered, and the solvent was removed in vacuo to give the crude product as a tan residue. Dichloromethane (3 mL) and diethyl ether (5 mL) were added, and the resulting white solid was filtered and washed with additional diethyl ether ether to give N-(4-amino-2-(1-(2-fluorobenzyl)-5-(isoxazol-3-yl)-1H-pyrazol-3-yl)pyrimidin-5-yl)acetamide (24 mg, 0.061 mmol, 79% yield) as a white solid. $^1H$ NMR (400 MHz, $CDCl_3$) δ 8.42 (d, 1H), 8.26 (s, 1H), 7.66 (br s, 1H), 7.34 (s, 1H), 7.18-7.13 (m, 1H), 7.01-6.96 (s, 1H), 6.92 (t, 1H), 6.77 (t, 1H), 6.56 (d, 1H), 5.96 (s, 2H), 5.57 (br s, 2H), 2.12 (s, 3H).

Compound I-118

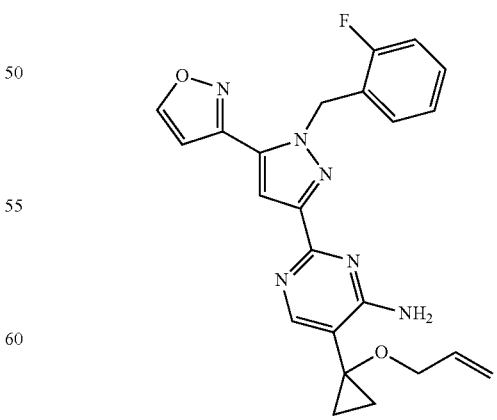

This compound was synthesized as a pale green solid (13% yield over 4 steps) following General Procedure F starting with Intermediate 7. The cyclization reaction (step 4) was conducted in anhydrous ethanol. ¹H NMR (400 MHz, CDCl₃) δ 8.42 (d, 1H), 8.13 (s, 1H), 7.46 (br s, 1H), 7.19-7.14 (m, 1H), 7.03-6.98 (m, 1H), 6.93 (t, 1H), 6.75 (t, 1H), 6.59 (br s, 1H), 6.01 (s, 2H), 5.84-5.75 (m, 1H), 5.20-5.09 (m, 2H), 3.86-3.84 (m, 2H), 1.21-1.17 (m, 2H), 0.96-0.93 (m, 2H).
Compound I-119

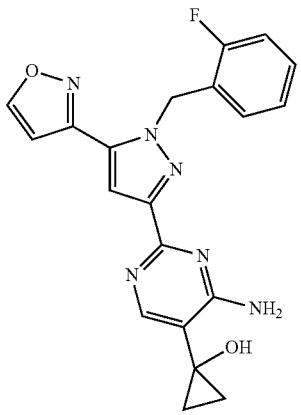 [SMILES: Nc1nc(-c2cc(-c3ccon3)n(Cc3ccccc3F)n2)ncc1C1(O)CC1]

To a solution of 5-(1-(allyloxy)cyclopropyl)-2-(1-(2-fluorobenzyl)-5-(isoxazol-3-yl)-1H-pyrazol-3-yl)pyrimidin-4-amine (I-118) (50 mg, 0.12 mmol), sodium acetate (20 mg, 0.26 mmol), and palladium(II) chloride (21 mg, 0.12 mmol) in acetic acid (0.6 mL) was added palladium tetrakistriphenylphosphine (17 mg, 0.015 mmol), followed by sodium benzenesulfinate (48 mg, 0.29 mmol). The heterogeneous mixture was stirred under argon at 50° C. for 1.75 hours. Ethyl acetate was added (3 mL) and the resulting suspension was filtered. The solvent was removed in vacuo and the crude orange solid was purified by silica gel chromatography (methanol in dichloromethane) to give 1-(4-amino-2-(1-(2-fluorobenzyl)-5-(isoxazol-3-yl)-1,4-pyrazol-3-yl)pyrimidin-5-yl)cyclopropanol (28 mg, 0.071 mmol, 62% yield) as a tan solid. ¹H NMR (400 MHz, CD₃OD) δ 8.76 (m, 1H), 8.10 (s, 1H), 7.42 (s, 1H) 7.29-7.23 (m, 1H), 7.11-7.06 (m, 1H), 7.03 (t, 1H), 6.87-6.82 (m, 2H), 5.95 (s, 2H), 1.10-1.07 (m, 2H), 0.94-0.91 (m, 2H).
Compound I-110

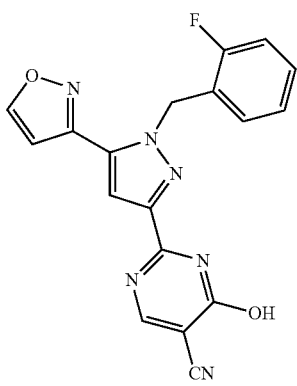 [SMILES: N#Cc1cnc(-c2cc(-c3ccon3)n(Cc3ccccc3F)n2)nc1O]

This compound was synthesized as a yellow solid (6% yield over 4 steps) following General Procedure F using Intermediate 7 as the starting compound. Ethanol was used as solvent, along with one equivalent of ethyl (ethoxymethylene)-cyanoacetate and one equivalent of DBU in the cyclization reaction (step 4) that was performed at 100° C. ¹H NMR (400 MHz, d-DMSO) δ 9.04 (d, 1H), 8.58 (s, 1H), 8.32 (s, 1H), 7.69 (s, 1H), 7.29-7.21 (m, 1H), 7.20-7.10 (m, 2H), 7.06-7.00 (m, 1H), 6.93-6.85 (m, 1H), 5.87 (s, 2H) ppm.
Compound I-130

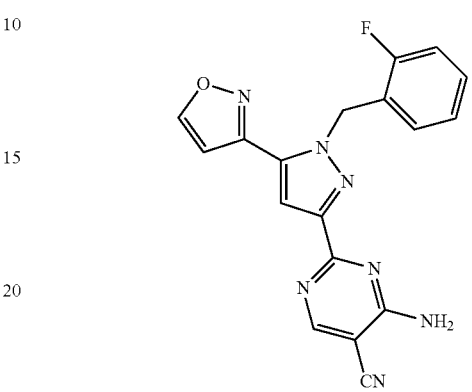

This compound was synthesized as a yellow solid (44% yield over 4 steps) following General Procedure F using Intermediate 7 as the starting compound. Ethanol was used as solvent, along with one equivalent of 2-(ethoxymethylene) malononitrile and one equivalent of Hunig's base in the cyclization reaction (step 4) that was performed at room temperature. ¹H NMR (400 MHz, d-DMSO) δ 9.01 (d, 1H), 8.61 (s, 1H), 7.53 (s, 1H), 7.28-7.21 (m, 1H), 7.18 (d, 1H), 7.16-7.10 (m, 1H), 7.05-6.99 (m, 1H), 6.81-6.75 (m, 1H), 5.83 (s, 2H) ppm.
Compound I-131

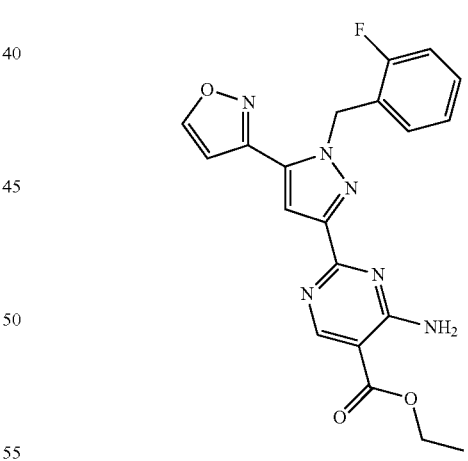

A mixture of Compound I-130 (150 mg) and HCl (10.09 ml, 4.0 M in dixoane) in ethanol (4.2 ml) was heated to 100° C. for 24 h. The mixture was cooled to room temperature and concentrated to give a white solid. The crude solid was purified using SiO₂ chromatography (acetone/hexanes) to give I-131 as a white solid (34%). ¹H NMR (400 MHz, d-DMSO) δ 9.07 (d, 1H), 8.79 (s, 1H), 8.20 (s, 2H), 7.60 (s, 1H), 7.34-7.27 (m, 1H), 7.24-7.17 (m, 2H), 7.11-7.05 (m, 1H), 6.88-6.81 (m, 1H), 5.90 (s, 2H), 4.30 (q, 2H), 1.30 (t, 3H) ppm.

Compound I-132

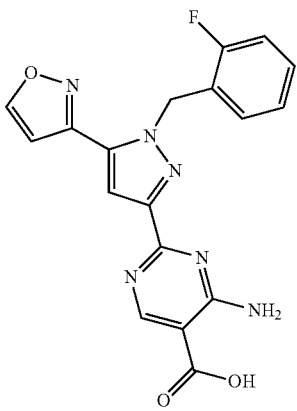 [SMILES: Nc1nc(-c2cc(-c3ccon3)n(Cc3ccccc3F)n2)ncc1C(=O)O]

In a sealed vial, a mixture of Compound I-130 (130 mg), acetic acid (1.0 ml), sulfuric acid (1 ml) and water (0.4 ml) was heated to 85° C. for 2 days. The mixture was cooled to rt and precipitate treated with excess sodium bicarbonate. The pH of the mixture was acidified to pH=3 and extracted with ethyl acetate (100 ml). The organic layer was dried, filtered and evaporated to give I-132 as a yellow solid (72%). $^1$H NMR (400 MHz, d-DMSO) δ 9.23 (s, 1H), 8.66-8.63 (m, 1H), 7.74-7.71 (m, 1H), 7.41-7.38 (m, 1H), 7.33 (s, 1H), 7.32-7.28 (m, 1H), 7.20-7.16 (m, 1H), 7.09-6.98 (m, 1H), 6.05 (s, 2H) ppm.

Compound I-136

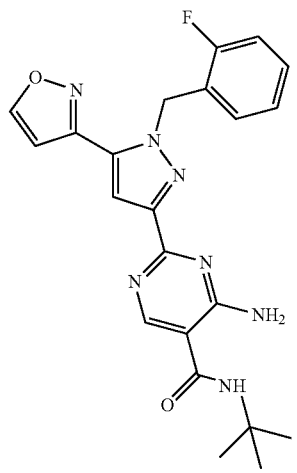 [SMILES: CC(C)(C)NC(=O)c1cnc(-c2cc(-c3ccon3)n(Cc3ccccc3F)n2)nc1N]

A mixture of Compound I-132 (80 mg), N-(3-dimethylaminopropyl)-N'-ethylcarbodiimide hydrochloride (101 mg), 1-hydroxybenzotriazole hydrate (81 mg), Hunig's base (147 µl) and 2-methylpropan-2-amine (33.2 µl, 0.316 mmol) in DMF (4.2 ml) was stirred at 25° C. for 24 h. The mixture was diluted with ethyl acetate (100 ml). The organic layer was washed with 1N HCl (50 ml×2), saturated solution of sodium bicarbonate (50 ml×2) and finally with brine (50 ml). The organic layer was dried, filtered and concentrated to give a white solid. The crude solid was purified using SiO$_2$ chromatography (ethyl acetate/hexanes) to give I-136 as a white solid (39%). $^1$H NMR (400 MHz, CDCl$_3$) δ 8.53 (s, 1H), 8.45 (d, 1H), 7.41 (s, 1H), 7.21-7.13 (m, 1H), 7.05-6.97 (m, 1H), 6.97-6.89 (m, 1H), 6.79-6.73 (m, 1H), 6.58 (d, 1H), 5.97 (s, 2H), 1.48 (s, 9H) ppm.

Compound I-138

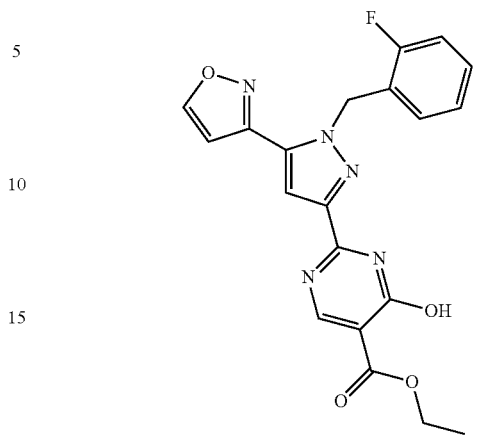

This was synthesized as a white solid (28% yield over 4 steps) following General Procedure F using ethyl 1-(2-fluorobenzyl)-5-(isoxazol-3-yl)-1H-pyrazole-3-carboxylate (Intermediate 7) as starting compound. Ethanol was used as solvent, along with one equivalent of diethyl ethoxymethylenemalonate in the cyclization reaction (step 4) that was carried out at 70° C. $^1$H NMR (400 MHz, d-DMSO) δ 13.13 (s, 1H), 9.13 (s, 1H), 8.61 (s, 1H), 7.78 (s, 1H), 7.39-7.31 (m, 1H), 7.29-7.19 (m, 1H), 7.17-7.10 (m, 1H), 7.07-6.97 (m, 1H), 5.95 (s, 2H), 4.25 (s, 2H), 1.29 (s, 3H) ppm.

Compound I-133

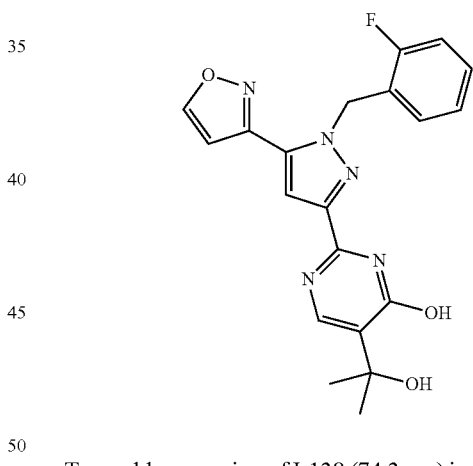

To a cold suspension of I-138 (74.3 mg) in THF (18 ml) at −20° C. and under argon, was added, very slowly, methylmagnesium bromide (0.24 ml, 3.0 M in diethyl ether). The mixture was removed from the dry ice-acetone bath and warmed to room temperature and stirred at this temperature for additional 30 min. The mixture subsequently turned green. The mixture was poured into ethyl acetate (300 ml) and washed with saturated solution of ammonium chloride (50 ml). The organic layer was dried, filtered and evaporated to give a yellow solid. It was dried under vacuum and treated with a minimal amount of methanol. Methanol was decanted and the remaining precipitate was collected and dried to give I-133 (38% yield) as an off-white solid. $^1$H NMR (400 MHz, d-DMSO) δ 12.46 (s, 1H), 9.13 (d, 1H), 8.14 (s, 1H), 7.68 (s, 1H), 7.37-7.30 (m, 1H), 7.29-7.20 (m, 2H), 7.15-7.09 (m, 1H), 7.05-6.97 (m, 1H), 5.92 (s, 2H), 5.19 (s, 1H), 1.47 (s, 6H) ppm.

Compound I-140

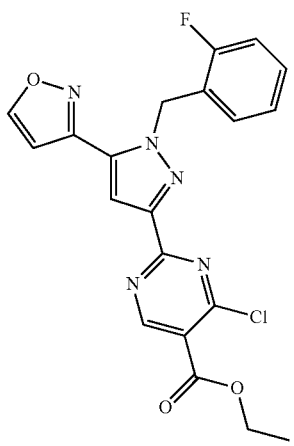

A heterogeneous mixture containing I-138 (300 mg), phosphorous (V) oxychloride (0.16 ml) and DMF (10 µl) in toluene (15 ml) was heated to 95° C. for 18 h. It was cooled to room temperature and concentrated under vacuum to give Compound I-140 (100% yield) as a white solid. $^1$H NMR (400 MHz, CDCl$_3$) δ 9.19 (s, 1H), 8.47-8.45 (m, 1H), 7.53 (s, 1H), 7.23-7.10 (m, 1H), 7.02-6.92 (m, 2H), 6.88-6.80 (m, 1H), 6.60-6.59 (m, 1H), 6.00 (s, 2H), 4.43 (q, 2H), 1.40 (t, 3H) ppm.

Compound I-134

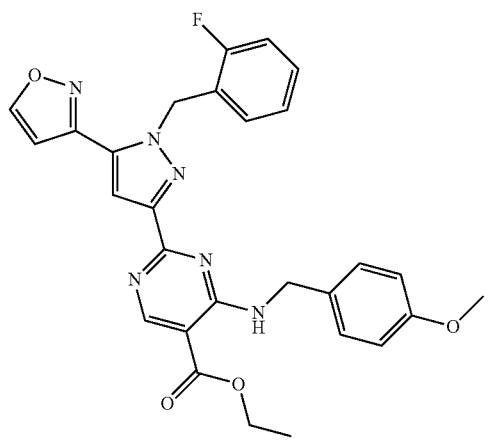 [SMILES: CCOC(=O)c1cnc(-c2cc(-c3ccon3)n(Cc3ccccc3F)n2)nc1NCc1ccc(OC)cc1]

To a solution of I-140 (375 mg) in THF (2.2 ml), was added a mixture of Hunig's base (0.6 ml) and 4-methoxybenzylamine (0.14 ml) in THF (2.2 ml). The mixture was stirred at 25° C. for 24 h. The mixture was diluted in ethyl acetate (100 ml) and sequentially washed with saturated solution of ammonium chloride (50 ml) then with brine (50 ml). The organic layer was dried, filtered and concentrated to give a white solid. The crude solid was purified using SiO$_2$ chromatography (ethyl acetate/hexanes) to give I-134 as a white solid (54%). $^1$H NMR (400 MHz, d-DMSO) δ 9.12 (d, 1H), 8.80 (s, 1H), 8.67 (t, 1H), 7.68 (s, 1H), 7.44-7.40 (m, 2H), 7.39-7.32 (m, 1H), 7.30 (d, 1H), 7.27-7.21 (m, 1H), 7.16-7.11 (s, 1H), 6.96-6.90 (s, 1H), 6.85-6.81 (m, 2H), 5.96 (s, 2H), 4.73 (d, 2H), 4.32 (q, 2H), 3.35 (s, 3H), 1.32 (t, 3H) ppm.

Compound I-135

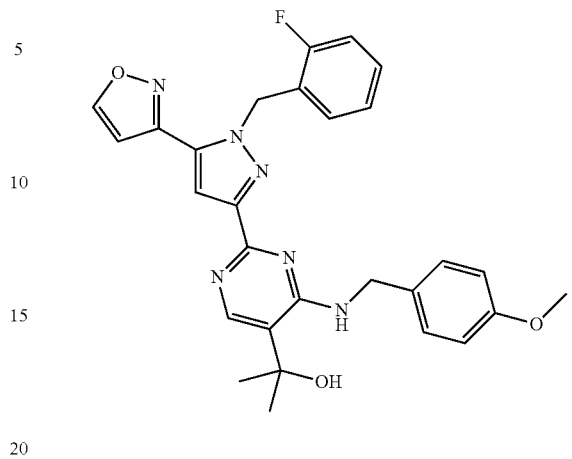

To a cold and clear solution of I-134 (165 mg) in THF (3.0 ml) at −20° C. under Argon, was added methylmagnesium bromide (1.0 ml, 3.0 M in diethyl ether) dropwise. The mixture turned yellow. The temperature was maintained at −20° C. for 4 h. To this cold mixture, was added saturated solution of ammonium chloride. The mixture was extracted with ethyl acetate (50 ml×2). The organic layers were combined, dried and filtered to give a crude solid. The crude solid was purified using SiO$_2$ chromatography (ethyl acetate/hexanes) to give I-135 (48% yield) as an off-white solid. $^1$H NMR (400 MHz, CDCl$_3$) δ 8.43 (d, 1H), 8.04 (s, 1H), 7.34 (s, 1H), 7.30-7.27 (m, 2H), 7.20-7.13 (m, 1H), 7.04-6.97 (m, 1H), 6.97-6.91 (m, 1H), 6.90-6.84 (m, 1H), 6.84-6.81 (m, 2H), 6.57 (d, 1H), 5.96 (s, 2H), 4.70 (d, 2H), 3.77 (s, 3H), 1.60 (s, 6H) ppm.

Compound I-137

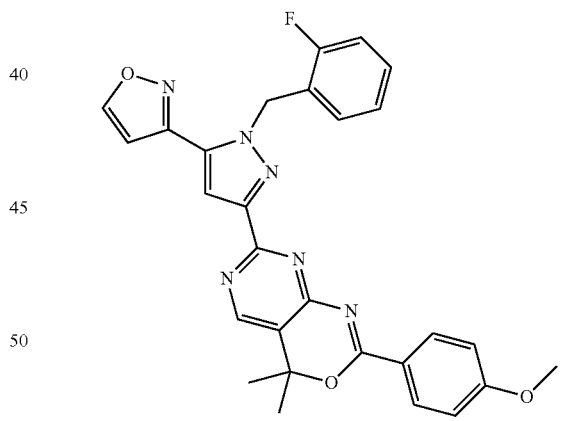

To a mixture of Compound I-135 (55 mg) in acetonitrile (0.71 ml) and acetic acid (0.71 ml), were added ammonium cerium (IV) nitrate (293 mg) followed by water (0.71 ml). The mixture was stirred for 24 h. The mixture was diluted in ethyl acetate (100 ml) and washed with 1 N NaOH (50 ml). The organic layer was dried, filtered and evaporated to give crude product. The crude solid was purified using SiO$_2$ chromatography (ethyl acetate/hexanes) to give I-137 (28% yield) as a light yellow solid. $^1$H NMR (400 MHz, CDCl$_3$) δ 8.53 (s, 1H), 8.46-8.44 (m, 1H), 8.27 (d, 2H), 7.67 (s, 1H), 7.23-7.14 (m, 1H), 7.07-6.99 (m, 1H), 6.99-6.93 (m, 3H), 6.87-6.79 (m, 1H), 6.62-6.60 (m, 1H), 6.04 (s, 2H), 3.90 (s, 3H), 1.81 (s, 6H) ppm.

Compound I-127

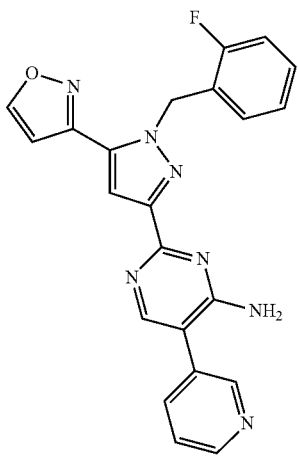 [SMILES: Nc1nc(-c2cc(-c3ccon3)n(Cc3ccccc3F)n2)ncc1-c1cccnc1]

This compound was synthesized as a light yellow solid (3% yield over 4 steps) following General Procedure F using Intermediate 7 as the starting compound. No solvent or additives were used in the cyclization reaction (step 4). $^1$H NMR (400 MHz, CDCl$_3$) δ 8.72 (d, 1H), 8.67 (dd, 1H), 8.43 (d, 1H), 8.26 (s, 1H), 7.79 (d, 1H), 7.45-7.41 (m, 2H), 7.20-7.14 (m, 1H), 7.00 (t, 1H), 6.93 (t, 1H), 6.76 (t, 1H), 6.58 (d, 1H), 6.02 (s, 2H), 5.21 (br s, 2H).

Compound I-128

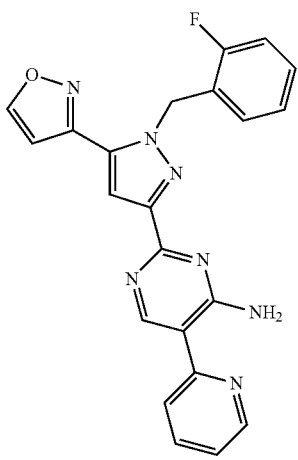 [SMILES: Nc1nc(-c2cc(-c3ccon3)n(Cc3ccccc3F)n2)ncc1-c1ccccn1]

This compound was synthesized as a light orange solid (26% yield over 4 steps) following General Procedure F using Intermediate 7 as a starting compound. No solvent or additives were used in the cyclization reaction (step 4). $^1$H NMR (400 MHz, CDCl$_3$) δ 8.82 (s, 1H), 8.60 (d, 1H), 8.42 (d, 1H), 7.82-7.78 (m, 2H), 7.44 (s, 1H), 7.26-7.22 (m, 1H), 7.19-7.13 (m, 1H), 7.00 (t, 1H), 6.93 (t, 1H), 6.76 (t, 1H), 6.57 (d, 1H), 6.02 (s, 2H).

Compound I-129

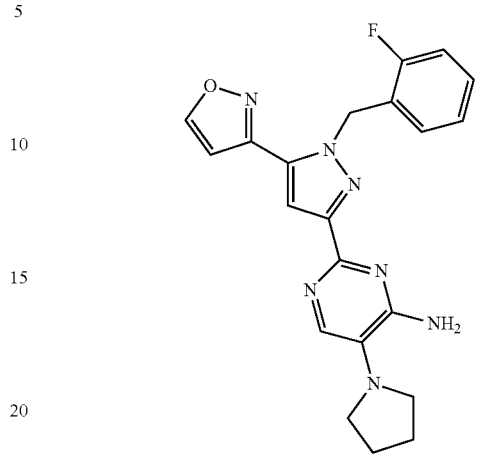

This compound was synthesized as a brown solid (6% yield over 4 steps) following General Procedure F using Intermediate 7 as the starting compound. No solvent or additives were used in the cyclization reaction (step 4). $^1$H NMR (400 MHz, CDCl$_3$) δ 8.40 (m, 1H), 8.01 (s, 1H), 7.32 (s, 1H), 7.14 (t, 1H), 6.99 (t, 1H), 6.91 (t, 1H), 6.73 (t, 1H), 6.55 (d, 1H), 5.99 (s, 2H), 5.18 (br s, 2H), 3.14-3.06 (br m, 4H), 1.98-1.90 (br m, 4H); MS m/z: 406.1 (M+1).

Compound I-120

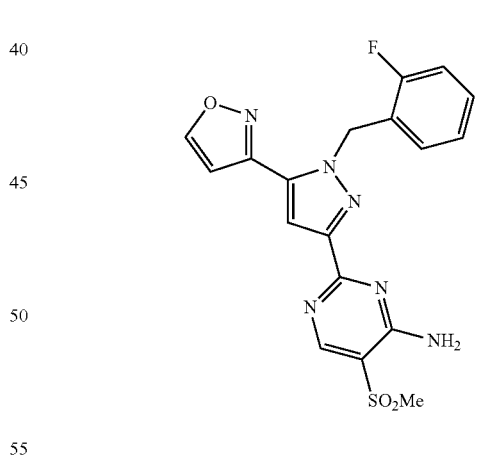

This compound was synthesized as a white solid (20% yield over 4 steps) following General Procedure F using Intermediate 7 as the starting compound. Cyclization conditions (step 4) consisted of stirring 3-(dimethylamino)-2-(methylsulfonyl)acrylonitrile (3 equiv), DBU (1 equiv), and the amidine (1 equiv) in pyridine at 110° C. $^1$H NMR (400 MHz, DMSO-d6) δ 9.11 (d, 1H), 8.60 (s, 1H), 7.66 (s, 1H), 7.36-7.30 (m, 1H), 7.28 (d, 1H), 7.25-7.20 (m, 1H), 7.11 (ddd, 1H), 6.86 (ddd, 1H), 5.93 (s, 2H), 3.28 (s, 3 h) ppm.

Compound I-121

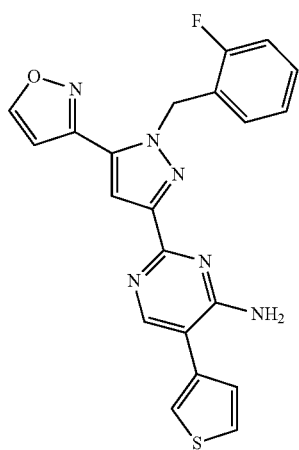 [SMILES: Nc1nc(-c2cc(-c3ccon3)n(Cc3ccccc3F)n2)ncc1-c1ccsc1]

This compound was synthesized as an off-white solid (1% yield over 4 steps) following General Procedure F using Intermediate 7 as the starting compound. Cyclization conditions (step 4) consisted of stirring 3-(dimethylamino)-2-(thiophen-3-yl)acrylonitrile (3 equiv) and the amidine (1 equiv) neat at 110° C. ¹H NMR (400 MHz, CDCl₃) δ 8.44 (d, 1H), 8.34 (s, 1H), 7.57-7.52 (m, 1H), 7.52 (dd, 1H), 7.46 (dd, 1H), 7.27-7.24 (m, 1H), 7.22-7.16 (m, 1H), 7.02 (ddd, 1H), 6.96 (ddd, 1H), 6.78 (ddd, 1H), 6.62 (d, 1H), 6.02 (s, 2H), 5.58 (bs, 2H) ppm.

Compound I-122

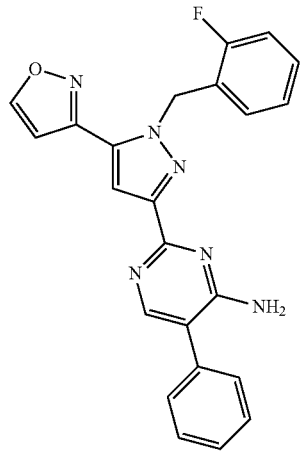 [SMILES: Nc1nc(-c2cc(-c3ccon3)n(Cc3ccccc3F)n2)ncc1-c1ccccc1]

This compound was synthesized as a white solid (8.5% yield over 4 steps) following General Procedure F using Intermediate 7 as the starting compound. Cyclization conditions (step 4) consisted of stirring 3-(dimethylamino)-2-phenylacrylonitrile (3 equiv), DBU (1 equiv), and the amidine (1 equiv) in pyridine at 110° C. ¹H NMR (400 MHz, CDCl₃) δ 8.40 (d, 1H), 8.23 (s, 1H), 7.71 (s, 1H), 7.48-7.38 (m, 5H), 7.15-7.10 (m, 1H), 7.00-6.87 (m, 2H), 6.79-6.70 (m, 1H), 6.60-6.55 (m, 1H), 5.98 (s, 2H), 5.30 (bs, 1H) ppm.

Example 8

General Procedure G

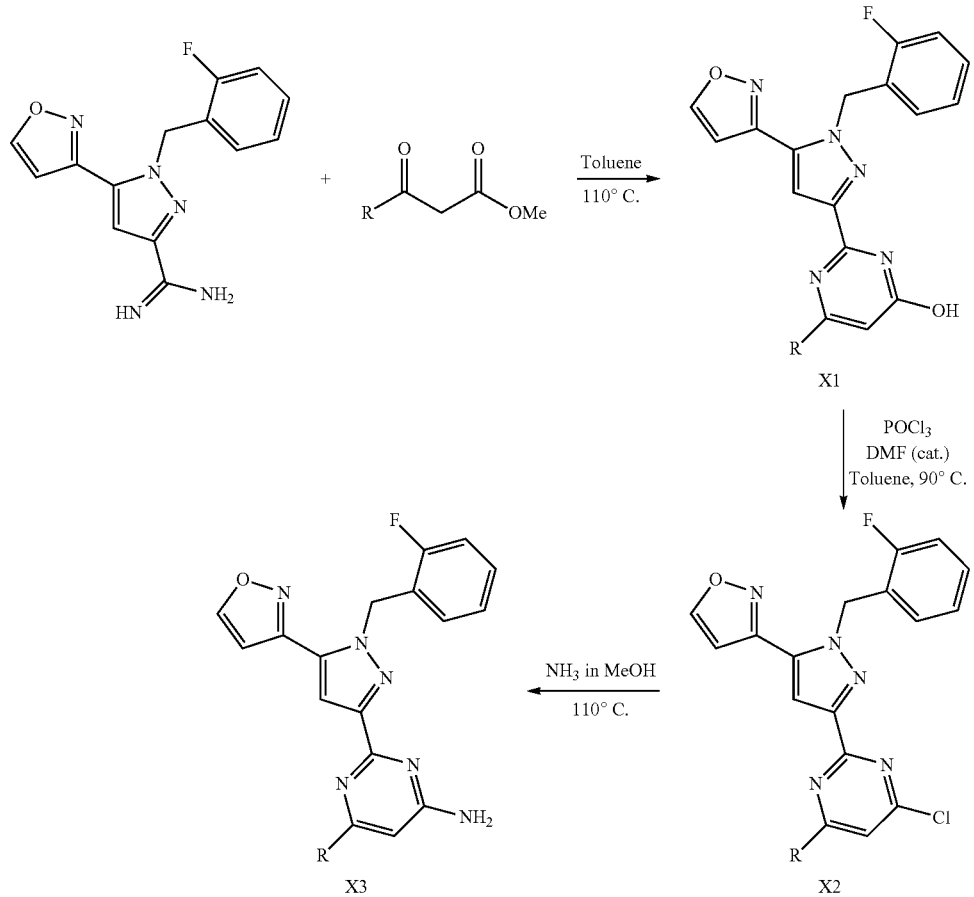

A solution of the requisite 1-(2-fluorobenzyl)-5-(isoxazol-3-yl)-1H-pyrazole-3-carboximidamide (1 equiv) and appropriate β-ketoester (1 equiv) in toluene was heated to 110° C. until consumption of starting material was complete. Evaporation of the solvent in vacuo, followed by purification via silica gel chromatography using the appropriate solvents, gave the desired pyrimidine X1. To a solution of X1 in toluene was added phosphoryl chloride (2.4 equiv), followed by a catalytic amount of N,N-dimethylformamide. The solution was heated to 90° C. until complete consumption of starting material was observed. The resulting suspension was partitioned between water and ethyl acetate. The layers were separated and the aqueous layer was extracted with ethyl acetate. The organics were combined, dried over magnesium sulfate, filtered, and the solvent was removed in vacuo to give the crude residue. Purification by silica gel chromatography using the appropriate solvent system delivered the intermediate aryl chloride X2. Conversion to the desired aminopyrimidine X3 was achieved by treating chloride X2 with 7N ammonia in methanol (100-150 equiv) and heating the solution to 110° C. for 4 h. The solvent was removed in vacuo and purification of the crude residue by silica gel chromatography (methanol in dichloromethane) provided the desired aminopyrimidine X3.

The Following Compounds were Synthesized According to General Procedure G

Compound I-111

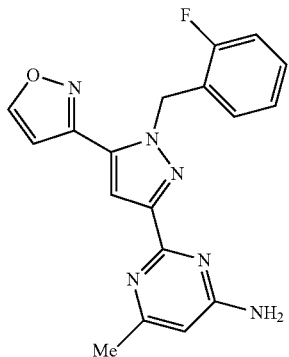 [SMILES: Cc1cc(N)nc(-c2cc(-c3ccon3)n(Cc3ccccc3F)n2)n1]

This compound was synthesized according as a white solid (18% yield over 3 steps) following General Procedure G using ethyl 1-(2-fluorobenzyl)-5-(isoxazol-3-yl)-1H-pyrazole-3-carboxylate as the starting compound. ¹H NMR (400 MHz, CDCl₃) δ 8.40 (d, 1H), 7.39 (s, 1H), 7.18-7.13 (m, 1H), 7.02-6.97 (m, 1H), 6.91 (t, 1H), 6.74-6.71 (m, 1H), 6.57 (d, 1H), 6.19 (s, 1H), 6.00 (s, 2H), 5.13 (br s, 2H), 2.40 (s, 3H).

Compound I-116

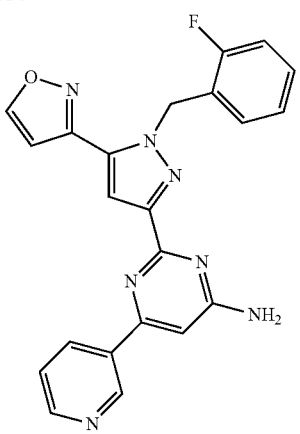 [SMILES: Nc1cc(-c2cccnc2)nc(-c2cc(-c3ccon3)n(Cc3ccccc3F)n2)n1]

This compound was synthesized as a white solid (9.2% yield over 3 steps) following General Procedure G using the required ethyl 1-(2-fluorobenzyl)-5-(isoxazol-3-yl)-1H-pyrazole-3-carboxylate as the starting compound. ¹H NMR (400 MHz, CDCl₃) δ 9.29 (br s, 1H), 8.72-8.70 (m, 1H), 8.48 (dt, 1H), 8.45 (d, 1H), 7.54 (s, 1H), 7.48 (dd, 1H), 7.20-7.15 (m, 1H), 7.04-6.99 (m, 1H), 6.95 (t, 1H), 6.87 (s, 1H), 6.83-6.79 (m, 1H), 6.63 (d, 1H), 6.02 (s, 2H), 5.71 (br s, 2H).

Compound I-117

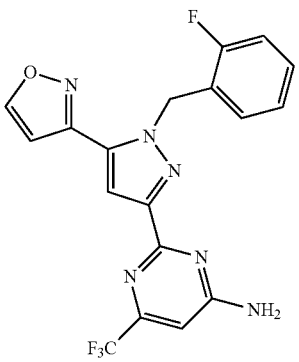 [SMILES: Nc1cc(C(F)(F)F)nc(-c2cc(-c3ccon3)n(Cc3ccccc3F)n2)n1]

This compound was synthesized as a white solid (13% yield over 3 steps) following General Procedure G using ethyl 1-(2-fluorobenzyl)-5-(isoxazol-3-yl)-1H-pyrazole-3-carboxylate as the starting compound. ¹H NMR (400 MHz, CDCl₃) δ 8.44 (d, 1H), 7.51 (s, 1H), 7.20-7.15 (m, 1H), 7.03-6.98 (m, 1H), 6.95 (t, 1H), 6.81 (t, 1H), 6.73 (s, 1H), 6.61 (d, 1H), 6.01 (s, 2H).

Example 9

Preparation of 1,3-diamine Compound I-103

Compound I-103

To a solution of 1-(2-fluorobenzyl)-5-(isoxazol-3-yl)-1H-pyrazole-3-carboximidamide (50 mg, 0.18 mmol) in ethanol (2 mL) was added malononitrile (35 mg, 0.53 mmol). After heating the solution to 110° C. for 6 hours, the solvent was removed in vacuo to give the crude product as a red oil. Purification by silica gel chromatography (0-10% methanol in dichloromethane) gave 2-(1-(2-fluorobenzyl)-5-(isoxazol-3-yl)-1H-pyrazol-3-yl)pyrimidine-4,6-diamine (I-103, 20 mg, 0.056 mmol, 32% yield) as a pink solid. ¹H NMR (400 MHz, CDCl₃) δ 8.45 (d, 1H), 7.31 (s, 1H), 7.19-7.14 (m, 1H), 7.01-6.96 (m, 1H), 6.92 (t, 1H), 6.74-6.71 (m, 1H), 6.58 (d, 1H), 5.90 (s, 2H), 5.57 (s, 1H), 5.03 (br s, 4H).

Example 10

The following compounds were synthesized with the procedures disclosed above.
Compound I-194

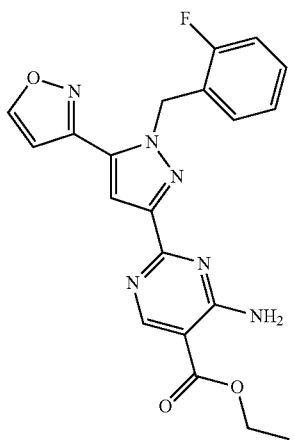 [SMILES: CCOC(=O)c1cnc(-c2cc(-c3ccon3)n(Cc3ccccc3F)n2)nc1N]

Compound I-194 was synthesized as a white solid (24% yield over 4 steps) following General Procedure F using ethyl 1-(2-fluorobenzyl)-5-(isoxazol-3-yl)-1H-pyrazole-3-carboxylate (Intermediate 7) as the starting compound. The cyclization reaction (step 4) was conducted in ethanol in the presence of one equivalents of diethyl 2-(ethoxymethylene)malonate and one equivalent of N,N-diisopropylethylamine. $^1$H NMR (400 MHz, DMSO-d6) δ 9.11 (d, 1H), 8.54 (bs, 1H), 7.75 (s, 1H), 7.36-7.30 (m, 1H), 7.25-7.17 (m, 1H), 7.23 (s, 1H), 7.13-7.07 (m, 1H), 7.05-6.94 (m, 1H), 5.92 (s, 2H), 4.22 (q, 2H), 1.26 (t, 3H).
Compound I-154

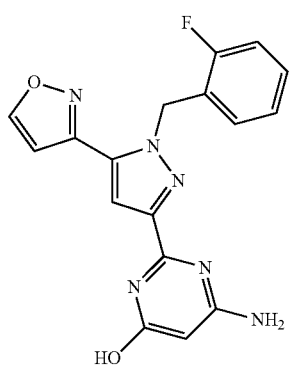

Compound I-154 was synthesized as a off-white solid (8% yield over 4 steps) following General Procedure F using ethyl 1-(2-fluorobenzyl)-5-(isoxazol-3-yl)-1H-pyrazole-3-carboxylate (Intermediate 7) as starting compound. Ethanol was used as solvent, along with one equivalents of ethyl cyanoacetate and four equivalents of sodium ethoxide in the cyclization reaction (step 4) that was carried out at 90° C. $^1$H NMR (400 MHz, DMSO-d6) δ 8.79 (d, 1H), 7.45 (s, 1H), 7.33-7.26 (m, 1H), 7.14-7.03 (m, 2H), 6.98-6.92 (m, 1H), 6.89-6.86 (m, 1H), 6.97-6.80 (m, 1H), 5.97 (s, 2H), 5.31 (s, 1H).

Compound I-146

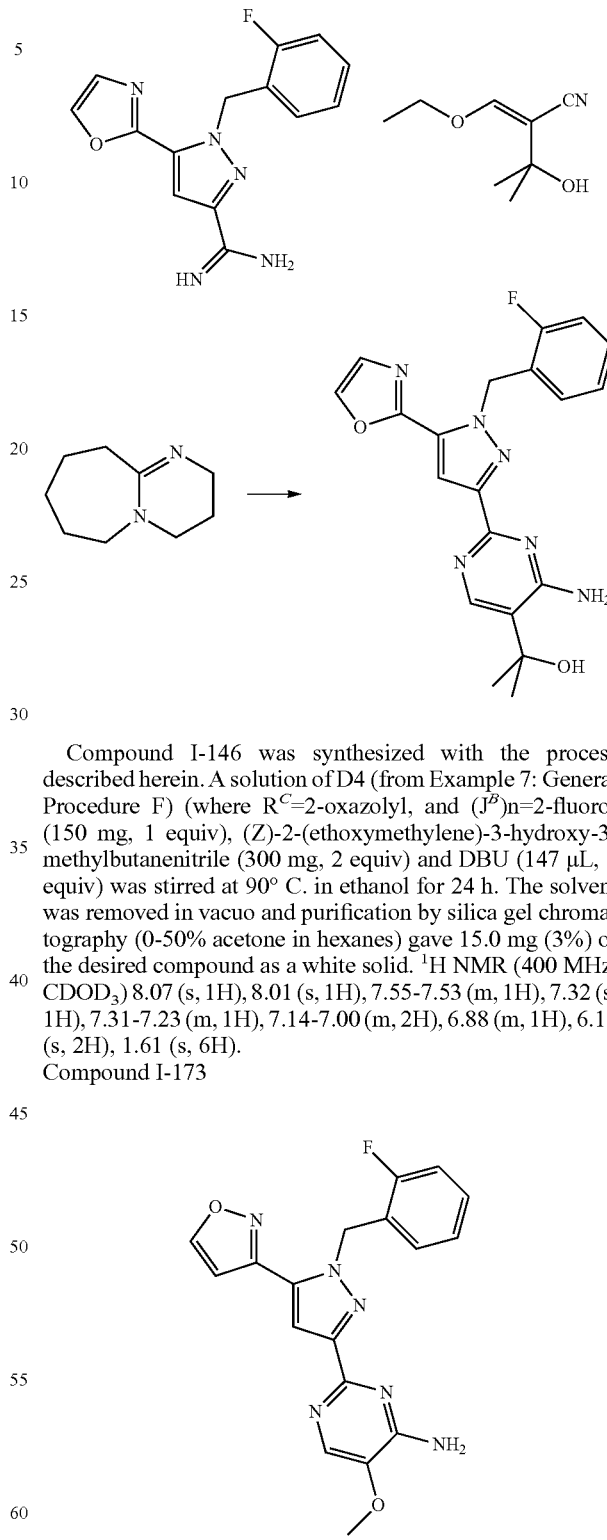

Compound I-146 was synthesized with the process described herein. A solution of D4 (from Example 7: General Procedure F) (where $R^C$=2-oxazolyl, and $(J^B)$n=2-fluoro) (150 mg, 1 equiv), (Z)-2-(ethoxymethylene)-3-hydroxy-3-methylbutanenitrile (300 mg, 2 equiv) and DBU (147 µL, 1 equiv) was stirred at 90° C. in ethanol for 24 h. The solvent was removed in vacuo and purification by silica gel chromatography (0-50% acetone in hexanes) gave 15.0 mg (3%) of the desired compound as a white solid. $^1$H NMR (400 MHz, CDOD$_3$) 8.07 (s, 1H), 8.01 (s, 1H), 7.55-7.53 (m, 1H), 7.32 (s, 1H), 7.31-7.23 (m, 1H), 7.14-7.00 (m, 2H), 6.88 (m, 1H), 6.11 (s, 2H), 1.61 (s, 6H).
Compound I-173

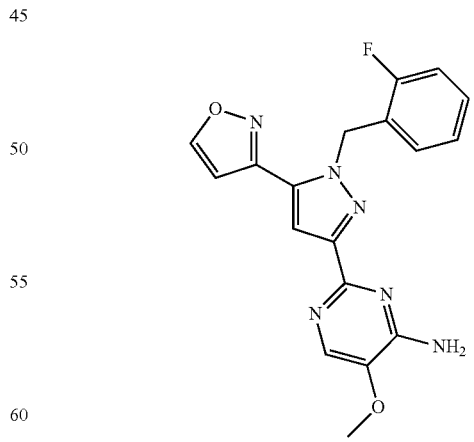

Compound I-173 was synthesized as a white solid (5% yield over 4 steps) following General Procedure F using ethyl 1-(2-fluorobenzyl)-5-(isoxazol-3-yl)-1H-pyrazole-3-carboxylate (Intermediate 7) as the starting compound. The cyclization reaction (step 4) was conducted in ethanol in the presence of three equivalents of 3-(dimethylamino)-2-methoxyacrylonitrile and one equivalent of 1,8-diazabicyclo[5.4.0]undec-7-ene. $^1$H NMR (400 MHz, DMSO-d6) δ 9.08 (d, 1H), 7.88 (s, 1H), 7.43 (s, 1H), 7.36-7.28 (m, 1H), 7.25-7.18 (m, 2H), 7.14-7.08 (m, 1H), 6.84 (t, 1H), 6.97-6.69 (bs, 2H), 5.87 (s, 2H), 3.86 (s, 3H).

Compound I-180

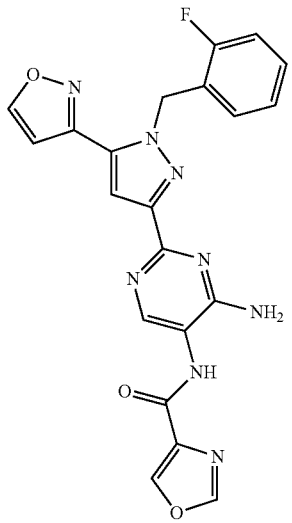 [SMILES: Nc1nc(-c2cc(-c3ccon3)n(Cc3ccccc3F)n2)ncc1NC(=O)c1cocn1]

Compound I-180 was synthesized as a light brown solid (42%) via the condensation of Compound I-107 (1 equiv) with oxazole-4-carbonyl chloride (1.5 equiv) in a solution of DCM/pyridine (2:1). (Purification was carried out using SiO$_2$ chromatography employing a 0-15% MeOH/DCM gradient following an EtOAc and NH$_4$Cl-based work-up). $^1$H NMR (400 MHz, DMSO-d6) δ 9.70 (s, 1H), 9.07 (d, 1H), 8.78-8.76 (m, 1H), 8.60-8.58 (m, 1H), 8.21-8.19 (m, 1H), 7.52 (s, 1H), 7.35-7.28 (m, 1H), 7.23 (d, 1H), 7.25-7.18 (m, 1H), 7.12-7.06 (m, 1H), 6.93 (bs, 2H), 6.87-6.81 (m, 1H), 5.88 (s, 2H).

Compound I-175

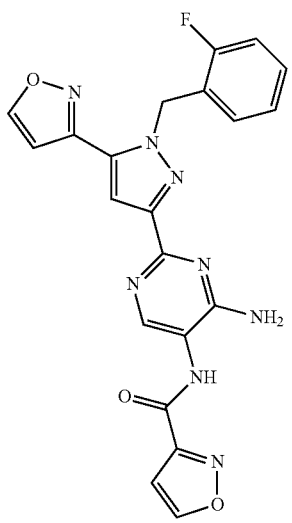 [SMILES: Nc1nc(-c2cc(-c3ccon3)n(Cc3ccccc3F)n2)ncc1NC(=O)c1ccon1]

Compound I-175 was synthesized as a light pink solid (35%) via the condensation of Compound I-107 (1 equiv) with isoxazole-3-carbonyl chloride (1.3 equiv) in a solution of DCM/pyridine (2:1). (Purification was carried out using SiO$_2$ chromatography employing a 0-15% MeOH/DCM gradient following an EtOAc and NH$_4$Cl-based work-up). $^1$H NMR (400 MHz, CDCl$_3$) δ 8.53 (s, 2H), 8.44 (s, 2H), 7.39 (s, 1H), 7.17 (q, 1H), 6.99 (t, 1H), 6.94 (t, 1H), 6.89 (s, 1H), 6.79 (t, 1H), 6.58 (s, 1H), 5.99 (s, 2H), 5.68 (bs, 2H).

Compound I-189

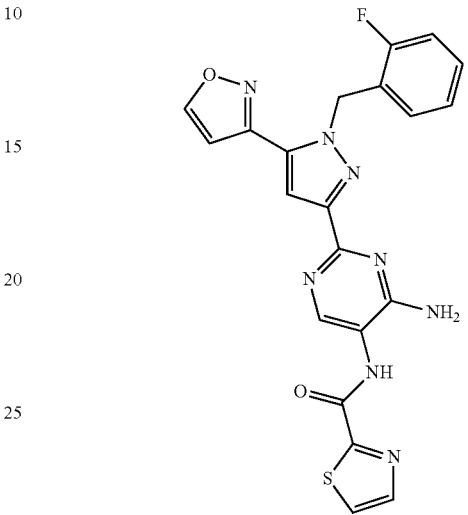

Compound I-189 was synthesized as a white solid (27%) via the condensation of Compound I-107 (1 equiv) with thiazole-2-carbonyl chloride (0.8 equiv) in a solution of DCM/pyridine (2:1). (Purification was carried out using SiO$_2$ chromatography employing a 0-15% MeOH/DCM gradient following an EtOAc and NH$_4$Cl-based work-up). $^1$H NMR (400 MHz, DMSO-d6) δ 10.25 (bs, 1H) 9.07 (d, 1H), 8.21 (s, 1H), 8.10 (q, 2H), 7.53 (s, 1H), 7.36-7.28 (m, 1H), 7.24 (d, 1H), 7.25-7.18 (m, 1H), 7.12-7.06 (m, 2H), 7.08 (bs, 1H), 6.87-6.81 (m, 1H), 5.89 (s, 2H).

Compound I-188

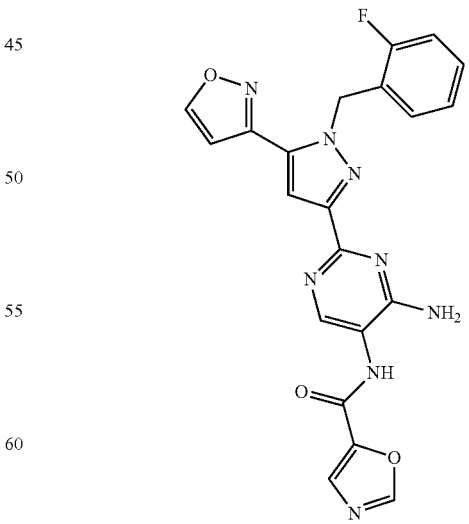

Compound I-188 was synthesized as a tan solid (55%) via the condensation of Compound I-107 (1 equiv) with oxazole-5-carbonyl chloride (2.2 equiv) in a solution of DCM/pyridine (2:1). (Purification was carried out using SiO$_2$ chromatography employing a 0-15% MeOH/DCM gradient following an EtOAc and NH$_4$Cl-based work-up). $^1$H NMR (400 MHz, DMSO-d6) δ9.93 (bs, 1H), 9.10 (d, 1H), 8.66 (s, 1H), 8.20 (s, 1H), 7.95 (s, 1H), 7.55 (s, 1H), 7.37-7.30 (m, 1H), 7.26 (d, 1H), 7.27-7.20 (m, 1H), 7.14-7.08 (m, 1H), 7.09 (bs, 2H), 6.90-6.83 (m, 1H), 5.90 (s, 2H).
Compound I-263

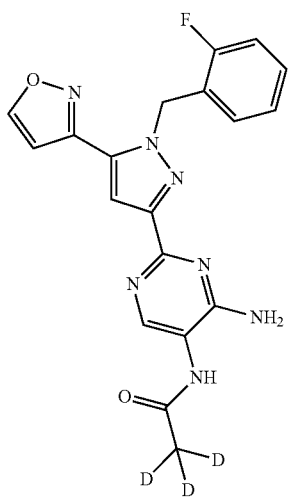 [SMILES: [2H]C([2H])([2H])C(=O)Nc1cnc(-c2cc(-c3ccon3)n(Cc3ccccc3F)n2)nc1N]

Compound I-263 was synthesized with the process described herein. A mixture of Compound I-107 (40 mg, 0.103 mmol) in acetic acid-d4 (3.1 mL) was heated to 110° C. for 24 h. After cooling to room temperature, the solution was partitioned between ethyl acetate (50 mL) and saturated aqueous sodium carbonate. The layers were separated and the aqueous layer was extracted with ethyl acetate (2×50 mL). The organics were dried over MgSO$_4$, filtered, and the solvent was removed in vacuo to give the crude product as a tan residue. Dichloromethane (3 mL) and diethyl ether (5 mL) were added, and the resulting tan solid was filtered and washed with additional diethyl ether to give the desired compound (24 mg, 58% yield) as a tan solid. $^1$H NMR (400 MHz, DMSO-d6) δ 9.25 (bs, 1H), 9.09 (d, 1H), 8.33 (s, 1H), 7.51 (s, 1H), 7.37-7.30 (m, 1H), 7.25-7.19 (m, 1H), 7.24 (d, 1H), 7.14-7.08 (m, 1H), 6.92 (bs, 2H), 6.88-6.82 (m, 1H), 5.89 (s, 2H).
Compound I-203

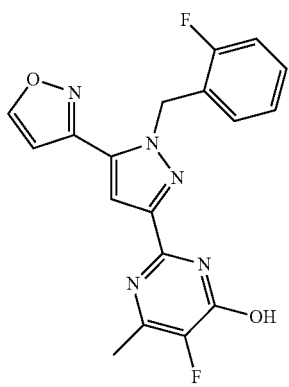 [SMILES: Cc1nc(-c2cc(-c3ccon3)n(Cc3ccccc3F)n2)nc(O)c1F]

Compound I-203 was synthesized as a white solid (11% yield over 4 steps) following General Procedure F using ethyl 1-(2-fluorobenzyl)-5-(isoxazol-3-yl)-1H-pyrazole-3-carboxylate (Intermediate 7) as starting compound. Ethanol was used as solvent, along with three equivalents of ethyl 2-fluoro-3-oxobutanoate and two equivalents of N,N-diisopropylethylamine in the cyclization reaction (step 4) that was carried out at 90° C. $^1$H NMR (400 MHz, DMSO-d6) δ 9.09 (d, 1H), 7.60 (s, 1H), 7.35-7.28 (m, 1H), 7.25-7.17 (m, 1H), 7.24 (d, 1H), 7.13-7.07 (m, 1H), 6.97-6.80 (m, 1H), 5.90 (s, 2H), 2.26 (d, 3H).
Compound I-196

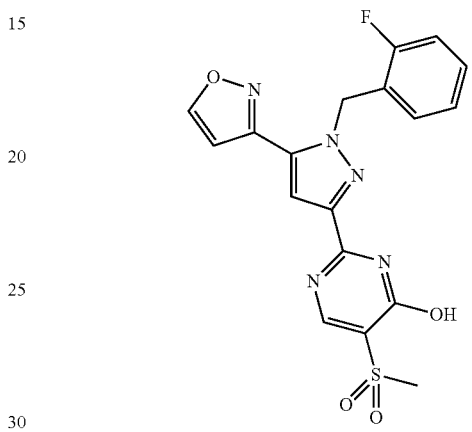

A solution of D4 (from Example 7: General Procedure F) (where R$^c$=3-isoxazolyl, and (JB)$_n$=2-fluoro) (85 mg, 1 equiv) and ethyl 3-(dimethylamino)-2-(methylsulfonyl)acrylate (65.9 mg, 1 equiv) was stirred at 90° C. in ethanol for 14 h. The solvent was removed in vacuo. The crude precipitate was suspended in methanol, collected by filtration, rinsed with a minimal amount of diethyl ether and methanol and dried in vacuo to give 58.0 mg (47.1%) of the desired compound as a white solid. $^1$H NMR (400 MHz, DMSO-d6) 9.05 (d, 1H), 8.42 (bs, 1H), 8.23 (s, 1H), 7.52 (s, 1H), 7.35-7.27 (m, 1H), 7.25-7.17 (m, 1H), 7.24 (d, 1H), 7.12-7.06 (m, 1H), 6.85-6.79 (m, 1H), 5.88 (s, 2H), 3.13 (s, 3H).
Compound I-217

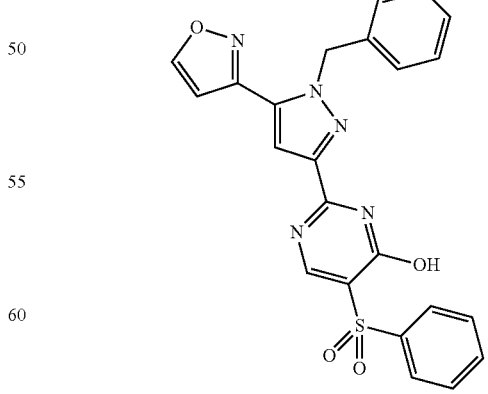

Compound I-217 was synthesized with a process described herein. A solution of D4 (from Example 7: General Procedure F) (where R$^c$=3-isoxazolyl, and (J$^B$)n=2-fluoro) (85 mg, 1 equiv), ethyl 3-(dimethylamino)-2-(phenylsulfonyl)acrylate (74.9 mg, 1 equiv) and N,N-diisopropylethylamine (46 µL, 1 equiv) was stirred at 100° C. in ethanol for 24 h. The solvent was removed in vacuo. The crude precipitate was suspended in methanol, collected by filtration, rinsed with a minimal amount of diethyl ether and methanol and dried in vacuo to give 58.0 mg (46%) of the desired compound as a white solid. $^1$H NMR (400 MHz, DMSO-d6) 9.03 (d, 1H), 8.44 (d, 1H), 8.43 (bs, 1H), 7.95-7.92 (m, 2H), 7.59-7.54 (m, 1H), 7.52-7.47 (m, 3H), 7.32-7.25 (m, 1H), 7.22 (d, 1H), 7.22-7.14 (m, 1H), 7.06 (t, 1H), 6.78 (t, 1H), 5.86 (s, 2H).
Compound I-254

(where $R^c$=3-isoxazolyl, and $(J^B)$n=2-fluoro) (86.7 mg, 1 equiv), ethyl 3-(dimethylamino)-2-(4-fluorophenylsulfonyl)acrylate (81.0 mg, 1 equiv) and N,N-diisopropylethylamine (47 µL, 1 equiv) was stirred at 100° C. in ethanol for 24 h. The solvent was removed in vacuo and purification by silica gel chromatography (0-20% ethyl acetate in hexanes) gave 14 mg (11%) of the desired compound as a white solid. $^1$H NMR (400 MHz, CD$_3$OD) 8.78 (d, 1H), 8.74 (s, 1H), 8.18-8.12 (m, 2H), 7.56 (s, 1H), 7.35-7.29 (m, 2H), 7.29-7.25 (m, 1H), 7.12-7.06 (m, 1H), 7.06-7.01 (m, 1H), 6.94-6.89 (m, 1H), 6.90 (d, 1H), 6.00 (s, 2H).
Compound I-253

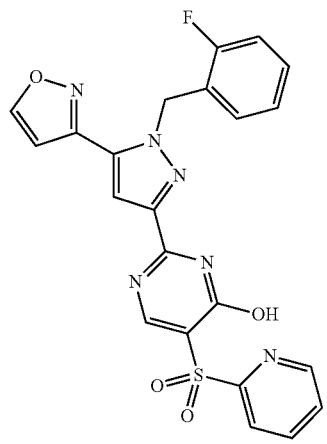 [SMILES: O=S(=O)(c1ccccn1)c1cnc(-c2cc(-c3ccon3)n(Cc3ccccc3F)n2)nc1O]

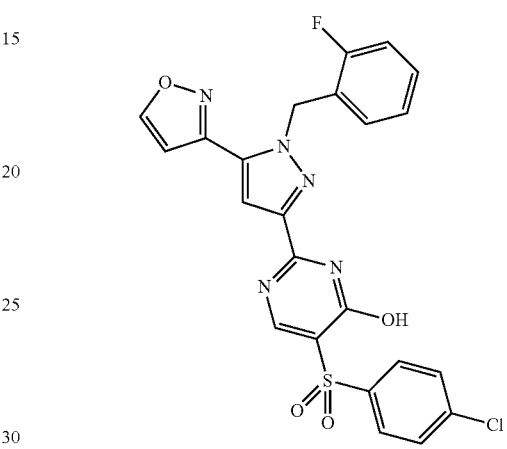

Compound I-254 was synthesized as described herein. A solution of D4 (from Example 7: General Procedure F) (where $R^c$=3-isoxazolyl, and $(J^B)$n=2-fluoro) (85 mg, 1 equiv), ethyl 3-(dimethylamino)-2-(pyridin-2-ylsulfonyl)acrylate (75 mg, 1 equiv) and N,N-diisopropylethylamine (46 µL, 1 equiv) was stirred at 100° C. in ethanol for 24 h. The solvent was removed in vacuo. The crude precipitate was suspended in methanol, collected by filtration, rinsed with a minimal amount of diethyl ether and methanol and dried in vacuo to give 53 mg (43%) of the desired compound as an off-white solid. $^1$H NMR (400 MHz, DMSO-d6) 9.13 (s, 1H), 8.68 (d, 1H), 8.24-8.15 (m, 1H), 8.21 (s, 1H), 7.81 (s, 1H), 7.75-7.70 (m, 1H), 7.38-7.31 (m, 1H), 7.31-7.19 (m, 2H), 7.12 (t, 1H), 6.94 (bs, 1H), 5.97 (s, 2H).
Compound I-241

Compound I-253 was synthesized as described herein. A solution of D4 (from Example 7: General Procedure F) (where $R^c$=3-isoxazolyl, and $(J^B)$n=2-fluoro) (86.9 mg, 1 equiv), ethyl 2-(4-chlorophenylsulfonyl)-3-(dimethylamino)acrylate (86 mg, 1 equiv) and N,N-diisopropylethylamine (47 µL, 1 equiv) was stirred at 100° C. in ethanol for 24 h. The solvent was removed in vacuo. The crude precipitate was suspended in methanol, collected by filtration, rinsed with a minimal amount of diethyl ether and methanol and dried in vacuo to give 53.9 mg (42.6%) of the desired compound as an off-white solid. $^1$H NMR (400 MHz, DMSO-d6) 9.13 (s, 1H), 8.74 (bs, 1H), 8.05-8.01 (m, 2H), 7.79 (s, 1H), 7.73-7.69 (m, 2H), 7.38-7.17 (m, 3H), 7.11 (t, 1H), 6.93 (bs, 1H), 5.97 (s, 2H).
Compound I-242

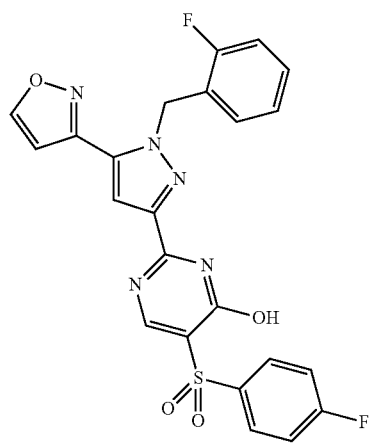 [SMILES: O=S(=O)(c1ccc(F)cc1)c1cnc(-c2cc(-c3ccon3)n(Cc3ccccc3F)n2)nc1O]

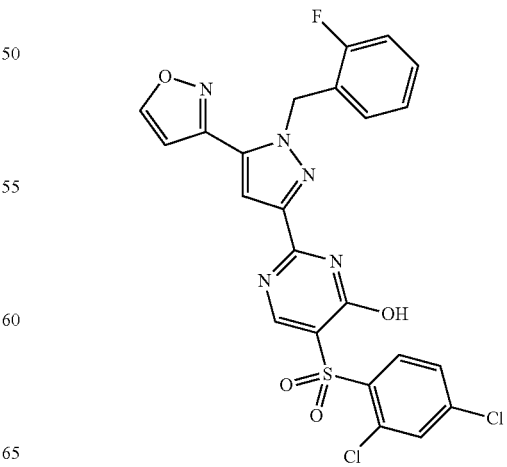

Compound I-241 was synthesized as described herein. A solution of D4 (from Example 7: General Procedure F)

Compound I-242 was synthesized as described herein. A solution of D4 (from Example 7: General Procedure F) (where R$^c$=3-isoxazolyl, and (J$^B$)n=2-fluoro) (85.0 mg, 1 equiv), ethyl 2-(2,5-dichlorophenylsulfonyl)-3-(dimethylamino)acrylate (93 mg, 1 equiv) and N,N-diisopropylethylamine (46 μL, 1 equiv) was stirred at 100° C. in ethanol for 24 h. The solvent was removed in vacuo. The crude precipitate was suspended in methanol, collected by filtration, rinsed with a minimal amount of diethyl ether and methanol and dried in vacuo to give 49.4 mg (34%) of the desired compound as a white solid. $^1$H NMR (400 MHz, DMSO-d6) 9.04 (d, 1H), 8.47 (s, 1H), 8.30 (bs, 1H), 8.10 (d, 1H), 7.71-7.65 (m, 1H), 7.54 (d, 1H), 7.49 (s, 1H), 7.34-7.25 (m, 1H), 7.23 (d, 1H), 7.22-7.16 (m, 1H), 7.11-7.05 (m, 1H), 6.84-6.79 (m, 1H), 5.86 (s, 2H).

Compound I-210

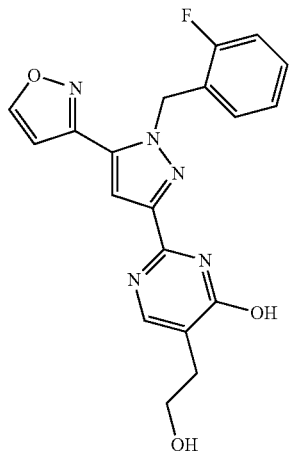 [SMILES: OCCc1cnc(-c2cc(-c3ccon3)n(Cc3ccccc3F)n2)nc1O]

Compound I-210 was synthesized as described herein. A solution of D4 (from Example 7: General Procedure F) (where R$^c$=3-isoxazolyl, and (J$^B$)n=2-fluoro) (50 mg, 1 equiv) and sodium (E)-(2-oxodihydrofuran-3(2H)-ylidene)methanolate (21 mg, 1 equiv) was stirred at 100° C. in ethanol for 24 h. The solvent was removed in vacuo and purification by silica gel chromatography (0-20% methanol in dichloromethane) gave 15 mg (20%) of the desired compound as a white solid. $^1$H NMR (400 MHz, CD$_3$OD) δ 8.79 (d, 1H), 7.90 (bs, 1H), 7.46 (s, 1H), 7.36-7.23 (m, 2H), 7.14-7.00 (m, 3H), 6.97-6.92 (m, 1H), 6.91-6.88 (m, 1H), 5.99 (s, 2H), 3.77 (t, 2H), 2.69 (t, 2H).

Compound I-158

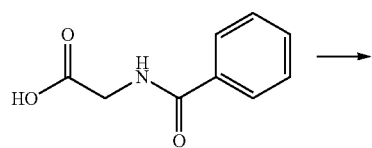

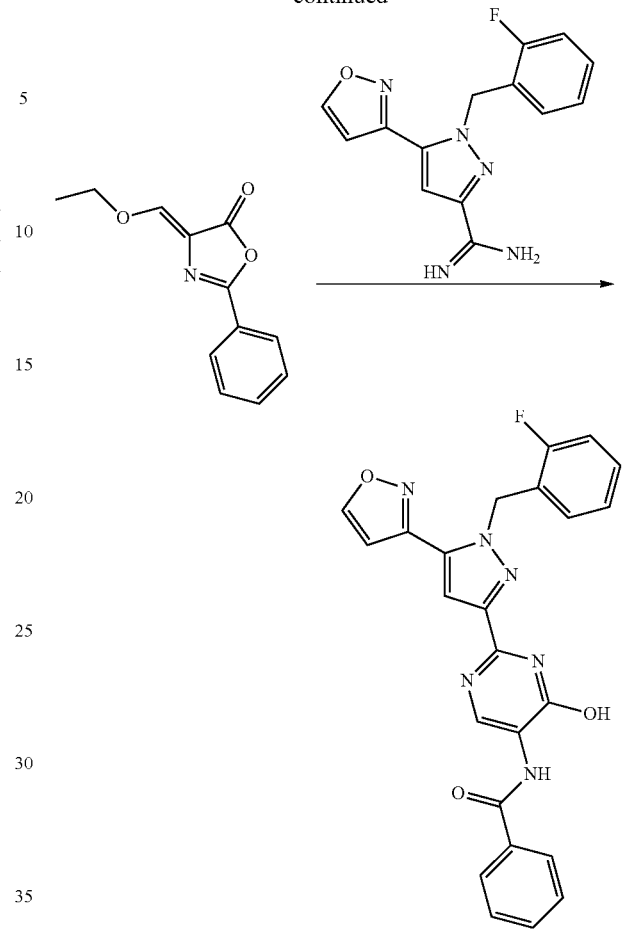

Compound I-158 was synthesized as described herein.

Step 1. Synthesis of (Z)-4-(ethoxymethylene)-2-phenyloxazol-5(4H)-one

To a mixture of 2-benzamidoacetic acid (2.5 g, 13.8 mmol), DMAP (0.017 g, 0.138 mmol) and triethoxymethane (2.3 ml, 13.8 mmol), was added acetic anhydride (2.6 ml, 27.6 mmol). The mixture was heated to 140° C. for 30 min. The solvent was removed in vacuo and purification by silica gel chromatography (0-30% ethyl acetate in hexanes) gave 1.4 g (47%) of (Z)-4-(ethoxymethylene)-2-phenyloxazol-5(4H)-one as an orange solid. $^1$H NMR (400 MHz, CDCl$_3$) 8.09-8.04 (m, 2H), 7.56-7.51 (m, 1H), 7.50-7.43 (m, 2H), 7.35 (s, 1H), 4.43 (q, 2H), 1.49 (t, 3H).

Step 2. Synthesis of Compound I-158

A solution of D4 (from Example 7: General Procedure F) (where R$^c$=3-isoxazolyl, and (J$^B$)n=2-fluoro) (150 mg, 1 equiv), (Z)-4-(ethoxymethylene)-2-phenyloxazol-5(4H)-one (114 mg, 1 equiv) and triethylamine (147 μL, 2 equiv) was stirred at 90° C. in ethanol for 24 h. The solvent was removed in vacuo and purification by silica gel chromatography (0-20% methanol in dichloromethane) gave 24 mg (10%) of the desired compound as a white solid. $^1$H NMR (400 MHz, DMSO-d6) 9.40 (bs, 1H), 9.12 (d, 1H), 8.81 (bs, 1H), 7.98-7.92 (m, 2H), 7.71 (s, 1H), 7.67-7.60 (m, 1H), 7.59-7.54 (m, 2H), 7.49-7.7.31 (m, 1H), 7.29-7.20 (m, 2H), 7.12 (t, 1H), 7.00 (bs, 1H), 5.97 (s, 2H).

Compound I-170

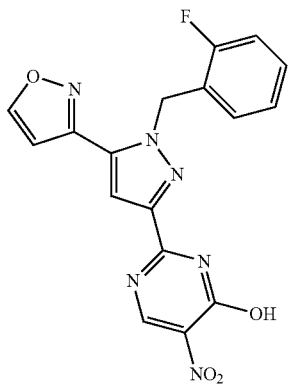 [SMILES: O=[N+]([O-])c1cnc(-c2cc(-c3ccon3)n(Cc3ccccc3F)n2)nc1O]

Compound I-170 was synthesized as described herein.

To a cold mixture of 2-(1-(2-fluorobenzyl)-5-(isoxazol-3-yl)-1H-pyrazol-3-yl)pyrimidin-4-ol Compound I-160 (100 mg, 1 equiv) in acetic acid (102 μl, 6 equiv) at 0° C., was added nitric acid (79 μl, 6 equiv). The mixture was heated to 80° C. for 1 h. The reaction was poured into ice and quenched with saturated solution of sodium bicarbonate (50 ml). The mixture was extracted with ethyl acetate (100 ml). The organic layer was dried, filtered and evaporated to give a white solid. The solid was suspended in methanol, collected by filtration and rinsed with a minimal amount of methanol to give 48 mg (42%) of the desired product as a white solid. $^1$H NMR (400 MHz, DMSO-d6) 9.15 (d, 1H), 8.31-8.25 (m, 1H), 8.02 (bs, 1H), 8.00-7.96 (m, 1H), 7.71 (s, 1H), 7.57 (t, 1H), 7.27 (s, 1H), 6.34 (bs, 1H), 6.01 (s, 2H).

Compound I-192

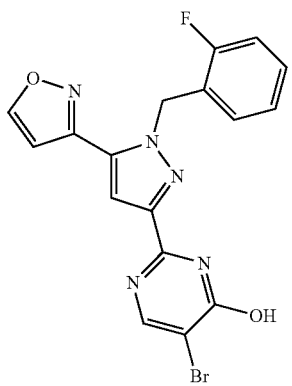 [SMILES: Oc1nc(-c2cc(-c3ccon3)n(Cc3ccccc3F)n2)ncc1Br]

Compound I-192 was synthesized as described herein.

To a solution of 2-(1-(2-fluorobenzyl)-5-(isoxazol-3-yl)-1H-pyrazol-3-yl)pyrimidin-4-ol Compound I-160 (276 mg, 1 equiv) in acetic acid (4 ml) at 0° C., was added bromine (59 μl, 1.4 equiv). The mixture was removed from the ice bath and stirred at 25° C. for 3 h. The mixture was concentrated under vacuum. The resulting residue was rinsed with a minimal amount of methanol and acetone. The precipitate was collected by filtration to give a mixture of the starting material as well as the desired 2-(1-(2-fluorobenzyl)-5-(isoxazol-3-yl)-1H-pyrazol-3-yl)pyrimidin-4-ol. Repeating and subjecting the solid under the bromination conditions gave 202 mg (59%) of the desired product as a white solid. $^1$H NMR (400 MHz, DMSO-d6) 9.10 (d, 1H), 8.40 (bs, 1H), 7.67 (s, 1H), 7.36-7.29 (m, 1H), 7.24-7.17 (m, 1H), 7.13-7.08 (m, 1H), 7.02-6.96 (m, 1H), 5.90 (s, 2H).

Compound I-216

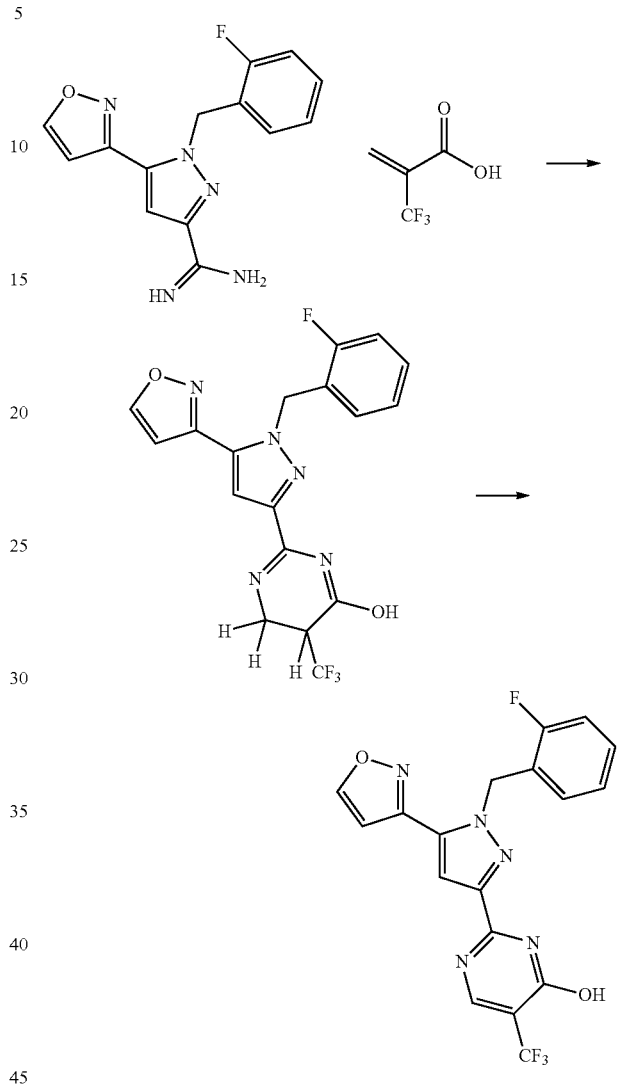

Compound I-216 was synthesized as described below.

Step 1. Synthesis of 2-(1-(2-fluorobenzyl)-5-(isoxazol-3-yl)-1H-pyrazol-3-yl)-5-(trifluoromethyl)-5,6-dihydropyrimidin-4(1H)-one A mixture of D4 (from Example 7: General Procedure F) (where $R^c$=3-isoxazolyl, and $(J^B)n$=2-fluoro) (500 mg, 1 equiv), 2-(trifluoromethyl)acrylic acid (218 mg, 1 equiv) and acetic anhydride (2.9 ml, 20 equiv) was heated to 100° C. for 1 h. The mixture was concentrated under vacuum to give thick oil. The oil was purified by column chromatography to give 372 mg (59%) of 2-(1-(2-fluorobenzyl)-5-(isoxazol-3-yl)-1H-pyrazol-3-yl)-5-(trifluoromethyl)-5,6-dihydropyrimidin-4(1H)-one. $^1$H NMR (400 MHz, CDCl$_3$) 8.87 (s, 1H), 8.45 (s, 1H), 7.11 (s, 1H), 7.04-6.92 (m, 3H), 6.60 (s, 1H), 5.87 (s, 2H), 4.12-3.99 (m, 2H), 3.29-3.25 (m, 1H).

Step 2. Synthesis of Compound I-216

A mixture of 2-(1-(2-fluorobenzyl)-5-(isoxazol-3-yl)-1H-pyrazol-3-yl)-5-(trifluoromethyl)-5,6-dihydropyrimidin-4

(1H)-one (131 mg, 1 equiv) and bromine (17 ml, 1 equiv) in acetic acid (6.4 ml) was heated to 100° C. for 2 h. The mixture was concentrated under vacuum to give oil. It was treated with diethyl ether. The precipitate formed was filtered, dried, rinsed with a minimal amount of warm methanol and dried under vacuum to give 42.9 mg (33%) of the desired product as a white solid. $^1$H NMR (400 MHz, DMSO-d6) 8.81 (d, 1H), 8.38 (bs, 1H), 7.58 (s, 1H), 7.33-7.26 (m, 1H), 7.14-7.08 (m, 1H), 7.08-7.04 (m, 1H), 6.99-6.93 (m, 1H), 6.93-6.92 (m, 1H), 6.03 (s, 2H).

Compound I-224

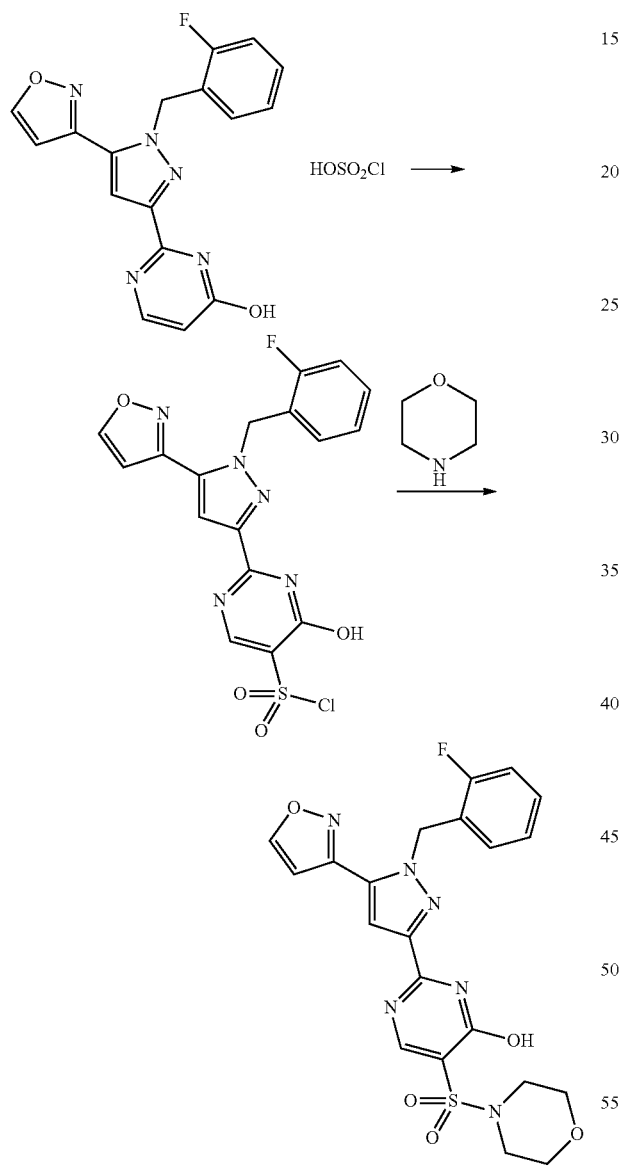

Compound I-224 was synthesized as described below.

A solution of 2-(1-(2-fluorobenzyl)-5-(isoxazol-3-yl)-1H-pyrazol-3-yl)pyrimidin-4-ol Compound I-160 (56 mg, 1 equiv) and sulfurochloridic acid (552 μl) in a sealed vial was heated to 100° C. for 30 min. The mixture was diluted in ethyl acetate (50 ml) and washed with water (50 ml). The organic layer was dried, filtered and evaporated to give 79 mg of crude 2-(1-(2-fluorobenzyl)-5-(isoxazol-3-yl)-1H-pyrazol-3-yl)-4-hydroxypyrimidine-5-sulfonyl chloride as a white solid. The solid was combined with morpholine (47.4 μl, 3.3 equiv) and stirred at 25° C. for 30 min. The mixture was diluted in ethyl acetate (100 ml) and washed with water (50 ml). The organic layer was dried, filtered and evaporated to give crude oil. Purification by column chromatography (0 to 10% methanol in dichloromethane) gave 40 mg of the desired product (45%) as a white solid. $^1$H NMR (400 MHz, DMSO-d6) 9.11 (d, 1H), 8.01 (bs, 1H), 7.74-7.67 (m, 1H), 7.66 (s, 1H), 7.51 (t, 1H), 7.35-7.30 (m, 1H) 7.22 (s, 1H), 6.33 (bs, 1H), 5.97 (s, 2H), 3.52-3.46 (m, 4H), 2.67-2.59 (m, 4H).

Compound I-147

Compound I-147 was synthesized as described herein.

A solution of D4, (from Example 7: General Procedure F, where $R^c$=2-oxazolyl, and $(J^B)n$=2-fluoro) (1 equiv) and 3-(dimethylamino)-2-fluoroacrylonitrile (3 equiv) was stirred neat at 110° C. for 14 h. The reaction mixture was purified by silica gel chromatography (0-100% 7:1 acetonitrile:methanol in dichloromethane) to deliver the desired compound as a solid (7%).

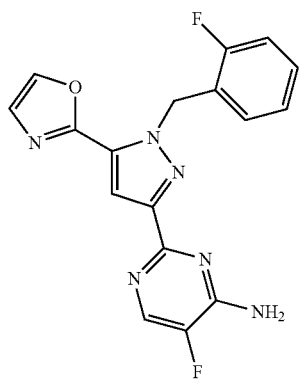 [SMILES: Nc1nc(-c2cc(-c3ncco3)n(Cc3ccccc3F)n2)ncc1F]

$^1$H NMR (400 MHz, DMSO-d6) 8.29 (s, 1H), 8.19 (d, 1H), 7.45 (s, 1H), 7.42 (br. s, 2H), 7.30-7.34 (m, 2H), 7.20 (dt, 1H), 7.10 (tt, 1H), 6.91 (dt, 1H), 6.0 (s, 2H).

Compound I-148

A solution of D4, (from Example 7: General Procedure F, where Rc=2-oxazolyl, and $(J^B)n$=2-fluoro) (1 equiv) and tert-butyl 1-cyano-2-(dimethylamino)vinylcarbamate was stirred neat at 110° C. for 14 h. The reaction mixture was purified by silica gel chromatography (0-100% 7:1 acetonitrile:methanol in dichloromethane) to deliver the desired compound I-148 as a solid (15.1%).

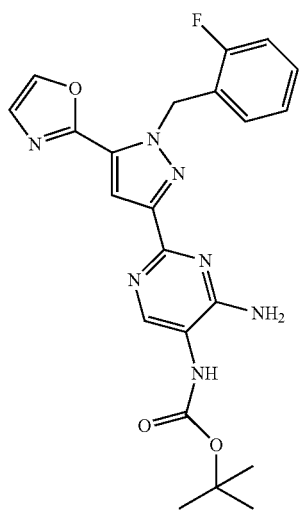 [SMILES: CC(C)(C)OC(=O)Nc1cnc(-c2cc(-c3ncco3)n(Cc3ccccc3F)n2)nc1N]

¹H NMR (400 MHz, CDCl₃) 8.31 (s, 1H), 7.67 (s, 1H), 7.55 (t, 1H), 7.19 (s, 1H), 7.15 (t, 1H), 6.99 (t, 1H), 6.92 (t, 1H), 6.77 (dt, 1H), 6.69-6.72 (m, 1H), 6.10 (s, 2H), 5.61 (br. s, 2H), 1.44 (s, 9H).

Compound I-269

A solution of D4, (from Example 7: General Procedure F, where Rc=2-oxazolyl, and (JB)n=2-fluoro) (1 equiv) and 3-(dimethylamino)-2-(diphenylmethyleneamino) acrylonitrile was stirred in 1,8-Diazabicyclo[5.4.0]undec-7-ene (2 equiv) and pyridine. The reaction was concentrated and purified by SiO2 chromatography to afford desired compound I-269 as a solid (26.9%).

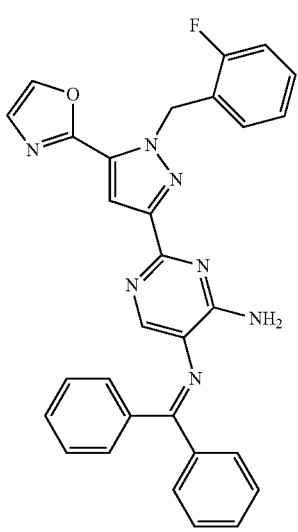 [SMILES: Nc1nc(-c2cc(-c3ncco3)n(Cc3ccccc3F)n2)ncc1N=C(c1ccccc1)c1ccccc1]

¹H NMR (400 MHz, CDCl₃) 7.76 (d, 2H), 7.63 (d, 1H), 7.47-7.51 (m, 2H), 7.36-7.42 (m, 2H), 7.31-7.35 (m, 4H), 7.11-7.18 (m, 4H), 6.96 (dt, 1H), 6.91 (dt, 1H), 6.74 (dt, 1H), 6.09 (s, 2H).

Compound I-149

A solution of Compound I-148 (1 equiv) and 4N HCl (50 equiv) was stirred under ambient conditions for 2 hr. The reaction was concentrated in vacuo and triturated with ethyl ether to afford desired compound I-149 as a solid (88%).

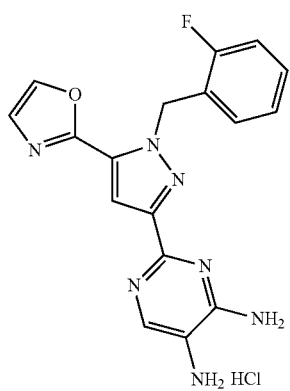 [SMILES: Nc1cnc(-c2cc(-c3ncco3)n(Cc3ccccc3F)n2)nc1N ; Cl]

¹H NMR (400 MHz, CD₃OD) 8.06 (s, 1H), 7.55 (s, 1H), 7.46 (s, 1H), 7.37 (s, 1H), 7.28-7.33 (m, 2H), 7.05-7.13 (m, 2H), 6.98-7.01 (tt, 1H), 6.14 (s, 2H).

Compound I-151

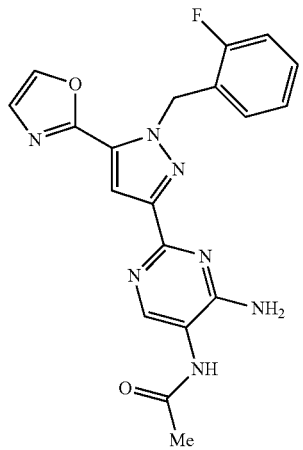 [SMILES: CC(=O)Nc1cnc(-c2cc(-c3ncco3)n(Cc3ccccc3F)n2)nc1N]

Acetic acid (500 equiv) was added to Compound I-149 and the solution was stirred at 110° C. for 14 hr. The reaction was quenched with saturated sodium carbonate and extracted with ethyl acetate. Following concentration, the crude mixture was triturated with ethyl ether to afford the desired compound I-151 as a solid (52.2%).

¹H NMR (400 MHz, CD₃OD) 8.27 (s, 1H), 8.00 (s, 1H), 7.53 (s, 1H), 7.31 (s, 1H), 7.25-7.27 (m, 1H), 7.01-7.11 (m, 2H), 6.84-6.88 (m, 1H), 6.10 (s, 2H), 2.18 (s, 3H).

Compound I-155

A solution of D4, (from Example 7: General Procedure F, where $R^c$=2-oxazolyl, and $(J^B)$n=2-fluoro) (1 equiv) and ethyl 2-cyano-3-ethoxyacrylate was stirred in 1,8-Diazabicyclo[5.4.0]undec-7-ene (3 equiv) and ethanol at 100° C. for 14 hr. The reaction mixture was concentrated in vacuo and purified by silica gel chromatography (0 to 100% ethyl acetate/hexanes) to afford desired compound I-155 as a solid (8.4%).

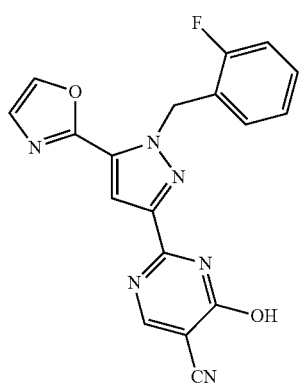 [SMILES: N#Cc1cnc(-c2cc(-c3ncco3)n(Cc3ccccc3F)n2)nc1O]

¹H NMR (400 MHz, DMSO-d6) 8.66 (br. s, 1H), 8.35 (s, 1H), 7.64 (s, 1H), 7.50 (s, 1H), 7.33-7.34 (m, 1H), 7.21 (t, 1H), 7.12 (t, 1H), 7.03-7.04 (m, 1H), 6.06 (s, 2H).

Compound I-186

A solution of Compound I-149 (1 equiv) and benzoyl chloride (2.5 equiv) was stirred in a 2:1 mixture of dichloromethane to pyridine. The reaction was quenched with brine and extracted with dichloromethane. The crude reaction mixture was triturated with ethyl ether to afford desired compound as a solid (38.1%).

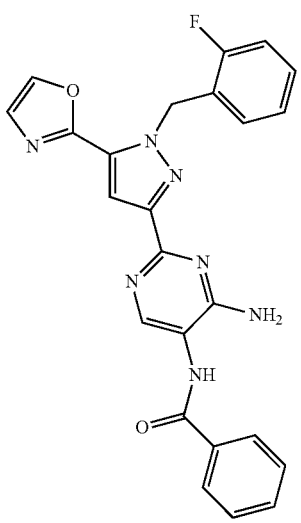 [SMILES: Nc1nc(-c2cc(-c3ncco3)n(Cc3ccccc3F)n2)ncc1NC(=O)c1ccccc1]

¹H NMR (400 MHz, CD₃OD) 8.37 (s, 1H), 8.01-8.05 (m, 3H), 7.60-7.64 (m, 2H), 7.52-7.56 (m, 2H), 7.34 (s, 1H), 7.27-7.30 (m, 1H), 7.04-7.13 (m, 2H) 6.91-6.95 (m, 1H), 6.14 (s, 2H).
Compound I-190

Compound I-190 was synthesized as a solid (23.1%) via the condensation of Compound I-107 (1 equiv) and thiazole-4-carbonyl chloride (2.5 equiv) in a 2:1 solution of dichloromethane and pyridine. The reaction was quenched with water to afford a grey solid which was then triturated with dichloromethane and ethyl acetate to afford the desired compound I-190 as a solid.

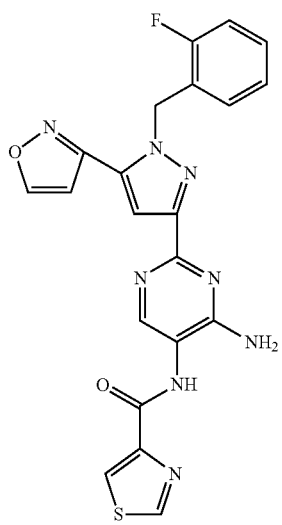 [SMILES: Nc1nc(-c2cc(-c3ccon3)n(Cc3ccccc3F)n2)ncc1NC(=O)c1cscn1]

¹H NMR (400 MHz, DMSO-d6) 9.89 (s, 1H), 9.24 (d, 1H), 9.07 (d, 1H), 8.47 (d, 1H), 8.23 (s, 1H), 7.53 (s, 1H), 7.30-7.32 (m, 1H), 7.19-7.24 (m, 1H), 7.09 (t, 1H), 6.95 (br. s, 2H), 6.82-6.86 (m, 1H), 5.89 (s, 2H).
Compound I-191

Compound I-191 was synthesized as a solid (52.6%) via the condensation of Compound I-149 (1 equiv) and pivaloyl chloride (2.5 equiv) in a 2:1 solution of dichloromethane and pyridine. The reaction was quenched with water and extracted with ethyl acetate and concentrated in vacuo. The desired product was obtained by crystallizing the crude mixture using dichloromethane/ethyl ether as co-solvents.

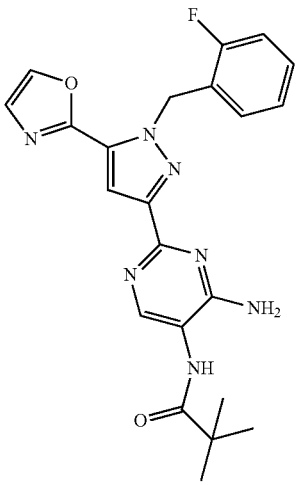 [SMILES: CC(C)(C)C(=O)Nc1cnc(-c2cc(-c3ncco3)n(Cc3ccccc3F)n2)nc1N]

¹H NMR (400 MHz, CD₃OD) 8.10 (s, 1H), 8.00 (s, 1H), 7.54 (s, 1H), 7.30 (s, 1H), 7.24-7.28 (m, 1H), 7.02-7.11 (m, 2H), 6.85-6.89 (m, 1H), 6.10 (s, 2H), 1.33 (s, 9H).
Compound I-197

A solution of D4, (from Example 7: General Procedure F, where $R^c$=2-oxazolyl, and $(J^B)$n=2-fluoro) (1 equiv) and ethyl 3-(dimethylamino)-2-fluoroacrylate (3 equiv) was stirred neat at 90° C. for 14 hr. Purification was achieved by silica gel chromatography (0 to 100% ethyl acetate in hexanes) to afford desired compound I-197 as a solid (5.85%).

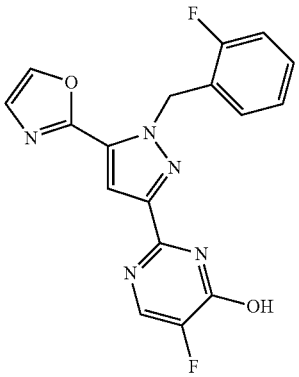 [SMILES: Oc1nc(-c2cc(-c3ncco3)n(Cc3ccccc3F)n2)ncc1F]

¹H NMR (400 MHz, CD₃OD) 8.03 (t, 2H), 7.52 (s, 1H), 7.34 (s, 1H), 7.27-7.31 (m, 1H), 7.05-7.12 (m, 2H), 6.96 (dt, 1H), 6.13 (s, 2H).
Compound I-214

Compound I-214 was synthesized as a solid (25%) via the condensation of Compound I-107 (1 equiv) and 3-(trifluoromethoxy)benzoyl chloride (5 equiv) with a catalytic amount of dimethylamino pyridine in a 2:1 solution of dichloromethane and pyridine. The reaction mixture was precipitated with the addition of ethyl ether followed by cooling at −20° C. The desired compound was vacuum filtered.

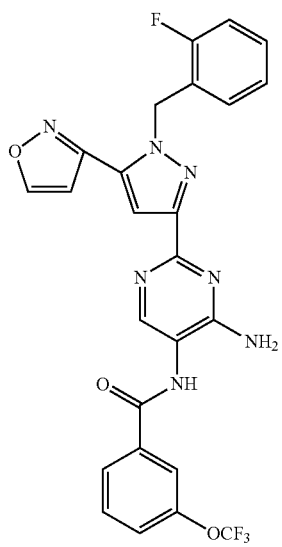 [SMILES: Nc1nc(-c2cc(-c3ccon3)n(Cc3ccccc3F)n2)ncc1NC(=O)c1cccc(OC(F)(F)F)c1]

¹H NMR (400 MHz, CD₃OD) 8.76 (d, 1H), 8.30 (s, 1H), 8.03 (d, 1H), 7.94 (s, 1H), 7.65 (t, 1H), 7.54 (td, 1H), 7.46 (s, 1H), 7.24-7.30 (m, 1H), 7.02-7.12 (m, 2H), 6.88 (d, 1H), 6.85 (dd, 1H), 5.97 (s, 2H).

Compound I-215

Compound I-215 was synthesized as a solid (69.4%) via the condensation of Compound I-107 (1 equiv) and 3-(trifluoromethyl)benzoyl chloride with a catalytic amount of dimethylaminopyridine in a 2:1 mixture of dichloromethane and pyridine. Purification was carried out by triturating the crude reaction mixture with ethyl ether following a brine and ethyl acetate work up.

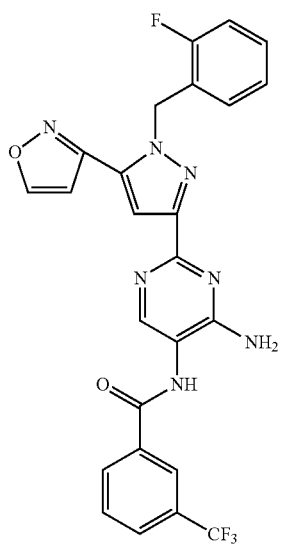 [SMILES: Nc1nc(-c2cc(-c3ccon3)n(Cc3ccccc3F)n2)ncc1NC(=O)c1cccc(C(F)(F)F)c1]

¹H NMR (400 MHz, CD₃OD) 8.76 (d, 1H), 8.36 (s, 1H), 8.29 (s, 1H), 8.28 (d, 1H), 7.92 (d, 1H), 7.45 (t, 2H), 7.46 (s, 1H), 7.25-7.30 (m, 1H), 7.02-7.12 (m, 2H), 6.88 (d, 1H), 6.84-6.86 (m, 1H), 5.97 (s, 2H).

Compound I-220

Compound I-220 was synthesized as a solid (39.7%) via the condensation of Compound I-107 (1 equiv) and 2,6-dimethylbenzoyl chloride (1.5 equiv) with a catalytic amount of dimethylaminopyridine in a 2:1 solution of dichloromethane and pyridine. Purification was carried out by triturating the reaction mixture with water and ethyl ether.

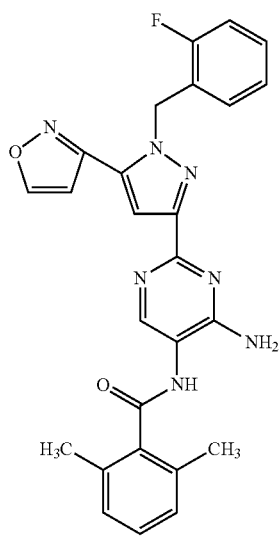 [SMILES: Cc1cccc(C)c1C(=O)Nc1cnc(-c2cc(-c3ccon3)n(Cc3ccccc3F)n2)nc1N]

¹H NMR (400 MHz, CD₃OD) 8.77 (d, 1H), 8.72 (s, 1H), 7.47 (s, 1H), 7.23-7.29 (m, 2H), 7.03-7.14 (m, 4H), 6.86-6.89 (m, 2H), 5.97 (s, 2H), 2.42 (s, 6H).

Compound I-235

A solution of Compound I-107 (1 equiv), bicyclo[2.2.1]hept-5-ene-2-carboxylic acid (2 equiv), N,N'-Dicyclohexylcarbodiimide (2 equiv), triethylamine (5 equiv) and a catalytic amount of dimethylaminopyridine in acetonitrile was heated to 75° C. for 14 hr. Purification was achieved by aqueous work-up followed by silica gel chromatography (0-100% 7:1 acetonitrile:methanol in dichloromethane) (36.3%). Compound I-235 was afforded as endo and exo mixture, most likely dictated by the original ratio of isomers found in the norbornene starting material.

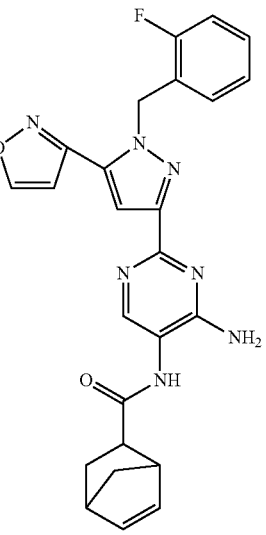

¹H NMR (400 MHz, CDCl₃) 8.42 (d, 1H), 8.29 (s, 0.5H), 8.16 (s, 0.5H), 7.80 (br. s, 0.5H), 7.50 (s, 0.5H), 7.34 (d, 1H), 7.15 (q, 1H), 6.90-7.00 (m, 2H), 6.73 (q, 1H), 6.57 (t, 1H), 6.31 (q, 0.5H), 6.21 (q, 0.25H), 6.15 (q, 0.5H), 6.05 (br. s, 1H), 5.98-6.00 (m, 0.5H), 5.94 (s, 2H), 5.65 (s, 1H), 5.48 (s, 1H), 3.24 (s, 1H), 3.06-3.10 (m, 0.5H), 2.94-3.01 (m, 2H), 2.20-2.23 (m, 0.5H), 1.89-2.01 (m, 2H), 1.67-1.72 (m, 1H), 1.42-1.49 (m, 2H), 1.28-1.37 (m, 3H), 1.08-1.17 (m, 1H).

Compound I-222

Compound I-222 was synthesized as a solid (37.7%) via the coupling of Compound I-107 (1 equiv), O-(7-Azabenzotriazol-1-yl)-N,N,N',N'-tetramethyluronium hexafluorophosphate (2 equiv), 2-(dimethylamino)benzoic acid (2 equiv) and Hunig's base (2 equiv) with a catalytic amount of dimethylaminopyridine in acetonitrile. Purification was achieved by precipitation from a 1:1 solution of ethyl ether and water.

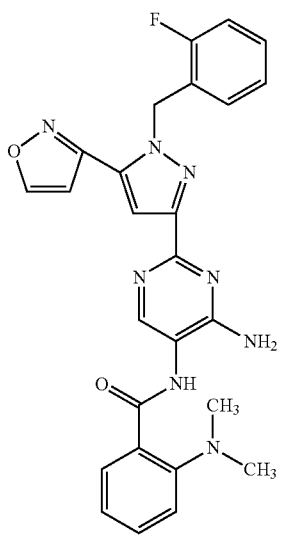 [SMILES: CN(C)c1ccccc1C(=O)Nc1cnc(-c2cc(-c3ccon3)n(Cc3ccccc3F)n2)nc1N]

$^1$H NMR (400 MHz, CD$_3$OD) 8.76 (d, 1H), 8.52 (s, 1H), 7.96 (dd, 1H), 7.52 (dt, 1H), 7.45 (s, 1H), 7.41 (d, 1H), 7.21-7.28 (m, 2H), 7.02-7.12 (m, 2H), 6.84-6.88 (m, 2H), 5.97 (s, 2H), 2.84 (s, 6H).

Compound I-271

A solution of D4, (from Example 7: General Procedure F, where R$^c$=2-oxazolyl, and (J$^B$)n=2-fluoro) (1 equiv) and ethyl 3-(dimethylamino)-2-(phenylsulfonyl)acrylate (1.2 equiv) and hunig's base (2 equiv) was stirred in ethanol at 100° C. for 14 hr. The reaction mixture was concentrated and purified by silica gel chromatography (0 to 100% ethyl acetate in hexanes) to afford desired compound I-271 as a solid (48.1%).

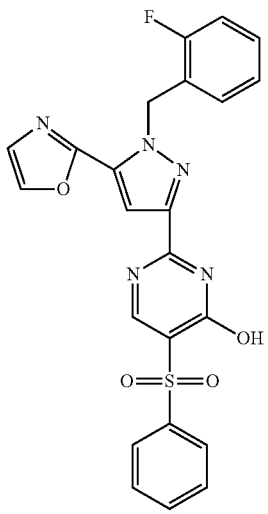 [SMILES: O=S(=O)(c1ccccc1)c1cnc(-c2cc(-c3ncco3)n(Cc3ccccc3F)n2)nc1O]

$^1$H NMR (400 MHz, CD$_3$OD) 8.72 (s, 1H), 8.04 (dd, 2H), 7.98 (d, 1H), 7.59 (tt, 1H), 7.50 (s, 1H), 7.48 (t, 2H), 7.26 (s, 1H), 7.21-7.25 (m, 1H), 6.99-7.07 (m, 2H), 6.85 (dt, 1H), 6.07 (s, 2H).

Compound I-272

To a solution of 1-(trifluoromethyl)cyclopropanecarboxylic acid (10 equiv) in dichloromethane was added oxalyl chloride (9 equiv) and catalytic N,N-dimethylformamide. Once gas evolution ceased, this crude reaction mixture was added portion-wise to a suspension of Compound I-149 (1 equiv) in dichloromethane/pyridine (1:1) until complete consumption of starting material was observed by LS/MS. Purification via silica gel chromatography (0-10% methanol in dichloromethane) following an aqueous ammonium chloride and dichloromethane workup provided the desired compound I-272 as a white solid (20.1%).

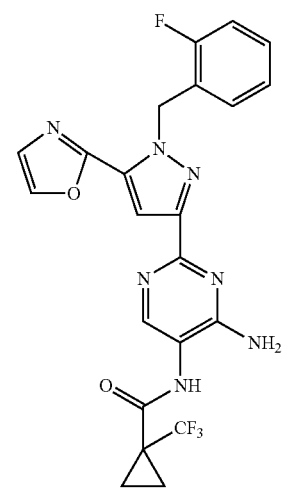 [SMILES: Nc1nc(-c2cc(-c3ncco3)n(Cc3ccccc3F)n2)ncc1NC(=O)C1(C(F)(F)F)CC1]

$^1$H NMR (400 MHz, CD$_3$OD) 8.09-8.12 (m, 1H), 7.98-7.99 (m, 1H), 7.52 (s, 1H), 7.30 (d, 1H), 7.23-7.29 (m, 1H), 7.00-7.09 (m, 2H), 6.85 (dt, 1H), 6.08 (s, 2H), 1.52-1.53 (m, 2H), 1.38 (q, 2H).

Compound I-275

To a solution of 1-methylcyclopropanecarboxylic acid (10 equiv) in dichloromethane was added oxalyl chloride (9 equiv) and catalytic N,N-dimethylformamide. Once gas evolution ceased, this crude reaction mixture was added portion-wise to a suspension of Compound I-149 (1 equiv) in dichloromethane/pyridine (1:1) until complete consumption of starting material was observed by LS/MS. Purification via silica gel chromatography (0-10% methanol in dichloromethane) following an aqueous ammonium chloride and dichloromethane workup provided the desired compound I-275 as a white solid (20.2%).

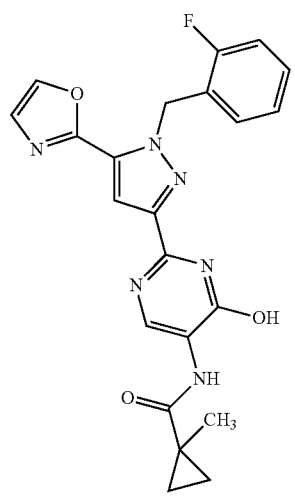 [SMILES: CC1(C(=O)Nc2cnc(-c3cc(-c4ncco4)n(Cc4ccccc4F)n3)nc2O)CC1]

¹H NMR (400 MHz, CDCl₃) 8.21 (s, 1H), 7.66 (s, 1H), 7.56 (s, 1H), 7.40 (br. s, 1H), 7.18 (s, 1H), 7.13-7.16 (m, 1H), 6.97-7.02 (m, 1H), 6.92-6.97 (m, 1H), 6.73-6.76 (m, 1H), 6.11 (s, 2H), 5.43 (s, 2H), 1.50 (s, 3H), 1.33 (q, 2H), 0.74 (q, 2H).

Compound I-276

To a solution of 2,2-difluoro-1-methylcyclopropanecarboxylic acid (10 equiv) in dichloromethane was added oxalyl chloride (9 equiv) and catalytic N,N-dimethylformamide. Once gas evolution ceased, this crude reaction mixture was added portion-wise to a suspension of Compound I-149 (1 equiv) in dichloromethane/pyridine (1:1) until complete consumption of starting material was observed by LS/MS. Purification via silica gel chromatography (0-10% methanol in dichloromethane) following an aqueous ammonium chloride and dichloromethane workup provided the desired compound I-276 as a white solid (39.3%).

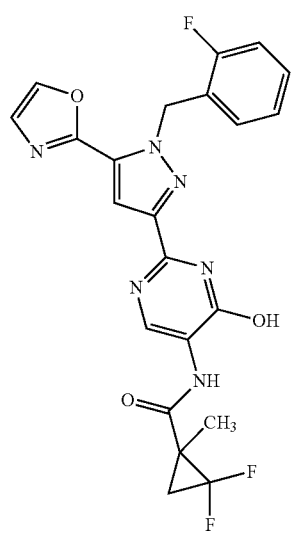 [SMILES: CC1(C(=O)Nc2cnc(-c3cc(-c4ncco4)n(Cc4ccccc4F)n3)nc2O)CC1(F)F]

¹H NMR (400 MHz, CDCl₃) 8.23 (s, 1H), 7.66 (s, 1H), 7.46 (s, 1H), 7.26 (br. s, 1H), 7.19 (s, 1H), 7.13-7.17 (m, 1H), 6.99 (dt, 1H), 6.93 (dt, 1H), 6.75 (dt, 1H), 6.11 (s, 2H), 5.30 (s, 2H), 2.27-2.34 (m, 1H), 1.61 (s, 3H), 1.37-1.43 (m, 1H).

Compound I-219

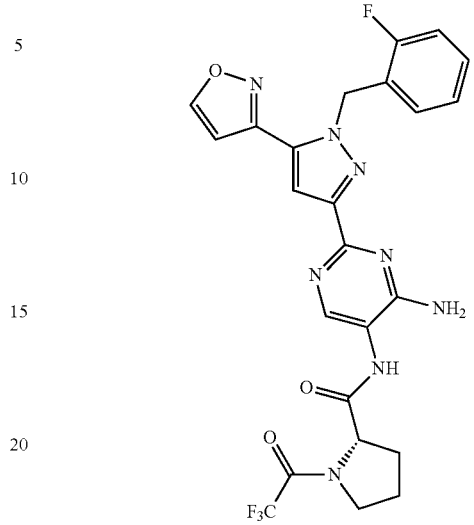

Compound I-219 was synthesized as an off-white solid (95%) via the condensation of Compound I-107 (1 equiv) with (S)-1-(2,2,2-trifluoroacetyl)pyrrolidine-2-carbonyl chloride (2 equiv, added as a 0.1 M solution in dichloromethane) in a solution of dichloromethane/pyridine (1:1). Purification was carried out using SiO₂ chromatography employing a 0-10% MeOH/DCM gradient following a DCM and NH₄Cl-based work-up. ¹H NMR (400 MHz, CDCl₃) (all peaks were broad singlets due to restricted rotation about the amide bond) 8.64-8.50 (bs, 1H), 8.46-8.42 (bs, 1H), 7.35-7.30 (bs, 1H), 7.20-7.12 (bs, 1H), 7.00-6.88 (bs, 2H), 6.62-6.58 (bs, 1H), 5.94-5.86 (bs, 2H), 4.92-4.82 (bs, 1H), 3.88-3.76 (bs, 2H), 2.46-2.02 (bs, 4H) ppm.

Compound I-225

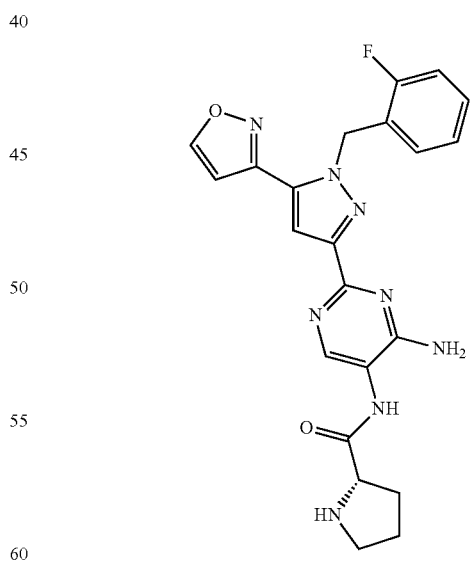

Compound I-225 was synthesized as a light yellow solid (95%) via the hydrolysis of Compound I-219 (1 equiv) with potassium carbonate (1 equiv) in methanol. After 10 minutes, the reaction was complete by LC/MS analysis. Reaction mixture was concentrated to ~⅕ original volume, charged with ammonium chloride, and then extracted with DCM. The organic portion was dried, filtered, and concentrated. The solid material (the desired compound I-225) was not purified further.

$^1$H NMR (400 MHz, DMSO-d6) 13.00 (bs, 1H), 9.08 (d, 1H), 8.71 (s, 1H), 7.51 (s, 1H), 7.35-7.30 (m, 1H), 7.24 (d, 1H), 7.22-7.20 (m, 1H), 7.11 (t, 1H), 7.08-7.03 (m, 1H), 6.85 (t, 1H), 5.88 (s, 2H), 4.15 (dd, 1H), 3.24-3.20 (m, 1H), 3.11-3.07 (m, 1H), 2.29-2.26 (m, 1H), 1.81-1.74 (m, 1H), 1.68-1.63 (m, 2H) ppm.

Compound I-227

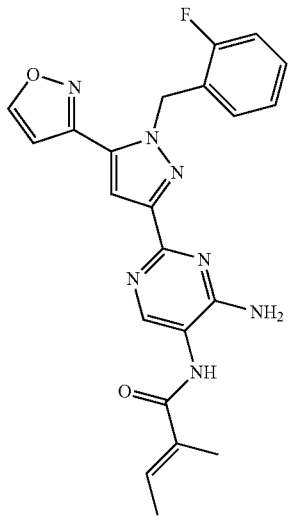 [SMILES: C/C=C(\C)C(=O)Nc1cnc(-c2cc(-c3ccon3)n(Cc3ccccc3F)n2)nc1N]

Compound I-227 was synthesized as a white solid (78%) via the condensation of Compound I-107 (1 equiv) with (E)-2-methylbut-2-enoyl chloride (1.5 equiv) in a solution of dichloromethane/pyridine (2:1). Purification was carried out by direct precipitation of the desired compound in a 1:1 mixture of diethyl ether and water followed by filtration.

$^1$H NMR (400 MHz, CD$_3$OD) 8.76 (d, 1H), 8.21 (s, 1H), 7.44 (s, 1H), 7.30-7.24 (m, 1H), 7.11-7.06 (m, 1H), 7.03 (t, 1H), 6.88 (d, 1H), 6.87-6.83 (m, 1H), 6.68-6.63 (m, 1H), 5.96 (s, 2H), 1.95 (s, 3H), 1.85 (d, 3H) ppm.

Compound I-229

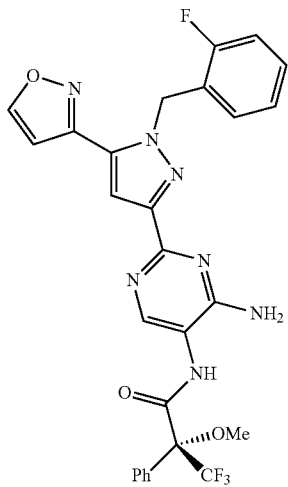 [SMILES: CO[C@@](C(=O)Nc1cnc(-c2cc(-c3ccon3)n(Cc3ccccc3F)n2)nc1N)(c1ccccc1)C(F)(F)F]

Compound I-229 was synthesized as a white solid (77%) via the condensation of Compound I-107 (1 equiv) with (S)-3,3,3-trifluoro-2-methoxy-2-phenylpropanoyl chloride (2 equiv) in a solution of dichloromethane/pyridine (2:1). Purification was carried out using SiO2 chromatography employing a 0-10% MeOH/DCM gradient following a diethyl ether and water-based work-up.

$^1$H NMR (400 MHz, CD$_3$OD) 8.76 (d, 1H), 8.25 (s, 1H), 7.69-7.65 (m, 2H), 7.51-7.48 (m, 3H), 7.44 (s, 1H), 7.29-7.24 (m, 1H), 7.11-7.05 (m, 1H), 7.03 (t, 1H), 6.87 (d, 1H), 6.86-6.82 (m, 1H), 5.96 (s, 2H), 3.61 (s, 3H) ppm.

Compound I-232

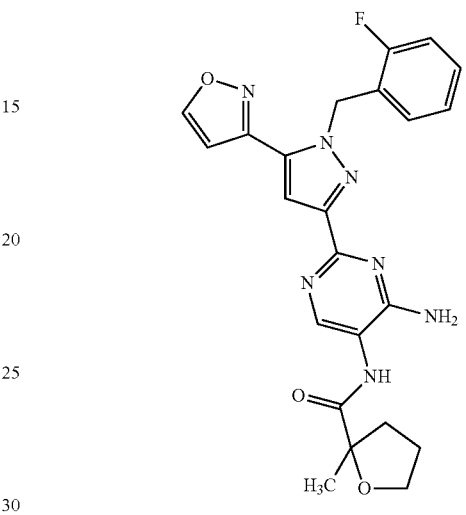

To a solution of 2-methyltetrahydrofuran-2-carbonyl chloride (16 equiv) in dichloromethane was added oxalyl chloride (80 equiv) and catalytic N,N-dimethylformamide. Once gas evolution ceased, this solvent was removed in vacuo. The crude acid chloride was redissolved in dichloromethane and added portion-wise to a suspension of Compound I-107 (1 equiv) in dichloromethane/pyridine (2:1) until the absence of starting material was observed by LC/MS. Purification via SiO2 chromatography employing a 0-10% MeOH/DCM gradient following a DCM and NH4Cl-based work-up provided the desired compound I-232 as an off-white solid (71%).

$^1$H NMR (400 MHz, CD$_3$OD) 8.76 (d, 1H), 8.23 (s, 1H), 7.43 (s, 1H), 7.29-7.24 (m, 1H), 7.11-7.01 (m, 2H), 6.87 (d, 1H), 6.86-6.23 (m, 1H), 5.96 (s, 2H), 4.11-4.00 (m, 2H), 2.43-2.36 (m, 1H) 2.08-1.90 (m, 3H), 1.51 (s, 3H) ppm.

Compound I-238

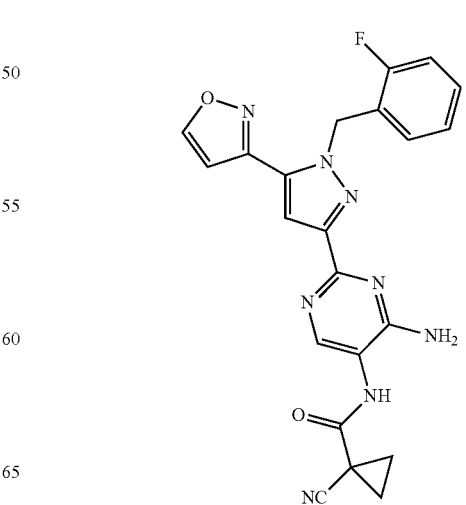

To a solution of 1-cyanocyclopropanecarboxylic acid (10 equiv) in dichloromethane was added oxalyl chloride (9 equiv) and catalytic N,N-dimethylformamide. Once gas evolution ceased, this crude reaction mixture was added portion-wise to a suspension of Compound I-107 (1 equiv) in dichloromethane/pyridine (1:1) until complete consumption of starting material was observed by LS/MS. Purification via washing residual solid with diethyl ether following an aqueous ammonium chloride and dichloromethane workup (and subsequent concentration of organics) provided the desired compound as a yellow solid (27%).

¹H NMR (400 MHz, DMSO-d6) 9.41 (s, 1H), 9.09 (d, 1H), 8.04 (s, 1H), 7.53 (s, 1H), 7.41-7.30 (m, 1H), 7.24 (d, 1H), 7.24-7.20 (m, 1H), 7.11 (t, 1H), 7.03 (bs, 1H), 6.86 (t, 1H), 5.90 (s, 2H), 1.72-1.64 (m, 4H) ppm.

Compound I-239

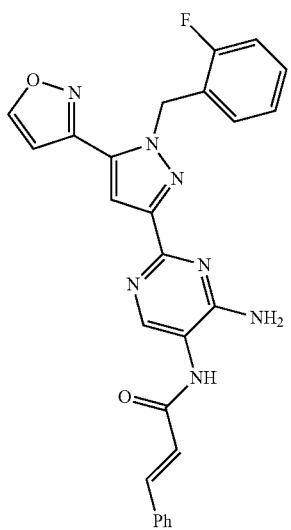 [SMILES: Nc1nc(-c2cc(-c3ccon3)n(Cc3ccccc3F)n2)ncc1NC(=O)/C=C/c1ccccc1]

Compound I-239 was synthesized as a white solid (56%) via the condensation of Compound I-107 (1 equiv) with cinnamoyl chloride (1.5 equiv) in a solution of dichloromethane/pyridine (2:1). Purification was carried out by direct precipitation of the desired compound I-239 in a 1:1 mixture of diethyl ether and water followed by filtration.

¹H NMR (400 MHz, DMSO-d6) 9.51 (bs, 1H), 9.08 (d, 1H), 8.58-8.55 (m, 1H), 8.54 (s, 1H), 7.63-7.61 (m, 2H), 7.52 (s, 1H), 7.46-7.39 (m, 3H), 7.34-7.29 (m, 1H), 7.23 (d, 1H), 7.21-7.19 (m, 1H), 7.10 (t, 2H), 6.87-6.81 (m, 2H), 5.89 (s, 2H) ppm.

Compound I-252

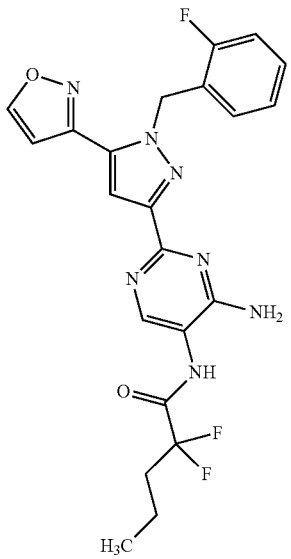 [SMILES: CCCC(F)(F)C(=O)Nc1cnc(-c2cc(-c3ccon3)n(Cc3ccccc3F)n2)nc1N]

To a solution of 2,2-difluoropentanoic acid (10 equiv) in dichloromethane was added oxalyl chloride (9 equiv) and catalytic N,N-dimethylformamide. Once gas evolution ceased, this crude reaction mixture was added portion-wise to a suspension of Compound I-107 (1 equiv) in dichloromethane/pyridine (1:1) until complete consumption of starting material was observed by LS/MS. Purification via washing residual solid with diethyl ether following an aqueous ammonium chloride and dichloromethane workup (and subsequent concentration of organics) provided the desired compound I-252 as a tan solid (26%).

¹H NMR (400 MHz, CD₃OD) 8.76 (d, 1H), 8.24 (s, 1H), 7.44 (s, 1H), 7.29-7.24 (m, 1H), 7.12-7.06 (m, 1H), 7.03 (t, 1H), 6.87 (d, 1H), 6.84 (t, 1H), 5.96 (s, 2H), 2.24-2.11 (m, 2H), 1.65-1.55 (m, 2H), 1.04 (t, 3H) ppm.

Compound I-266

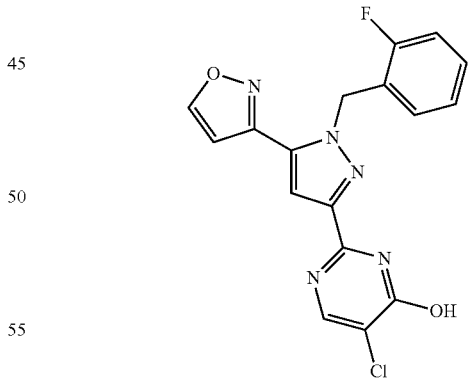

Compound I-266 was synthesized as an off-white solid (44%) via the treatment of Compound I-160 (1 equiv) with N-chlorosuccinimide (1 equiv) in DMF at 70° C. Purification was carried out using SiO₂ chromatography employing a 0-100% ethyl acetate/hexane gradient following an ethyl acetate and water-based work-up.

¹H NMR (400 MHz, CDCl₃) 10.32 (bs, 1H), 8.52 (d, 1H), 8.11 (s, 1H), 7.27 (s, 1H), 7.10-7.04 (m, 4H), 6.60 (d, 1H), 5.89 (s, 2H) ppm.

Compound I-268

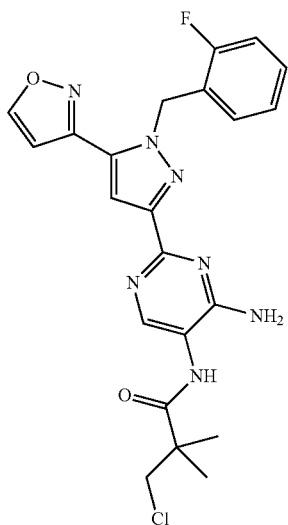 [SMILES: CC(C)(CCl)C(=O)Nc1cnc(-c2cc(-c3ccon3)n(Cc3ccccc3F)n2)nc1N]

Compound I-268 was synthesized as a white solid (45%) via the condensation of Compound I-107 (1 equiv) with 3-chloro-2,2-dimethylproponyl chloride (1.5 equiv) in a solution of dichloromethane/pyridine (2:1). Purification was carried out by direct precipitation of the desired compound in a 1:1 mixture of diethyl ether and water followed by filtration.

$^1$H NMR (400 MHz, DMSO-d6) 9.00 (d, 1H), 9.04 (bs, 1H), 8.06 (s, 1H), 7.51 (s, 1H), 7.32-7.27 (m, 1H), 7.22 (d, 1H), 7.22-7.17 (m, 1H), 7.10-7.06 (m, 1H), 5.87 (s, 2H), 3.82 (s, 2H), 1.29 (s 6H) ppm.

Compound I-141

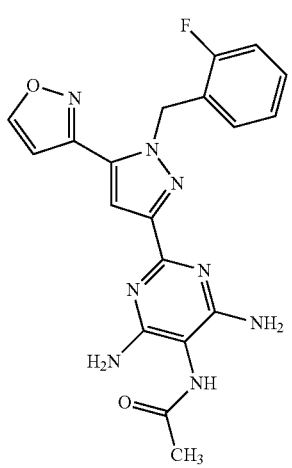 [SMILES: CC(=O)Nc1c(N)nc(-c2cc(-c3ccon3)n(Cc3ccccc3F)n2)nc1N]

Compound I-141 was synthesized as a brown solid (34%, two-steps) in an analogous fashion to Compound I-94.

$^1$H NMR (400 MHz, DMSO-d6) 9.09 (d, 1H), 8.82 (s, 1H), 7.34 (s, 1H), 7.33-7.29 (m, 1H), 7.24-7.20 (m, 1H), 7.21 (d, 1H), 7.11-7.07 (m, 1H), 6.11 (s, 4H), 5.92 (s, 2H), 2.02 (s, 3H) ppm.

Compound I-152

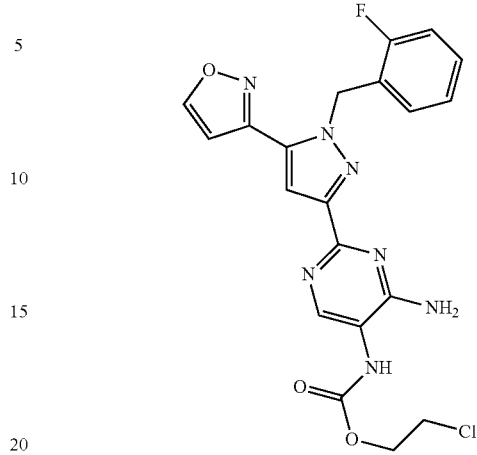

Compound I-152 was synthesized as an off-white solid (95%) via the condensation of Compound I-107 (1 equiv) with 2-chloroethyl cabonochloridate (1.1 equiv) in a solution of dichloromethane/pyridine (1:1). Purification was carried out by direct precipitation of the desired compound with diethyl ether following an ethyl acetate and NH$_4$Cl-based work-up (organic was concentrated to near dryness then charged with the diethyl ether).

$^1$H NMR (400 MHz, CD$_3$OD) 8.76-8.75 (m, 1H), 8.37 (bs, 1H), 7.41 (s, 1H), 7.29-7.23 (m, 1H), 7.11-7.01 (m, 2H), 6.87-6.86 (m, 1H), 6.86-6.81 (m, 1H), 5.95 (s, 2H), 4.41 (t, 2H), 3.80 (t, 2H) ppm.

Compound I-153

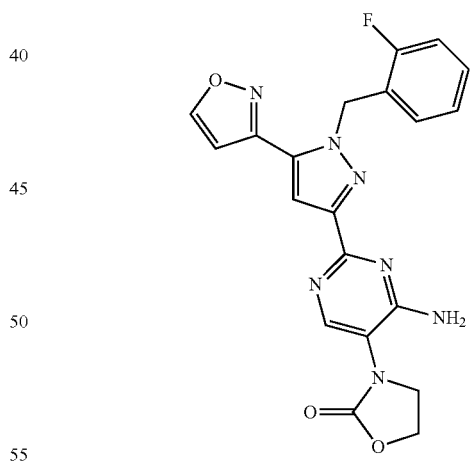

Compound I-153 was synthesized as a white solid (0.9%) via the treatment of Compound I-152 (1 equiv) with sodium hydride (2 equiv, 60% in dispersion oil) in THF. Purification was carried out using SiO$_2$ chromatography employing a 0-10% MeOH/DCM gradient following an EtOAc and NH$_4$Cl-based work-up.

$^1$H NMR (400 MHz, CD$_3$OD) 8.76 (d, 1H), 8.26 (s, 1H), 7.45 (s, 1H), 7.29-7.24 (m, 1H), 7.09 (t, 1H), 7.03 (t, 1H), 6.87 (d, 1H), 6.87-6.83 (m, 1H), 5.96 (s, 2H), 4.58 (t, 2H), 3.95 (t, 2H) ppm.

Compound I-156

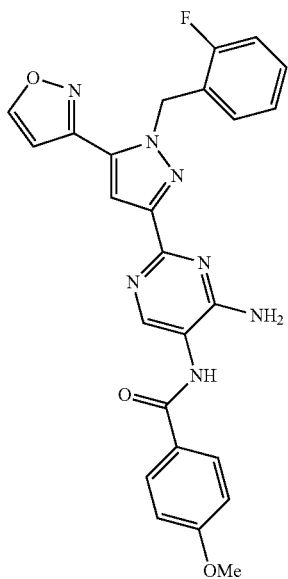 [SMILES: COc1ccc(C(=O)Nc2cnc(-c3cc(-c4ccon4)n(Cc4ccccc4F)n3)nc2N)cc1]

Compound I-156 was synthesized as a white solid (55%) via the condensation of Compound I-107 (1 equiv) with 4-methoxybenzoyl chloride (1.25 equiv) in a solution of dichloromethane/pyridine (2:1). Purification was carried out using SiO$_2$ chromatography employing a 0-10% MeOH/DCM gradient following a DCM/EtOAc and NH$_4$Cl-based work-up.

$^1$H NMR (400 MHz, CD$_3$OD) 8.77-8.75 (m, 1H), 8.29 (s, 1H), 8.00-7.98 (m, 2H), 7.45 (s, 1H), 7.29-7.24 (m, 1H), 7.12-6.96 (m, 4H), 6.89-6.83 (m, 2H), 5.96 (s, 2H), 3.88 (s, 3H) ppm.

Compound I-157

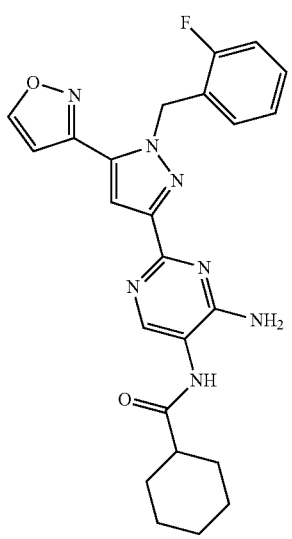 [SMILES: Nc1nc(-c2cc(-c3ccon3)n(Cc3ccccc3F)n2)ncc1NC(=O)C1CCCCC1]

Compound I-157 was synthesized as a white solid (72%) via the condensation of Compound I-107 (1 equiv) with cyclohexanecarbonyl chloride (1.6 equiv) in a solution of dichloromethane/pyridine (2:1). Purification was carried out using SiO$_2$ chromatography employing a 0-10% MeOH/DCM gradient following a DCM/EtOAc and NH$_4$Cl-based work-up.

$^1$H NMR (400 MHz, CD$_3$OD) 8.76 (d, 1H), 8.34 (s, 1H), 7.43 (s, 1H), 7.29-7.24 (m, 1H), 7.11-7.01 (m, 2H), 6.87 (d, 1H), 6.87-6.83 (m, 1H), 5.96 (s, 2H), 2.49-2.41 (m, 1H), 1.97-1.30 (m, 10H) ppm.

Compound I-162

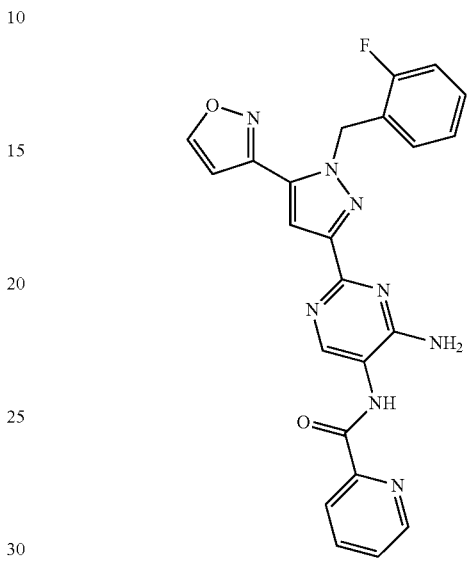

Compound I-162 was synthesized as a grey solid (80%) via the condensation of Compound I-107 (1 equiv) with picolinoyl chloride (2.5 equiv) in a solution of dichloromethane/pyridine (2:1). Purification was carried out by direct precipitation of the desired compound from a mixture of diethyl ether and hexane (20:1) and water followed by filtration.

$^1$H NMR (400 MHz, CD$_3$OD) 8.77 (d, 1H), 8.74-8.72 (m, 1H), 8.43 (s, 1H), 8.22-8.20 (m, 1H), 8.05-8.01 (m, 1H), 7.64-7.61 (m, 1H), 7.46 (s, 1H), 7.28-7.25 (m, 1H), 7.12-7.02 (m, 2H), 6.89 (d, 1H), 6.86-6.83 (m, 1H), 5.97 (s, 2H) ppm.

Compound I-177

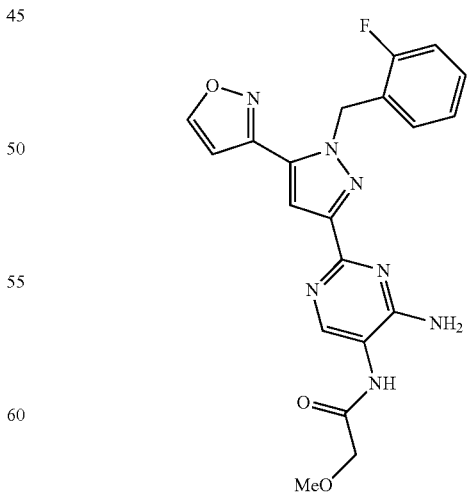

Compound I-177 was synthesized as a tan solid (63%) via the condensation of Compound I-107 (1 equiv) with 2-methoxyacetyl chloride (1.1 equiv) in a solution of dichloromethane/pyridine (2:1). Purification was carried out using SiO₂ chromatography employing a 0-10% MeOH/DCM gradient following a DCM and NH₄Cl-based work-up.

¹H NMR (400 MHz, CD₃OD) 8.76 (d, 1H), 8.22 (s, 1H), 7.44 (s, 1H), 7.29-7.24 (m, 1H), 7.08 (ddd, 1H), 7.03 (ddd, 1H), 6.87 (d, 1H), 6.86-6.82 (m, 1H), 5.96 (s, 2H), 3.51 (s, 3H) ppm.

Compound I-179

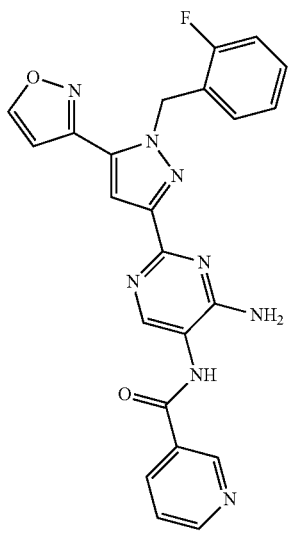 [SMILES: Nc1nc(-c2cc(-c3ccon3)n(Cc3ccccc3F)n2)ncc1NC(=O)c1cccnc1]

Compound I-179 was synthesized as a light tan solid (30%) via the condensation of Compound I-107 (1 equiv) with nicotinoyl chloride (2.0 equiv) in a solution of dichloromethane/pyridine (2:1). Purification was carried out using SiO₂ chromatography employing a 0-15% MeOH/DCM gradient following a DCM and NH₄Cl-based work-up.

¹H NMR (400 MHz, CD₃OD) 8.77 (d, 1H), 8.76-8.73 (m, 2H), 8.32 (s, 1H), 7.98-7.96 (m, 2H), 7.46 (s, 1H), 7.30-7.24 (m, 1H), 7.09 (ddd, 1H), 7.04 (ddd, 1H), 6.88 (d, 1H), 6.88-6.83 (m, 1H), 5.97 (s, 2H) ppm.

Compound I-176

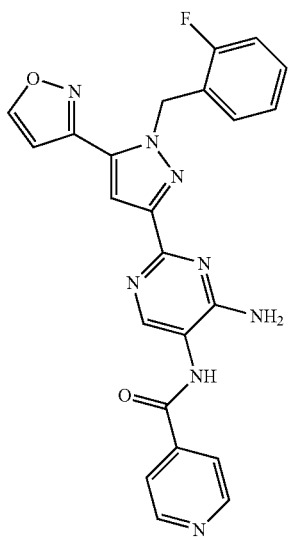 [SMILES: Nc1nc(-c2cc(-c3ccon3)n(Cc3ccccc3F)n2)ncc1NC(=O)c1ccncc1]

Compound I-176 was synthesized as a tan solid (51%) via the condensation of Compound I-107 (1 equiv) with isonicotinoyl chloride (2.0 equiv) in a solution of dichloromethane/pyridine (2:1). Purification was carried out using SiO₂ chromatography employing a 0-15% MeOH/DCM gradient following a DCM and NH₄Cl-based work-up.

¹H NMR (400 MHz, CD₃OD) 8.85 (d, 1H), 8.82-8.79 (m, 2H), 8.47 (s, 1H), 8.02-7.98 (m, 2H), 7.62 (s, 1H), 7.35-7.27 (m, 1H), 7.14-7.06 (m, 2H), 7.05-6.95 (m, 1H), 6.93 (d, 1H), 6.04 (s, 2H) ppm.

Compound I-193

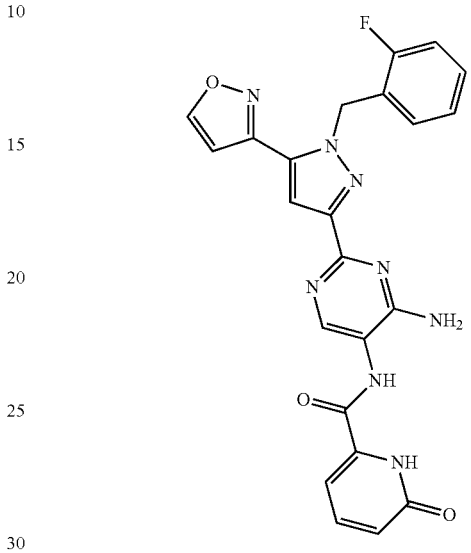

Compound I-193 was synthesized as a yellow solid (33%) via the condensation of Compound I-107 (1 equiv) with 6-hydroxypicolinic acid (3.0 equiv), HATU (2.5 equiv) and Hunig's base (5 equiv) in acetonitrile at 45° C. Purification was carried out using SiO₂ chromatography employing a 0-40% (7:1 acetonitrile/MeOH)/DCM gradient following a DCM and sodium bicarbonate-based work-up.

¹H NMR (400 MHz, CD₃OD) 8.85 (d, 1H), 8.82-8.79 (m, 2H), 8.47 (s, 1H), 8.02-7.98 (m, 2H), 7.62 (s, 1H), 7.35-7.27 (m, 1H), 7.14-7.06 (m, 2H), 7.05-6.95 (m, 1H), 6.93 (d, 1H), 6.04 (s, 2H) ppm. ¹H NMR (400 MHz, CD₃OD) 8.81 (d, 1H), 8.45 (s, 1H), 7.85-7.77 (m, 1H), 7.77-7.40 (bs, 1H), 7.55 (s, 1H), 7.33-7.27 (m, 1H), 7.13-7.05 (m, 2H), 6.98-6.93 (m, 1H), 6.91 (d, 1H), 6.91-6.86 (m, 1H), 6.01 (s, 2H) ppm.

Compound I-211

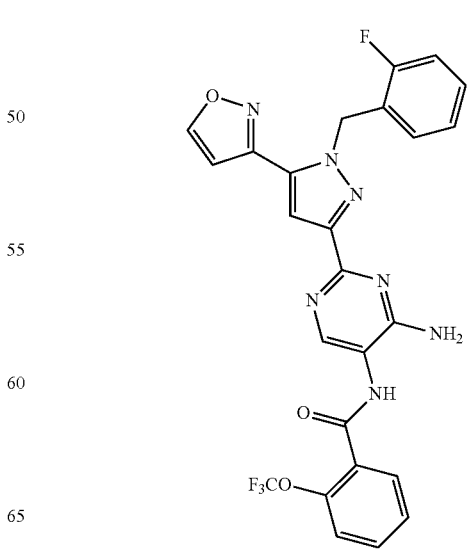

Compound I-211 was synthesized as a white solid (51%) via the condensation of Compound I-107 (1 equiv) with 2(trifluoromethoxy)benzoyl chloride (6.25 equiv) in a solution of dichloromethane/pyridine (2:1). Purification was carried out by direct precipitation of the desired compound in a 1:1 mixture of diethyl ether and water followed by filtration.

$^1$H NMR (400 MHz, CD$_3$OD) 8.77 (d, 1H), 8.45 (s, 1H) 7.86 (dd, 1H), 7.66 (ddd, 1H), 7.55-7.51 (m, 1H), 7.49-7.46 (m, 1H), 7.46 (s, 1H), 7.30-7.24 (m, 1H), 7.09 (ddd, 1H), 7.04 (t, 1H), 6.88 (d, 1H), 6.88-6.85 (m, 1H), 5.97 (s, 2H) ppm.

Compound I-212

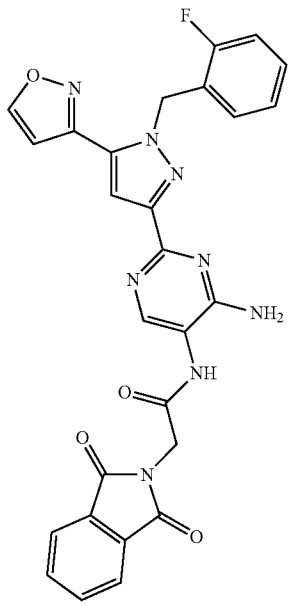 [SMILES: Nc1nc(-c2cc(-c3ccon3)n(Cc3ccccc3F)n2)ncc1NC(=O)CN1C(=O)c2ccccc2C1=O]

Compound I-212 was synthesized as an off-white solid (85%) via the condensation of Compound I-107 (1 equiv) with 2-(1,3-dioxoisoindolin-2-yl)acetyl chloride (1.25 equiv) in a solution of dichloromethane/pyridine (2:1). Purification was carried out using SiO$_2$ chromatography employing a 0-10% MeOH/DCM gradient following a DCM and NH$_4$Cl-based work-up. LRMS Calculated for C$_{27}$H$_{19}$FN$_8$O$_4$ [M+H]+539.15, observed 539.

Compound I-213

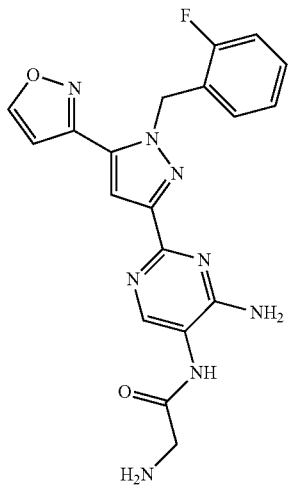 [SMILES: NCC(=O)Nc1cnc(-c2cc(-c3ccon3)n(Cc3ccccc3F)n2)nc1N]

Compound I-213 was synthesized as a white solid (33%) via the treatment of Compound I-211 (1 equiv) with hydrazine hydrate (5.0 equiv) in ethanol at 45° C. Purification was carried out by evaporation of the crude reaction to dryness, followed by washing the residual material with a 9:1 ether/water mixture, and collection of the solid by vacuum filtration.

$^1$H NMR (400 MHz, DMSO-d6) 9.09 (s, 1H), 8.26 (s, 1H), 7.52 (s, 1H), 7.33 (dd, 1H), 7.24 (s, 1H), 7.24-7.20 (m, 1H), 7.11 (t, 1H), 6.91 (bs, 2H), 6.86 (t, 1H), 5.89 (s, 2H), 3.12 (bs, 2H), 3.34 (s, 2H) ppm.

Compound I-161

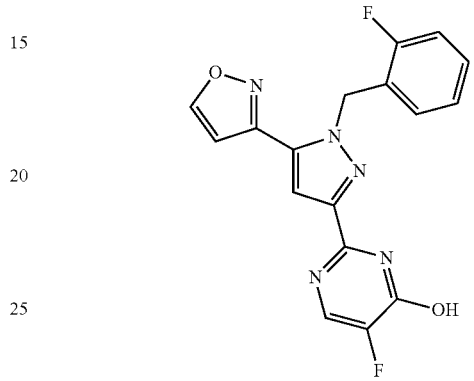

A solution of D4 (from Example 7: General Procedure F) (1 equiv) and ethyl 3-(dimethylamino)-2-fluoroacrylate (3 equiv) was stirred at 85° C. in ethanol for 14 h. The solvent was removed in vacuo and purification by silica gel chromatography (0-50% 7:1 acetonitrile:methanol in dichloromethane) delivered the desired compound as a white solid (47.6%).

$^1$NMR (400 MHz, DMSO-d6) 13.28 (bs, 1H), 9.12 (d, 1H), 8.16 (bs, 1H), 7.65 (s, 1H), 7.37-7.32 (m, 1H), 7.25-7.20 (m, 2H), 7.12 (t, 1H), 7.02-6.96 (m, 1H), 5.92 (s, 2H) ppm.

Compound I-160

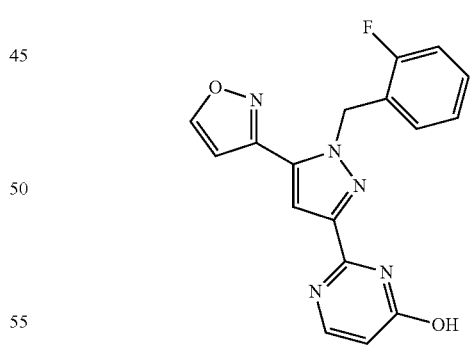

A mixture of D4 (from Example 7: General Procedure F) (1 equiv) and methyl 3-methoxyacrylate (3 equiv) was stirred at 90° C. for 6 h. The solvent was removed in vacuo and purification by silica gel chromatography (0-7% methanol/dichloromethane) delivered the desired compound as a colorless solid (41%).

$^1$H NMR (400 MHz, CDCl$_3$) δ 10.46 (br s, 1H), 8.51 (d, 1H), 7.96 (d, 1H), 7.31 (s, 1H), 7.31-7.24 (m, 1H), 7.07-7.02 (m, 3H), 6.60 (d, 1H), 6.38 (d, 1H), 5.89 (s, 2H).

Compound I-168

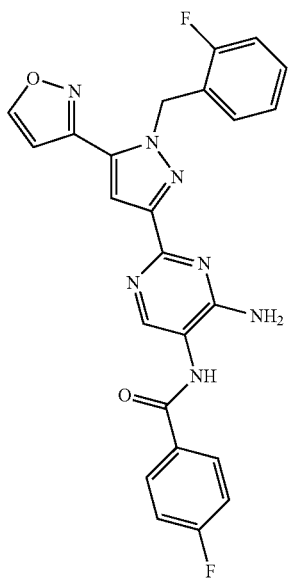 [SMILES: Nc1nc(-c2cc(-c3ccon3)n(Cc3ccccc3F)n2)ncc1NC(=O)c1ccc(F)cc1]

Compound I-168 was synthesized as a faint tan solid (59%) via the acylation of Compound I-107 (1 equiv) with 4-fluorobenzoyl chloride (2 equiv) in a solution of dichloromethane/pyridine (2:1). Purification was carried out by direct precipitation of the desired compound in a 1:1 mixture of diethyl ether and water followed by filtration.

$^1$H NMR (400 MHz, CDCl$_3$) δ 8.45 (s, 1H), 8.33 (s, 1H), 7.95 (dd, 2H), 7.84 (br s, 1H), 7.40 (s, 1H), 7.21-7.16 (m, 3H), 7.01 (t, 1H), 6.95 (t, 1H), 6.78 (t, 1H), 6.59 (s, 1H), 5.99 (s, 2H), 5.49 (br s, 2H).

Compound I-171

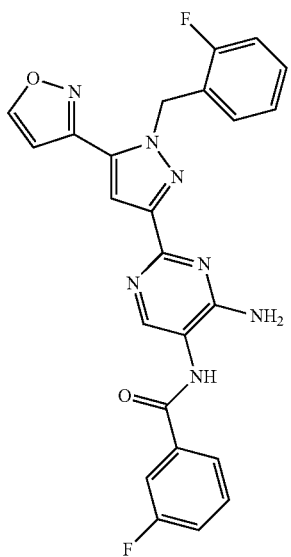 [SMILES: Nc1nc(-c2cc(-c3ccon3)n(Cc3ccccc3F)n2)ncc1NC(=O)c1cccc(F)c1]

Compound I-171 was synthesized as a faint tan solid (75%) via the acylation of Compound I-107 (1 equiv) with 3-fluorobenzoyl chloride (2 equiv) in a solution of dichloromethane/pyridine (2:1). Purification was carried out by direct precipitation of the desired compound in a 1:1 mixture of diethyl ether and water followed by filtration.

$^1$H NMR (400 MHz, CDCl$_3$) δ 8.45 (s, 1H), 8.35 (s, 1H), 7.82 (br s, 1H), 7.70-7.64 (m, 2H), 7.52-7.46 (m, 1H), 7.41 (d, 1H), 7.34-7.15 (m, 2H), 7.01 (t, 1H), 6.95 (t, 1H), 6.78 (t, 1H), 6.59 (s, 1H), 6.00 (s, 2H), 5.50 (br s, 2H).

Compound I-172

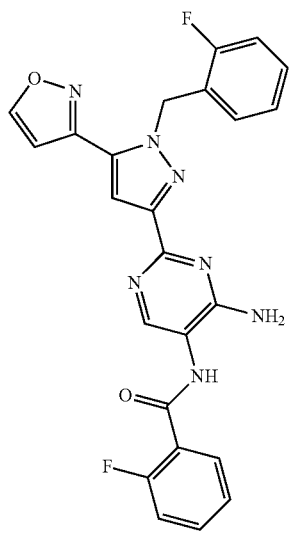

Compound I-172 was synthesized as a faint tan solid (75%) via the acylation of Compound I-107 (1 equiv) with 2-fluorobenzoyl chloride (3 equiv) in a solution of dichloromethane/pyridine (2:1). Purification was carried out by direct precipitation of the desired compound in a 1:1 mixture of diethyl ether and water followed by filtration.

$^1$H NMR (400 MHz, CDCl$_3$) δ 8.44 (s, 1H), 8.42 (s, 1H), 7.26-7.18 (m, 2H), 7.60 (dd, 1H), 7.43 (d, 1H), 7.36 (t, 1H), 7.26-7.16 (m, 2H), 7.02 (t, 1H), 6.96 (t, 1H), 6.78 (t, 1H), 6.59 (s, 1H), 6.03 (s, 2H), 5.45 (s, 2H).

Compound I-181

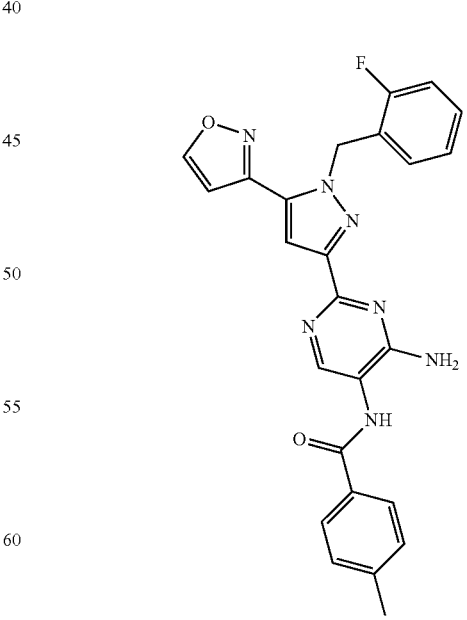

Compound I-181 was synthesized as a faint tan solid (81%) via the acylation of Compound I-107 (1 equiv) with 4-methylbenzoyl chloride (2.6 equiv) in a solution of dichloromethane/pyridine (2:1). Purification was carried out by direct precipitation of the desired compound in a 1:1 mixture of diethyl ether and water followed by filtration.

$^1$H NMR (400 MHz, CDCl$_3$) δ 8.44 (s, 1H), 8.34 (s, 1H), 7.82 (d, 2H), 7.73 (br s, 1H), 7.41 (d, 1H), 7.32 (d, 2H), 7.18 (dd, 1H), 7.02 (t, 1H), 6.95 (t, 1H), 6.78 (t, 1H), 6.59 (s, 1H), 6.02 (s, 2H), 5.54 (br s, 2H), 2.45 (s, 3H).

Compound I-182

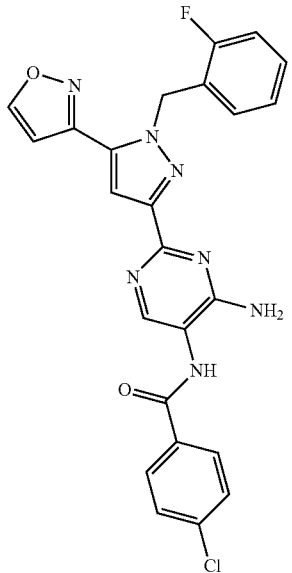

Compound I-182 was synthesized as a faint tan solid (75%) via the acylation of Compound I-107 (1 equiv) with 4-chlorobenzoyl chloride (2.5 equiv) in a solution of dichloromethane/pyridine (2:1). Purification was carried out by direct precipitation of the desired compound in a 1:1 mixture of diethyl ether and water followed by filtration.

$^1$H NMR (400 MHz, CDCl$_3$) δ 8.45 (s, 1H), 8.32 (s, 1H), 7.97 (br s, 1H), 7.86 (d, 2H), 7.46 (d, 2H), 7.39 (d, 1H), 7.17 (dd, 1H), 7.00 (t, 1H), 6.94 (t, 1H), 6.78 (t, 1H), 6.59 (s, 1H), 5.97 (s, 2H), 5.50 (br s, 2H).

Compound I-183

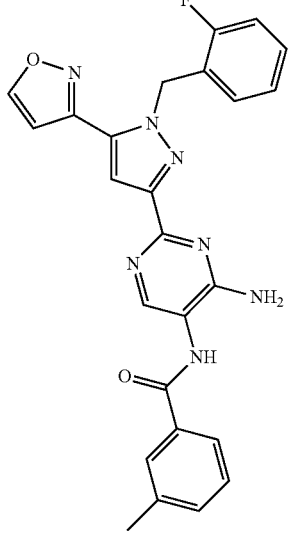

Compound I-183 was synthesized as a faint tan solid (82%) via the acylation of Compound I-107 (1 equiv) with 3-methylbenzoyl chloride (2.2 equiv) in a solution of dichloromethane/pyridine (2:1). Purification was carried out by quenching with a small amount of methanol, diluting with water, extracting with DCM (3×), drying the combined organic layers with magnesium sulfate, and concentrating under a stream of nitrogen. The resulting solid was triturated with diethyl ether and filtered.

$^1$H NMR (400 MHz, CDCl$_3$) δ 8.44 (s, 1H), 8.35 (s, 1H), 7.73 (d, 2H), 7.71 (br s, 1H), 7.44-7.40 (m, 3H), 7.18 (dd, 1H), 7.02 (t, 1H), 6.96 (t, 1H), 6.78 (t, 1H), 6.59 (s, 1H), 6.02 (s, 2H), 5.51 (br s, 2H), 2.45 (s, 3H).

Compound I-187

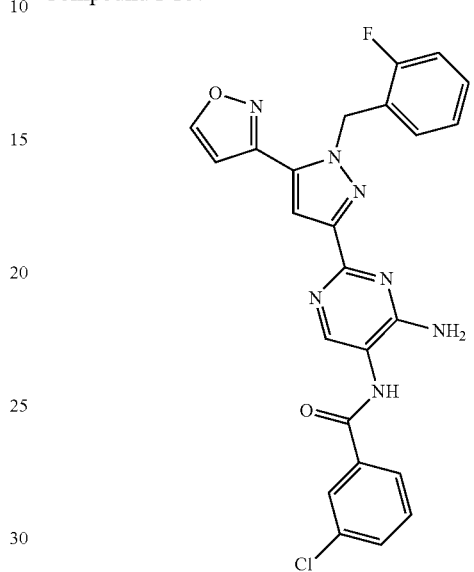

Compound I-187 was synthesized as a faint tan solid (82%) via the acylation of Compound I-107 (1 equiv) with 3-chlorobenzoyl chloride (2.5 equiv) in a solution of dichloromethane/pyridine (2:1). Purification was carried out by quenching with a small amount of methanol, diluting with water, extracting with DCM (3×), drying the combined organic layers with magnesium sulfate, and concentrating under a stream of nitrogen. The resulting solid was triturated with diethyl ether and filtered.

$^1$H NMR (400 MHz, CD$_3$OD) δ 8.76 (d, 1H), 8.30 (s, 1H), 8.06-8.04 (m, 1H), 7.95 (d, 1H), 7.64-7.60 (m, 1H), 7.53 (t, 1H), 7.45 (s, 1H), 7.27 (dd, 1H), 7.09 (t, 1H), 7.04 (t, 1H), 6.88 (d, 1H), 6.85 (t, 1H), 5.97 (s, 2H).

Compound I-184

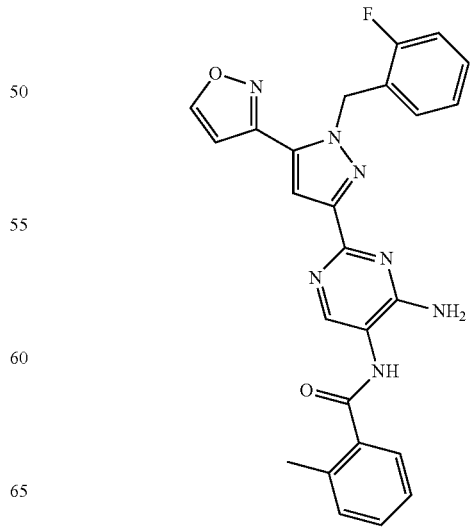

Compound I-184 was synthesized as a faint tan solid (66%) via the acylation of Compound I-107 (1 equiv) with 2-methylbenzoyl chloride (2.5 equiv) in a solution of dichloromethane/pyridine (2:1). Purification was carried out by direct precipitation of the desired compound in a 1:1 mixture of diethyl ether and water followed by filtration.

¹H NMR (400 MHz, CDCl₃) δ 8.44 (s, 1H), 8.34 (s, 1H), 7.58 (d, 1H), 7.44-7.40 (m, 3H), 7.34-7.26 (m, 2H), 7.18 (dd, 1H), 7.02 (t, 1H), 6.96 (t, 1H), 6.77 (t, 1H), 6.59 (s, 1H), 6.02 (s, 2H), 5.57 (br s, 2H), 2.56 (s, 3H).

Compound I-185

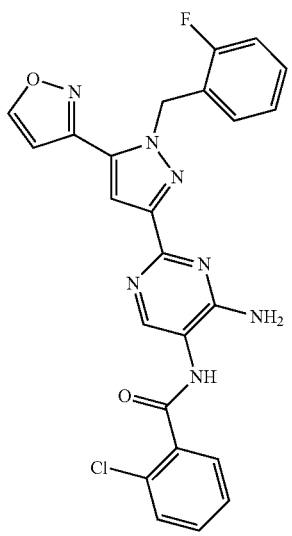

Compound I-185 was synthesized as a faint tan solid (79%) via the acylation of Compound I-107 (1 equiv) with 2-chlorobenzoyl chloride (2.7 equiv) in a solution of dichloromethane/pyridine (2:1). Purification was carried out by direct precipitation of the desired compound in a 1:1 mixture of diethyl ether and water followed by filtration.

¹H NMR (400 MHz, CDCl₃) δ 8.45 (s, 1H), 8.41 (s, 1H), 7.86 (d, 1H), 7.76 (br s, 1H), 7.50 (td, 2H), 7.48-7.40 (m 2H), 7.21-7.16 (m, 1H), 7.02 (t, 1H), 6.96 (t, 1H), 6.77 (t, 1H), 6.60 (s, 1H), 6.03 (s, 2H), 5.51 (br s, 2H).

Intermediate 8

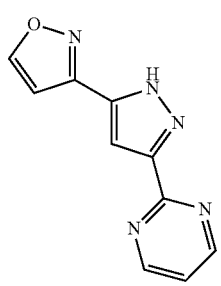 [SMILES: c1cnc(-c2cc(-c3ccon3)[nH]n2)nc1]

This compound was synthesized by the following procedure:

To a −78° C. cooled solution of 1-(isoxazol-3-yl)ethanone (2.01 g, 18.09 mmol) in THF (50 mL) was added lithium hexamethyldisilazide (15.5 mL, 15.50 mmol) (1M solution in toluene) slowly. Reaction mixture became yellow-orange. Reaction mixture was stirred at this temperature for 10 min. Reaction mixture was warmed to 0° C. for 30 min. Methyl pyrimidine-2-carboxylate (2.499 g, 18.09 mmol) in THF (25 mL) was added slowly and stirring continued at this temperature for 15 min. Reaction mixture stirred at room temperature for 1.83 h. EtOH (60 mL), AcOH (6 mL), and hydrazine hydrate (1.014 mL, 20.81 mmol) were added and the reaction mixture was heated at 65° C. for 2.25 h. Concentrated in vacuo. The reaction mixture was diluted with water and ether, and then filtered and washed with water and ether. The ether contained some of the desired product. NMR is consistent with product. Product was a faint tan solid (39%). ¹H NMR (400 MHz, CD₃OD) δ 8.85 (d, 2H), 8.73 (s, 1H), 7.46 (s, 1H), 7.40 (t, 1H), 6.92 (d, 1H).

Compound I-223

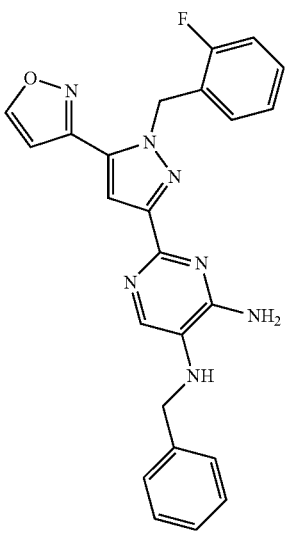 [SMILES: Nc1nc(-c2cc(-c3ccon3)n(Cc3ccccc3F)n2)ncc1NCc1ccccc1]

To a suspension of 2-(1-(2-fluorobenzyl)-5-(isoxazol-3-yl)-1H-pyrazol-3-yl)pyrimidine-4,5-diamine hydrochloride (26.9 mg, 0.069 mmol) in DCM (3 mL) was added benzaldehyde (7.01 μl, 0.069 mmol), triethylamine (0.039 mL, 0.277 mmol), powdered molecular sieves, and sodium triacetoxyborohydride (58.8 mg, 0.277 mmol). The reaction mixture was stirred at room temperature for 24 h. The reaction mixture appeared to be stopped at an imine or cyclic derivative. Additional reducing agent was added and the reaction mixture was refluxed for 3.5 h, filtered, concentrated and subjected to chromatography, 0-10% MeOH/DCM. The product was a colorless solid (18%).

¹H NMR (400 MHz, CDCl₃) δ 8.42 (d, 1H), 7.86 (s, 1H), 7.39-7.26 (m, 6H), 7.20-7.13 (m, 1H), 7.00 (t, 1H), 6.93 (t, 1H), 6.77 (t, 1H), 6.56 (d, 1H), 5.98 (s, 2H), 5.10 (br s, 2H), 4.32 (s, 2H).

Compound I-228

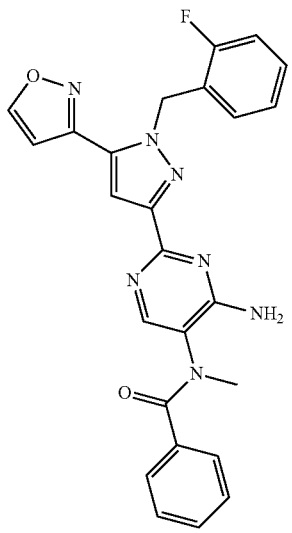 [SMILES: CN(C(=O)c1ccccc1)c1cnc(-c2cc(-c3ccon3)n(Cc3ccccc3F)n2)nc1N]

To a suspension of 2-(1-(2-fluorobenzyl)-5-(isoxazol-3-yl)-1H-pyrazol-3-yl)-N-5-methylpyrimidine-4,5-diamine hydrochloride (50.2 mg, 0.125 mmol) in DCM (2 mL) and pyridine (1.00 mL) was added benzoyl chloride (39.1 µl, 0.337 mmol). The reaction mixture took a while to go completely into solution and was stirred at room temperature for ~40 min. The reaction mixture was then diluted with saturated ammonium chloride. The mixture was extracted 3× with DCM, and concentrated under a stream of nitrogen. The solid was triturated with ether and water, and filtered yielding a colorless solid as the product (81%).

$^1$H NMR (400 MHz, CDCl$_3$) δ 8.43 (d, 1H), 7.91 (br s, 1H), 7.40-7.34 (m, 2H), 7.34-7.15 (m, 5H), 7.04-6.99 (m, 1H), 6.94 (t, 1H), 6.75 (t, 1H), 6.54 (d, 1H), 5.99 (s, 2H), 5.34 (br s, 2H), 3.36 (s, 3H).

Compound I-234

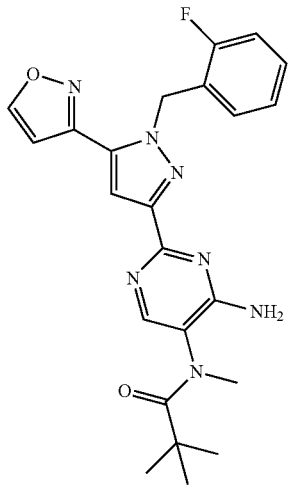 [SMILES: CN(C(=O)C(C)(C)C)c1cnc(-c2cc(-c3ccon3)n(Cc3ccccc3F)n2)nc1N]

To a suspension of 2-(1-(2-fluorobenzyl)-5-(isoxazol-3-yl)-1H-pyrazol-3-yl)-N5-methylpyrimidine-4,5-diamine hydrochloride (44 mg, 0.110 mmol) in DCM (3 mL) was added triethylamine (153 µl, 1.096 mmol) followed by pivaloyl chloride (67.4 µm, 0.548 mmol). Stir 3 h 20 min. Trace MeOH was added. The mixture was concentrated, followed by purification with silica gel chromatography (0-30% [MeOH/CH3CN-1/7]/DCM), yielding a colorless solid as the product (86%). $^1$H NMR (400 MHz, CDCl$_3$) δ 8.45 (d, 1H), 8.22 (s, 1H), 7.41 (s, 1H), 7.22-7.16 (m, 1H), 7.02 (t, 1H), 6.96 (t, 1H), 6.79 (t, 1H), 6.58 (d, 1H), 6.02 (s, 2H), 5.42 (br s, 2H), 3.14 (s, 3H), 1.15 (s, 9H).

Compound I-233

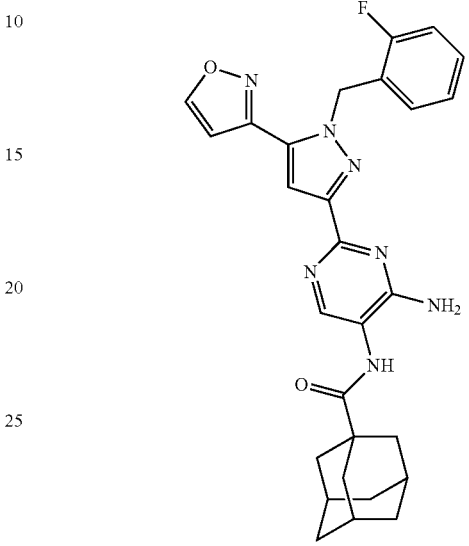

To a suspension of 2-(1-(2-fluorobenzyl)-5-(isoxazol-3-yl)-1H-pyrazol-3-yl)pyrimidine-4,5-diamine hydrochloride (42.5 mg, 0.110 mmol) and (3r,5r,7r)-adamantane-1-carbonyl chloride (63.1 mg, 0.318 mmol) in DCM (3 mL) was added triethylamine (153 µl, 1.096 mmol). The reaction mixture was stirred for 20 min. Trace MeOH was added. The reaction mixture was extracted with water and DCM, and dried with magnesium sulfate. The reaction mixture was then triturated with ether and filtered. The product was a colorless solid (81%).

$^1$H NMR (400 MHz, CDCl$_3$) δ 8.45 (d, 1H), 8.38 (s, 1H), 7.84 (br s, 1H), 7.43 (s, 1H), 7.24-7.16 (m, 1H), 7.02 (t, 1H), 6.96 (t, 1H), 6.81 (t, 1H), 6.59 (d, 1H), 6.10 (br s, 2H), 5.99 (s, 1H), 2.13 (br s, 3H), 2.07-2.04 (br m, 6H), 1.80-1.76 (br m, 6H).

Compound I-237

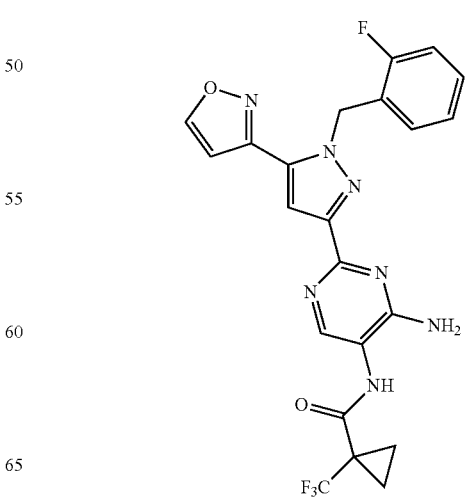

To an ice-cooled solution of 1-(trifluoromethyl)cyclopropanecarboxylic acid (0.180 g, 1.168 mmol) in DCM (2 mL) was added a drop of a DMF solution (2 drops DMF in 1 mL DCM). Oxalyl chloride (0.088 mL, 1.003 mmol) was added and the reaction mixture was brought to room temperature. Stirring was continued for 1 h. Initially bubbling picked up at room temperature and then by 1 h the bubbling had somewhat subsided. Then 70% of this solution (~7 eq acid chloride) was slowly added to a stirring suspension of 2-(1-(2-fluorobenzyl)-5-(isoxazol-3-yl)-1H-pyrazol-3-yl)pyrimidine-4,5-diamine hydrochloride (0.0401 g, 0.103 mmol) in DCM (2 mL) and Py (1 mL). Bubbling ensued as the solution was added (presumably oxalyl chloride remained, but was broken down by pyridine on addition). Eventually the SM went into solution, and the reaction mixture was stirred ~30 min. The reaction mixture was then quenched by adding saturated ammonium chloride and extracted with DCM. The extract was dried with magnesium sulfate. The extract was then concentrated, and triturated with ether. Filtration yielded a faint tan solid as the product (69%).

$^1$H NMR (400 MHz, CDCl$_3$) δ 8.44 (d, 1H), 8.31 (s, 1H), 7.50 (br s, 1H), 7.40 (s, 1H), 7.21-7.15 (m, 1H), 7.02 (t, 1H), 6.95 (t, 1H), 6.76 (t, 1H), 6.58 (d, 1H), 6.02 (s, 2H), 5.26 (br s, 2H), 1.56 (br s, 2H), 1.41 (dd, 2H).

Compound I-240

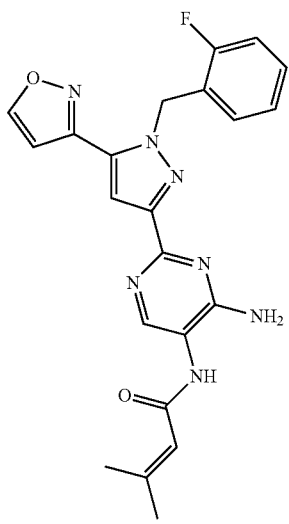 [SMILES: CC(C)=CC(=O)Nc1cnc(-c2cc(-c3ccon3)n(Cc3ccccc3F)n2)nc1N]

This compound was synthesized as a colorless solid (79%) via the acylation of Compound I-107 (1 equiv) with 3-methylbut-2-enoyl chloride (3 equiv) in a solution of dichloromethane/pyridine (2:1). Purification was carried out by quenching with a small amount of methanol, diluting with water, extracting with DCM (3×), drying the combined organic layers with magnesium sulfate, and concentrating under a stream of nitrogen. The resulting solid was triturated with diethyl ether and filtered.

$^1$H NMR (400 MHz, CDCl$_3$) δ 8.43 (d, 1H), 8.23 (s, 1H), 7.39 (s, 1H), 7.21-7.14 (m, 1H), 7.01 (t, 1H), 6.97-6.90 (m, 2H), 6.77 (t, 1H), 6.58 (dd, 1H), 6.01 (s, 2H), 5.79 (br s, 1H), 5.54 (br s, 2H), 2.24 (s, 3H), 1.94 (s, 3H).

Compound I-246

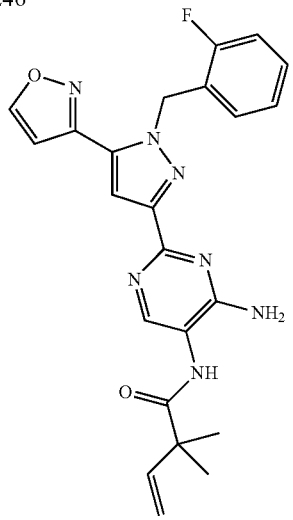

To a solution of 2,2-dimethylbut-3-enoic acid (135 mg, 1.184 mmol) in DCM (2 mL) was added a drop of a DMF solution (2 drops DMF in 1 mL DCM). Oxalyl chloride (0.088 mL, 1.003 mmol) was added and the reaction was brought to rt. Stirring continued 1.66 h. Initially bubbling picked up at rt and then by 1 h the bubbling had somewhat subsided. Slowly 60% of this solution (~5.5 eq acid chloride) was added to a stirring suspension of 2-(1-(2-fluorobenzyl)-5-(isoxazol-3-yl)-1H-pyrazol-3-yl)pyrimidine-4,5-diamine hydrochloride (0.0401 g, 0.103 mmol) in DCM (2 mL) and Py (1 mL). Bubbling ensued as the solution was added (presumably oxalyl chloride remained, but was broken down by pyridine on addition). Eventually the SM went into solution and the mixture was stirred ~30 min. The reaction mixture was quenched by the addition of saturated ammonium chloride and extracted with DCM. The extract was dried with magnesium sulfate and concentrated. The mixture was triturated with ether and the solid was filtered. The product was a faint tan solid (70%).

$^1$H NMR (400 MHz, CDCl$_3$) δ 8.43 (d, 1H), 8.19 (s, 1H), 7.39 (s, 1H), 7.21-7.15 (m, 1H), 7.02 (t, 1H), 6.95 (t, 1H), 6.76 (t, 1H), 6.57 (d, 1H), 6.17 (dd, 1H), 6.01 (s, 2H), 5.44 (d, 1H), 5.41 (d, 1H), 5.34 (br s, 2H), 1.56 (s, 6H).

Compound I-260

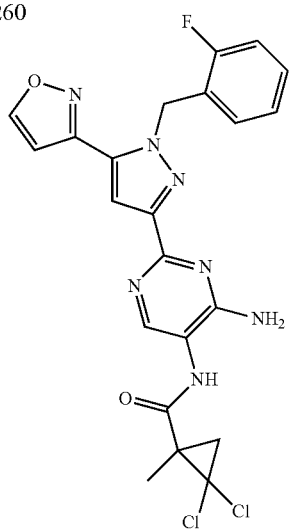

To a solution of 2,2-dichloro-1-methylcyclopropanecarboxylic acid (192 mg, 1.137 mmol) in DCM (2 mL) was added a drop of a DMF solution (2 drops DMF in 1 mL DCM). Oxalyl chloride (0.088 mL, 1.003 mmol) was added and the reaction was brought to rt. Stirring continued 2 h. Initially bubbling picked up at rt and then by 1 h had somewhat subsided. Slowly 55% of this solution was added to a stirring suspension of 2-(1-(2-fluorobenzyl)-5-(isoxazol-3-yl)-1H-pyrazol-3-yl)pyrimidine-4,5-diamine hydrochloride (0.0401 g, 0.103 mmol) in DCM (2 mL) and Py (1 mL). Bubbling ensued as solution was added (presumably oxalyl chloride remained, but was broken down by pyridine on addition). Eventually the SM went into solution. The reaction mixture was stirred ~30 min, quenched by addition of saturated ammonium chloride and extracted with DCM. The extract was dried with magnesium sulfate, concentrated and triturated with ether. The mixture was filtered yielding a colorless solid (77%) as the product.

$^1$H NMR (400 MHz, CDCl$_3$) δ 8.42 (d, 1H), 8.26 (s, 1H), 7.38 (s, 1H), 7.27 (br s, 1H), 7.20-7.13 (m, 1H), 7.00 (td, 1H), 6.93 (t, 1H), 6.75 (td, 1H), 6.56 (d, 1H), 6.00 (s, 2H), 5.34 (br s, 2H), 2.36 (d, 1H), 1.77 (s, 3H), 1.51 (d, 1H).

Compound I-267

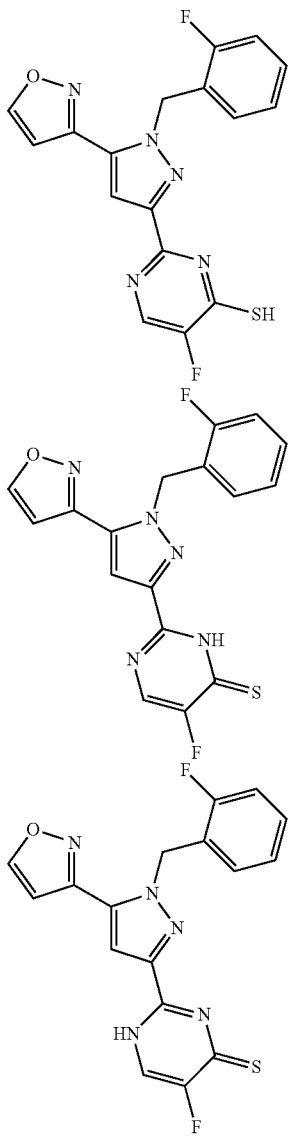

To a solution of 5-fluoro-2-(1-(2-fluorobenzyl)-5-(isoxazol-3-yl)-1H-pyrazol-3-yl)pyrimidin-4-ol (31.4 mg, 0.088 mmol) in pyridine (1.5 mL) was added phosphorous pentasulfide (25.5 mg, 0.115 mmol). Reaction mixture was heated with stirring at 70° C. for 30 min. The reaction mixture was heat refluxed for 2 h, more P2S5 was added, and heat refluxed for 1 h. The mixture was poured onto ice, diluted with DCM/IPA and extract 4×. The extract was dried with magnesium sulfate and concentrated. The product was a yellow solid (88%). NMR appears to contain either closely related impurities or possibly other tautomers of the pyrimidinone. NMR may be a mixture of multiple isomers such as the 2nd and 3rd compounds shown above.

$^1$H NMR (400 MHz, (CD$_3$)$_2$SO) δ 9.13 (d, 1H), 8.76-8.73 (m, 1H), 8.18 (br s, 1H), 7.74 (s, 1H), 7.72-7.68 (m, 1H), 7.36-7.31 (m, 1H), 7.25-7.20 (m, 1H), 7.13 (td, 1H), 7.00 (td, 1H), 5.94 (s, 2H).

Compound I-270

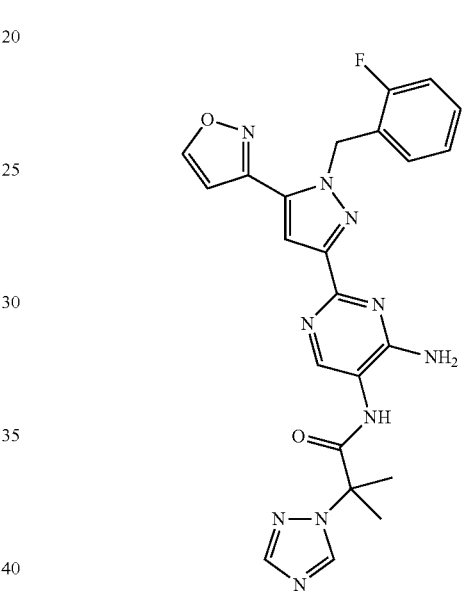

To a suspension of 2-methyl-2-(1H-1,2,4-triazol-1-yl)propanoic acid hydrochloride (198 mg, 1.031 mmol) and oxalyl dichloride (81 μl, 0.928 mmol) in DCM (2 mL) was added a couple drops of a DMF solution (2 drops DMF in 1 mL DCM). Bubbling ensued. The rxn stirred at rt for ~3 h. A precipitate remained as if SM went into solution and came back out. Slowly about ¾ of this suspension was added to a stirring suspension of 2-(1-(2-fluorobenzyl)-5-(isoxazol-3-yl)-1H-pyrazol-3-yl)pyrimidine-4,5-diamine hydrochloride (40 mg, 0.103 mmol) in DCM (2 mL) and Py (1 mL). The starting material did not go into solution. Precipitate remained. Triethylamine (~1 mL) was added. No further reaction was observed. The rest of 'acid chloride' suspension was added. More product was formed (~1/1). The mixture was diluted with water and DCM, extracted and the extract dried with magnesium sulfate and concentrated. To separate from remaining diamine, acylation with benzoyl chloride was conducted. Same workup as other benzoylations above was applied. Purification by silica gel chromatography (0-100% [MeOH/CH3CN-1/7]/DCM) yielded a faint tan solid as the product (28%).

$^1$H NMR (400 MHz, CD$_3$OD) δ 8.77 (s, 1H), 8.74 (d, 1H), 8.11 (s, 1H), 8.06 (s, 1H), 7.42 (s, 1H), 7.28-7.20 (m, 1H), 7.06 (td, 1H), 7.00 (td, 1H), 6.85 (d, 1H), 6.80 (td, 1H), 5.94 (s, 2H), 1.95 (s, 6H).

Compound I-142

Compound I-142 was synthesized as a tan solid (34%) via the condensation of Compound I-107 (1 equiv) with methylchloroformate (3 equiv) in a solution of dichloromethane/pyridine (2:1). Purification was carried out by washing the crude solid obtained after aqueous ammonium chloride and ethyl acetate workup with 3:1 diethyl ether/dichloromethane.

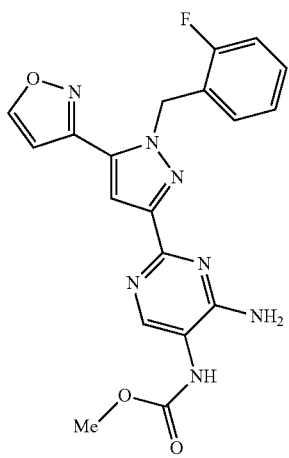 [SMILES: COC(=O)Nc1cnc(-c2cc(-c3ccon3)n(Cc3ccccc3F)n2)nc1N]

Product exists as rotameric mixture by $^1$H-NMR. $^1$H NMR (400 MHz, DMSO) δ 9.09 (s, 1H), 7.51 (s, 1H), 7.33-7.30 (m, 1H), 7.24-7.09 (m, 7H), 6.93 (br s, 1H), 6.96-6.83 (m, 1H), 5.89 (s, 2H), 3.67 (s, 3H).

Compound I-277

Compound I-277 was synthesized as a light brown solid (69%) via the condensation of Compound I-107 (1 equiv) with pivaloyl chloride (5 equiv) in a solution of dichloromethane/pyridine (2:1). Purification was carried out using silica gel chromatography (0-10% methanol in dichloromethane) following an aqueous ammonium chloride and ethyl acetate workup.

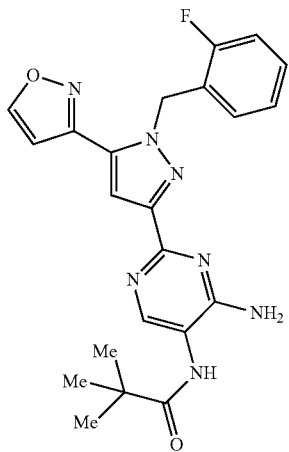 [SMILES: CC(C)(C)C(=O)Nc1cnc(-c2cc(-c3ccon3)n(Cc3ccccc3F)n2)nc1N]

$^1$H NMR (400 MHz, CDCl$_3$) δ 8.42 (s, 1H), 8.23 (s, 1H), 7.63 (br s, 1H), 7.35 (s, 1H), 7.18-7.13 (m, 1H), 7.01-6.90 (m, 2H), 6.76-6.72 (m, 1H), 6.56 (s, 1H), 5.95 (s, 2H), 5.63 (br s, 2H), 1.35 (s, 9H).

Compound I-144

Compound I-144 was synthesized as a tan solid (31%) via the condensation of Compound I-107 (1 equiv) with cyclopropanecarbonyl chloride (1.3 equiv) in a solution of dichloromethane/pyridine (2:1). Purification was carried out by washing the crude solid obtained after aqueous ammonium chloride and ethyl acetate workup with diethyl ether.

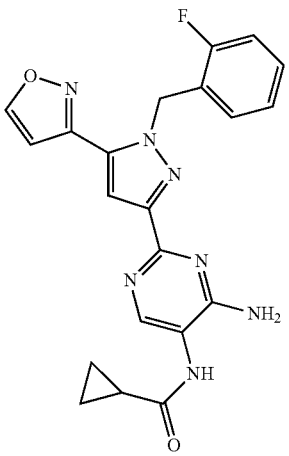 [SMILES: Nc1nc(-c2cc(-c3ccon3)n(Cc3ccccc3F)n2)ncc1NC(=O)C1CC1]

1H NMR (400 MHz, CD$_3$OD) δ 8.76 (s, 1H), 8.34 (s, 1H), 7.42 (s, 1H), 7.28-7.24 (m, 1H), 7.11-7.01 (m, 2H), 6.87-6.82 (m, 2H), 5.96 (s, 2H), 1.88-1.81 (m, 1H), 1.10-0.96 (m, 2H), 0.94-0.89 (m, 2H).

Compound I-145

This compound was synthesized as a white solid (45%) via the condensation of Compound I-107 (1 equiv) with methanesulfonyl chloride (1.3 equiv) in a solution of dichloromethane/pyridine (2:1). Purification was carried out using silica gel chromatography (0-10% methanol in dichloromethane) following an aqueous ammonium chloride and ethyl acetate workup.

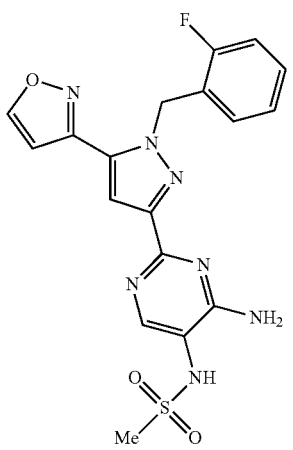 [SMILES: CS(=O)(=O)Nc1cnc(-c2cc(-c3ccon3)n(Cc3ccccc3F)n2)nc1N]

$^1$H NMR (400 MHz, CD$_3$OD) δ 8.78 (s, 1H), 8.17 (s, 1H), 7.46 (s, 1H), 7.30-7.25 (m, 1H), 7.12-7.02 (m, 2H), 6.88-6.84 (m, 2H), 5.97 (s, 2H), 3.07 (s, 3H).

Compound I-150

Compound I-150 was synthesized as a light brown solid (53%) via the condensation of Compound I-107 (1 equiv) with isobutyl chloroformate (1.9 equiv) in a solution of dichloromethane/pyridine (2:1). Purification was carried out using silica gel chromatography (0-5% methanol in dichloromethane) following an aqueous ammonium chloride and ethyl acetate workup.

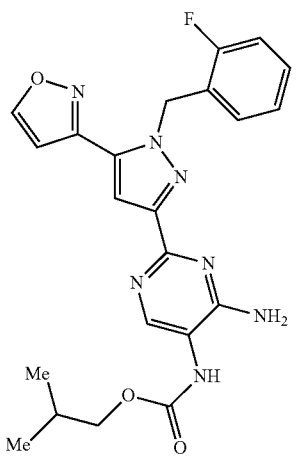 [SMILES: CC(C)COC(=O)Nc1cnc(-c2cc(-c3ccon3)n(Cc3ccccc3F)n2)nc1N]

1H NMR (400 MHz, CDCl₃) δ 8.42 (m, 1H), 8.35 (br s, 1H), 7.33 (s, 1H), 7.25 (br s, 1H), 7.17-7.11 (m, 1H), 6.99-6.94 (m, 1H), 6.91 (t, 1H), 6.79-6.76 (m, 1H), 6.56 (m, 1H), 5.93 (s, 2H), 5.80 (br s, 2H), 3.85 (d, 2H), 1.85 (sept, 1H), 0.84 (d, 6H).

Compound I-165

This compound was synthesized as a white solid (81%) via the condensation of Compound I-107 (1 equiv) with isobutyryl chloride (2.8 equiv) in a solution of dichloromethane/pyridine (2:1). Purification was carried out using silica gel chromatography (0-10% methanol in dichloromethane) following an aqueous ammonium chloride and ethyl acetate workup.

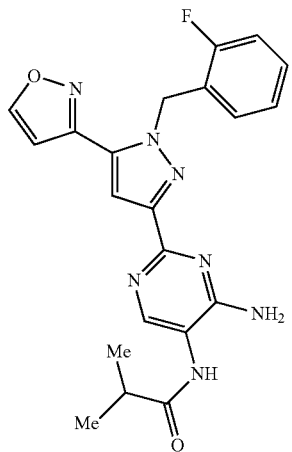 [SMILES: CC(C)C(=O)Nc1cnc(-c2cc(-c3ccon3)n(Cc3ccccc3F)n2)nc1N]

1H NMR (400 MHz, CD₃OD) δ 8.76 (d, 1H), 8.31 (s, 1H), 7.42 (s, 1H), 7.29-7.24 (m, 1H), 7.11-7.06 (m, 1H), 7.03 (t, 1H), 6.87 (d, 1H), 6.86-6.82 (m, 1H), 5.96 (s, 2H), 2.71 (quint, 1H), 1.24 (d, 6H).

Compound I-166

Compound I-166 was synthesized as a white solid (59%) via the condensation of Compound I-107 (1 equiv) with 2-methoxybenzoyl chloride (2.0 equiv) in a solution of dichloromethane/pyridine (2:1). After an aqueous ammonium chloride and ethyl acetate workup, column chromatography (0-10% methanol in dichloromethane) followed by washing the resulting impure product with diethyl ether provided the desired compound.

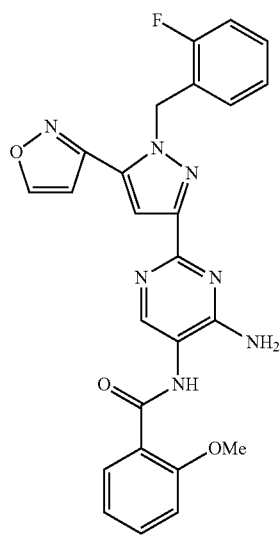 [SMILES: COc1ccccc1C(=O)Nc1cnc(-c2cc(-c3ccon3)n(Cc3ccccc3F)n2)nc1N]

1H NMR (400 MHz, CD₃OD) δ 8.76 (d, 1H), 8.41 (s, 1H), 7.97 (dd, 1H), 7.59-7.55 (m, 1H), 7.46 (s, 1H), 7.30-7.21 (m, 2H), 7.13-7.07 (m, 2H), 7.04 (t, 1H), 6.88 (d, 1H), 6.88-6.83 (m, 1H), 5.97 (s, 2H), 4.04 (s, 3H).

Compound I-167

Compound I-167 was synthesized as a pink solid (quantitative yield) via the condensation of Compound I-107 (1 equiv) with 4-chlorobutanoyl chloride (2.2 equiv) in a solution of dichloromethane/pyridine (2:1). Purification was carried out using silica gel chromatography (0-10% methanol in dichloromethane) following an aqueous ammonium chloride and ethyl acetate workup.

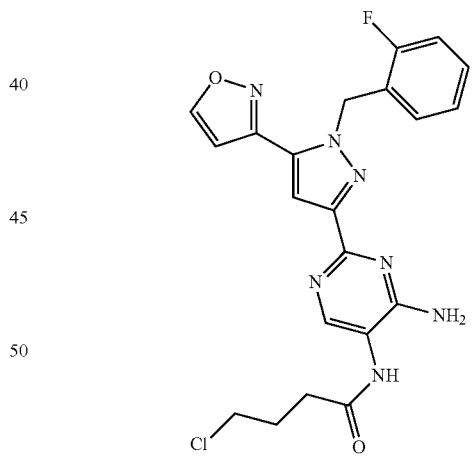

1H NMR (400 MHz, CDCl₃) δ 8.75 (br s, 1H), 8.43 (s, 1H), 8.38 (s, 1H), 7.15-7.11 (m, 1H), 6.96-6.88 (m, 2H), 6.80-6.76 (m, 1H), 6.58 (s, 1H), 6.12 (br s, 2H), 5.87 (s, 2H), 3.54 (t, 2H), 2.48 (t, 2H), 2.05 (quint, 2H).

Compound I-174

Compound I-174 was synthesized as a tan solid (52%) via the condensation of Compound I-107 (1 equiv) with 3-methoxybenzoyl chloride (1.8 equiv) in a solution of dichloromethane/pyridine (2:1). Purification was carried out using silica gel chromatography (30-95% ethyl acetate in hexanes) following an aqueous ammonium chloride and ethyl acetate workup.

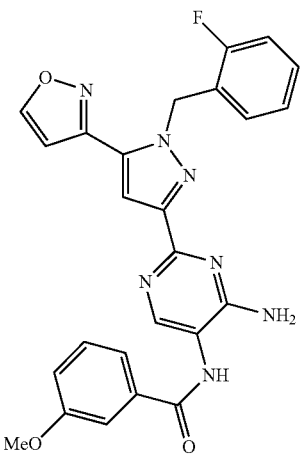 [SMILES: COc1cccc(C(=O)Nc2cnc(-c3cc(-c4ccon4)n(Cc4ccccc4F)n3)nc2N)c1]

1H NMR (400 MHz, CDCl₃) δ 9.47 (s, 1H), 8.40 (s, 1H), 8.24 (s, 1H), 7.37 (m, 2H), 7.22 (s, 1H), 7.13 (t, 1H), 7.06-7.01 (m, 1H), 6.93-6.91 (m, 1H), 6.86-6.78 (m, 2H), 6.74-6.70 (m, 1H), 6.53 (s, 1H), 5.83 (br s, 2H), 5.70 (s, 2H), 3.62 (s, 3H).

Compound I-205

Compound I-205 was synthesized as a solid (35%) via the condensation of Compound I-107 (1 equiv) with 2-fluoro-2-methylpropanoic acid (2.75 equiv) in the presence of HATU (2.5 equiv) and N,N-diisopropylethylamine (5 equiv) in acetonitrile. Purification was carried out using silica gel chromatography (0-10% methanol in dichloromethane) following an aqueous 1 N sodium hydroxide and ethyl acetate workup.

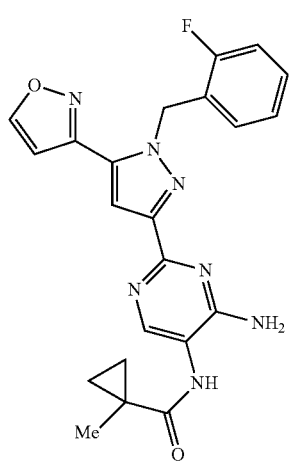

1H NMR (400 MHz, CD₃OD) δ 8.74 (s, 1H), 8.10 (s, 1H), 7.41 (s, 1H), 7.27-7.22 (m, 1H), 7.09-7.05 (m, 1H), 7.01 (t, 1H), 6.85-6.81 (m, 2H), 5.94 (s, 2H), 1.48 (s, 3H), 1.25-1.23 (m, 2H), 0.75-0.72 (m, 2H).

Compound I-278

Compound I-278 was synthesized as a tan solid (94%) via the condensation of Compound I-107 (1 equiv) with 2-acetoxyisobutyryl chloride (3 equiv) in a solution of dichloromethane/pyridine (2:1). Purification was carried out using silica gel chromatography (0-10% methanol in dichloromethane) following an aqueous ammonium chloride and dichloromethane workup.

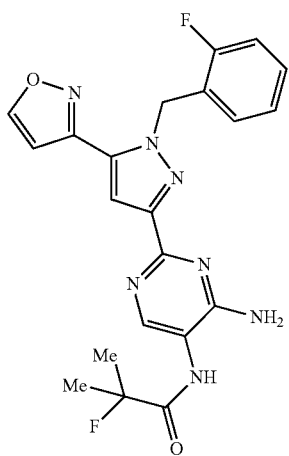 [SMILES: CC(C)(F)C(=O)Nc1cnc(-c2cc(-c3ccon3)n(Cc3ccccc3F)n2)nc1N]

1H NMR (400 MHz, CD₃OD) δ 8.75 (d, 1H), 8.23 (s, 1H), 7.43 (s, 1H), 7.29-7.23 (m, 1H), 7.11-7.01 (m, 2H), 6.87-6.82 (m, 2H), 5.95 (s, 2H), 1.66 (d, 6H).

Compound I-206

Compound I-206 was synthesized as an orange solid (65%) via the condensation of Compound I-107 (1 equiv) with 1-methylcyclopropanecarboxylic acid (3.0 equiv) in the presence of HATU (2.5 equiv) and N,N-diisopropylethylamine (5 equiv) in acetonitrile. Purification was carried out using silica gel chromatography (0-10% methanol in dichloromethane) following an aqueous 1 N sodium hydroxide and ethyl acetate workup.

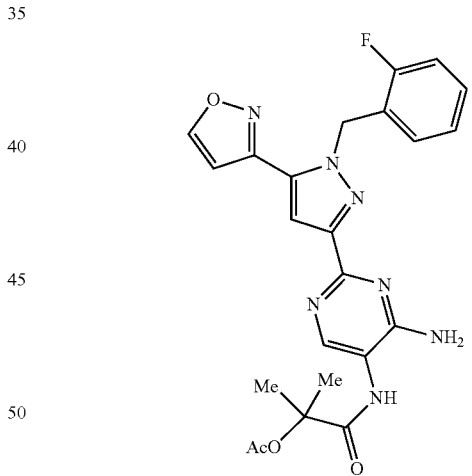

¹H NMR (400 MHz, CD₃OD) δ 8.74 (d, 1H), 8.04 (s, 1H), 7.42 (s, 1H), 7.28-7.22 (m, 1H), 7.10-7.05 (m, 1H), 7.02 (t, 1H), 6.85-6.81 (m, 2H), 5.95 (s, 2H), 2.12 (s, 3H), 1.65 (s, 6H).

Compound I-218

Compound I-218 was synthesized as a white solid (94%) via the condensation of Compound I-107 (1 equiv) with 1-phenylcyclobutanecarbonyl chloride (2 equiv) in a solution of dichloromethane/pyridine (2:1). Purification was carried out using silica gel chromatography (ethyl acetate in hexanes) following an aqueous ammonium chloride and dichloromethane workup.

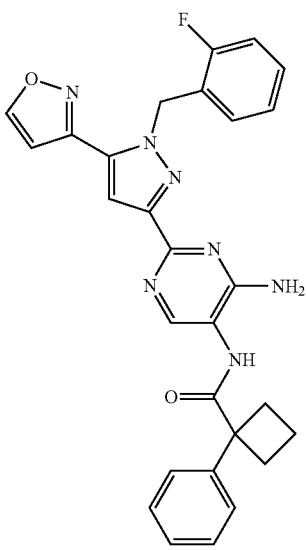 [SMILES: Nc1nc(-c2cc(-c3ccon3)n(Cc3ccccc3F)n2)ncc1NC(=O)C1(c2ccccc2)CCC1]

¹H NMR (400 MHz, CD₃OD) δ 8.74 (s, 1H), 8.02 (s, 1H), 7.52-7.50 (m, 2H), 7.43-7.39 (m, 3H), 7.31-7.23 (m, 2H), 7.10-7.05 (m, 1H), 7.01 (t, 1H), 6.85-6.80 (m, 2H), 5.93 (s, 2H), 2.99-2.92 (m, 2H), 2.63-2.56 (m, 2H), 2.04-1.92 (m, 2H).

Compound I-226

Compound I-226 was synthesized as a white solid (59%) via the condensation of Compound I-107 (1 equiv) with 2,2-difluoropropanoic acid (3 equiv) in the presence of N,N'-dicyclohexylcarbodiimide (3 equiv), triethylamine (3 equiv), and 4-dimethylaminopyridine (0.25 equiv) in dichloromethane. Purification was carried out using silica gel chromatography (0-10% methanol in dichloromethane) following filtration of the crude reaction mixture through celite.

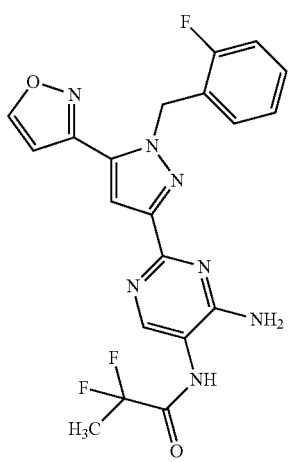 [SMILES: CC(F)(F)C(=O)Nc1cnc(-c2cc(-c3ccon3)n(Cc3ccccc3F)n2)nc1N]

¹H NMR (400 MHz, CD₃OD) δ 8.76 (d, 1H), 8.24 (s, 1H), 7.44 (s, 1H), 7.29-7.24 (m, 1H), 7.11-7.06 (m, 1H), 7.03 (t, 1H), 6.87-6.83 (m, 2H), 5.96 (s, 2H), 1.90 (t, 3H).

Compound I-231

Compound I-231 was synthesized as an orange solid (86%) via the condensation of Compound I-107 (1 equiv) with 1-methylcyclohexanecarbonyl chloride (4.5 equiv) in a solution of dichloromethane/pyridine (2:1). Purification was carried out using silica gel chromatography (ethyl acetate in hexanes) following an aqueous ammonium chloride and dichloromethane workup.

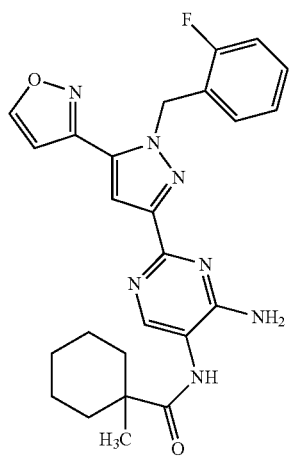 [SMILES: CC1(C(=O)Nc2cnc(-c3cc(-c4ccon4)n(Cc4ccccc4F)n3)nc2N)CCCCC1]

¹H NMR (400 MHz, CD₃OD) δ 8.74 (m, 1H), 8.13 (s, 1H), 7.42 (s, 1H), 7.27-7.22 (m, 1H), 7.09-7.05 (m, 1H), 7.01 (t, 1H), 6.85-6.81 (m, 2H), 5.94 (s, 2H), 2.12-2.07 (m, 2H), 1.63-1.39 (m, 8H), 1.29 (s, 3H).

Compound I-236

To a solution of 2-methyl-2-phenylpropanoic acid (11 equiv) in dichloromethane was added oxalyl chloride (33 equiv) and catalytic N,N-dimethylformamide. Once gas evolution ceased, this solvent was removed in vacuo. The crude acid chloride was redissolved in dichloromethane and added portion-wise to a suspension of Compound I-107 (1 equiv) in dichloromethane/pyridine (2:1) until the absence of starting material was observed by LC/MS. Following an aqueous ammonium chloride and dichloromethane workup, purification via silica gel chromatography (0-10% methanol in dichloromethane) did not provide sufficiently pure material. Repurification using ethyl acetate in hexanes as an eluent provided the desired compound as a white solid (57%).

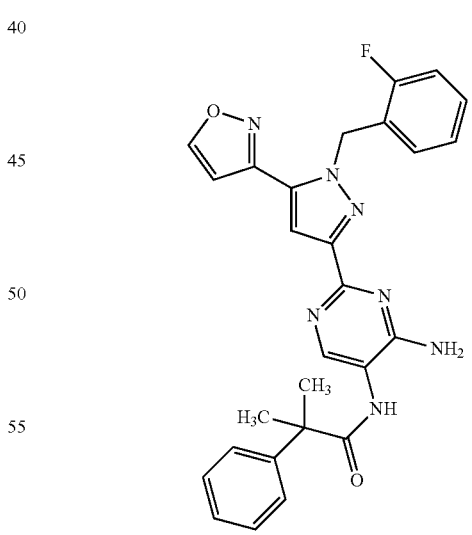

¹H NMR (400 MHz, CD₃OD) δ 8.74 (m, 1H), 8.03 (s, 1H), 7.48-7.46 (m, 2H), 7.41-7.36 (m, 3H), 7.30-7.21 (m, 2H), 7.09-7.04 (m, 1H), 7.01 (t, 1H), 6.85-6.79 (m, 2H), 5.93 (s, 2H), 1.67 (s, 6H).

Compound I-243

To a solution of 1-(trifluoromethyl)cyclobutanecarboxylic acid (18 equiv) in dichloromethane was added oxalyl chloride (16 equiv) and catalytic N,N-dimethylformamide. Once gas evolution ceased, this crude reaction mixture was added portion-wise to a suspension of Compound I-107 (1 equiv) in dichloromethane/pyridine (2:1) until complete consumption of starting material was observed by LS/MS. Purification via silica gel chromatography (0-10% methanol in dichloromethane) following an aqueous ammonium chloride and dichloromethane workup provided the desired compound as a white solid (74%).

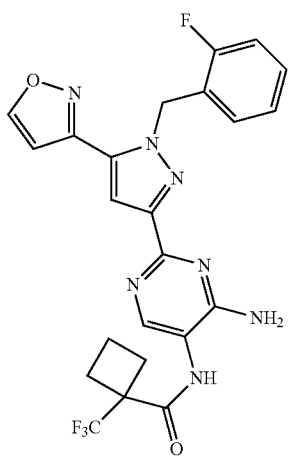 [SMILES: Nc1nc(-c2cc(-c3ccon3)n(Cc3ccccc3F)n2)ncc1NC(=O)C1(C(F)(F)F)CCC1]

$^1$H NMR (400 MHz, CD$_3$OD) δ 8.76 (d, 1H), 8.16 (s, 1H), 7.44 (s, 1H), 7.29-7.24 (m, 1H), 7.11-7.06 (m, 1H), 7.03 (t, 1H), 6.87-6.81 (m, 2H), 5.96 (s, 2H), 2.85-2.77 (m, 2H), 2.58-2.51 (m, 2H), 2.14-1.97 (m, 2H).

Compound I-244

Compound I-244 was synthesized as a yellow solid (55%) via the condensation of Compound I-107 (1 equiv) with 2,2-difluoro-2-phenylacetyl chloride (10 equiv) in a solution of dichloromethane/pyridine (2:1). After an aqueous ammonium chloride and dichloromethane workup, column chromatography (0-10% methanol in dichloromethane) followed by washing the resulting impure product with diethyl ether provided the desired compound.

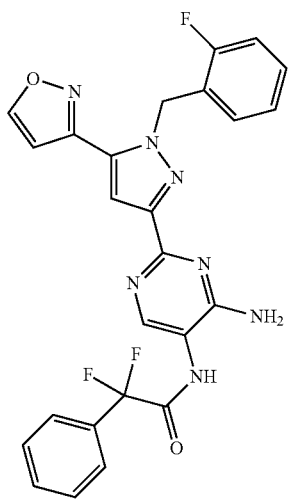 [SMILES: Nc1nc(-c2cc(-c3ccon3)n(Cc3ccccc3F)n2)ncc1NC(=O)C(F)(F)c1ccccc1]

$^1$H NMR (400 MHz, CD$_3$OD) δ 8.75 (d, 1H), 8.18 (s, 1H), 7.74-7.72 (m, 2H), 7.59-7.52 (m, 3H), 7.43 (s, 1H), 7.29 (m, 1H), 7.10-7.06 (m, 1H), 7.02 (t, 1H), 6.86-6.82 (m, 2H), 5.95 (s, 2H).

Compound I-257

To a solution of 3,3,3-trifluoro-2,2-dimethylpropanoic acid (18 equiv) in dichloromethane was added oxalyl chloride (16 equiv) and catalytic N,N-dimethylformamide. Once gas evolution ceased, this crude reaction mixture was added portion-wise to a suspension of Compound I-107 (1 equiv) in dichloromethane/pyridine (2:1) until complete consumption of starting material was observed by LS/MS. After an aqueous ammonium chloride and dichloromethane workup, column chromatography (0-10% methanol in dichloromethane) followed by washing the resulting impure product with diethyl ether provided the desired compound as a white solid (34%).

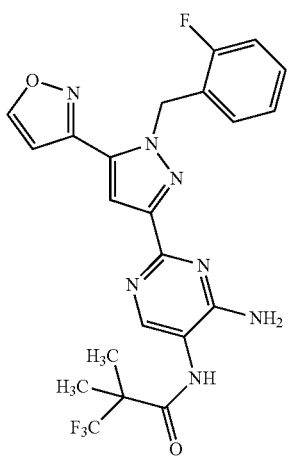 [SMILES: CC(C)(C(=O)Nc1cnc(-c2cc(-c3ccon3)n(Cc3ccccc3F)n2)nc1N)C(F)(F)F]

$^1$H NMR (400 MHz, CD$_3$OD) δ 8.76 (m, 1H), 8.08 (s, 1H), 7.44 (s, 1H), 7.29-7.24 (m, 1H), 7.11-7.06 (m, 1H), 7.03 (t, 1H), 6.87-6.83 (m, 2H), 5.96 (s, 2H), 1.57 (s, 6H).

Compound I-280

To a solution of 3-acetoxy-2,2-dimethylpropanoic acid (19 equiv) in dichloromethane was added oxalyl chloride (14 equiv) and catalytic N,N-dimethylformamide. Once gas evolution ceased, this crude reaction mixture was added portion-wise to a suspension of Compound I-107 (1 equiv) in dichloromethane/pyridine (2:1) until complete consumption of starting material was observed by LS/MS. After an aqueous ammonium chloride and dichloromethane workup, column chromatography (50-100% ethyl acetate in hexanes) provided the desired product as a yellow film (18%).

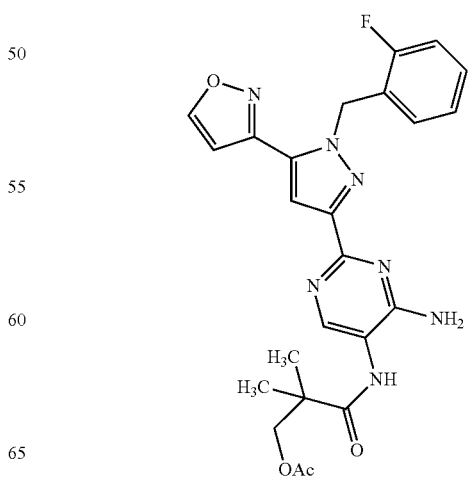

$^1$H NMR (400 MHz, CD$_3$OD) δ 8.74 (d, 1H), 8.09 (s, 1H), 7.42 (s, 1H), 7.28-7.22 (m, 1H), 7.09-7.05 (m, 1H), 7.01 (dt, 1H), 6.86-6.80 (m, 2H), 5.94 (s, 2H), 4.20 (s, 2H), 2.06 (s, 3H), 1.34 (s, 6H).

Compound I-265

To a solution of Compound I-280 (1 equiv) in tetrahydrofuran, methanol, and water (3:1:1) was added lithium hydroxide (2 equiv). After 30 min, the solution was diluted with saturated aqueous ammonium chloride and dichloromethane. The layers were separated and the aqueous layer was extracted with dichloromethane. The organics were dried over magnesium sulfate, filtered, and the solvent was removed in vacuo. To the crude solid was added diethyl ether, and filtration provided the desired product as a white solid (84%).

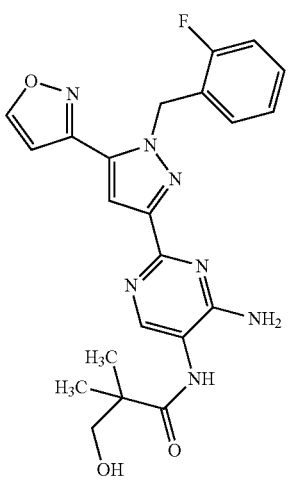 [SMILES: CC(C)(CO)C(=O)Nc1cnc(-c2cc(-c3ccon3)n(Cc3ccccc3F)n2)nc1N]

$^1$H NMR (400 MHz, CD$_3$OD) δ 8.74 (d, 1H), 8.09 (s, 1H), 7.41 (s, 1H), 7.27-7.23 (m, 1H), 7.09-7.05 (m, 1H), 7.02 (t, 1H), 6.86-6.81 (m, 2H), 5.94 (s, 2H), 3.62 (s, 2H), 1.26 (s, 6H).

Compound I-143 tert-Butyl (4-amino-2-(1-(2-fluorobenzyl)-5-(isoxazol-3-yl)-1H-pyrazol-3-yl)pyrimidin-5-yl)(methyl)carbamate and hydrochloric acid (4 N solution in dioxane, 55 equiv) were stirred for 15 minutes. Solvent removal under a stream of nitrogen provided the desired product as a solid (quantitative yield).

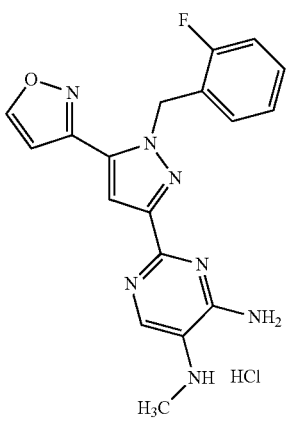 [SMILES: CNc1cnc(-c2cc(-c3ccon3)n(Cc3ccccc3F)n2)nc1N ; Cl]

$^1$H NMR (400 MHz, CD$_3$OD) δ 8.83 (s, 1H), 7.48 (s, 1H), 7.33-7.28 (m, 1H), 7.22 (s, 1H), 7.13-7.05 (m, 2H), 6.99-6.95 (m, 1H), 6.90 (s, 1H), 5.99 (s, 2H), 2.91 (s, 3H).

Compound I-281

To a suspension of Compound I-107 (1 equiv) in dichloromethane/pyridine (2:1) was added phenyl chloroformate (10 equiv). After 25 min, the solution was diluted with ethyl acetate and aqueous saturated ammonium chloride. The layers were separated and the aqueous layer was extracted with ethyl acetate. The organics were combined, dried over magnesium sulfate, filtered, and the solvent was removed in vacuo. Purification of the crude product by silica gel chromatography (0-10% methanol in dichloromethane) delivered the tetracylated product. This compound was treated with methanolic 1 N NaOH. After stirring for 20 min, the methanol was removed in vacuo and the crude residue was portioned between ethyl acetate and water. The layers were separated and the aqueous layer was extracted with ethyl acetate. The organics were combined, dried over magnesium sulfate, filtered, and the solvent was removed in vacuo. Purification by silica gel chromatography (0-10% methanol in dichloromethane) afforded the desired product as a white solid (16%, 2 steps).

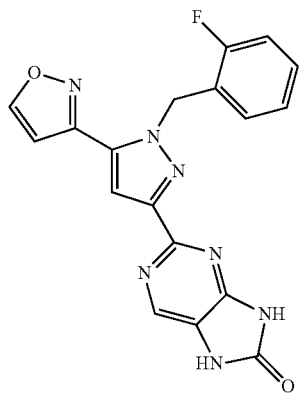 [SMILES: O=c1[nH]c2cnc(-c3cc(-c4ccon4)n(Cc4ccccc4F)n3)nc2[nH]1]

$^1$H NMR (400 MHz, DMSO) δ 11.91 (s, 1H), 11.21 (s, 1H), 9.10 (s, 1H), 8.23 (s, 1H), 7.54 (s, 1H), 7.36-7.31 (m, 1H), 7.28 (m, 1H), 7.25-7.20 (m, 1H), 7.14-7.10 (m, 1H), 6.94-6.90 (m, 1H), 5.90 (s, 2H).

Compound I-163

A solution of D4 (from Example 7: General Procedure F) (1 equiv) and methyl 3-(dimethylamino)-2-(pyridin-4-yl) acrylate (3 equiv) were stirred at 90° C. in ethanol for 23 h. The solvent was removed in vacuo and purification by silica gel chromatography chromatography (0-50% 7:1 acetonitrile:methanol in dichloromethane) delivered impure product. Successive washings with diethyl ether and dichloromethane provided the desired product as a yellow film (0.3%).

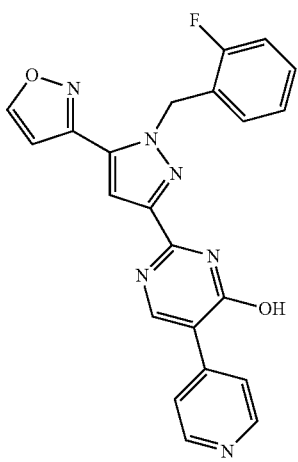 [SMILES: Oc1nc(-c2cc(-c3ccon3)n(Cc3ccccc3F)n2)ncc1-c1ccncc1]

¹H NMR (400 MHz, CD₃OD) δ 8.82 (m, 1H), 8.77 (d, 2H), 8.69 (br s, 1H), 8.51 (d, 2H), 7.61 (s, 1H), 7.33-7.29 (m, 1H), 7.14-7.06 (m, 2H), 6.99-6.94 (m, 2H), 6.05 (s, 2H).

Compound I-164

A solution of D4 (from Example 7: General Procedure F) (1 equiv) and methyl 2-(tert-butoxycarbonylamino)-3-(dimethylamino)acrylate (3 equiv) were stirred at 90° C. in ethanol for 23 h. The solvent was removed in vacuo and purification by silica gel chromatography (0-100% ethyl acetate in hexanes) delivered impure product. Washing of the resulting material with diethyl ether provided the desired product as a white solid (8%).

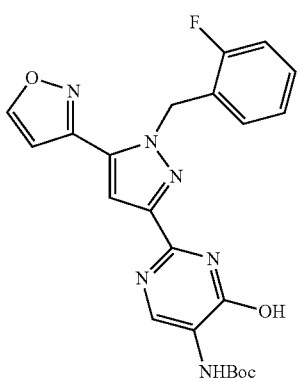 [SMILES: CC(C)(C)OC(=O)Nc1cnc(-c2cc(-c3ccon3)n(Cc3ccccc3F)n2)nc1O]

¹H NMR (400 MHz, CDCl₃) δ 10.18 (br s, 1H), 8.69 (br s, 1H), 8.52 (d, 1H), 7.32-7.26 (m, 3H), 7.10-7.04 (m, 3H), 6.62 (d, 1H), 5.90 (s, 2H), 1.52 (s, 9H).

Compound I-169

To a solution of Compound I-167 (1 equiv) in tetrahydrofuran was added sodium hydride (1 equiv). After stirring for 15 min, the solution was poured into water and the solution was extracted with ethyl acetate. The organics were dried over magnesium sulfate, filtered, the solvent was removed in vacuo, and the crude residue was purified by silica gel chromatography (0-10% methanol in dichloromethane) to give the desired product as a white solid (66%).

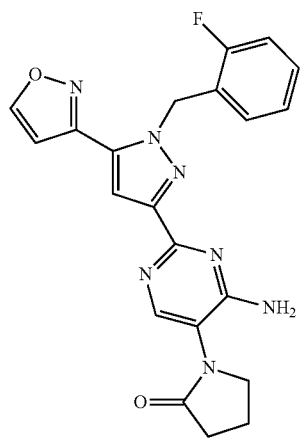 [SMILES: Nc1nc(-c2cc(-c3ccon3)n(Cc3ccccc3F)n2)ncc1N1CCCC1=O]

1H NMR (400 MHz, CDCl₃) δ 8.44 (s, 1H), 8.28 (s, 1H), 7.43 (s, 1H), 7.20-7.15 (m, 1H), 7.04-6.99 (m, 1H), 6.95 (t, 1H), 6.79-6.75 (m, 1H), 6.59 (s, 1H), 6.01 (s, 2H), 5.65 (br s, 2H), 3.88 (t, 2H), 2.64 (t, 2H), 2.29 (quint, 2H).

Compound I-209

To a solution of 1-((4-amino-2-(1-(2-fluorobenzyl)-5-(isoxazol-3-yl)-1H-pyrazol-3-yl)pyrimidin-5-yl)amino)-2-methyl-1-oxopropan-2-yl acetate in tetrahydrofuran, methanol, and water (3:1:1) was added lithium hydroxide (1 equiv). After stirring for 30 min, the solution was partitioned between dichloromethane and saturated aqueous ammonium chloride. The layers were separated and the aqueous layer was extracted with dichloromethane. The organics were dried over magnesium sulfate, filtered, and the solvent was removed to give the desired product as a white solid (94%).

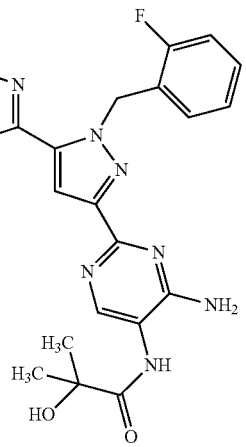

1H NMR (400 MHz, CD₃OD) δ 8.76 (d, 1H), 8.25 (s, 1H), 7.43 (s, 1H), 7.29-7.24 (m, 1H), 7.11-7.06 (m, 1H), 7.03 (t, 1H), 6.87 (d, 1H), 6.86-6.82 (m, 1H), 5.96 (s, 2H), 1.49 (s, 6H).

Compound I-259

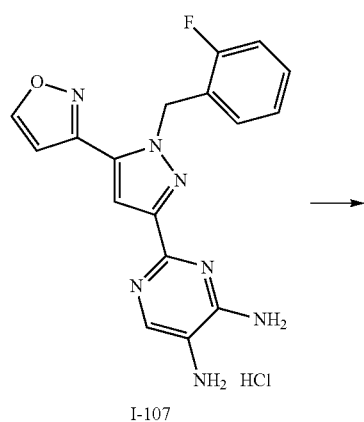

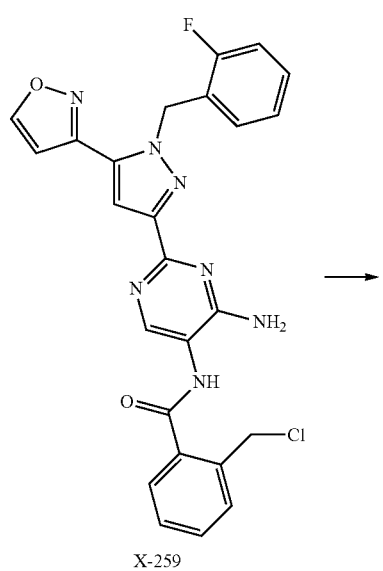

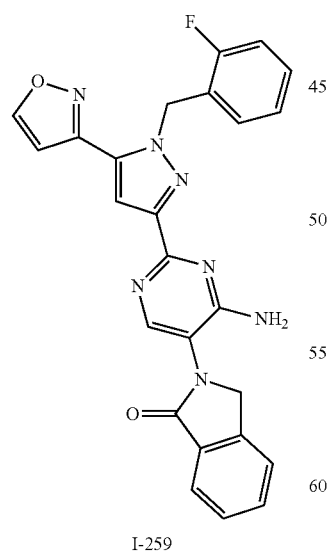

A solution of crude 2-(chloromethyl)benzoyl chloride (prepared by heating a neat mixture of isobenzofuran-1(3H)-one (14.5 equiv) and PPh$_3$Cl2 (15.1 equiv) at 180° C. for 4 h) in dichloromethane was added portion-wise to a suspension of Compound I-107 in dichloromethane and pyridine (2:1) until one-half of the crude material was added and the solution became homogeneous. The solution was partitioned between saturated aqueous ammonium chloride and dichloromethane. The layers were separated and the aqueous layer was extracted with dichloromethane. The organics were dried over magnesium sulfate, filtered, the solvent was removed in vacuo, and purification by silica gel chromatography (0-10% methanol in dichloromethane) provided intermediate X-259 as a yellow film (12%). The benzyl chloride intermediate was stirred with 1,8-diazabicyclo[5.4.0]undec-7-ene (28 equiv) in dichloromethane for 1.5 h. The solution was partitioned between saturated aqueous ammonium chloride and dichloromethane. The layers were separated and the aqueous layer was extracted with dichloromethane. The organics were dried over magnesium sulfate, filtered, the solvent was removed in vacuo, and purification by silica gel chromatography (ethyl acetate in hexanes) provided the desired product as a white solid (52%).

LRMS Calcd for C$_{25}$H$_{19}$FN$_7$O$_2$ [M+H]+468.16, observed 468.1.

Compound I-178

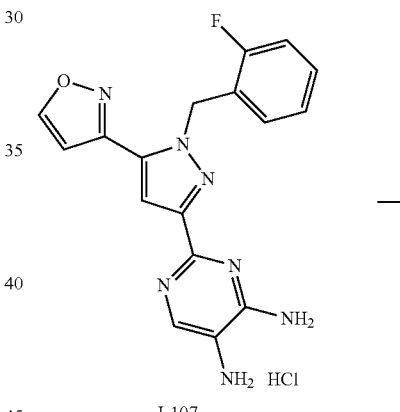

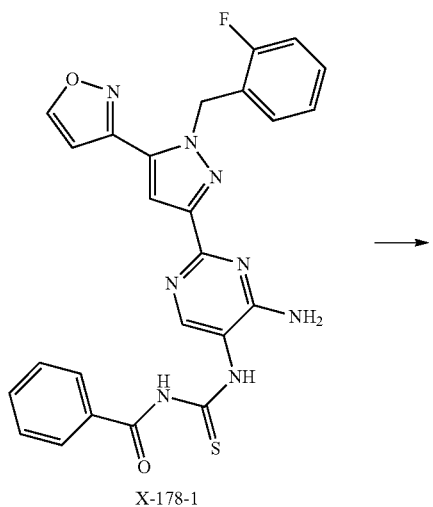

-continued

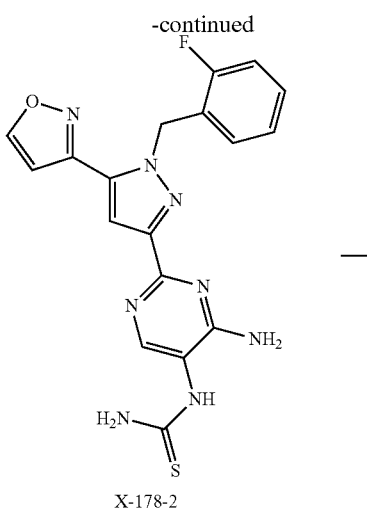

X-178-2

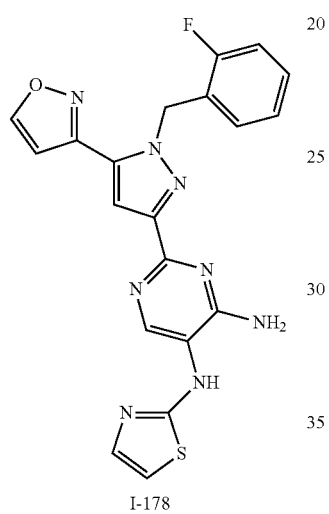

I-178

Benzoyl isothiocyanate (1.3 equiv) was added to a solution of Compound I-107 (1.0 equiv) and N,N-diisopropylethylamine (2.0 equiv) in acetone. After stirring for 15 minutes, the solution was partitioned between water and ethyl acetate. The layers were separated and the aqueous layer was extracted with ethyl acetate. The organics were combined, dried over magnesium sulfate, filtered, and the solvent was removed in vacuo. Purification by silica gel chromatography (ethyl acetate in hexanes) provided intermediate X-178-1 as a brown solid. To a methanol and water (2:1) solution of the intermediate was added potassium carbonate (3 equiv). After 1.25 h, the solution was partitioned between water and ethyl acetate. The layers were separated and the aqueous layer was extracted with ethyl acetate. The organics were dried over magnesium sulfate, filtered, and the solvent was removed in vacuo to give the crude product intermediate X-178-2 as a film. This intermediate was treated with 2-chloro-1,1-dimethoxyethane (1090 equiv) and p-toluensulfonic acid monohydrate (1.3 equiv) at 60° C. for 1.25 h, at which point the reaction mixture was poured into saturated aqueous sodium carbonate and extracted with ethyl acetate. The organic extracts were dried over magnesium sulfate, filtered, and the solvent was removed in vacuo. The crude product was purified via silica gel chromatography (0-10% methanol in dichloromethane) to provide the desired product I-178 (10%, 3 steps).

$^1$H NMR (400 MHz, CD$_3$OD) δ 8.87 (br s, 1H), 8.79 (d, 1H), 7.48 (s, 1H), 7.31-7.26 (m, 1H), 7.23 (d, 1H), 7.12-7.03 (m, 2H), 6.92-6.86 (m, 3H), 5.98 (s, 2H).

Compound I-245

To a solution of 2,2-difluoro-1-methylcyclopropanecarboxylic acid (135 mg, 0.995 mmol) (10 equiv) in dichloromethane was added oxalyl chloride (9 equiv) and catalytic N,N-dimethylformamide. Once gas evolution ceased, this crude reaction mixture was added portion-wise to a suspension of Compound I-107 (1 equiv) in dichloromethane/pyridine (2:1) until complete consumption of starting material was observed by LC/MS. Purification by precipitation from diethyl ether following an aqueous ammonium chloride and dichloromethane workup provided the desired compound as an off-white solid (76%).

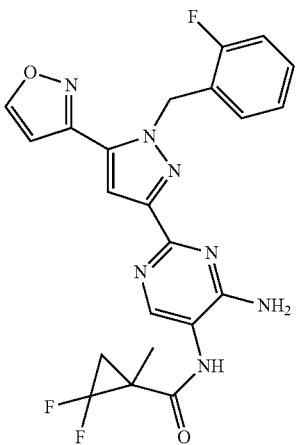 [SMILES: CC1(C(=O)Nc2cnc(-c3cc(-c4ccon4)n(Cc4ccccc4F)n3)nc2N)CC1(F)F]

$^1$H NMR (400 MHz, CDCl$_3$) δ 8.44 (d, 1H), 8.26 (s, 1H), 7.42 (br. s, 1H), 7.39 (s, 1H), 7.15-7.30 (m, 1H), 7.02 (m, 1H), 6.95 (m, 1H), 6.77 (m, 1H), 6.58 (d, 1H), 6.01 (s, 2H), 5.31 (br. s, 2H), 2.29-2.36 (m, 1H), 1.64 (s, 3H), 1.39-1.46 (m, 1H).

Compound I-247

This compound was synthesized as an off-white solid (57%) via the condensation of Compound I-107 (1 equiv) with 2,2-dimethylbutanoyl chloride (3 equiv) in a solution of dichloromethane/pyridine (2:1). Purification was carried out using silica gel chromatography (10% of a 7:1 acetonitrile/methanol mixture in dichloromethane) following an aqueous ammonium chloride and dichloromethane workup.

¹H NMR (400 MHz, CDCl₃) δ 8.44 (d, 1H), 8.19 (s, 1H), 7.39 (s, 1H), 7.16-7.21 (m, 2H), 6.93-7.04 (m, 2H), 6.77 (m, 1H), 6.58 (d, 1H), 6.01 (s, 2H), 5.39 (br. s, 2H), 1.70 (q, 2H), 1.33 (s, 6H), 0.97 (t, 3H).

Compounds I-250 and I-251

Compounds I-250 and I-251 were synthesized via the condensation of Compound I-107 (1 equiv) with 2-methylpropane-2-sulfinic chloride (6 equiv) in a solution of dichloromethane/pyridine (2:1). Purification was carried out using silica gel chromatography (3% to 8% of a 7:1 acetonitrile/methanol mixture in dichloromethane over 40 minutes) following an aqueous ammonium chloride and dichloromethane workup. Compound I-250 was isolated as an off-white solid (19%) while compound I-251 was isolated as a light tan solid (12%).

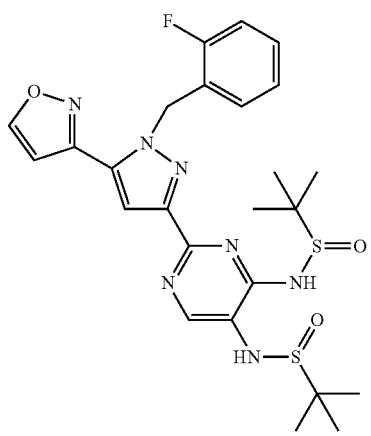 [SMILES: CC(C)(C)S(=O)Nc1cnc(-c2cc(-c3ccon3)n(Cc3ccccc3F)n2)nc1NS(=O)C(C)(C)C]

1H NMR (400 MHz, CDCl₃) δ 8.44 (d, 1H), 8.02 (s, 1H), 7.27 (s, 1H), 7.16-7.21 (m, 1H), 7.01 (m, 1H), 6.96 (m, 1H), 6.76 (m, 1H), 6.57 (d, 1H), 5.98 (s, 2H), 1.54 (s, 9H), 1.31 (s, 9H).

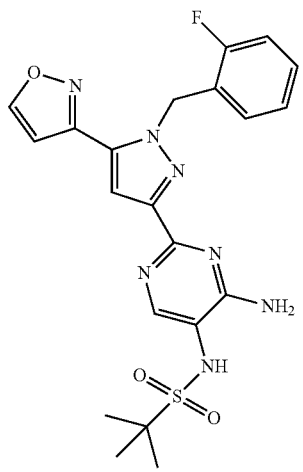 [SMILES: CC(C)(C)S(=O)(=O)Nc1cnc(-c2cc(-c3ccon3)n(Cc3ccccc3F)n2)nc1N]

1H NMR (400 MHz, CDCl₃) δ 8.44 (dd, 1H), 8.33 (s, 1H), 7.37 (d, 1H), 7.26 (s, 1H, isochronous with CDCl₃), 7.15-7.21 (m, 1H), 7.01 (m, 1H), 6.94 (m, 1H), 6.76 (m, 1H), 6.58 (d, 1H), 5.99 (s, 2H), 5.80 (br. s, 2H), 1.49 (s, 9H).

Compound I-258

This compound was synthesized as a yellow solid (13%) via a microwave mediated condensation carried out at 100° C. of Compound I-107 (1 equiv) with 2-bromo-2-methylpropanoyl bromide (10 equiv) and N,N-diisopropylethylamine (4.5 equiv) in a (1:1) solution of dichloromethane/dimethylformamide. Purification was carried out by flash chromatography (0-5% methanol in dichloromethane) of the crude solid obtained after water and dichloromethane workup.

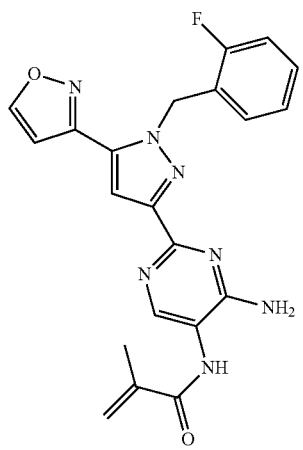 [SMILES: C=C(C)C(=O)Nc1cnc(-c2cc(-c3ccon3)n(Cc3ccccc3F)n2)nc1N]

¹H NMR (400 MHz, CDCl₃) δ 8.43 (d, 1H), 8.26 (s, 1H), 7.51-7.59 (m, 1H), 7.38 (s, 1H), 7.15-7.20 (m, 1H), 7.01 (t, 1H), 6.95 (t, 1H), 6.78 (t, 1H), 6.58 (d, 1H), 5.99 (s, 2H), 5.91 (s, 1H), 5.55 (s, 1H), 5.49 (br s, 2H), 2.08 (s, 3H).

Compound I-230

To a solution of 2-methyl-2-phenoxypropanoic acid (4.5 equiv) in dichloromethane was added oxalyl chloride (6.8 equiv) and catalytic N,N-dimethylformamide. Once gas evolution ceased, this solvent was removed in vacuo. The crude acid chloride was redissolved in dichloromethane and added portion-wise to a suspension of Compound I-107 (1 equiv) in dichloromethane/pyridine (2:1) until the absence of starting material was observed by LC/MS. Following an aqueous ammonium chloride and dichloromethane workup, purification via silica gel chromatography (50% ethyl acetate in hexanes) provided the desired compound as a white solid (71%).

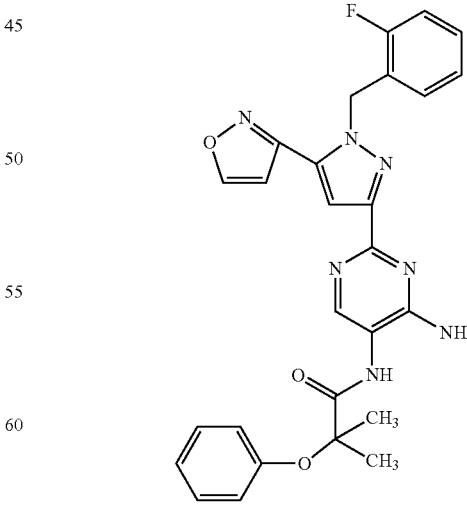

1H NMR (400 MHz, CD₃OD) δ 8.76 (d, 1H), 8.19 (s, 1H), 7.43 (s, 1H), 7.33 (app. t, 2H), 7.27 (m, 1H), 7.12-7.01 (m, 5H), 6.87 (d, 1H), 6.84 (app. t, 1H), 5.96 (s, 2H), 1.65 (s, 6H).

To a solution of 1-methylcyclopentanecarboxylic acid (6.8 equiv) in dichloromethane was added oxalyl chloride (6.1 equiv) and catalytic N,N-dimethylformamide. Once gas evolution ceased, this crude reaction mixture was added portionwise to a suspension of Compound I-107 (1 equiv) in dichloromethane/pyridine (1:1) until the absence of starting material was observed by LC/MS. Following an aqueous ammonium chloride and dichloromethane workup, purification via silica gel chromatography (50-70% ethyl acetate in hexanes) provided the desired compound as an off-white solid (60%).

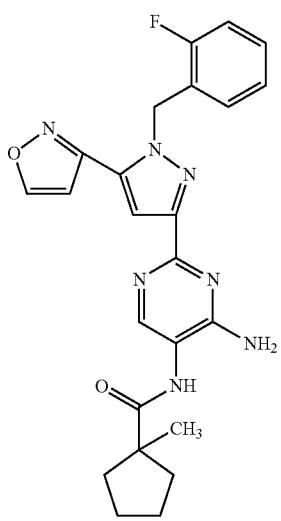 [SMILES: CC1(C(=O)Nc2cnc(-c3cc(-c4ccon4)n(Cc4ccccc4F)n3)nc2N)CCCC1]

1H NMR (400 MHz, CDCl₃) δ 8.43 (d, 1H), 8.20 (s, 1H), 7.38 (s, 1H), 7.24 (s, 1H), 7.18 (m, 1H), 7.01 (m, 1H), 6.95 (app. t, 1H), 6.76 (app. t, 1H), 6.57 (d, 1H), 6.01 (s, 2H), 5.41 (s, 2H), 2.16 (m, 2H), 1.78 (m, 4H), 1.64 (m, 2H), 1.40 (s, 3H).

Compound I-249

A solution of 1-(2-fluorobenzyl)-5-(isoxazol-3-yl)-1H-pyrazole-3-carboximidamide D4 (from Example 7: General Procedure F) (1 equiv) and N-(3-(dimethylamino)-2-((dimethylamino)methyleneamino)allylidene)-N-methylmethanaminium perchlorate (1.5 equiv) were stirred at 60° C. in pyridine for 4 h. Water was added and the product was collected by filtration as a tan solid (80%).

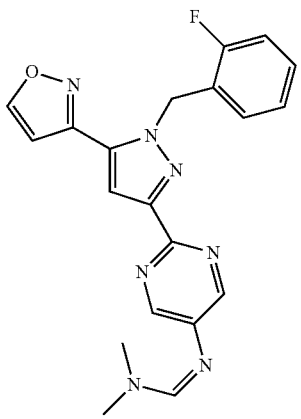 [SMILES: CN(C)/C=N\c1cnc(-c2cc(-c3ccon3)n(Cc3ccccc3F)n2)nc1]

1H NMR (400 MHz, CDCl₃) δ 8.53 (br s, 2H), 8.44 (d, 1H), 7.69 (br s, 1H), 7.40 (s, 1H), 7.18 (m, 1H), 7.02 (app. t, 1H), 6.96 (app. t, 1H), 6.85 (app. t, 1H), 6.60 (d, 1H), 6.01 (s, 2H), 3.14 (s, 6H).

Compound I-144

Compound I-144 was synthesized as a tan solid (31%) via the condensation of Compound I-107 (1 equiv) with cyclopropanecarbonyl chloride (1.3 equiv) in a solution of dichloromethane/pyridine (2:1). Purification was carried out by washing the crude solid obtained after aqueous ammonium chloride and ethyl acetate workup with diethyl ether.

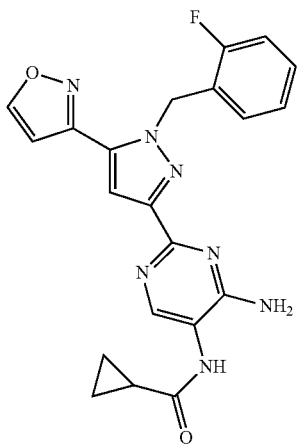 [SMILES: Nc1nc(-c2cc(-c3ccon3)n(Cc3ccccc3F)n2)ncc1NC(=O)C1CC1]

1H NMR (400 MHz, CD₃OD) δ 8.76 (s, 1H), 8.34 (s, 1H), 7.42 (s, 1H), 7.28-7.24 (m, 1H), 7.11-7.01 (m, 2H), 6.87-6.82 (m, 2H), 5.96 (s, 2H), 1.88-1.81 (m, 1H), 1.10-0.96 (m, 2H), 0.94-0.89 (m, 2H).

Compound I-165

Compound I-165 was synthesized as a white solid (81%) via the condensation of Compound I-107 (1 equiv) with isobutyryl chloride (2.8 equiv) in a solution of dichloromethane/pyridine (2:1). Purification was carried out using silica gel chromatography (0-10% methanol in dichloromethane) following an aqueous ammonium chloride and ethyl acetate workup.

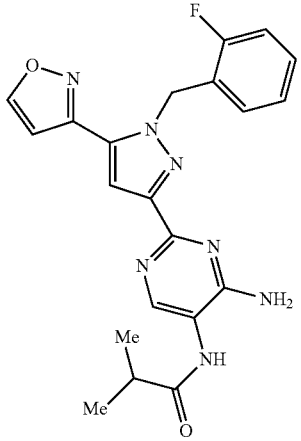 [SMILES: CC(C)C(=O)Nc1cnc(-c2cc(-c3ccon3)n(Cc3ccccc3F)n2)nc1N]

1H NMR (400 MHz, CD₃OD) δ 8.76 (d, 1H), 8.31 (s, 1H), 7.42 (s, 1H), 7.29-7.24 (m, 1H), 7.11-7.06 (m, 1H), 7.03 (t, 1H), 6.87 (d, 1H), 6.86-6.82 (m, 1H), 5.96 (s, 2H), 2.71 (quint, 1H), 1.24 (d, 6H).

Compound I-284

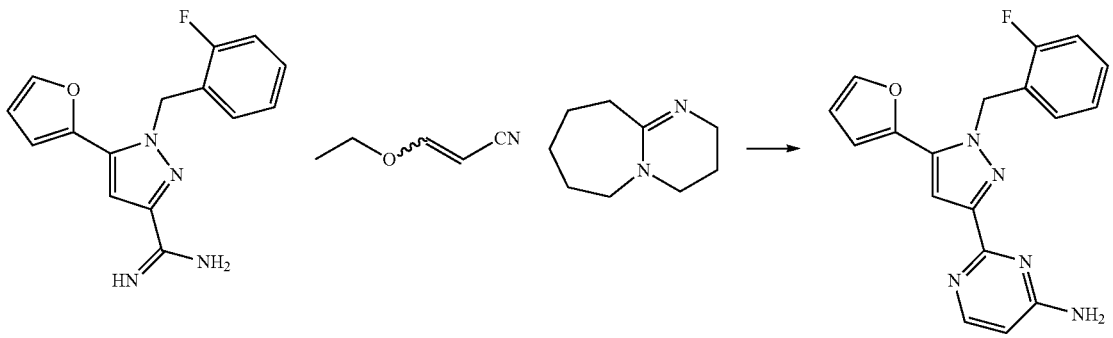

A solution of D4 (from Example 7: General Procedure F) (where $R^c$=2-furyl, and $(J^B)$n=2-fluoro) (811 mg, 1 equiv), 3-ethoxyacrylnitrile (1.39 g, 5 equiv) and DBU (430 μL, 1 equiv) was stirred at 90° C. in toluene for 24 h. The solvent was removed in vacuo and purification by silica gel chromatography (0 to 40% 7:1 Acetonitrile:methanol in dichloromethane) gave 167 mg (17%) of the desired compound as off-white solid.

$^1$H NMR (400 MHz, CDOD) 8.30 (s, 1H), 7.44-7.42 (m, 1H), 7.27 (s, 1H), 7.23-7.16 (m, 1H), 7.08-7.00 (m, 1H), 6.99-6.94 (m, 1H), 6.84-6.79 (m, 1H), 6.47-6.40 (m, 2H), 6.34 (d, 1H), 5.78 (s, 2H), 5.20 (bs, 2H).

Compound I-146

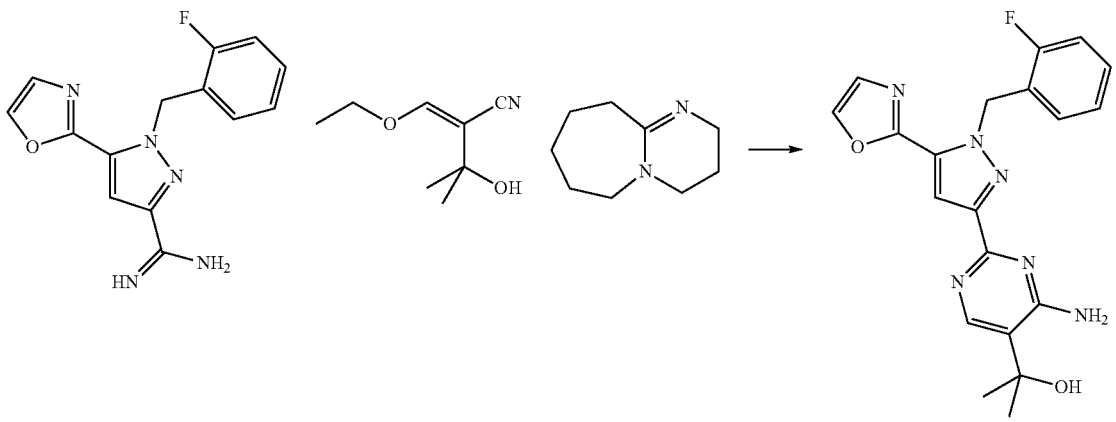

A solution of D4 (from Example 7: General Procedure F) (where $R^c$=2-oxazolyl, and $(J^B)$n=2-fluoro) (150 mg, 1 equiv), (Z)-2-(ethoxymethylene)-3-hydroxy-3-methylbutanenitrile (300 mg, 2 equiv) and DBU (147 L, 1 equiv) was stirred at 90° C. in ethanol for 24 h. The solvent was removed in vacuo and purification by silica gel chromatography (0-50% acetone in hexanes) gave 15.0 mg (3%) of the desired compound as a white solid.

$^1$H NMR (400 MHz, CDOD$_3$) 8.07 (s, 1H), 8.01 (s, 1H), 7.55-7.53 (m, 1H), 7.32 (s, 1H), 7.31-7.23 (m, 1H), 7.14-7.00 (m, 2H), 6.88 (m, 1H), 6.11 (s, 2H), 1.61 (s, 6H).

Compound I-303

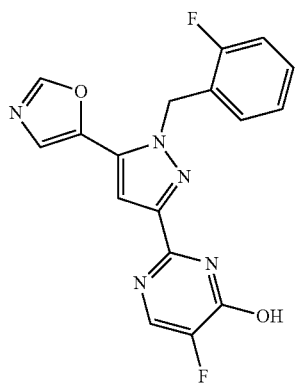 [SMILES: Oc1nc(-c2cc(-c3cnco3)n(Cc3ccccc3F)n2)ncc1F]

A solution of D4, (from Example 7: General Procedure F) (where R$^c$=5-oxazolyl, and (J$^B$)n=2-fluoro) (1 equiv) and ethyl 3-(dimethylamino)-2-fluoroacrylate (3 equiv) was stirred at 85° C. in ethanol for 5 h. The solvent was removed in vacuo and purification by silica gel chromatography (0-50% 7:1 acetonitrile:methanol in dichloromethane) delivered the desired compound as a yellow solid (5%).

$^1$H NMR (400 MHz, DMSO-d6) δ 13.25 (bs, 1H), 8.55 (s, 1H), 8.12 (s, 1H), 7.62 (s, 1H), 7.36-7.30 (m, 1H), 7.31 (s, 1H), 7.20 (t, 1H), 7.12 (dt, 1H), 7.08-7.04 (m, 1H), 5.66 (s, 2H) ppm.
Compound I-302

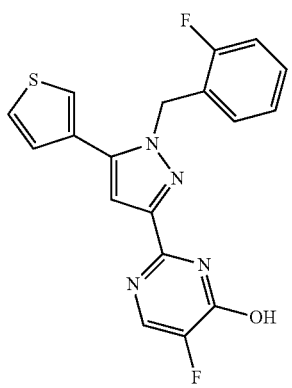 [SMILES: Oc1nc(-c2cc(-c3ccsc3)n(Cc3ccccc3F)n2)ncc1F]

A solution of D4, from Example 7: General Procedure F (where R$^c$=3-thiophenyl, and (J$^B$)n=2-fluoro) (1 equiv) and ethyl 3-(dimethylamino)-2-fluoroacrylate (3 equiv) was stirred at 85° C. in ethanol for 3 h. The solvent was removed in vacuo and purification by silica gel chromatography (0-100% ethyl acetate in dichloromethane) delivered the desired compound as an off-white solid (13%).

$^1$H NMR (400 MHz, CD$_3$OD) δ 8.01 (s, 1H), 7.55-7.52 (m, 2H), 7.33-7.27 (m, 1H), 7.18 (dd, 1H), 7.11-7.06 (m, 1H), 7.06 (s, 1H), 6.95-6.90 (m, 1H), 5.60 (s, 2H) ppm.
Compound I-296

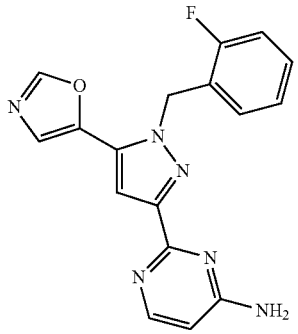 [SMILES: Nc1ccnc(-c2cc(-c3cnco3)n(Cc3ccccc3F)n2)n1]

This compound was synthesized as a pink solid (58% yield over 4 steps) following General Procedure D using 5-acetyloxazole en route to the required ethyl 1-(2-fluorobenzyl)-5-(oxazol-2-yl)-1H-pyrazole-3-carboxylate starting unit. Pyridine was used as solvent in the cyclization reaction.

$^1$H NMR (400 MHz, CDCl$_3$) δ 8.33 (d, 1H), 7.91 (s, 1H), 7.34 (s, 1H), 7.28-7.19 (m, 1H), 7.13 (s, 1H), 7.08-7.02 (m, 1H), 7.01-6.96 (m, 1H), 6.82 (t, 1H), 6.37 (d, 1H), 5.75 (s, 2H), 5.12 (bs, 2H) ppm.
Compound I-297

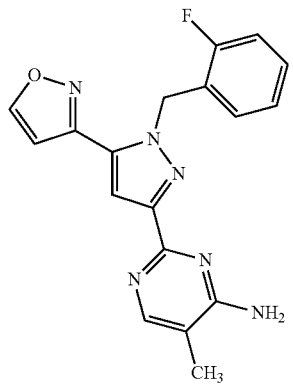

This compound was synthesized as an off-white solid (2% yield over 4 steps) following General Procedure D using 3-acetylisoxazole en route to the required ethyl 1-(2-fluorobenzyl)-5-(isoxazol-3-yl)-1H-pyrazole-3-carboxylate starting unit. Cyclization with 3-bromo-2-methylacrylonitrile (3 equiv) was conducted in toluene at 120° C. with one equivalent of 1,8-diazabicyclo[5.4.0]undec-7-ene.

LRMS Calcd for C$_{27}$H$_{19}$FN$_8$O$_4$ [M+H]+351.13, observed 351.1.
Compound I-309

This was synthesized as a solid (1.3% yield over 3 steps) following General Procedure A using 2-acetyloxazole and methylpyrimidine-2-carboxylate in step 1 and 2-fluorobenzyl bromide in step 3.

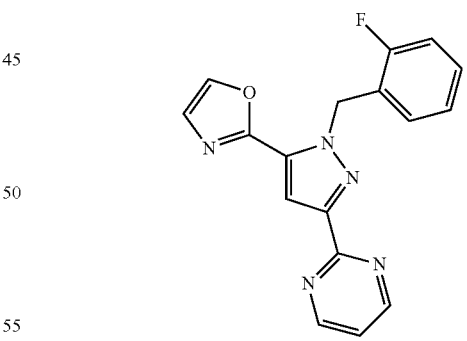

$^1$H NMR (400 MHz, CDCl$_3$) δ 8.82 (d, 2H), 7.67 (d, 2H), 7.26-7.15 (m, 3H), 7.04-6.99 (m, 1H), 6.97-6.93 (m, 1H), 6.86-6.83 (m, 1H), 6.15 (s, 2H).
Compound I-307

This compound was synthesized as a yellow oil (44% yield over 3 steps) following General Procedure A using 1-cyclobutylethanone and methylpyrimidine-2-carboxylate in step 1 and 2-fluorobenzyl bromide in step 3.

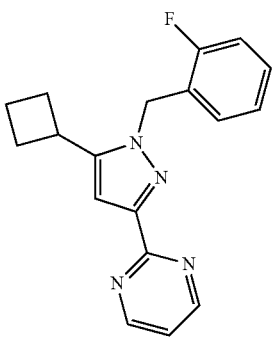 [SMILES: Fc1ccccc1Cn1nc(-c2ncccn2)cc1C1CCC1]

¹H NMR (400 MHz, CDCl₃) δ 8.80 (d, 2H), 7.26-7.17 (m, 2H), 7.08-6.98 (m, 3H), 6.89-6.86 (m, 1H), 5.44 (s, 2H), 3.44-3.36 (quint, 1H), 2.29-2.21 (m, 2H), 2.16-2.06 (m, 2H), 2.03-1.84 (m, 2H).

Compound I-305

This compound was synthesized as a yellow solid (1.3% yield over 3 steps) following General Procedure A using 5-acetyl isoxazole and methylpyrimidine-2-carboxylate in step 1 and 2-fluorobenzyl bromide in step 3. Base and solvent used in step 3 were sodium hydride (1.1 equiv) and N,N-dimethylformamide, respectively.

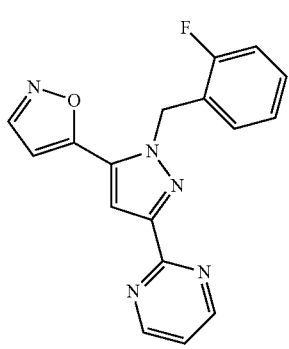 [SMILES: Fc1ccccc1Cn1nc(-c2ncccn2)cc1-c1ccno1]

¹H NMR (400 MHz, CDCl₃) δ 8.84 (d, 2H), 8.28 (m, 1H), 7.54 (s, 1H), 7.28-7.20 (m, 2H), 7.08-7.03 (m, 1H), 6.99 (t, 1H), 6.92-6.90 (m, 1H), 6.40 (m, 1H), 5.86 (s, 2H).

Compounds I-313 and I-308

2-Bromo-6-(1-(2-fluorobenzyl)-3-(pyridin-2-yl)-1H-pyrazol-5-yl)pyridine

I-313 and 2-Bromo-6-(1-(2-fluorobenzyl)-5-(pyridin-2-yl)-1H-pyrazol-3-yl)pyridine (I-308) were synthesized as a off-white solid (12% yield over 3 steps) and an yellow solid (12% yield over 3 steps) respectively following General Procedure A using 1-(6-bromopyridin-2-yl)ethanone, and methyl picolinate in step 1 and 2-fluorobenzyl bromide in step 3.

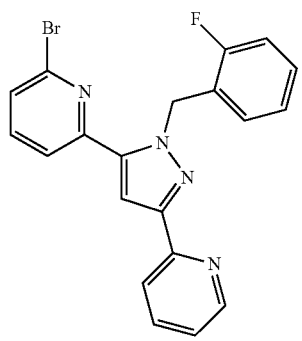 [SMILES: Fc1ccccc1Cn1nc(-c2ccccn2)cc1-c1cccc(Br)n1]

¹H NMR (400 MHz, CDCl₃) δ 8.64 (d, 1H), 8.05 (d, 1H), 7.74 (m, 1H), 7.60 (d, 1H), 7.56 (app. t, 1H), 7.37 (d, 1H), 7.36 (s, 1H), 7.23 (m, 1H), 7.18 (m, 1H), 7.02 (m, 1H), 6.96 (app. t, 1H), 6.91 (m, 1H), 6.08 (s, 2H) ppm.

MS: [M+H]=409 and 411.

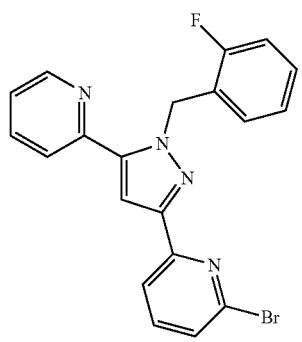 [SMILES: Fc1ccccc1Cn1nc(-c2cccc(Br)n2)cc1-c1ccccn1]

¹H NMR (400 MHz, CDCl₃) δ 8.60 (d, 1H), 8.00 (d, 1H), 7.73 (m, 1H), 7.67 (d, 1H), 7.57 (app. t, 1H), 7.39 (d, 1H), 7.37 (s, 1H), 7.21 (m, 1H), 7.15 (m, 1H), 6.99 (m, 1H), 6.94 (m, 1H), 6.86 (app. t, 1H), 6.12 (s, 2H) ppm.

MS: [M+H]=409 and 411.

The Following Compounds were Made Via General Procedure A, p.53. Only Structural and NMR Data are Included Compound I-310

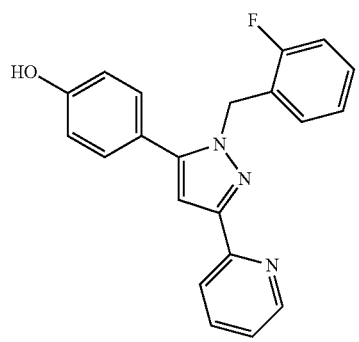

¹H NMR (400 MHz, CDCl₃) 8.63 (ddd, 1H), 8.01 (ddd, 1H), 7.74 (ddd, 1H), 7.22-7.25 (m, 2H), 7.16-7.21 (m, 2H), 7.03-7.05 (m, 1H), 6.98-7.01 (m, 1H), 6.95 (s, 1H), 6.90-6.94 (m, 1H), 6.83-6.86 (m, 2H), 5.45 (s, 2H).

Compound I-311

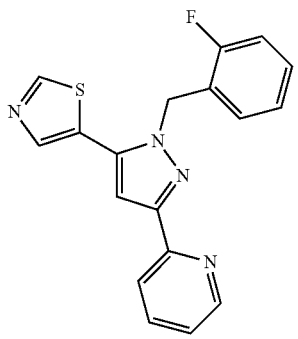 [SMILES: Fc1ccccc1Cn1nc(-c2ccccn2)cc1-c1cncs1]

¹H NMR (400 MHz, CDCl₃) 8.84 (s, 1H), 8.64-8.66 (m, 1H), 7.99-8.01 (m, 1H), 7.84 (s, 1H), 7.74 (ddd, 1H), 7.22-7.29 (m, 2H), 7.17 (s, 1H), 7.02-7.09 (m, 2H), 6.85-6.89 (m, 1H), 5.58 (s, 2H).

Compound I-306

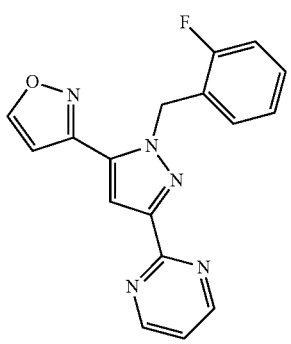

¹H NMR (400 MHz, CDCl₃) 8.82 (d, 2H), 7.45-7.46 (m, 1H), 7.34 (s, 1H), 7.17-7.19 (m, 2H), 7.02-7.07 (m, 1H), 6.96-6.99 (m, 1H), 6.85-6.89 (m, 1H), 6.48 (d, 1H), 6.42-6.44 (m, 1H), 5.00 (s, 2H).

Compound I-285

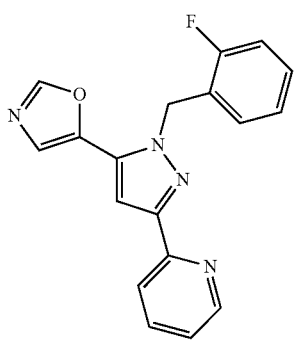 [SMILES: Fc1ccccc1Cn1nc(-c2ccccn2)cc1-c1cnco1]

¹H NMR (400 MHz, CDCl₃) 8.59-8.60 (m, 1H), 7.92-7.94 (m, 1H), 7.87 (s, 1H), 7.69-7.73 (m, 1H), 7.16-7.23 (m, 3H), 7.13 (br. s, 1H), 6.95-7.03 (m, 2H), 6.86-6.88 (m, 1H), 5.63 (s, 2H).

Compound I-294

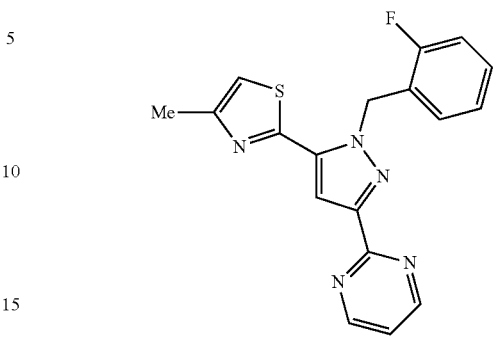

¹H NMR (400 MHz, CDCl₃) 8.83 (d, 2H), 7.49 (s, 1H), 7.24 (t, 2H), 7.13-7.18 (m, 1H), 6.87-7.02 (m, 3H), 6.15 (s, 2H), 2.43 (d, 3H).

Example 11

General Procedure H

This general procedure, described below, may be used to synthesize various compounds, such as Compound I-195.

Compound I-195

To a suspension of 3-(3-(pyrimidin-2-yl)-1H-pyrazol-5-yl) isoxazole (intermediate 8, 73.9 mg, 0.347 mmol) and cesium carbonate (181 mg, 0.555 mmol) in acetonitrile (2 mL) was added 1-(bromomethyl)-2-fluorobenzene (0.059 mL, 0.485 mmol). The suspension was heated to 60° C. for 1 h, at which point the solution had turned faint yellow. LCMS analysis indicated the absence of the starting material. The heterogenous solution was filtered, concentrated, and purified by silica gel chromatography (EtOAc/hex 10-100%). The compound above is the more polar isomer of the alkylation of the central pyrazole. The product was a colorless solid (23%).

¹H NMR (400 MHz, CDCl₃) δ 8.83 (d, 2H), 8.45 (d, 1H), 7.47 (s, 1H), 7.24 (t, 1H), 7.20-7.15 (m, 1H), 7.02 (td, 1H), 6.96 (td, 1H), 6.84 (td, 1H), 6.59 (d, 1H), 6.03 (s, 2H).

The Following Compounds were Synthesized
According to General Procedure H

Compound I-198

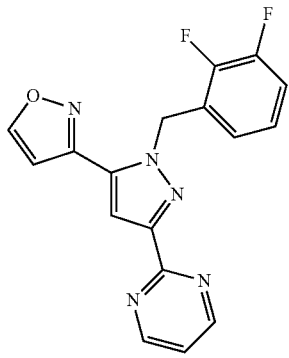 [SMILES: Fc1cccc(Cn2nc(-c3ncccn3)cc2-c2ccon2)c1F]

General Procedure H was used to synthesize Compound I-198. The alkylation was performed with 1-(bromomethyl)-2,3-difluorobenzene. The compound above is the more polar isomer of the alkylation of the central pyrazole. The product was a colorless solid (19%). $^1$H NMR (400 MHz, CDCl$_3$) δ 8.84 (d, 2H), 8.47 (d, 1H), 7.47 (s, 1H), 7.26 (t, 1H), 7.06-6.98 (m, 1H), 6.93-6.86 (m, 1H), 6.65-6.59 (m, 2H), 6.06 (s, 2H).

Compound I-199

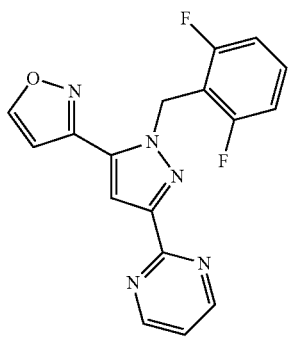 [SMILES: Fc1cccc(F)c1Cn1nc(-c2ncccn2)cc1-c1ccon1]

General Procedure H was used to synthesize Compound I-199. The alkylation was performed with 2-(bromomethyl)-1,3-difluorobenzene. The compound above is the more polar isomer of the alkylation of the central pyrazole. The product was a colorless solid (20%). $^1$H NMR (400 MHz, CDCl$_3$) δ 8.80 (d, 2H), 8.50 (d, 1H), 7.38 (s, 1H), 7.23-7.16 (m, 2H), 6.85-6.78 (m, 2H), 6.65 (d, 1H), 6.07 (s, 2H).

Compound I-200

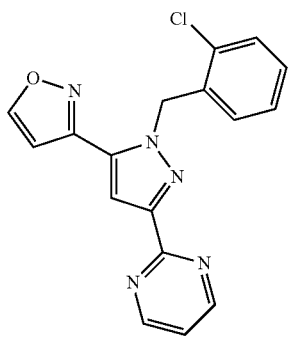

General Procedure H was used to synthesize Compound I-200. The alkylation was performed with 1-(bromomethyl)-2-chlorobenzene. The compound above is the more polar isomer of the alkylation of the central pyrazole. The product was a colorless solid (21%). $^1$H NMR (400 MHz, CDCl$_3$) δ 8.84 (dd, 2H), 8.45 (dd, 1H), 7.51 (d, 1H), 7.36 (dt, 1H), 7.27-7.24 (m, 1H), 7.15 (t, 1H), 7.06 (t, 1H), 6.60-6.55 (m, 2H), 6.05 (s, 2H).

Compound I-201

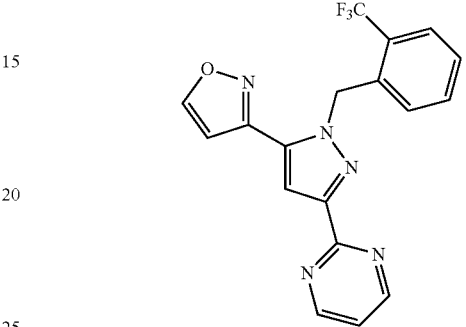

General Procedure H was used to synthesize Compound I-201. The alkylation was performed with 1-(bromomethyl)-2-(trifluoromethyl)benzene. The compound above is the more polar isomer of the alkylation of the central pyrazole. The product is a colorless solid (17%). $^1$H NMR (400 MHz, CDCl$_3$) δ 8.85 (d, 2H), 8.44 (d, 1H); 7.69-7.65 (m, 1H), 7.54 (s, 1H), 7.34-7.25 (m, 3H), 6.59 (d, 1H), 6.55-6.52 (m, 1H), 6.21 (s, 2H).

Compound I-202

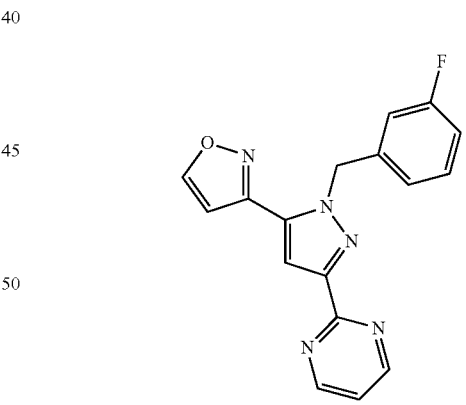

General Procedure H was used to synthesize Compound I-202. The alkylation was performed with 1-(bromomethyl)-3-fluorobenzene. The compound above is the more polar isomer of the alkylation of the central pyrazole. The product was a colorless solid (20%). $^1$H NMR (400 MHz, CDCl$_3$) δ 8.83 (d, 2H), 8.46 (d, 1H), 7.44 (s, 1H), 7.25-7.19 (m, 2H), 7.07 (dd, 1H), 6.96 (dt, 1H), 6.90 (td, 1H), 6.59 (d, 1H), 5.96 (d, 2H).

Compound I-204

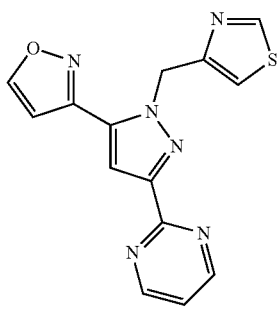 [SMILES: c1cnc(-c2cc(-c3ccon3)n(Cc3cscn3)n2)nc1]

General Procedure H was used to synthesize Compound I-204. The alkylation was performed with 4-(chloromethyl)thiazole hydrochloride. The compound above is the more polar isomer of the alkylation of the central pyrazole. The product was a yellow solid (23%).

$^1$H NMR (400 MHz, CDCl$_3$) δ 8.84 (d, 2H), 8.75 (d, 1H), 8.48 (d, 1H), 7.49 (s, 1H), 7.25 (t, 1H), 7.04 (d, 1H), 6.69 (d, 1H), 6.13 (s, 2H).

Compound I-208

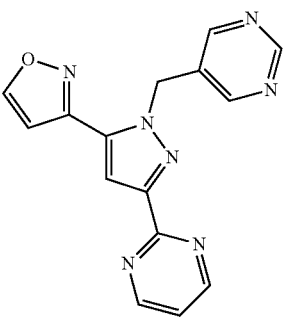 [SMILES: c1cnc(-c2cc(-c3ccon3)n(Cc3cncnc3)n2)nc1]

General Procedure H was used to synthesize Compound I-208. The alkylation was performed with 5-(chloromethyl)pyrimidine. The compound above is the more polar isomer of the alkylation of the central pyrazole. The product is a colorless solid (5.6%). $^1$H NMR (400 MHz, CDCl$_3$) δ 9.12 (s, 1H), 8.85 (d, 2H), 8.80 (s, 2H), 8.50 (dd, 1H), 7.48 (s, 1H), 7.28 (t, 1H), 6.65 (dd, 1H), 6.02 (s, 2H).

Compound I-221

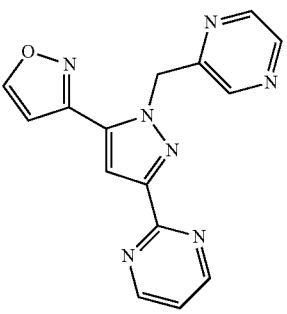 [SMILES: c1cnc(-c2cc(-c3ccon3)n(Cc3cnccn3)n2)nc1]

General Procedure H was used to synthesize Compound I-221: The alkylation was performed with 2-(chloromethyl)pyrazine. The compound above is the more polar isomer of the alkylation of the central pyrazole. The product was a tan solid (63%). $^1$H NMR (400 MHz, CDCl$_3$) δ 8.81 (d, 2H), 8.47 (dd, 1H), 8.44 (d, 1H), 8.41 (d, 1H), 8.26 (d, 1H), 7.50 (s, 1H), 7.23 (t, 1H), 6.66 (d, 1H), 6.15 (s, 2H).

Compound I-207

Step 1: Synthesis of the Protected Alcohol

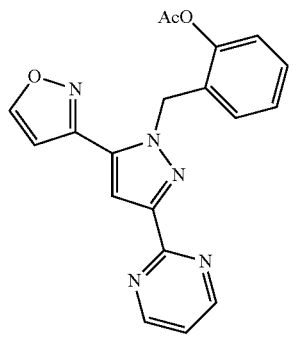

General Procedure H was used to synthesize 2-((5-(isoxazol-3-yl)-3-(pyrimidin-2-yl)-1H-pyrazol-1-yl)methyl)phenyl acetate. The alkylation was performed with 2-(chloromethyl)phenyl acetate. The compound above is the more polar isomer of the alkylation of the central pyrazole. The product was a colorless solid (56%).

$^1$H NMR (400 MHz, CDCl$_3$) δ 8.79 (d, 2H), 8.39 (d, 1H), 7.41 (s, 1H), 7.24-7.18 (m, 2H), 7.07-7.02 (m, 3H), 6.49 (d, 1H), 5.91 (s, 2H), 2.33 (s, 3H).

Step 2: Hydrolysis

Compound I-207 was synthesized as a white solid (60%) via the hydrolysis of 2-((5-(isoxazol-3-yl)-3-(pyrimidin-2-yl)-1H-pyrazol-1-yl)methyl)phenyl acetate (1 equiv) with lithium hydroxide monohydrate (2.0 equiv) in a solution of THF/methanol/water (3:1:1). Purification was carried out by: (i) acidifying the crude reaction mixture with 1N HCl; (ii) concentration to near dryness in vacuo; and (iii) precipitation of the desired compound in a 3:1 mixture of diethyl ether and water followed by filtration.

$^1$H NMR (400 MHz, DMSO-d6) 9.77 (bs, 1H), 9.09 (d, 1H), 8.87 (d, 2H), 7.67 (s, 1H), 7.46 (t, 1H), 7.25 (d, 1H), 7.07 (ddd, 1H), 6.83 (dd, 1H), 6.66 (ddd, 1H), 6.48 (dd, 1H), 5.78 (s, 2H) ppm.

Compound I-261

Compound I-261 was synthesized as a white solid (42%) via a microwave mediated condensation carried out at 150° C. between 1-(2-fluorobenzyl)-5-(isoxazol-3-yl)-1H-pyrazole-3-carboximidamide (1 equiv) and diethyl malonate (15 equiv). Purification was carried out by first diluting the reaction mixture with a mixture of dichloromethane/methanol (1:1) followed by filtration and washing of the crude solid with a (1:1) dichloromethane/methanol mixture.

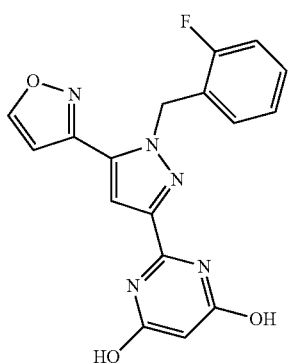 [SMILES: Oc1cc(O)nc(-c2cc(-c3ccon3)n(Cc3ccccc3F)n2)n1]

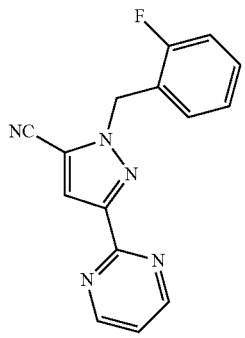

¹H NMR (400 MHz, DMSO-d₆) δ 9.13 (d, 1H), 7.60 (s, 1H), 7.31-7.37 (m, 1H), 7.19-7.24 (m, 1H), 7.16 (d, 1H), 7.12 (dt, 1H), 6.99 (dt, 1H), 5.89 (s, 2H), 5.34 (s, 1H).

Compound I-283

Compound I-283 was synthesized as a white solid (17%) in a two-step process starting from Compound I-270. In the first step, Compound I-270 (1 equiv) was reacted with phosphoryl chloride (25 equiv) and N,N-diisopropylethylamine (1.5 equiv) to afford the intermediate 2,4-chloro-3-nitropyrimidine compound. This crude solid was isolated following an aqueous sodium bicarbonate and dichloromethane workup. The second step was carried out by treatment of the crude intermediate with 7N ammonia in methanol (20 equiv) at 50° C. The solid was obtained by filtration and washing of the residue with methanol.

A solution of 1-(2-fluorobenzyl)-3-(pyrimidin-2-yl)-1H-pyrazole-5-carboxylic acid, intermediate 8 (100 mg, 1 equiv), triethylamine (51 µL, 1.1 equiv), ammonium chloride (27 mg, 1.5 equiv) and propylphosphonic anhydride [50 wt % in ethyl acetate] (1.0 mL, 5.0 M) was heated to 65° C. for 3 days. The mixture was poured into ethyl acetate (100 ml) and washed with saturated solution of sodium bicarbonate (50 ml×2). The organic layer was dried, filtered, and evaporated to give oil. Purification by column chromatography (0 to 80% ethyl acetate in hexanes) gave 19 mg of the desired product (19%) as a yellow solid.

¹H NMR (400 MHz, CDCl₃) δ 8.83 (s, 1H), 8.82 (s, 1H), 7.59 (s, 1H), 7.36-7.29 (m, 1H), 7.28-7.26 (m, 1H), 7.25-7.21 (m, 1H), 7.14-7.11 (m, 1H), 7.11-7.08 (m, 1H), 5.70 (s, 2H).

Compound I-295

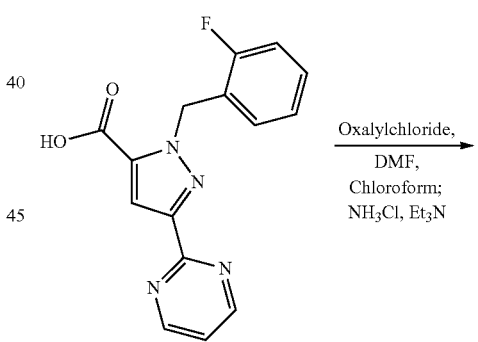

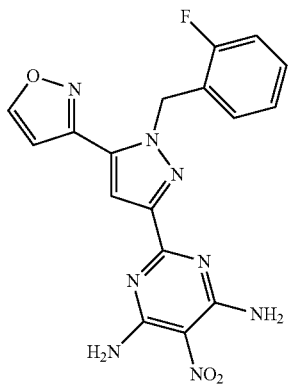 [SMILES: Nc1nc(-c2cc(-c3ccon3)n(Cc3ccccc3F)n2)nc(N)c1[N+](=O)[O-]]

¹H NMR (400 MHz, DMSO-d₆) δ 9.11 (d, 1H), 8.65 (br s, 3H), 7.42 (s, 1H), 7.30-7.35 (m, 1H), 7.20-7.25 (m, 1H), 7.18 (d, 1H), 7.11 (dt, 1H), 6.84 (dt, 1H), 5.89 (s, 2H).

Compound I-293

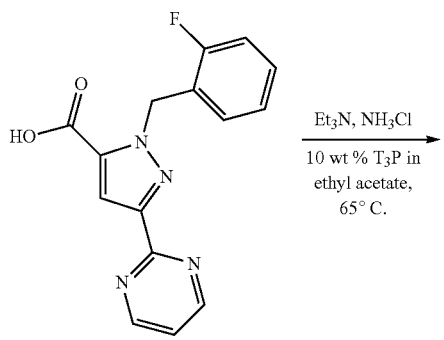

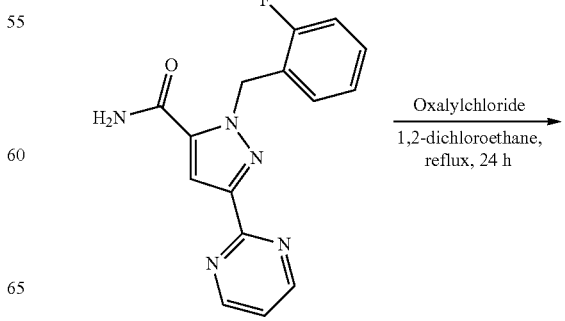

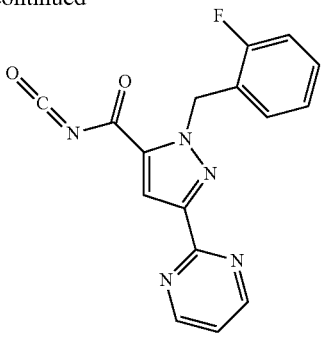

TMS-diazomethane, Acetonitrile, rt, 1 h.

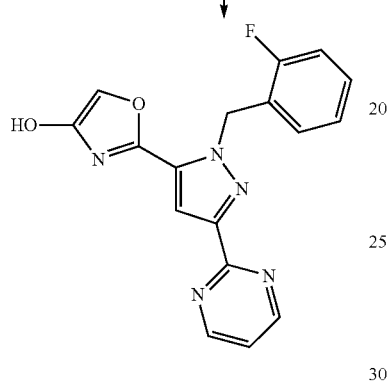

Step 1: Synthesis of 1-(2-fluorobenzyl)-3-(pyrimidin-2-yl)-1H-pyrazole-5-carboxamide To a mixture of 1-(2-fluorobenzyl)-3-(pyrimidin-2-yl)-1H-pyrazole-5-carboxylic acid, intermediate 9 (133 mg, 1 equiv) and oxalyl chloride (60 μL, 1.5 equiv) in chloroform (2.2 ml), was added DMF (3 μL, 0.1 equiv). The mixture was allowed to stir at room temperature and until the bubbling ceased. Then, to this mixture, was added a solution of 0.5 M ammonia in dioxane (2.7 ml, 3.0 equiv). The mixture was stirred at room temperature for 1 h. It was concentrated under vacuum. The resulting residue was suspended in ethyl acetate (200 ml) and washed with saturated solution of sodium bicarbonate (50 ml×2). The organic layer was washed with brine (10 ml), dried, filtered and evaporated to give 120 mg of 1-(2-fluorobenzyl)-3-(pyrimidin-2-yl)-1H-pyrazole-5-carboxamide (91%) as an orange solid.

$^1$H NMR (400 MHz, CDCl$_3$) δ 8.83 (d, 2H), 7.59 (s, 1H), 7.39-7.21 (m, 3H), 7.19-7.26 (m, 2H), 5.69 (s, 2H).

Step 2: Synthesis of 1-(2-fluorobenzyl)-3-(pyrimidin-2-yl)-1H-pyrazole-5-carbonyl isocyanate A mixture of 1-(2-fluorobenzyl)-3-(pyrimidin-2-yl)-1H-pyrazole-5-carboxamide (120 mg, 1 equiv) and oxalyl chloride (106 μl, 3 equiv) in 1,2-dichloroethane (2.0 ml) was heated to reflux for 24 h. The mixture was cooled to room temperature and purified by column chromatography (0 to 100% ethyl acetate in hexanes) to give 68 mg of 1-(2-fluorobenzyl)-3-(pyrimidin-2-yl)-1H-pyrazole-5-carbonyl isocyanate (52% yield) as a brown solid.

$^1$H NMR (400 MHz, CDCl$_3$) δ 8.82 (bs, 2H), 7.93 (s, 1H), 7.39-7.21 (m, 3H), 7.12-6.71 (m, 2H), 5.82 (s, 2H).

Step 3: Synthesis of Compound I-295

To a solution of 1-(2-fluorobenzyl)-3-(pyrimidin-2-yl)-1H-pyrazole-5-carbonyl isocyanate (68 mg, 1 equiv) in acetonitrile (1.0 ml), was added 2.0 M solution of TMS-diazomethane in diethyl ether (126 μl, 1.2 equiv). Exothermic process was observed. The mixture was stirred at room temperature for 30 min. The mixture was concentrated under vacuum. It was purified by column chromatography (0 to 100% ethyl acetate in hexanes) to give 24 mg of the title compound (33% yield) as a brown solid.

$^1$H NMR (400 MHz, CDCl$_3$) δ 8.84 (d, 2H), 7.42 (s, 1H), 7.30-7.19 (m, 2H), 7.09-6.98 (m, 2H), 6.91-6.85 (m, 2H), 6.05 (s, 2H).

Compound I-274

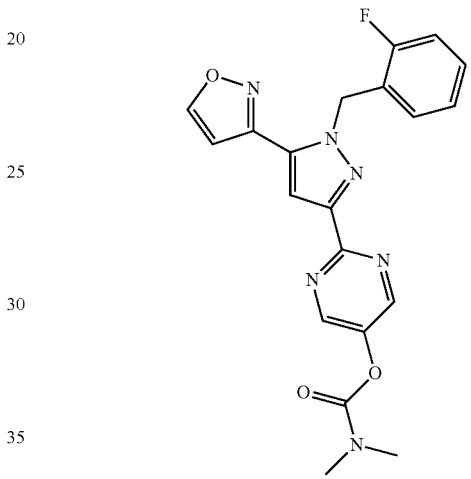

This compound was synthesized as an off-white solid (72%) via the sodium hydride (1.75 equiv, 60% in dispersion oil)-mediated condensation of 1-255 (1 equiv) with dimethylcarbamic chloride (1 equiv). Purification was carried out via washing residual solid with diethyl ether following an aqueous ammonium chloride and dichloromethane workup (and subsequent concentration of organics).

$^1$H NMR (400 MHz, DMSO-d6) δ 9.07 (d, 1H), 8.75 (s, 2H), 7.66 (s, 1H), 7.34-7.27 (m, 1H), 7.26 (d, 1H), 7.22-7.17 (m, 1H), 7.09 (dt, 1H), 6.90 (dt, 1H), 5.90 (s, 2H), 3.07 (s, 3H), 2.92 (s, 3H) ppm.

Compound I-304

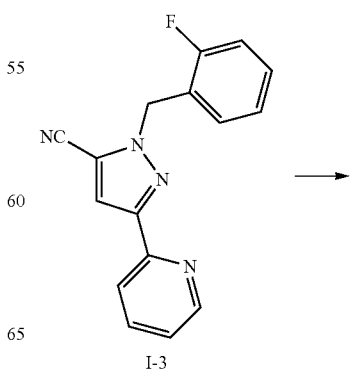

I-3

-continued

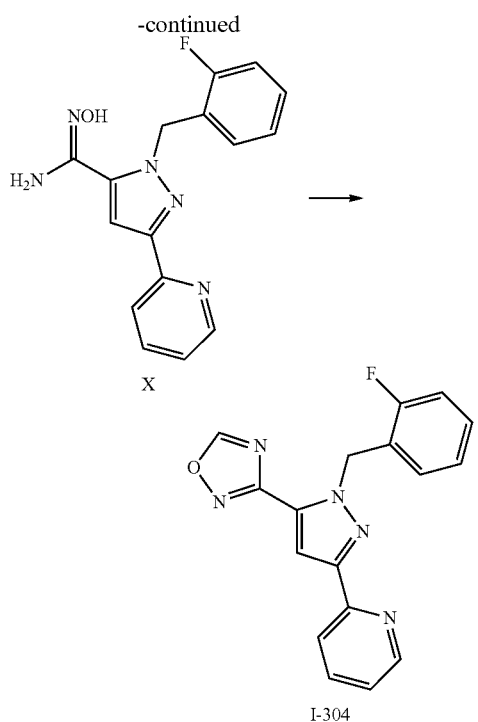

X

I-304

To a solution of I-3 (6.1 mg, 0.02 mmol) and potassium carbonate (12.1 mg, 0.09 mmol) in ethanol (438 μL) was added hydroxylamine hydrochloride (4.6 mg, 0.07 mmol). The solution was heated to 80° C. for 4 h and then cooled to room temperature, diluted ethyl acetate, and the solids were removed by filtration. The solvent was removed in vacuo to give intermediate X, which was suspended in trimethyl orthoformate (200 μl, 1.8 mmol) and treated with catalytic p-toluenesulfonic acid monohydrate (0.2 mg, 0.8 μmol). The vial was heated to 100° C. for 1.5 h. The solvent was removed in vacuo and the crude residue was purified by silica gel chromatography (0-100% ethyl acetate in hexanes) to deliver I-304 as a white solid (35% yield, two steps).

$^1$H NMR (400 MHz, CDCl$_3$) δ 8.76 (s, 1H), 8.68-6.66 (m, 1H), 8.01-7.99 (m, 1H), 7.75 (dt, 1H), 7.68 (s, 1H), 7.26-7.19 (m, 2H), 7.07-7.03 (m, 1H), 6.99 (t, 1H), 6.87-6.84 (m, 1H), 6.02 (s, 2H).

Example 12

General Procedure K

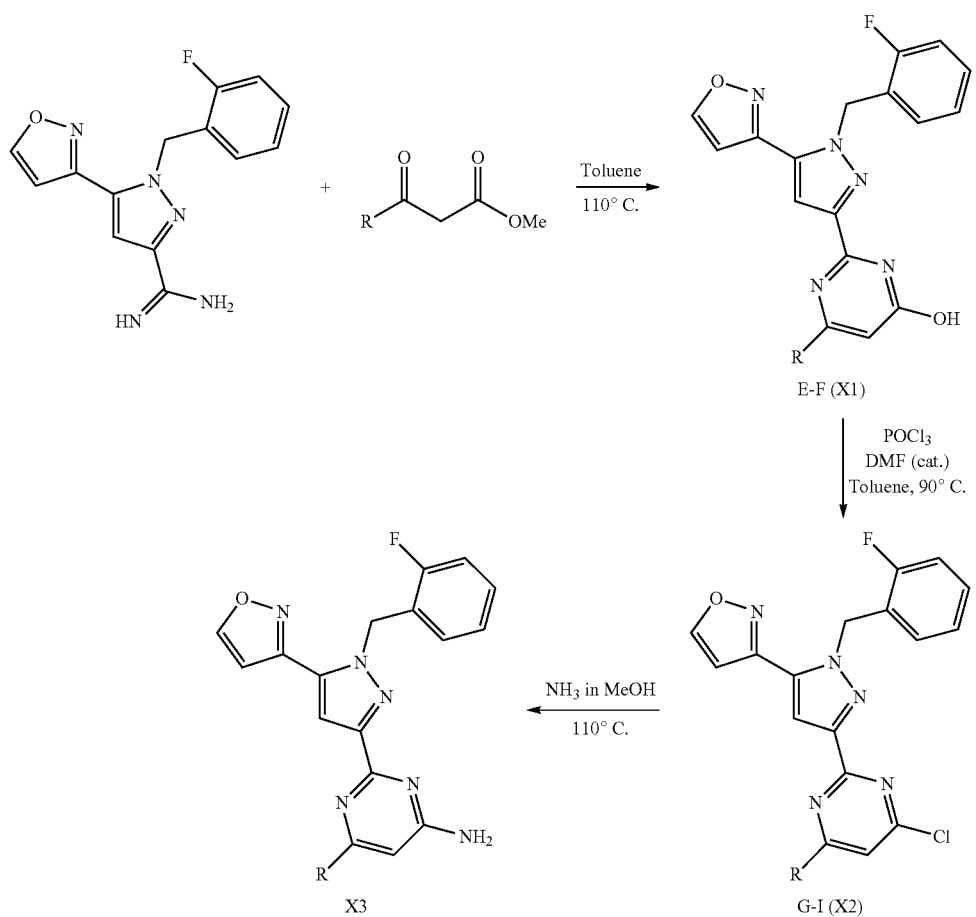

Step 1:

A solution of the requisite 1-(2-fluorobenzyl)-5-(isoxazol-3-yl)-1H-pyrazole-3-carboximidamide (1 equiv) and appropriate β-ketoester (1 equiv) in toluene was heated to 110° C. until consumption of starting material was complete. Evaporation of the solvent in vacuo, followed by purification via silica gel chromatography using the appropriate solvents, gave the desired pyrimidine X1.

Step 2:

To a solution of X1 in toluene was added phosphoryl chloride (2.4 equiv), followed by a catalytic amount of N,N-dimethylformamide. The solution was heated to 90° C. until complete consumption of starting material was observed. The resulting suspension was partitioned between water and ethyl acetate. The layers were separated and the aqueous layer was extracted with ethyl acetate. The organics were combined, dried over magnesium sulfate, filtered, and the solvent was removed in vacuo to give the crude residue. Purification by silica gel chromatography using the appropriate solvent system delivered the intermediate aryl chloride X2.

Step 3:

Conversion to the desired aminopyrimidine X3 was achieved by treating chloride X2 with 7N ammonia in methanol (100-150 equiv) and heating the solution to 110° C. for 4 h. The solvent was removed in vacuo and purification of the crude residue by silica gel chromatography (methanol in dichloromethane) provided the desired aminopyrimidine X3.

The Following Compounds were Prepared According to General Procedure K

Compound I-298

Compound I-298 was prepared according to the first step of General Procedure K using methyl acetoacetate. Purification by silica gel chromatography (50-100% ethyl acetate in hexanes) provided the desired product as a white solid (49% yield).

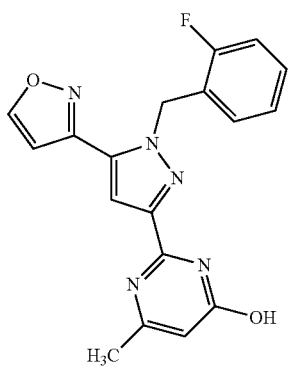 [SMILES: Cc1cc(O)nc(-c2cc(-c3ccon3)n(Cc3ccccc3F)n2)n1]

$^1$H NMR (400 MHz, CDCl$_3$) δ 9.94 (br s, 1H), 8.51 (d, 1H), 7.30-7.23 (m, 2H), 7.08-7.03 (m, 3H), 6.61 (d, 1H), 6.22 (s, 1H), 5.89 (s, 2H), 2.33 (s, 3H).

Compound I-300

This compound was prepared according to the first step of General Procedure K using 1.25 equivalents of methyl 3-oxo-3-(pyridin-3-yl)propanoate. Purification by silica gel chromatography (0-5% methanol in dichloromethane) provided the desired product as a white solid (52% yield).

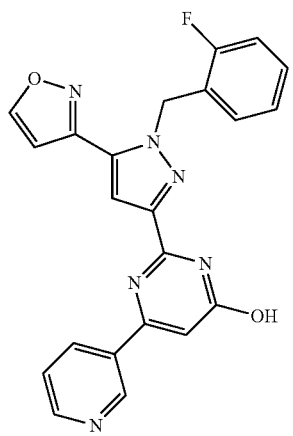

$^1$H NMR (400 MHz, CDCl$_3$) δ 10.12 (br s, 1H), 9.35 (s, 1H), 8.74-8.72 (d, 1H), 8.54 (d, 1H), 8.38 (d, 1H), 7.55-7.50 (m, 1H), 7.42 (s, 1H), 7.32-7.26 (m, 1H), 7.10-7.04 (m, 3H), 6.84 (s, 1H), 6.68 (d, 1H), 5.92 (s, 2H).

Compound I-273

Compound I-273 was prepared according to the second step of General Procedure K. Purification by silica gel chromatography (20-30% ethyl acetate in hexanes) provided the desired product as a white solid (67% yield).

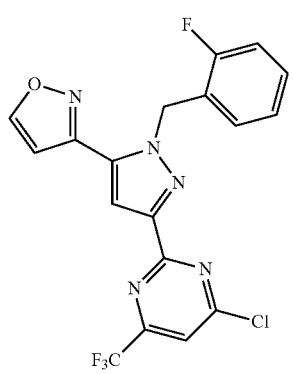

$^1$H NMR (400 MHz, CDCl$_3$) δ 8.46 (d, 1H), 7.57 (s, 1H), 7.53 (s, 1H), 7.23-7.17 (m, 1H), 7.05-7.00 (m, 1H), 6.96 (t, 1H), 6.83-6.79 (m, 1H), 6.61 (d, 1H), 6.04 (s, 2H).

Compound I-299

Compound I-299 was prepared according to the second step of General Procedure K. Purification by silica gel chromatography (20-70% ethyl acetate in hexanes) provided the desired product as a white solid (82% yield).

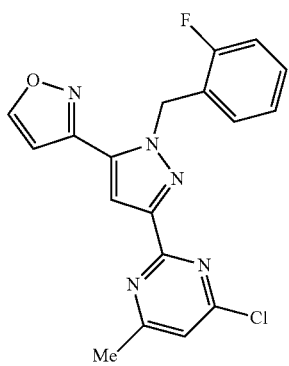 [SMILES: Cc1cc(Cl)nc(-c2cc(-c3ccon3)n(Cc3ccccc3F)n2)n1]

¹H NMR (400 MHz, CDCl₃) δ8.41 (m, 1H), 7.45 (s, 1H), 7.16-7.10 (m, 2H), 6.99-6.95 (m, 1H), 6.90 (t, 1H), 6.76-6.72 (m, 1H), 6.55 (m, 1H), 6.01 (s, 2H), 2.56 (s, 3H).

Compound I-301

This compound was prepared according to the second step of General Procedure K. Purification by silica gel chromatography (100% ethyl acetate followed by 10% methanol in dichloromethane) provided the desired product as a white solid (43% yield).

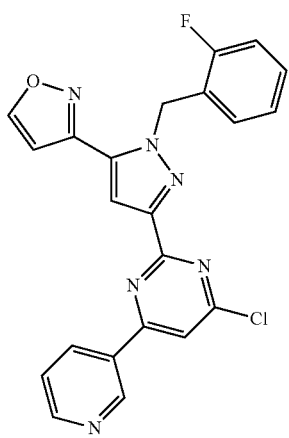 [SMILES: Fc1ccccc1Cn1nc(-c2nc(Cl)cc(-c3cccnc3)n2)cc1-c1ccon1]

¹H NMR (400 MHz, CDCl₃) δ9.36 (d, 1H), 8.77 (dd, 1H), 8.51-8.47 (m, 2H), 7.68 (s, 1H), 7.56 (s, 1H), 7.52-7.48 (m, 1H), 7.24-7.17 (m, 1H), 7.05-7.01 (m, 1H), 6.99-6.95 (m, 1H), 6.87-6.83 (m, 1H), 6.63 (d, 1H), 6.04 (s, 2H).

Example 13

General Procedure M (Amination)

The following compounds were made utilizing the following amination conditions

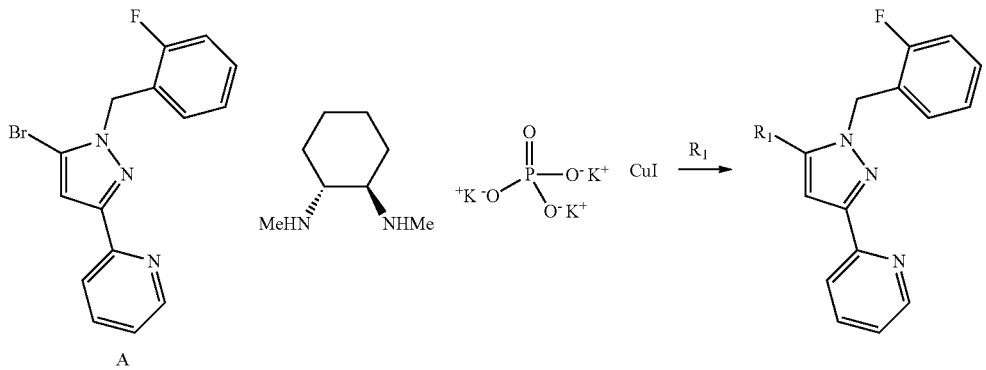

Compound I-286

To a stirring solution of A, (2-(5-bromo-1-(2-fluorobenzyl)-1H-pyrazol-3-yl)pyridine (1 equiv)) in Dioxane was added N1,N2-dimethylcyclohexane-1,2-diamine (0.1 equiv), potassium phosphate (2 equiv), copper(I) iodide (0.1 equiv) and R₁, 1H-pyrazole (1 equiv). The reaction was stirred 16 hr at 110° C. After concentration, product was afforded by both silica gel chromatography as a solid (7.66%).

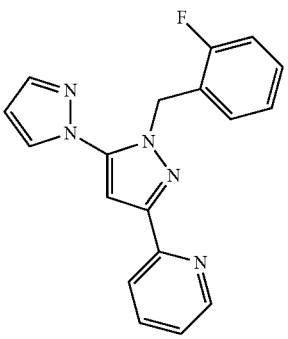 [SMILES: Fc1ccccc1Cn1nc(-c2ccccn2)cc1-n1cccn1]

¹H NMR (400 MHz, CDCl₃) 8.56-8.57 (m, 1H), 7.93-7.95 (m, 1H), 7.69-7.70 (m, 1H), 7.65-7.69 (m, 1H), 7.54-7.55 (m, 1H), 7.11-7.17 (m, 2H), 6.92-6.96 (m, 3H), 6.91- (s, 1H), 6.36-6.37 (m, 1H), 5.55 (s, 2H).

Compound I-287

To a stirring solution of A, (2-(5-bromo-1-(2-fluorobenzyl)-1H-pyrazol-3-yl)pyridine (1 equiv.)) in Dioxane was added N1,N2-dimethylcyclohexane-1,2-diamine (0.1 equiv), potassium phosphate (2 equiv), copper(I) iodide (0.1 equiv) and R₁, azetidine (1 equiv). The reaction was stirred 16 hr at 110° C. After concentration, product was afforded by both silica gel chromatography as a solid (6.65%).

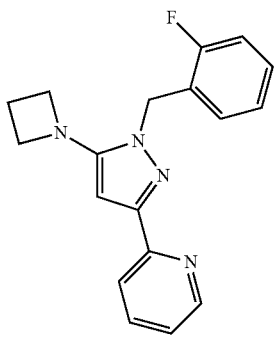

¹H NMR (400 MHz, CDCl₃) 8.62-8.63 (m, 1H), 7.93-7.95 (m, 1H), 7.70 (ddd, 1H), 7.47 (d, 1H), 7.29-7.32 (m, 1H), 7.16-7.20 (m, 2H), 7.07-7.12 (m, 1H), 6.90 (d, 1H), 5.45 (s, 2H), 3.79 (t, 2H), 3.69 (t, 2H), 2.36-2.41 (m, 2H).

Compound I-288

To a stirring solution of A, (2-(5-bromo-1-(2-fluorobenzyl)-1H-pyrazol-3-yl)pyridine (1 equiv.)) in Dioxane was added N1,N2-dimethylcyclohexane-1,2-diamine (0.1 equiv), potassium phosphate (2 equiv), copper(I) iodide (0.1 equiv) and R₁, pyrrolidine (1 equiv). The reaction was stirred 16 hr at 110° C. After concentration, product was afforded by both silica gel chromatography as a solid (16.82%).

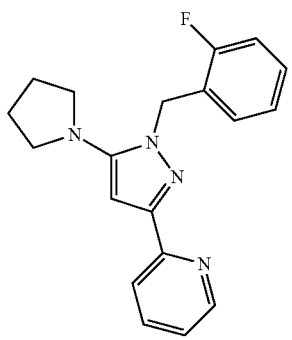 [SMILES: Fc1ccccc1Cn1nc(-c2ccccn2)cc1N1CCCC1]

¹H NMR (400 MHz, CDCl₃) 8.61 (ddd, 1H), 7.95 (ddd, 1H), 7.68 (ddd, 1H), 7.16-7.25 (m, 2H), 7.01-7.07 (m, 2H), 6.93-6.97 (m, 1H), 6.92 (s, 1H), 5.43 (s, 2H), 3.09-3.13 (m, 4H), 1.87-1.90 (m, 4H).

Compound I-289

To a stirring solution of A, (2-(5-bromo-1-(2-fluorobenzyl)-1H-pyrazol-3-yl)pyridine (1 equiv.)) in Dioxane was added N1,N2-dimethylcyclohexane-1,2-diamine (0.1 equiv), potassium phosphate (2 equiv), copper(I) iodide (0.1 equiv) and R₁, 1,2,4-pyrazole (1 equiv). The reaction was stirred 16 hr at 110° C. After concentration, product was afforded by both silica gel chromatography as a solid (2.68%).

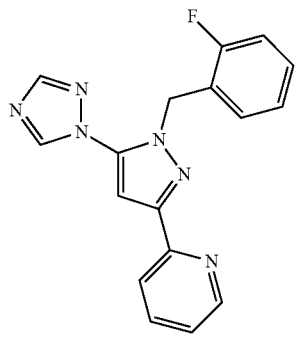 [SMILES: Fc1ccccc1Cn1nc(-c2ccccn2)cc1-n1cncn1]

¹H NMR (400 MHz, CDCl₃) 8.63 (ddd, 1H), 8.24 (s, 1H), 8.17 (s, 1H), 8.01 (ddd, 1H), 7.75 (ddd, 1H), 7.09-7.28 (m, 1H), 7.09 (s, 1H), 7.05-7.06 (m, 1H), 6.97-7.02 (m, 3H), 5.54 (s, 2H).

Example 14

General Procedure O

The following compounds were made utilizing the following procedure

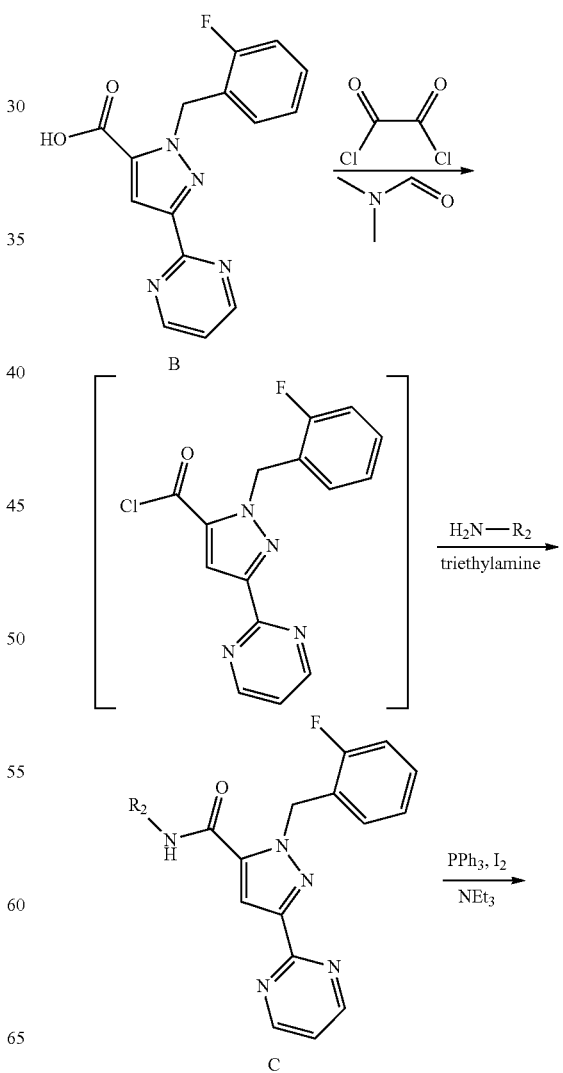

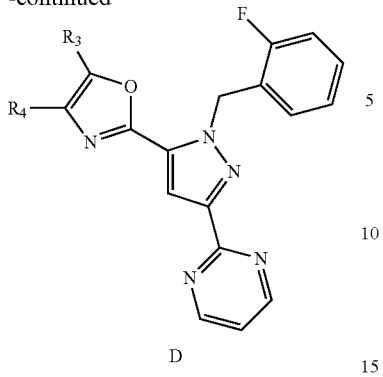

D

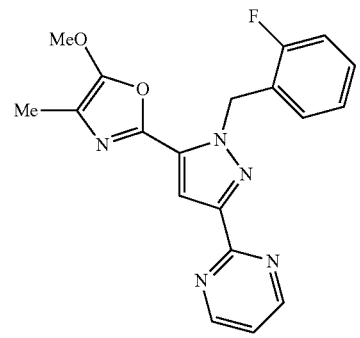

¹H NMR (400 MHz, CDCl₃) 8.82 (d, 2H), 7.52 (d, 1H), 7.20-7.23 (m, 1H), 7.16-7.19 (m, 1H), 6.94-7.04 (m, 2H), 6.85-6.89 (m, 1H), 6.08 (s, 2H), 3.93 (s, 3H), 2.04 (s, 3H).

Compound I-292

To a solution of B, 1-(2-fluorobenzyl)-3-(pyrimidin-2-yl)-1H-pyrazole-5-carboxylic acid (1 equiv) stirring in DCM was added oxalyl chloride (1.1 equiv) and a catalytic amount of N,N-dimethylformamide. This reaction generated gas and was stirred for 2 hr. The reaction mixture was then concentrated, dried under reduced pressure and subsequently added to a stirring solution of benzene and triethylamine in a 5:1 solution and R₂—NH₂, ethyl 2-aminoacetate to afford C, where R₂ is ethyl acetate. This reaction was purified by silica gel chromatography, concentrated and then subsequently treated with triphenylphosphine (2 equiv), iodine (2 equiv) and triethylamine (4 equiv). After stirring for 16 hr under ambient conditions, the reaction was purified by silica gel chromatography to afford D, where R₃ is ethoxy and R₄ is hydrogen, as desired solid (63.0%).

Compound I-290

To a solution of B, 1-(2-fluorobenzyl)-3-(pyrimidin-2-yl)-1H-pyrazole-5-carboxylic acid (1 equiv) stirring in DCM was added oxalyl chloride (1.1 equiv) and a catalytic amount of N,N-dimethylformamide. This reaction generated gas and was stirred for 2 hr. The reaction mixture was then concentrated, dried under reduced pressure and subsequently added to a stirring solution of benzene and triethylamine in a 5:1 solution and R₂—NH₂, 2-bromoethanamine hydrobromide (2 equiv). The temperature was raised to 90° C. and stirred for 16 hr to afford C, where R₂ is the closed oxazoline. The reaction was concentrated and purified by silica gel chromatography to afford a solid (10.16%).

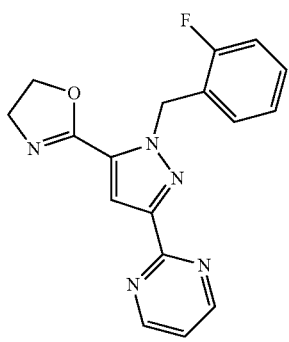 [SMILES: Fc1ccccc1Cn1nc(-c2ncccn2)cc1C1=NCCO1]

¹H NMR (400 MHz, CDCl₃) 8.81 (d, 2H), 7.55 (s, 1H), 7.21 (t, 1H), 7.16-7.18 (m, 1H), 6.96-7.04 (m, 2H), 6.79-6.83 (m, 1H), 6.09 (s, 2H), 4.35 (t, 2H), 4.03 (t, 2H).

Compound I-291

To a solution of B, 1-(2-fluorobenzyl)-3-(pyrimidin-2-yl)-1H-pyrazole-5-carboxylic acid (1 equiv) stirring in DCM was added oxalyl chloride (1.1 equiv) and a catalytic amount of N,N-dimethylformamide. This reaction generated gas and was stirred for 2 hr. The reaction mixture was then concentrated, dried under reduced pressure and subsequently added to a stirring solution of benzene and triethylamine in a 5:1 solution and R₂—NH₂, (S)-methyl 2-aminopropanoate hydrochloride (2 equiv) to afford C, where R₂ is (S)-methyl 2-aminopropane. This reaction was purified by silica gel chromatography, concentrated and then subsequently treated with triphenylphosphine (2 equiv), iodine (2 equiv) and triethylamine (4 equiv). After stirring for 16 hr under ambient conditions, the reaction was purified by silica gel chromatography to afford D, where R₃ is methoxy and R₄ is methyl, as desired solid (38.2%).

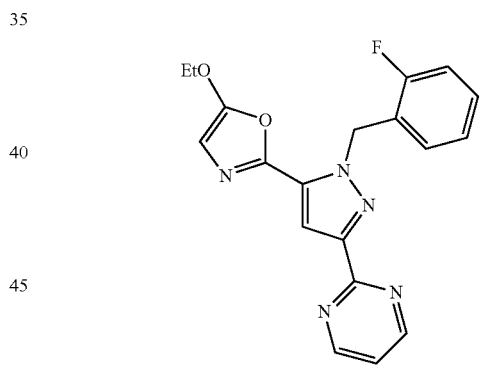

¹H NMR (400 MHz, CDCl₃) 8.82 (d, 2H), 7.53 (s, 1H), 7.23 (t, 1H), 7.15-7.20 (m, 1H), 7.01-7.05 (m, 1H), 6.96 (dt, 1H), 6.83 (dt, 1H), 6.19 (s, 1H), 6.09 (s, 2H), 4.17 (q, 2H), 1.43 (t, 3H).

Example 15

Compounds Prepared by Other Synthetic Methods

Compound I-248

This compound was synthesized as a yellow solid (64%) via a microwave mediated condensation carried out at 220° C. between 1-(2-fluorobenzyl)-5-(isoxazol-3-yl)-1H-pyrazole-3-carboximidamide (1 equiv) and diethyl malonate (6 equiv) in dimethylformamide. Isolation and purification was done by first diluting the reaction mixture with dichloromethane followed by filtration and washing of the crude solid with dichloromethane.

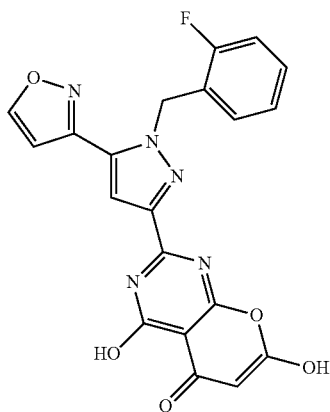 [SMILES: O=c1cc(O)oc2nc(-c3cc(-c4ccon4)n(Cc4ccccc4F)n3)nc(O)c12]

¹H NMR (400 MHz, DMSO-d₆) δ 9.08 (8, 1H), 7.60 (s, 1H), 7.30-7.35 (m, 1H), 7.29 (d, 1H), 7.22 (t, 1H), 7.11 (t, 1H), 6.85 (dt, 1H), 5.92 (s, 2H), 4.93 (s, 1H).

Compound I-261

This compound was synthesized as a white solid (42%) via a microwave mediated condensation carried out at 150° C. between 1-(2-fluorobenzyl)-5-(isoxazol-3-yl)-1H-pyrazole-3-carboximidamide (1 equiv) and diethyl malonate (15 equiv). Purification was carried out by first diluting the reaction mixture with a mixture of dichloromethane/methanol (1:1) followed by filtration and washing of the crude solid with a (1:1) dichloromethane/methanol mixture.

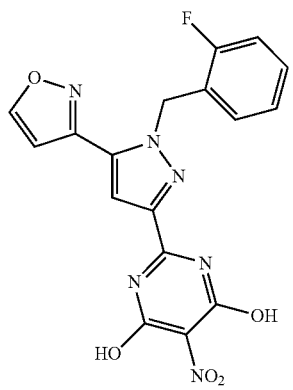

¹H NMR (400 MHz, DMSO-d₆) δ 9.17 (d, 1H), 7.73 (s, 1H), 7.32-7.39 (m, 1H), 7.19-7.24 (m, 1H), 7.13 (dt, 1H), 7.11 (d, 1H), 7.07 (dt, 1H), 5.90 (s, 2H).

Compound I-283

This compound was synthesized as a white solid (17%) in a two-step process starting from Compound I-282. In the first step, Compound I-282 (1 equiv) was reacted with phosphoryl chloride (25 equiv) and N,N-diisopropylethylamine (1.5 equiv) to afford the intermediate 2,4-chloro-3-nitropyrimidine compound. This crude solid was isolated following an aqueous sodium bicarbonate and dichloromethane workup.

The second step was carried out by treatment of the crude intermediate with 7N ammonia in methanol (20 equiv) at 50° C. The solid was obtained by filtration and washing

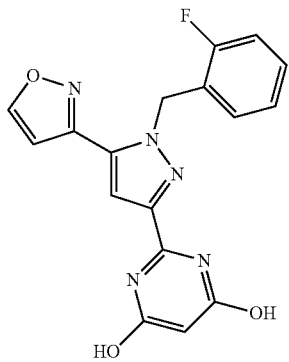 [SMILES: Oc1cc(O)nc(-c2cc(-c3ccon3)n(Cc3ccccc3F)n2)n1]

¹H NMR (400 MHz, DMSO-d₆) δ 9.13 (d, 1H), 7.60 (s, 1H), 7.31-7.37 (m, 1H), 7.19-7.24 (m, 1H), 7.16 (d, 1H), 7.12 (dt, 1H), 6.99 (dt, 1H), 5.89 (s, 2H), 5.34 (s, 1H).

Compound I-282

Compound I-282 was synthesized as a purple solid (63%) via the reaction of Compound I-261 (1 equiv) with fuming, red nitric acid (1.1 equiv) in a solution of trifluororoacetic acid maintained at 0° C. Purification was carried out by diluting the reaction mixture with a 1:1 water/methanol mixture and filtration followed by washing of the crude solid with (1:1) methanol/dichloromethane mixture.

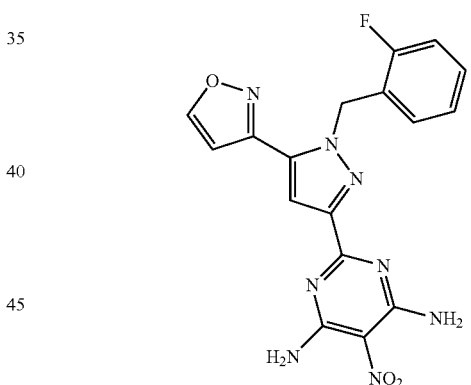

¹H NMR (400 MHz, DMSO-d₆) δ 9.11 (d, 1H), 8.65 (br s, 3H), 7.42 (s, 1H), 7.30-7.35 (m, 1H), 7.20-7.25 (m, 1H), 7.18 (d, 1H), 7.11 (dt, 1H), 6.84 (dt, 1H), 5.89 (s, 2H).

Compound I-262

A suspension of N'-(2-(1-(2-fluorobenzyl)-5-(isoxazol-3-yl)-1H-pyrazol-3-yl)pyrimidin-5-yl)-N,N-dimethylformimidamide Compound I-249 (1 equiv) in methanol-acetic acid (16:1) was treated with hydrazine hydrate (10 equiv) and stirred at room temperature for 18 h. The reaction mixture was concentrated in vacuo. The crude material was redissolved in dichloromethane/iso-propanol (4:1) and washed with saturated sodium bicarbonate solution. A significant amount of insoluble material was removed by filtration. The organic layer was collected, dried over sodium sulfate, filtered, the solvent was removed in vacuo, and purification by silica gel chromatography (50-100% ethyl acetate in hexanes) provided the desired compound as an off-white solid (13%).

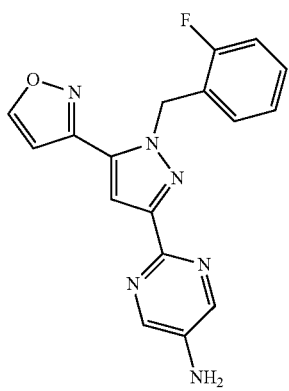

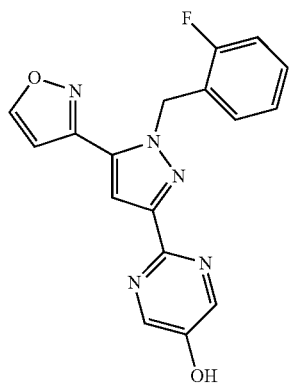

¹H NMR (400 MHz, CDCl₃) δ 8.44 (d, 1H), 8.31 (s, 2H), 7.33 (s, 1H), 7.18 (m, 1H), 7.02 (m, 1H), 6.95 (app. t, 1H), 6.82 (app. t, 1H), 6.58 (d, 1H), 6.00 (s, 2H), 3.81 (br s, 2H).

Compound I-264

This compound was synthesized as a white solid (32%) via the condensation of Compound I-262 (1 equiv) with pivaloyl chloride (1.5 equiv) in a solution of dichloromethane/pyridine (2:1). Saturated ammonium chloride solution was added at the end of the reaction. The crude product was collected by filtration and washed with water and ether. Purification was carried out using silica gel chromatography (60% ethyl acetate in hexanes).

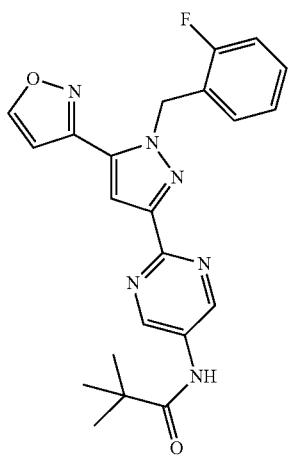

1H NMR (400 MHz, CDCl₃) δ 9.07 (s, 2H), 8.46 (d, 1H), 7.44 (s, 1H), 7.36 (s, 1H), 7.19 (m, 1H), 7.02 (m, 1H), 6.96 (app. t, 1H), 6.83 (app. t, 1H), 6.60 (d, 1H), 6.02 (s, 2H), 1.37 (s, 9H).

Compound I-255

A suspension of N'-(2-(1-(2-fluorobenzyl)-5-(isoxazol-3-yl)-1H-pyrazol-3-yl)pyrimidin-5-yl)-N,N-dimethylformimidamide Compound I-249 (1 equiv) in ethanol and 2N aqueous HCl solution (1:1) was heated at 80° C. for 8 h. The reaction mixture was diluted with water and neutralized with 2N aqueous NaOH solution. Product was collected by filtration as a tan solid (85%).

¹H NMR (400 MHz, DMSO) δ 10.6 (s, 1H), 9.09 (d, 1H), 8.39 (s, 2H), 7.54 (s, 1H), 7.33 (m, 1H), 7.26 (d, 1H), 7.23 (m, 1H), 7.11 (app. t, 1H), 6.91 (app. t, 1H), 5.89 (s, 2H).

Example 16

Biological Activity Measurement by the sGC-HEK-cGMP Assay

A) Assay Run in the Absence of SNP

Human embryonic kidney cells (HEK293), endogenously expressing soluble guanylate cyclase (sGC), were used to evaluate the activity of test compounds. Compounds stimulating the sGC receptor should cause an increase in the intracellular concentration of cGMP. HEK 293 cells were seeded in Dulbecco's Modification of Eagle's Medium supplemented with fetal bovine serum (10% final) and L-glutamine (2 mM final) in a 200 μL volume at a density of 1×10⁵ cells/well in a poly-D-lysine coated 96 well flat bottom plate and grown overnight at 37° C. Medium was aspirated and cells were washed with 1× Hank's Buffered Saline Salt Solution (200 μL). Cells were then incubated for 15 minutes at 37° C. with 0.5 mM 3-isobutyl-1-methylxanthine (200 μL). Test article was then added to the assay mixture (2 μL) and incubated at 37° C. for 10 minutes. After the 10 minute incubation, the assay mixture was aspirated and 0.1M HCl (200 μL) was added to the cells. The plate was incubated at 4° C. for 30 minutes in the 0.1M HCl to stop the reaction and lysed the cells. The plates were then centrifuged at 1,200 g for 5 minutes at room temperature. Supernatants were collected and transferred to a new flat bottom 96 well plate for analysis. Vehicle controls were carried out using DMSO (1%). A known sGC stimulator, BAY 41-2272, was used as the positive control. Samples were diluted with an equal volume of 1 M Ammonium Acetate (pH 7) to neutralize samples for better chromatography. A 2×cGMP standard curve was prepared in 0.1 M HCl and then diluted with an equal volume of 1 M Ammonium Acetate, with the following final concentrations in nM: 1024, 512, 256, 128, 64, 32, 16, 8, 4, 2, 1.cGMP concentrations were determined from each sample using the LC/MS conditions (Table 2 below) and calculated standard curve. $EC_{50}$ values were calculated from concentration-response curves generated with GraphPad Prism Software.

The biological activities of some of the compounds according to Formula I determined with the sGC-HEK assay are summarized in Tables 3A, 3B and 3C below.

TABLE 2

(LC/MS experimental conditions)

| | |
|---|---|
| MS: | Thermo Quantum or Waters LCMS |
| Ion Mode: | ESI+ |
| Scan Type: | MRM |

| Compound: | Transition | Dwell Time (msec) | Collision Energy (V) | Tube Lens | Retention Time (min) |
|---|---|---|---|---|---|
| cGMP | 346 > 152 | 100 | 28 | 139 | 1.0 |

| | |
|---|---|
| HPLC: | Agilent Technologies 1200 Series with CTC Analytics HTS PAL |
| Column: | Thermo Hypersil Gold 2.1 × 50 mm 5 micron particle size |
| Flow Rate: | 400 uL/min |
| Column Temperature: | RT |
| Autosampler Temperature: | 6° C. |
| Injection Volume: | 20 uL |
| Mobile Phases: | A = 98:2 Water:Acetonitrile + 0.1% Formic Acid<br>B = 2:98 Water:Acetonitrile + 0.1% Formic Acid |

| Gradient: | Time (min) | % A | % B |
|---|---|---|---|
| | 0 | 100 | 0 |
| | 0.3 | 30 | 70 |
| | 2.00 | 30 | 70 |
| | 2.01 | 100 | 0 |
| | 4 | 100 | 0 |

B) Assay run with SNP Incubation

Human embryonic kidney cells (HEK293), endogenously expressing soluble guanylate cyclase (sGC), were used to evaluate the activity of test compounds. Compounds stimulating the sGC receptor should cause an increase in the intracellular concentration of cGMP. HEK 293 cells were seeded in Dulbecco's Modification of Eagle's Medium supplemented with fetal bovine serum (10% final) and L-glutamine (2 mM final) in a 200 µL volume at a density of 1×10$^5$ cells/well in a poly-D-lysine coated 96 well flat bottom plate and grown overnight at 37° C. Medium was aspirated and cells were washed with 1× Hank's Buffered Saline Salt Solution (200 µL). Cells were then incubated for 15 minutes at 37° C. with 0.5 mM 3-isobutyl-1-methylxanthine (200 µL). Test article and sodium nitroprusside were then added to the assay mixture (2 µL each) and incubated at 37° C. for 10 minutes. After the minute incubation, the assay mixture was aspirated and 0.1M HCl (200 µL) was added to the cells. The plate was incubated at 4° C. for 30 minutes in the 0.1M HCl to stop the reaction and lysed the cells. The plates were then centrifuged at 1,200 g for 5 minutes at room temperature. Supernatants were collected and transferred to a new flat bottom 96 well plate for analysis. Vehicle controls were carried out using DMSO (1%). A known sGC stimulator, BAY 41-2272, was used as the positive control. Samples were diluted with an equal volume of 1 M Ammonium Acetate (pH 7) to neutralize samples for better chromatography. A 2×cGMP standard curve was prepared in 0.1 M HCl and then diluted with an equal volume of 1 M Ammonium Acetate, with the following final concentrations in nM: 1024, 512, 256, 128, 64, 32, 16, 8, 4, 2, 1. cGMP concentrations were determined from each sample using the LC/MS conditions (Table 2 below) and calculated standard curve. EC$_{50}$ values were calculated from concentration-response curves generated with GraphPad Prism Software.

The biological activities of some of the compounds according to Formula I determined with the sGC-HEK assay with SNP incubation are summarized in Tables 3A, 3B, 4A, 4B, and 5 below.

TABLE 3A

| Compound | HEK WC Assay (fold increase at 10 µM)* | HEK WC Assay (fold increase at 30 µM)* | HEK WC Assay (% Emax at 10 uM/with 10 uM SNP)** | HEK WC Assay (% Emax at 30 uM/with 10 uM SNP)** |
|---|---|---|---|---|
| I-1 | A | C | A | B |
| I-2 | A | B | B | C |
| I-3 | A | D | C | D |
| I-4 | A | D | B | C |
| I-5 | A | A | A | B |
| I-6 | B | C | C | C |
| I-7 | | | A | A |
| I-8 | | | A | A |
| I-9 | | | A | A |
| I-10 | A | A | A | A |
| I-11 | A | A | A | A |
| I-12 | | | A | A |
| I-13 | | | A | A |
| I-14 | | | A | A |
| I-15 | A | A | A | A |
| I-19 | A | A | ND | ND |
| I-20 | A | A | ND | ND |
| I-21 | A | A | A | B |
| I-22 | ND | ND | A | A |
| I-23 | | | A | A |
| I-25 | | | A | B |
| I-26 | | | C | D |
| I-27 | | | C | D |
| I-31 | | | A | B |
| I-32 | A | A | A | A |
| I-33 | B | C | C | D |
| I-34 | A | A | A | A |
| I-35 | | | B | B |
| I-40 | | | A | A |
| I-41 | A | A | A | A |
| I-42 | | | A | B |
| I-43 | | | A | A |
| I-45 | | | C | C |
| I-46 | | | A | A |
| I-47 | | | A | A |
| I-48 | | | A | A |
| I-49 | | | C | D |
| I-50 | | | A | A |
| I-51 | | | A | A |

TABLE 3A-continued

| Compound | HEK WC Assay (fold increase at 10 μM)* | HEK WC Assay (fold increase at 30 μM)* | HEK WC Assay (% Emax at 10 uM/with 10 uM SNP)** | HEK WC Assay (% Emax at 30 uM/with 10 uM SNP)** |
|---|---|---|---|---|
| I-52 |  |  | A | A |
| I-53 |  |  | A | A |
| I-54 |  |  | A | A |
| I-55 |  |  | B | C |
| I-56 |  |  | A | A |
| I-57 |  |  | A | A |
| I-58 |  |  | A | A |
| I-59 |  |  | A | A |
| I-60 |  |  | A | A |
| I-61 |  |  | C | C |
| I-62 |  |  | A | A |
| I-63 |  |  | A | A |
| I-64 |  |  | A | A |
| I-65 |  |  | A | A |
| I-66 |  |  | C | C |
| I-67 |  |  | A | A |
| I-68 |  |  | A | A |
| I-69 |  |  | A | A |

*The compounds were tested at a concentration of 10 or 30 μM. The code for the increase in the sGC receptor activity obtained is: A = no increase to <1 fold increase B = 1 to <2 fold increase C = 2 to <5 fold increase D = 5 to <10 fold increase E = 10 or >10 fold increase
**The code for the sGC receptor activity, expressed as % $E_{max}$ in the presence of 10 uM of SNP (wherein $E_{max}$ = 100% was the activity in the HEK assay obtained with the positive control BAY 41-2272 in the presence 10 uM SNP) obtained is: A = 0 to <10% B = 10 to <20% C = 20 to <40% D = 40 to <60 E = 60 or <80% F = 80 to <100% G = 100 to 120%

TABLE 3B

| Compound | HEK WC Assay in the presence of 10 uM SNP $EC_{50}$ (μM)* |
|---|---|
| I-1 | E |
| I-3 | B |
| I-26 | D |
| I-27 | B |
| I-33 | B |
| I-42 | E |
| I-45 | D |
| I-4 | D |
| I-49 | A |
| I-55 | E |
| I-6 | C |
| I-61 | C |
| I-66 | D |

*The code for the $EC_{50}$ value obtained is: A = 0 to <20 μM B = 20 to <40 μM C = 40 to <60 μM D = 60 to <100 μM E = 100 to <300 μM

TABLE 3C

| Compound | HEK WC Assay (fold increase at 30 μM in the absence of SNP)* | HEK WC Assay (fold increase at 30 μM in the presence of 10 μM SNP)* |
|---|---|---|
| I-244 | D | E |
| I-243 | D | E |
| I-242 | C | D |
| I-241 | D | E |
| I-240 | E | E |
| I-239 | D | E |
| I-238 | E | E |
| I-237 | E | F |
| I-236 | C | E |
| I-235 | E | E |
| I-234 | C | E |
| I-233 | E | F |
| I-232 | C | E |
| I-231 | E | E |
| I-230 | C | E |
| I-229 | C | E |
| I-228 | C | E |
| I-227 | F | F |
| I-226 | E | F |
| I-225 | C | E |
| I-224 | C | E |
| I-223 | C | E |
| I-222 | E | F |
| I-221 | B | C |
| I-220 | D | F |
| I-219 | D | E |
| I-218 | D | E |
| I-217 | D | F |
| I-216 | C | E |
| I-215 | E | F |
| I-214 | D | E |
| I-213 | D | E |
| I-212 | D | E |
| I-211 | D | E |
| I-210 | C | D |
| I-209 | C | E |
| I-208 | B | D |
| I-207 | B | C |
| I-278 | D | E |
| I-206 | E | F |
| I-205 | D | E |
| I-204 | B | C |
| I-203 | B | D |
| I-202 | C | E |
| I-201 | B | B |
| I-200 | B | C |
| I-199 | C | E |
| I-198 | D | E |
| I-197 | C | E |
| I-196 | C | E |
| I-195 | D | E |
| I-194 | C | C |
| I-193 | E | E |
| I-192 | D | E |
| I-191 | C | E |
| I-190 | E | F |
| I-188 | E | F |
| I-187 | D | F |
| I-186 | D | F |
| I-185 | E | E |
| I-184 | E | E |
| I-183 | E | D |
| I-182 | E | E |
| I-181 | E | E |
| I-180 | D | E |
| I-179 | E | E |
| I-178 | E | E |
| I-177 | D | E |
| I-176 | E | E |
| I-175 | E | E |
| I-174 | E | F |
| I-173 | C | D |
| I-172 | E | E |
| I-171 | E | E |
| I-170 | B | B |
| I-169 | C | D |
| I-168 | E | G |
| I-167 | D | G |
| I-166 | D | G |
| I-165 | D | F |
| I-164 | C | E |
| I-163 | C | E |
| I-162 | E | G |
| I-161 | D | F |
| I-160 | C | E |
| I-159 | B | D |
| I-158 | C | E |
| I-154 | B | B |
| I-153 | C | D |
| I-152 | E | E |
| I-151 | C | D |

TABLE 3C-continued

| Compound | HEK WC Assay (fold increase at 30 μM in the absence of SNP)* | HEK WC Assay (fold increase at 30 μM in the presence of 10 μM SNP)* |
|---|---|---|
| I-150 | E | E |
| I-149 | C | D |
| I-148 | D | E |
| I-147 | D | E |
| I-137 | C | D |
| I-126 | E | F |
| I-277 | D | E |
| I-281 | D | E |
| I-125 | D | F |
| I-143 | C | D |
| I-142 | E | F |
| I-124 | E | F |
| I-136 | D | E |
| I-135 | C | D |
| I-134 | B | B |
| I-119 | C | E |
| I-118 | D | E |
| I-123 | B | C |
| I-117 | B | B |
| I-141 | B | C |
| I-300 | B | B |
| I-299 | C | F |
| I-298 | B | C |
| I-296 | C | E |
| I-295 | B | C |
| I-294 | B | D |
| I-293 | C | C |
| I-292 | B | B |
| I-291 | B | B |
| I-290 | B | C |
| I-289 | B | B |
| I-288 | C | C |
| I-287 | B | C |
| I-285 | C | D |
| I-313 | C | C |
| I-308 | B | B |
| I-307 | C | C |
| I-306 | D | E |
| I-304 | C | E |
| I-309 | B | E |
| I-311 | B | C |
| I-310** | B | |

*The compounds were tested at a concentration of 30 μM of the compound in the absence or presence of 10 μM SNP. The code for the increase in the sGC receptor activity obtained is: A = no increase to <1 fold increase B = 1 to <2 fold increase C = 2 to <5 fold increase D = 5 to <10 fold increase E = 10 to <20 fold increase F = 20 to <30 fold increase G = 30 to <40 fold increase
**Compound I-310 was also tested at 10 μm in the absence of SNP, and the code for the fold increase was B.

TABLE 4A

| Compound | HEK WC Assay (% $E_{max}$ at 10 μM/with 10 uM SNP)* | HEK WC Assay (% $E_{max}$ at 30 μM/with 10 uM SNP)* |
|---|---|---|
| I-70 | A | A |
| I-71 | B | B |
| I-72 | C | C |
| I-73 | A | A |
| I-75 | B | C |
| I-79 | A | A |
| I-80 | A | A |
| I-81 | A | A |
| I-82 | B | B |
| I-85 | | G |
| I-86 | D | E |
| I-87 | E | G |
| I-88 | A | A |
| I-89 | A | A |
| I-90 | A | A |
| I-91 | A | B |
| I-92 | C | C |
| I-93 | B | C |
| I-94 | A | A |
| I-95 | B | C |
| I-96 | C | C |
| I-97 | D | D |
| I-98 | C | C |
| I-99 | C | D |
| I-100 | C | D |
| I-101 | E | C |
| I-102 | D | C |
| I-103 | C | C |
| I-104 | D | H |
| I-105 | F | G |
| I-106 | N | N |
| I-107 | E | A |
| I-108 | C | C |
| I-109 | E | E |
| I-110 | E | E |
| I-111 | E | D |
| I-112 | G | F |
| I-113 | C | D |
| I-114 | D | D |
| I-115 | F | E |
| I-116 | C | C |
| I-117 | B | A |
| I-118 | E | D |
| I-119 | H | H |
| I-120 | A | A |
| I-121 | N | N |
| I-122 | C | E |
| I-123 | B | C |
| I-124 | H | E |
| I-125 | F | F |
| I-126 | H | G |
| I-127 | E | E |
| I-128 | E | D |
| I-130 | N | N |
| I-131 | E | D |
| I-132 | D | C |
| I-133 | C | D |
| I-134 | C | D |
| I-135 | A | A |
| I-136 | C | C |
| I-137 | G | C |
| I-138 | D | D |
| I-139 | N | N |
| I-140 | E | D |

*The compounds were tested at a concentration of 10 or 30 μM. The code for the sGC receptor activity, expressed as % $E_{max}$ in the presence of 10 μM SNP (wherein $E_{max}$ = 100% was the activity in the HEK assay obtained with the positive control BAY 41-2272 in the presence of 10 uM SNP) obtained is: A = 0 to <10% B = 10 to <20% C = 20 to <40% D = 40 to <60 E = 60 or <80% F = 80 to <100% G = 100 to <120% H = >120% N or ND = not determined

TABLE 4B

| Compound | HEK WC Assay (% $E_{max}$ at 1 μM with 10 uM SNP)* | HEK WC Assay (% $E_{max}$ at 10 μM with 10 uM SNP)* | HEK WC Assay (% $E_{max}$ at 30 μM with 10 uM SNP)* |
|---|---|---|---|
| I-272 | E | F | F |
| I-274 | C | E | E |
| I-271 | D | E | F |
| I-270 | B | D | E |
| I-282 | A | A | A |
| I-269 | A | A | B |
| I-268 | D | G | F |
| I-267 | C | E | F |
| I-266 | C | E | E |
| I-265 | D | E | F |
| I-264 | C | D | A |
| I-263 | D | G | G |
| I-280 | C | E | G |
| I-262 | C | E | E |
| I-261 | A | A | A |

TABLE 4B-continued

| Compound | HEK WC Assay (% $E_{max}$ at 1 μM with 10 uM SNP)* | HEK WC Assay (% $E_{max}$ at 10 μM with 10 uM SNP)* | HEK WC Assay (% $E_{max}$ at 30 μM with 10 uM SNP)* |
| --- | --- | --- | --- |
| I-260 | F | G | F |
| I-259 | C | E | E |
| I-258 | D | E | E |
| I-252 | D | D | E |
| I-251 | B | C | C |
| I-250 | A | B | B |
| I-249 | C | D | E |
| I-248 | A | A | A |
| I-247 | C | E | F |
| I-246 | E | G | G |
| I-245 | F | G | G |
| I-244 | C | D | D |
| I-243 | D | D | E |
| I-242 | B | C | C |
| I-241 | C | E | D |
| I-240 | E | E | E |
| I-239 | D | E | E |
| I-238 | F | G | G |
| I-237 | F | G | G |
| I-236 | C | E | E |
| I-235 | D | F | E |
| I-234 | C | D | D |
| I-233 | F | F | F |
| I-232 | C | E | E |
| I-231 | E | F | F |
| I-230 | B | C | C |
| I-229 | C | D | C |
| I-228 | B | D | D |
| I-227 | D | E | E |
| I-226 | D | F | E |
| I-225 | A | C | C |
| I-224 | C | D | D |
| I-223 | A | B | B |
| I-222 | C | C | C |
| I-221 | A | A | B |
| I-220 | D | E | E |
| I-219 | C | E | E |
| I-218 | D | D | C |
| I-217 | E | G | |
| I-216 | C | D | D |
| I-215 | F | F | F |
| I-214 | C | D | E |
| I-213 | A | B | C |
| I-212 | E | E | E |
| I-211 | C | C | D |
| I-210 | A | B | C |
| I-209 | B | C | D |
| I-208 | A | B | B |
| I-207 | A | A | A |
| I-278 | B | D | D |
| I-206 | G | G | G |
| I-205 | D | F | F |
| I-204 | A | A | A |
| I-203 | A | B | C |
| I-202 | C | D | D |
| I-201 | A | A | A |
| I-200 | A | A | A |
| I-199 | B | C | D |
| I-198 | D | D | E |
| I-197 | B | D | D |
| I-196 | C | E | F |
| I-195 | D | E | E |
| I-194 | A | C | D |
| I-193 | B | D | E |
| I-192 | C | D | D |
| I-191 | C | D | F |
| I-190 | E | E | E |
| I-189 | E | E | E |
| I-188 | D | E | E |
| I-187 | D | E | E |
| I-186 | E | E | F |
| I-185 | E | F | G |
| I-184 | E | G | F |
| I-183 | E | G | F |
| I-182 | E | F | F |
| I-181 | E | F | H |
| I-180 | D | F | F |
| I-179 | D | E | F |
| I-178 | D | F | E |
| I-177 | D | F | F |
| I-176 | C | E | E |
| I-175 | E | F | G |
| I-174 | E | F | G |
| I-173 | A | D | B |
| I-172 | F | E | F |
| I-171 | E | G | F |
| I-170 | A | A | |
| I-169 | C | D | E |
| I-168 | G | G | G |
| I-167 | E | F | G |
| I-166 | E | F | G |
| I-165 | D | F | G |
| I-164 | | C | C |
| I-163 | | D | D |
| I-162 | | F | E |
| I-161 | D | E | E |
| I-160 | B | D | D |
| I-159 | | C | C |
| I-158 | A | C | C |
| I-157 | | G | F |
| I-156 | | F | E |
| I-155 | | D | E |
| I-154 | | A | B |
| I-153 | | D | E |
| I-152 | | E | D |
| I-151 | | E | E |
| I-150 | | F | F |
| I-149 | | E | F |
| I-148 | | G | G |
| I-147 | | F | E |
| I-146 | | D | D |
| I-145 | | C | C |
| I-312 | C | C | C |
| I-144 | | G | E |
| I-137 | | D | D |
| I-126 | | G | G |
| I-277 | E | F | F |
| I-281 | | E | D |
| I-125 | | F | F |
| I-143 | | D | D |
| I-142 | | G | G |
| I-124 | | G | E |
| I-136 | D | E | C |
| I-135 | | B | B |
| I-134 | | A | A |
| I-119 | | G | G |
| I-118 | | E | D |
| I-123 | | B | C |
| I-273 | | C | C |
| I-117 | | B | A |
| I-141 | | A | A |
| I-301 | | D | E |
| I-299 | | E | E |
| I-298 | | B | C |
| I-297 | | D | F |
| I-296 | | C | E |
| I-295 | | A | B |
| I-294 | | C | C |
| I-293 | | C | C |
| I-292 | | A | A |
| I-291 | | A | A |
| I-290 | | B | C |
| I-289 | | A | A |
| I-287 | | A | A |
| I-286 | | A | B |
| I-285 | | C | C |
| I-284 | | E | E |
| I-313 | | A | A |
| I-308 | | A | A |
| I-307 | | A | A |

TABLE 4B-continued

| Compound | HEK WC Assay (% $E_{max}$ at 1 μM with 10 uM SNP)* | HEK WC Assay (% $E_{max}$ at 10 μM with 10 uM SNP)* | HEK WC Assay (% $E_{max}$ at 30 μM with 10 uM SNP)* |
| --- | --- | --- | --- |
| I-306 | | C | D |
| I-304 | | C | D |
| I-309 | | C | C |
| I-311 | | A | A |
| I-310 | | A | A |

*The compounds were tested at a concentration of 1, 10 or 30 μM. The code for the sGC receptor activity, expressed as % $E_{max}$ in the presence of 10 uM SNP (wherein $E_{max}$ = 100% was the activity in the HEK assay obtained with the positive control BAY 41-2272 in the presence of 10 uM SNP) obtained is: A = 0 to <10% B = 10 to <20% C = 20 to <40% D = 40 to <60% E = 60 to <80% F = 80 to <100% G = 100 to <120% H = >120% Blank cell = not tested

TABLE 5A

| Compound | HEK WC Assay in the presence of 10 uM SNP $EC_{50}$ (μM)* |
| --- | --- |
| I-71 | E |
| I-72 | B |
| I-75 | C |
| I-83 | E |
| I-84 | C |
| I-85 | A |
| I-86 | A |
| I-87 | A |
| I-92 | C |
| I-93 | E |
| I-96 | A |
| I-97 | A |
| I-98 | A |
| I-99 | B |
| I-100 | E |
| I-101 | C |
| I-102 | A |
| I-103 | C |
| I-104 | A |
| I-105 | A |
| I-106 | A |
| I-107 | A |
| I-108 | E |
| I-109 | A |
| I-110 | A |
| I-111 | B |
| I-112 | A |
| I-113 | D |
| I-114 | A |
| I-115 | A |
| I-116 | B |
| I-117 | N |
| I-118 | D |
| I-119 | A |
| I-120 | N |
| I-121 | B |
| I-122 | B |
| I-123 | N |
| I-124 | N |
| I-125 | A |
| I-126 | A |
| I-127 | A |
| I-128 | B |
| I-129 | A |
| I-130 | A |
| I-131 | E |
| I-132 | B |
| I-133 | A |
| I-134 | N |
| I-135 | N |
| I-136 | N |
| I-137 | C |

TABLE 5A-continued

| Compound | HEK WC Assay in the presence of 10 uM SNP $EC_{50}$ (μM)* |
| --- | --- |
| I-138 | N |
| I-139 | A |

*The code for the $EC_{50}$ value in the presence of 10 uM SNP obtained is: A = 0 to <20 μM B = 20 to <40 μM C = 40 to <60 μM D = 60 to <100 μM E = 100 to <300 μM

TABLE 5B

| Compound | HEK WC Assay in the presence of 10 uM SNP $EC_{50}$ (μM)* |
| --- | --- |
| I-272 | A |
| I-274 | A |
| I-271 | A |
| I-270 | A |
| I-282 | H |
| I-269 | E |
| I-268 | A |
| I-267 | A |
| I-266 | A |
| I-265 | A |
| I-264 | F |
| I-263 | A |
| I-280 | A |
| I-262 | A |
| I-261 | F |
| I-260 | A |
| I-259 | A |
| I-258 | A |
| I-252 | A |
| I-251 | B |
| I-250 | E |
| I-249 | A |
| I-248 | G |
| I-247 | A |
| I-246 | A |
| I-245 | A |
| I-244 | B |
| I-243 | A |
| I-242 | D |
| I-241 | A |
| I-240 | A |
| I-239 | A |
| I-238 | A |
| I-237 | A |
| I-236 | A |
| I-235 | A |
| I-234 | A |
| I-233 | A |
| I-232 | A |
| I-231 | A |
| I-230 | D |
| I-229 | B |
| I-228 | B |
| I-227 | A |
| I-226 | A |
| I-225 | D |
| I-224 | A |
| I-223 | E |
| I-222 | C |
| I-220 | A |
| I-219 | A |
| I-218 | B |
| I-217 | A |
| I-216 | A |
| I-215 | A |
| I-214 | A |
| I-213 | D |
| I-212 | A |
| I-211 | B |
| I-210 | D |
| I-209 | B |
| I-208 | E |
| I-207 | H |

TABLE 5B-continued

| Compound | HEK WC Assay in the presence of 10 uM SNP $EC_{50}$ (μM)* |
|---|---|
| I-278 | A |
| I-206 | A |
| I-205 | A |
| I-203 | D |
| I-202 | A |
| I-200 | F |
| I-199 | B |
| I-198 | A |
| I-197 | B |
| I-196 | A |
| I-195 | A |
| I-194 | B |
| I-193 | A |
| I-192 | A |
| I-191 | A |
| I-190 | A |
| I-189 | A |
| I-188 | A |
| I-187 | A |
| I-186 | A |
| I-185 | A |
| I-184 | A |
| I-183 | A |
| I-182 | A |
| I-181 | A |
| I-180 | A |
| I-179 | A |
| I-178 | A |
| I-177 | A |
| I-176 | A |
| I-175 | A |
| I-174 | A |
| I-173 | E |
| I-172 | A |
| I-171 | A |
| I-169 | A |
| I-168 | A |
| I-167 | A |
| I-166 | A |
| I-165 | A |
| I-162 | A |
| I-161 | A |
| I-160 | A |
| I-158 | E |
| I-156 | A |
| I-155 | A |
| I-153 | A |
| I-152 | A |
| I-151 | A |
| I-150 | A |
| I-149 | B |
| I-148 | A |
| I-147 | A |
| I-312 | C |
| I-144 | A |
| I-137 | C |
| I-126 | A |
| I-277 | A |
| I-281 | B |
| I-125 | A |
| I-143 | C |
| I-142 | A |
| I-124 | A |
| I-136 | A |
| I-119 | A |
| I-118 | D |
| I-301 | A |
| I-299 | A |
| I-297 | A |
| I-296 | A |
| I-295 | C |
| I-294 | C |
| I-293 | C |
| I-306 | A |
| I-304 | B |
| I-309 | A |

*The code for the $EC_{50}$ value in the presence of 10 uM SNP obtained is: A = 0 to <20 μM B = 20 to <40 μM C = 40 to <60 μM D = 60 to <100 μM E = 100 to <300 μM F = 300 to <600 μM G = 600 to <900 μM H = 900 to <1,200 μM

Example 17

Biological Activity Measurements by the Purified Human sGC Enzyme Activity Assay Human soluble guanylate cyclase enzyme (hsGC) obtained from Enzo Inc. (P/N: ALX-201-177) was used to evaluate the activity of test compounds. The assay reactions contained 0.1 M Tris (pH 8.0), 0.5 mg/mL BSA (pH 8.0), 2 mM DTT, 2 mM $MgCl_2$, 300 μM GTP, 1 mM 3-isobutyl-1-methylxanthine (IBMX) and 5 ng human soluble guanylate cyclase enzyme. Test compounds in DMSO were then added (2 μL, 10 or 30 μM final concentration) and incubated (200 μL, 96-well plate format) at 37° C. for 30 minutes. The controls were carried out using 2 μL, DMSO. After the 30 minute incubation, the reaction was stopped with the addition of 200 μL of cold methanol. The plate was then centrifuged at 3,200 rpm for 10 minutes at room temperature. Supernatants (200 μL) were collected and transferred to a new 96 well plate for analysis.

An 8 point cGMP (Sigma-Aldrich P/N: G6129) standard curve was prepared in assay buffer ranging from 0.156-20 μM. Samples for the cGMP standard curve were then diluted with an equal volume of methanol resulting in final cGMP concentrations of 0.078-10 μM.

cGMP concentrations in all samples were determined using LC/MS/MS analysis, using the conditions listed in Table 6 below. The cGMP standard curve was generated using GraphPad Prism Software.

Calculations: Specific Activity was determined by the amount of cGMP formed (nmoles) per mg of sGC per min. Enzyme "fold-change" was calculated by dividing Specific Activity for test compounds by Specific Activity of DMSO controls.

TABLE 6

LC/MS/MS method for detection of cGMP

Inlet Method:

| | | | | |
|---|---|---|---|---|
| HPLC: | Waters Acquity | | | |
| Column: | Thermo Hypersile Gold PFP, 2.1 × 30 mm, 3 μm | | | |
| Guard Column: | Thermo Hypersile Gold, 2.1 × 10 mm | | | |
| Column Temp: | 25° C. | | | |
| Flow Rate: | 0.4 mL/min | | | |
| Auto sampler: | Acquity; 6° C. | | | |
| Injection Volume: | 10 uL | | | |
| Mobile Phases: | A = 0.1% Acetic Acid (v/v) in 100% water | | | |
| | B = 0.1% Acetic Acid (v/v) in 100 methanol | | | |
| | Time (min) | % A | % B | Curve |
| Gradient: | 0 | 95 | 5 | 6 |
| | 0.5 | 95 | 5 | 6 |
| | 0.6 | 10 | 90 | 6 |
| | 2.0 | 10 | 90 | 6 |
| | 2.1 | 95 | 5 | 6 |
| | 4 | (end) | | |

TABLE 6-continued

LC/MS/MS method for detection of cGMP

MS File: cGMP.exp

| Mass Spectrum: | Waters Quattro micro |
|---|---|
| Ionization: | ES+ |
| Source, Desolvation: | 150° C., 450° C. |
| MS Function: | MRM |

| Compound | Transition | Dwell (sec) | Cone (V) | Collision Energy (eV) |
|---|---|---|---|---|
| cGMP | 346 > 152 | 0.1 | 35 | 20 |

Example 18

Biological Measurement by the Purified Human sGC Enzyme Synergy Performed in the Presence of Sodium Nitroprusside (SNP), a Nitric Oxide Donor Enzyme assays were performed as described above, but was done in the presence of 1 μM sodium nitroprusside (SNP). Specific activities are reported for selected test compounds in the presence of both SNP and test compounds and compared to specific activity of SNP alone and compound alone.

TABLE 7

(Enzyme Data With or Without SNP)

| Comp # | sGC Enzyme (fold increase at 10 μM without SNP)* | sGC Enzyme (fold increase at 30 μM without SNP)* | sGC Enzyme (specific activity at 10 μM) | sGC Enzyme (specific activity at 30 μM) | sGC Enzyme (fold increase at 10 μM with SNP)* | sGC Enzyme (fold increase at 30 μM with SNP)* |
|---|---|---|---|---|---|---|
| I-1 | B | C | B | C | — | |
| I-2 | B | B | B | A | — | |
| I-3 | B | C | D | D/E*** | C | C |
| I-4 | B | C | E | E | B | C |
| I-5 | B | B | D | D | B | B |
| I-6 | B | B | D | D | B | D |
| I-7 | B | B | D | D | B | C |
| I-8 | A | B | C | D | — | |
| I-9 | A | B | C | C | — | |
| I-10 | B | B | D | D | — | |
| I-11 | A | A | B/C*** | C | — | |
| I-12 | A | A | C | C | — | |
| I-13 | A | A | B | C | A | A |
| I-14 | A | A | C | C | — | |
| I-15 | A | A | C | C | — | |
| I-16 | A | A | B | B | — | — |
| I-17 | A | A | B | B | — | — |
| I-18 | A | A | C | C | A | A |
| I-19 | A | A | — | — | — | — |
| I-20 | A | A | C | D | — | |
| I-21 | A | A | C | C | — | |
| I-22 | A | B | C | C | A | A |
| I-23 | B | B | C | D | B | B |
| I-24 | A | A | C | C | A | A |
| I-25 | A | A | C | D | B | C |
| I-26 | B | C | D | D | C | D |
| I-27 | B | B | C | D | — | |
| I-31 | A | B | C | C | B | C |
| I-32 | A | A | C | D | — | |
| I-33 | A | C | C | D | | D |
| I-34 | A | A | B | C | — | |
| I-35 | B | B | D | D | B | C |
| I-36 | A | A | C | C | A | A |
| I-37 | A | A | C | C | A | A |
| I-38 | A | A | C | C | A | A |
| I-40 | A | A | C | C | A | B |
| I-41 | A | B | B | C | — | |
| I-42 | B | C | D | E | B | C |
| I-43 | A | A | C | C | A | A |
| I-44 | A | A | B | B | A | A |
| I-45 | A | B | C | C | C | D |
| I-46 | A | A | C | D | A | A |
| I-47 | A | B | D | D | B | B |
| I-48 | B | B | D | E | B | C |
| I-59 | B | B | B | C | B | C |
| I-64 | A | A | A | B | A | B |
| I-65 | B | B | B | C | B | C |
| I-66 | B | C | B | C | C | D |
| I-67 | A | A | C | D | A | A |
| I-68 | A | A | | | — | |
| I-69 | A | A | | | A | A |
| I-63 | A | A | B | B | A | A |
| I-62 | A | A | B | B | A | A |
| I-61 | B | C | C | D | D | D |

TABLE 7-continued (Enzyme Data With or Without SNP)

| Comp # | sGC Enzyme (fold increase at 10 μM without SNP)* | sGC Enzyme (fold increase at 30 μM without SNP)* | sGC Enzyme (specific activity at 10 μM) | sGC Enzyme (specific activity at 30 μM) | sGC Enzyme (fold increase at 10 μM with SNP)* | sGC Enzyme (fold increase at 30 μM with SNP)* |
|---|---|---|---|---|---|---|
| I-60 | A | B | B | C | A | A |
| I-58 | A | B | B | B | B | B |
| I-57 | A | A | B | B | A | B |
| I-56 | A | A | B | B | A | A |
| I-55 | A | B | | | B | B |
| I-54 | A | A | | | A | A |
| I-53 | A | A | | | A | A |
| I-52 | A | A | | | A | A |
| I-51 | A | A | | | A | A |
| I-50 | A | A | B | B | | |
| I-49 | C | D | D | E | — | |

*The compounds were tested at a concentration of 10 or 30 μM. The code for the fold increase in enzyme activity is:
A = no increase to <2 fold increase
B = 2 to <5 fold increase
C = 5 to <10 fold increase
D = equal or >10 fold increase

**The compounds were tested at a concentration of 10 or 30 μM. The code for the specific activity (nmoles of cGMP formed per mg of sGC per minute) is:
A = 0 to <50
B = 50 to <100
C = 100 to <200
D = 200 to <500
E = 500 to <1000

***For each of I-3 and I-11, two results were obtained falling within two codes.

TABLE 8

(Enzyme Data With or Without SNP)

| Compound | sGC Enzyme (fold increase at 10 μM)* | sGC Enzyme (fold increase at 30 μM)* | sGC Enzyme (fold increase at 10 μM with SNP)** | sGC Enzyme (fold increase at 30 μM with SNP)** |
|---|---|---|---|---|
| I-70 | N | A | N | A |
| I-71 | N | C | N | D |
| I-72 | N | D | N | D |
| I-75 | A | B | N | D |
| I-77 | A | A | N | N |
| I-78 | A | A | N | N |
| I-79 | A | A | A | A |
| I-80 | A | A | N | N |
| I-81 | N | A | N | A |
| I-82 | N | C | N | C |
| I-83 | N | D | N | C |
| I-84 | N | C | N | B |
| I-85 | N | C | N | D |
| I-86 | N | C | N | D |
| I-87 | N | D | N | D |
| I-88 | N | A | N | A |
| I-89 | N | A | N | A |
| I-90 | N | A | N | B |
| I-91 | N | B | N | C |
| I-92 | N | B | N | D |
| I-93 | N | B | N | C |
| I-94 | N | A | N | B |
| I-95 | N | A | N | C |
| I-96 | N | B | N | C |
| I-97 | N | D | N | D |
| I-98 | N | B | N | D |
| I-103 | | A | | B |
| I-104 | | B | | C |
| I-105 | | C | | C |
| I-106 | | D | | D |
| I-107 | | B | | C |
| I-108 | | A | | B |
| I-109 | | D | | D |
| I-99 | N | B | N | C |
| I-100 | N | B | N | C |
| I-101 | N | B | N | D |
| I-102 | | B | | C |
| I-110 | | B | | C |
| I-111 | | B | | C |
| I-112 | | C | | D |
| I-113 | | A | | C |
| I-114 | | B | | D |
| I-115 | | C | | D |
| I-116 | | B | | C |
| I-117 | | A | | A |
| I-118 | | C | | D |
| I-119 | | B | | D |
| I-120 | | A | | C |
| I-121 | | C | | D |
| I-122 | | C | | D |
| I-123 | | A | | B |
| I-124 | | D | | D |
| I-125 | | C | | D |
| I-126 | | D | | D |
| I-127 | | C | | D |
| I-128 | | B | | C |
| I-129 | | B | | D |
| I-130 | | C | | D |
| I-131 | | B | | D |
| I-132 | | B | | C |
| I-133 | | A | | B |
| I-136 | | C | | D |
| I-137 | | B | | C |
| I-139 | | C | | C |

*The compounds were tested at a concentration of 10 or 30 μM. The code for the fold increase in enzyme activity obtained without the addition of SNP is: A = no increase to <2 fold increase B = 2 to <5 fold increase C = 5 to <10 fold increase D = 10 to <30 fold increase N = not determined

**The compounds were tested at a concentration of 10 or 30 μM. The code for the fold increase in enzyme activity obtained with the addition of SNP is: A = no increase to <2 fold increase B = 2 to <5 fold increase C = 5 to <10 fold increase D = 10 to <30 fold increase N = not determined

Example 19a

Biological Activity Measurement by the Thoracic Aortic Rings Assay

Thoracic aortic rings were dissected from anesthetized (isoflurane) male Sprague-Dawley rats weighing 275-299 g. Tissues were immediately transferred to ice-cold Krebs-Henseleit solution, which had been aerated with 95% $O_2$ and 5% $CO_2$ for 30 minutes. Following removal of connective tissue, aortic sections were cut into 4 rings (~2 mm each) and suspended on 2 L-shaped hooks, with one hook fixed at the bottom of the tissue bath (Schuler Organ Bath, Harvard Apparatus) and the other connected to a force transducer (F30 Force Transducer, Harvard Apparatus). Baths contained Krebs Henseleit solution (10 mL) heated to 37° C. and aerated with 95% $O_2$ and 5% $CO_2$. Rings were brought to an initial tension of 0.3-0.5 g and gradually raised to a resting tension of 1.0 g over 60 minutes. Rings were rinsed with Krebs Henseleit solution (heated to 37° C. and aerated with 95% $O_2$ and 5% $CO_2$) at 15 minute intervals until a stable baseline was obtained. Rings were considered to be stable after a resting tension of 1.0 g was maintained (for approximately 10 minutes) without need for adjustment. Rings were then contracted with 100 ng/mL phenylephrine by adding 100 uL of a 10 μg/mL phenylephrine stock solution. Tissues achieving a stable contraction were then treated in a cumulative, dose dependent manner with test compounds prepared in dimethylsulfoxide (DMSO). In some cases, tissues were rinsed three times over a 5 minute period with Krebs-Heinseleit's solution (heated to 37° C. and aerated with 95% $O_2$ and 5% $CO_2$), allowed to stabilize at baseline, and then used for characterization of other test articles or DMSO effects. All data were collected using the HSE-ACAD software provided by Harvard Apparatus. Percent relaxation effects were calculated in Microsoft Excel using the recorded tension value of 100 ng/mL phenylephrine treatment as 0% inhibition and treatment with 100 μM 3-isobutyl-1-methylxanthine as 100% inhibition. $EC_{50}$ values were calculated from concentration-response curves generated with GraphPad Prism Software.

Example 19b

Biological Activity Measurement by the Thoracic Aortic Rings Assay

As an alternative thoracic aortic rings assay, the procedure of Example 11a was used except that percent relaxation effects were calculated in Microsoft Excel using the recorded tension value of 100 ng/mL phenylephrine treatment as 0% inhibition and, after washing the tissue with buffer, the original resting tension of the tissue was used as 100% inhibition.

The biological data for some of the compounds of Formula I, in comparison with the known compound, BAY 41-2272, as the reference compound, determined by the thoracic aorta ring assay are presented in Table 9 below.

TABLE 9

Thoracic Aortic Ring Assay Result*

| Compound Tested | Percent Relaxation at 10 μM |
|---|---|
| Reference Compound | 100 |
| I-1 | 53.7 |
| I-2 | 100.8 |
| I-3 | 92 |
| I-4 | 102.2 |

TABLE 9-continued

Thoracic Aortic Ring Assay Result*

| Compound Tested | Percent Relaxation at 10 μM |
|---|---|
| I-5 | 55.6 |
| I-6 | 101.8 |
| I-7 | 60.4 |
| I-26 | 85.3 |
| I-27 | 77.2 |
| I-31 | 93.15 |
| I-33 | 110.25 |
| I-42 | 72.1 |
| I-45 | 94.9 |
| I-49 | 105.5 |
| I-61 | 103.3 |
| I-66 | 103.3 |

*The compounds were tested at a concentration of 10 μM to obtain data using the method described in Example 13a.

The aortic ring assay data for other compounds are presented in Tables 10A and 10B.

TABLE 10A

Thoracic Ring Assay Results*

| Compound Tested | Percent Relaxation at 1 μM* | Percent Relaxation at 3 μM* | Percent Relaxation at 10 μM* | Aortic Ring $EC_{50}$ (μM)** |
|---|---|---|---|---|
| I-71 | No relaxation | B | E | |
| I-72 | 3.1 | C | E | |
| I-75 | B | C | E | B |
| I-82 | B | C | F | C |
| I-83 | B | C | E | C |
| I-84 | no relaxation | no relaxation | C | D |
| I-85 | E | F | G | A |
| I-86 | D | F | G | A |
| I-87 | E | F | G | A |
| I-92 | E | F | N | A |
| I-97 | F | G | G | A |
| I-98 | E | G | G | A |
| I-99 | A | C | F | A |
| I-100 | C | E | G | A |
| I-102 | C | E | F | A |
| I-105 | E | F | G | A |
| I-106 | C | E | G | A |
| I-109 | F | E | G | A |
| I-110 | D | E | F | A |
| I-112 | F | H | G | A |
| I-115 | C | D | F | B |
| I-119 | C | E | G | A |
| I-126 | F | G | | A |
| I-138 | C | D | | B |
| I-140 | C | E | F | A |

*The compounds were tested at a concentration of 1, 3 or 10 μM to obtain data using the method described in Example 13b. The code for the percent relaxation of the aotic ring is: A = 0 to <10% B = 10 to <20% C = 20 to <40% D = 40 to <60% E = 60 or <80% F = 80 to <100% G = 100 to <120% H = higher than 120% N = not determined
**The code for the $EC_{50}$ value obtained is: A = 0 to <2 μM B = 2 to <4 μM C = 4 to <8 μM D = 8 to <12 μM

TABLE 10B

| Compound Tested | Percent Relaxation at 1 μM* | Percent Relaxation at 3 μM* | Percent Relaxation at 10 μM* | Aortic Ring $EC_{50}$ (μM)** |
|---|---|---|---|---|
| I-245 | F | G | G | A |
| I-238 | F | G | G | A |
| I-237 | E | F | G | A |
| I-217 | D | E | F | A |
| I-216 | D | F | G | A |
| I-206 | C | E | F | A |
| I-205 | E | F | G | A |
| I-196 | E | F | F | A |
| I-189 | F | F | | A |
| I-188 | F | G | G | A |

TABLE 10B-continued

| Compound Tested | Percent Relaxation at 1 μM* | Percent Relaxation at 3 μM* | Percent Relaxation at 10 μM* | Aortic Ring EC$_{50}$ (μM)** |
|---|---|---|---|---|
| I-186 | E | F | G | A |
| I-185 | E | G | G | A |
| I-184 | F | G |   | A |
| I-178 | E | G | G | A |
| I-177 | F | F |   | A |
| I-176 | F | G |   | A |
| I-174 | F | F |   | A |
| I-172 | F | G | G | A |
| I-169 | D | F |   | A |
| I-168 | E | G | G | A |
| I-166 | D | F | G | A |
| I-165 | E | F | G | A |
| I-162 | G | H |   | A |
| I-161 | F | G |   | A |
| I-158 | B | D | F | C |
| I-156 | E | F |   | A |
| I-153 | E | E | F | A |
| I-152 | E | F | G | A |
| I-151 | F | G | G | A |
| I-150 | D | F | F | A |
| I-148 | F | F |   | A |
| I-147 | E | F | F | A |
| I-144 | F | G |   | A |
| I-126 | F | G |   | A |
| I-277 | E | F | G | A |
| I-142 | F | G |   | A |
| I-119 | C | E | G | A |
| I-297 | C | E |   | A |
| I-296 | C | D | F |   |
| I-294 | C | E | G | A |
| I-305 | D | F | G | A |
| I-304 | C | E | F | A |

*The compounds were tested at a concentration of 1, 3 or 10 μM to obtain data using the method described in Example 13b. The code for the percent relaxation of the aotic ring is: A = 0 to <10% B = 10 to <20% C = 20 to <40% D = 40 to <60% E = 60 or <80% F = 80 to <100% G = 100 to <120% H = higher than 120% Blank cell = not tested
**The code for the EC$_{50}$ value obtained is: A = 0 to <2 μM B = 2 to <4 μM C = 4 to <8 μM D = 8 to <12 μM A number of embodiments have been described. Nevertheless, it will be understood that various modifications may be made without departing from the spirit and scope of the invention.

The invention claimed is:

1. A compound according to Formula I, or a pharmaceutically acceptable salt thereof,

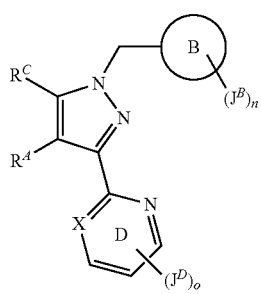

Formula I wherein:
ring B is a phenyl or a 6-membered heteroaryl ring, containing 1 or 2 nitrogen atoms in the ring;
n is an integer selected from 0 to 3;
each $J^B$ is independently selected from halogen, —CN, —NO$_2$, a C$_{1-6}$ aliphatic, —OR$^B$ or a C$_{3-8}$ cycloaliphatic group; wherein each said C$_{1-6}$ aliphatic and each said C$_{3-8}$ cycloaliphatic group is optionally and independently substituted with up to 3 instances of R$^3$;

each R$^B$ is independently selected from hydrogen, a C$_{1-6}$ aliphatic or a C$_{3-8}$ cycloaliphatic; wherein each said C$_{1-6}$ aliphatic and each said C$_{3-8}$ cycloaliphatic ring is optionally and independently substituted with up to 3 instances of R$^3$;
each R$^3$ is independently selected from halogen, —CN, C$_{1-4}$ alkyl, C$_{1-4}$ haloalkyl, —O(C$_{1-4}$ alkyl) or —O(C$_{1-4}$ haloalkyl);
X is selected from N, C-J$^D$ or C—H;
o is an integer selected from 0 to 3;
each J$^D$ is independently selected from halogen, —NO$_2$, —OR$^D$, —SR$^D$, —C(O)R$^D$, —C(O)OR$^D$, —C(O)N(R$^D$)$_2$, —CN, —N(R$^D$)$_2$, —N(R$^d$)C(O)R$^D$, —N(R$^d$)C(O)OR$^D$, —SO$_2$R$^D$, —SO$_2$N(R$^D$)$_2$, —N(R$^d$)SO$_2$R$^D$, a C$_{1-6}$ aliphatic, —(C$_{1-6}$ aliphatic)-R$^D$, a C$_{3-8}$ cycloaliphatic ring, a 6 to 10-membered aryl ring, a 4 to 8-membered heterocyclic ring or a 5 to 10-membered heteroaryl ring; wherein each said 4 to 8-membered heterocylic ring and each said 5 to 10-membered heteroaryl ring contains between 1 and 3 heteroatoms independently selected from O, N or S; and wherein each said C$_{1-6}$ aliphatic, each said C$_{3-8}$ cycloaliphatic ring, each said 6 to 10-membered aryl ring, each said 4 to 8-membered heterocyclic ring and each said 5 to 10-membered heteroaryl ring is optionally and independently substituted with up to 3 instances of R$^5$;
each R$^D$ is independently selected from hydrogen, a C$_{1-6}$ aliphatic, —(C$_{1-6}$ aliphatic)-R$^f$, a C$_{3-8}$ cycloaliphatic ring, a 4 to 8-membered heterocyclic ring, phenyl or a 5 to 6-membered heteroaryl ring; wherein each said 4 to 8-membered heterocyclic ring and each said 5 to 6-membered heteroaryl ring contains between 1 and 3 heteroatoms independently selected from O, N or S; and wherein each said C$_{1-6}$ aliphatic, each said C$_{3-8}$ cycloaliphatic ring, each said 4 to 8-membered heterocyclic ring, each said phenyl and each said 5 to 6-membered heteroaryl ring is optionally and independently substituted with up to 3 instances of R$^5$;
each R$^d$ is independently selected from hydrogen, a C$_{1-6}$ aliphatic, —(C$_{1-6}$ aliphatic)-R$^f$, a C$_{3-8}$ cycloaliphatic ring, a 4 to 8-membered heterocyclic ring, phenyl or a 5 to 6-membered heteroaryl ring; wherein each said heterocylic ring and each said heteroaryl ring contains between 1 and 3 heteroatoms independently selected from O, N or S; and wherein each said C$_{1-6}$ aliphatic, each said C$_{3-8}$ cycloaliphatic ring, each said 4 to 8-membered heterocyclic ring, each said phenyl and each said 5 to 6-membered heteroaryl ring is optionally and independently substituted by up to 3 instances of R$^5$;
each R$^f$ is independently selected from a C$_{3-8}$ cycloaliphatic ring, a 4 to 8-membered heterocyclic ring, phenyl or a 5 to 6-membered heteroaryl ring; wherein each said heterocylic ring and each said heteroaryl ring contains between 1 and 3 heteroatoms independently selected from O, N or S; and wherein each said C$_{1-6}$ aliphatic, each said C$_{3-8}$ cycloaliphatic ring, each said 4 to 8-membered heterocyclic ring, each said phenyl and each said 5 to 6-membered heteroaryl ring is optionally and independently substituted by up to 3 instances of R$^5$;
alternatively, two instances of R$^D$ linked to the same nitrogen atom of J$^D$, together with said nitrogen atom of J$^D$, form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of $R^5$; or alternatively, one instance of $R^D$ linked to a carbon, oxygen or sulfur atom of $J^D$ and one instance of $R^d$ linked to a nitrogen atom of the same $J^D$, together with said carbon, oxygen or sulfur and said nitrogen atom of that same $J^D$, form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of $R^5$;

each $R^5$ is independently selected from halogen, —CN, —NO$_2$, $C_{1-4}$ alkyl, a $C_{7-12}$ aralkyl, $C_{3-8}$ cycloalkyl ring, $C_{1-4}$ haloalkyl, $C_{1-4}$ cyanoalkyl, —OR$^6$, —SR$^6$, —COR$^6$, —OC(O)R$^6$, —C(O)OR$^6$, —C(O)N(R$^6$)$_2$, —N(R$^6$)C(O)R$^6$, —N(R$^6$)$_2$, —SO$_2$R$^6$, —SO$_2$N(R$^6$)$_2$, —N(R$^6$)SO$_2$R$^6$, phenyl or an oxo group; wherein each said phenyl group is optionally and independently substituted with up to 3 instances of halogen, —OH, —NH$_2$, —NH(C$_{1-4}$ alkyl), —N(C$_{1-4}$ alkyl)$_2$, —NO$_2$, —CN, C$_{1-4}$ alkyl, C$_{1-4}$ haloalkyl, —O(C$_{1-4}$ alkyl) or —O(C$_{1-4}$ haloalkyl); and wherein each said C$_{7-12}$ aralkyl and each said cycloalkyl group is optionally and independently substituted with up to 3 instances of halogen;

with the proviso that when X is C—H, each $R^5$ is independently selected from halogen, —CN, —NO$_2$, methyl, ethyl, a C$_{7-12}$ aralkyl, C$_{3-8}$ cycloalkyl ring, C$_{1-4}$ haloalkyl, C$_{1-4}$ cyanoalkyl, —OR$^6$, —SR$^6$, —COR$^6$, —OC(O)R$^6$, —C(O)OR$^6$, —C(O)N(R$^6$)$_2$, —N(R$^6$)C(O)R$^6$, —N(R$^6$)$_2$, —SO$_2$R$^6$, —SO$_2$N(R$^6$)$_2$, —N(R$^6$)SO$_2$R$^6$, phenyl or an oxo group; wherein each said phenyl group is optionally and independently substituted with up to 3 instances of halogen, —OH, —NH$_2$, —NH(C$_{1-4}$ alkyl), —N(C$_{1-4}$ alkyl)$_2$, —NO$_2$, —CN, C$_{1-4}$ alkyl, C$_{1-4}$ haloalkyl, —O(C$_{1-4}$ alkyl) or —O(C$_{1-4}$ haloalkyl); and wherein each said C$_{7-12}$ aralkyl and each said cycloalkyl group is optionally and independently substituted with up to 3 instances of halogen;

each $R^6$ is independently selected from hydrogen, a C$_{1-4}$ alkyl, a C$_{2-4}$ alkenyl, phenyl, a C$_{7-12}$ aralkyl or a C$_{3-8}$ cycloalkyl ring; wherein each of said C$_{1-4}$ alkyl, each said C$_{2-4}$ alkenyl, each said phenyl, each said C$_{7-12}$ aralkyl and each said cycloalkyl group is optionally and independently substituted with up to 3 instances of halogen;

alternatively, two instances of $R^6$ linked to the same nitrogen atom of $R^5$, together with said nitrogen atom of $R^5$, form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S; or alternatively, one instance of $R^6$ linked to a nitrogen atom of $R^5$ and one instance of $R^6$ linked to a carbon or sulfur atom of the same $R^5$, together with said nitrogen and said carbon or sulfur atom of the same $R^5$, form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S;

or, alternatively, two $J^D$ groups attached to two vicinal ring D atoms, taken together with said two vicinal ring D atoms, form a 5 to 7-membered heterocycle resulting in a fused ring D wherein said 5 to 7-membered heterocycle contains from 1 to 3 heteroatoms independently selected from N, O or S; and wherein said 5 to 7-membered heterocycle is optionally and independently substituted by up to 3 instances of halogen, —OH, —NH$_2$, —NH(C$_{1-4}$ alkyl), —N(C$_{1-4}$ alkyl)$_2$, —CN, C$_{1-4}$ alkyl, C$_{1-4}$ haloalkyl, —O(C$_{1-4}$ alkyl), —O(C$_{1-4}$ haloalkyl) oxo or phenyl; wherein said phenyl is optionally and independently substituted by up to three instances of halogen, —OH, —NH$_2$, —NH(C$_{1-4}$ alkyl), —N(C$_{1-4}$ alkyl)$_2$, —NO$_2$, —CN, C$_{1-4}$ alkyl, C$_{1-4}$ haloalkyl, —O(C$_{1-4}$ alkyl) or —O(C$_{1-4}$ haloalkyl);

$R^C$ is selected from —CN, C$_{1-6}$ alkyl or a ring C;

ring C is a phenyl ring, a monocyclic 5 or 6-membered heteroaryl ring, a bicyclic 8 to 10-membered heteroaryl ring, a monocyclic 3 to 10-membered cycloaliphatic ring, or a monocyclic 4 to 10-membered heterocycle; wherein said monocyclic 5 or 6-membered heteroaryl ring, said bicyclic 8 to 10-membered heteroaryl ring, or said monocyclic 4 to 10-membered heterocycle contain between 1 and 4 heteroatoms selected from N, O or S; wherein said monocyclic 5 or 6-membered heteroaryl ring is not a 1,3,5-triazinyl ring; and wherein said phenyl, monocyclic 5 to 6-membered heteroaryl ring, bicyclic 8 to 10-membered heteroaryl ring, or monocyclic 4 to 10-membered heterocycle is optionally and independently substituted with up to 3 instances of $J^C$;

each $J^C$ is independently selected from halogen, —CN, —NO$_2$, a C$_{1-6}$ aliphatic, —OR$^H$, —SR$^H$, —N(R$^H$)$_2$, a C$_{3-8}$ cycloaliphatic ring or a 4 to 8-membered heterocyclic ring; wherein said 4 to 8-membered heterocyclic ring contains 1 or 2 heteroatoms independently selected from N, O or S; wherein each said C$_{1-6}$ aliphatic, each said C$_{3-8}$ cycloaliphatic ring and each said 4 to 8-membered heterocyclic ring, is optionally and independently substituted with up to 3 instances of $R^7$; or alternatively, two $J^C$ groups attached to two vicinal ring C atoms, taken together with said two vicinal ring C atoms, form a 5 to 7-membered heterocycle resulting in a fused ring C; wherein said 5 to 7-membered heterocycle contains from 1 to 2 heteroatoms independently selected from N, O or S;

each $R^H$ is independently selected from hydrogen, a C$_{1-6}$ aliphatic, a C$_{3-8}$ cycloaliphatic ring or a 4 to 8-membered heterocyclic ring; wherein each said 4 to 8-membered heterocylic ring contains between 1 and 3 heteroatoms independently selected from O, N or S; and wherein each said C$_{1-6}$ aliphatic, each said C$_{3-8}$ cycloaliphatic ring, each said 4 to 8-membered heterocyclic ring, is optionally and independently substituted with up to 3 instances of $R^7$;

alternatively, two instances of $R^H$ linked to the same nitrogen atom of $J^C$, together with said nitrogen atom of $J^C$, form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of $R^7$; or each $R^7$ is independently selected from halogen, —CN, —NO$_2$, C$_{1-4}$ alkyl, C$_{1-4}$ haloalkyl, C$_{3-8}$ cycloalkyl ring, —OR⁸, —SR⁸, —N(R⁸)₂, or an oxo group; wherein each said cycloalkyl group is optionally and independently substituted with up to 3 instances of halogen;

each R⁸ is independently selected from hydrogen, a $C_{1-4}$ alkyl, $C_{1-4}$ haloalkyl or a $C_{3-8}$ cycloalkyl ring; wherein each said cycloalkyl group is optionally and independently substituted with up to 3 instances of halogen;

alternatively, two instances of R⁸ linked to the same nitrogen atom of R⁷, together with said nitrogen atom of R⁷, form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S;

$R^A$ is selected from hydrogen, halogen, $C_{1-4}$ alkyl or $C_{1-4}$ haloalkyl, with the proviso that when ring B is unsubstituted phenyl and ring D is unsubstituted pyrimidinyl (X is N and o is zero), $R^C$ is not methyl or ethyl.

2. The compound of claim 1, or a pharmaceutically acceptable salt thereof, wherein ring B is phenyl.

3. The compound of claim 1 or claim 2, or a pharmaceutically acceptable salt thereof, wherein n is an integer selected from 1 to 3 and wherein each $J^B$ is independently selected from halogen, a $C_{1-6}$ aliphatic or —OR$^B$.

4. The compound of claim 3, or a pharmaceutically acceptable salt thereof, wherein each $J^B$ is independently selected from halogen atoms.

5. The compound of claim 4, or a pharmaceutically acceptable salt thereof, wherein each $J^B$ is independently selected from fluoro or chloro.

6. The compound of claim 5, or a pharmaceutically acceptable salt thereof, wherein each $J^B$ is fluoro.

7. The compound of claim 3, or a pharmaceutically acceptable salt thereof, wherein each $J^B$ is a $C_{1-6}$ aliphatic.

8. The compound of claim 7, or a pharmaceutically acceptable salt thereof, wherein each $J^B$ is methyl or ethyl.

9. The compound of claim 3, or a pharmaceutically acceptable salt thereof, wherein n is 1.

10. The compound of claim 9, or a pharmaceutically acceptable salt thereof, wherein $J^B$ is selected from halogen atoms.

11. The compound of claim 10, or a pharmaceutically acceptable salt thereof, wherein $J^B$ is fluoro or chloro.

12. The compound of claim 11, or a pharmaceutically acceptable salt thereof, wherein $J^B$ is fluoro.

13. The compound of claim 3, or a pharmaceutically acceptable salt thereof, wherein at least one $J^B$ is ortho to the attachment of the methylene linker between ring B and the pyrazolyl ring.

14. The compound of claim 13, or a pharmaceutically acceptable salt thereof, wherein each $J^B$ is independently selected from halogen atoms.

15. The compound of claim 14, or a pharmaceutically acceptable salt thereof, wherein each $J^B$ is independently selected from fluoro or chloro.

16. The compound of claim 15, or a pharmaceutically acceptable salt thereof, wherein each $J^B$ is fluoro.

17. The compound of claim 13, or a pharmaceutically acceptable salt thereof, wherein n is 1 and the $J^B$ ortho to the attachment of the methylene linker between ring B and the pyrazolyl ring is fluoro.

18. The compound of claim 1, or a pharmaceutically acceptable salt thereof, wherein ring B is a 6-membered heteroaryl ring.

19. The compound of claim 18, or a pharmaceutically acceptable salt thereof, wherein ring B is a pyridyl ring.

20. The compound of claim 18, or a pharmaceutically acceptable salt thereof, wherein ring B is a pyrimidinyl ring.

21. The compound of claim 1, or a pharmaceutically acceptable salt thereof, wherein X in ring D is C-$J^D$ or C—H.

22. The compound of claim 1, or a pharmaceutically acceptable salt thereof, wherein X in ring D is N.

23. The compound of either of claims 21 or 22, or a pharmaceutically acceptable salt thereof, wherein o is 0.

24. The compound of either of claims 21 or 22, or a pharmaceutically acceptable salt thereof, wherein o is an integer selected between 1 and 3 and each $J^D$ is independently selected from halogen, a $C_{1-6}$ aliphatic, —N(R$^D$)₂, —N(R$^d$)C(O)R$^D$, —N(R$^d$)C(O)OR$^D$, —SO₂R$^D$, —SO₂N(R$^D$)₂, —N(R$^d$)SO₂R$^D$, —SR$^D$, —OR$^D$ or an optionally substituted $C_{3-8}$ cycloaliphatic ring.

25. The compound of claim 24, or a pharmaceutically acceptable salt thereof, wherein each $J^D$ is independently selected from halogen atoms.

26. The compound of claim 25, or a pharmaceutically acceptable salt thereof, wherein each $J^D$ is independently selected from a chloro or fluoro.

27. The compound of claim 24, or a pharmaceutically acceptable salt thereof, wherein each $J^D$ is independently selected from a $C_{1-6}$ aliphatic or a $C_{3-8}$ cycloaliphatic ring.

28. The compound of claim 27, or a pharmaceutically acceptable salt thereof, wherein each $J^D$ is independently methyl or ethyl, propyl, cyclobutyl, cyclopropyl or isopropyl.

29. The compound of claim 28, or a pharmaceutically acceptable salt thereof, wherein each $J^D$ is independently methyl, ethyl or cyclopropyl.

30. The compound of claim 24, or a pharmaceutically acceptable salt thereof, wherein each $J^D$ is independently selected from —N(R$^D$)₂, —N(R$^d$)C(O)R$^D$, —N(R$^d$)C(O)OR$^D$, —SO₂R$^D$, —SO₂N(R$^D$)₂, —N(R$^d$)SO₂R$^D$ or —OR$^D$.

31. The compound of claim 30, or a pharmaceutically acceptable salt thereof, wherein each R$^d$ is independently selected from a $C_{1-4}$ alkyl or hydrogen and each R$^D$ is independently selected from hydrogen or $C_{1-4}$ alkyl.

32. The compound of claim 31, or a pharmaceutically acceptable salt thereof, wherein each R$^d$ is independently selected from hydrogen or methyl and each R$^D$ is independently selected from hydrogen, methyl, ethyl, propyl or isopropyl.

33. The compound of claim 32, or a pharmaceutically acceptable salt thereof, wherein each R$^d$ and each R$^D$ is independently selected from hydrogen or methyl.

34. The compound of claim 24, wherein o is 1, 2 or 3 and each $J^D$ is independently selected from methyl, fluoro, —N(R$^D$)₂, —N(R$^d$)C(O)R$^D$, —N(R$^d$)C(O)OR$^D$, —SO₂R$^D$, —SO₂N(R$^D$)₂ or —N(R$^d$)SO₂R$^D$; wherein each R$^d$ and each R$^D$ is independently selected from hydrogen or methyl.

35. The compound of claim 1, or a pharmaceutically acceptable salt thereof, wherein $R^C$ is —CN.

36. The compound of claim 1, or a pharmaceutically acceptable salt thereof, wherein $R^C$ is a $C_{1-6}$ alkyl.

37. The compound of claim 36, or a pharmaceutically acceptable salt thereof, wherein $R^C$ is selected from methyl, ethyl, propyl, isopropyl or butyl.

38. The compound of claim 1, or a pharmaceutically acceptable salt thereof, wherein $R^C$ is a ring C.

39. The compound of claim 38, or a pharmaceutically acceptable salt thereof, wherein ring C is a phenyl, a monocyclic 5 or 6-membered heteroaryl ring, a monocyclic 3 to 10-membered cycloaliphatic ring or a monocyclic 4 to 10-membered heterocycle; each of them optionally and independently substituted with up to 3 instances of $J^C$.

40. The compound of claim 39, or a pharmaceutically acceptable salt thereof, wherein ring C is a phenyl, a monocyclic 5 or 6-membered heteroaryl ring, a monocyclic 3 to 6-membered cycloaliphatic ring or a monocyclic 4 to 6-membered heterocycle; each of them optionally and independently substituted with up to 3 instances of $J^C$.

41. The compound of claim 40, or a pharmaceutically acceptable salt thereof, wherein ring C is a monocyclic 3 to 6-membered cycloaliphatic ring, optionally substituted with up to 2 instances of $J^C$.

42. The compound of claim 41, or a pharmaceutically acceptable salt thereof, wherein ring C is cyclopropyl.

43. The compound of claim 41, or a pharmaceutically acceptable salt thereof, wherein ring C is cyclobutyl.

44. The compound of claim 41, or a pharmaceutically acceptable salt thereof, wherein ring C is cyclopentyl.

45. The compound of claim 41, or a pharmaceutically acceptable salt thereof, wherein ring C is cyclohexyl.

46. The compound of claim 41, or a pharmaceutically acceptable salt thereof, wherein ring C is a 4-membered cycloaliphatic ring substituted by 1 to 3 instances of $J^C$, a 5-membered cycloaliphatic ring substituted by 1 to 3 instances of $J^C$ or a 6-membered cycloaliphatic ring substituted by 1 to 3 instances of $J^C$, and wherein each $J^C$ is independently selected from halogen or a $C_{1-6}$ aliphatic.

47. The compound of claim 40, or a pharmaceutically acceptable salt thereof, wherein ring C is phenyl, optionally and independently substituted by up to 3 instances of $J^C$.

48. The compound of claim 47, or a pharmaceutically acceptable salt thereof, wherein ring C is phenyl and it is unsubstituted.

49. The compound of claim 47, or a pharmaceutically acceptable salt thereof, wherein ring C is substituted by 1 to 3 instances of $J^C$ and wherein each $J^C$ is independently selected from halogen, a $C_{1-6}$ aliphatic, —$NH_2$, —CN or —$O(C_{1-6}$ aliphatic).

50. The compound of claim 49, or a pharmaceutically acceptable salt thereof, wherein each $J^C$ is independently selected from halogen, a $C_{1-4}$ alkyl, —$O(C_{1-4}$alkyl), —CN or —$NH_2$.

51. The compound of claim 50, or a pharmaceutically acceptable salt thereof, wherein ring C is phenyl substituted by 1 to 2 instances of $J^C$.

52. The compound of either of claims 50 or 51, or a pharmaceutically acceptable salt thereof, wherein each $J^C$ is independently selected from fluoro, methyl, —CN or —$OCH_3$.

53. The compound of claim 40, or a pharmaceutically acceptable salt thereof, wherein ring C is a 5 to 6-membered heteroaryl ring, optionally substituted by up to 3 instances of $J^C$.

54. The compound of claim 40, or a pharmaceutically acceptable salt thereof, wherein ring C is a 5 to 6-membered heteroaryl ring and it is unsubstituted.

55. The compound of either of claims 53 or 54, or a pharmaceutically acceptable salt thereof, wherein said 5 to 6-membered heteroaryl ring is selected from thienyl, thiazolyl, oxadiazolyl, oxazolyl, isooxazolyl, tetrazolyl, pyrrolyl, triazolyl, furanyl, pyridinyl, pyrimidinyl, pyrazinyl or pyridazinyl.

56. The compound of claim 55, or a pharmaceutically acceptable salt thereof, wherein said 5 to 6-membered heteroaryl ring is selected from furanyl, thienyl, thiazolyl, 1,3,4-oxadiazolyl, pyridinyl, pyrimidinyl or pyrazin-3-yl.

57. The compound of claim 56, or a pharmaceutically acceptable salt thereof, wherein said 5 to 6-membered heteroaryl ring is selected from thienyl, thiazolyl, 1,3,4-oxadiazolyl or pyridinyl.

58. The compound of claim 56, or a pharmaceutically acceptable salt thereof, wherein the 5 to 6-membered heteroaryl ring is selected from furan-2-yl, furan-3-yl, thien-3-yl, thien-2-yl, thiazol-2-yl, pyridin-2-yl, pyridin-3-yl, pyridin-4-yl, pyrimidin-2-yl or pyrimidin-4-yl; and is optionally substituted with up to 2 instances of $J^C$.

59. The compound of claim 53, or a pharmaceutically acceptable salt thereof, wherein each $J^C$ is independently selected from halogen, a $C_{1-6}$ aliphatic, —CN, —$NH_2$ or —$O(C_{1-6}$ aliphatic).

60. The compound of claim 53, or a pharmaceutically acceptable salt thereof, wherein ring C is thienyl or pyridinyl substituted by 1 to 3 instances of $J^C$ and each $J^C$ is independently selected from a halogen, a $C_{1-6}$ aliphatic, —$NH_2$ or —$O(C_{1-6}$ aliphatic).

61. The compound of claim 60, or a pharmaceutically acceptable salt thereof, wherein each $J^C$ is independently selected from a $C_{1-6}$ aliphatic.

62. The compound of claim 61, or a pharmaceutically acceptable salt thereof, wherein each $J^C$ is independently selected from methyl, ethyl, propyl or isopropyl.

63. The compound of claim 60, or a pharmaceutically acceptable salt thereof, wherein each $J^C$ is independently selected from a halogen atom, methyl, —$NH_2$ or —$OCH_3$.

64. The compound of claim 38, or a pharmaceutically acceptable salt thereof, wherein ring C is a bicyclic 7 to 10-membered heteroaryl ring.

65. The compound of claim 64, or a pharmaceutically acceptable salt thereof, wherein ring C is benzofuran-2-yl, furo[3,2-b]pyridinyl, furo[2,3-b]pyridinyl, benzothienyl or indolyl.

66. The compound of claim 65, or a pharmaceutically acceptable salt thereof, wherein ring C is benzofuran-2-yl, furo[3,2-b]pyridinyl or benzothienyl.

67. The compound of claim 1, or a pharmaceutically acceptable salt thereof, wherein $J^D$ is —$N(R^d)C(O)OR^D$ or —$N(R^D)_2$, or two $J^D$ groups attached to two vicinal ring D atoms, taken together with said two vicinal ring D atoms, form a 5-membered heterocycle containing from 1 to 3 heteroatoms independently selected from N, O or S resulting in a fused ring D wherein said 5-membered heterocycle is optionally and independently substituted by up to 3 instances of halogen, —OH, —$NH_2$, —$NH(C_{1-4}$ alkyl), —$N(C_{1-4}$ alkyl)$_2$, —CN, $C_{1-4}$ alkyl, $C_{1-4}$ haloalkyl, —$O(C_{1-4}$ alkyl), —$O(C_{1-4}$ haloalkyl) or oxo having Formula II:

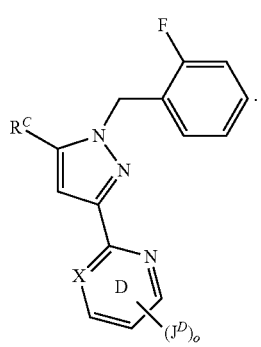

Formula II

68. The compound of claim 1, or a pharmaceutically acceptable salt thereof, having Formula III or Formula IV:

Formula III

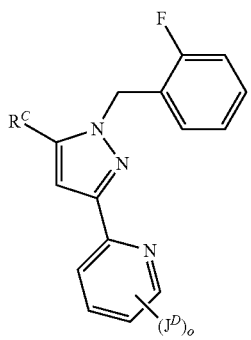

Formula IV

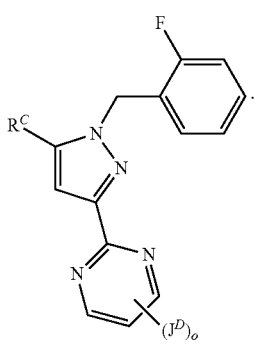

69. The compound of claim 68, or a pharmaceutically acceptable salt thereof, having one of Formulae VA, VC, VD and VF, wherein the symbol of the letter C surrounded by a circle represents ring C:

VA

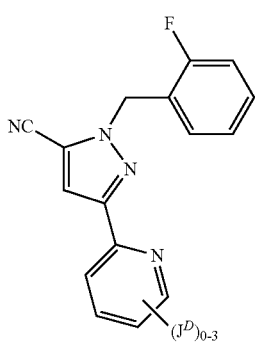

VC

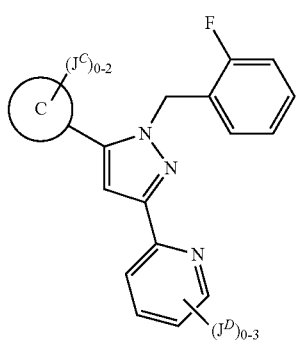

VD

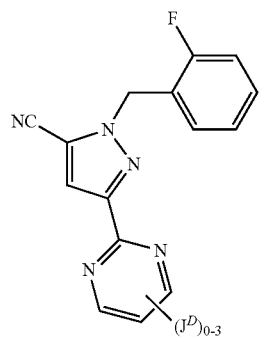

VF

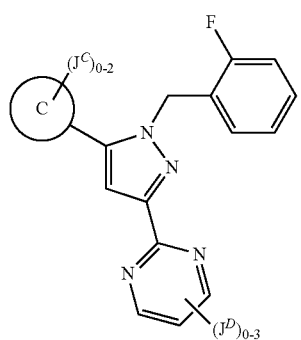

70. The compound of claim 68, or a pharmaceutically acceptable salt thereof, wherein $R^C$ is oxazolyl optionally and independently substituted by up to 3 instances of $J^C$.

71. The compound of claim 70, wherein $J^D$ is selected from —N($R^d$)C(O)O$R^D$ or —N($R^D$)$_2$.

72. The compound of claim 71, wherein $J^D$ is —N($R^D$)$_2$.

73. The compound of one of claims 70, 71 or 72, or a pharmaceutically acceptable salt thereof, having Formula IV, wherein $R^C$ is oxazolyl optionally and independently substituted by up to 3 instances of $J^C$.

74. The compound of claim 1, selected from Table IA, IB, IC or ID, or a pharmaceutically acceptable salt thereof.

75. The compound of claim 20, or a pharmaceutically acceptable salt thereof, wherein X in ring D is C-$J^D$ or C—H.

76. The compound of claim 20, or a pharmaceutically acceptable salt thereof, wherein X in ring D is N.

77. The compound of either claims 75 or 76, or a pharmaceutically acceptable salt thereof, wherein o is 0.

78. A pharmaceutical composition comprising the compound of claim 1, or a pharmaceutically acceptable salt thereof, and at least one pharmaceutically acceptable excipient.

79. A method of treating a disease, health condition or disorder in a subject, comprising administering a therapeutically effective amount of the compound of claim 1, or a pharmaceutically acceptable salt thereof, to the subject in need of the treatment, wherein the disease, health condition or disorder is pulmonary hypertension, pulmonary arterial hypertension, and associated pulmonary vascular remodeling, pulmonary hypertonia, primary pulmonary hypertension, secondary pulmonary hypertension, familial pulmonary hypertension, sporadic pulmonary hypertension, pre-capillary pulmonary hypertension or idiopathic pulmonary hypertension.

* * * * *

(12) EX PARTE REEXAMINATION CERTIFICATE (51st)
Ex Parte Reexamination Ordered under 35 U.S.C. 257

United States Patent
Kim et al.

(10) Number: US 8,748,442 C1
(45) Certificate Issued: Apr. 15, 2016

(54) SGC STIMULATORS

(75) Inventors: Charles Kim, Cambridge, MA (US); Takashi Nakai, Newton, MA (US); Thomas Wai-Ho Lee, Lexington, MA (US); Joel Moore, Lexington, MA (US); Nicholas Robert Perl, Brookline, MA (US); Jason Rohde, Andover, MA (US); Rajesh R Iyengar, West Newton, MA (US); Ara Mermerian, Melrose, MA (US); Angelika Fretzen, Somerville, MA (US)

(73) Assignee: Ironwood Pharmaceuticals, Inc., Cambridge, MA (US)

Supplemental Examination Request:
No. 96/000,110, Jul. 20, 2015

Reexamination Certificate for:
Patent No.: 8,748,442
Issued: Jun. 10, 2014
Appl. No.: 13/174,676
Filed: Jun. 30, 2011

Related U.S. Application Data

(60) Provisional application No. 61/360,236, filed on Jun. 30, 2010, provisional application No. 61/406,845, filed on Oct. 26, 2010, provisional application No. 61/474,563, filed on Apr. 12, 2011.

(51) Int. Cl.
| | | |
|---|---|---|
| *A01N 43/54* | (2006.01) | |
| *C07D 419/00* | (2006.01) | |
| *C07D 413/00* | (2006.01) | |
| *C07D 417/00* | (2006.01) | |
| *C07D 411/00* | (2006.01) | |
| *C07D 409/00* | (2006.01) | |
| *C07D 405/00* | (2006.01) | |
| *C07D 403/00* | (2006.01) | |
| *C07D 401/00* | (2006.01) | |
| *A61K 31/44* | (2006.01) | |
| *A01N 43/40* | (2006.01) | |
| *A61K 31/505* | (2006.01) | |
| *C07D 401/04* | (2006.01) | |
| *A61K 31/506* | (2006.01) | |
| *C07D 401/14* | (2006.01) | |
| *C07D 405/14* | (2006.01) | |
| *C07D 413/14* | (2006.01) | |
| *C07D 417/14* | (2006.01) | |
| *A61K 31/4155* | (2006.01) | |
| *A61K 45/06* | (2006.01) | |
| *C07D 473/34* | (2006.01) | |
| *C07D 409/14* | (2006.01) | |
| *C07D 403/14* | (2006.01) | |
| *C07D 403/04* | (2006.01) | |
| *A61K 31/5365* | (2006.01) | |
| *A61K 31/522* | (2006.01) | |
| *C07D 498/04* | (2006.01) | |
| *A61K 31/497* | (2006.01) | |
| *A61K 31/444* | (2006.01) | |
| *A61K 31/4439* | (2006.01) | |
| *C07D 491/048* | (2006.01) | |

(52) U.S. Cl.
CPC .......... *C07D 401/04* (2013.01); *A61K 31/4155* (2013.01); *A61K 31/444* (2013.01); *A61K 31/4439* (2013.01); *A61K 31/497* (2013.01); *A61K 31/506* (2013.01); *A61K 31/522* (2013.01); *A61K 31/5365* (2013.01); *A61K 45/06* (2013.01); *C07D 401/14* (2013.01); *C07D 403/04* (2013.01); *C07D 403/14* (2013.01); *C07D 405/14* (2013.01); *C07D 409/14* (2013.01); *C07D 413/14* (2013.01); *C07D 417/14* (2013.01); *C07D 473/34* (2013.01); *C07D 491/048* (2013.01); *C07D 498/04* (2013.01)

(58) Field of Classification Search
None
See application file for complete search history.

(56) References Cited

To view the complete listing of prior art documents cited during the supplemental examination proceeding and the resulting reexamination proceeding for Control Number 96/000,110, please refer to the USPTO's public Patent Application Information Retrieval (PAIR) system under the Display References tab.

*Primary Examiner* — Evelyn Huang

(57) ABSTRACT

Compounds of Formula I are described. They are useful as stimulators of sGC, particularly NO-independent, heme-dependent stimulators. These compounds may be useful for treating, preventing or managing various disorders that are herein disclosed.

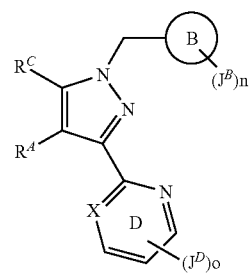

Formula I

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPH OF THE SPECIFICATION AFFECTED BY AMENDMENT ARE PRINTED HEREIN.

Column 74, line 23 to Column 117, line 22:

TABLE 1B

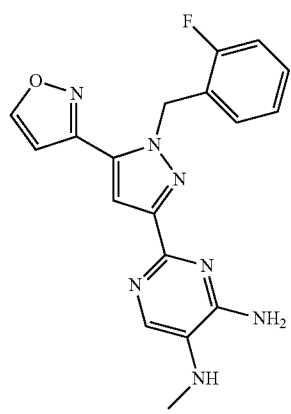

I-141

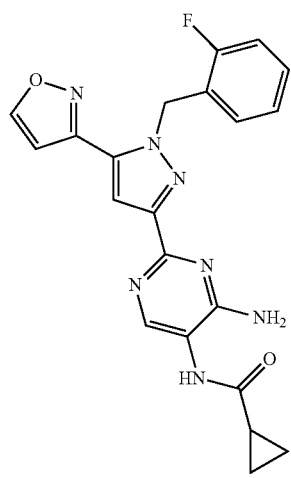

I-142

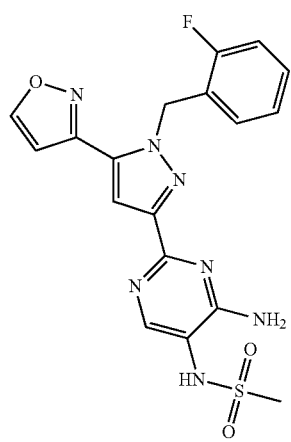

I-143

TABLE 1B-continued

I-144

I-145

TABLE 1B-continued
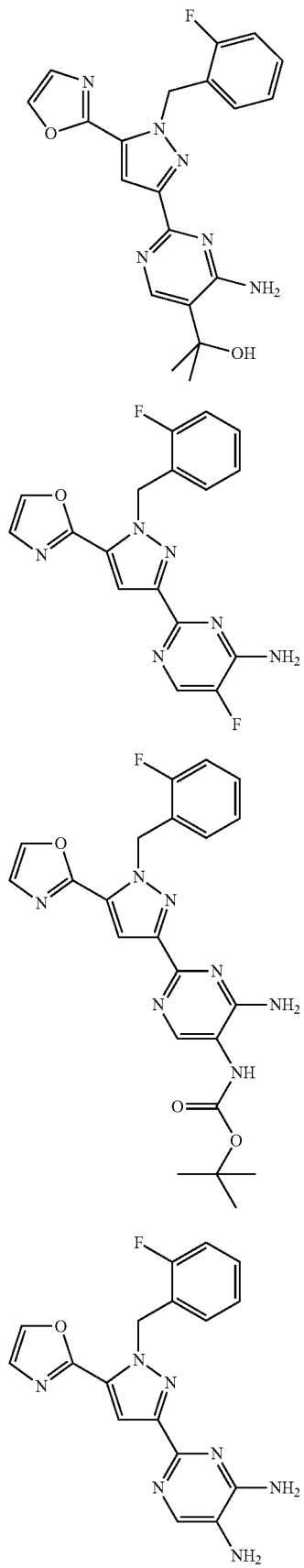
I-146
I-147
I-148
I-149
TABLE 1B-continued
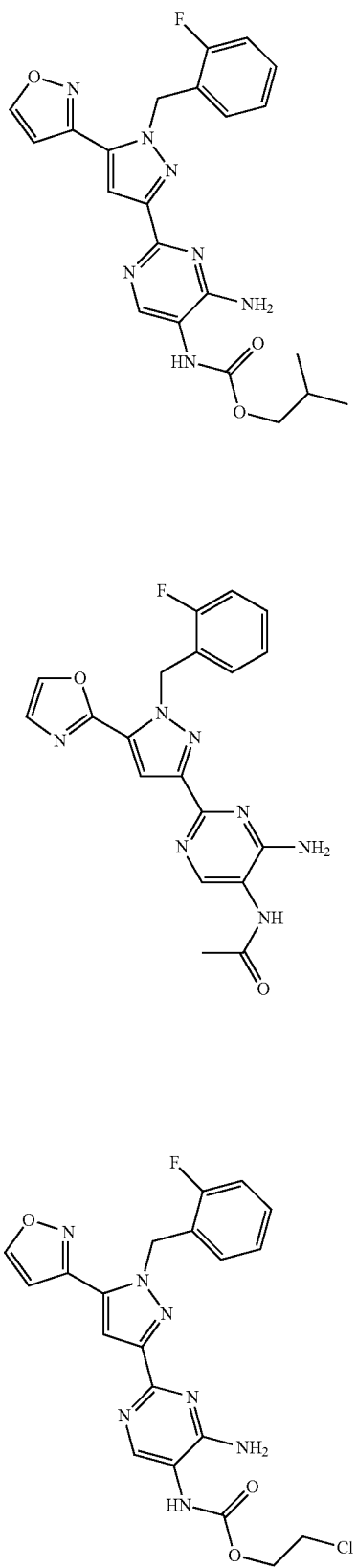
I-150
I-151
I-152

TABLE 1B-continued
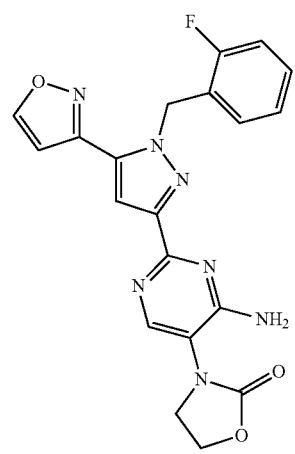
I-153
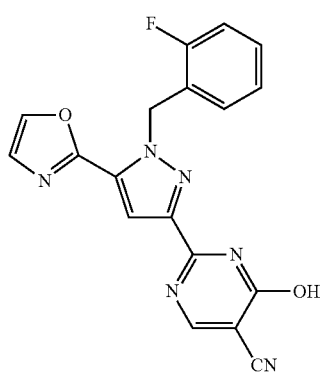
I-154
I-155
TABLE 1B-continued
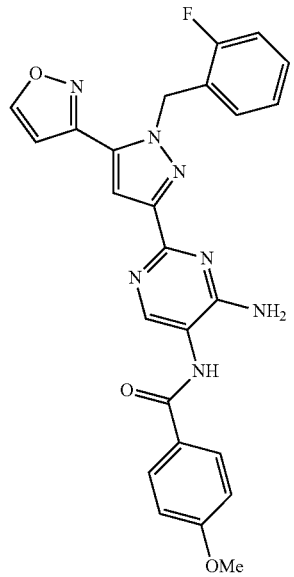
I-156
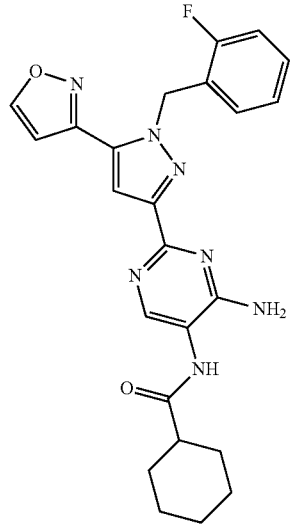
I-157
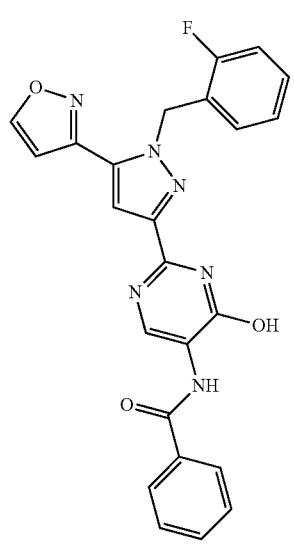
I-158

TABLE 1B-continued
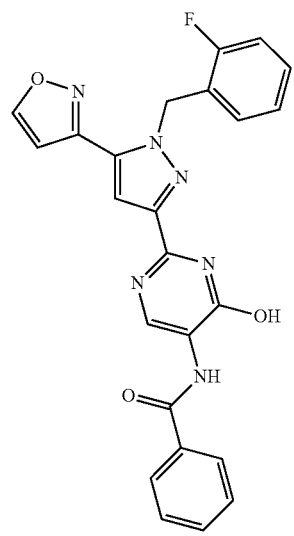
I-159
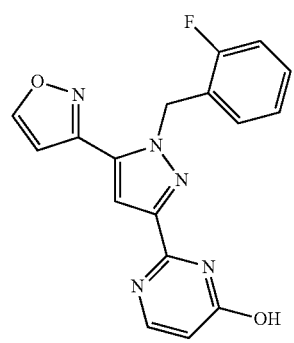
I-160
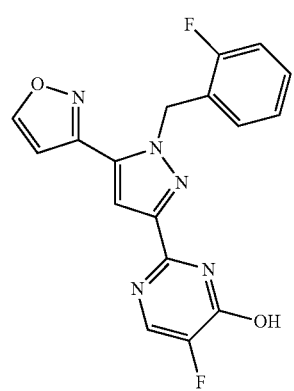
I-161
TABLE 1B-continued
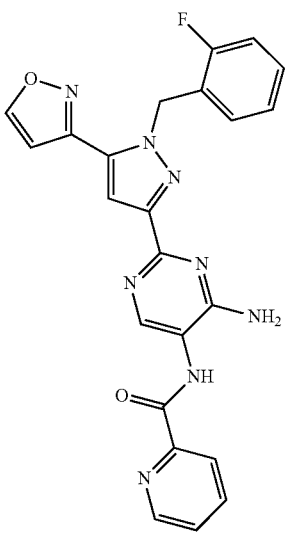
I-162
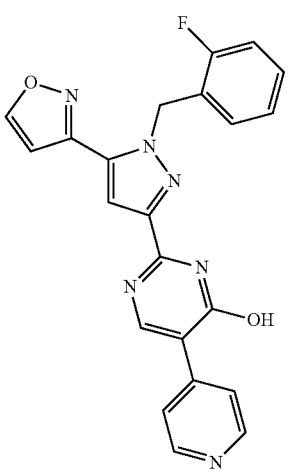
I-163
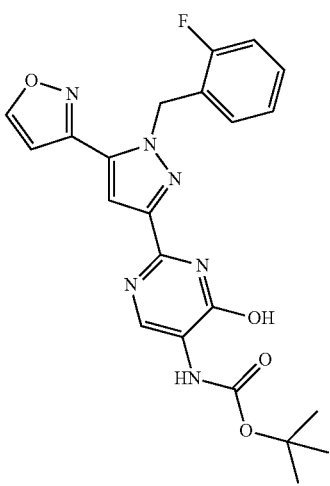
I-164

TABLE 1B-continued
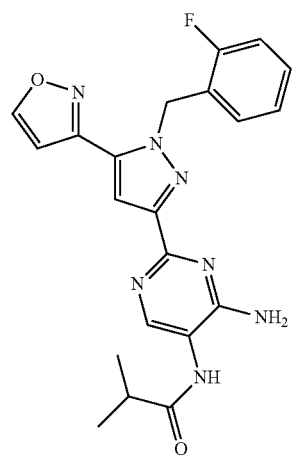
I-165
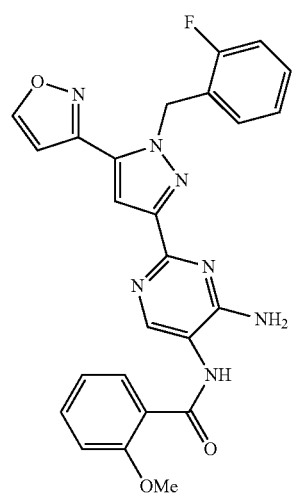
I-166
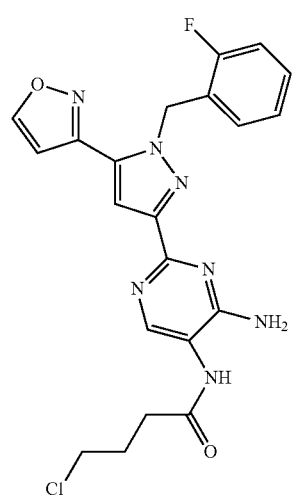
I-167
TABLE 1B-continued
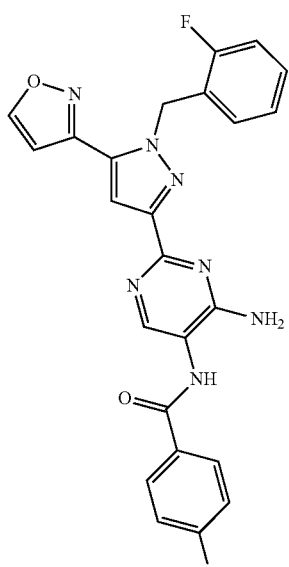
I-168
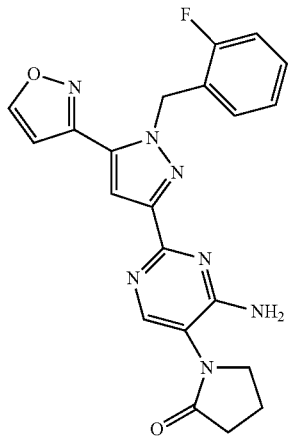
I-169
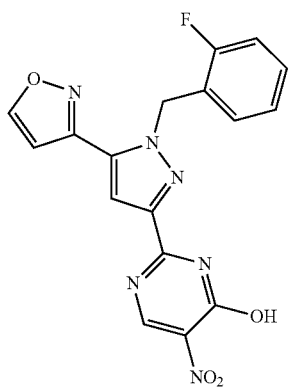
I-170

TABLE 1B-continued
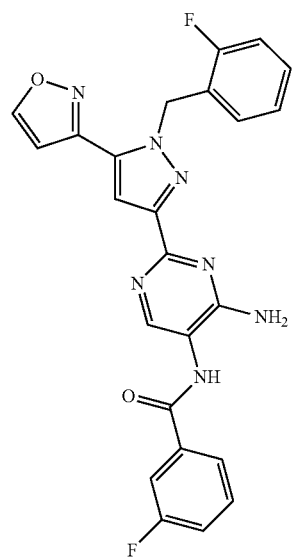
I-171
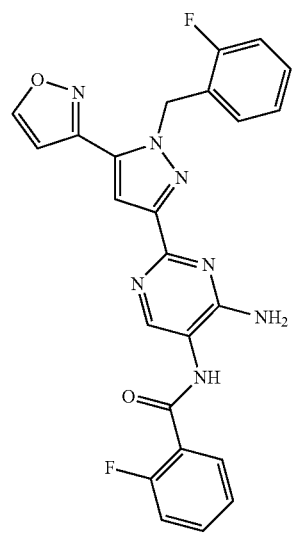
I-172
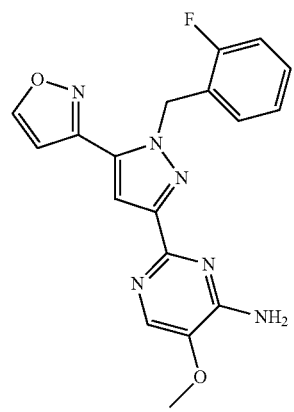
I-173
TABLE 1B-continued
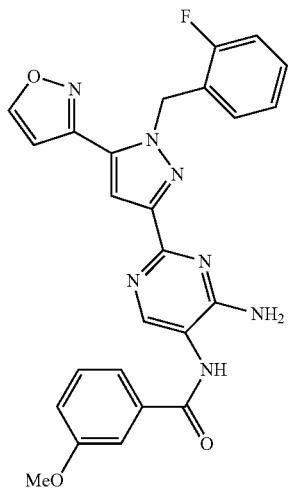
I-174
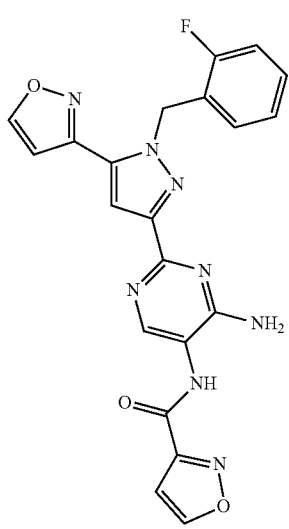
I-175
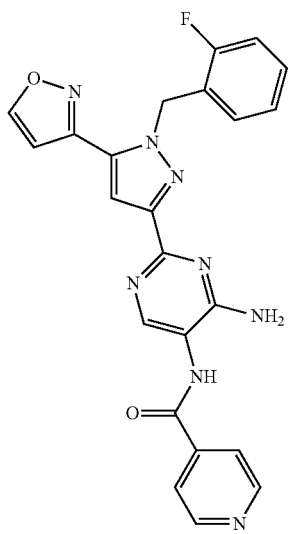
I-176

TABLE 1B-continued
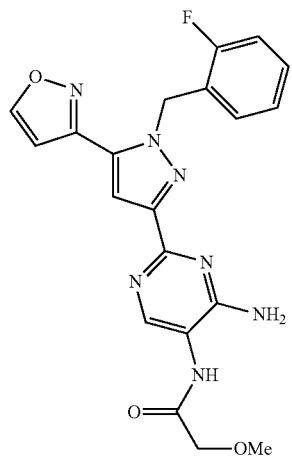
I-177
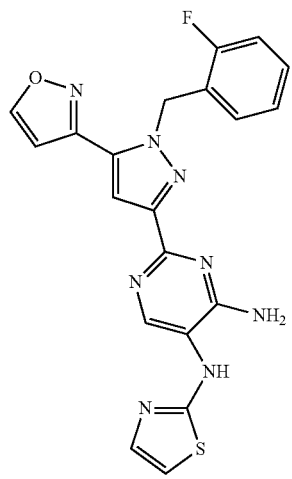
I-178
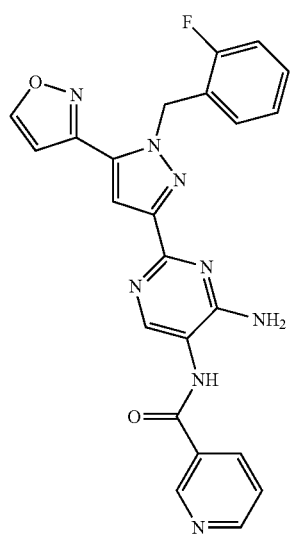
I-179
TABLE 1B-continued
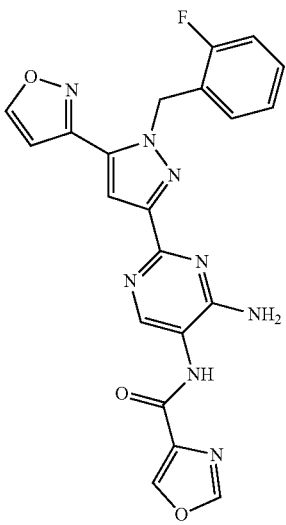
I-180
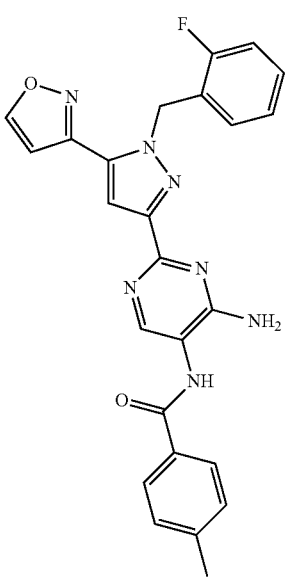
I-181
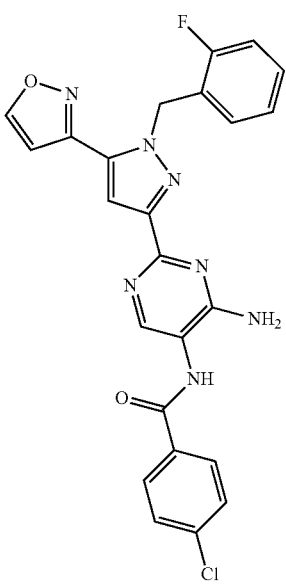
I-182

TABLE 1B-continued
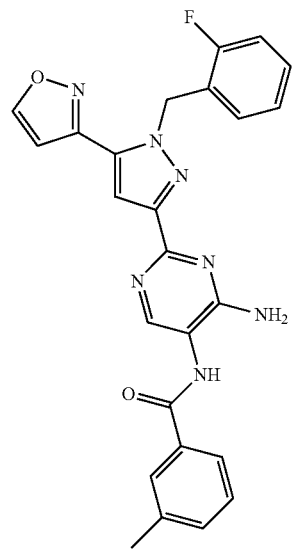
I-183
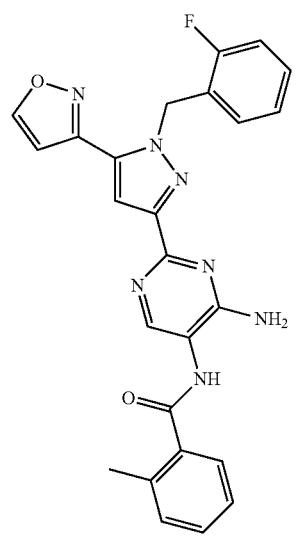
I-184
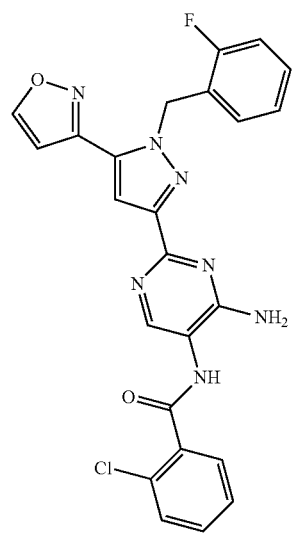
I-185
TABLE 1B-continued
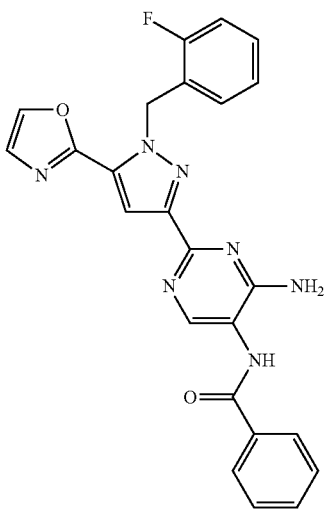
I-186
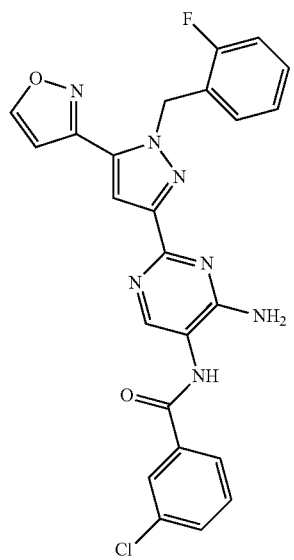
I-187
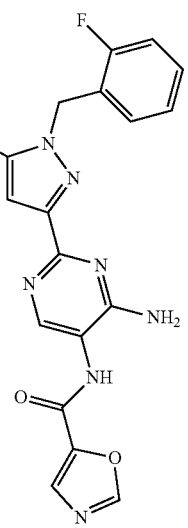
I-188

TABLE 1B-continued
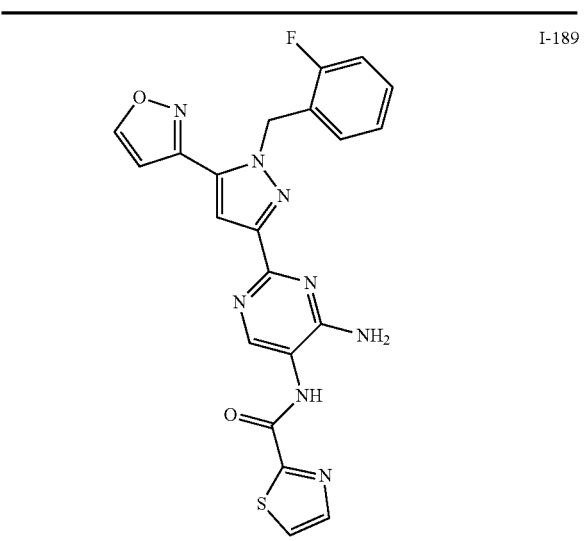
I-189
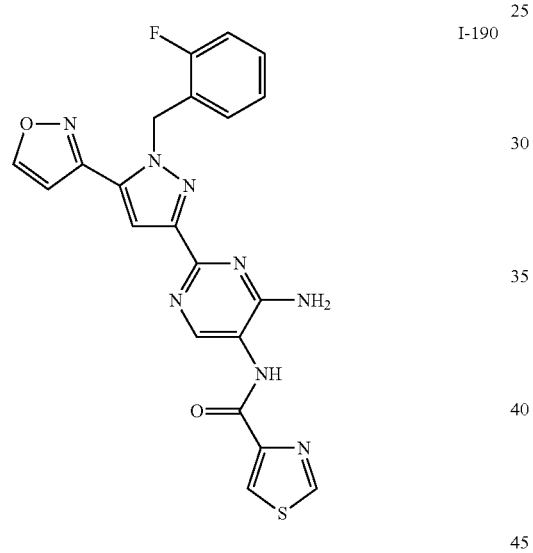
I-190
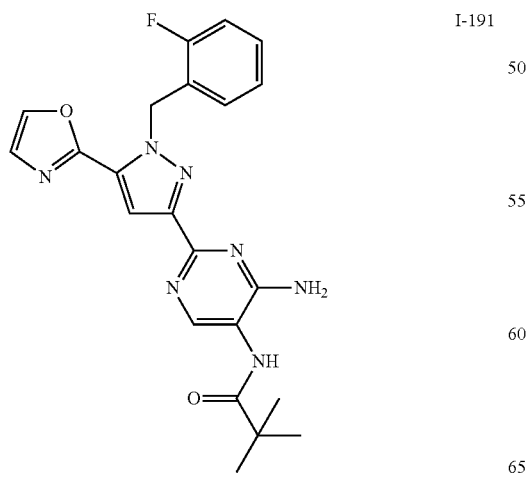
I-191
TABLE 1B-continued
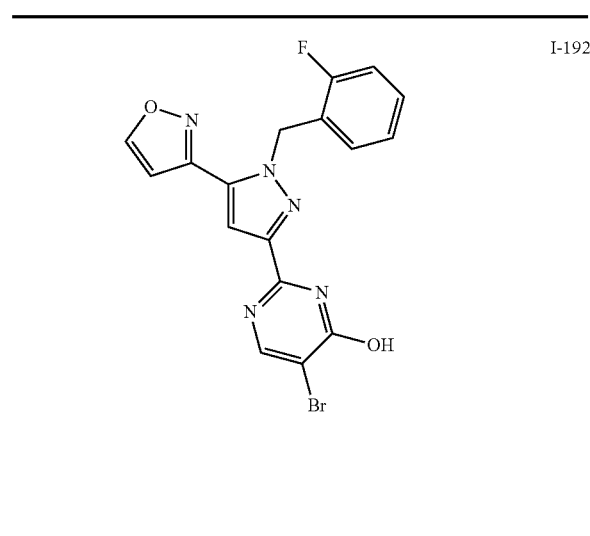
I-192
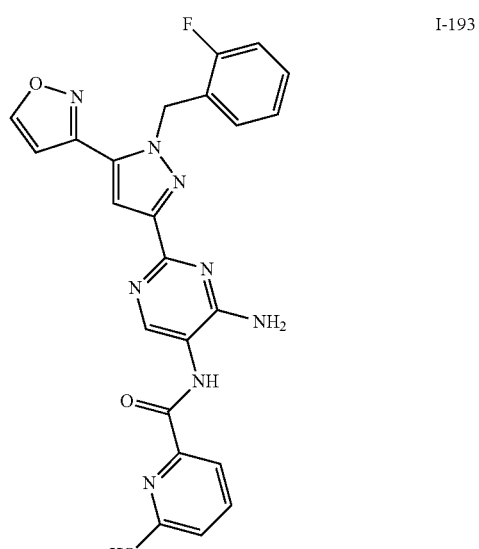
I-193
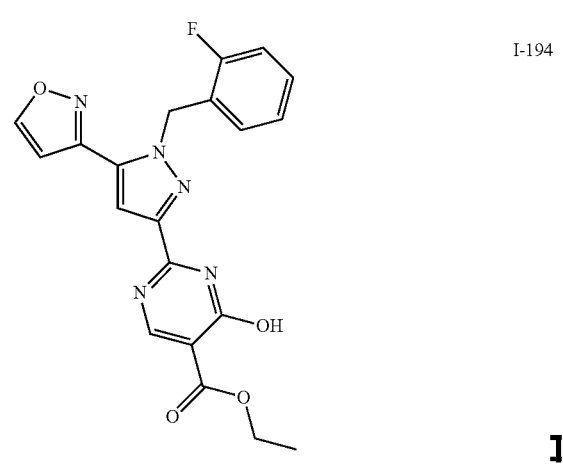
I-194

TABLE 1B-continued
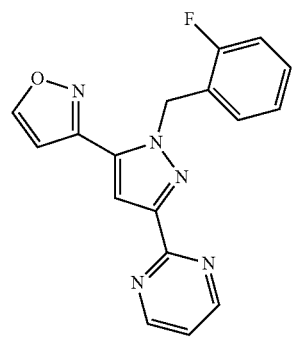
I-195
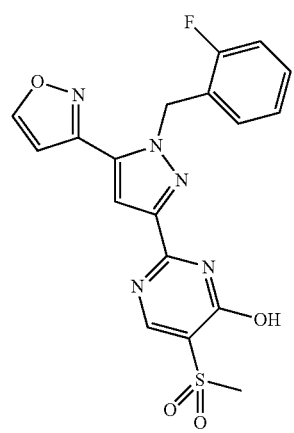
I-196
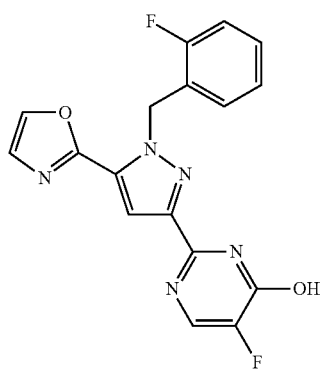
I-197
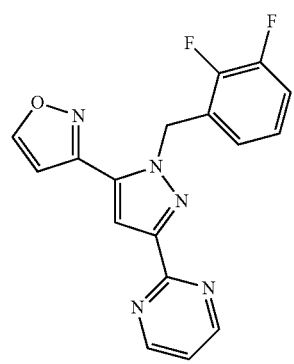
I-198
TABLE 1B-continued
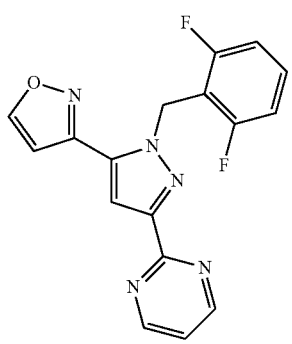
I-199
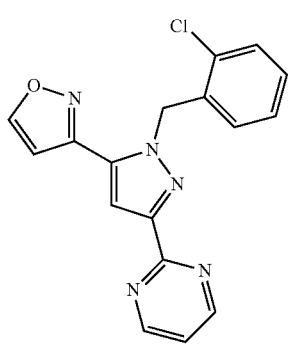
I-200
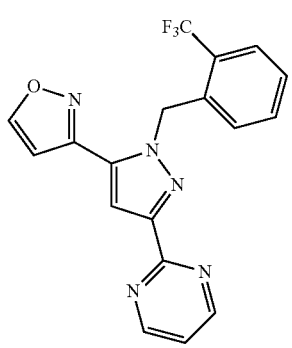
I-201
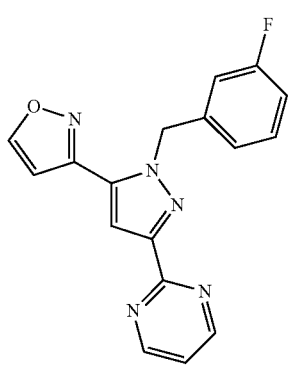
I-202

TABLE 1B-continued
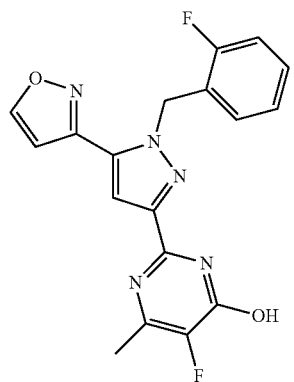
1-203
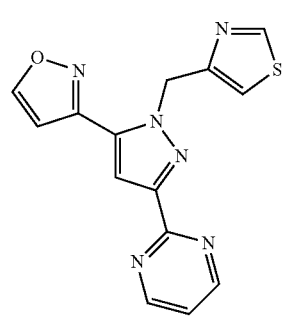
1-204
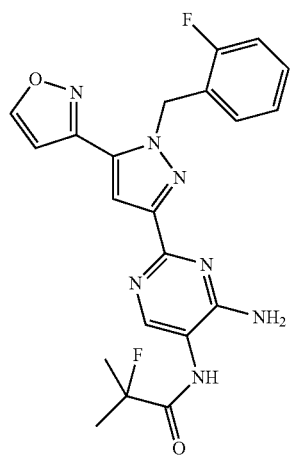
1-205
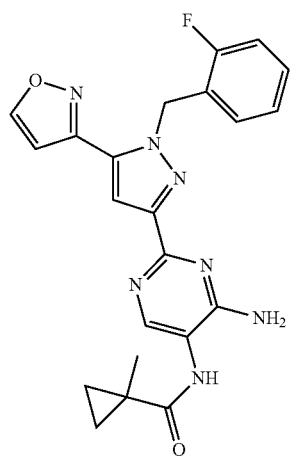
1-206
TABLE 1B-continued
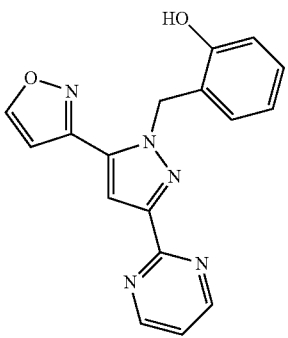
1-207
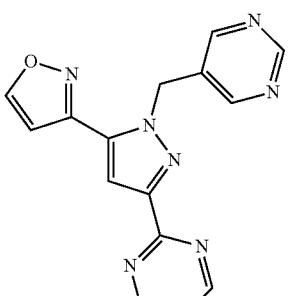
1-208
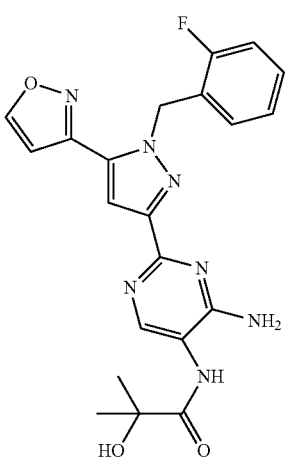
1-209
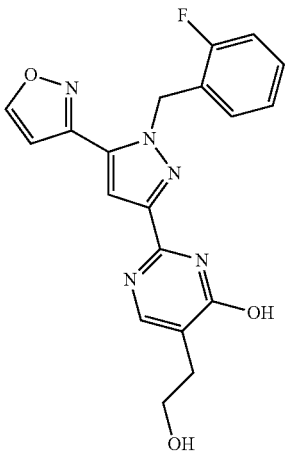
1-210

TABLE 1B-continued
1-211
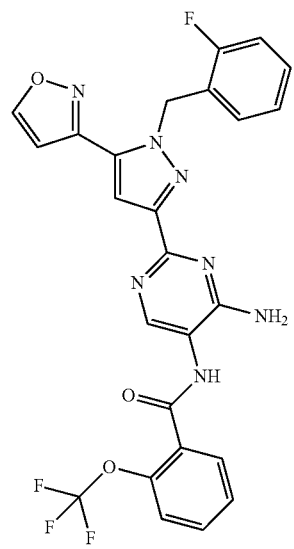
1-212
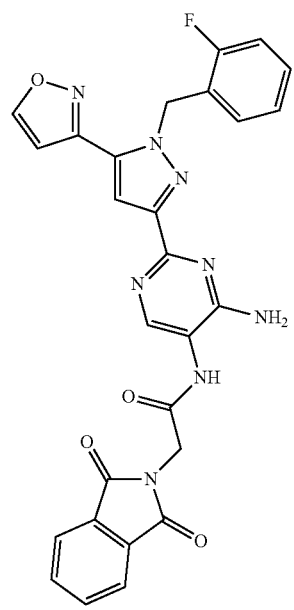
1-213
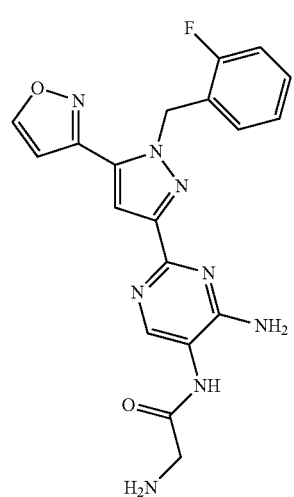
TABLE 1B-continued
1-214
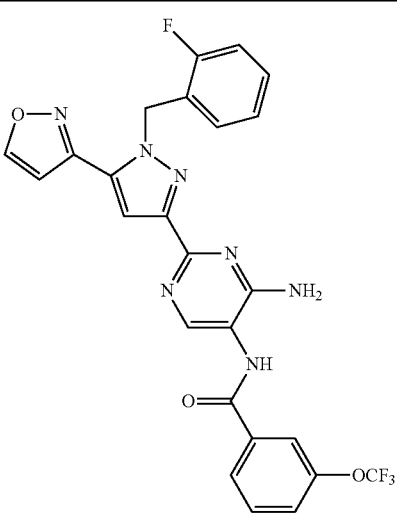
1-215
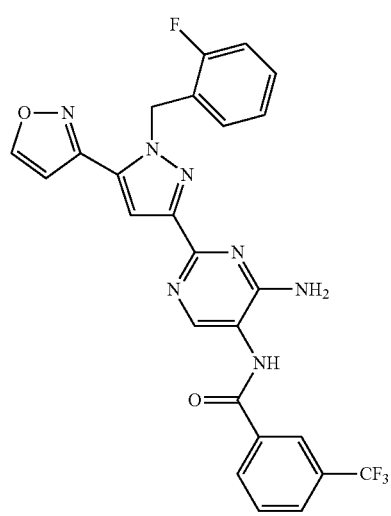
1-216
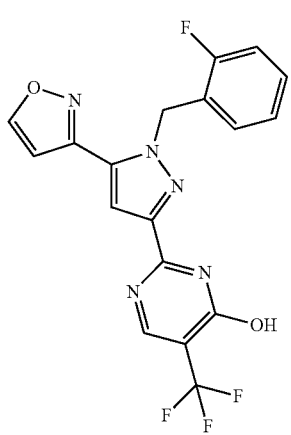

TABLE 1B-continued
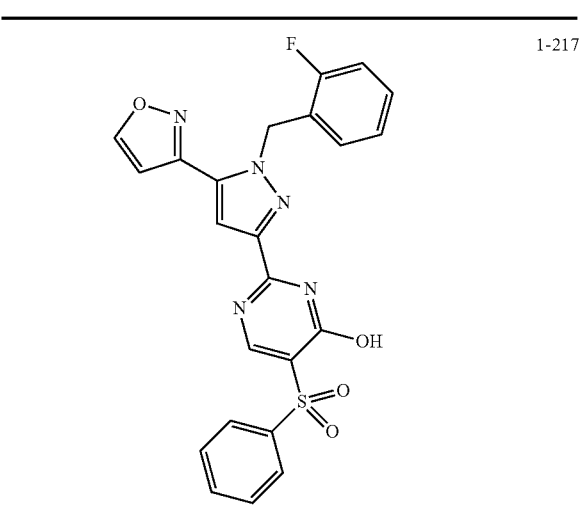
1-217
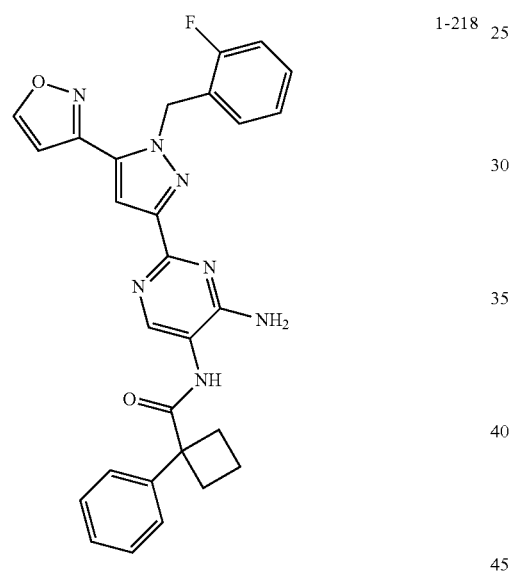
1-218
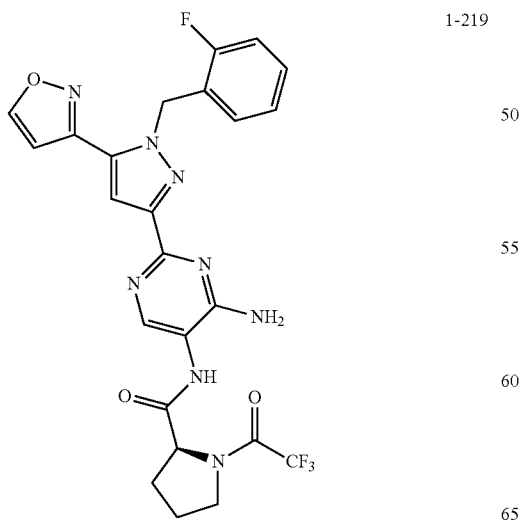
1-219
TABLE 1B-continued
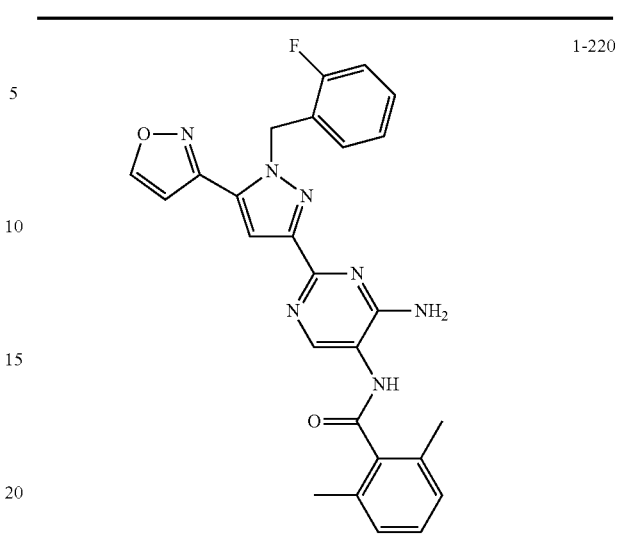
1-220
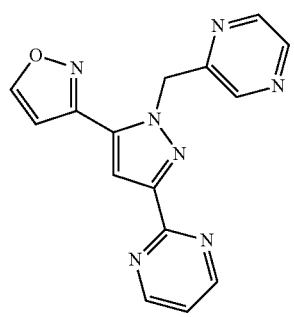
1-221
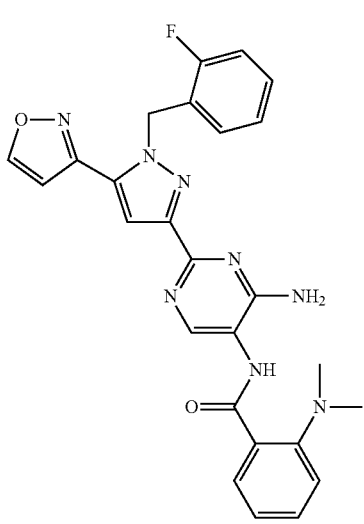
1-222

TABLE 1B-continued
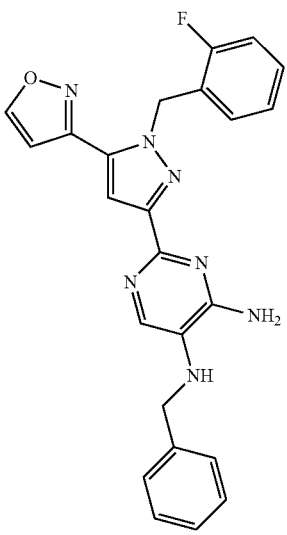
1-223
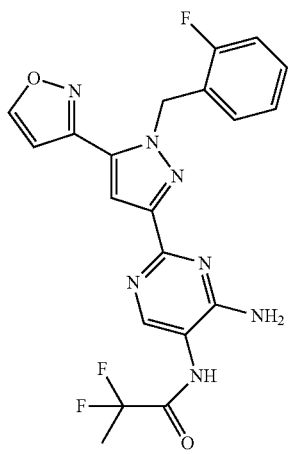
1-226
1-224
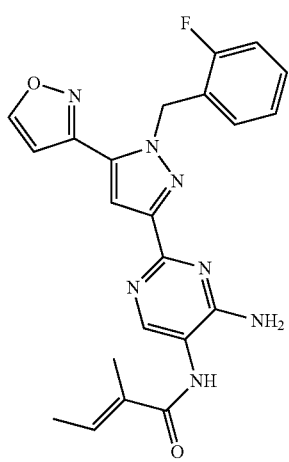
1-227
1-225
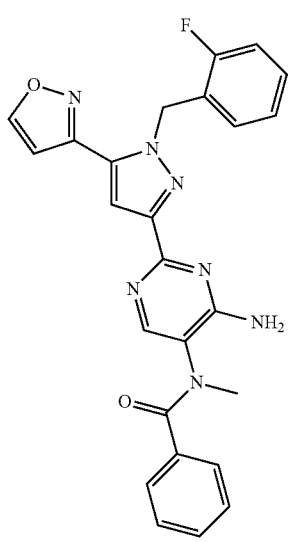
1-228

TABLE 1B-continued
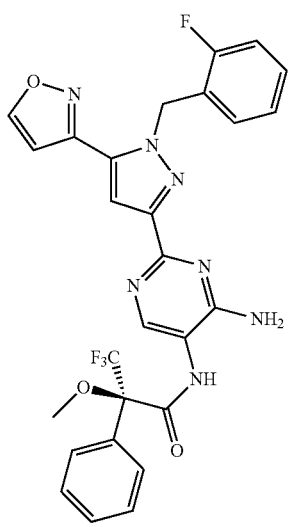
1-229
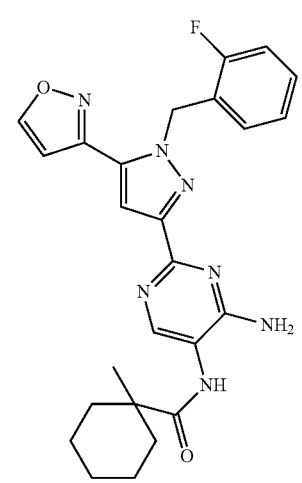
1-230
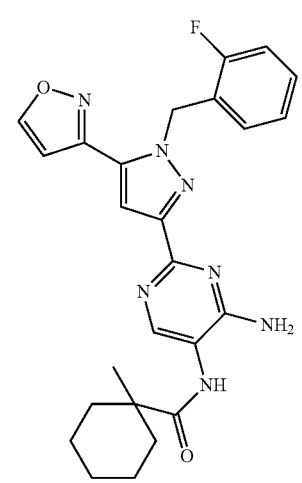
1-231
TABLE 1B-continued
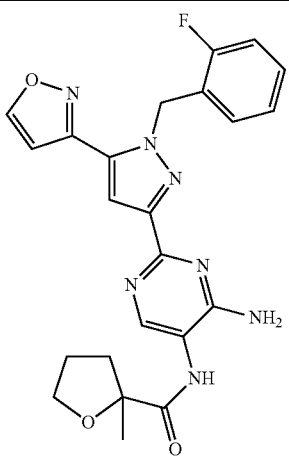
1-232
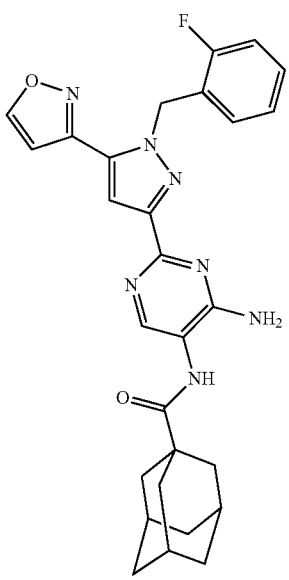
1-233
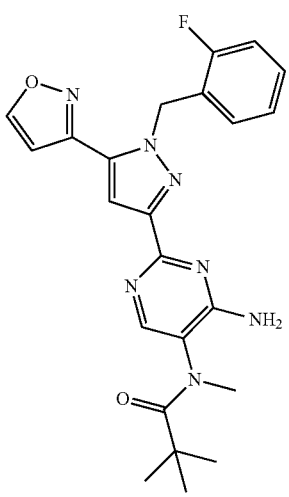
1-234

TABLE 1B-continued
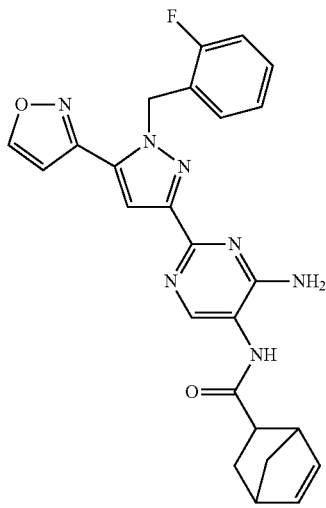
1-235
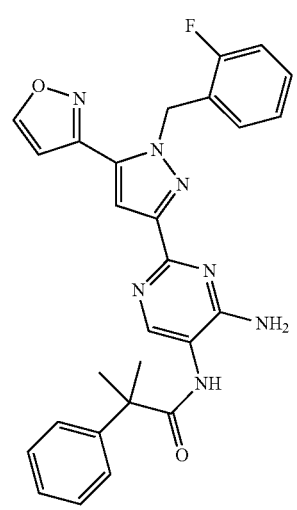
1-236
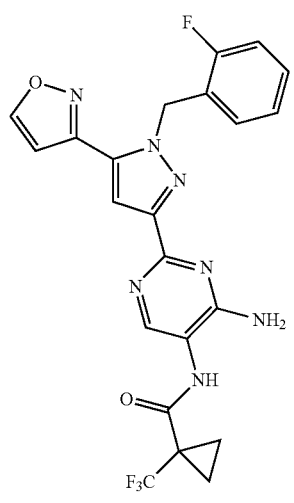
1-237
TABLE 1B-continued
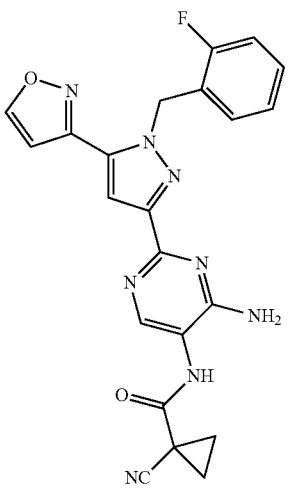
1-238
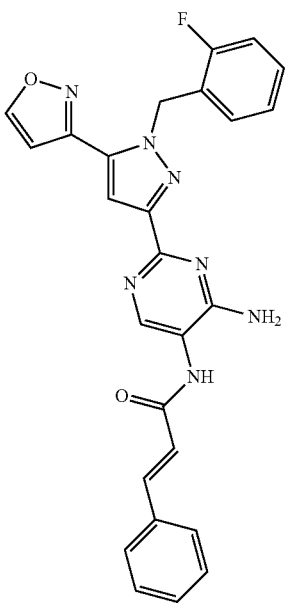
1-239
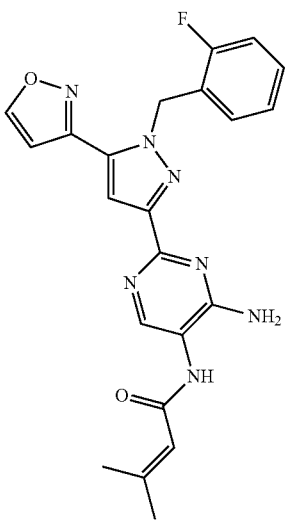
1-240

TABLE 1B-continued
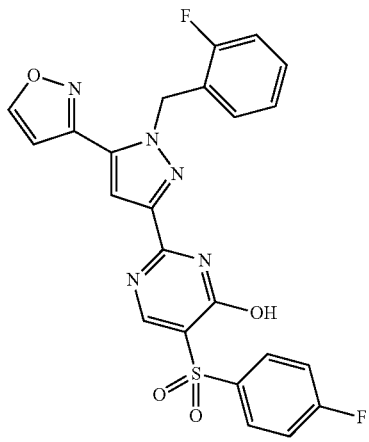
1-241
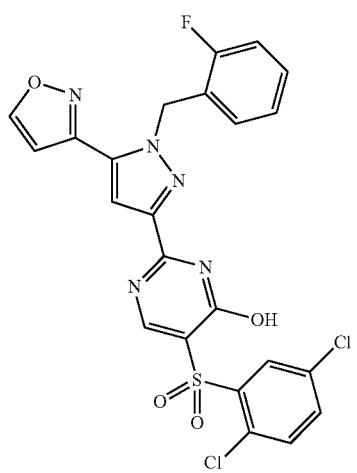
1-242
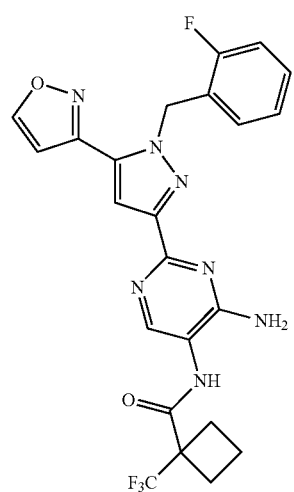
1-243
TABLE 1B-continued
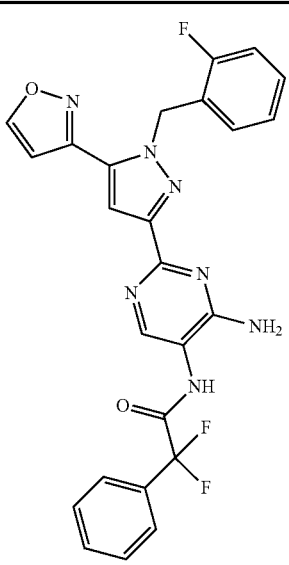
1-244
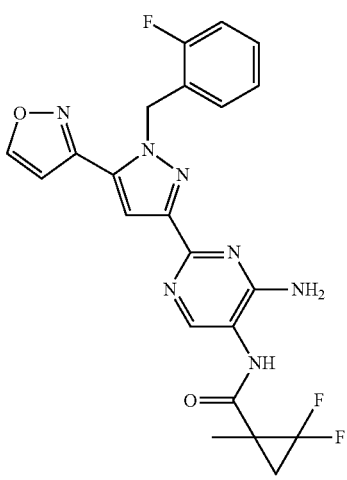
1-245
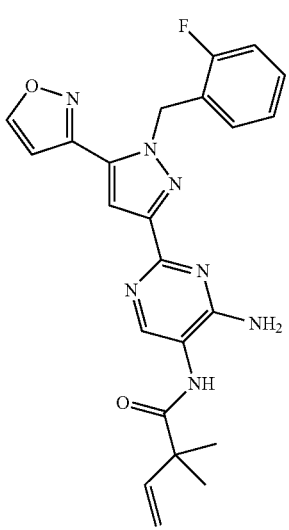
1-246

TABLE 1B-continued
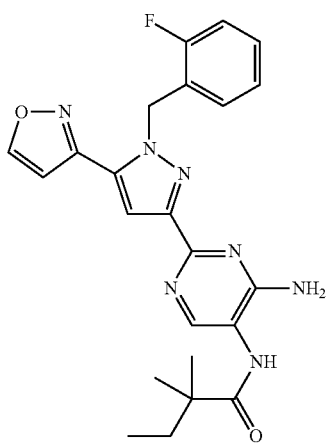
1-247
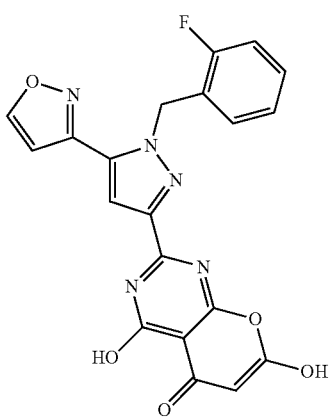
1-248
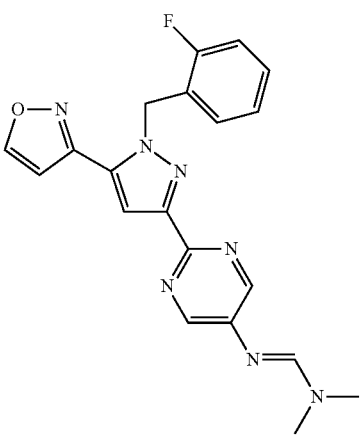
1-249
TABLE 1B-continued
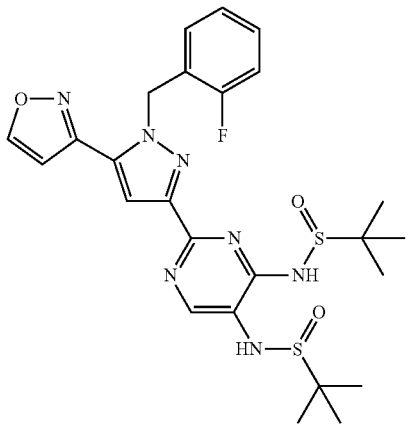
1-250
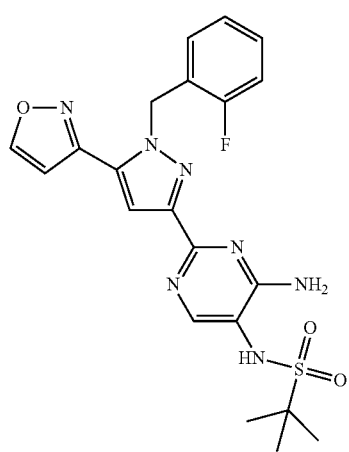
1-251
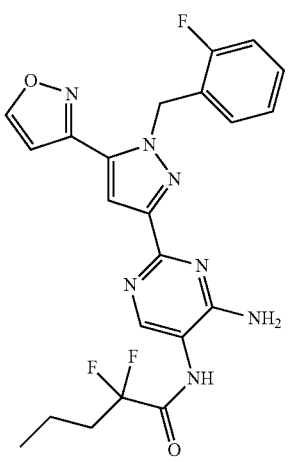
1-252

TABLE 1B-continued
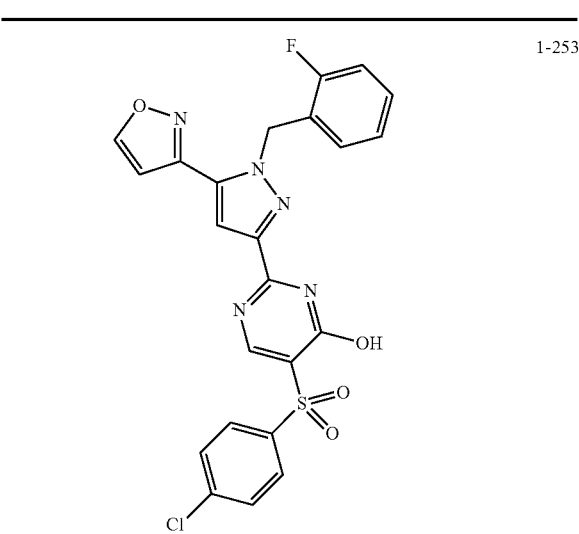
1-253
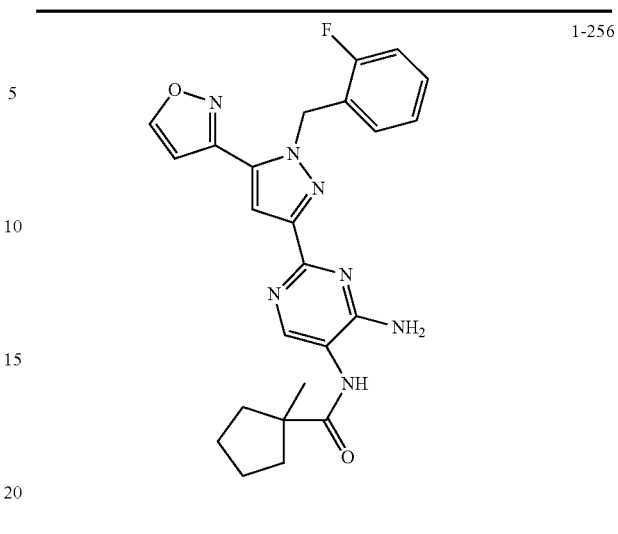
1-256
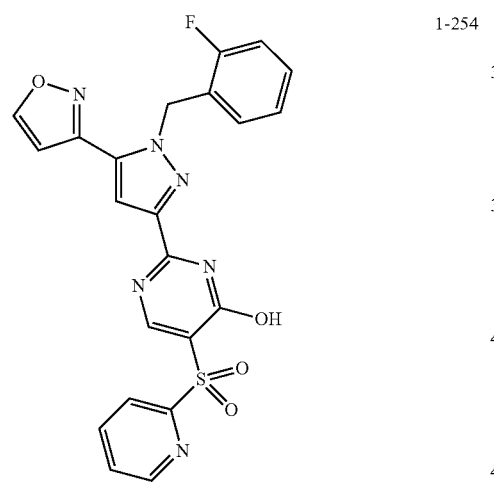
1-254
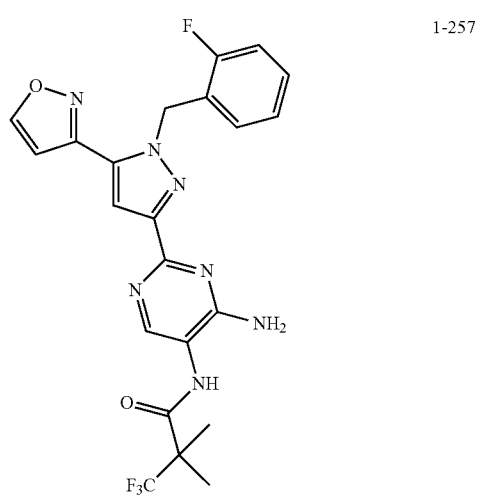
1-257
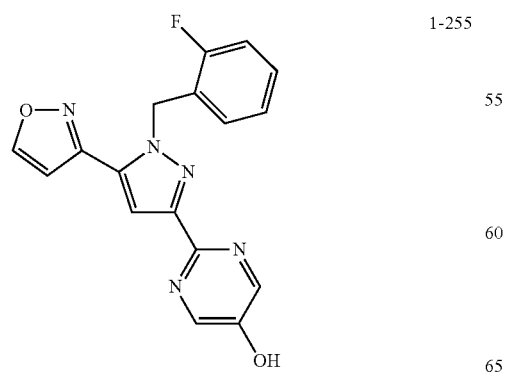
1-255
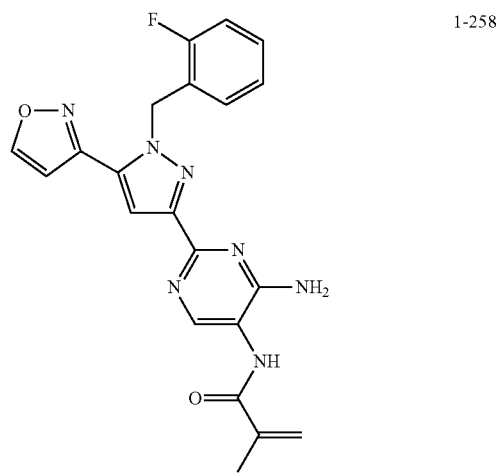
1-258

TABLE 1B-continued
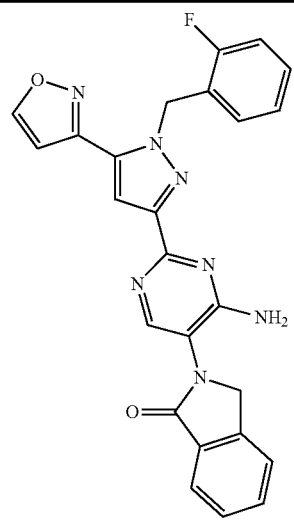
1-259
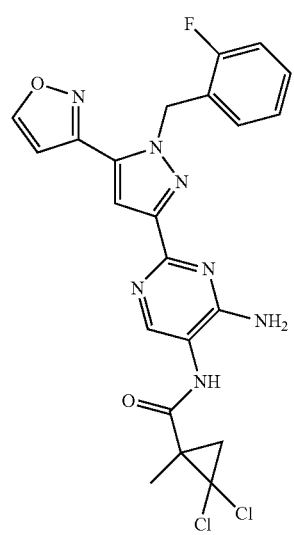
1-260
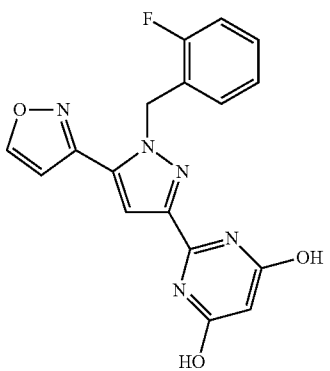
1-261
TABLE 1B-continued
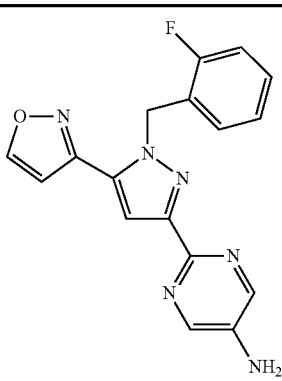
1-262
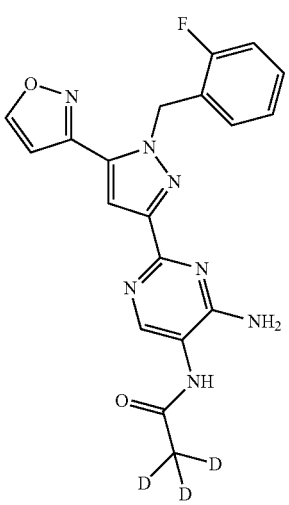
1-263
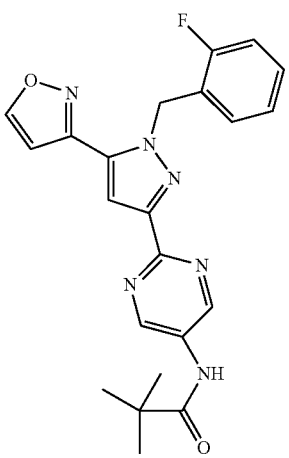
1-264

TABLE 1B-continued
1-265
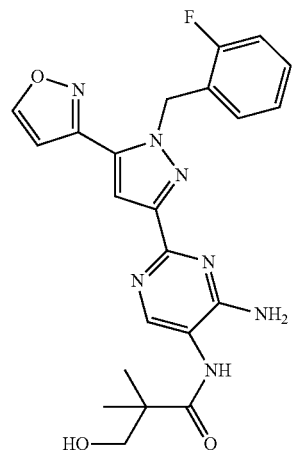
1-266
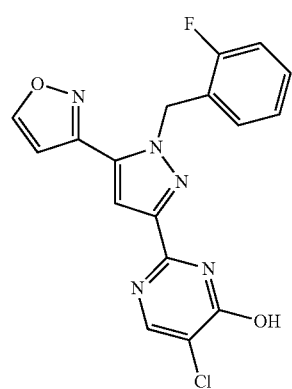
1-267
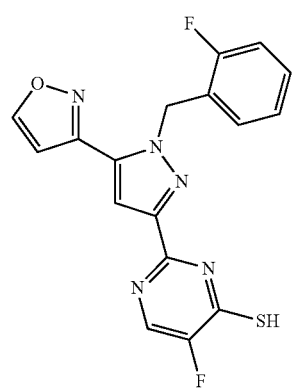
TABLE 1B-continued
1-268
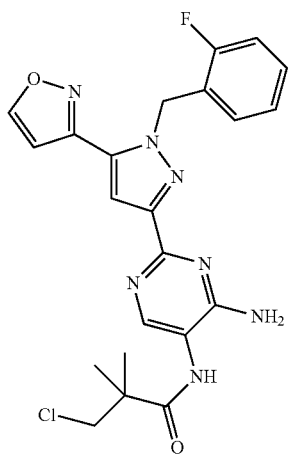
1-269
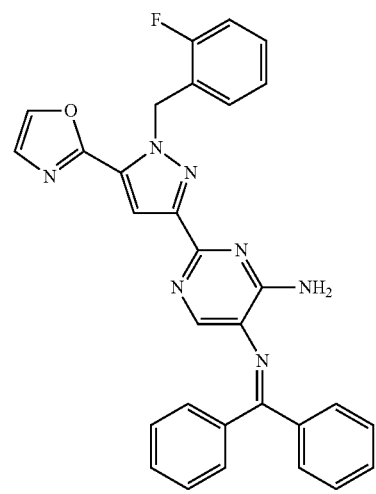
1-270
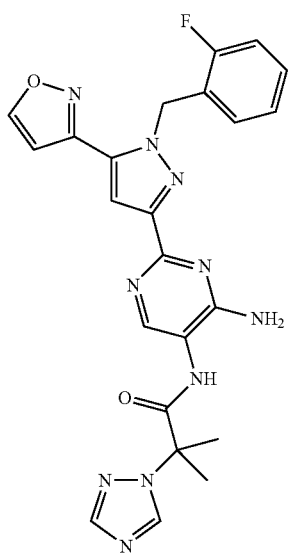

TABLE 1B-continued
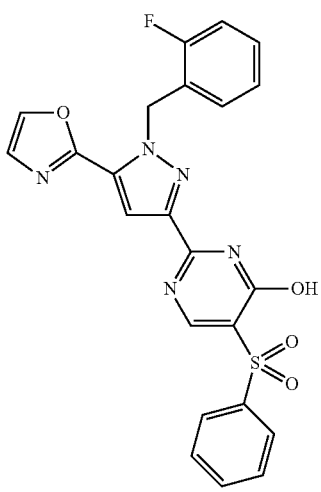
1-271
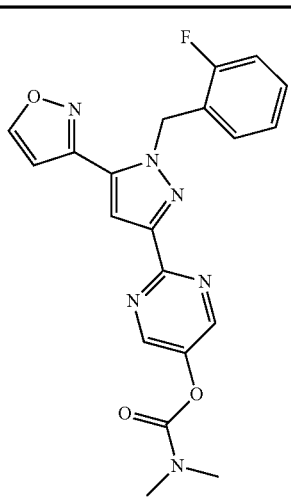
1-274
Column 117, line 24 to Column 119, line 36:
TABLE 1C
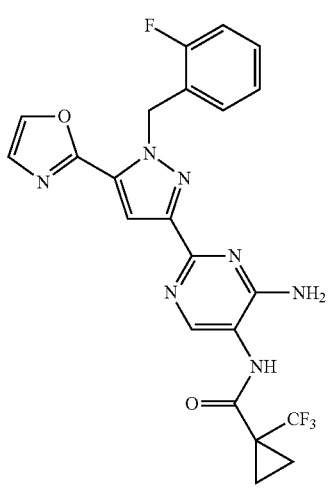
1-272
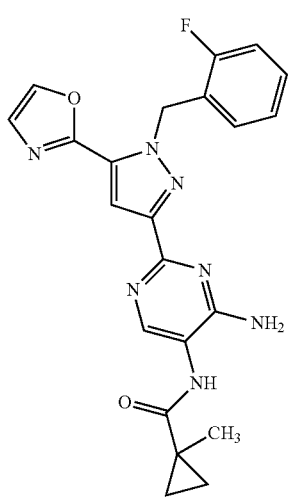
1-275
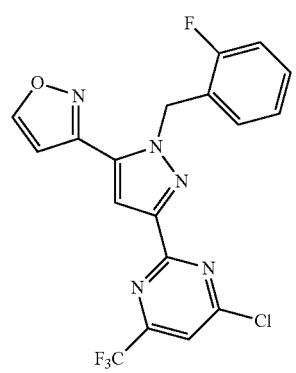
1-273
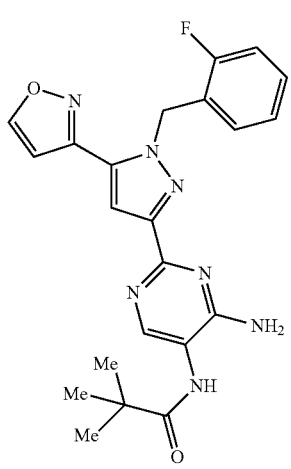
1-277

TABLE 1C-continued
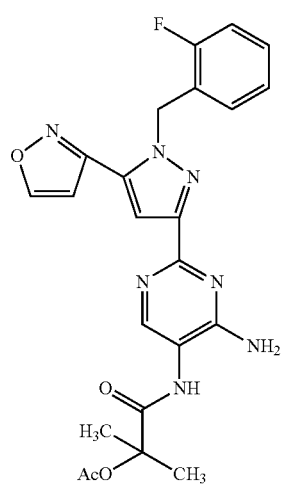
1-278
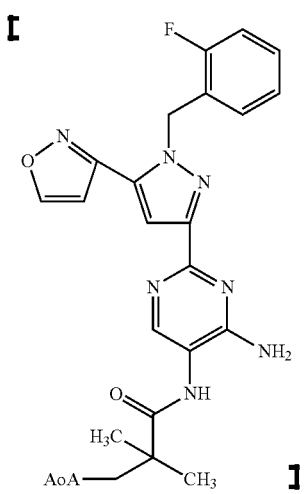
1-280
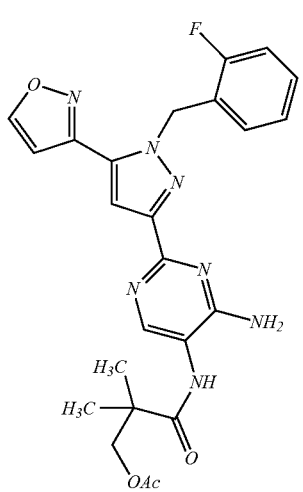
TABLE 1C-continued
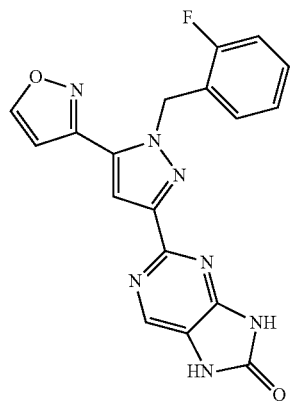
1-281
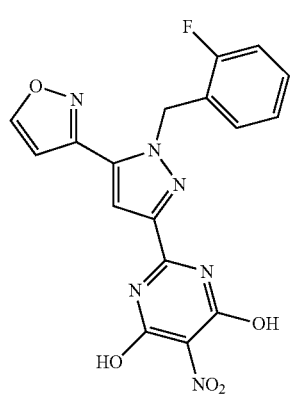 [SMILES: O=[N+]([O-])c1c(O)nc(-c2cc(-c3ccon3)n(Cc3ccccc3F)n2)nc1O]
1-282
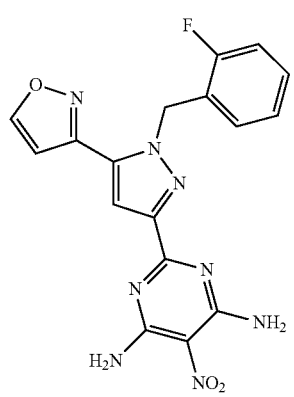 [SMILES: Nc1nc(-c2cc(-c3ccon3)n(Cc3ccccc3F)n2)nc(N)c1[N+](=O)[O-]]
1-283
Column 119, line 38 to Column 126, line 47:
TABLE 1D
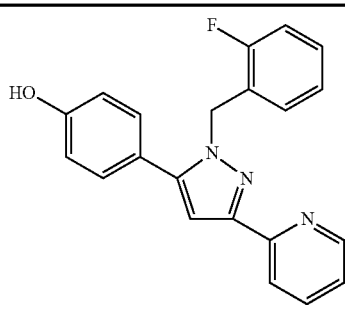
1-310

TABLE 1D-continued
| | |
|---|---|
| 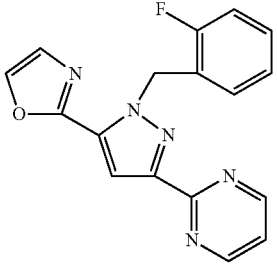 | 1-309 |
| 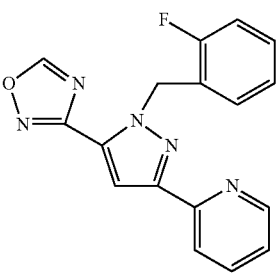 | 1-311 |
| 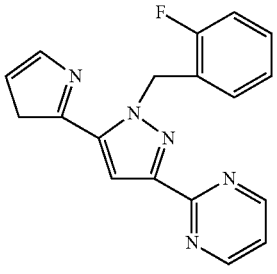 | 1-304 |
| 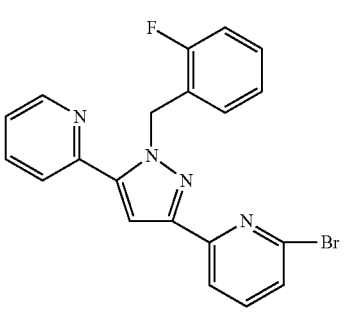 | 1-305 |
| 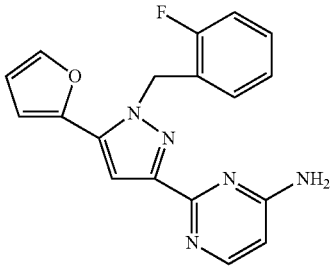 | 1-306 |
TABLE 1D-continued
| | |
|---|---|
| 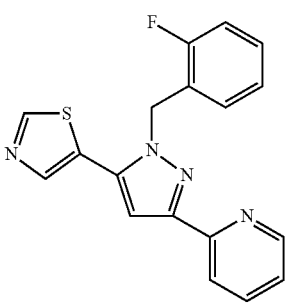 | 1-307 |
| 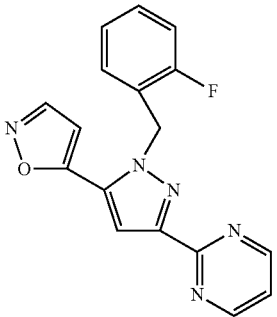 | 1-308 |
| 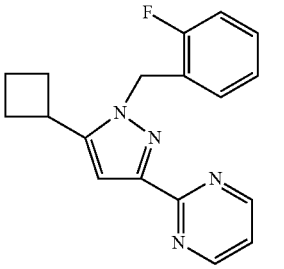 | 1-313 |
| 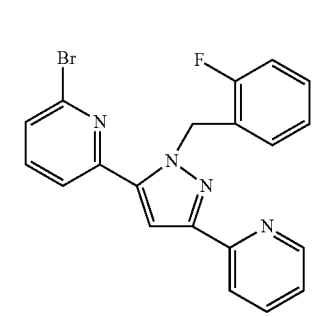 | 1-284 |
| 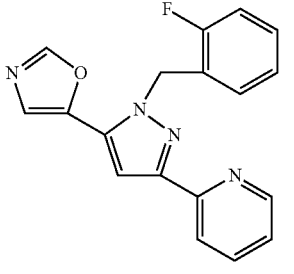 | 1-285 |

TABLE 1D-continued
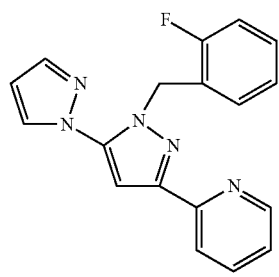 1-286
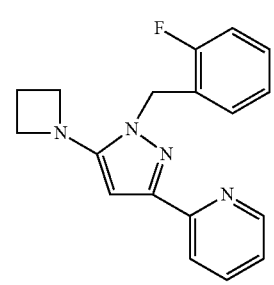 1-287
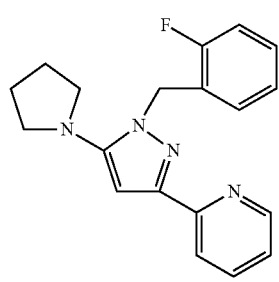 1-288
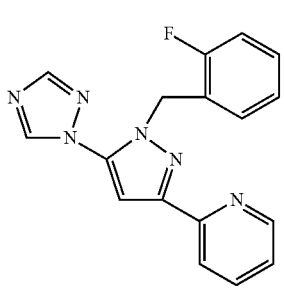 1-289
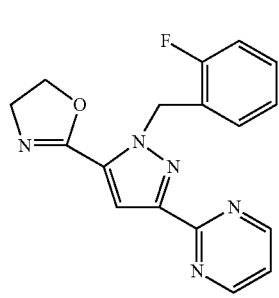 1-290
TABLE 1D-continued
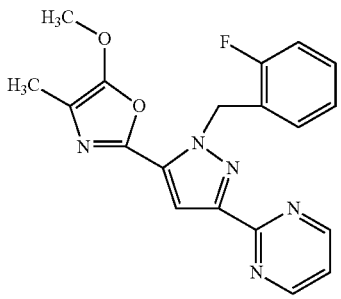 1-291
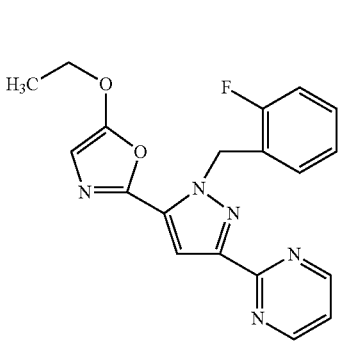 1-292
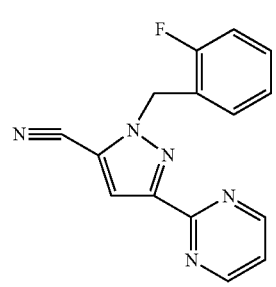 1-293
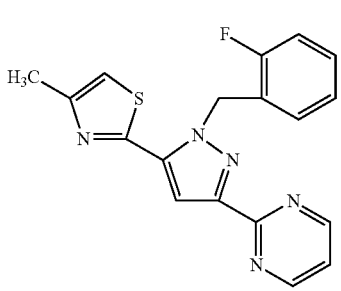 1-294
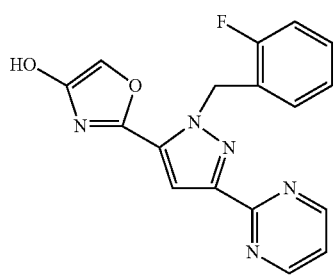 1-295

TABLE 1D-continued
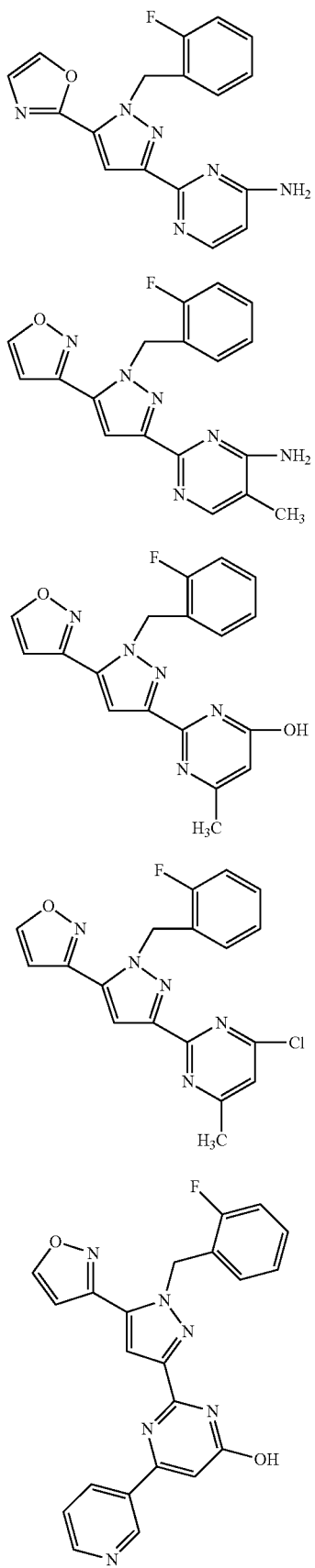
1-296
1-297
1-298
1-299
1-300
TABLE 1D-continued
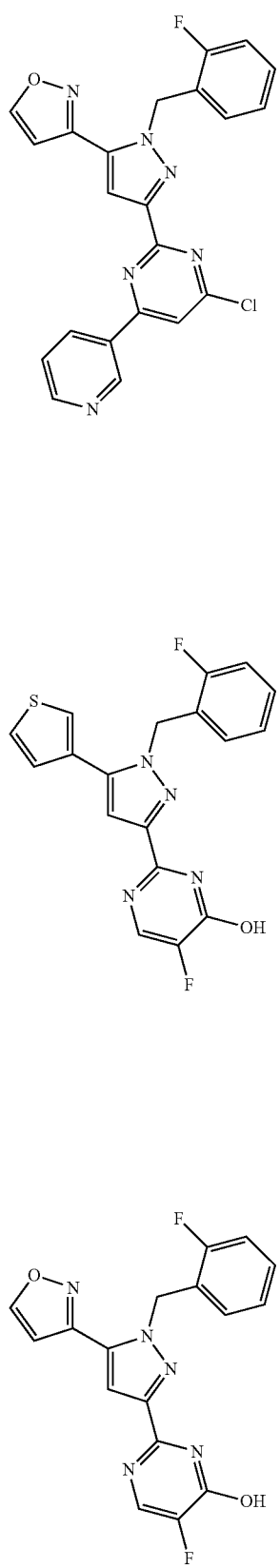
1-301
1-302
1-303

TABLE 1D-continued

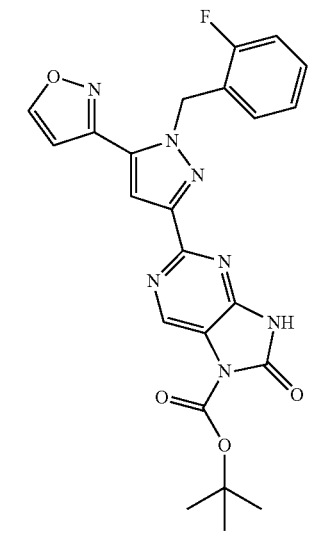

1-312

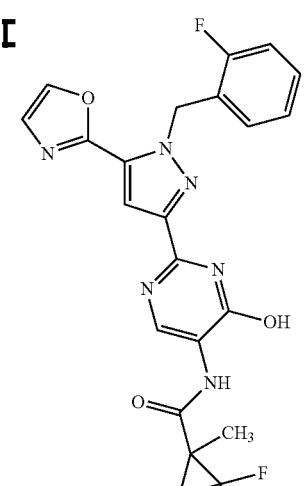

1-276

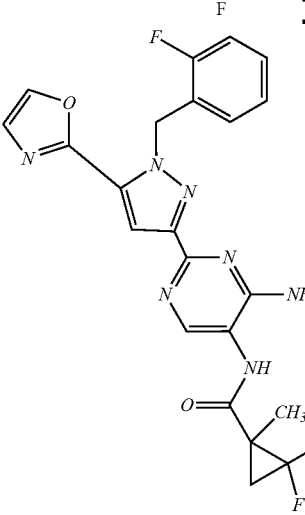

Column 245, lines 6-39:

The following compounds were synthesized with the procedures disclosed above.

[Compound I-194

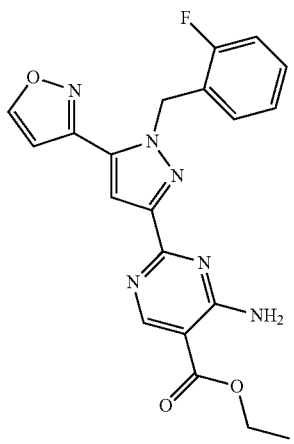

Compound I-194 was synthesized as a white solid (24% yield over 4 steps) following General Procedure F using ethyl 1-(2-fluorobenzyl)-5-(isoxazol-3-yl)-1H-pyrazole-3-carboxylate (Intermediate 7) as the starting compound. The cyclization reaction (step 4) was conducted in ethanol in the presence of one equivalents of diethyl 2-(ethoxymethylene)malonate and one equivalent of N,N-diisopropylethylamine. $^1$H NMR (400 MHz, DMSO-d6) δ 9.11 (d, 1H), 8.54 (bs, 1H), 7.75 (s, 1H), 7.36-7.30 (m, 1H), 7.25-7.17 (m, 1H), 7.23 (s, 1H), 7.13-7.07 (m, 1H), 7.05-6.94 (m, 1H), 5.92 (s, 2H), 4.22 (q, 2H), 1.26 (t, 3H).]

Column 266, line 55, to Column 267, line 26:

To a solution of 1-methylcyclopropanecarboxylic acid (10 equiv) in dichloromethane was added oxalyl chloride (9 equiv) and catalytic N,N-dimethylformamide. Once gas evolution ceased, this crude reaction mixture was added portionwise to a suspension of Compound I-149 (1 equiv) in dichloromethane/pyridine (1:1) until complete consumption of starting material was observed by LS/MS. Purification via silica gel chromatography (0-10% methanol in dichloromethane) following an aqueous ammonium chloride and dichloromethane workup provided the desired compound I-275 as a white solid (20.2%).

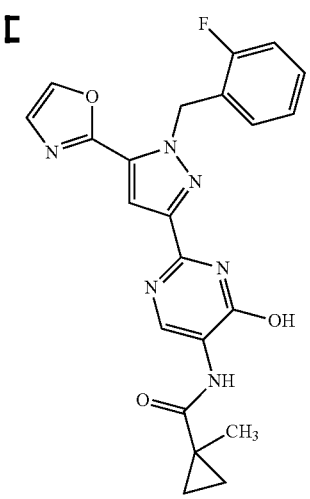

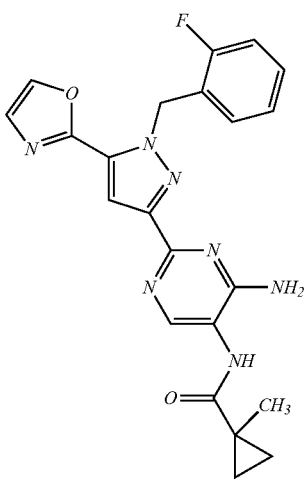

¹H NMR (400 MHz, CDCl₃) 8.21 (s, 1H), 7.66 (s, 1H), 7.56 (s, 1H), 7.40 (br. s, 1H), 7.18 (s, 1H), 7.13-7.16 (m, 1H), 6.97-7.02 (m, 1H), 6.92-6.97 (m, 1H), 6.73-6.76 (m, 1H), 6.11 (s, 2H), 5.43 (s, 2H), 1.50 (s, 3H), 1.33 (q, 2H), 0.74 (q, 2H).

Column 267, lines 29-67:

To a solution of 2,2-difluoro-1-methylcyclopropanecarboxylic acid (10 equiv) in N,N-dichloromethane was added oxalyl chloride (9 equiv) and catalytic dimethylformamide. Once gas evolution ceased, this crude reaction mixture was added portion-wise to a suspension of Compound I-149 (1 equiv) in dichloromethane/pyridine (1:1) until complete consumption of starting material was observed by LS/MS. Purification via silica gel chromatography (0-10% methanol in dichloromethane) following an aqueous ammonium chloride and dichloromethane workup provided the desired compound I-276 as a white solid (39.3%).

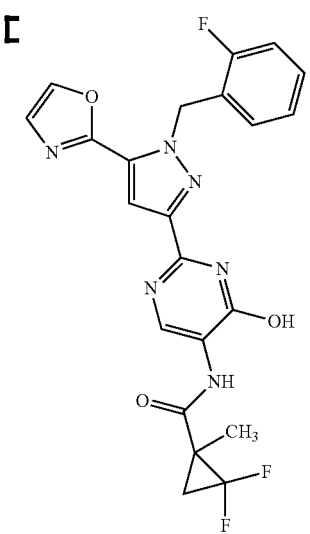

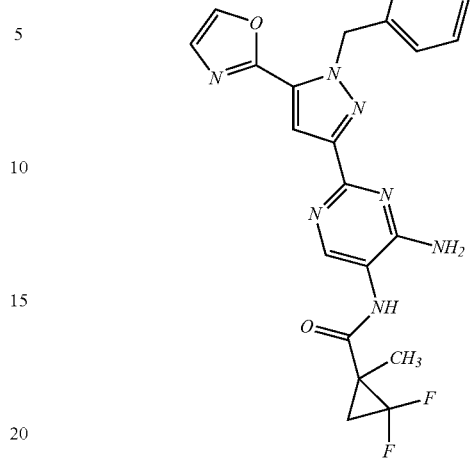

¹H NMR (400 MHz, CDCl₃) 8.23 (s, 1H), 7.66 (s, 1H), 7.46 (s, 1H), 7.26 (br. s, 1H), 7.19 (s, 1H), 7.13-7.17 (m, 1H), 6.99 (dt, 1H), 6.93 (dt, 1H), 6.75 (dt, 1H), 6.11 (s, 2H), 5.30 (s, 2H), 2.27-2.34 (m, 1H), 1.61 (s, 3H), 1.37-1.43 (m, 1H).

Column 313, lines 1-11:

*Compound I-256*

To a solution of 1-methylcyclopentanecarboxylic acid (6.8 equiv) in dichloromethane was added oxalyl chloride (6.1 equiv) and catalytic N,N-dimethylformamide. Once gas evolution ceased, this crude reaction mixture was added portion-wise to a suspension of Compound I-107 (1 equiv) in dichloromethane/pyridine (1:1) until the absence of starting material was observed by LC/MS. Following an aqueous ammonium chloride and dichloromethane workup, purification via silica gel chromatography (50-70% ethyl acetate in hexanes) provided the desired compound as an off-white solid (60%).

AS A RESULT OF REEXAMINATION, IT HAS BEEN DETERMINED THAT:

Claims 21, 22, 75 and 76 are cancelled.

Claims 1, 23, 24, 39, 40, 41, 46, 68, 69, 74 and 77 are determined to be patentable as amended.

Claims 2-20, 25-38, 42-45, 47-67, 70-73, 78 and 79, dependent on an amended claim, are determined to be patentable.

1. A compound according to Formula I, or a pharmaceutically acceptable salt thereof,

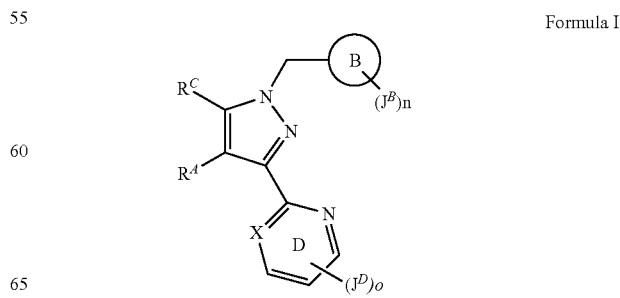

Formula I wherein:
ring B is a phenyl or a 6-membered heteroaryl ring, containing 1 or 2 nitrogen atoms in the ring;
n is an integer selected from 0 to 3;
each $J^B$ is independently selected from halogen, —CN, $NO_2$, —$OR^B$ or a $C_{3-8}$ cycloaliphatic group; wherein each said $C_{1-6}$ aliphatic and each said $C_{3-8}$ cycloaliphatic group is optionally and independently substituted with up to 3 instances of $R^3$;
each $R^B$ is independently selected from hydrogen, a $C_{1-6}$ aliphatic or a $C_{3-8}$ cycloaliphatic; wherein each said $C_{1-6}$ aliphatic and each said $C_{3-8}$ cycloaliphatic ring is optionally and independently substituted with up to 3 instances of $R^3$;
each $R^3$ is independently selected from halogen, —CN, $C_{1-4}$ alkyl, $C_{1-4}$ haloalkyl, —O($C_{1-4}$ alkyl) or —O($C_{1-4}$ haloalkyl);
X is [selected from] N[, C-$J^D$ or C-H];
o is an integer selected from 0 to 3;
each $J^D$ is independently selected from halogen, —$NO_2$, —$OR^D$, —$SR^D$, —C(O)$R^D$, —C(O)O$R^D$, —C(O)N($R^D$)$_2$, —CN, —N($R^D$)$_2$, —N($R^d$)C(O)$R^D$, —N($R^d$)C(O)O$R^D$, —$SO_2R^D$, —$SO_2$N($R^D$)$_2$, —N($R^d$)$SO_2R^D$, a $C_{1-6}$ aliphatic, —($C_{1-6}$ aliphatic)-$R^D$, a $C_{3-8}$ cycloaliphatic ring, a 6 to 10-membered aryl ring, a 4 to 8-membered heterocyclic ring or a 5 to 10-membered heteroaryl ring; wherein each said 4 to 8-membered heterocylic ring and each said 5 to 10-membered heteroaryl ring contains between 1 and 3 heteroatoms independently selected from O, N or S; and wherein each said $C_{1-6}$ aliphatic, each said $C_{3-8}$ cycloaliphatic ring, each said 6 to 10-membered aryl ring, each said 4 to 8-membered heterocyclic ring and each said 5 to 10-membered heteroaryl ring is optionally and independently substituted with up to 3 instances of $R^5$;
each $R^D$ is independently selected from hydrogen, a $C_{1-6}$ aliphatic, —($C_{1-6}$ aliphatic)-$R^f$, a $C_{3-8}$ cycloaliphatic ring, a 4 to 8-membered heterocyclic ring, phenyl or a 5 to 6-membered heteroaryl ring; wherein each said 4 to 8-membered heterocylic ring and each said 5 to 6-membered heteroaryl ring contains between 1 and 3 heteroatoms independently selected from O, N or S; and wherein each said $C_{1-6}$ aliphatic, each said $C_{3-8}$ cycloaliphatic ring, each said 4 to 8-membered heterocyclic ring, each said phenyl and each said 5 to 6-membered heteroaryl ring is optionally and independently substituted with up to 3 instances of $R^5$;
each $R^d$ is independently selected from hydrogen, a $C_{1-6}$ aliphatic, —($C_{1-6}$ aliphatic)-$R^f$, a $C_{3-8}$ cycloaliphatic ring, a 4 to 8-membered heterocyclic ring, phenyl or a 5 to 6-membered heteroaryl ring; wherein each said heterocylic ring and each said heteroaryl ring contains between 1 and 3 heteroatoms independently selected from O, N or S; and wherein each said $C_{1-6}$ aliphatic, each said $C_{3-8}$ cycloaliphatic ring, each said 4 to 8-membered heterocyclic ring, each said phenyl and each said 5 to 6-membered heteroaryl ring is optionally and independently substituted by up to 3 instances of $R^5$;
each $R^f$ is independently selected from a $C_{3-8}$ cycloaliphatic ring, a 4 to 8-membered heterocyclic ring, phenyl or a 5 to 6-membered heteroaryl ring; wherein each said heterocylic ring and each said heteroaryl ring contains between 1 and 3 heteroatoms independently selected from O, N or S; and wherein each said $C_{1-6}$ aliphatic, each said $C_{3-8}$ cycloaliphatic, each said 4 to 8-membered heterocyclic ring, each said phenyl and each said 5 to 6-membered heteroaryl ring is optionally and independently substituted by up to 3 instances of $R^5$;
alternatively, two instances of $R^D$ linked to the same nitrogen atom of $J^D$, together with said nitrogen atom of $J^D$, form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of $R^5$;
or alternatively, one instance of $R^D$ linked to a carbon, oxygen or sulfur atom of $J^D$ and one instance of $R^d$ linked to a nitrogen atom of the same $J^D$, together with said carbon, oxygen or sulfur and said nitrogen atom of that same $J^D$, form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of $R^5$;
each $R^5$ is independently selected from halogen, —CN, —$NO_2$, $C_{1-4}$ alkyl, a $C_{7-12}$ aralkyl, $C_{3-8}$ cycloalkyl ring, $C_{1-4}$ haloalkyl, $C_{1-4}$ cyanoalkyl, —$OR^6$, —$SR^6$, —$COR^6$, —OC(O)$R^6$, —C(O)O$R^6$, —C(O)N($R^6$)$_2$, —N($R^6$)C(O)$R^6$, —N($R^6$)$_2$, —$SO_2R^6$, —$SO_2$N($R^6$)$_2$, —N($R^6$)$SO_2R^6$, phenyl or an oxo group; wherein each said phenyl group is optionally and independently substituted with up to 3 instances of halogen, —OH, —$NH_2$, —NH($C_{1-4}$ alkyl), —N($C_{1-4}$ alkyl)$_2$, —$NO_2$, —CN, $C_{1-4}$ alkyl, $C_{1-4}$ haloalkyl, —O($C_{1-4}$ alkyl) or O($C_{1-4}$ haloalkyl); and wherein each said $C_{7-12}$ aralkyl and each said cycloalkyl group is optionally and independently substituted with up to 3 instances of halogen;
[with the proviso that when X is C-H, each $R^5$ is independently selected from halogen, —CN, —$NO_2$, methyl, ethyl, a $C_{7-12}$ aralkyl, $C_{3-8}$ cycloalkyl ring, $C_{1-4}$ haloalkyl, $C_{1-4}$ cyanoalkyl, —$OR^6$, —$SR^6$, —$COR^6$, —OC(O)$R^6$, —C(O)O$R^6$, —C(O)N($R^6$)$_2$, —N($R^6$)C(O)$R^6$, —N($R^6$)$_2$, —$SO_2R^6$, —$SO_2$N($R^6$)$_2$, —N($R^6$)$SO_2R^6$, phenyl or an oxo group; wherein each said phenyl group is optionally and independently substituted with up to 3 instances of halogen, —OH, —$NH_2$, —NH($C_{1-4}$ alkyl), —N($C_{1-4}$ alkyl)$_2$, —$NO_2$, —CN, $C_{1-4}$ alkyl, $C_{1-4}$ haloalkyl, —O($C_{1-4}$ alkyl) or —O($C_{1-4}$ haloalkyl); and wherein each said $C_{7-12}$ aralkyl and each said cycloalkyl group is optionally and independently substituted with up to 3 instances of halogen;]
each $R^6$ is independently selected from hydrogen, a $C_{1-4}$ alkyl, a $C_{2-4}$ alkenyl, phenyl, a $C_{7-12}$ aralkyl or a $C_{3-8}$ cycloalkyl ring; wherein each of said $C_{1-4}$ alkyl, each said $C_{2-4}$ alkenyl, each said phenyl, each said $C_{7-12}$ aralkyl and each said cycloalkyl group is optionally and independently substituted with up to 3 instances of halogen;
alternatively, two instances of $R^6$ linked to the same nitrogen atom of $R^5$, together with said nitrogen atom of $R^5$, form a 5 to 8-membered heterocyclic ring or a 5-membered heteroaryl ring; wherein each said 5 to 8-membered heterocyclic ring and each said 5-independently membered heteroaryl ring optionally contains up to 2 additional heteroatoms selected from N, O or S; or alternatively, one instance of $R^6$ linked to a nitrogen atom of $R^5$ and one instance of $R^6$ linked to a carbon or sulfur atom of the same $R^5$, together with said nitrogen and said carbon or sulfur atom of the same $R^5$, form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S;

or, alternatively, two $J^D$ groups attached to two vicinal ring D atoms, taken together with said two vicinal ring D atoms, form a 5 to 7-membered heterocycle resulting in a fused ring D wherein said 5 to 7-membered heterocycle contains from 1 to 3 heteroatoms independently selected from N, O or S; and wherein said 5 to 7-membered heterocycle is optionally and independently substituted by up to 3 instances of halogen, —OH, —NH$_2$, —NH(C$_{1-4}$ alkyl), —N(C$_{1-4}$ alkyl)$_2$, —CN, C$_{1-4}$ alkyl, C$_{1-4}$ haloalkyl, —O(C$_{1-4}$ alkyl), —O(C$_{1-4}$ haloalkyl) oxo or phenyl; wherein said phenyl is optionally and independently substituted by up to three instances of halogen, —OH, —NH$_2$, —NH(C$_{1-4}$ alkyl), —N(C$_{1-4}$ alkyl)$_2$, —NO$_2$, —CN, C$_{1-4}$ alkyl, C$_{1-4}$ haloalkyl, —O(C$_{1-4}$ alkyl) or —O(C$_{1-4}$ haloalkyl);

$R^C$ is selected from —CN, C$_{1-6}$ alkyl or a ring C;

ring C is a phenyl ring, a monocyclic 5 or 6-membered heteroaryl ring, a bicyclic 8 to 10-membered heteroaryl ring, a monocyclic 3 to 10-membered cycloaliphatic ring, or a monocyclic 4 to 10-membered heterocycle; wherein said monocyclic 5 or 6-membered heteroaryl ring, said bicyclic 8 to 10-membered heteroaryl ring, or said monocyclic 4 to 10-membered heterocycle contain between 1 and 4 heteroatoms selected from N, O or S; wherein said monocyclic 5 or 6-membered heteroaryl ring is not a 1,3,5-triazinyl ring; and wherein said phenyl, monocyclic 5 to 6-membered heteroaryl ring, bicyclic 8 to 10-membered heteroaryl ring, or monocyclic 4 to 10-membered heterocycle is optionally and independently substituted with up to 3 instances of $J^C$;

each $J^C$ is independently selected from halogen, —CN, —NO$_2$, a C$_{1-6}$ aliphatic, —OR$^H$, —SR$^H$, —N(R$^H$)$_2$, a C$_{3-8}$ cycloaliphatic ring or a 4 to 8-membered heterocyclic ring; wherein said 4 to 8-membered heterocyclic ring contains 1 or 2 heteroatoms independently selected from N, O or S; wherein each said C$_{1-6}$ aliphatic, each said C$_{3-8}$ cycloaliphatic ring and each said 4 to 8-membered heterocyclic ring, is optionally and independently substituted with up to 3 instances of $R^7$; or alternatively, two $J^C$ groups attached to two vicinal ring C atoms, taken together with said two vicinal ring C atoms, form a 5 to 7-membered heterocycle resulting in a fused ring C; wherein said 5 to 7-membered heterocycle contains from 1 to 2 heteroatoms independently selected from N, O or S;

each $R^H$ is independently selected from hydrogen, a C$_{1-6}$ aliphatic, a C$_{3-8}$ cycloaliphatic ring or a 4 to 8-membered heterocyclic ring,; wherein each said 4 to 8-membered heterocylic ring contains between 1 and 3 heteroatoms independently selected from O, N or S; and wherein each said C$_{1-6}$ aliphatic, each said C$_{3-8}$ cycloaliphatic ring, each said 4 to 8-membered heterocyclic ring, is optionally and independently substituted with up to 3 instances of $R^7$;

alternatively, two instances of $R^H$ linked to the same nitrogen atom of $J^C$, together with said nitrogen atom of $J^C$, form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of $R^7$;

or each $R^7$ is independently selected from halogen, —CN, —NO$_2$, C$_{1-4}$ alkyl, C$_{1-4}$ haloalkyl, C$_{3-8}$ cycloalkyl ring, —OR$^8$, —SR$^8$, —N(R$^8$)$_2$, or an oxo group; wherein each said cycloalkyl group is optionally and independently substituted with up to 3 instances of halogen;

each $R^8$ is independently selected from hydrogen, a C$_{1-4}$ alkyl, C$_{1-4}$ haloalkyl or a C$_{3-8}$ cycloalkyl ring; wherein each said cycloalkyl group is optionally and independently substituted with up to 3 instances of halogen;

alternatively, two instances of $R^8$ linked to the same nitrogen atom of $R^7$, together with said nitrogen atom of $R^7$, form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S;

$R^A$ is selected from hydrogen, halogen, C$_{1-4}$ alkyl or C$_{1-4}$ haloalkyl, with the proviso that when ring B is unsubstituted phenyl and ring D is unsubstituted pyrimidinyl (X is N and o is zero), $R^C$ is not methyl or ethyl.

23. The compound of [either of claims 21 or 22] *claim 1*, or a pharmaceutically acceptable salt thereof, wherein o is 0.

24. The compound of [either of claims 21 or 22] *claim 1*, or a pharmaceutically acceptable salt thereof, wherein o is an integer selected between 1 and 3 and each $J^D$ is independently selected from halogen, a C$_{1-6}$ aliphatic, —N(R$^D$)$_2$, —N(R$^d$)C(O)R$^D$, —N(R$^d$)C(O)OR$^D$, —SO$_2$R$^D$, —SO$_2$N(R$^D$)$_2$, —N(R$^d$)SO$_2$R$^D$, —SR$^D$, —OR$^D$ or an optionally substituted C$_{3-8}$ cycloaliphatic ring.

39. The compound of claim 38, or a pharmaceutically acceptable salt thereof, wherein ring C is a phenyl, a monocyclic 5 or 6-membered heteroaryl ring, a monocyclic 3 to 10-membered cycloaliphatic ring or a monocyclic 4 to 10-membered heterocycle; wherein each of [them] *said phenyl, monocyclic 5 or 6-membered heteroaryl ring or monocyclic 4 to 10-membered heterocycle is* optionally and independently substituted with up to 3 instances of $J^C$.

40. The compound of claim 39, or a pharmaceutically acceptable salt thereof, wherein ring C is a phenyl, a monocyclic 5 or 6-membered heteroaryl ring, a monocyclic 3 to 6-membered cycloaliphatic ring or a monocyclic 4 to 6-membered heterocycle; *wherein* each of [them] *said phenyl, monocyclic 5 or 6-membered heteroaryl ring or monocyclic 4 to 6-membered heterocycle is* optionally and independently substituted with up to 3 instances of $J^C$.

41. The compound of claim 40, or a pharmaceutically acceptable salt thereof, wherein ring C is a monocyclic 3 to 6-membered cycloaliphatic ring[, optionally substituted with up to 2 instances of $J^C$].

46. The compound of claim 41, or a pharmaceutically acceptable salt thereof, wherein ring C is a 4-membered cycloaliphatic ring [substituted by 1 to 3 instances of $J^C$], a 5-membered cycloaliphatic ring [substituted by 1 to 3 instances of $J^C$] or a 6-membered cycloaliphatic ring [substituted by 1 to 3 instances of $J^C$, and wherein each $J^C$ is independently selected from halogen or a C$_{1-6}$ aliphatic].

68. The compound of claim 1, or a pharmaceutically acceptable salt thereof, having [Formula III or] Formula IV:

Formula III
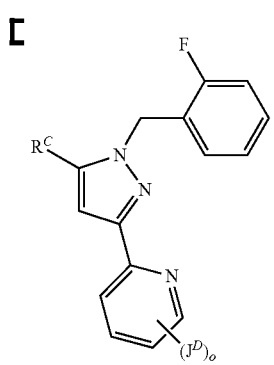
Formula IV
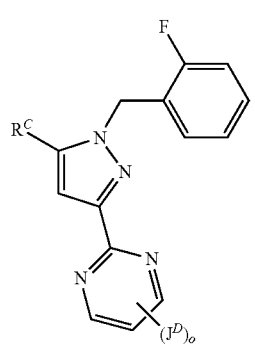
69. The compound of claim 68, or a pharmaceutically acceptable salt thereof, having one of Formulae [VA, VC,] VD [and] or VF, wherein the symbol of the letter C surrounded by a circle represents ring C:
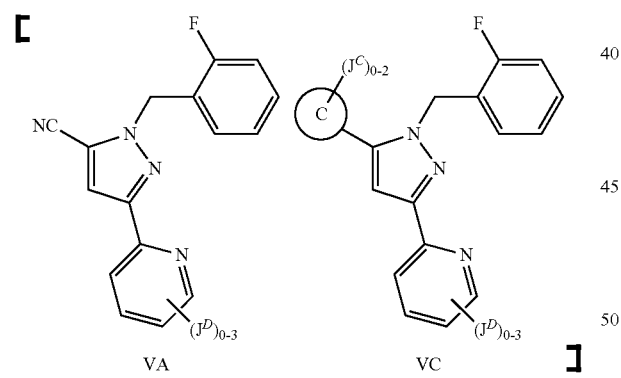
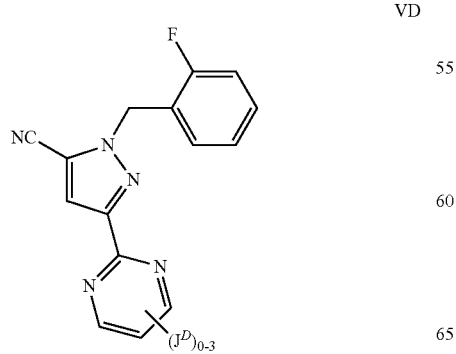
VF
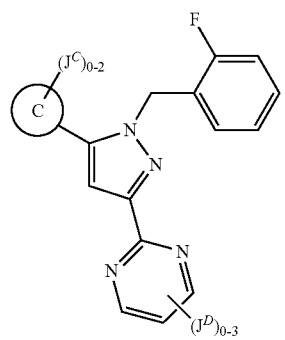
74. [The] A compound [of claim 1,] selected from [Table IA, IB, IC or ID] one below, or a pharmaceutically acceptable salt thereof[.]:
I-2
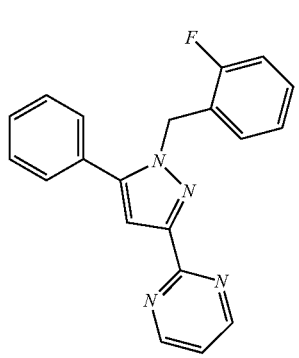
I-4
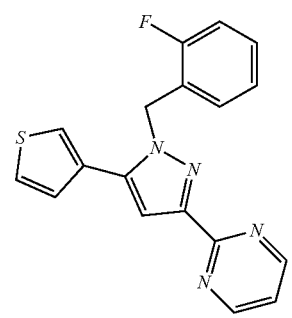
I-6
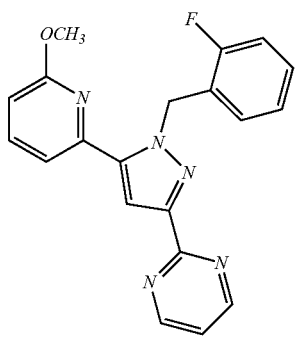

-continued
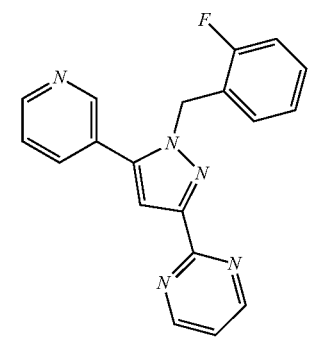
I-10
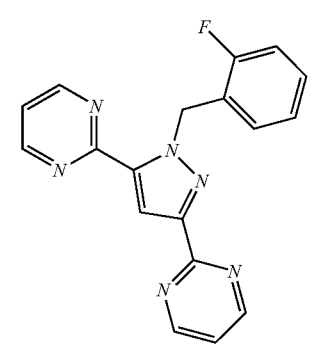
I-13
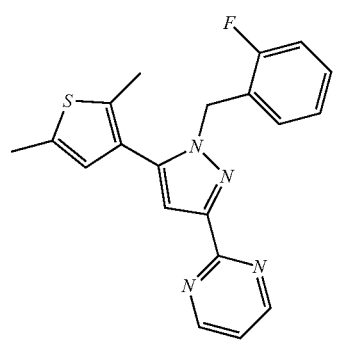
I-14
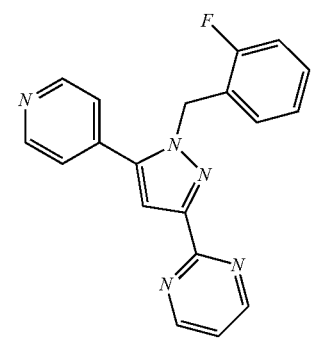
I-19
-continued
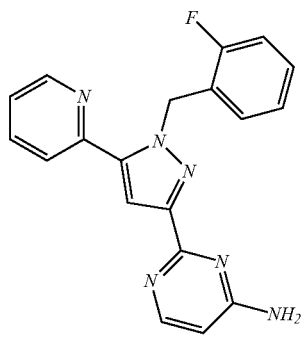
I-31
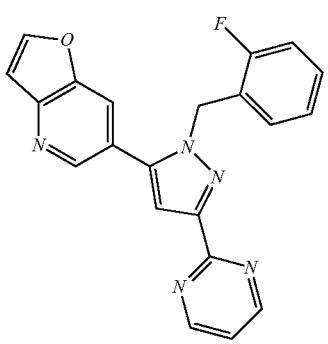
I-32
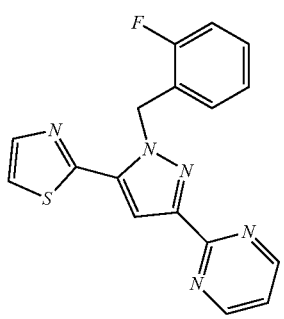
I-33
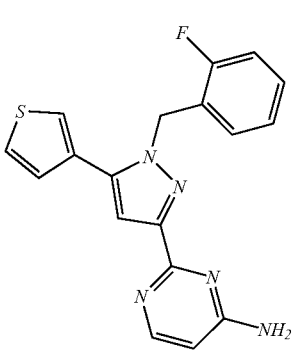
I-49
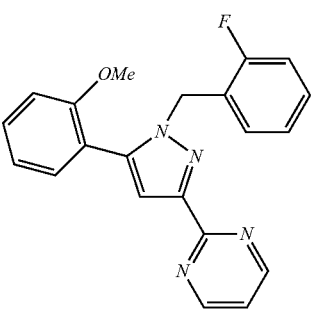
I-37

I-58
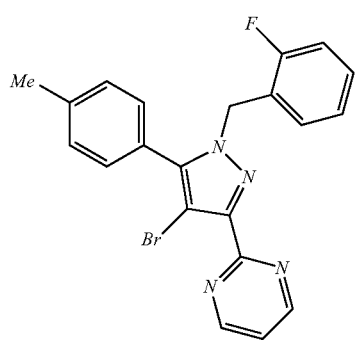
I-59
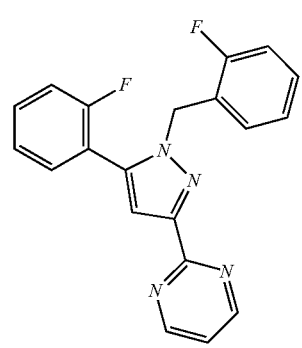
I-60
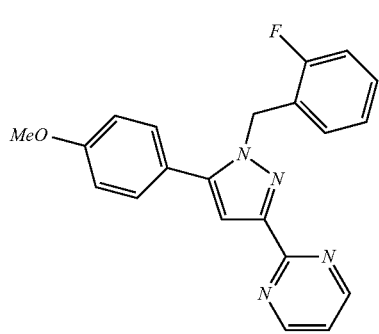
I-65
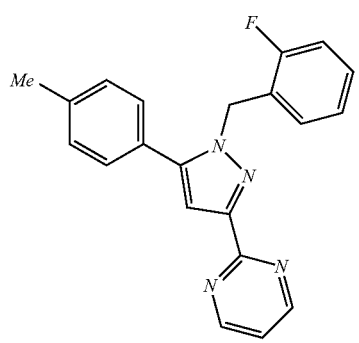
I-66
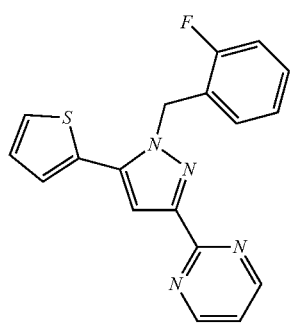
I-68
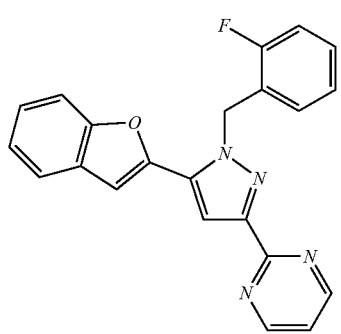
I-69
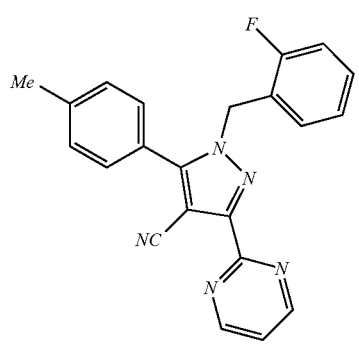
I-70
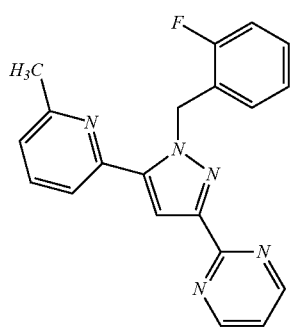

-continued
I-71
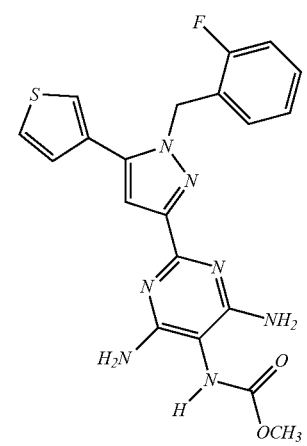
I-72
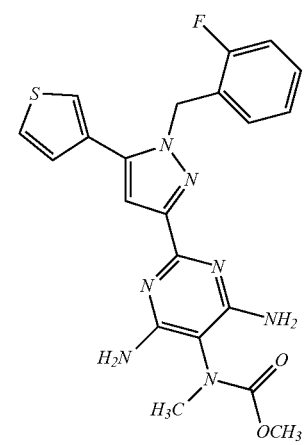
I-75
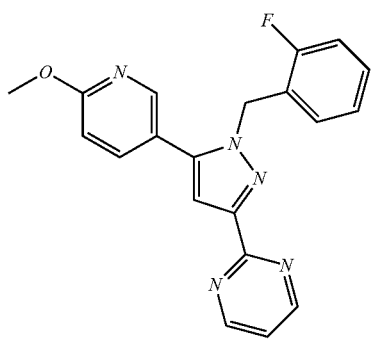
I-77
-continued
I-83
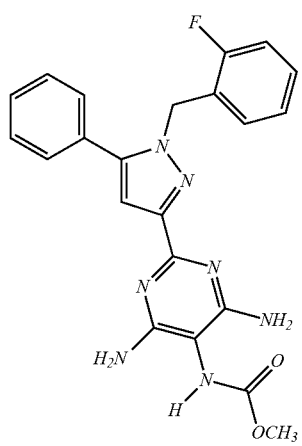
I-84
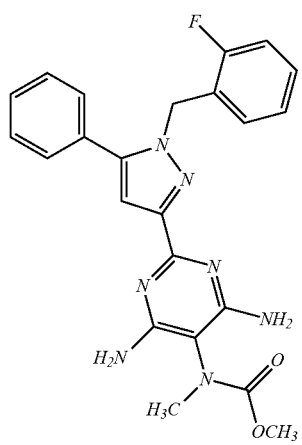
I-85
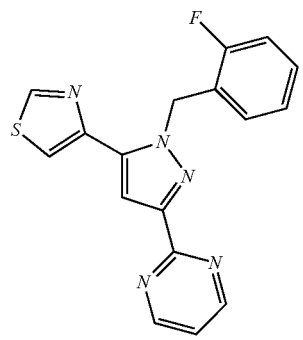
I-86
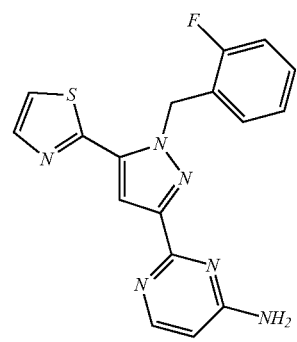

I-87
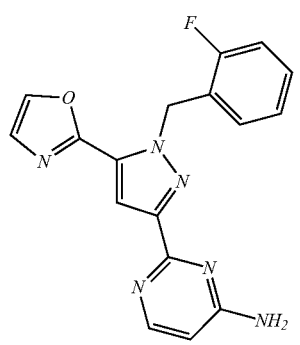
I-88
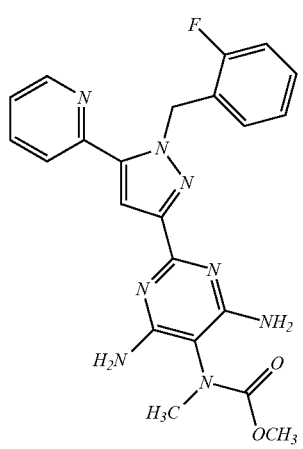
I-89
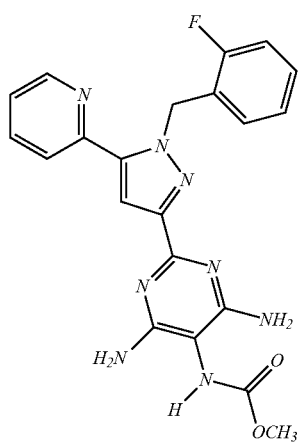
I-90
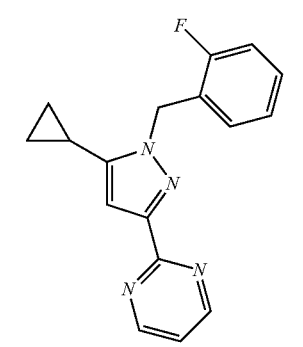
I-91
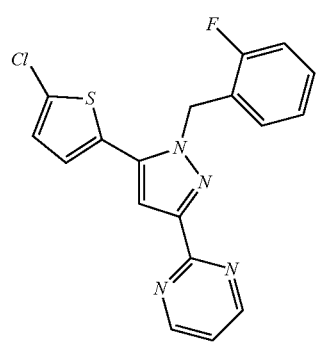
I-92
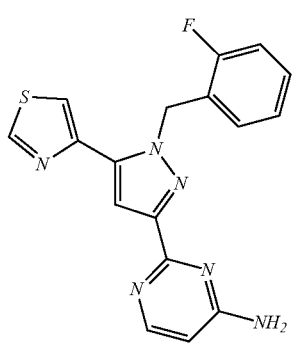
I-93
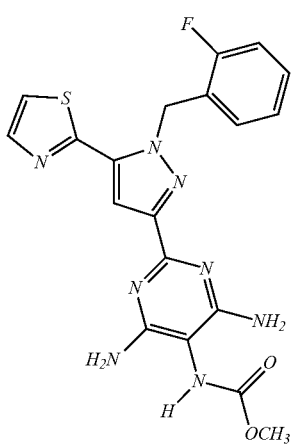
I-94
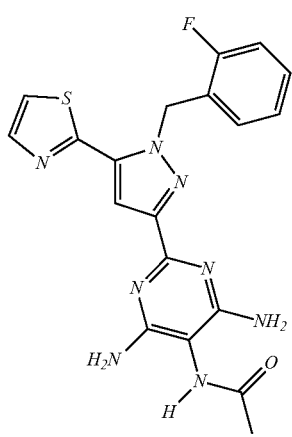

I-95
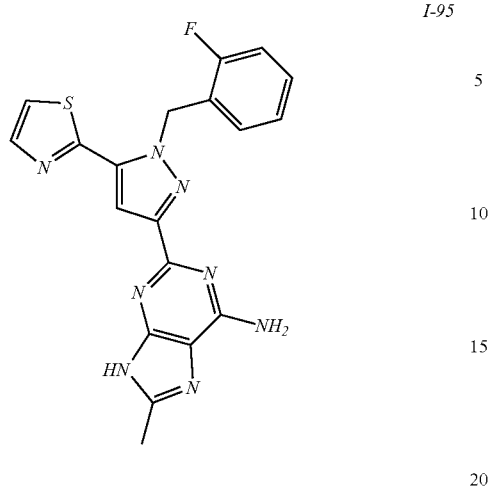
I-96
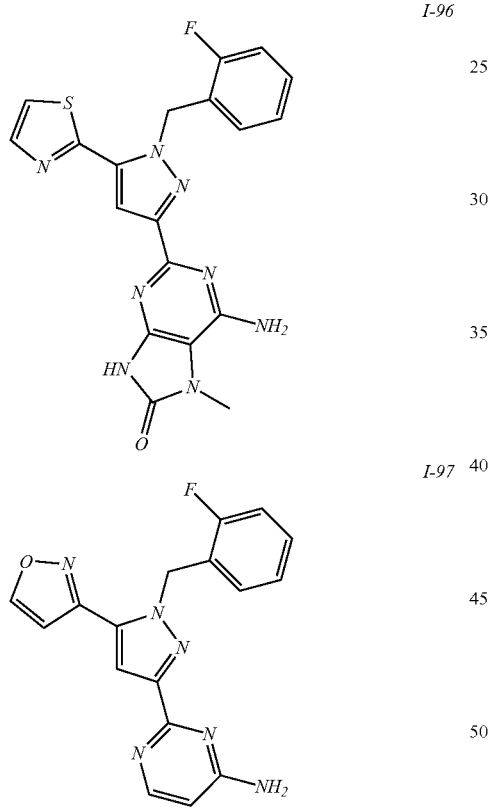
I-97
I-98
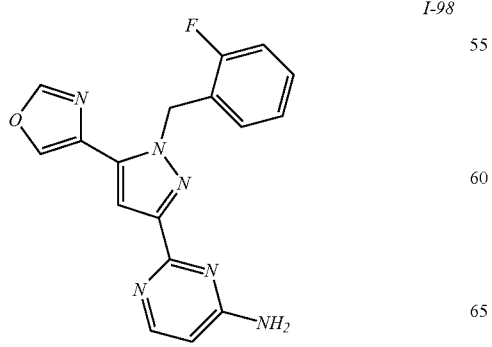
I-99
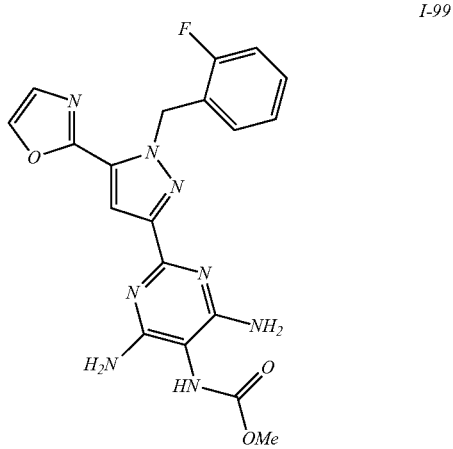
I-100
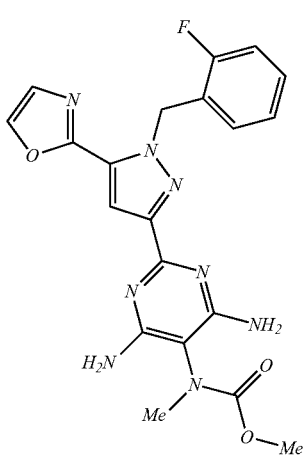
I-101
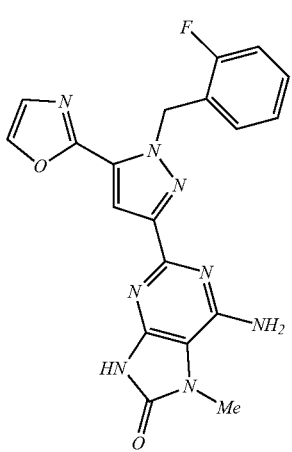

I-102
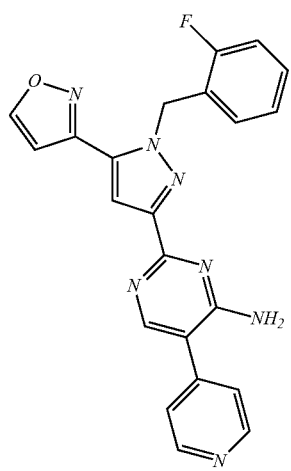
I-103
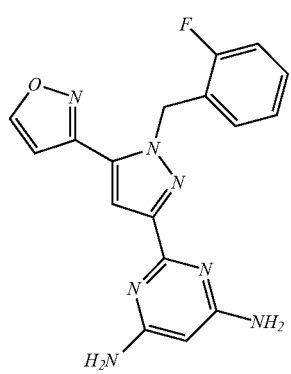
I-104
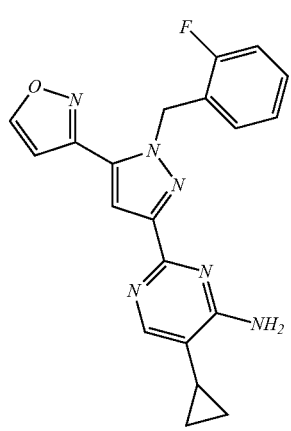
I-105
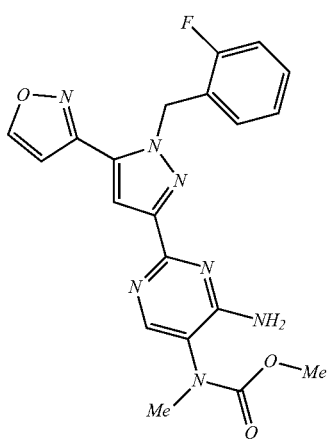
I-106
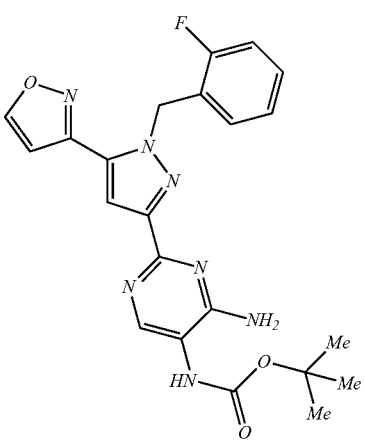
I-107
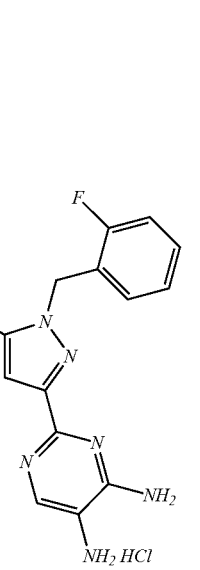

-continued
I-108
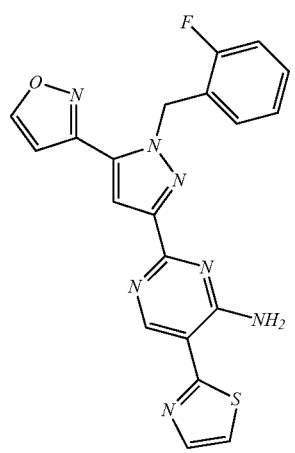
I-109
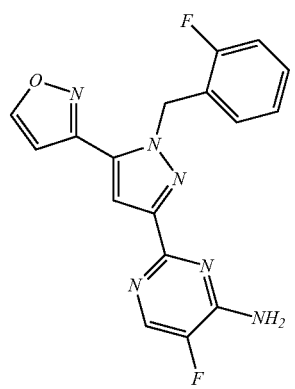
I-110
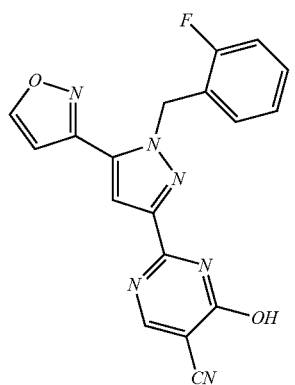
I-111
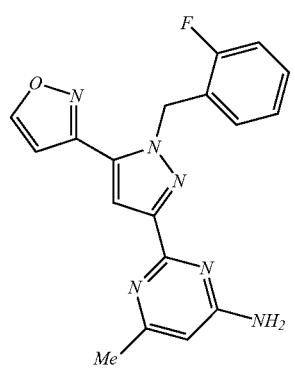
-continued
I-112
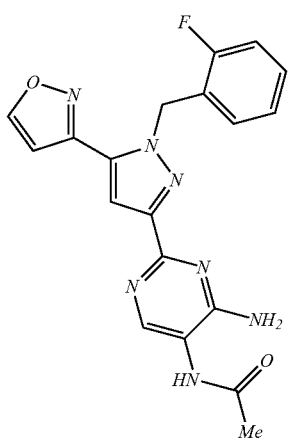
I-113
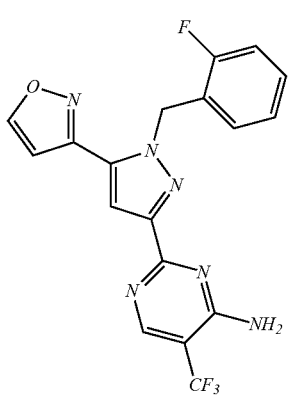
I-114
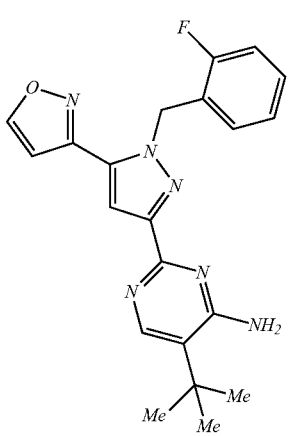

I-115
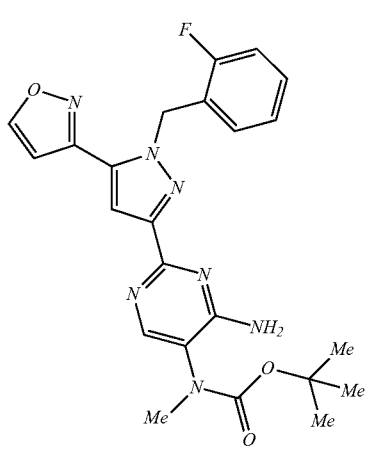
I-116
I-117
I-118
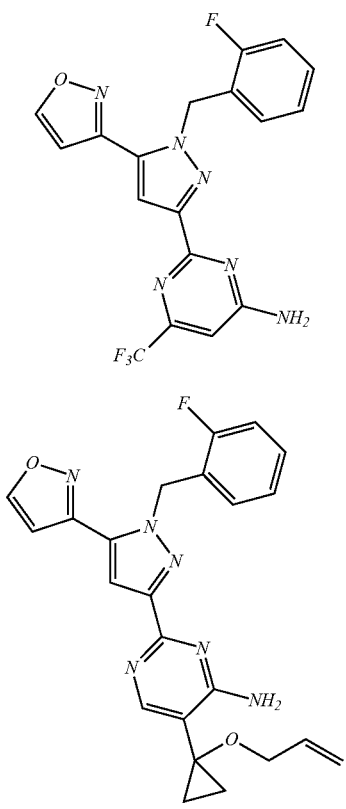
I-119
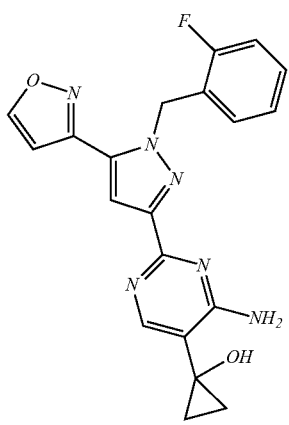
I-120
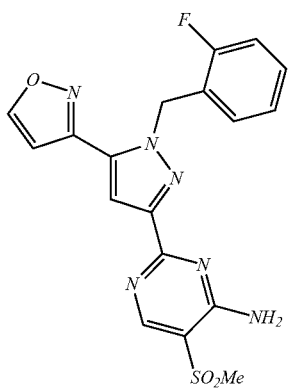
I-121
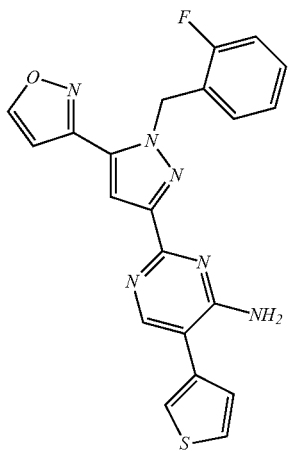

-continued
I-122
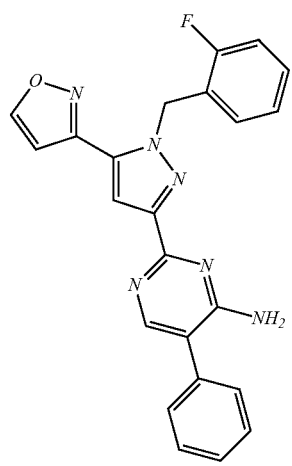
I-124
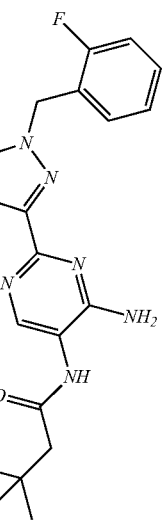
I-123
-continued
I-125
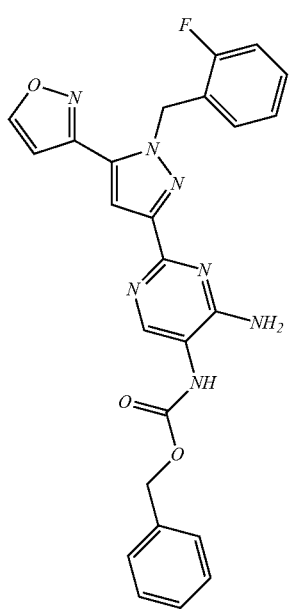
I-126
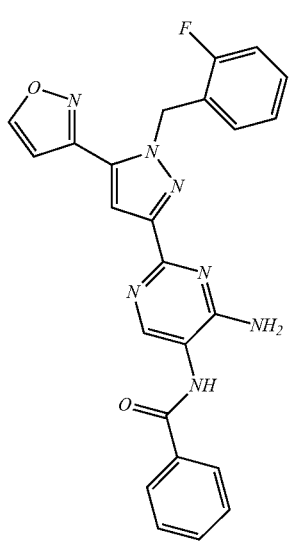
I-127
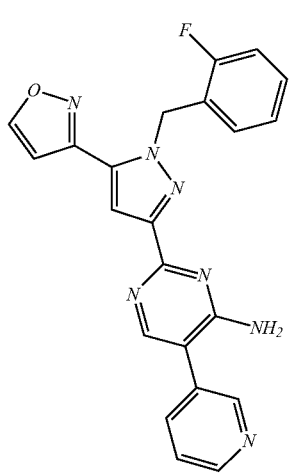

I-128
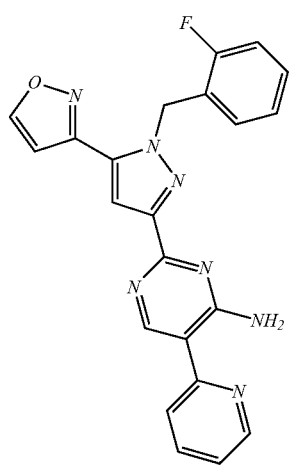
I-129
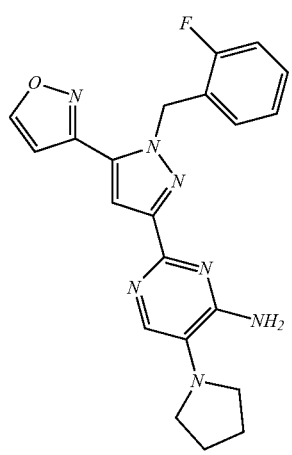
I-130
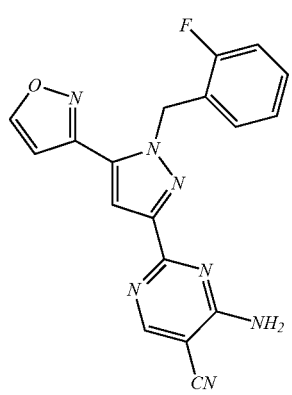
I-131
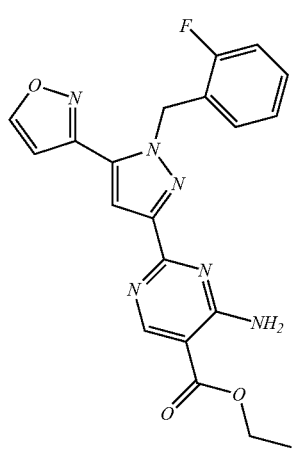
I-132
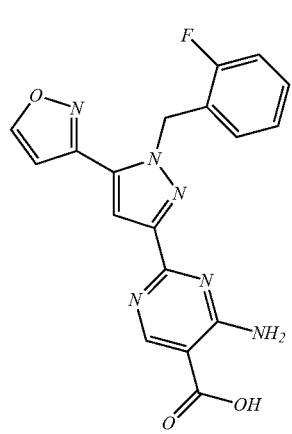
I-133
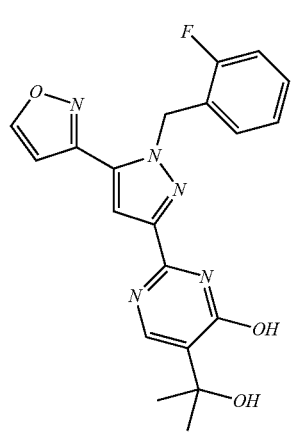

I-134
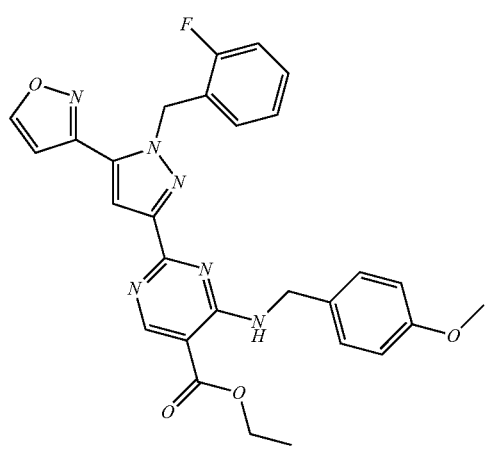
I-135
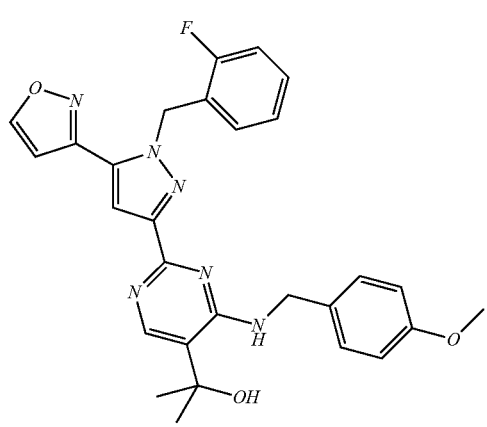
I-136
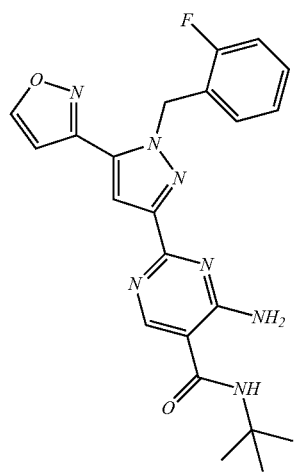
I-137
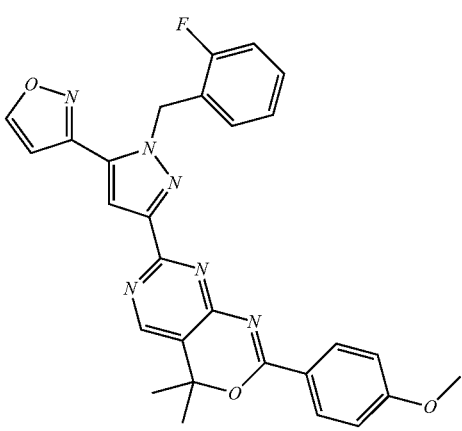
I-138
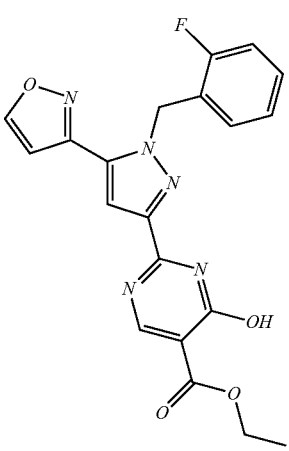
I-139
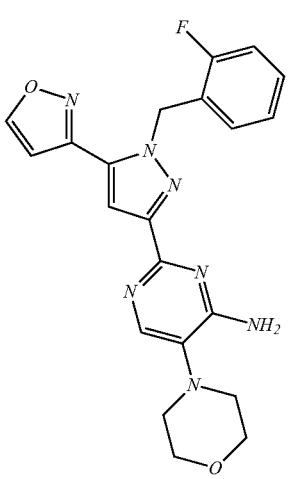

I-140
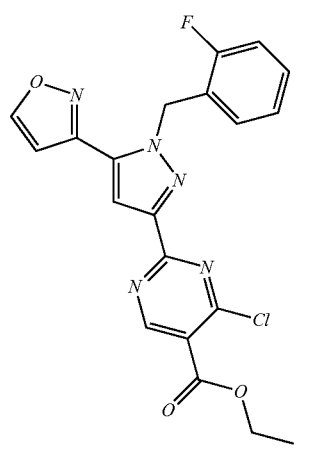
I-143
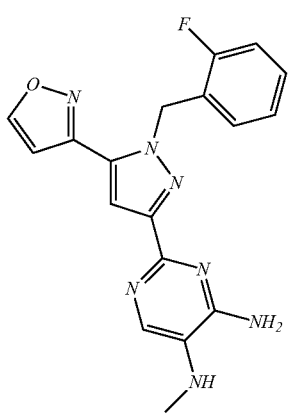
I-141
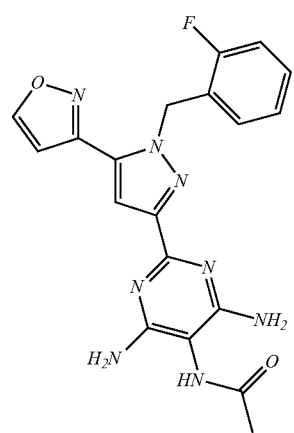
I-144
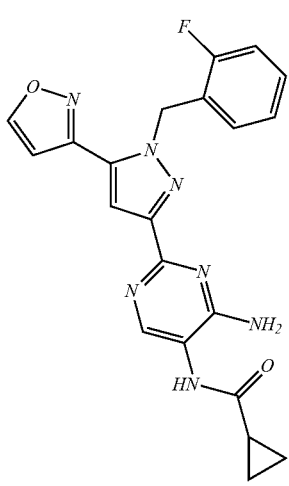
I-142
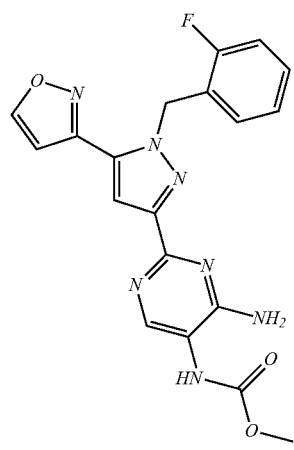
I-145
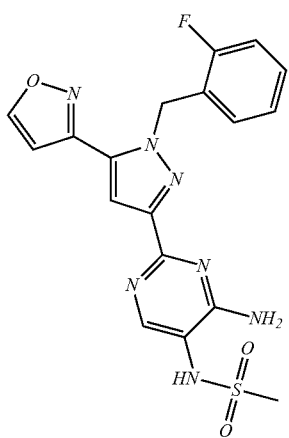

I-146
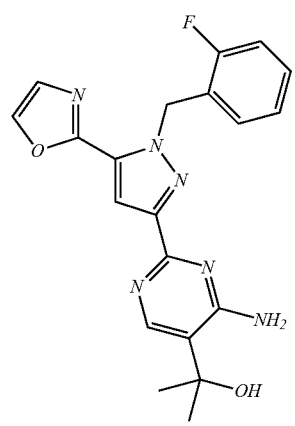
I-149
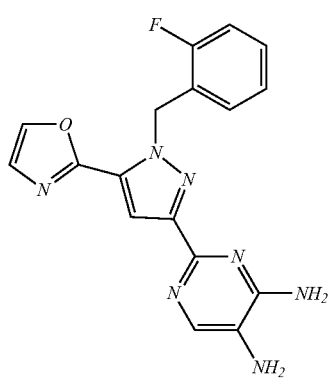
I-147
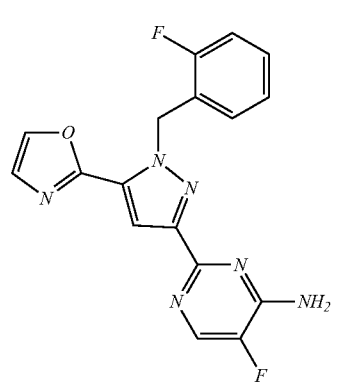
I-150
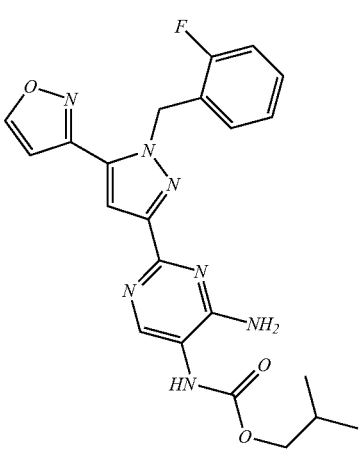
I-148
I-151
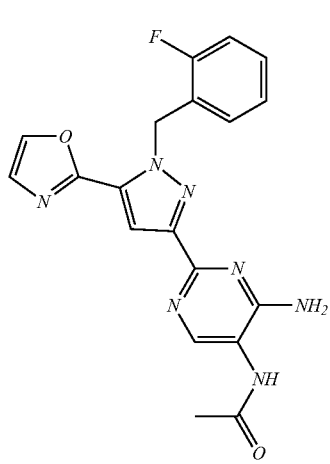

I-152
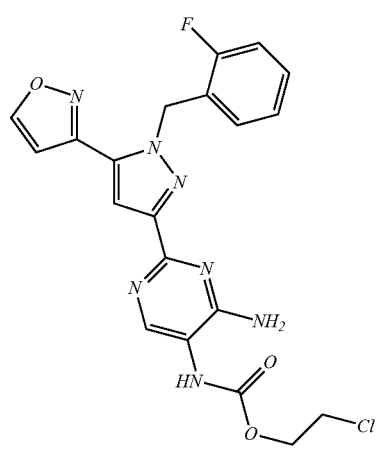
I-153
I-154
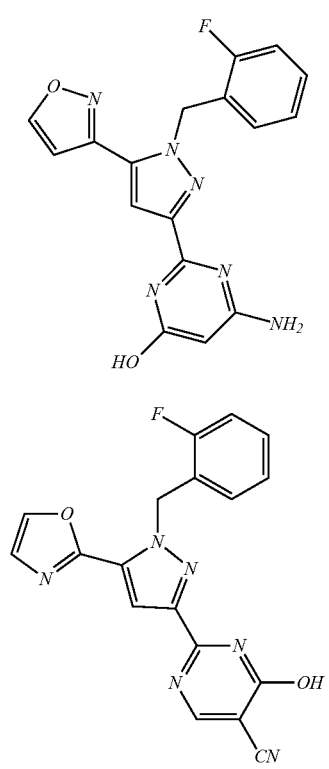
I-155
I-156
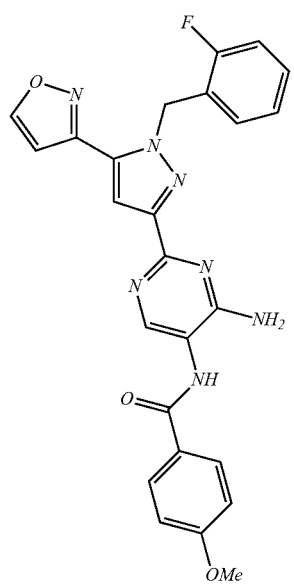
I-157
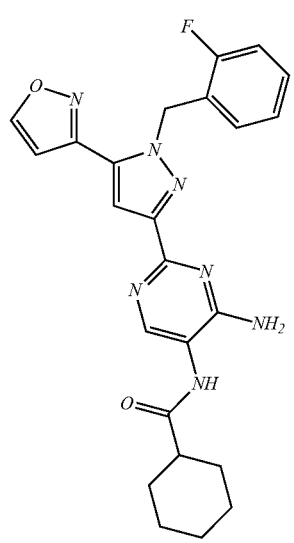
I-158
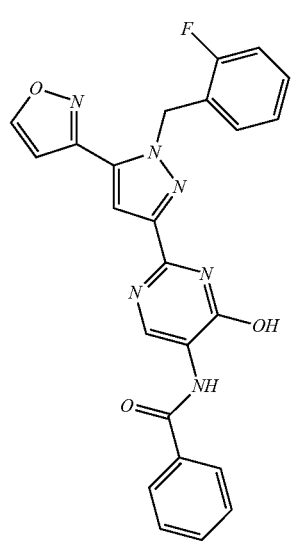

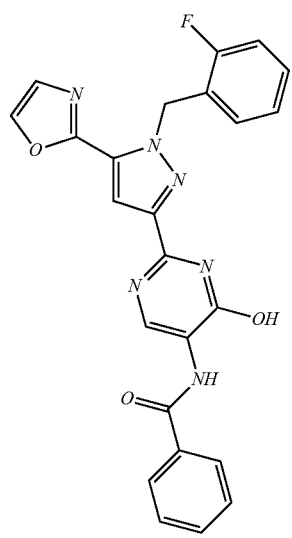
I-159
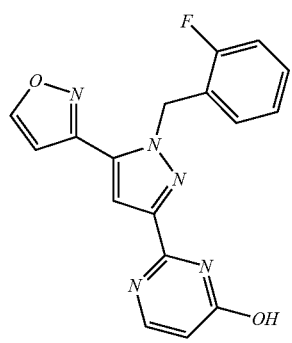
I-160
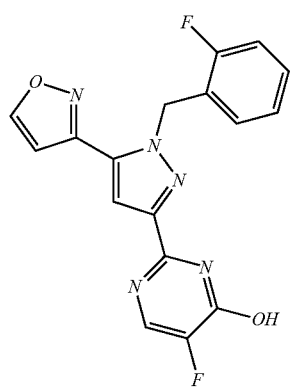
I-161
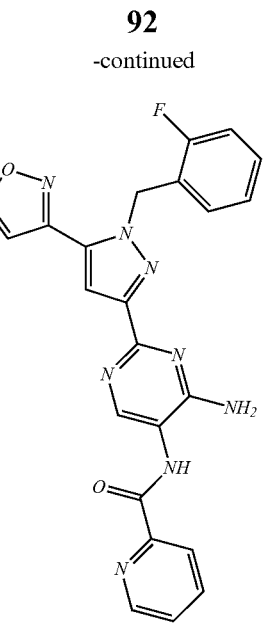
I-162
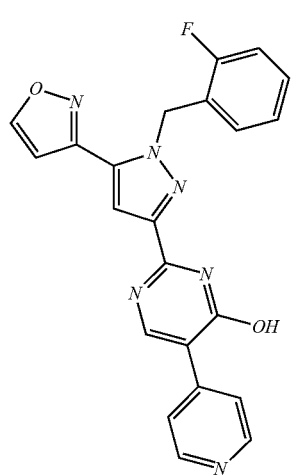
I-163
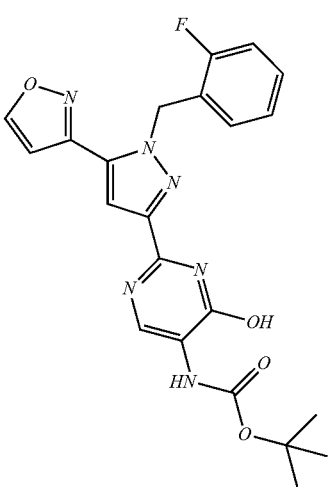
I-164

I-165
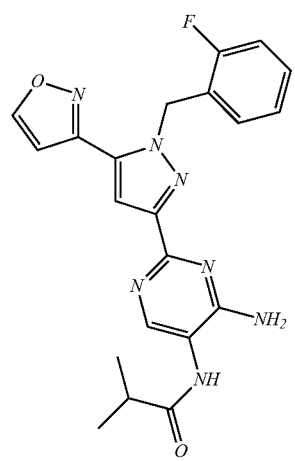
I-166
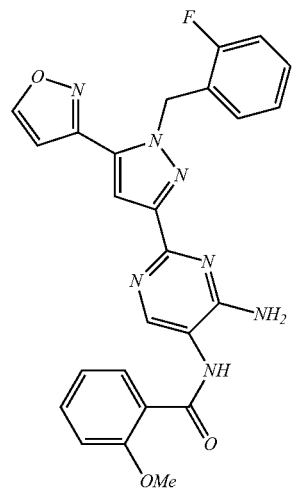
I-167
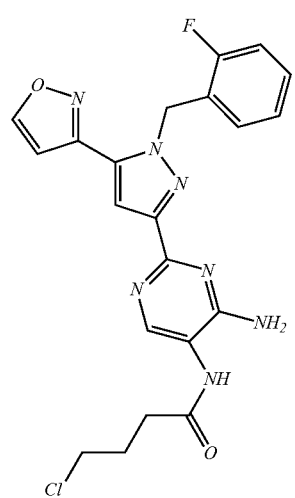
I-168
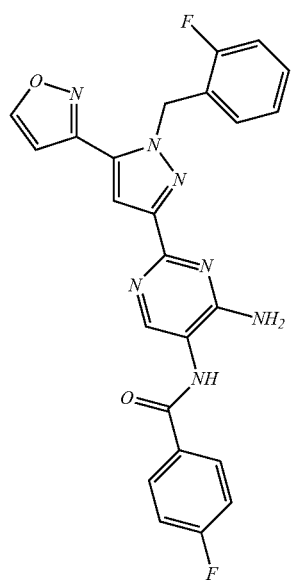
I-169
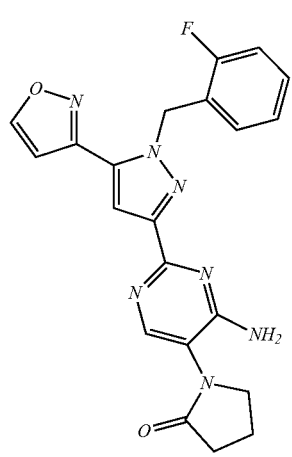
I-170
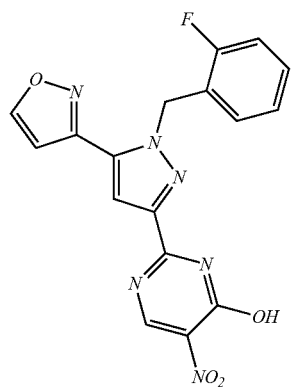

I-171
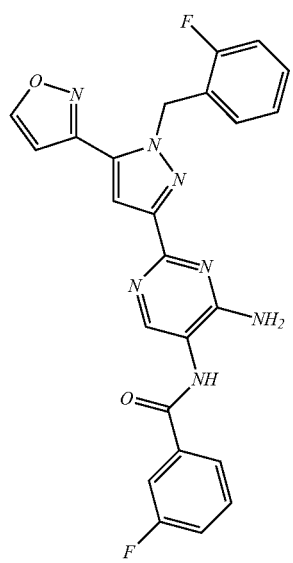
I-172
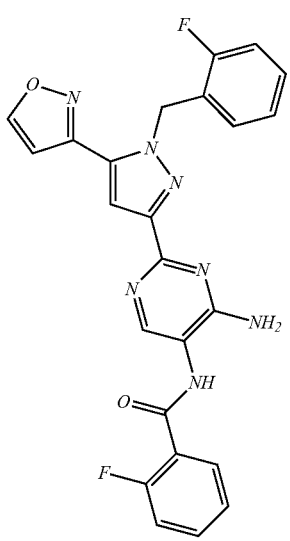
I-173
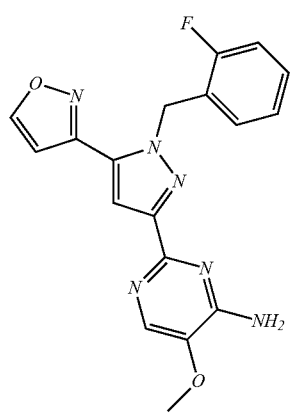
I-174
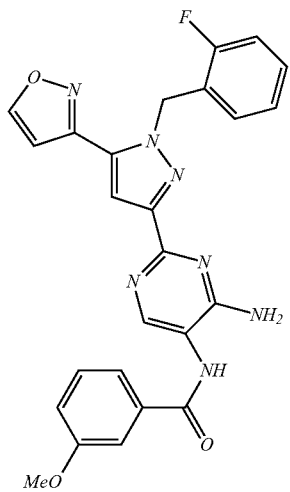
I-175
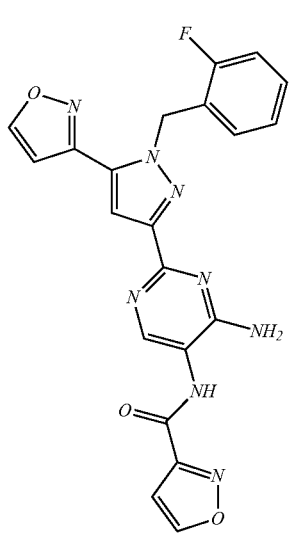
I-176
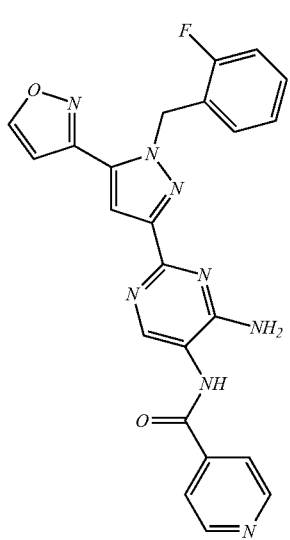

I-177
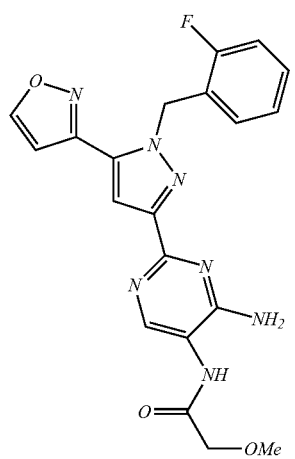
I-178
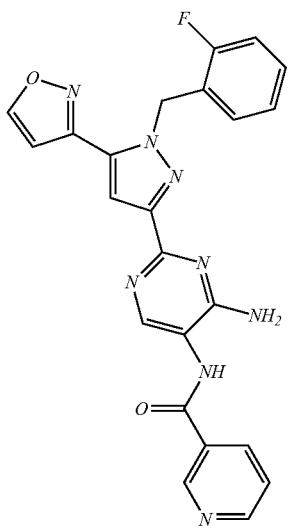
I-179
I-180
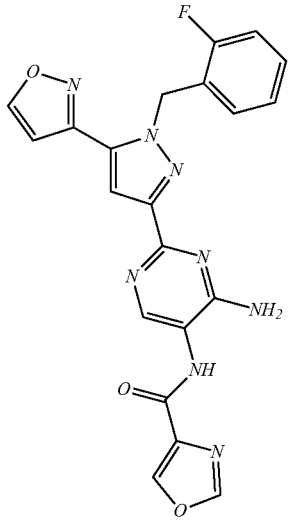
I-181
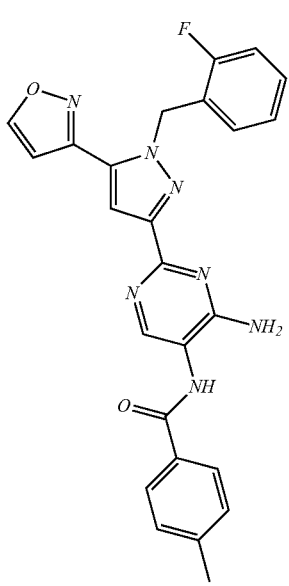
I-182
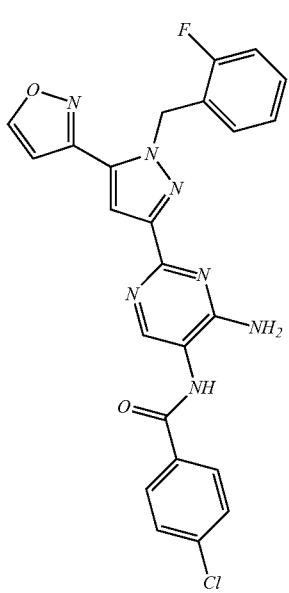

I-183
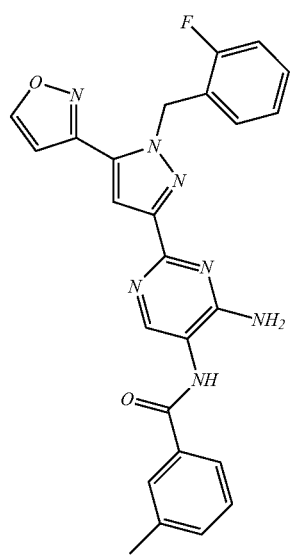
I-184
I-185
I-186
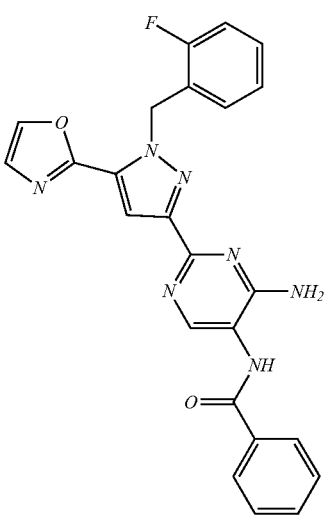
I-187
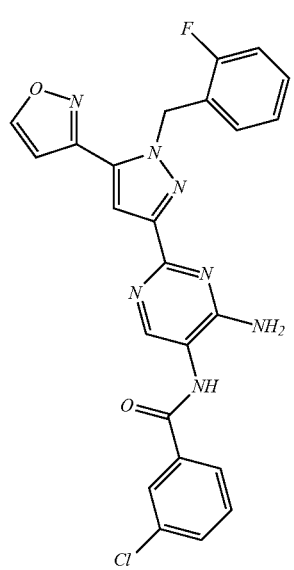
I-188
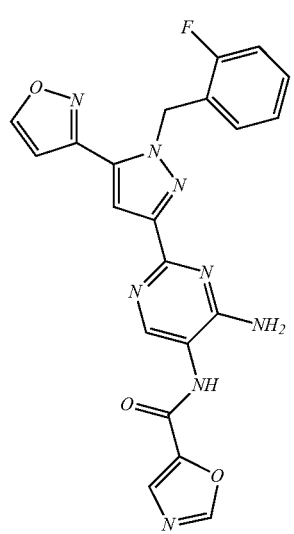

-continued
I-189
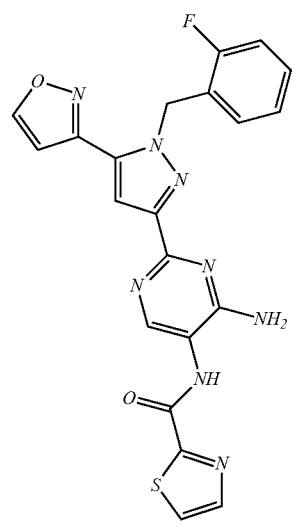
I-190
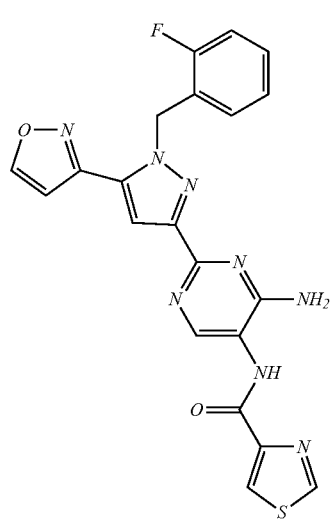
I-191
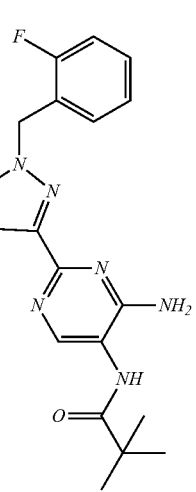
-continued
I-192
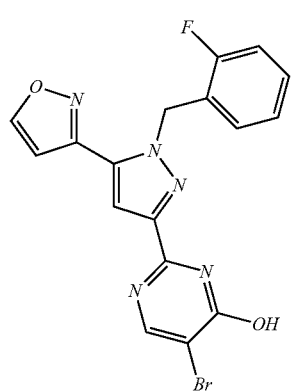
I-193
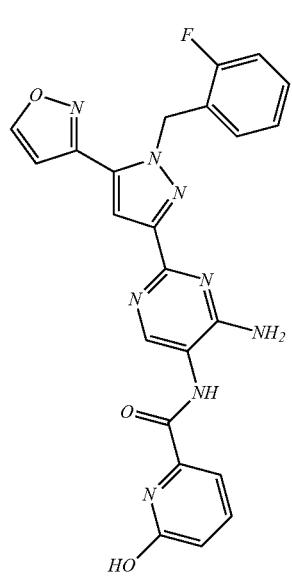
I-195
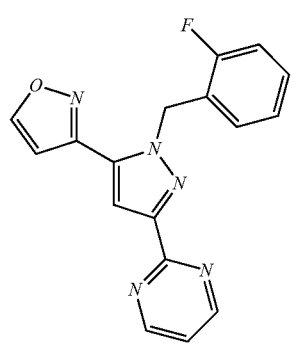

-continued
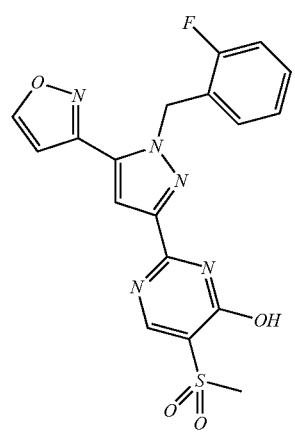
I-196
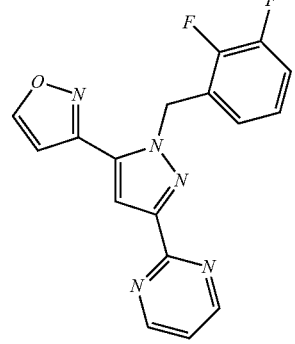
I-197
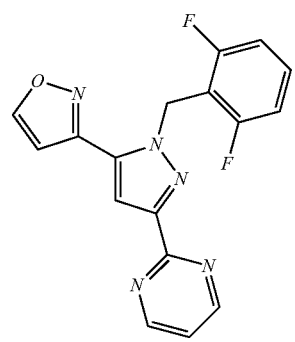
I-198
I-199
-continued
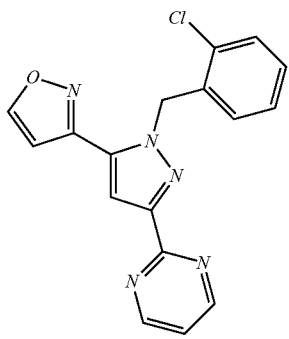
I-200
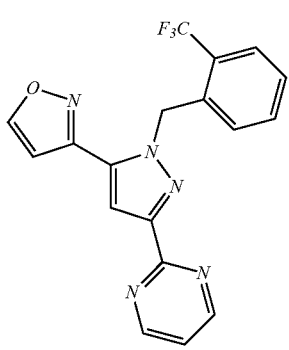
I-201
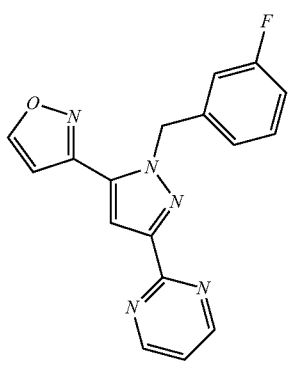
I-202
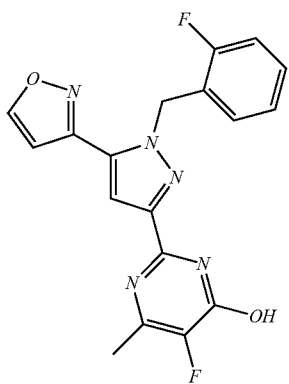
I-203

I-204
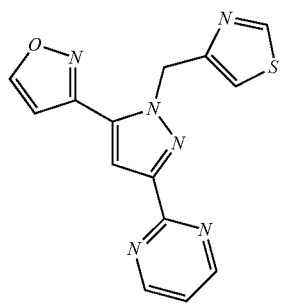
I-212
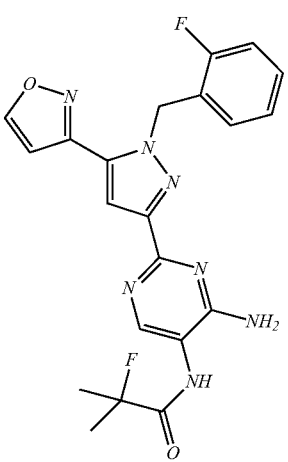
I-205
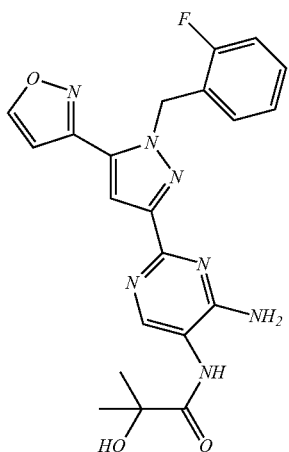
I-206
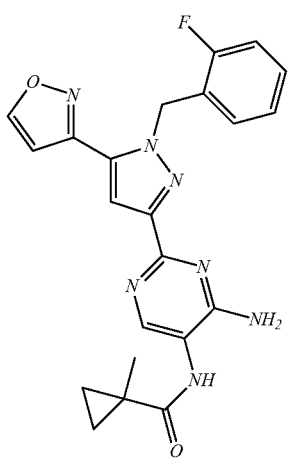
I-207
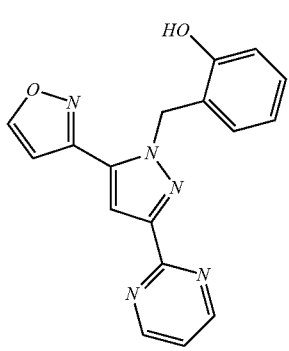
I-208
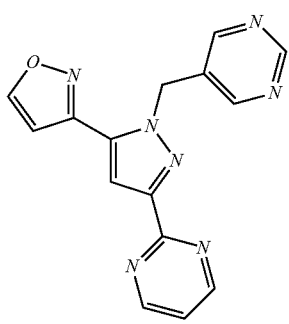
I-209
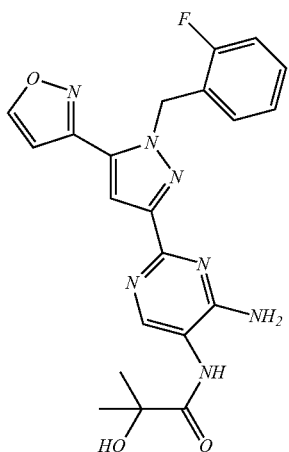

I-210
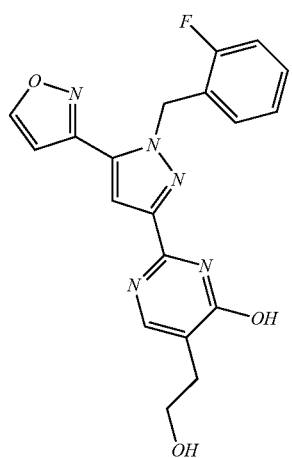
I-211
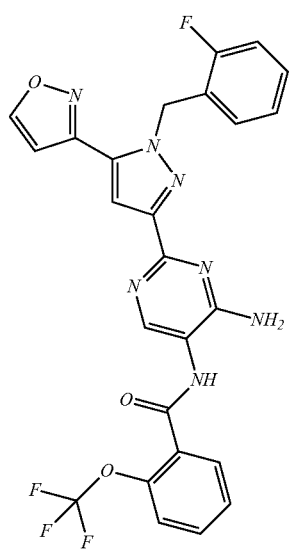
I-213
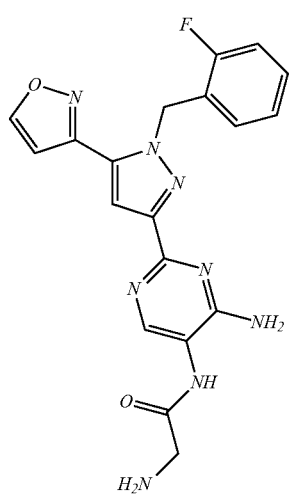
I-214
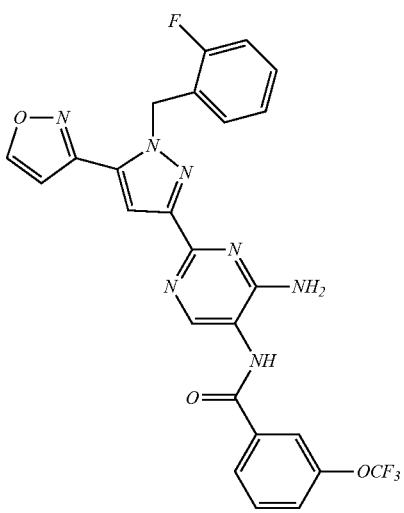
I-215
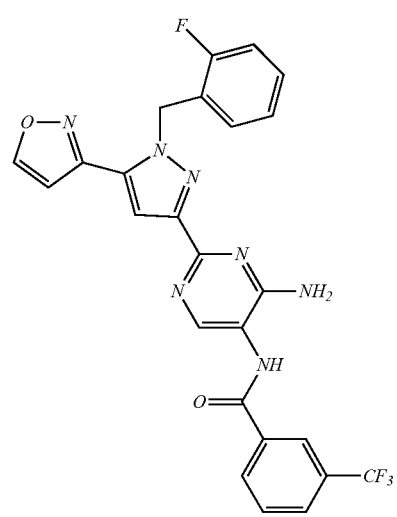
I-216
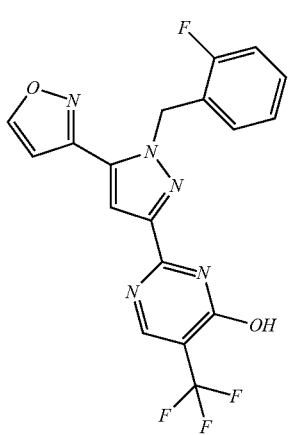

I-217
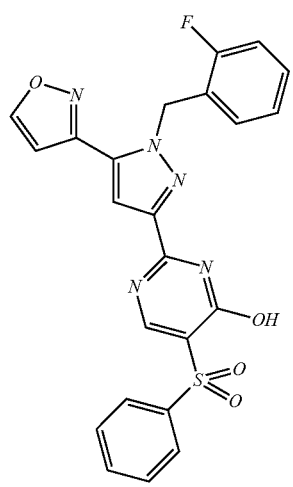
I-218
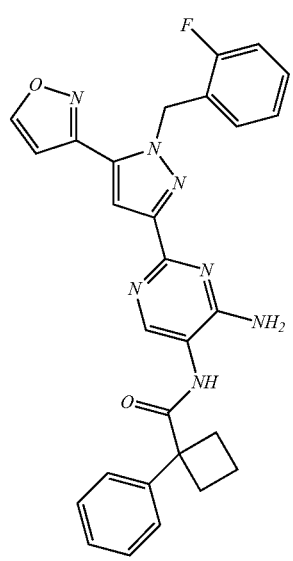
I-219
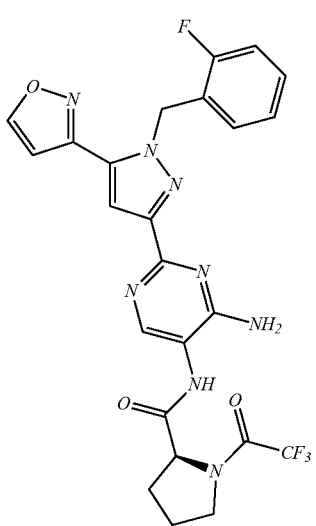
I-220
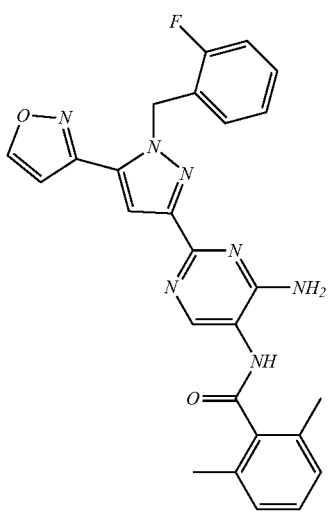
I-221
I-222
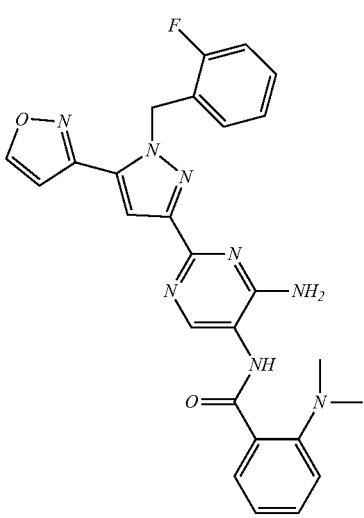

I-223
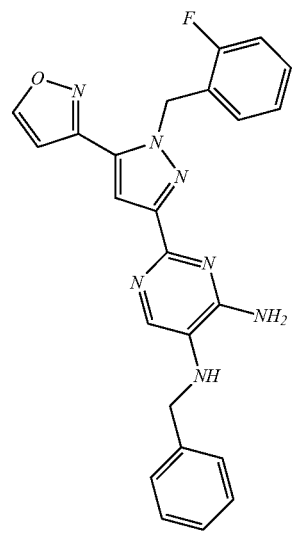
I-224
I-225
I-226
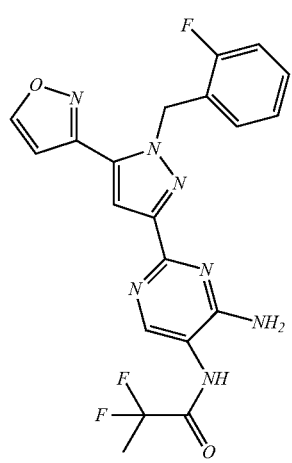
I-227
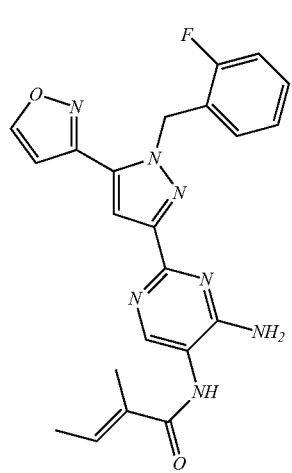
I-228
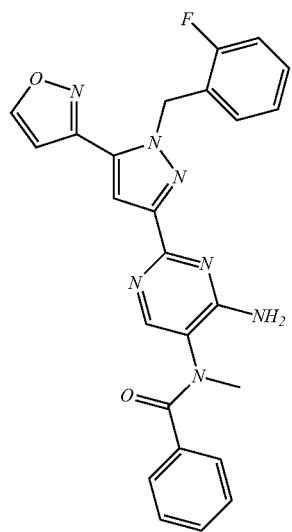

I-229
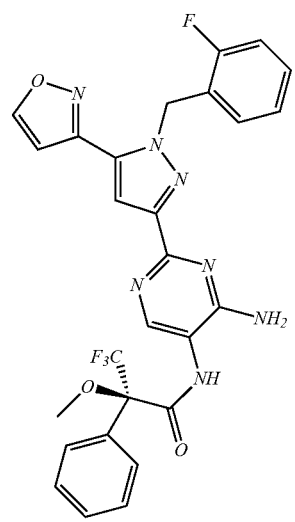
I-230
I-231
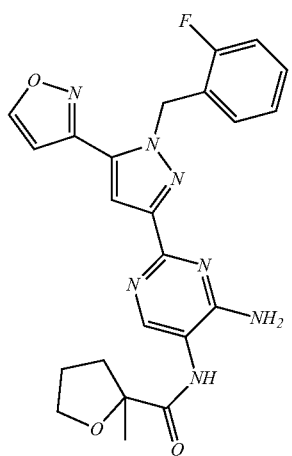
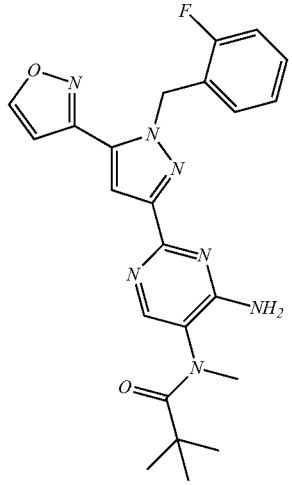
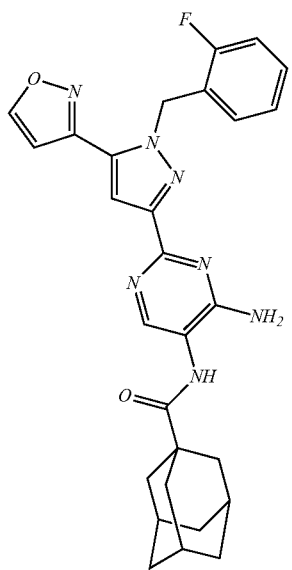
I-232
I-234
I-233

I-235
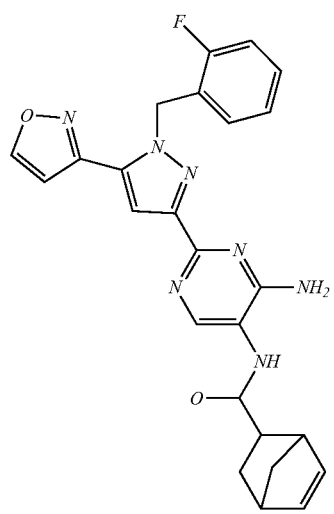
I-236
I-238
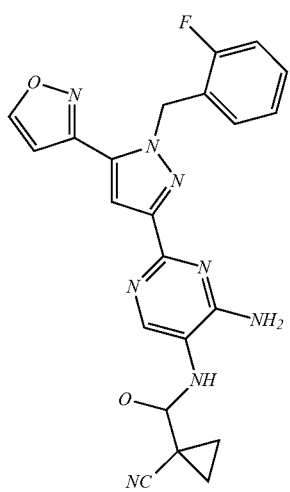
I-239
I-237
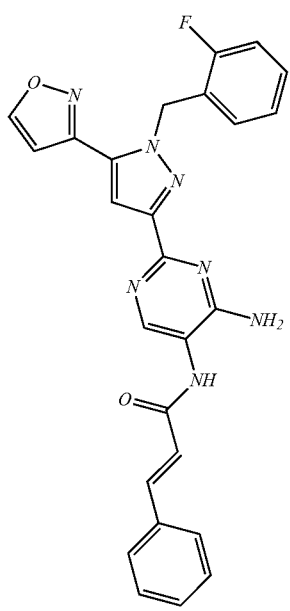
I-240
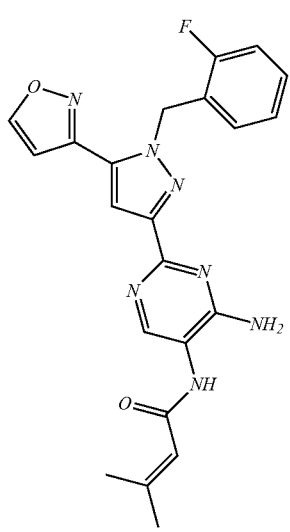

I-241
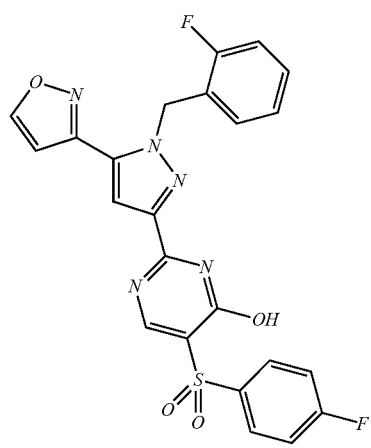
I-242
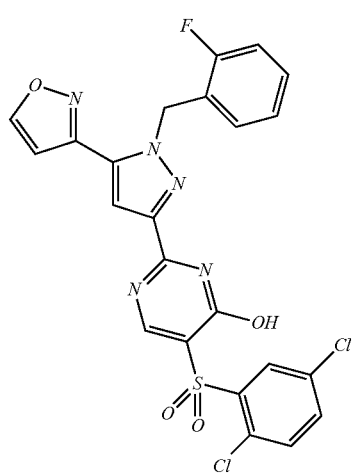
I-243
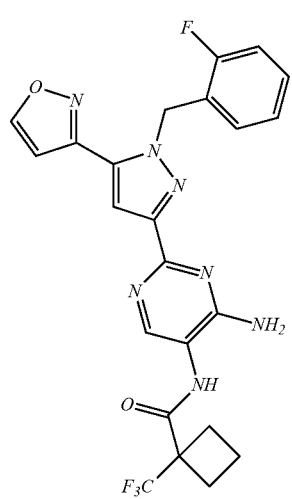
I-244
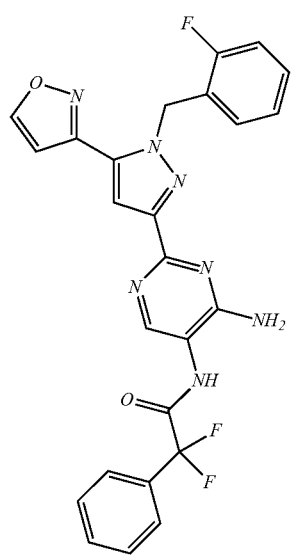
I-245
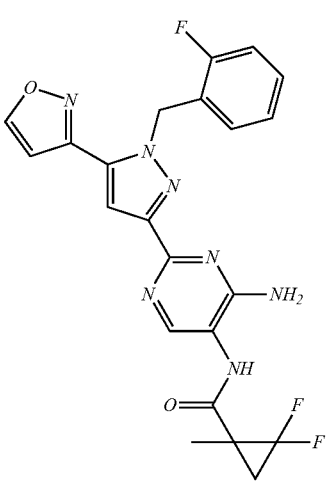
I-246
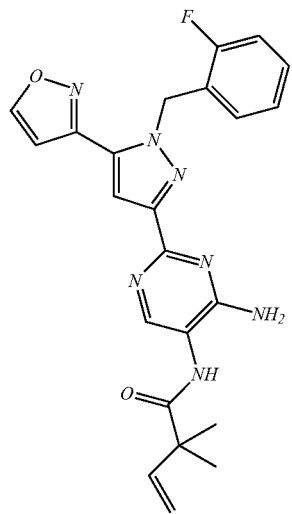

I-247
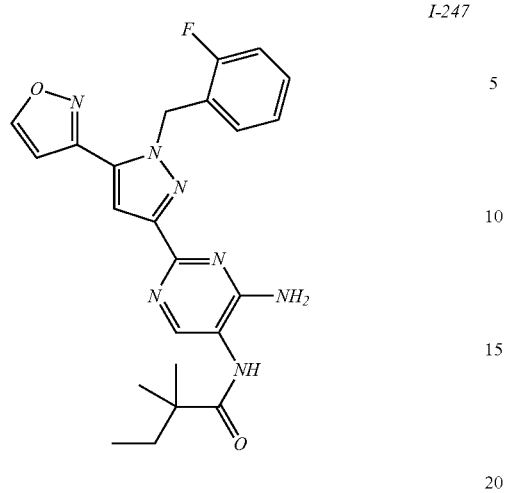
I-248
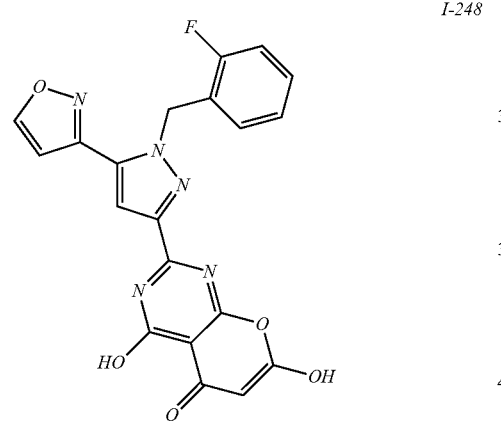
I-249
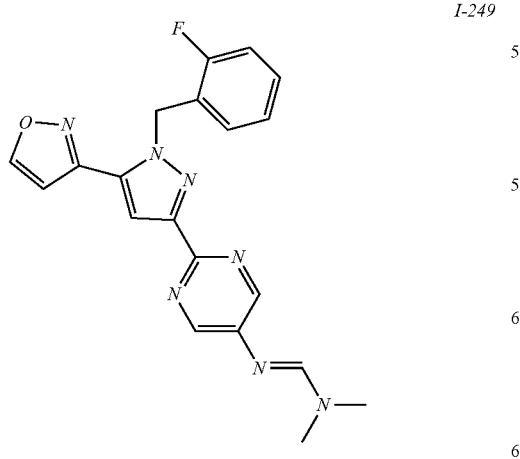
I-250
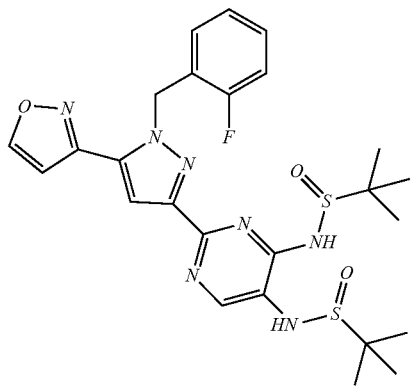
I-251
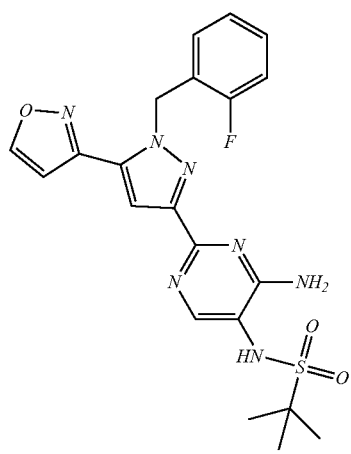
I-252
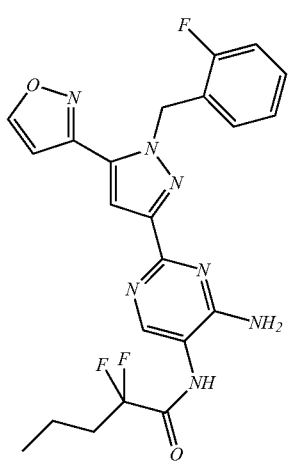

-continued
I-253
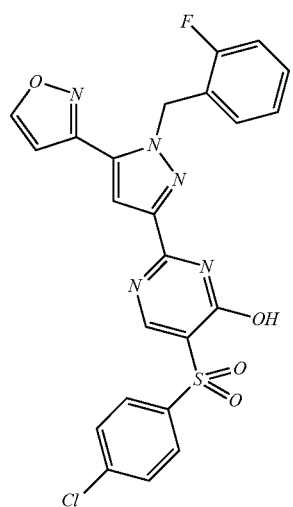
I-254
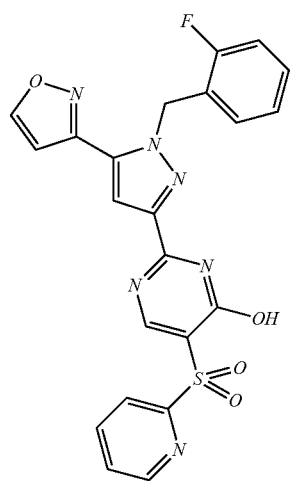
I-255
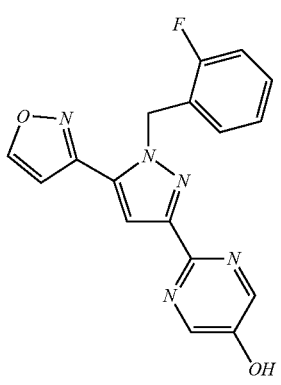
-continued
I-256
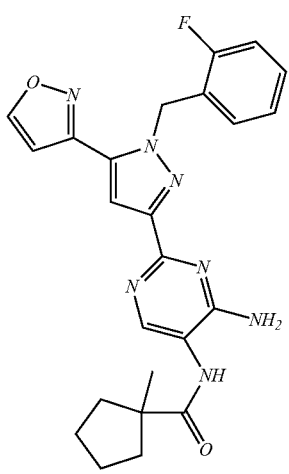
I-257
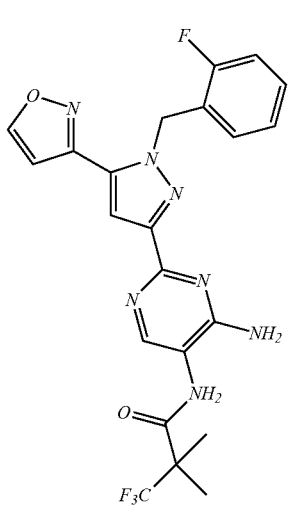
I-258
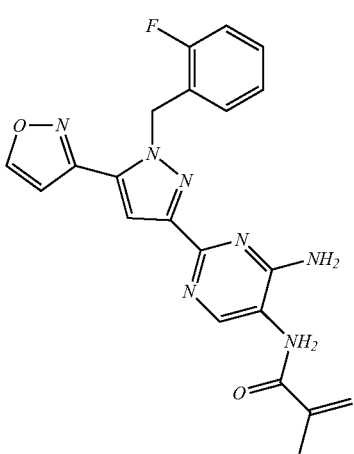

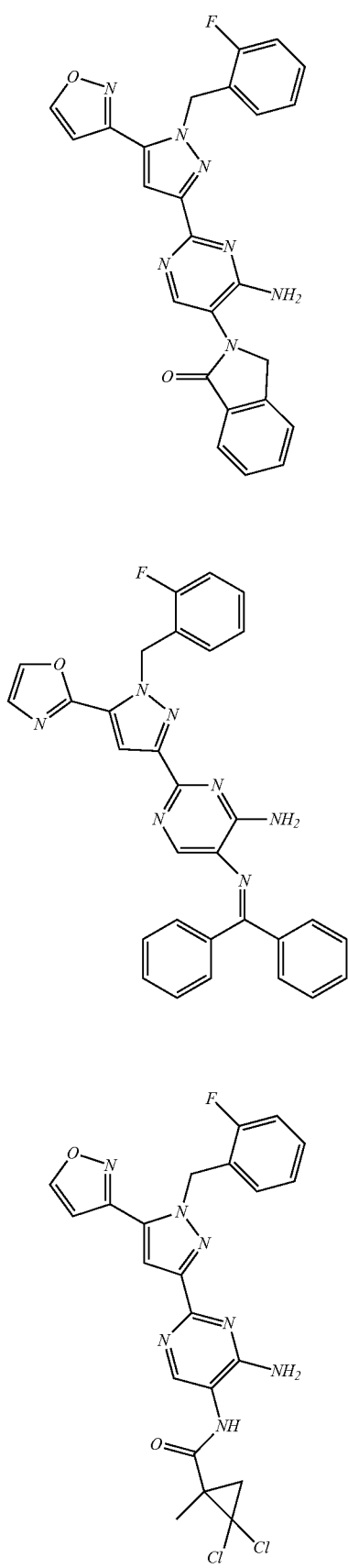
I-259
I-269
I-260
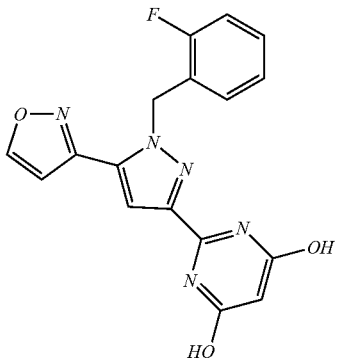
I-261
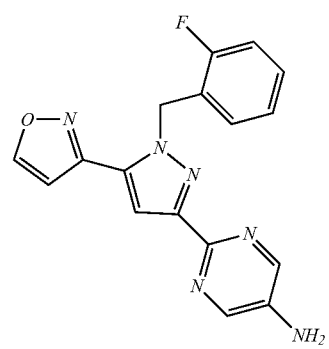
I-262
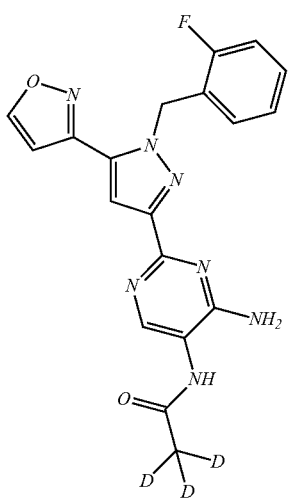
I-263
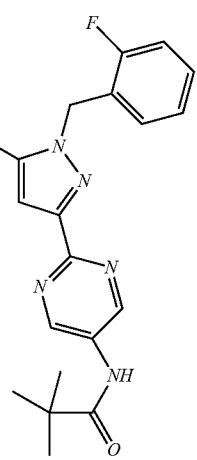
I-264

I-265
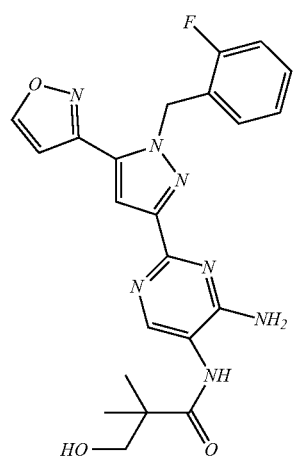
I-266
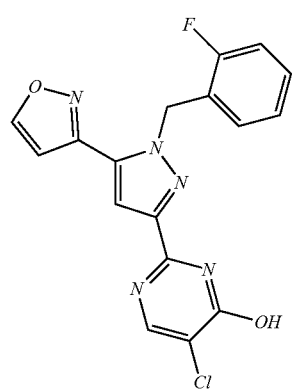
I-267
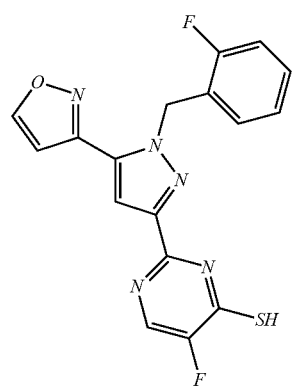
I-268
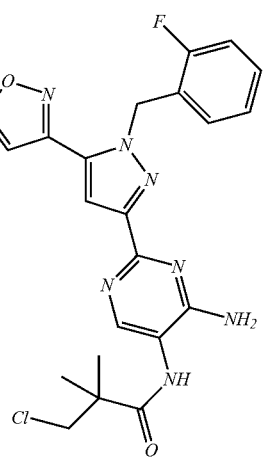
I-270
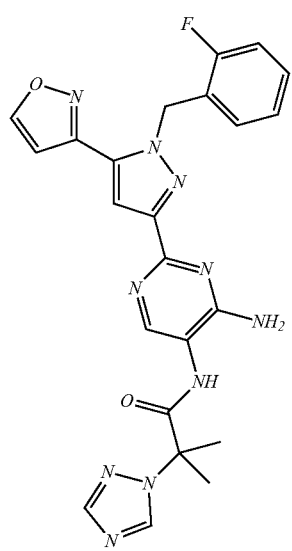
I-271
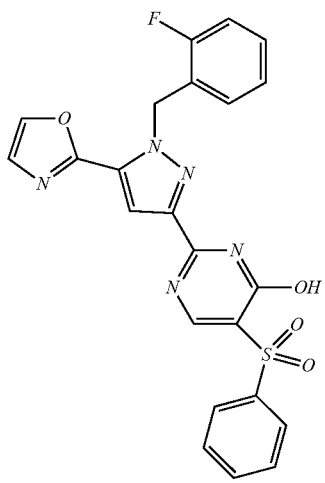

-continued
I-272
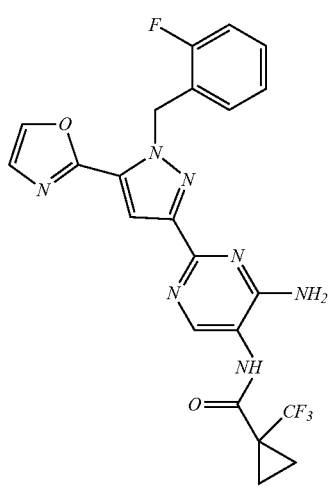
I-273
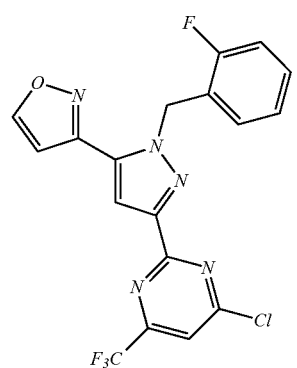
I-274
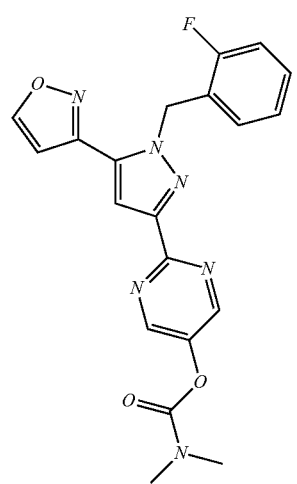
-continued
I-275
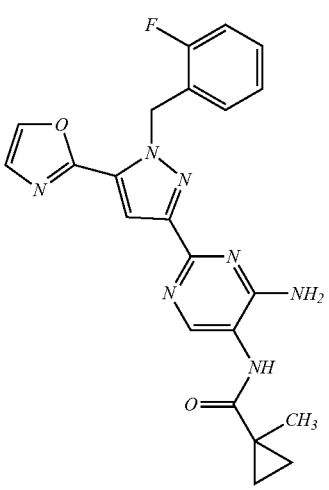
I-277
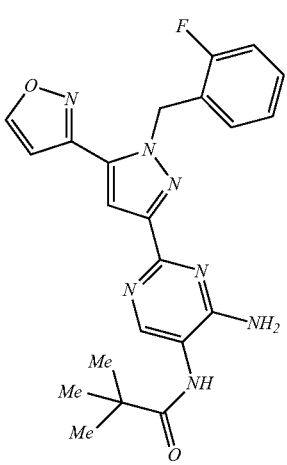
I-278
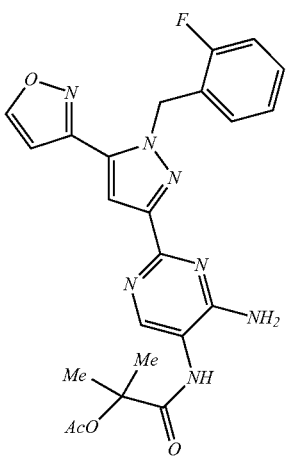

I-280
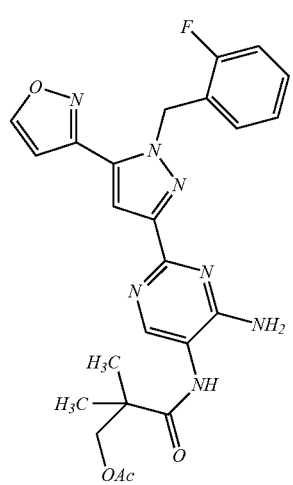
I-281
I-276
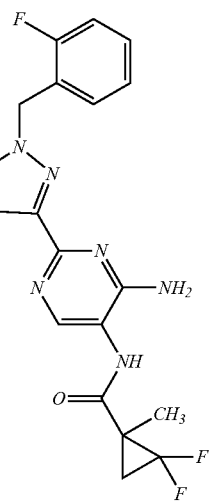
I-305
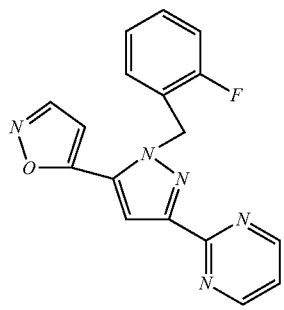
I-282
I-309
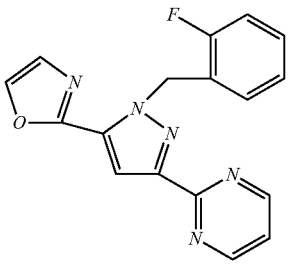
I-307
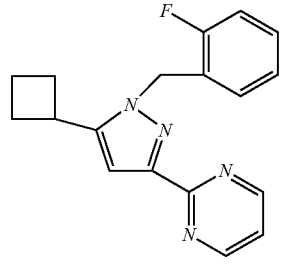
I-283
I-306
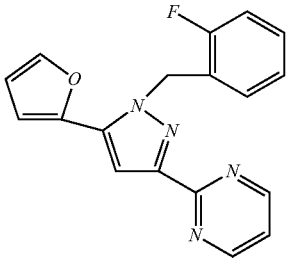

I-284
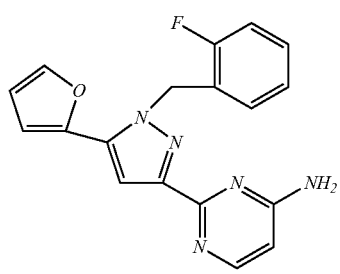
I-290
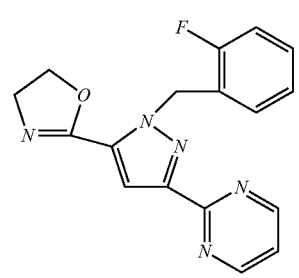
I-291
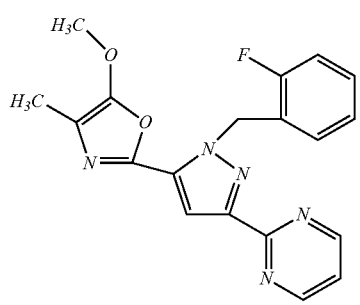
I-292
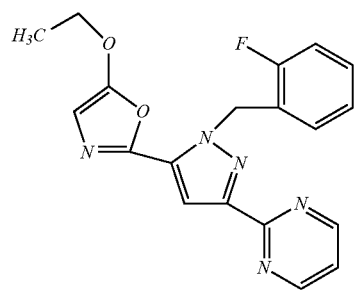
I-293
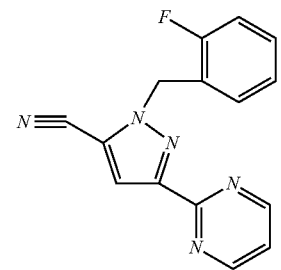
I-294
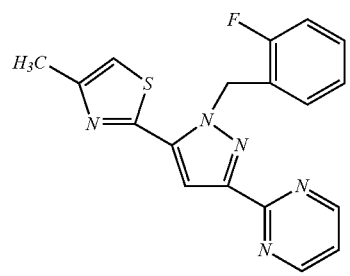
I-295
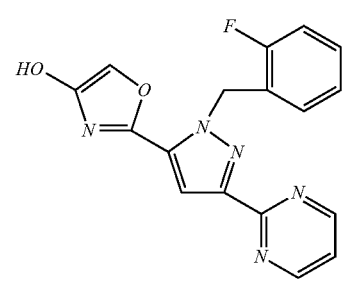
I-296
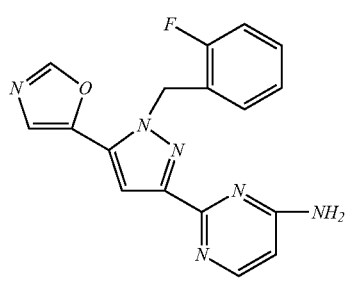
I-297
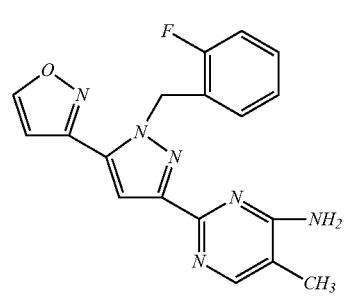
I-298
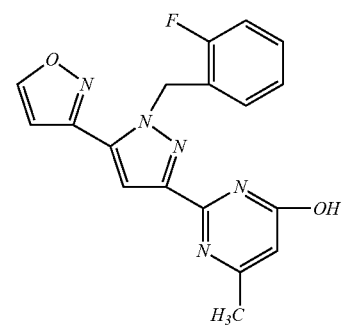

-continued
I-299
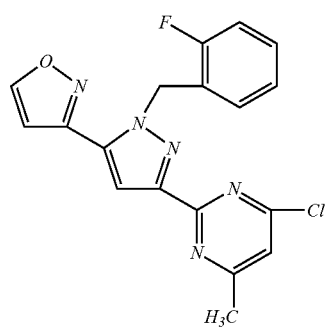
I-300
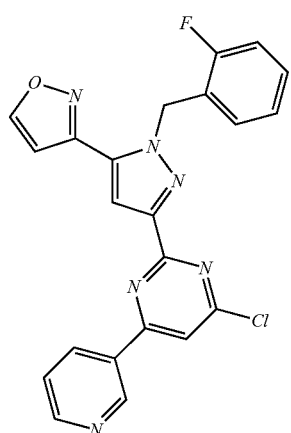
I-301
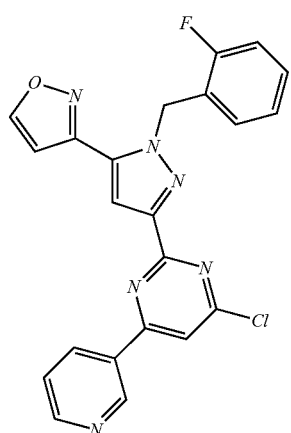
-continued
I-302
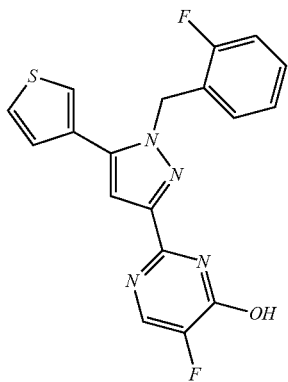
I-303
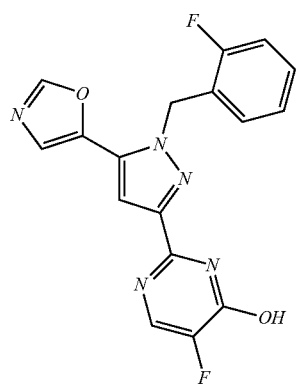
I-312
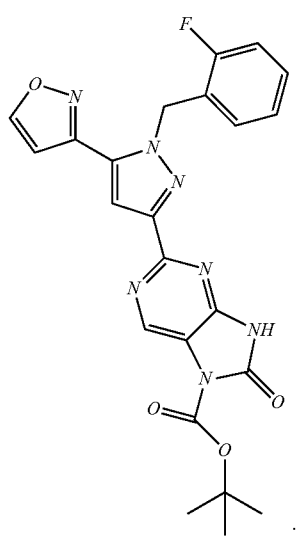
77. The compound of [either claims 75 or 76] claim 20, or a pharmaceutically acceptable salt thereof, wherein o is 0.
* * * * *